(12) United States Patent
Taylor et al.

(10) Patent No.: US 9,284,283 B2
(45) Date of Patent: Mar. 15, 2016

(54) MACROCYCLIC COMPOUNDS FOR MODULATING IL-17

(71) Applicant: ENSEMBLE THERAPEUTICS CORPORATION, Cambridge, MA (US)

(72) Inventors: Michael Taylor, Lexington, MA (US); Nicholas K. Terrett, Sherborn, MA (US); William H. Connors, Lynnfield, MA (US); Cheri Snedeker, Nashua, NH (US); Kelley C. Shortsleeves, Maynard, MA (US); Benjamin A. Seigal, Newton, MA (US); Stephen P. Hale, Belmont, MA (US); Timothy F. Briggs, Cambridge, MA (US); Frank G. Favaloro, Jr., North Attleboro, MA (US); Tyler J. Cipriani, North Stonington, CT (US); Dingxue Yan, South Grafton, MA (US); Sethu L. Alexander, Westford, MA (US); Atli Thorarensen, Stow, MA (US); Li Xing, Lexington, MA (US)

(73) Assignee: Ensemble Therapeutics Corporation, Cambridge, MA (US)

( * ) Notice: Subject to any disclaimer, the term of this patent is extended or adjusted under 35 U.S.C. 154(b) by 0 days.

(21) Appl. No.: 14/376,247

(22) PCT Filed: Feb. 1, 2013

(86) PCT No.: PCT/US2013/024386
§ 371 (c)(1),
(2) Date: Aug. 1, 2014

(87) PCT Pub. No.: WO2013/116682
PCT Pub. Date: Aug. 8, 2013

(65) Prior Publication Data
US 2015/0005319 A1    Jan. 1, 2015

Related U.S. Application Data

(60) Provisional application No. 61/593,993, filed on Feb. 2, 2012, provisional application No. 61/725,878, filed on Nov. 13, 2012.

(51) Int. Cl.
| | |
|---|---|
| *C07D 257/10* | (2006.01) |
| *C07D 273/00* | (2006.01) |
| *C07D 401/12* | (2006.01) |
| *C07D 409/14* | (2006.01) |
| *C07D 413/12* | (2006.01) |
| *C07D 409/12* | (2006.01) |
| *C07D 405/12* | (2006.01) |
| *C07D 257/02* | (2006.01) |
| *C07D 403/12* | (2006.01) |
| *C07D 417/12* | (2006.01) |
| *A61K 31/4965* | (2006.01) |
| *A61K 31/33* | (2006.01) |
| *A61K 31/44* | (2006.01) |
| *A61K 31/445* | (2006.01) |
| *A61K 31/425* | (2006.01) |

(Continued)

(52) U.S. Cl.
CPC ............ *C07D 257/10* (2013.01); *A61K 31/366* (2013.01); *A61K 31/42* (2013.01); *A61K 38/00* (2013.01); *C07D 255/02* (2013.01); *C07D 257/02* (2013.01); *C07D 273/00* (2013.01); *C07D 401/12* (2013.01); *C07D 403/12* (2013.01); *C07D 405/12* (2013.01); *C07D 409/12* (2013.01); *C07D 409/14* (2013.01); *C07D 413/12* (2013.01); *C07D 417/12* (2013.01)

(58) Field of Classification Search
USPC ............ 514/255.05, 183, 256, 278, 326, 365, 514/374, 444, 451; 540/453, 460, 461
See application file for complete search history.

(56) References Cited

U.S. PATENT DOCUMENTS

| | | |
|---|---|---|
| 5,952,320 A | 9/1999 | Davidsen et al. |
| 6,100,235 A | 8/2000 | Yao et al. |

(Continued)

FOREIGN PATENT DOCUMENTS

| | | |
|---|---|---|
| WO | WO-0168705 | 9/2001 |
| WO | WO-0208285 | 1/2002 |

(Continued)

OTHER PUBLICATIONS

Cancer [online], [retrieved on Jul. 6, 2007] Retrieved from the Internet, URL: http://www.nlm.nih.gov/medlineplus/cancer.html.*

(Continued)

*Primary Examiner* — Kristin Vajda
(74) *Attorney, Agent, or Firm* — Goodwin Procter LLP

(57) ABSTRACT

The invention relates generally to macrocyclic compounds of formula I and their therapeutic use. More particularly, the invention relates to macrocyclic compounds that modulate the activity of IL-17 and/or are useful in the treatment of medical conditions, such as inflammatory diseases and other IL-17-associated disorders.

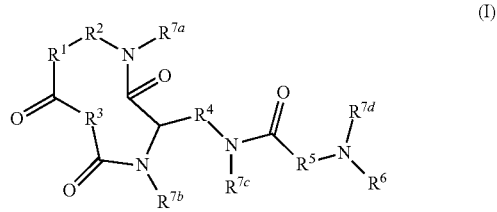

16 Claims, 284 Drawing Sheets

(51) Int. Cl.
*A61K 31/42* (2006.01)
*A61K 31/38* (2006.01)
*A61K 31/35* (2006.01)
*A61K 38/00* (2006.01)
*A61K 31/366* (2006.01)
*C07D 255/02* (2006.01)

(56) References Cited

U.S. PATENT DOCUMENTS

| | | |
|---|---|---|
| 7,427,402 B2 | 9/2008 | Kastelein et al. |
| 7,501,247 B2 | 3/2009 | Kastelein et al. |
| 7,510,709 B2 | 3/2009 | Gurney |
| 7,611,857 B2 | 11/2009 | Medlock et al. |
| 7,622,116 B2 | 11/2009 | Kuestner et al. |
| 7,740,848 B2 | 6/2010 | Kastelein et al. |
| 7,776,540 B2 | 8/2010 | Kastelein et al. |
| 7,790,163 B2 | 9/2010 | Jaspers et al. |
| 7,790,862 B2 | 9/2010 | Lewis et al. |
| 7,807,155 B2 | 10/2010 | Di Padova et al. |
| 7,910,540 B2 | 3/2011 | Levin et al. |
| 7,910,703 B2 | 3/2011 | Lewis et al. |
| 8,119,131 B2 | 2/2012 | Di Padova et al. |
| 8,178,095 B2 | 5/2012 | Kastelein et al. |
| 8,183,040 B2 | 5/2012 | Manel et al. |
| 8,268,773 B2 | 9/2012 | Presnell et al. |
| 8,287,869 B2 | 10/2012 | Gurney |
| 8,338,565 B2 | 12/2012 | Lee et al. |
| 2002/0037524 A1 | 3/2002 | Medlock et al. |
| 2003/0124092 A1 | 7/2003 | Medlock et al. |
| 2004/0136992 A1 | 7/2004 | Burton et al. |
| 2005/0287593 A1 | 12/2005 | Kastelein et al. |
| 2006/0270003 A1 | 11/2006 | Arnott et al. |
| 2007/0123459 A1 | 5/2007 | Medlock et al. |
| 2007/0154487 A1 | 7/2007 | Littman et al. |
| 2007/0160576 A1 | 7/2007 | Arnott et al. |
| 2007/0212362 A1 | 9/2007 | Filvaroff |
| 2007/0238658 A1 | 10/2007 | Levin et al. |
| 2007/0249533 A1 | 10/2007 | Levin et al. |
| 2008/0031882 A1 | 2/2008 | Liang et al. |
| 2008/0199460 A1 | 8/2008 | Cua et al. |
| 2008/0241130 A1 | 10/2008 | Wright et al. |
| 2008/0248025 A1 | 10/2008 | Roark et al. |
| 2008/0269467 A1 | 10/2008 | Allan et al. |
| 2009/0274703 A1 | 11/2009 | Mohler |
| 2009/0300776 A1 | 12/2009 | Lecron et al. |
| 2010/0021456 A1 | 1/2010 | Miossec et al. |
| 2010/0111950 A1 | 5/2010 | Cua et al. |
| 2010/0111954 A1 | 5/2010 | Cua et al. |
| 2010/0239590 A1 | 9/2010 | Bowman et al. |
| 2010/0247547 A1 | 9/2010 | Dong et al. |
| 2011/0033451 A1 | 2/2011 | Carreno et al. |
| 2011/0091378 A1 | 4/2011 | Dudas et al. |
| 2011/0104236 A1 | 5/2011 | Dana et al. |
| 2011/0142831 A1 | 6/2011 | Cua et al. |
| 2011/0144303 A1 | 6/2011 | Nash et al. |
| 2011/0152173 A1 | 6/2011 | Lofquist et al. |
| 2011/0159589 A1 | 6/2011 | Lewis et al. |
| 2011/0177578 A1 | 7/2011 | Nakamura et al. |
| 2011/0212099 A1 | 9/2011 | Liang et al. |
| 2011/0212100 A1 | 9/2011 | Keller et al. |
| 2011/0236390 A1 | 9/2011 | Almagro et al. |
| 2011/0256126 A1 | 10/2011 | Arnott et al. |
| 2011/0263479 A1 | 10/2011 | Jacobsen et al. |
| 2011/0289608 A1 | 11/2011 | Schnell et al. |
| 2011/0293629 A1 | 12/2011 | Bastid et al. |
| 2011/0311519 A1 | 12/2011 | Teitelbaum et al. |
| 2011/0318301 A1 | 12/2011 | Arnott et al. |
| 2012/0009190 A1 | 1/2012 | Gaffen et al. |
| 2012/0107325 A1 | 5/2012 | Di Padova et al. |
| 2012/0142755 A1 | 6/2012 | Lecron et al. |
| 2012/0196861 A1 | 8/2012 | Leban et al. |
| 2012/0196862 A1 | 8/2012 | Leban et al. |
| 2012/0244543 A1 | 9/2012 | Manel et al. |
| 2012/0252896 A1 | 10/2012 | Ernst et al. |
| 2012/0263729 A1 | 10/2012 | Burton et al. |
| 2012/0276105 A1 | 11/2012 | Kastelein et al. |
| 2014/0309265 A1 | 10/2014 | Seigal et al. |

FOREIGN PATENT DOCUMENTS

| | | |
|---|---|---|
| WO | WO-03055980 | 7/2003 |
| WO | WO-03057722 A2 | 7/2003 |
| WO | WO-2004019866 A2 | 3/2004 |
| WO | WO-2004042009 A2 | 5/2004 |
| WO | WO-2005010044 A2 | 2/2005 |
| WO | WO-2005098435 A2 | 10/2005 |
| WO | WO-2005108616 A1 | 11/2005 |
| WO | WO-2005123778 A2 | 12/2005 |
| WO | WO-2006013107 A1 | 2/2006 |
| WO | WO-2006063864 A2 | 6/2006 |
| WO | WO-2006088833 A2 | 8/2006 |
| WO | WO-2007027761 A2 | 3/2007 |
| WO | WO-2007038703 A2 | 4/2007 |
| WO | WO-2007147019 A2 | 12/2007 |
| WO | WO-2007149814 A1 | 12/2007 |
| WO | WO-2008039553 A1 | 4/2008 |
| WO | WO-2008067223 A2 | 6/2008 |
| WO | WO-2008104000 A2 | 8/2008 |
| WO | WO-2008118792 A2 | 10/2008 |
| WO | WO-2008121865 A1 | 10/2008 |
| WO | WO-2008131315 A2 | 10/2008 |
| WO | WO-2008134659 A2 | 11/2008 |
| WO | WO-2008150885 A1 | 12/2008 |
| WO | WO-2008156865 A2 | 12/2008 |
| WO | WO-2009015063 A2 | 1/2009 |
| WO | WO-2009023267 A2 | 2/2009 |
| WO | WO-2009047523 A1 | 4/2009 |
| WO | WO-2009082624 A2 | 7/2009 |
| WO | WO-2009089036 A2 | 7/2009 |
| WO | WO-2010003108 A2 | 1/2010 |
| WO | WO-2010022249 A2 | 2/2010 |
| WO | WO-2010062858 A1 | 6/2010 |
| WO | WO-2010144344 A2 | 12/2010 |
| WO | WO-2011053763 A2 | 5/2011 |
| WO | WO-2011061667 A1 | 5/2011 |
| WO | WO-2011062628 A1 | 5/2011 |
| WO | WO-2011100567 A1 | 8/2011 |
| WO | WO-2011141823 A2 | 11/2011 |
| WO | WO-2011143608 A1 | 11/2011 |
| WO | WO-2011163452 A2 | 12/2011 |
| WO | WO-2012059598 A2 | 5/2012 |
| WO | WO-2012082573 A1 | 6/2012 |
| WO | WO-2012101261 A1 | 8/2012 |
| WO | WO-2012101263 A1 | 8/2012 |
| WO | WO-2013016220 A1 | 1/2013 |
| WO | WO-2013071027 A1 | 5/2013 |
| WO | WO-2013071035 A1 | 5/2013 |
| WO | WO-2013071039 A1 | 5/2013 |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Appel et al. (2011) "Analysis of IL-17+ cells in facet joints of patients with spondyloarthritis suggests that the innate immune pathway might be of greater relevance than the Th17-mediated adaptive immune response," Arthritis Research and Therapy 13:R95.
Bednarek et al. (2001) "Selective, high affinity peptide antagonists of alpha-melanotropin action at human melanocortin receptor 4: Their synthesis and biological evaluation in vitro," Journal of Medicinal Chemistry 44(22): 3665-3672.
Dudler et al. (2000) "Effect of interleukin 17 on proteoglycan degradation in murine knee joints," Ann Rheum Dis 59:529-32.
Flygare et al. (2010) "Small-molecule pan-IAP antagonists: a patent review," Expert Opinion on Therapeutic Patents 20(2): 251-267.
Gaffen (2004) "Biology of recently discovered cytokines: Interleukin-17—a unique inflammatory cytokine with roles in bone biology and arthritis," Arthritis Research & Therapy 6: 240-247.

(56) References Cited

OTHER PUBLICATIONS

Gaffen (2009) "Structure and signalling in the IL-17 receptor family," Nature Rev Immunol, 9: 556-567.

Giolitti et al. (2002) "Monocyclic human tachykinin NK-2 receptor antagonists as evolution of a potent bicyclic antagonist: QSAR and site-directed mutagenesis studies," Journal of Medicinal Chemistry 45(16): 3418-3429.

International Search Report and Written Opinion for International Patent Application No. PCT/US2009/054487, mailed on Feb. 15, 2010 (18 pages).

International Search Report and Written Opinion for International Patent Application No. PCT/US2012/064332, mailed on Feb. 21, 2013 (7 pages).

International Search Report and Written Opinion for International Patent Application No. PCT/US2012/064342, mailed on Jan. 24, 2013 (8 pages).

International Search Report and Written Opinion for International Patent Application No. PCT/US2012/064349, mailed on Jan. 30, 2013 (10 pages).

Ji et al. (2010) "Th17 cells: positive or negative role in tumor?" Cancer Immunol Immunother 59: 979-987.

Lubberts et al. (2001) "IL-1 Independent Role of IL-17 in Synovial Inflammation and Joint Destruction During Collagen-Induced Arthritis," J Immunol 167:1004-1013.

Matusevicius et al. (1999) "Interleukin-17 mRNA expression in blood and CSF mononuclear cells is augmented in multiple sclerosis," Multiple Sclerosis 5:101-104.

McInnes et al. (2011) "Anti-Interleukin 17A Monoclonal Antibody Secukinumab Reduces Signs and Symptoms of Psoriatic Arthritis in a 24-Week Multicenter, Double-Blind, Randomized, Placebo-Controlled Trial. [abstract]," Arthritis & Rheumatism 63: Suppl.10:779.

Miyazaki et al. (2004) "Design and synthesis of nobel type somatostatin analogs with antiproliferative activities on A431 tumor cells," Tetrahedrin Letters 45(33): 6323-6327.

Nakae et al. (2003) "Suppression of Immune Induction of Collagen-Induced Arthritis in IL-17-Deficient Mice," J Immunol 171:6173-6177.

Nikolovska-Coleska et al. (2008) "Interaction of a Cyclic. Bivalent Smac Mimetic with the X-Linked Inhibitor of Apoptosis Protein," Biochemistry 47(37): 9811-9824.

Pedersen et al. (2011) "1.2.3-Triazoles in Peptidomimetic Chemistry," European Journal of Organic Chemistry 13: 2399-2411.

Prabhala et al. (2010) "Elevated IL-17 produced by Th17 cells promotes myeloma cell growth and inhibits immune function in multiple myeloma," Blood 115(26): 5385-5392.

Rothe et al. (1976) "Makrocyclische Peptide in Anionischen Polymerisaten Von Aminosaeure-N-Carbonsaeureanhydriden," Angewandte Chemie 88(10): 338-339.

Schwyzer et al. (1956) "Synthesen zyklischer Polypeptide. c-Tetraglycyl and c-Hexaglycyl. Uber aktivierte Ester VII," Helvetica Chimica Acta 39(3): 872-883.

Sheh et al. (1985) "Cyclization Studies of Tetrapeptide Homologs," Tetrahedron Letters 26(47): 5755-5758.

Shlezinger et al. (2011) "Apoptosis-like programmed cell death in the grey mould fungus Botrytis cinerea: genes and their role in pathogenicity," Biochemical Society Transactions 39(5): 1493-1498.

Smolewski et al. (2011) "Inhibitors of apoptosis proteins (IAPs) as potential molecular targets for therapy of hematological malignancies," Current Molecular Medicine 11(8): 633-49.

Spriggs et al. (1997) "Interleukin-17 and Its Receptor," J Clin Immunol, 17: 366-369.

STN Search Transcript Registry/Caplus Databases (2013) 162 pages.

Sun et al. (2010) "Cyclopeptide Smac mimetics as antagonists of IAP proteins," Bioorganic & Medicinal Chemistry Letters 20(10): 3043-3046.

Zhang et al. (2009) "Increased intratumoral IL-17-producing cells correlate with poor survival in hepatocellular carcinoma patients" J Hepatology 50: 980-89.

\* cited by examiner

Figure 12

Table 1. Exemplary Compounds of the Invention

| Compound No. | Structure |
|---|---|
| 100 | 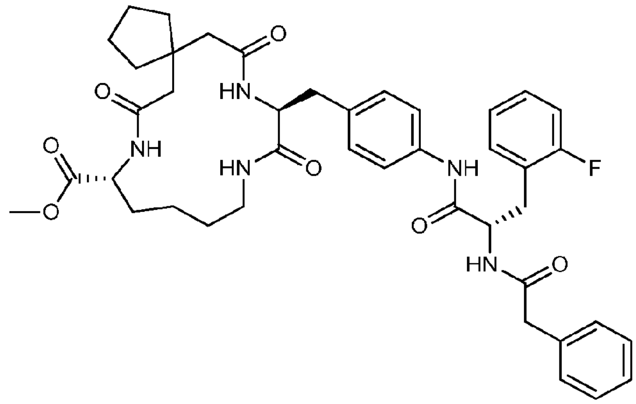 |
| 101 | 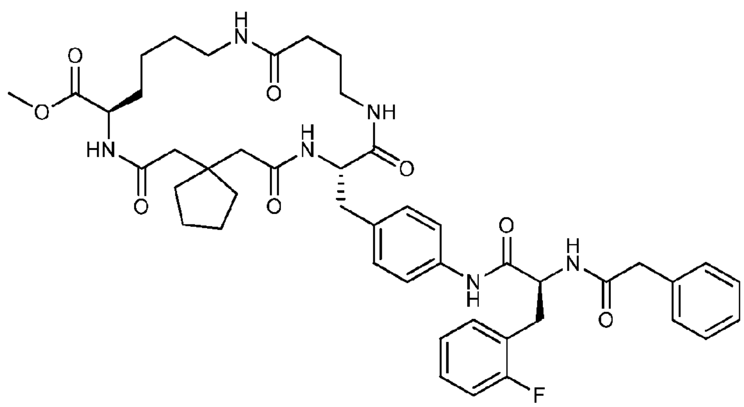 |
| 102 | 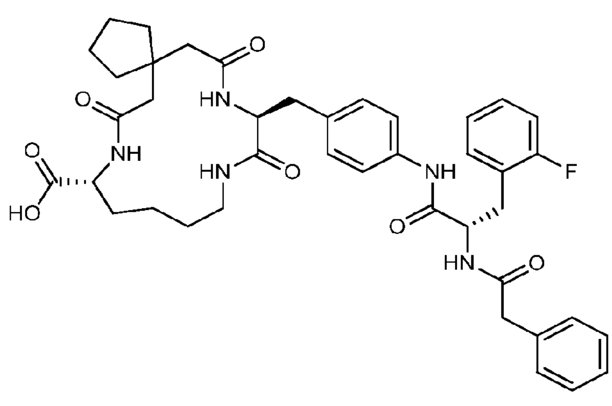 |

FIG. 12-1

| Compound No. | Structure |
|---|---|
| 103 | 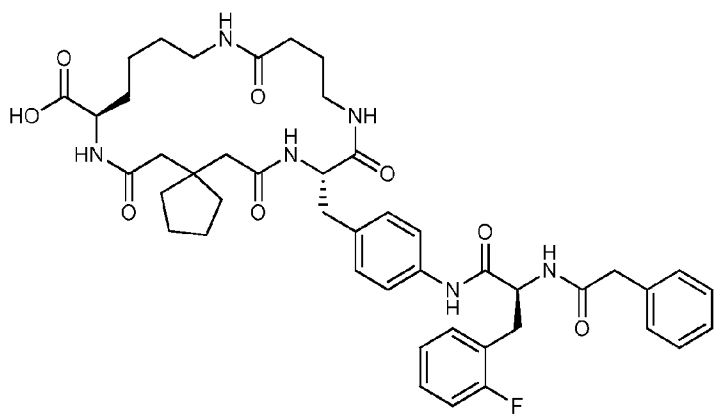 |
| 104 | 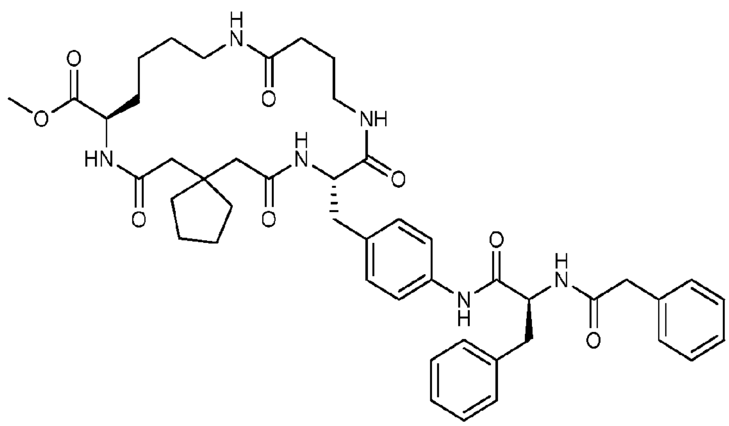 |
| 105 | 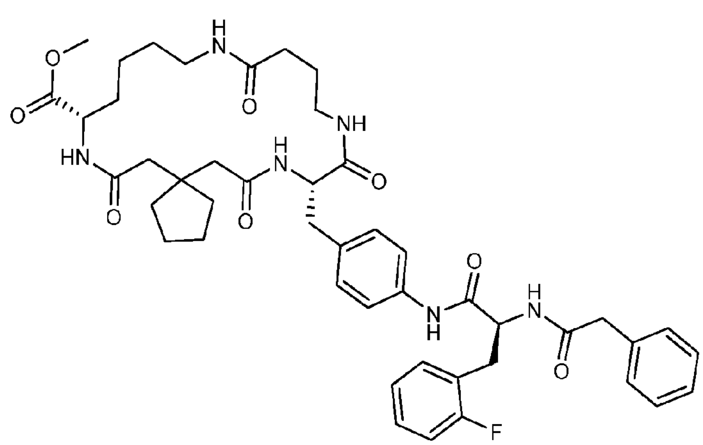 |

FIG. 12-2

| Compound No. | Structure |
|---|---|
| 106 | 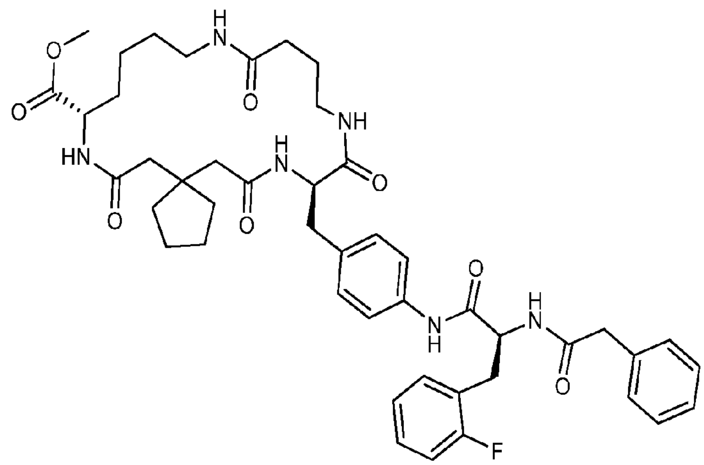 |
| 107 | 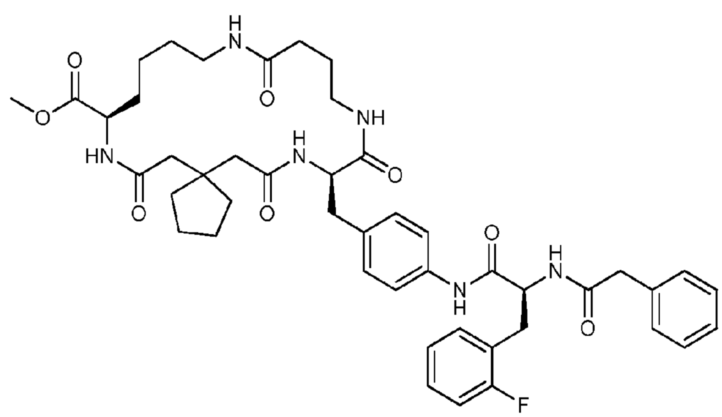 |
| 108 | 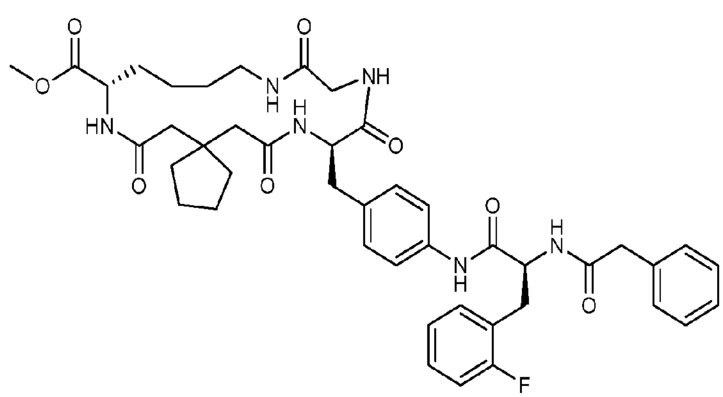 |

FIG. 12-3

| Compound No. | Structure |
|---|---|
| 109 | 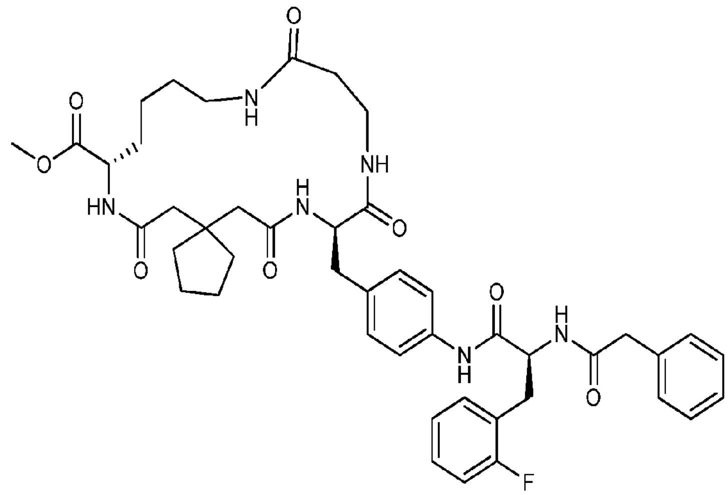 |
| 110 | 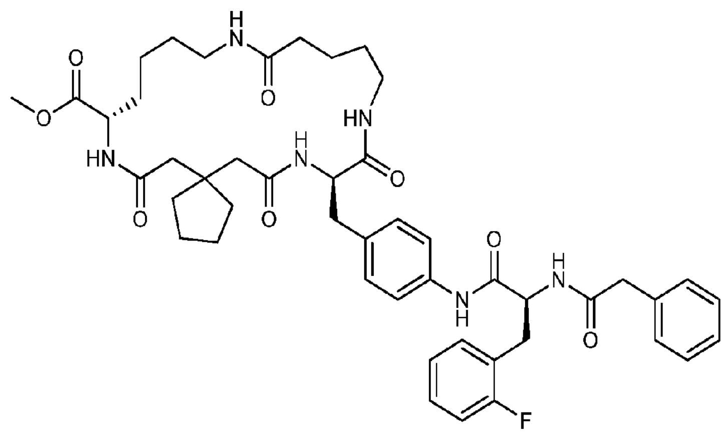 |

FIG. 12-4

| Compound No. | Structure |
|---|---|
| 111 | 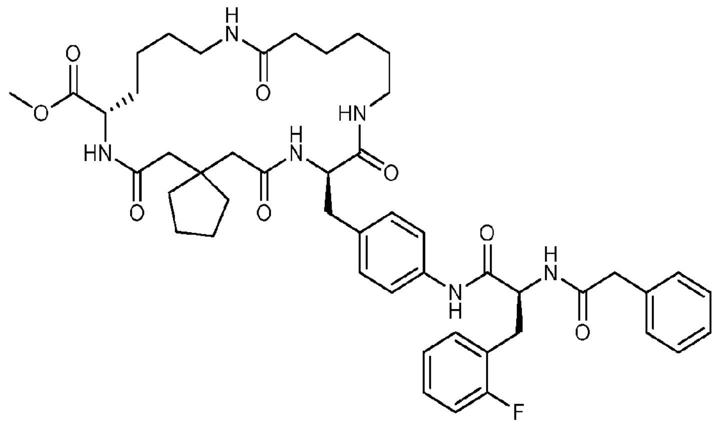 |
| 112 | 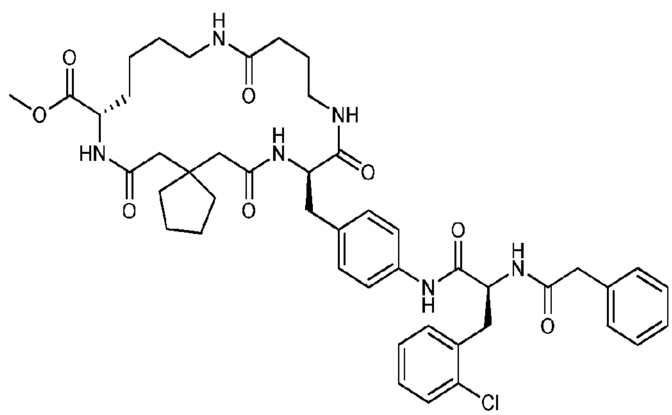 |
| 113 | 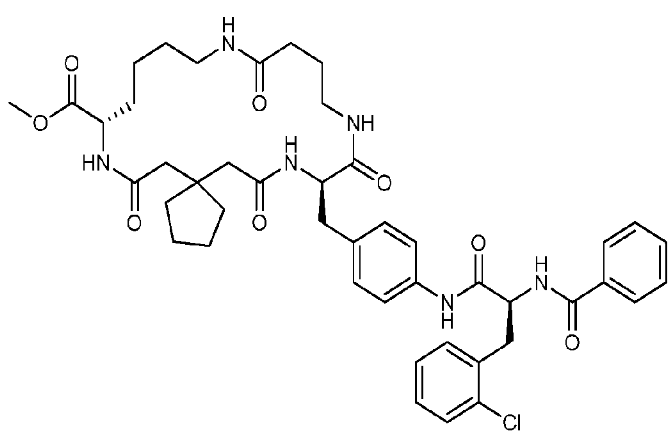 |

FIG. 12-5
| Compound No. | Structure |
|---|---|
| 114 | 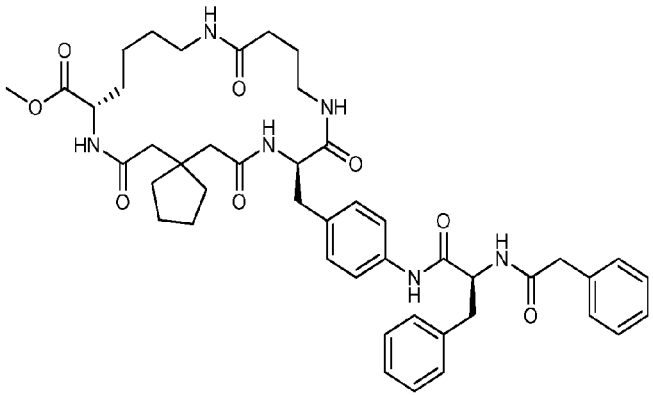 |
| 115 | 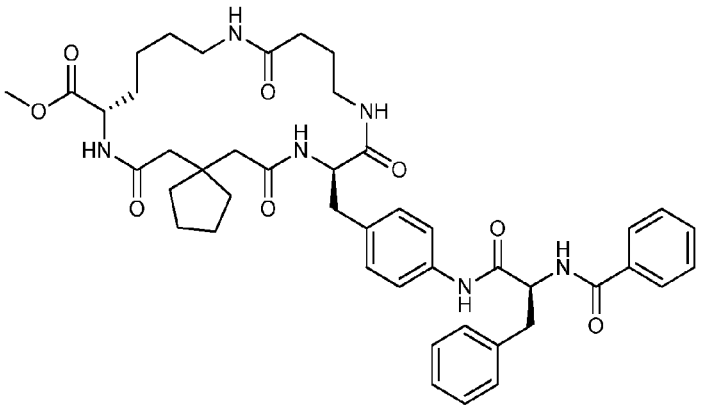 |
| 116 | 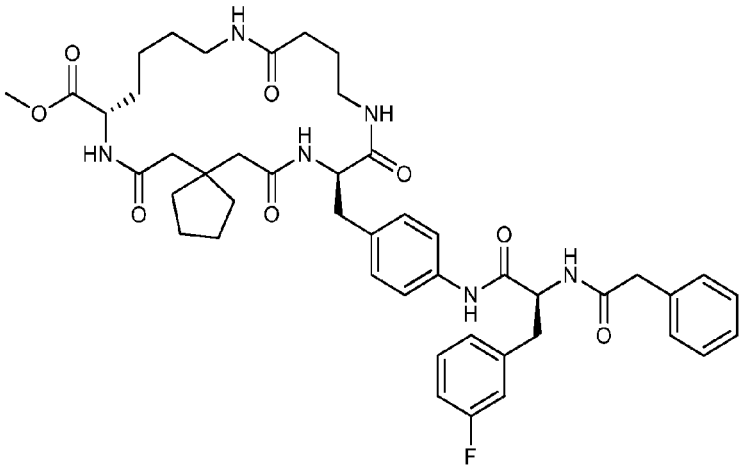 |

| Compound No. | Structure |
|---|---|
| 117 | 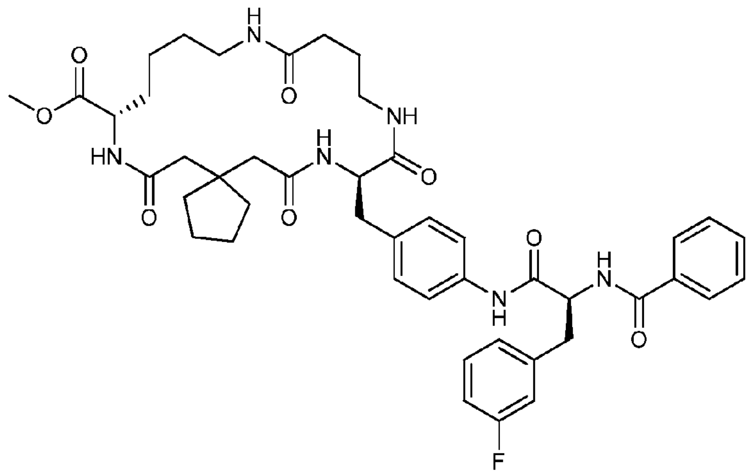 |
| 118 | 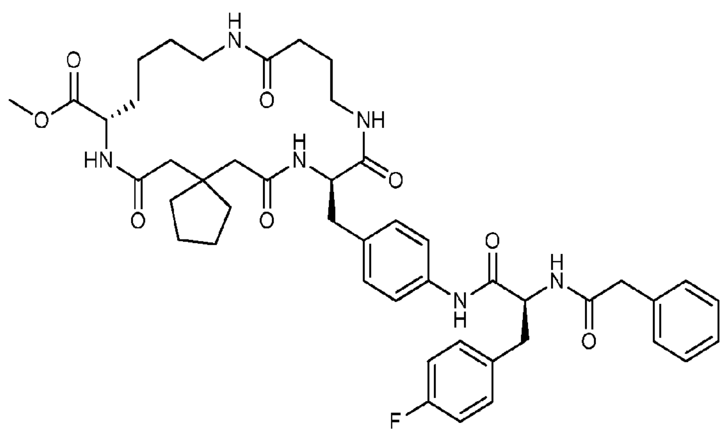 |

FIG. 12-7

| Compound No. | Structure |
|---|---|
| 119 | 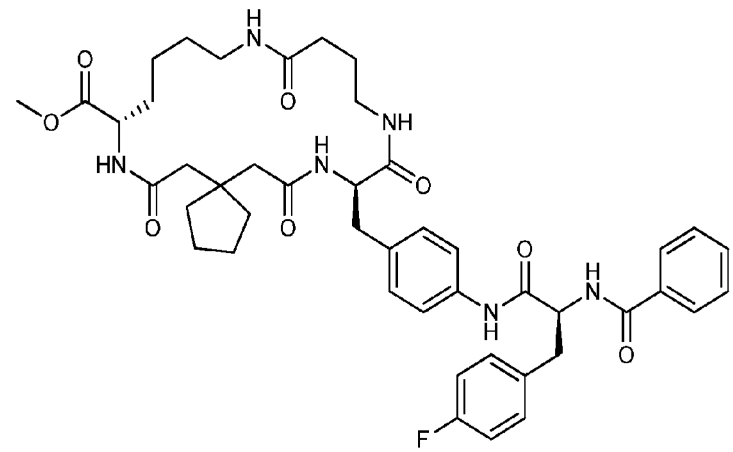 |
| 120 | 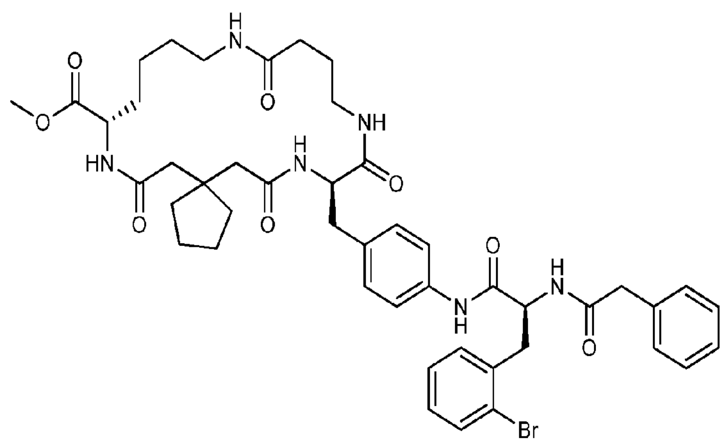 |

FIG. 12-8
| Compound No. | Structure |
|---|---|
| 121 | 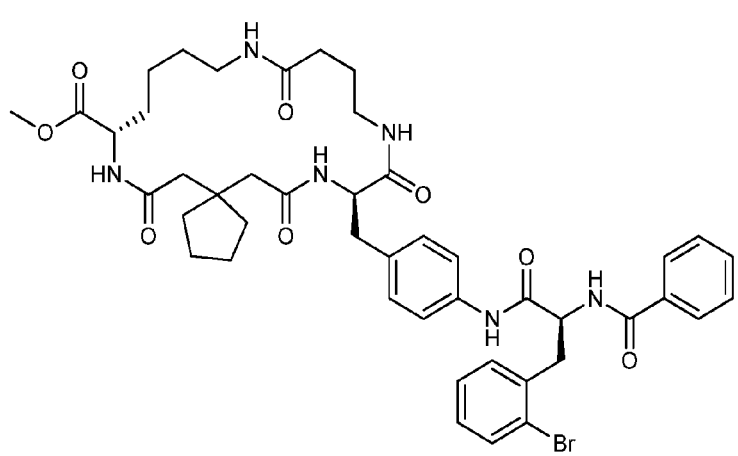 |
| 122 | 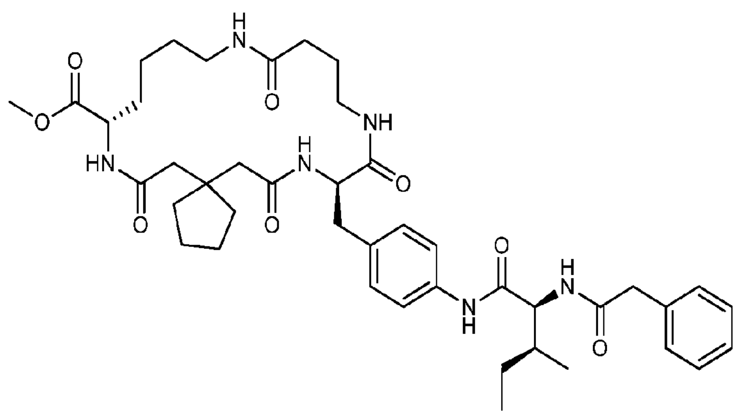 |
| 123 | 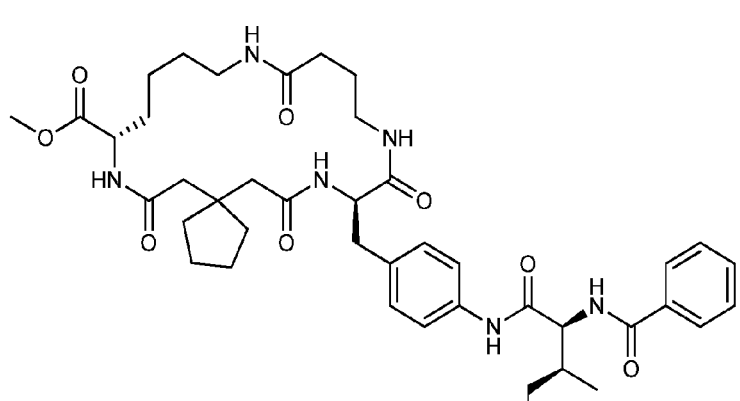 |

| Compound No. | Structure |
|---|---|
| 124 | 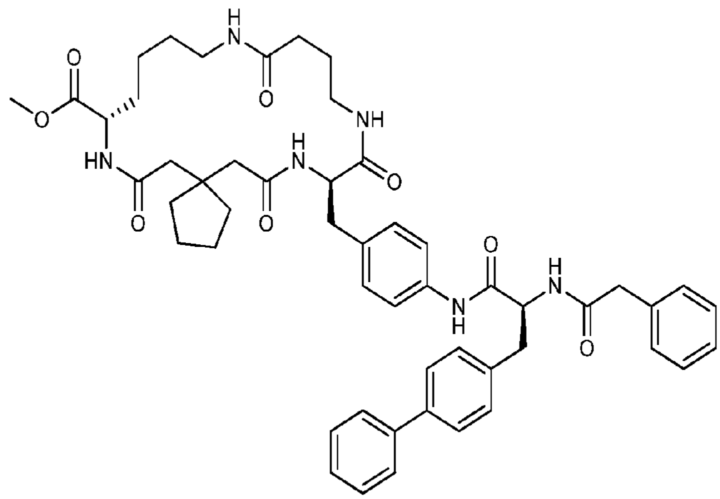 |
| 125 | 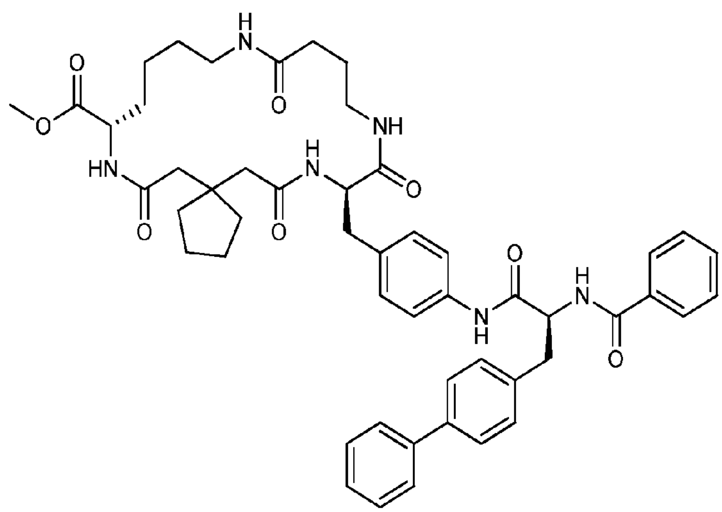 |

FIG. 12-10
| Compound No. | Structure |
|---|---|
| 126 | 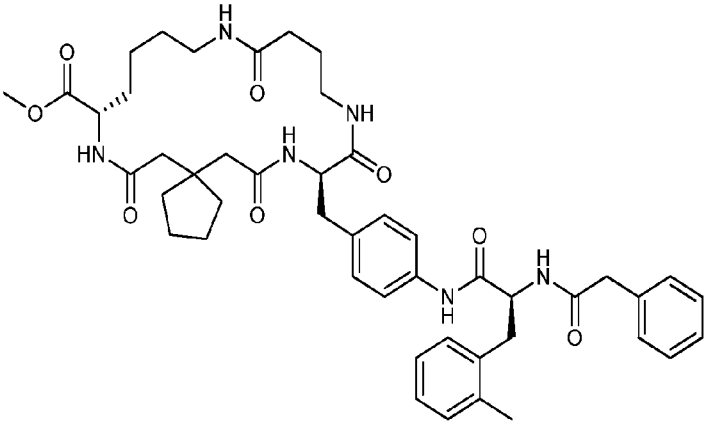 |
| 127 | 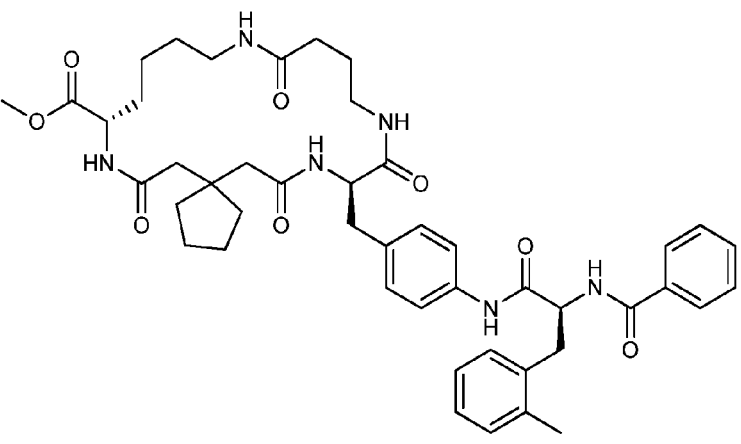 |
| 128 | 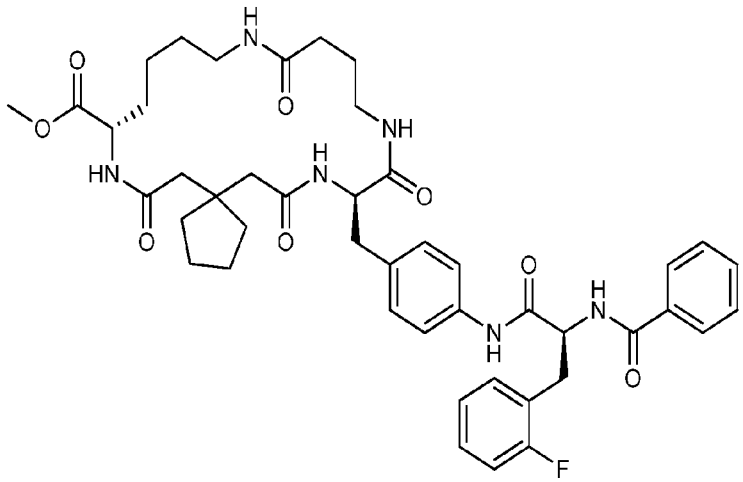 |

FIG. 12-11

| Compound No. | Structure |
|---|---|
| 129 | 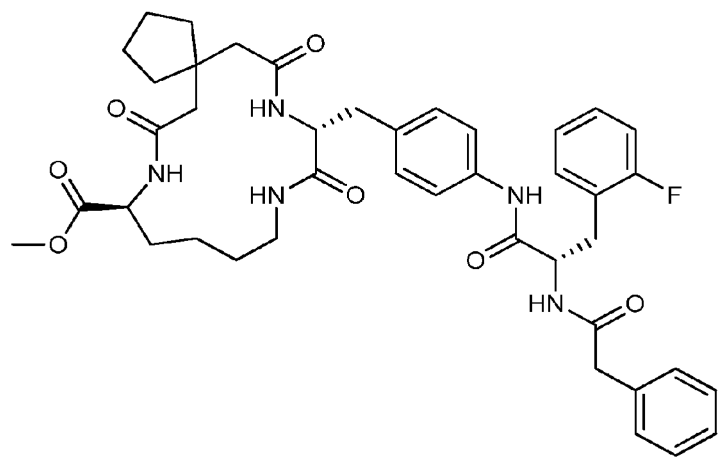 |
| 130 | 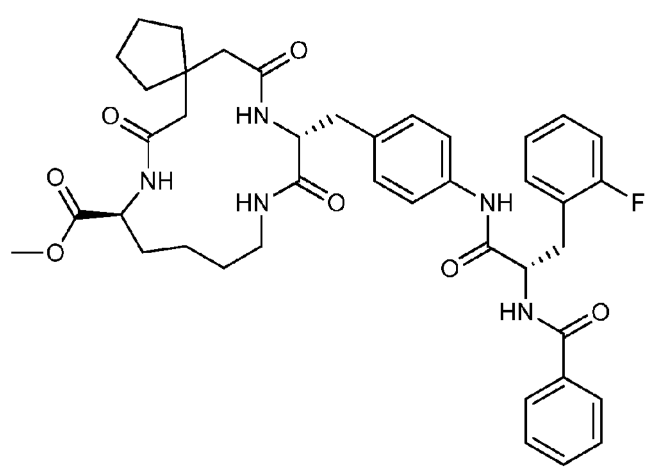 |
| 131 | 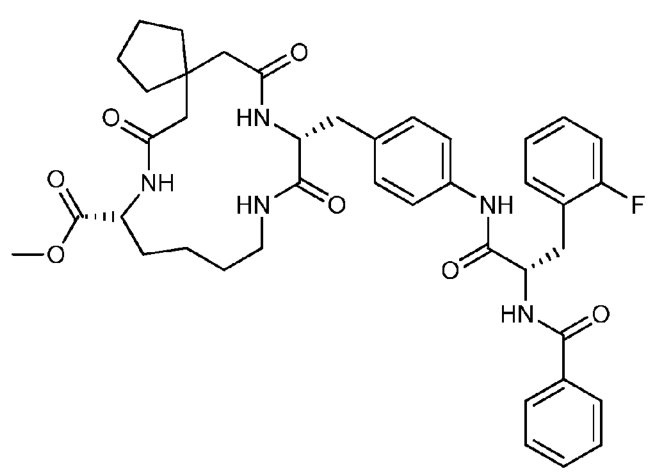 |

FIG. 12-12

| Compound No. | Structure |
|---|---|
| 132 | 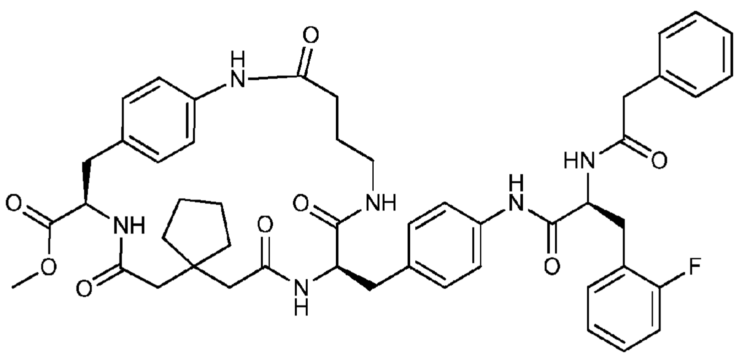 |
| 133 | 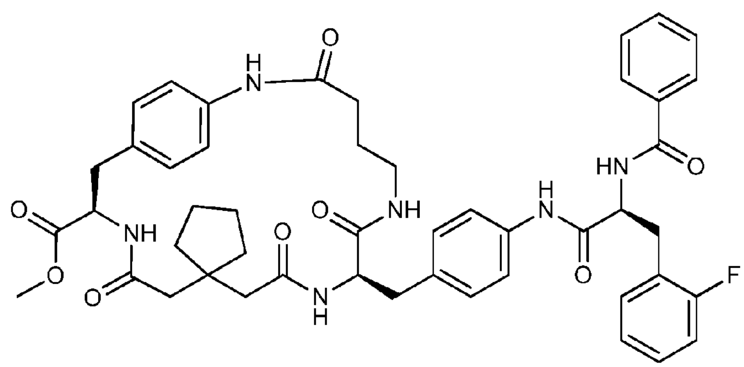 |
| 134 | 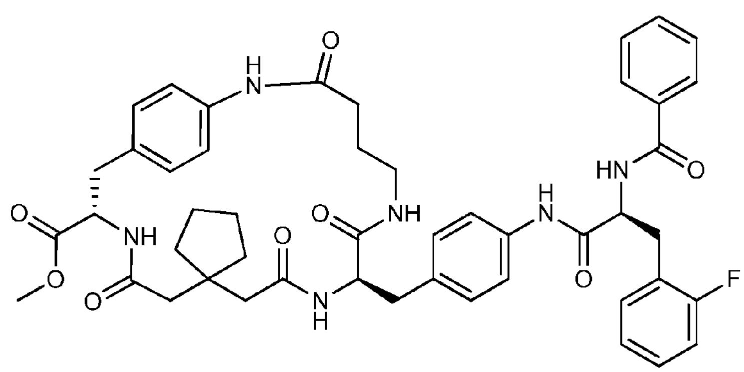 |

FIG. 12-13

| Compound No. | Structure |
|---|---|
| 135 | 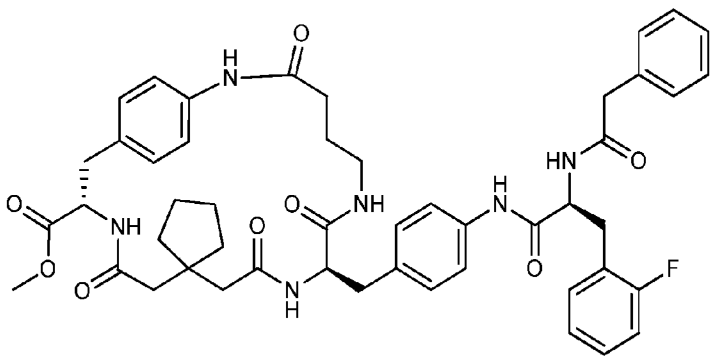 |
| 136 | 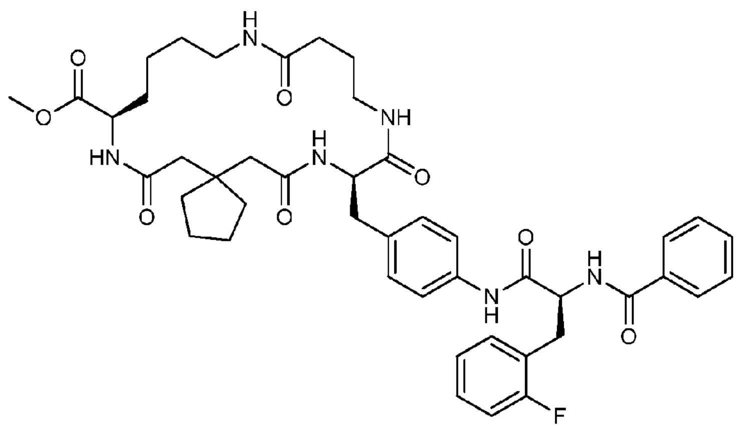 |
| 137 | 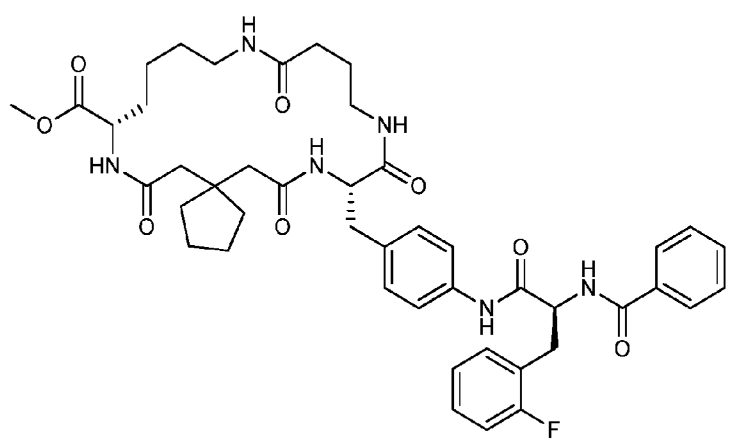 |

FIG. 12-14

| Compound No. | Structure |
|---|---|
| 138 | 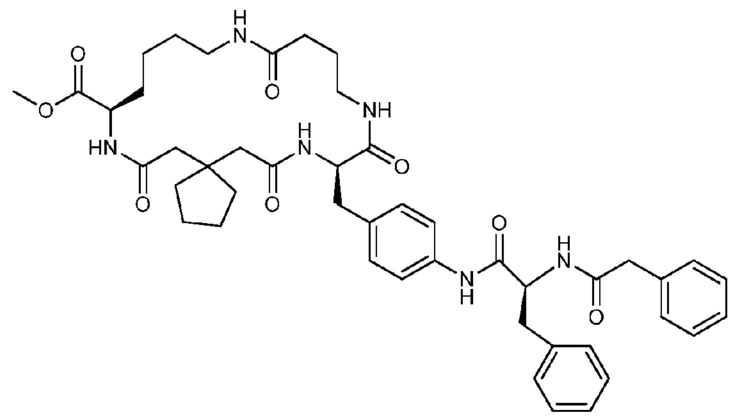 |
| 139 | 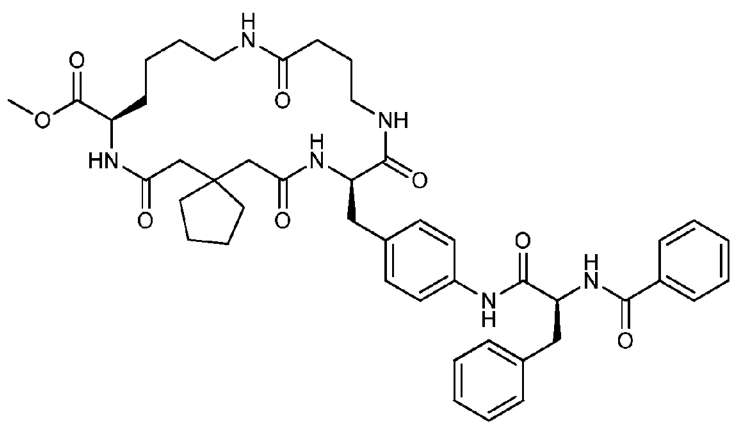 |
| 140 | 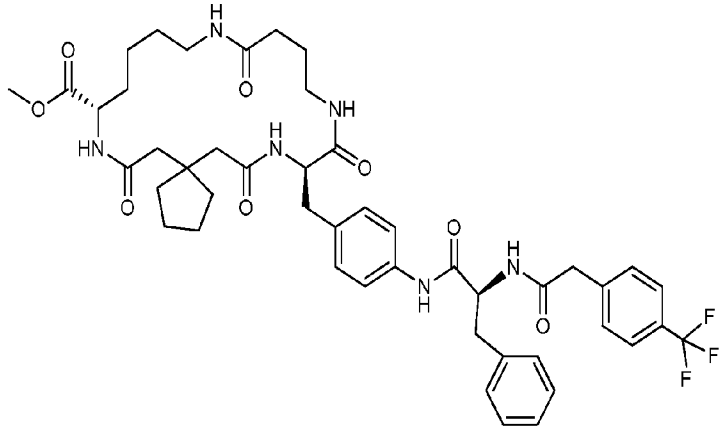 |

FIG. 12-15
| Compound No. | Structure |
|---|---|
| 141 | 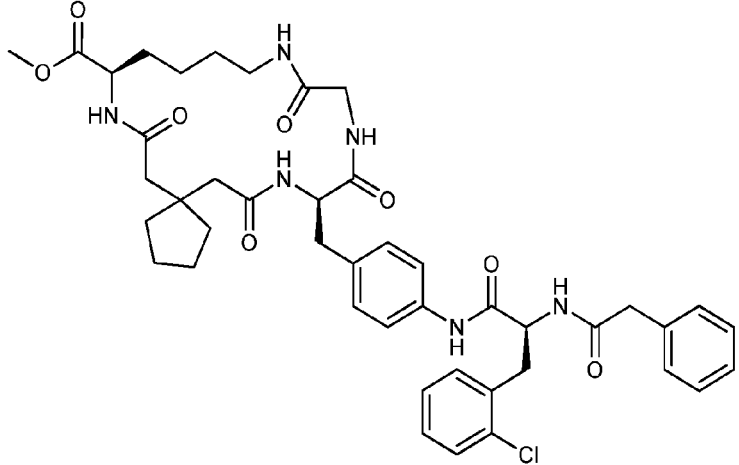 |
| 142 | 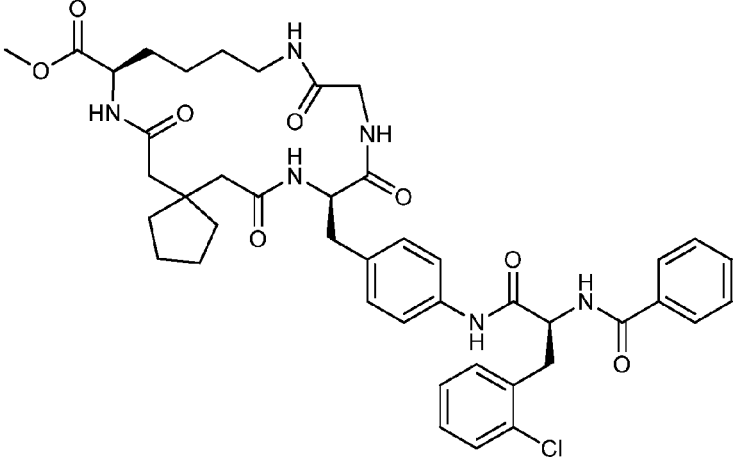 |

FIG. 12-16
| Compound No. | Structure |
|---|---|
| 143 | 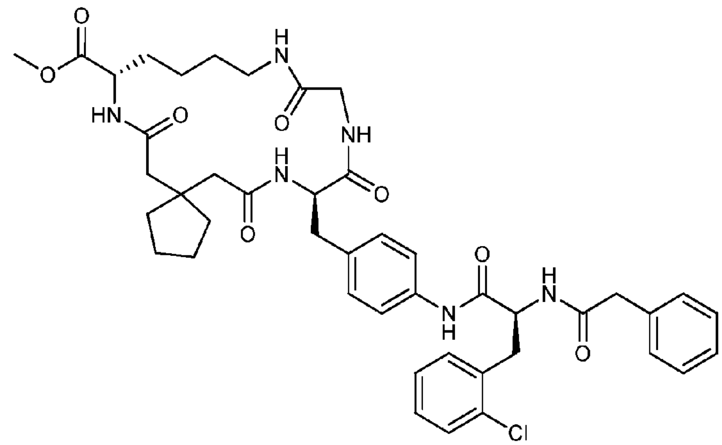 |
| 144 | 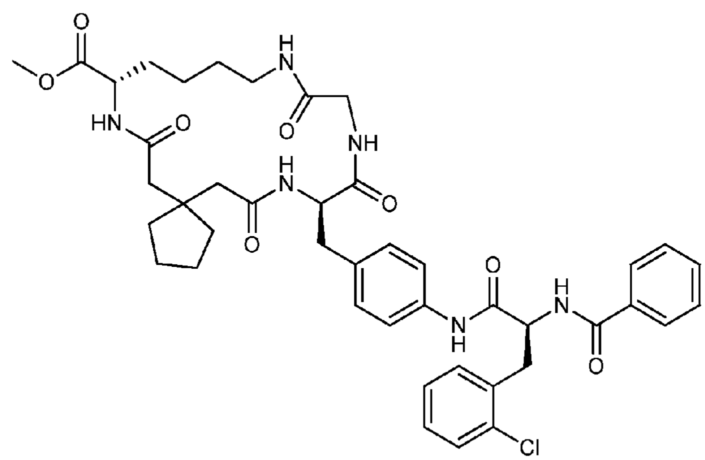 |

FIG. 12-17
| Compound No. | Structure |
|---|---|
| 145 | 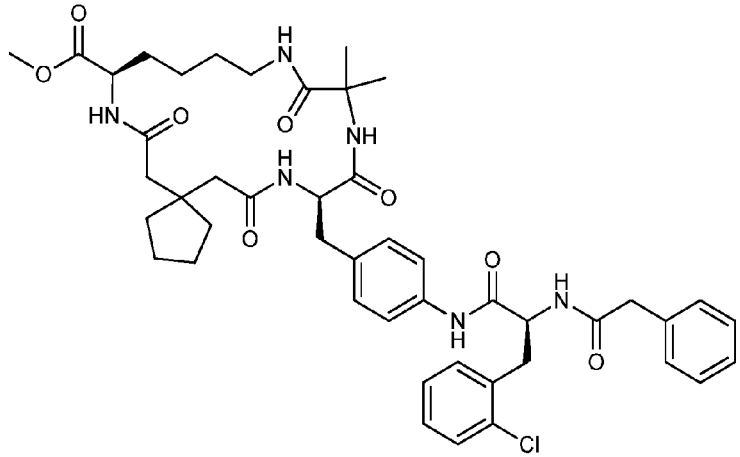 |
| 146 | 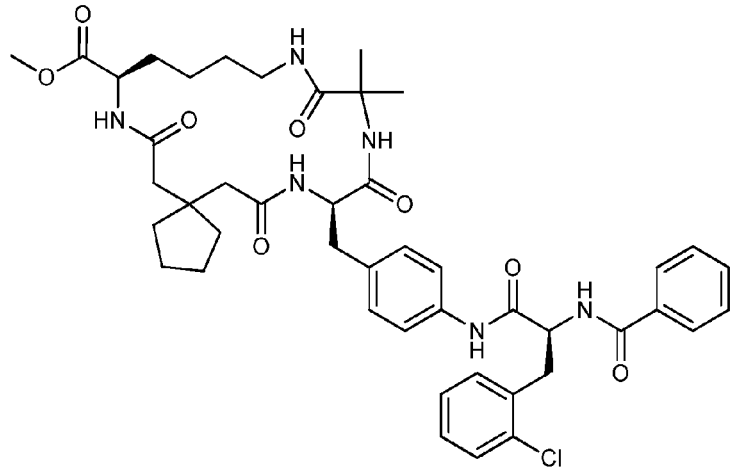 |

FIG. 12-18
| Compound No. | Structure |
|---|---|
| 147 | 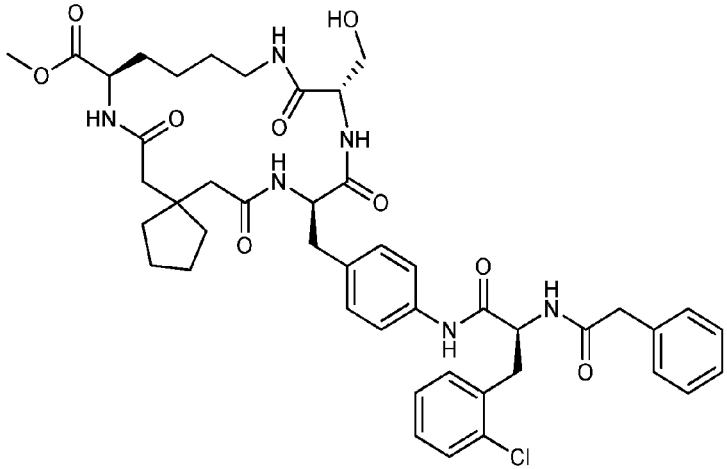 |
| 148 | 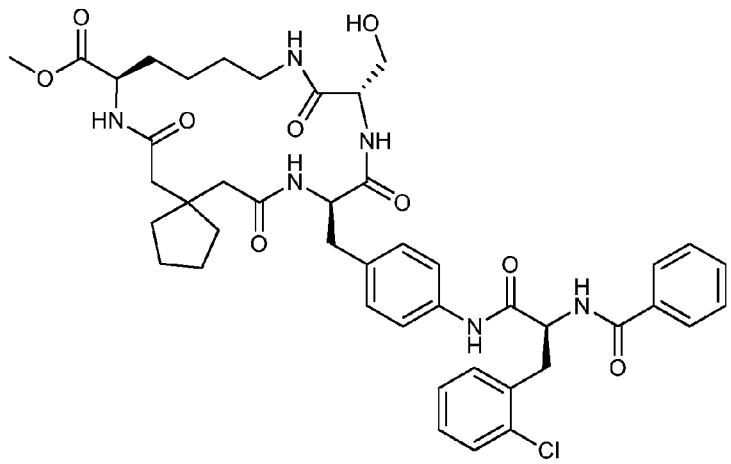 |

FIG. 12-19
| Compound No. | Structure |
|---|---|
| 149 | 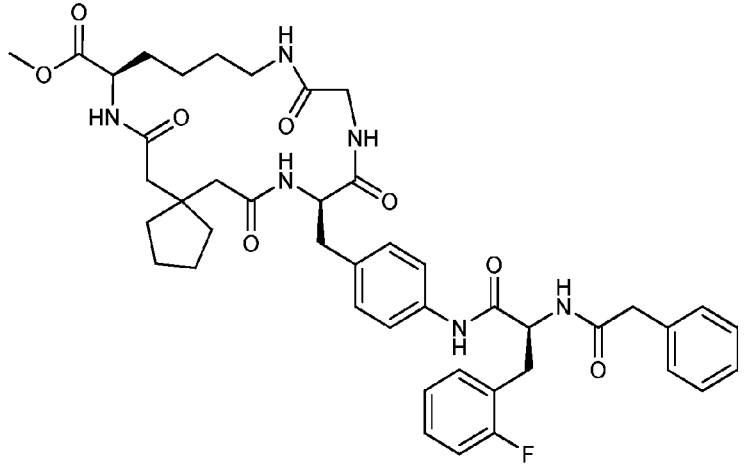 |
| 150 | 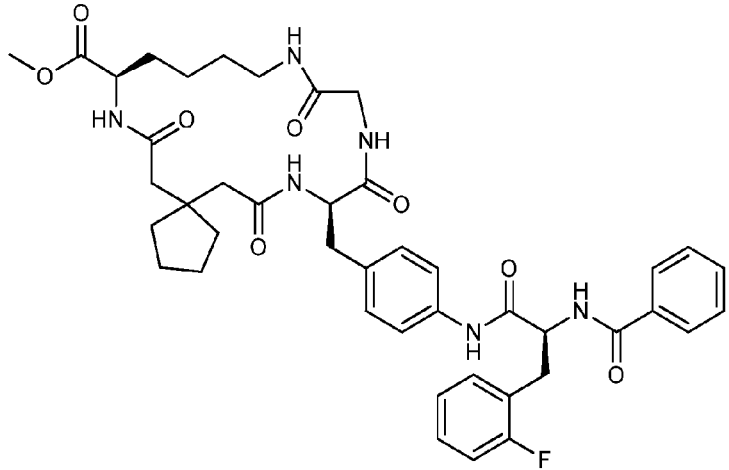 |

FIG. 12-20
| Compound No. | Structure |
|---|---|
| 151 | 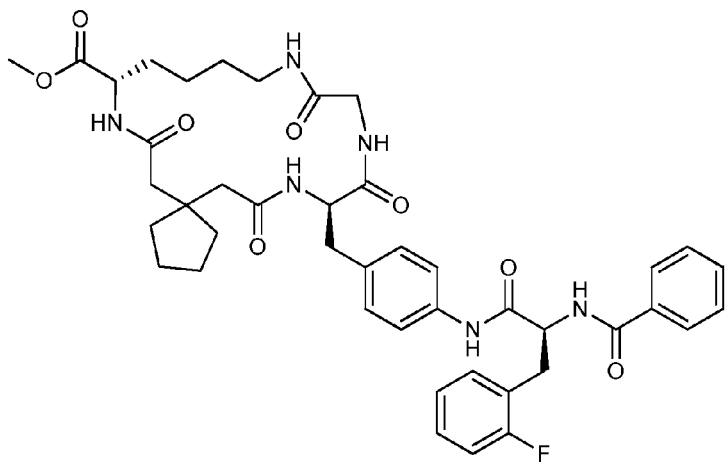 |
| 152 | 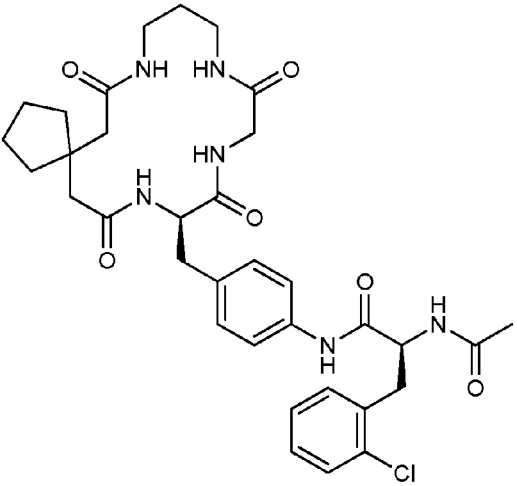 |

FIG. 12-21
| Compound No. | Structure |
|---|---|
| 153 | 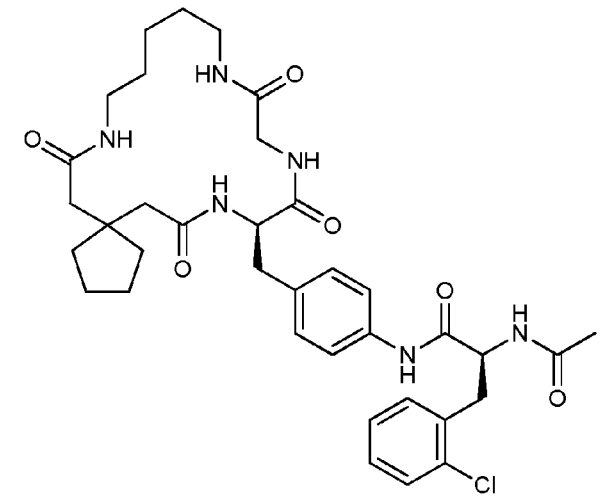 |
| 154 | 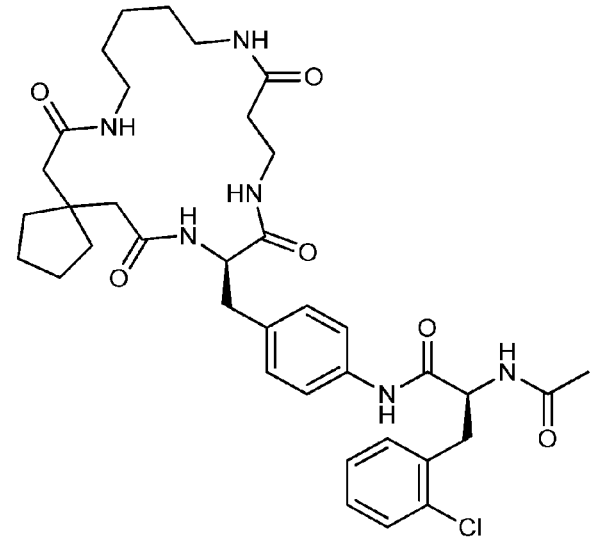 |

FIG. 12-22
| Compound No. | Structure |
|---|---|
| 155 | 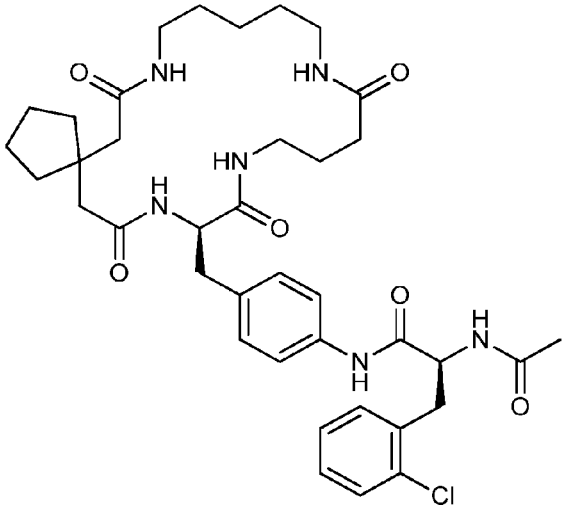 |
| 156 | 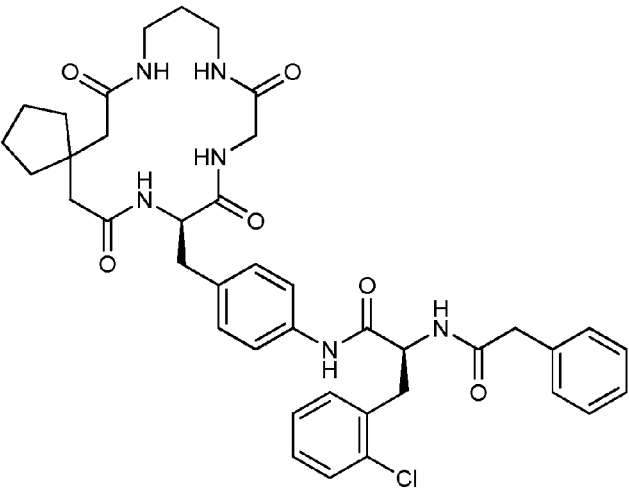 |

FIG. 12-23

| Compound No. | Structure |
|---|---|
| 157 | 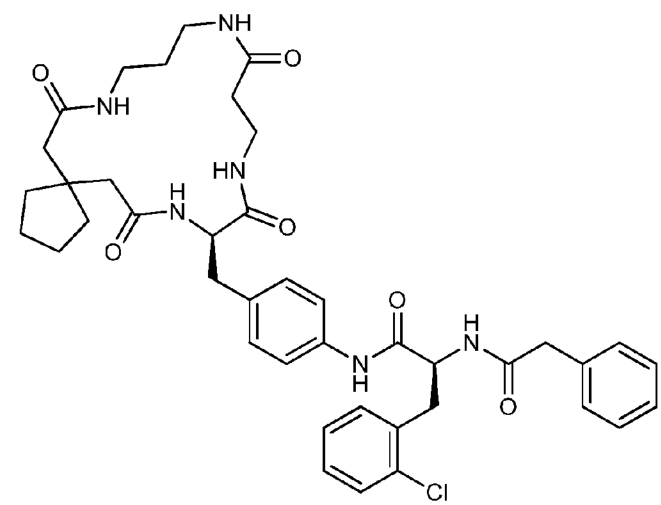 |
| 158 | 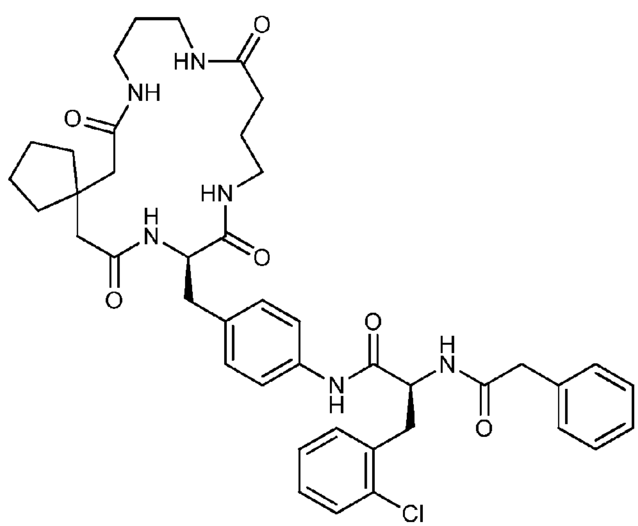 |

FIG. 12-24
| Compound No. | Structure |
|---|---|
| 159 | 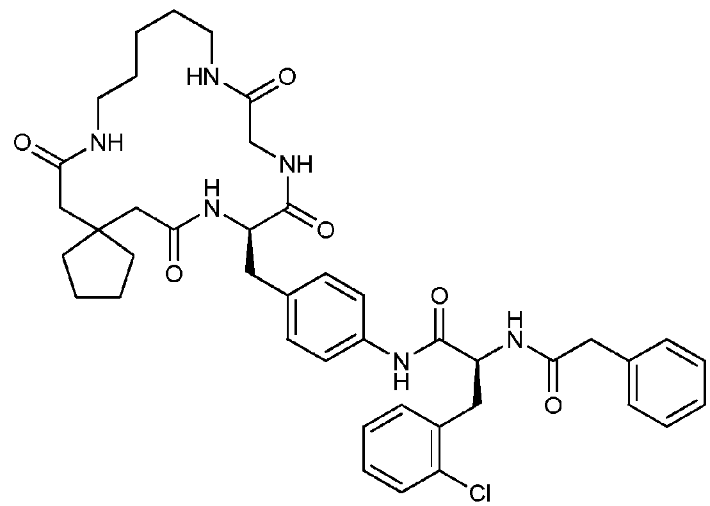 |
| 160 | 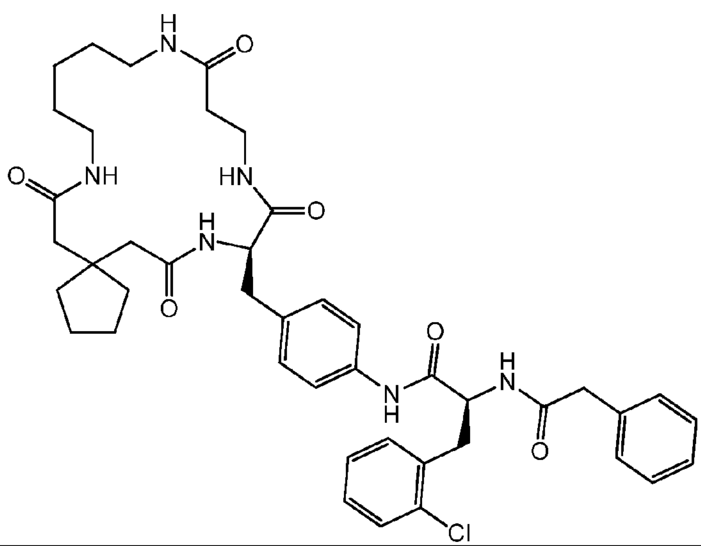 |

FIG. 12-25
| Compound No. | Structure |
|---|---|
| 161 | 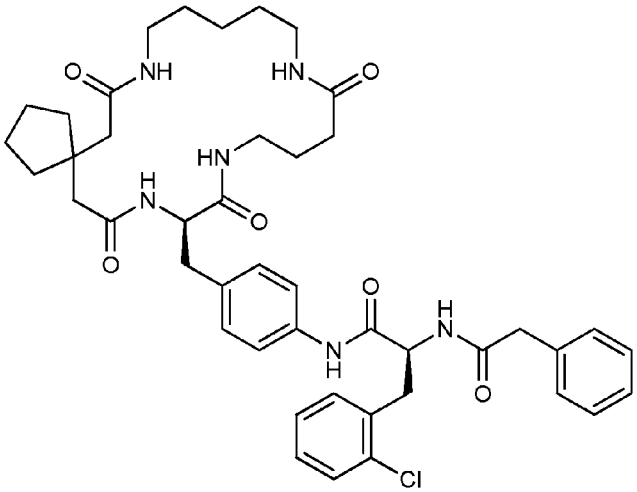 |
| 162 | 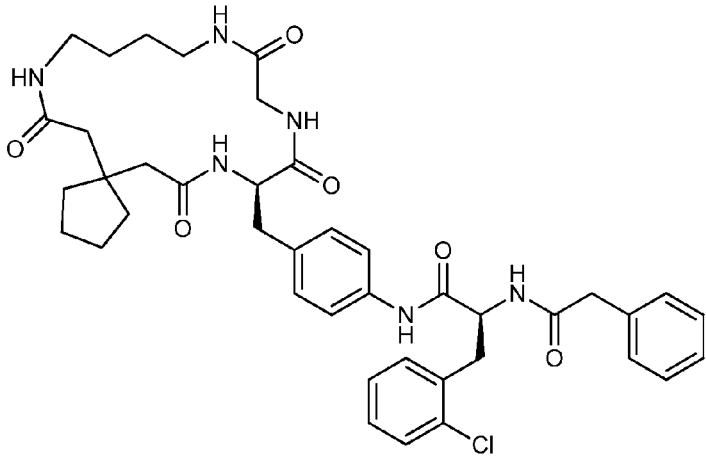 |

FIG. 12-26
| Compound No. | Structure |
|---|---|
| 163 | 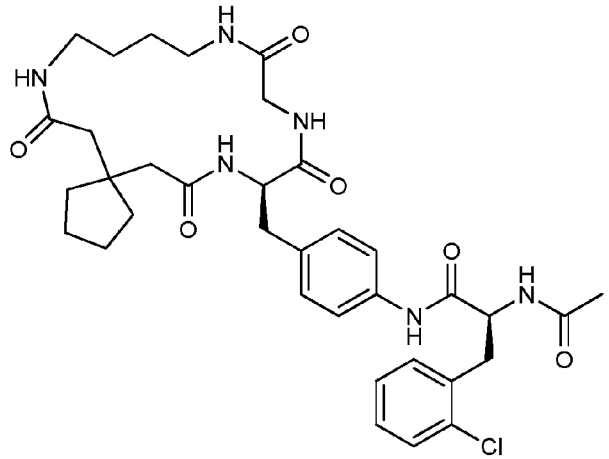 |
| 164 | 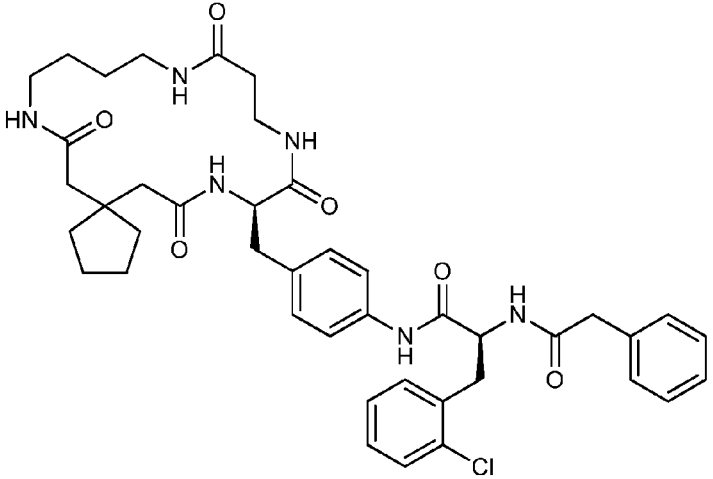 |

FIG. 12-27
| Compound No. | Structure |
|---|---|
| 165 | 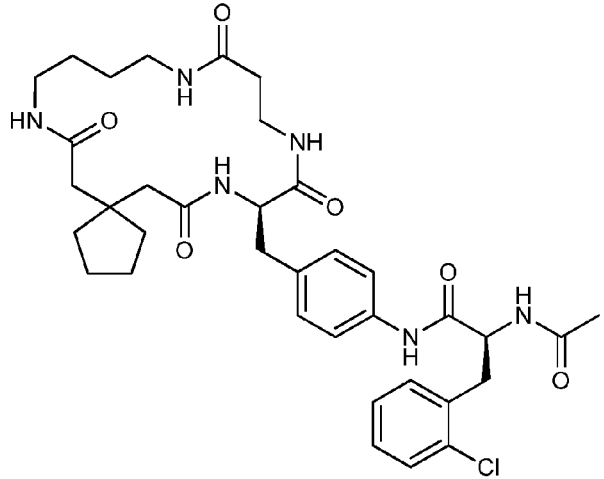 |
| 166 | 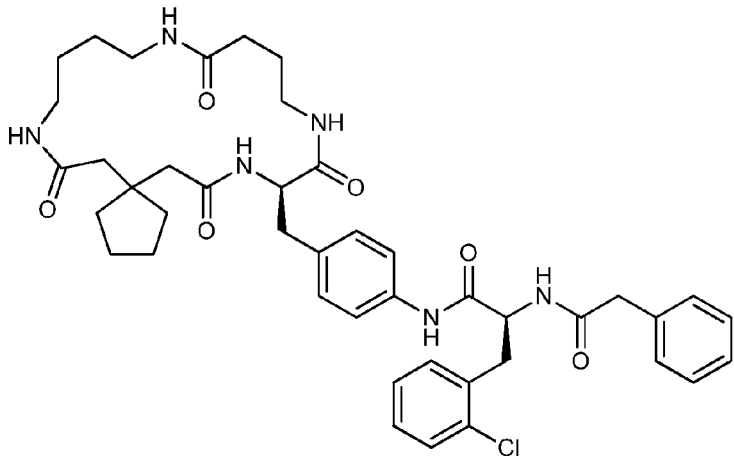 |
| 167 | 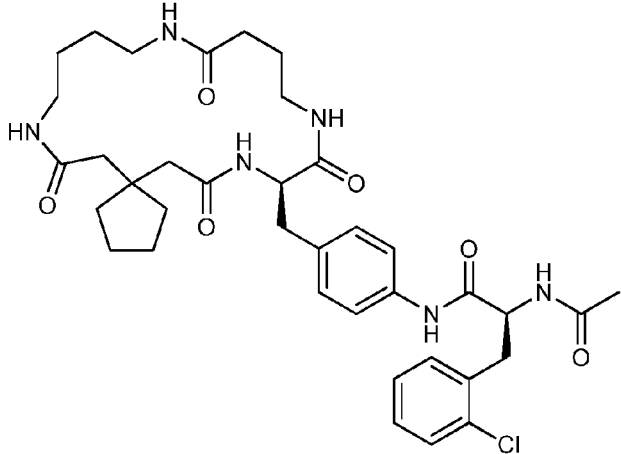 |

FIG. 12-28
| Compound No. | Structure |
|---|---|
| 168 | 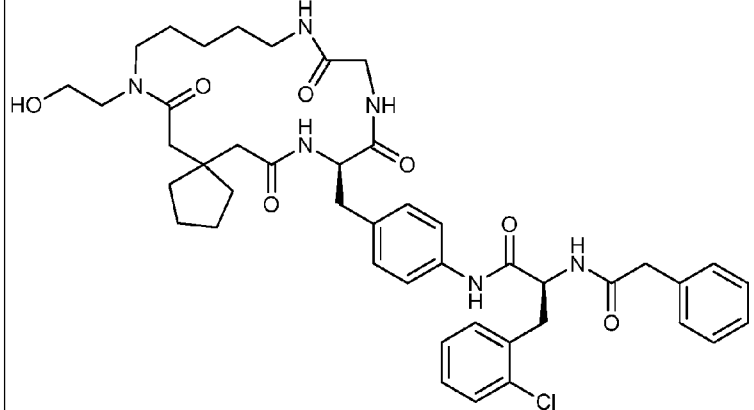 |
| 169 | 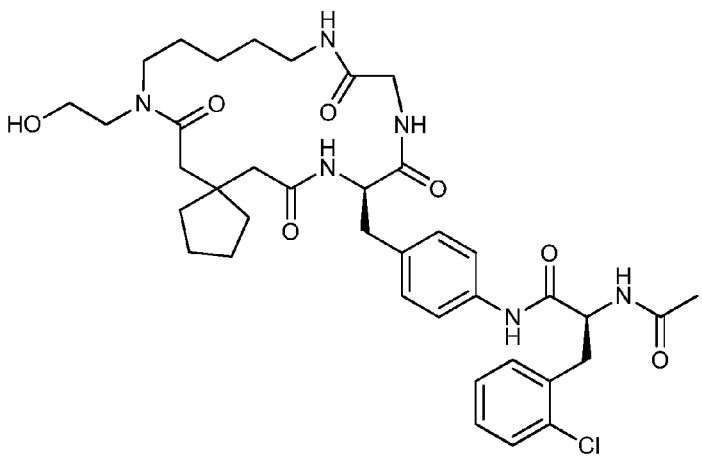 |
| 170 | 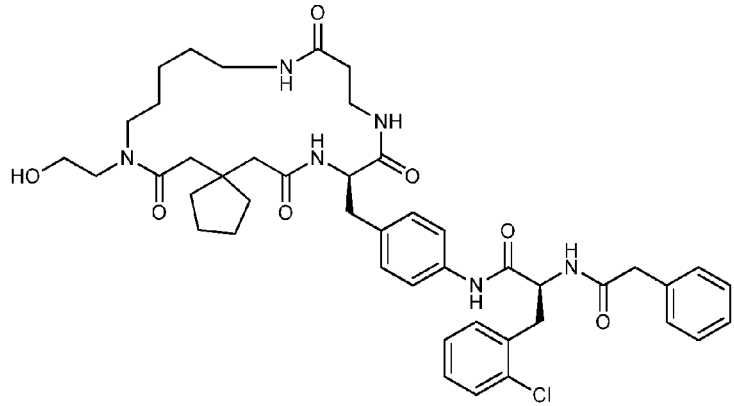 |

FIG. 12-29
| Compound No. | Structure |
|---|---|
| 171 | 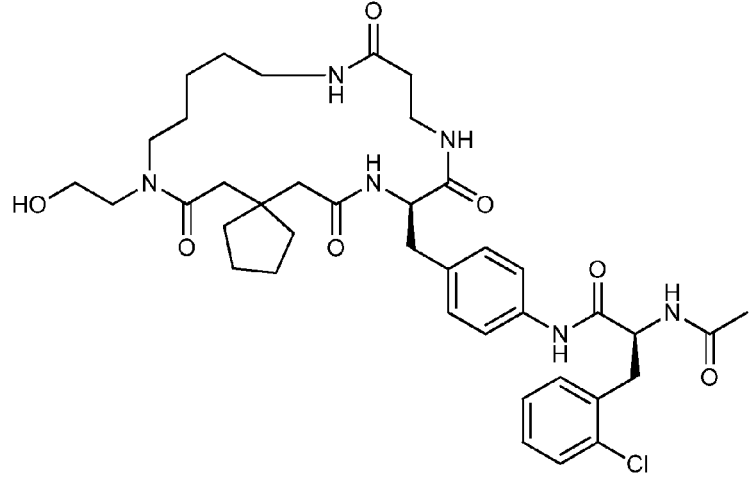 |
| 172 | 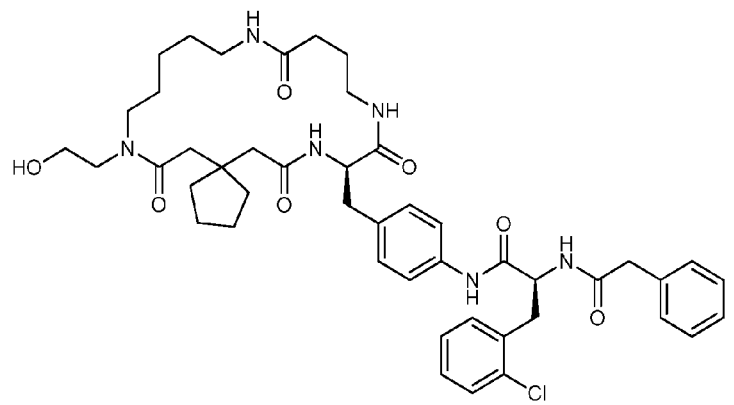 |
| 173 | 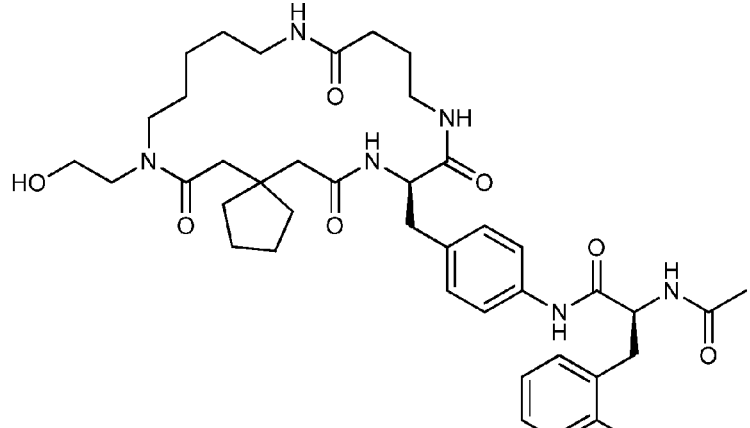 |

FIG. 12-30
| Compound No. | Structure |
|---|---|
| 174 | 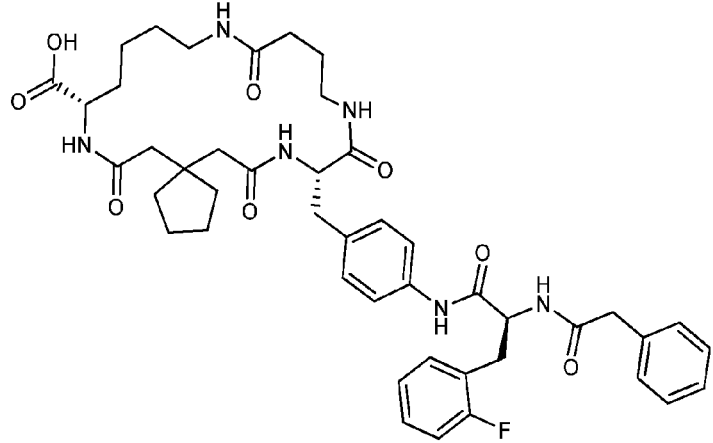 |
| 175 | 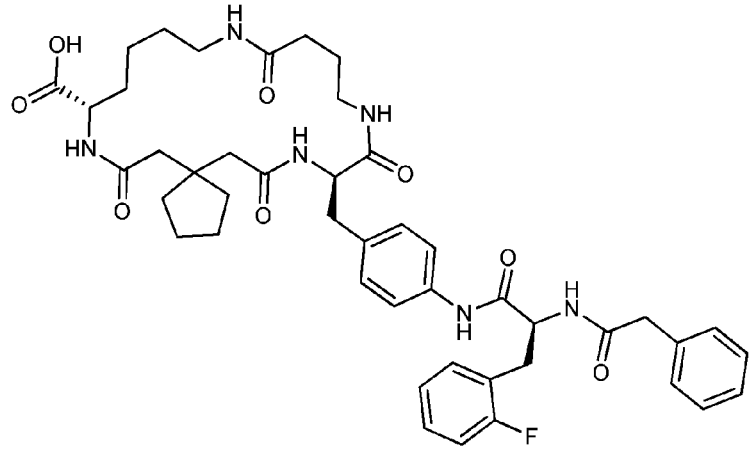 |

FIG. 12-31

| Compound No. | Structure |
|---|---|
| 176 | 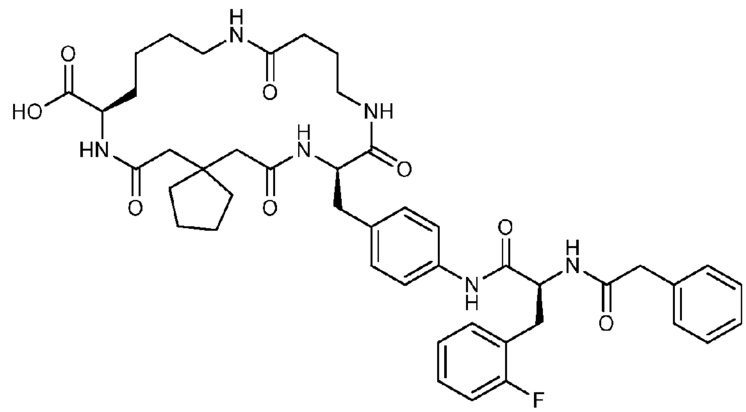 |
| 177 | 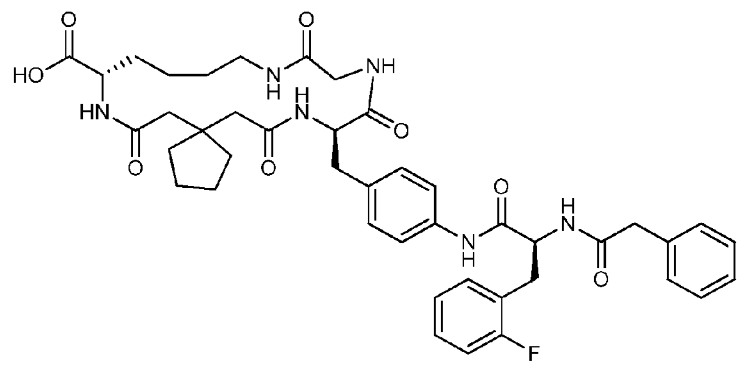 |
| 178 | 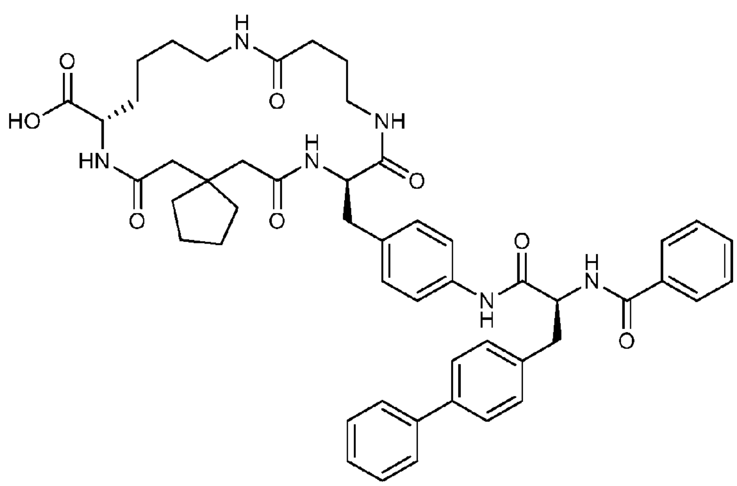 |

FIG. 12-32
| Compound No. | Structure |
|---|---|
| 179 | 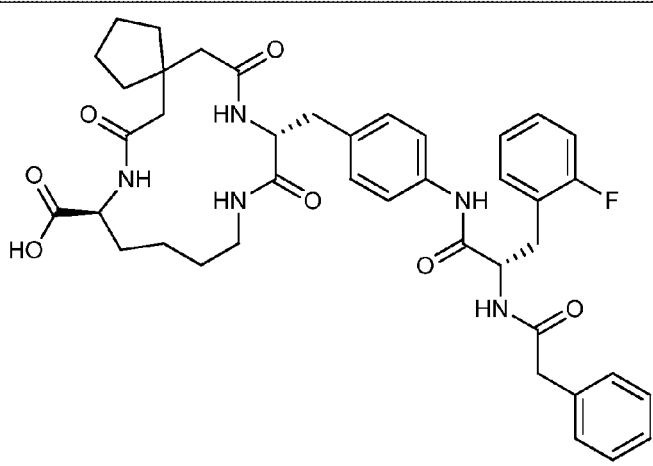 |
| 180 | 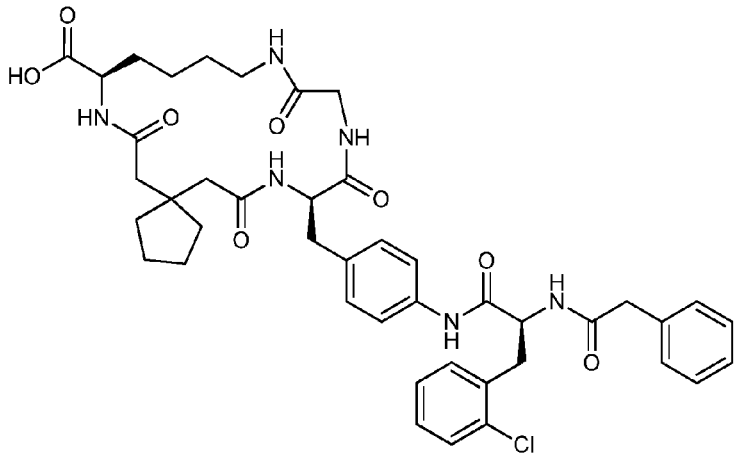 |

FIG. 12-33
| Compound No. | Structure |
|---|---|
| 181 | 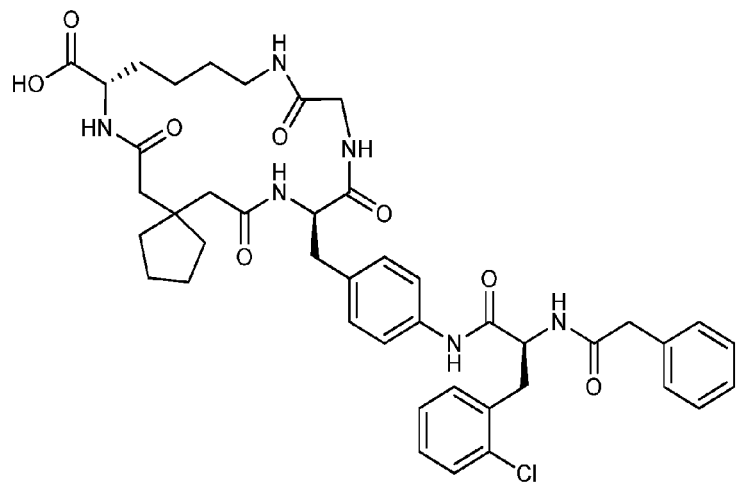 |
| 182 | 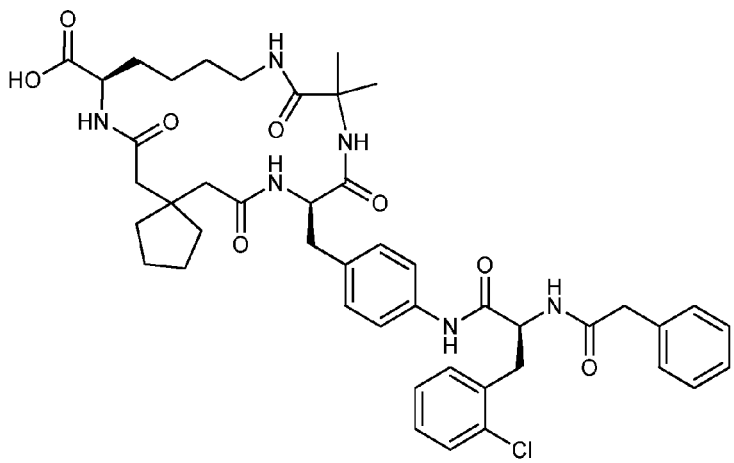 |

FIG. 12-34
| Compound No. | Structure |
|---|---|
| 183 | 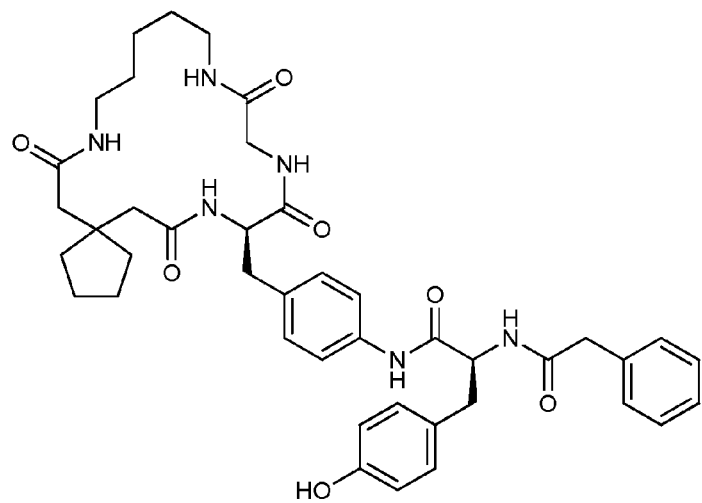 |
| 184 | 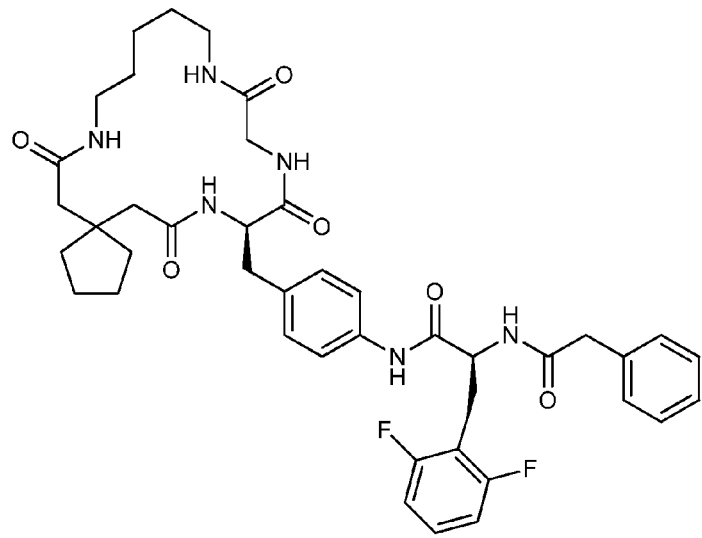 |

FIG. 12-35
| Compound No. | Structure |
|---|---|
| 185 | 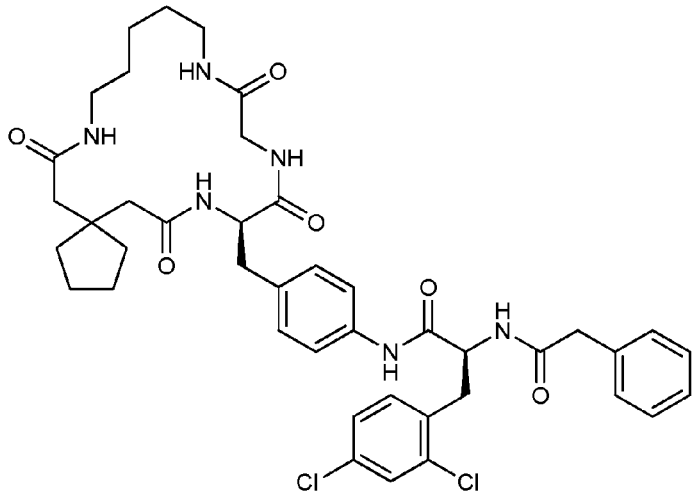 |
| 186 | 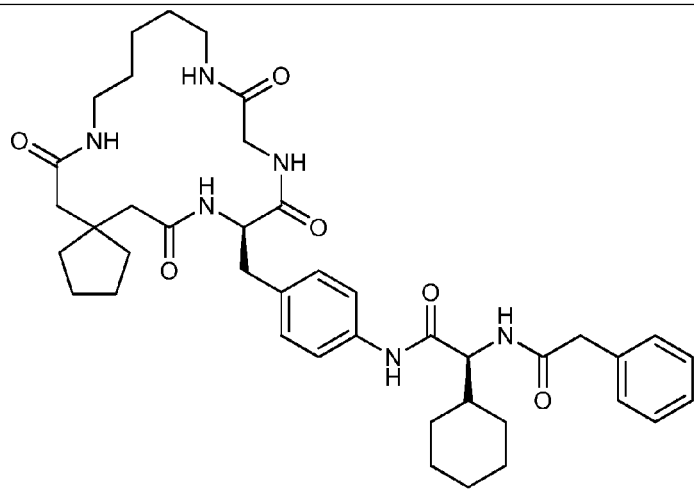 |

FIG. 12-36
| Compound No. | Structure |
|---|---|
| 187 | 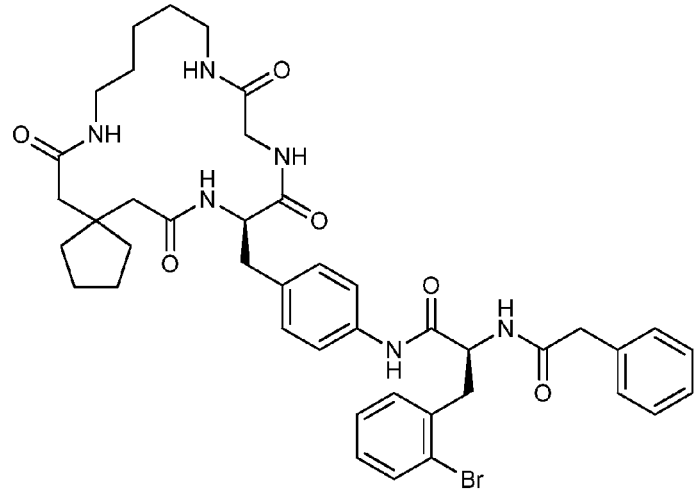 |
| 188 | 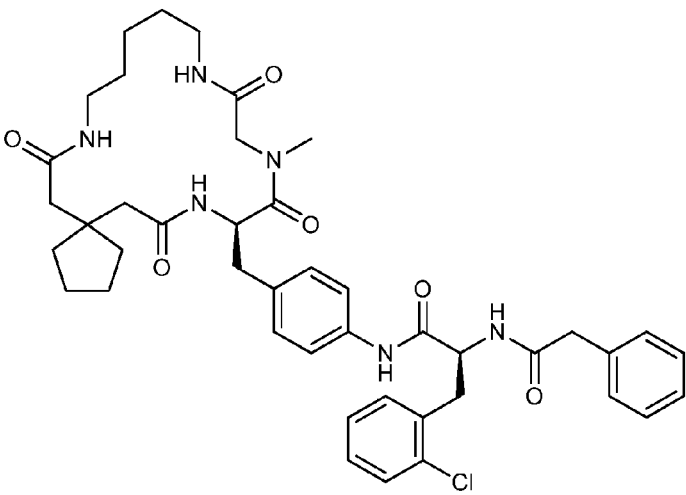 |

FIG. 12-37
| Compound No. | Structure |
|---|---|
| 189 | 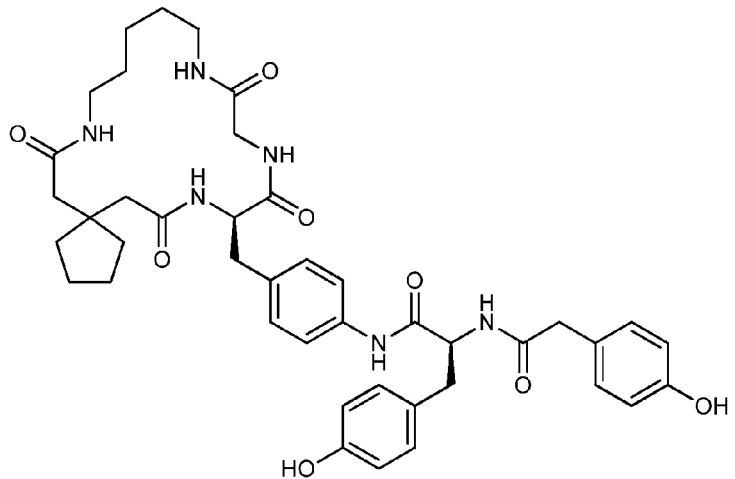 |
| 190 | 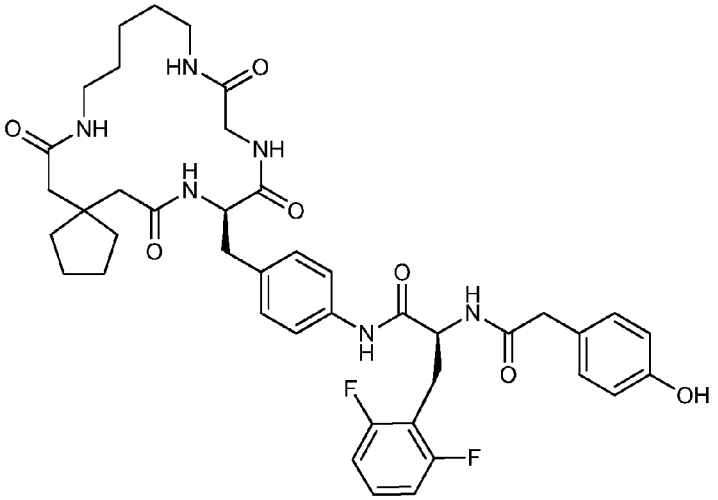 |

FIG. 12-38
| Compound No. | Structure |
|---|---|
| 191 | 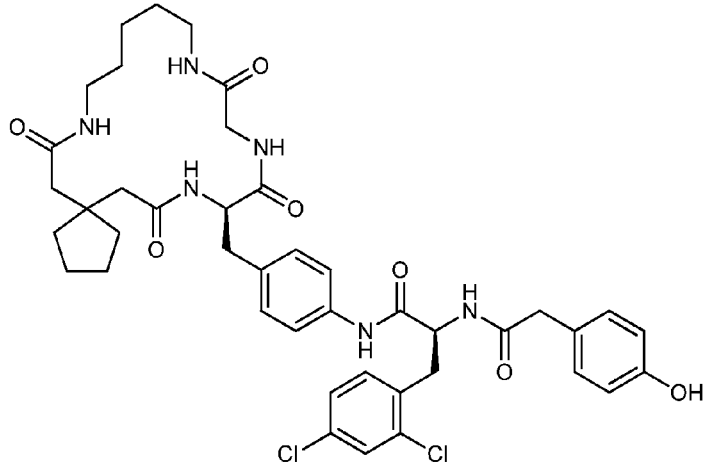 |
| 192 | 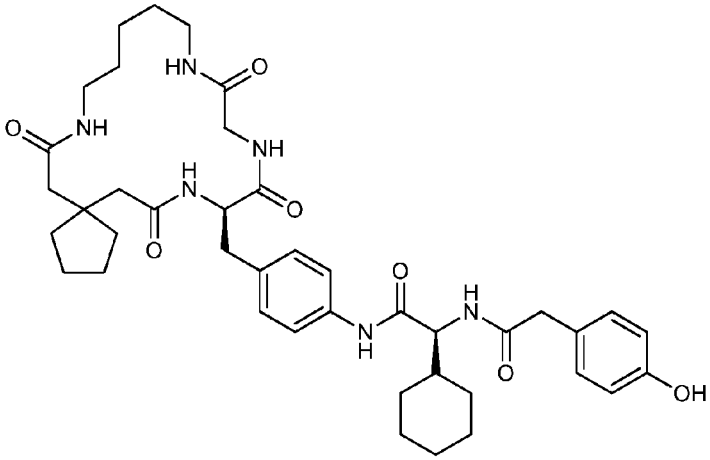 |

FIG. 12-39
| Compound No. | Structure |
|---|---|
| 193 | 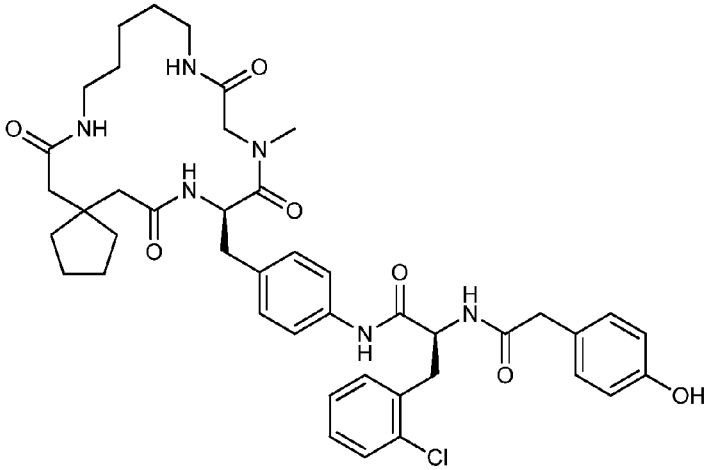 |
| 194 | 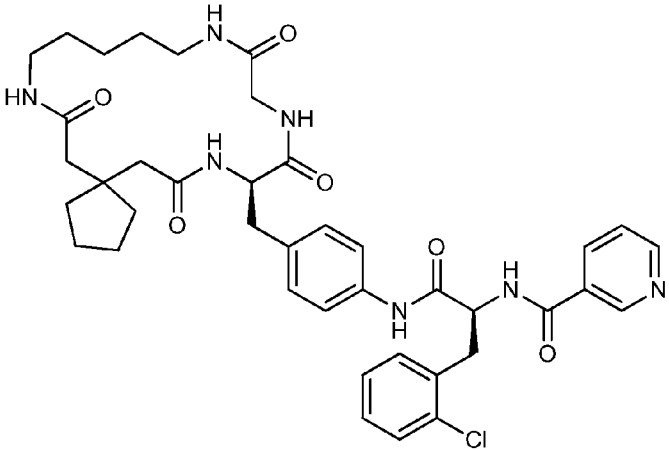 |

FIG. 12-40
| Compound No. | Structure |
|---|---|
| 195 | 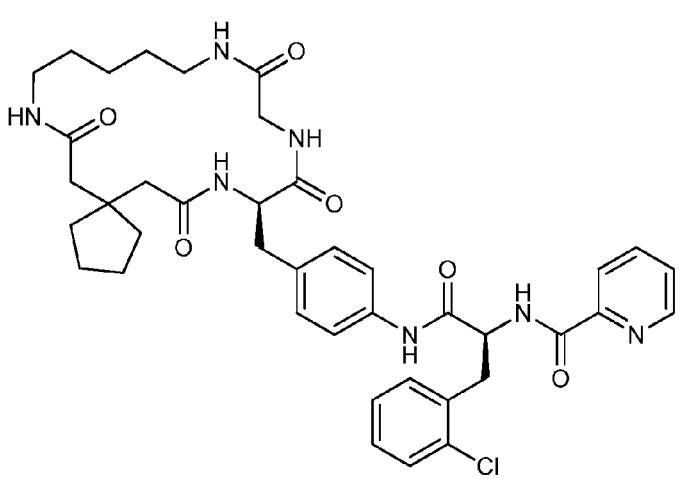 |
| 196 | 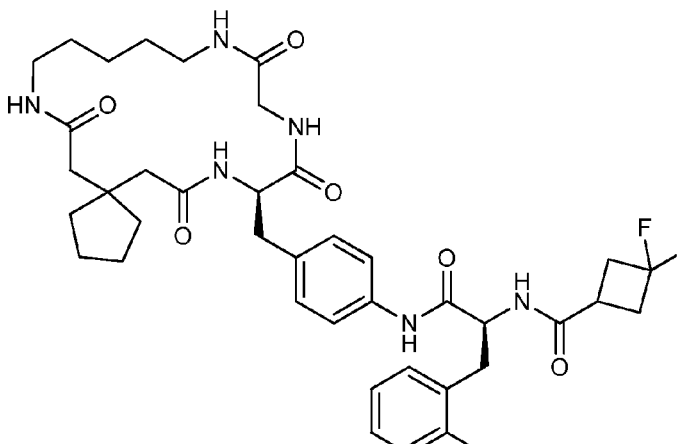 |

FIG. 12-41
| Compound No. | Structure |
|---|---|
| 197 | 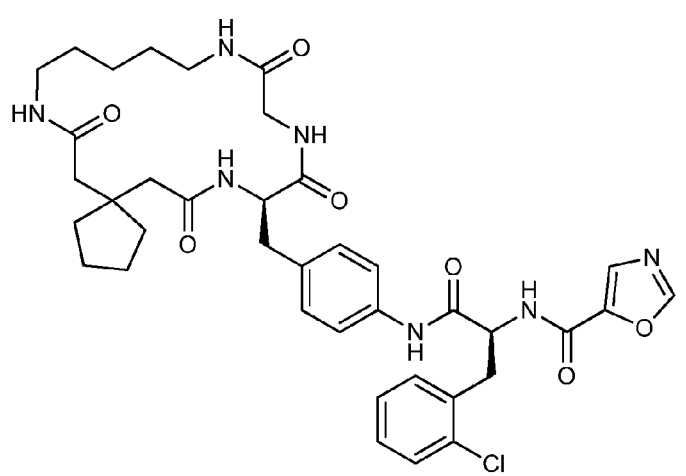 |
| 198 | 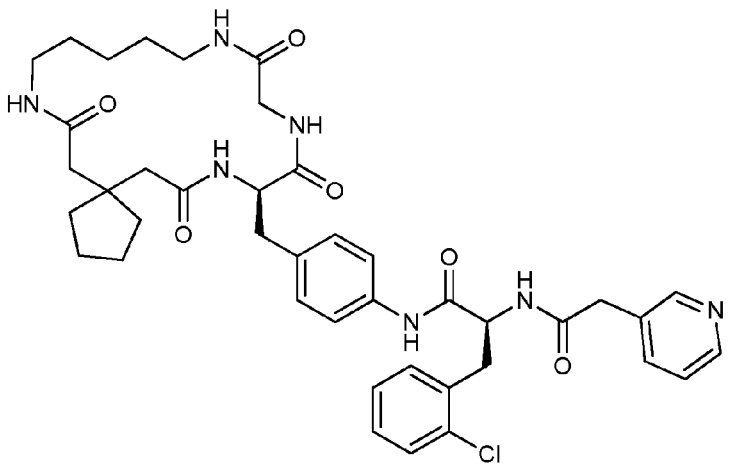 |
| 199 | 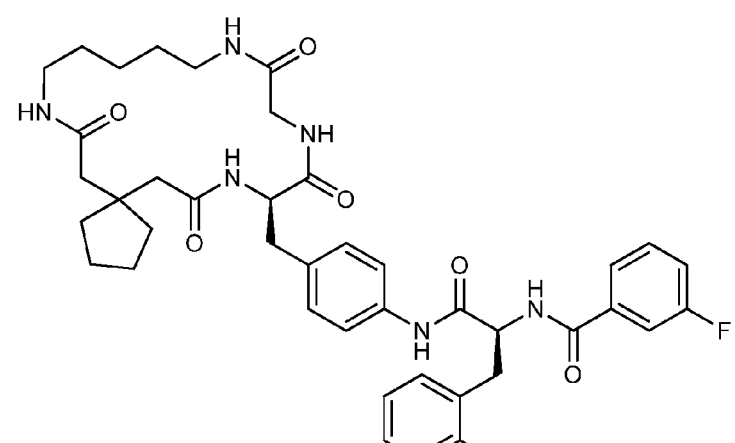 |

FIG. 12-42
| Compound No. | Structure |
|---|---|
| 200 | 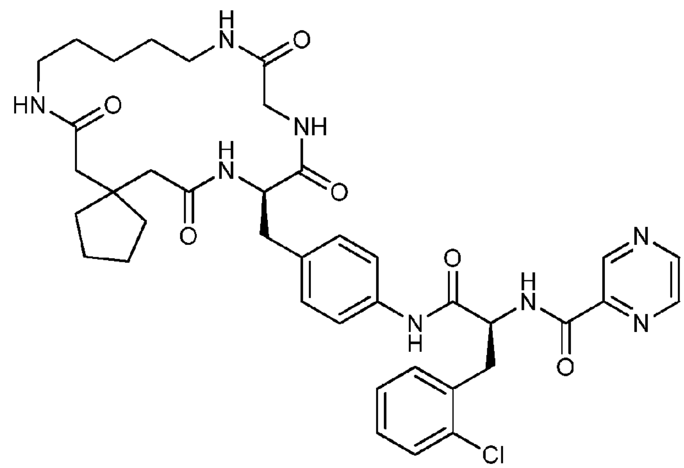 |
| 201 | 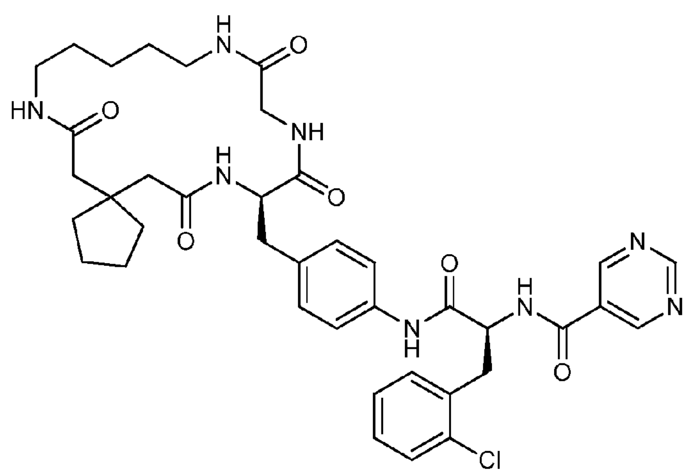 |
| 202 | 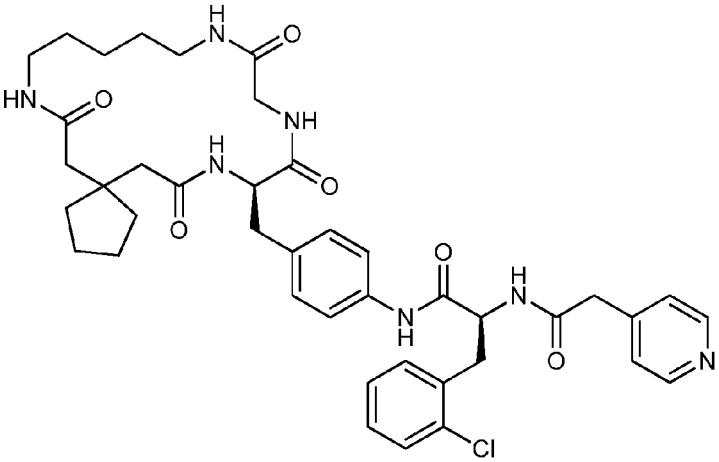 |

FIG. 12-43
| Compound No. | Structure |
|---|---|
| 203 | 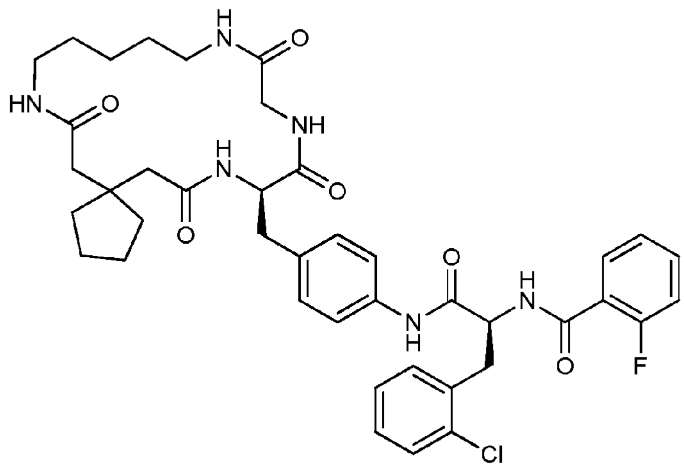 |
| 204 | 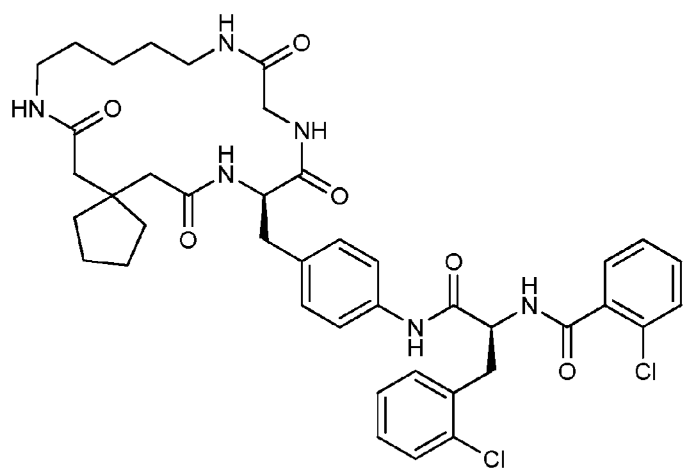 |

FIG. 12-44
| Compound No. | Structure |
|---|---|
| 205 | 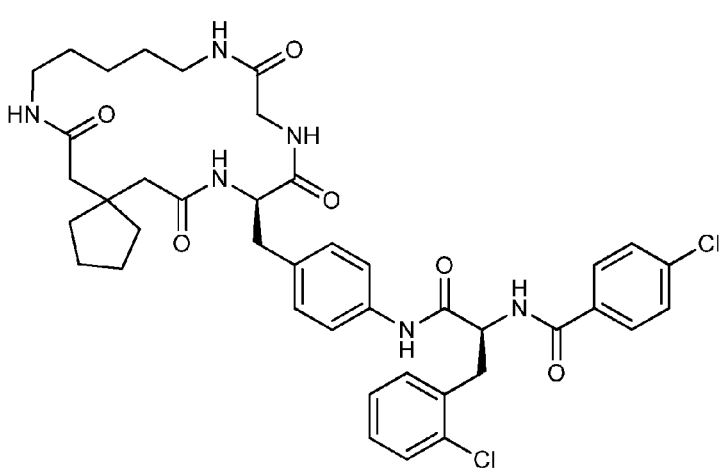 |
| 206 | 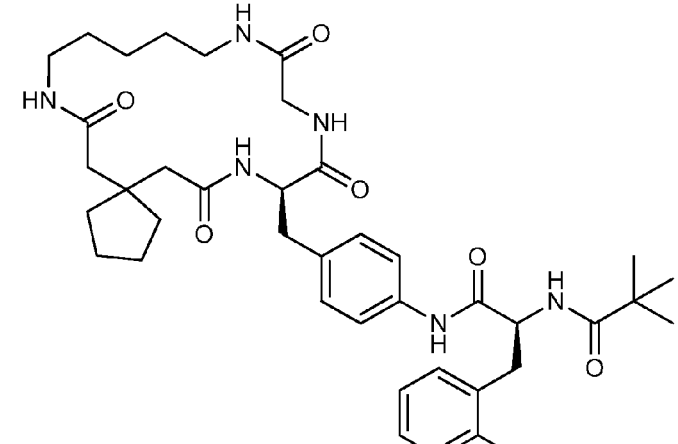 |

FIG. 12-45

| Compound No. | Structure |
|---|---|
| 207 | 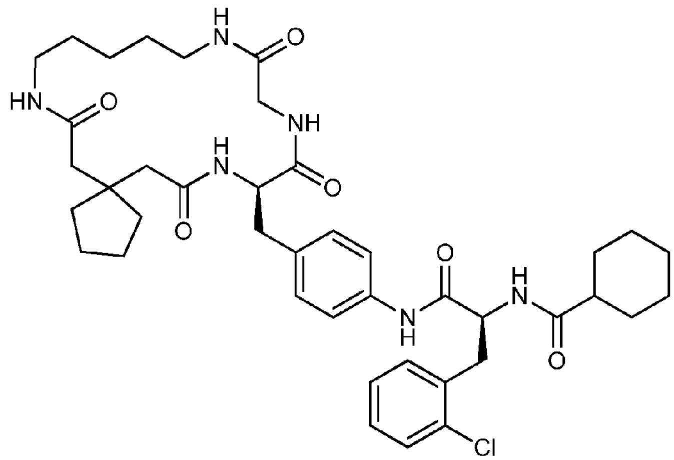 |
| 208 | 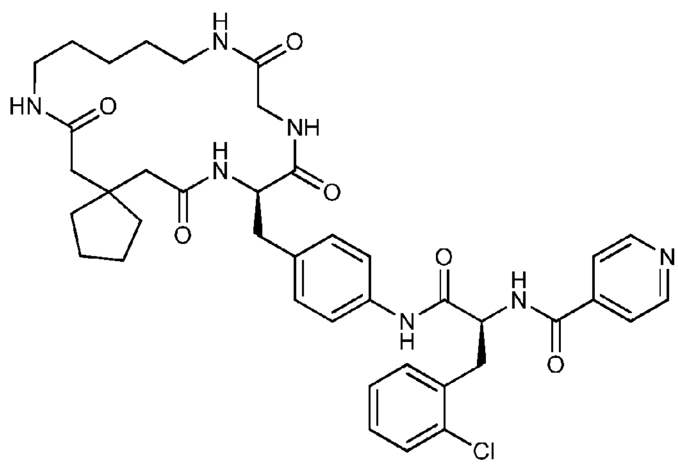 |

FIG. 12-46

| Compound No. | Structure |
|---|---|
| 209 | (chemical structure) |
| 210 | (chemical structure) |

FIG. 12-47

| Compound No. | Structure |
|---|---|
| 211 | 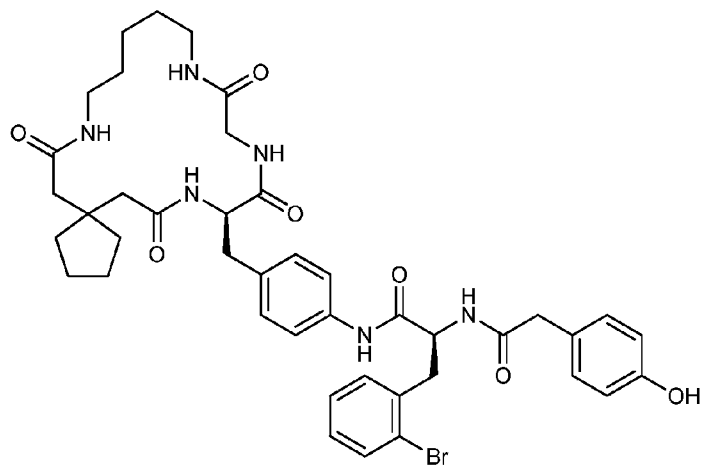 |
| 212 | 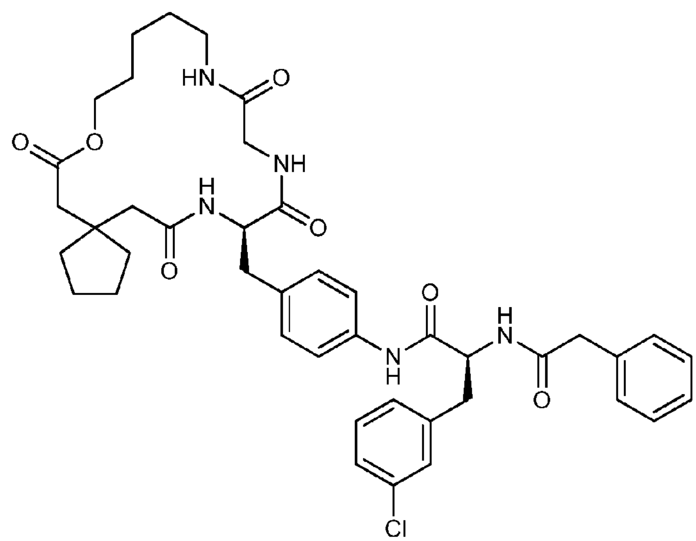 |

FIG. 12-48
| Compound No. | Structure |
|---|---|
| 213 | 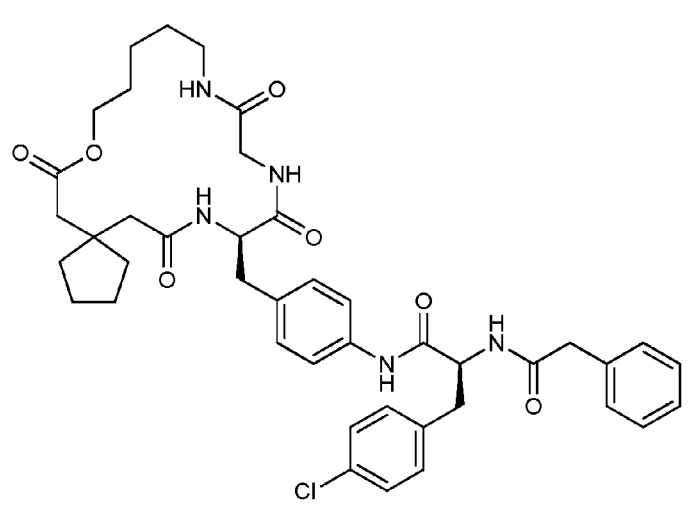 |
| 214 | 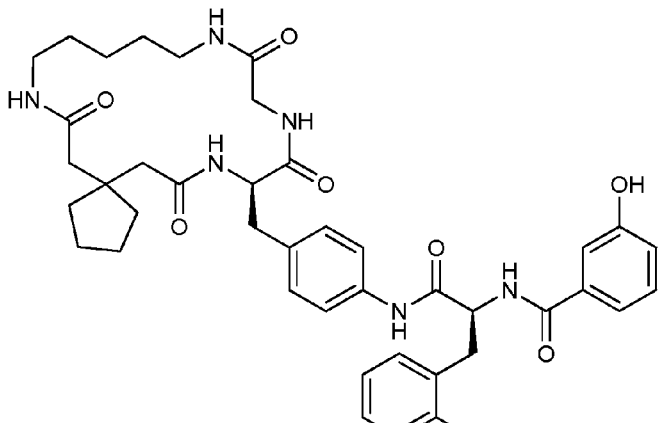 |

FIG. 12-49

| Compound No. | Structure |
|---|---|
| 215 | 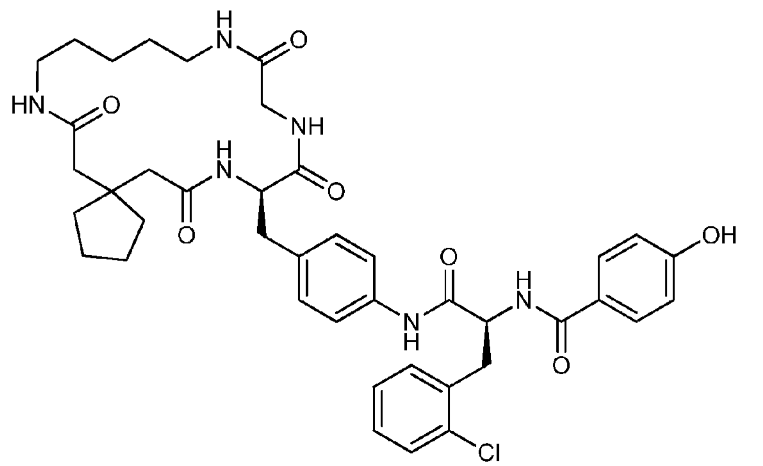 |
| 216 | 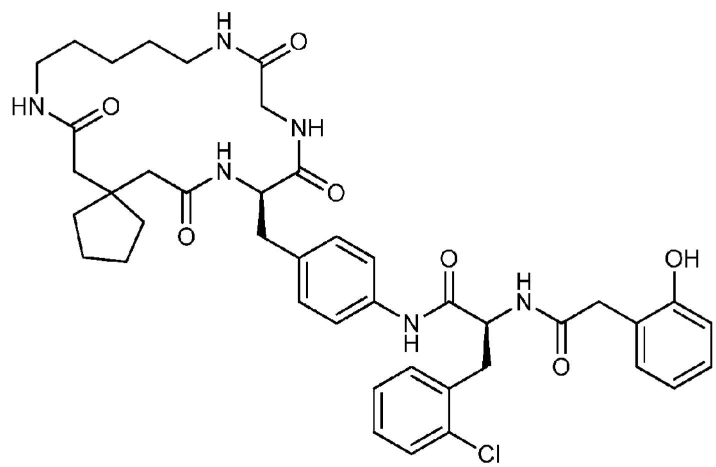 |

FIG. 12-50
| Compound No. | Structure |
|---|---|
| 217 | 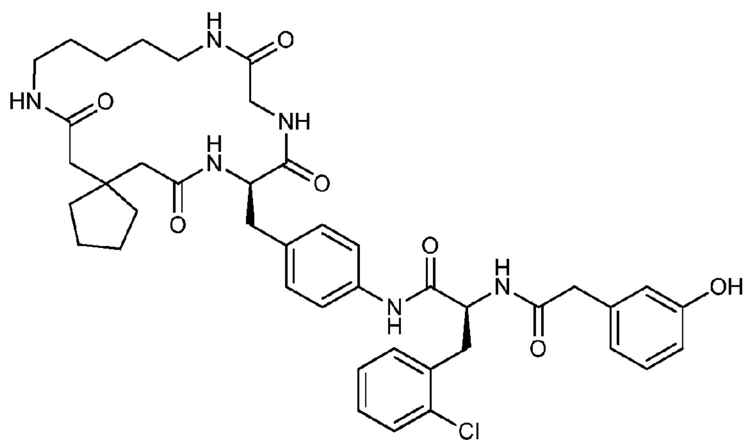 |
| 218 | 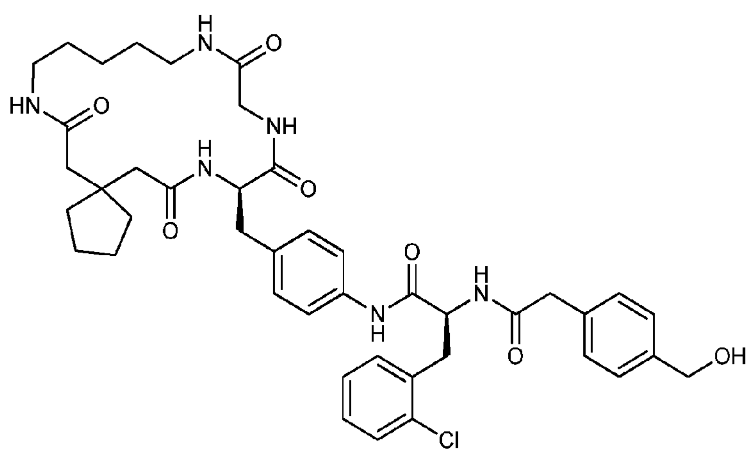 |

FIG. 12-51

| Compound No. | Structure |
|---|---|
| 219 | 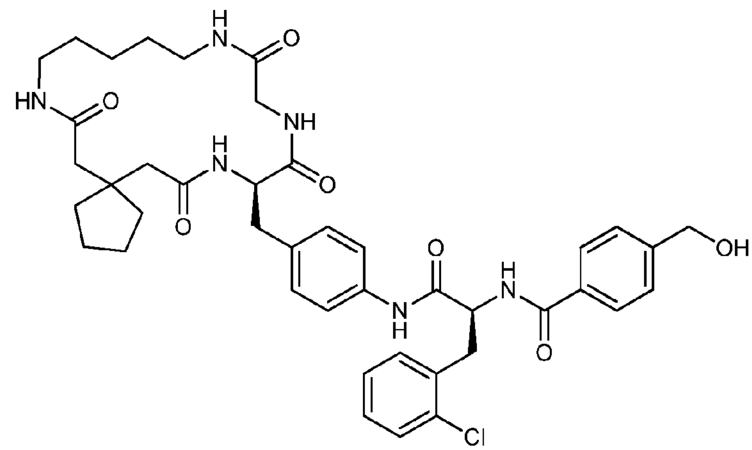 |
| 220 | 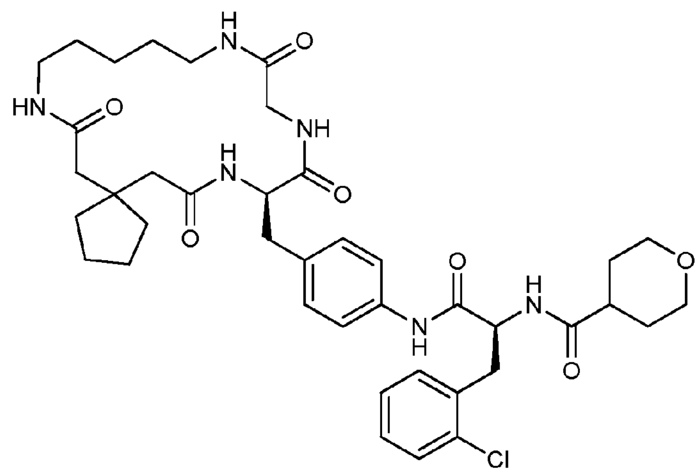 |

FIG. 12-52

| Compound No. | Structure |
|---|---|
| 221 | 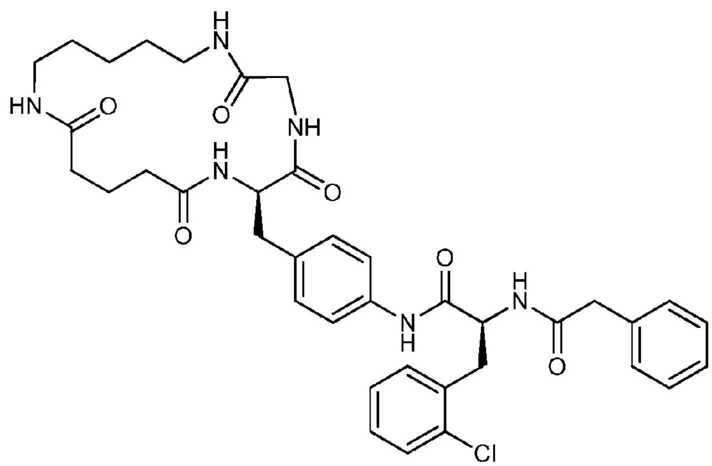 |
| 222 | 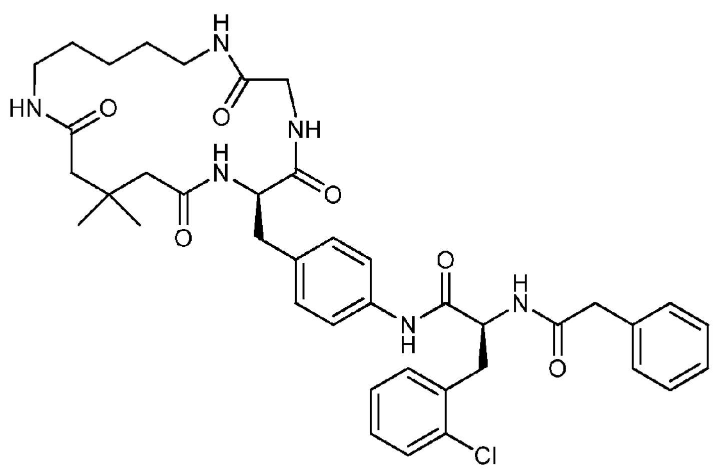 |

FIG. 12-53
| Compound No. | Structure |
|---|---|
| 223 | 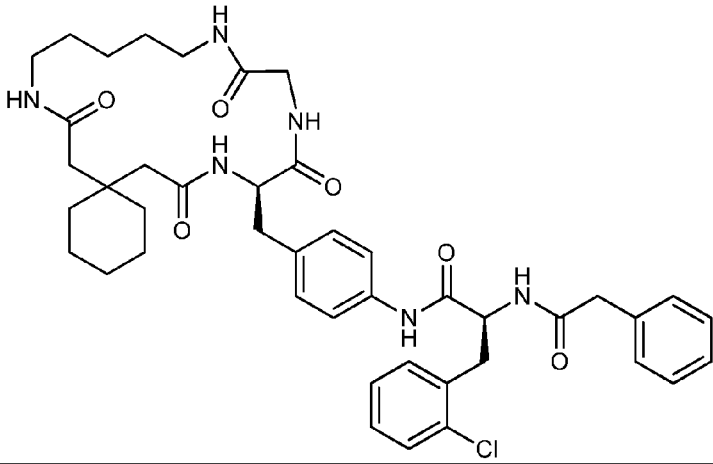 |
| 224 | 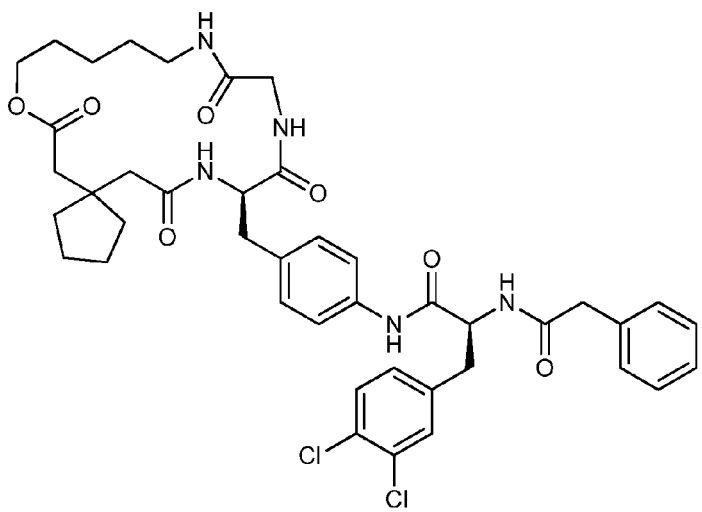 |

FIG. 12-54
| Compound No. | Structure |
|---|---|
| 225 | 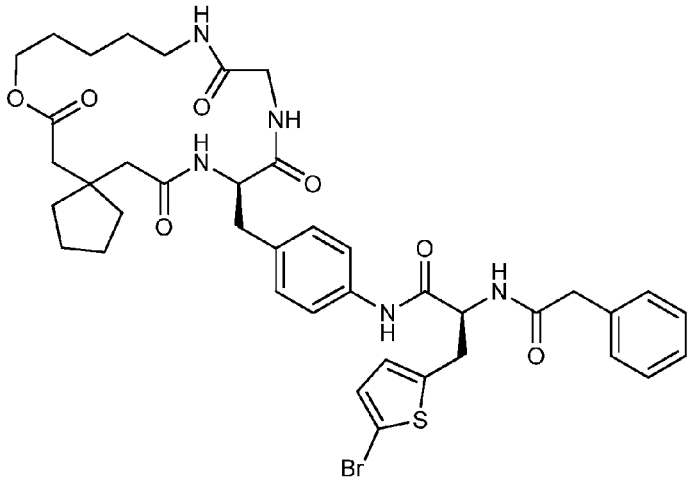 |
| 226 | 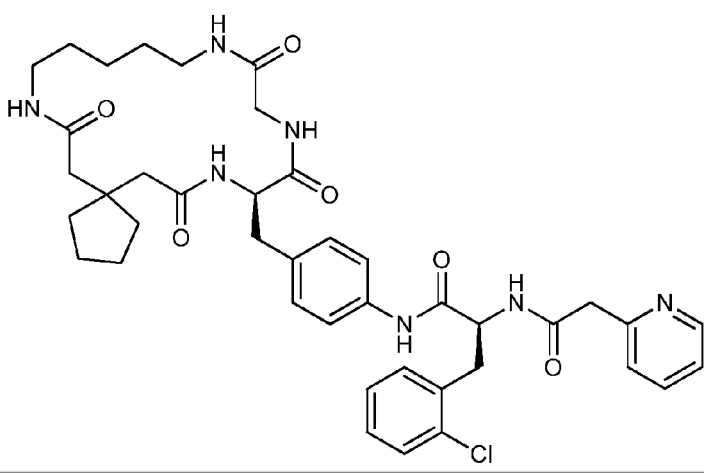 |

FIG. 12-55
| Compound No. | Structure |
|---|---|
| 227 | 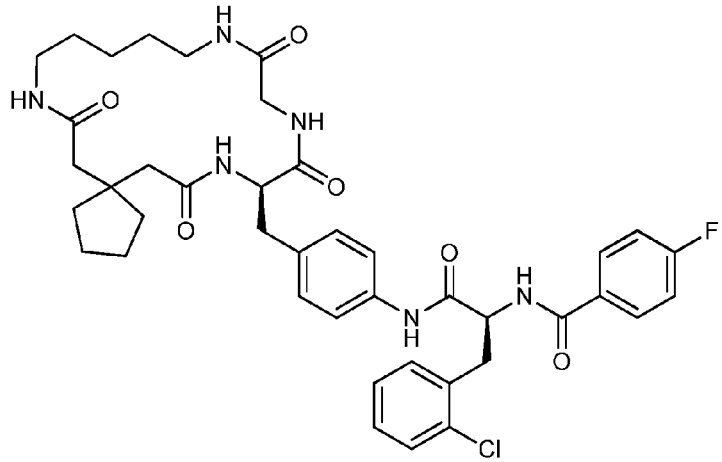 |
| 228 | 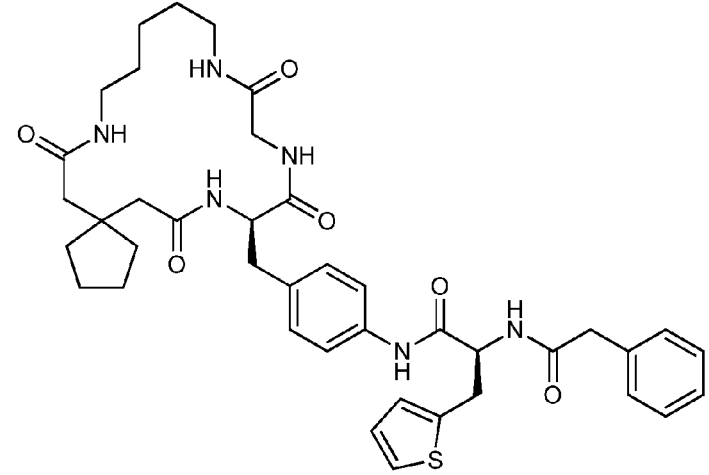 |

FIG. 12-56
| Compound No. | Structure |
|---|---|
| 229 | 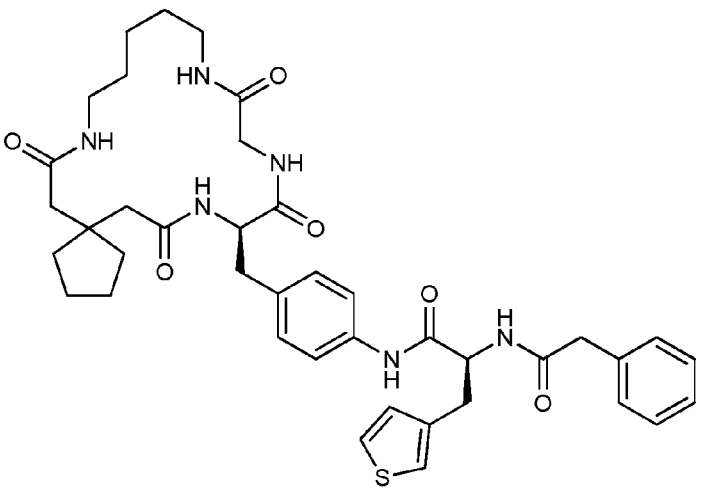 |
| 230 | 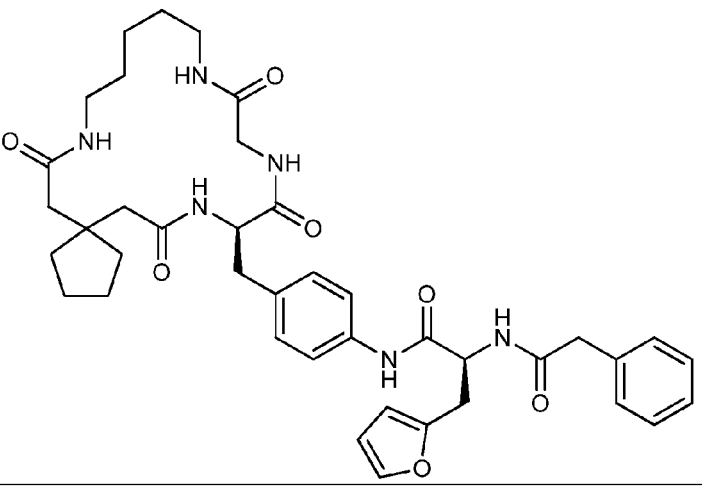 |

FIG. 12-57
| Compound No. | Structure |
|---|---|
| 231 | 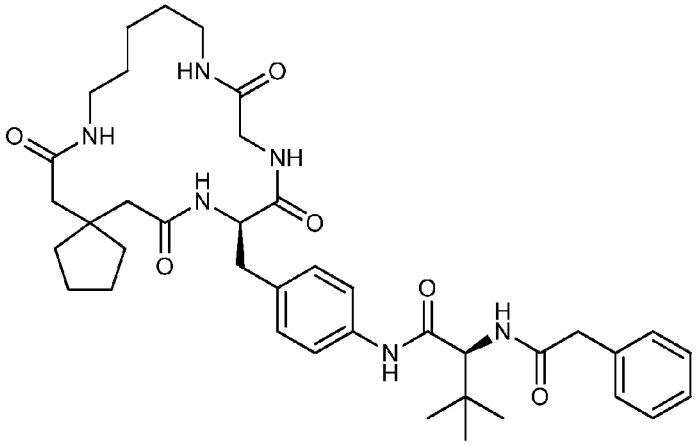 |
| 232 | 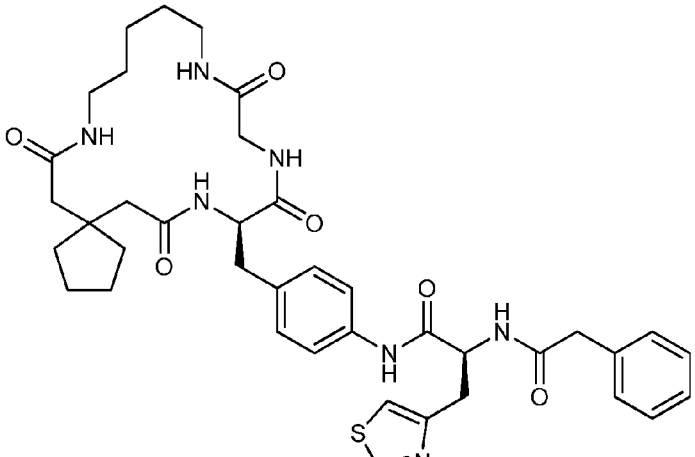 |

FIG. 12-58
| Compound No. | Structure |
|---|---|
| 233 | 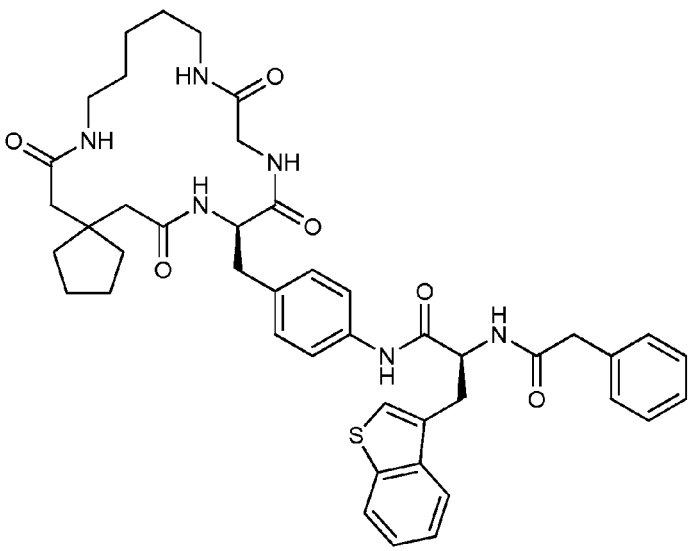 |
| 234 | 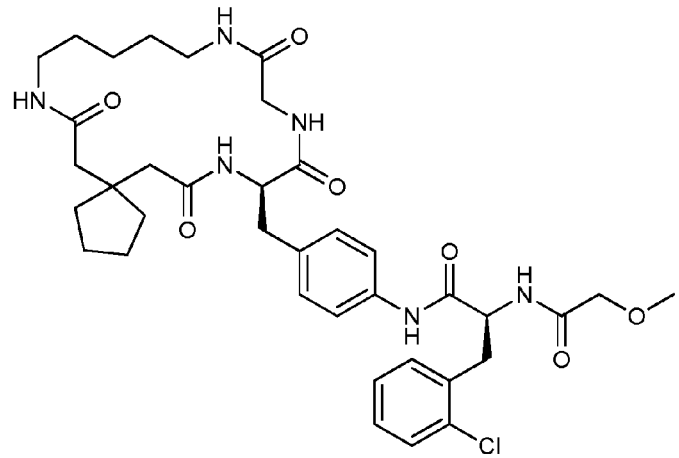 |

FIG. 12-59
| Compound No. | Structure |
|---|---|
| 235 | 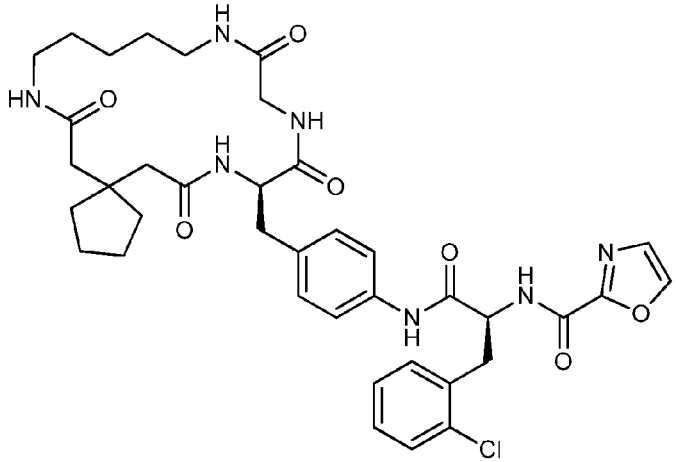 |
| 236 | 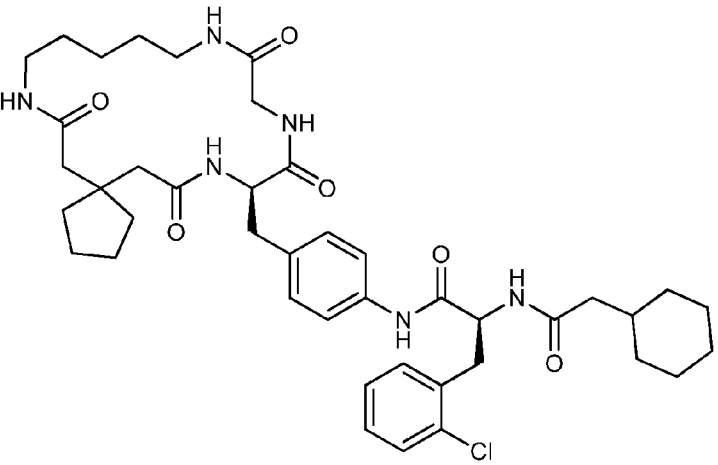 |

FIG. 12-60
| Compound No. | Structure |
|---|---|
| 237 | 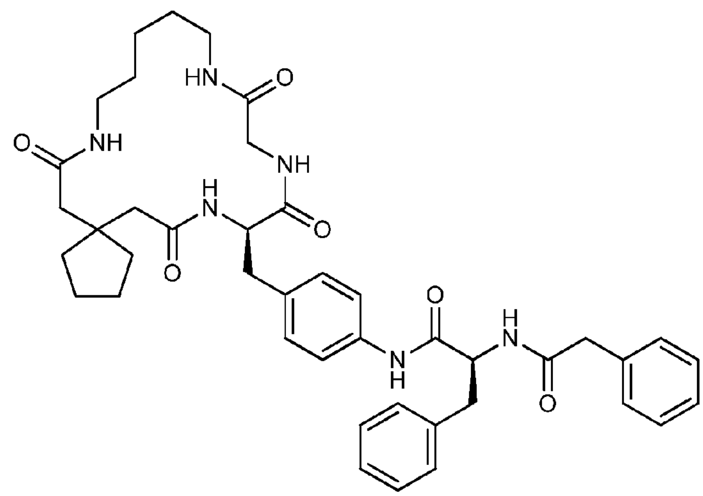 |
| 238 | 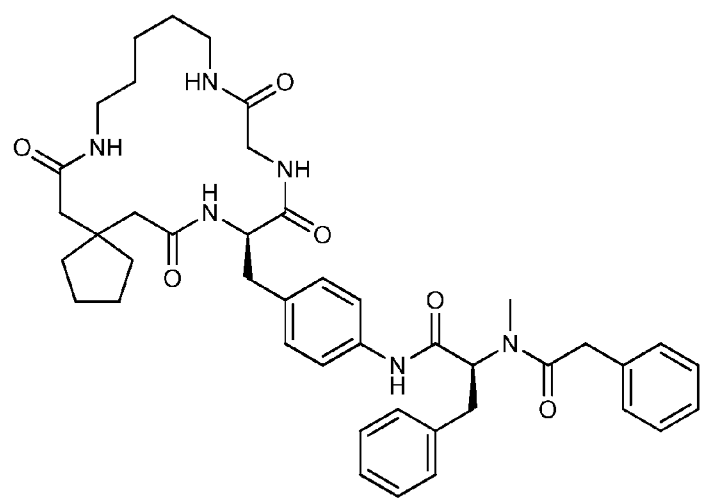 |

FIG. 12-61
| Compound No. | Structure |
|---|---|
| 239 | 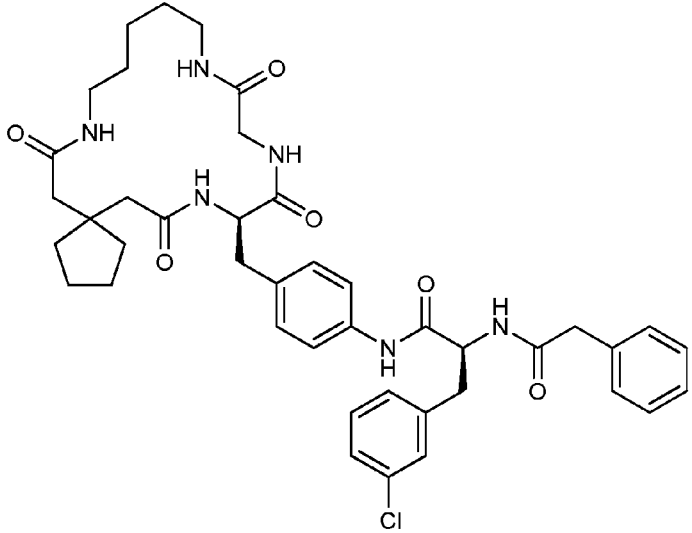 |
| 240 | 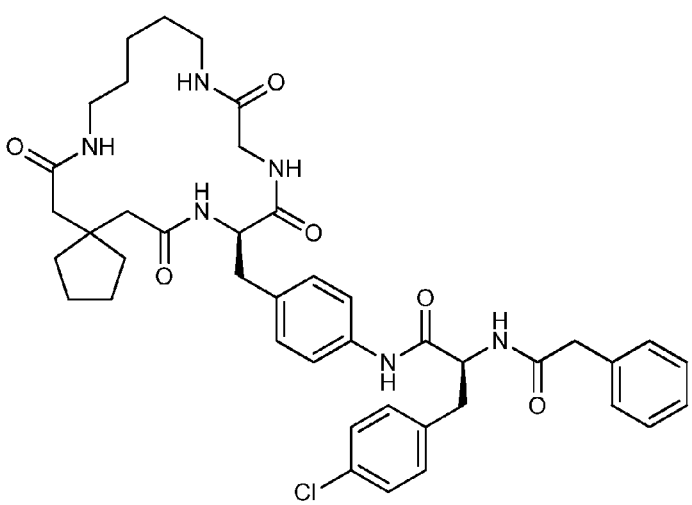 |

FIG. 12-62
| Compound No. | Structure |
|---|---|
| 241 | 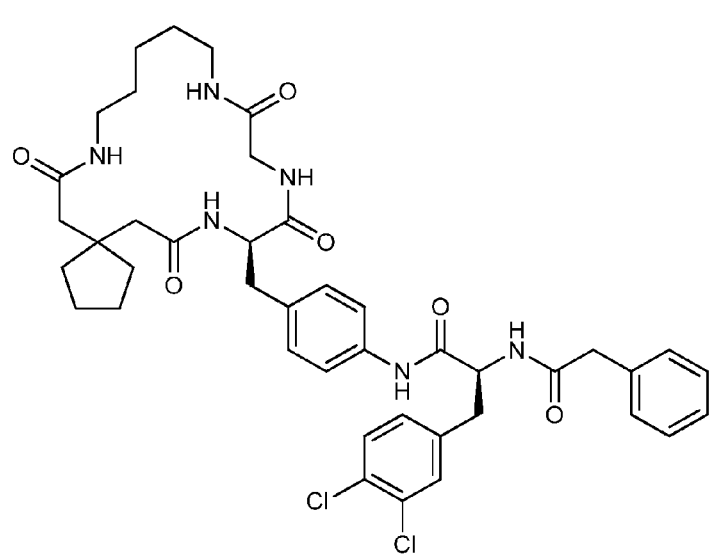 |
| 242 | 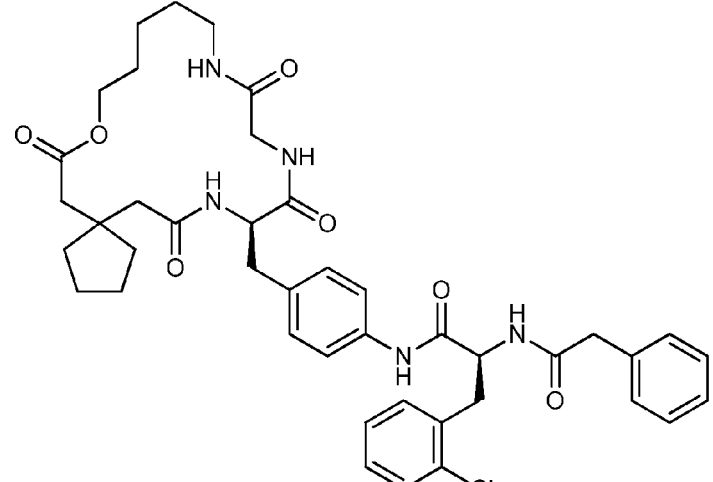 |

FIG. 12-63
| Compound No. | Structure |
|---|---|
| 243 | 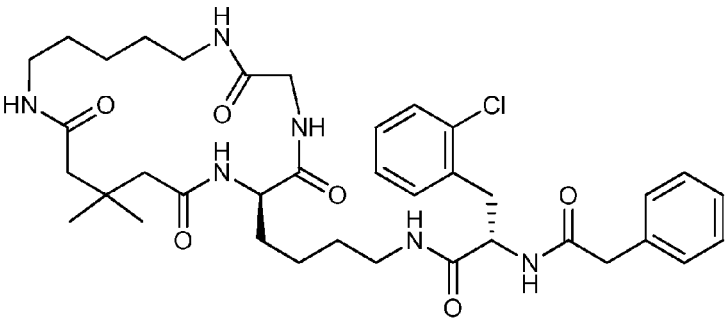 |
| 244 | 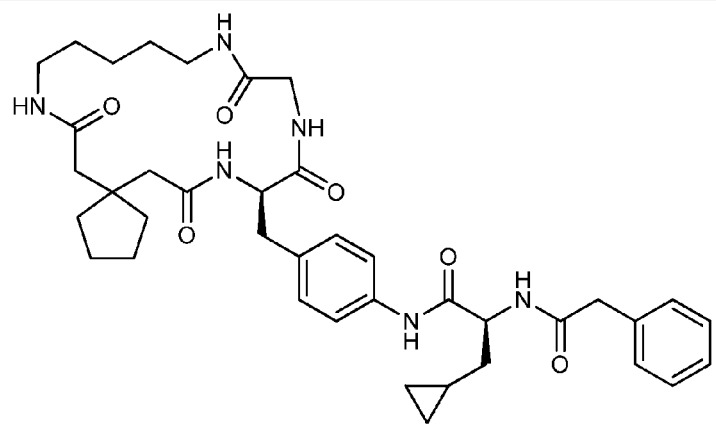 |
| 245 | 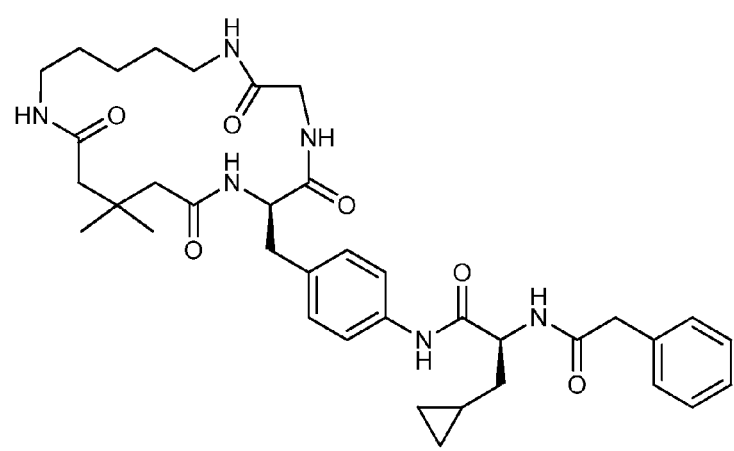 |

| Compound No. | Structure |
|---|---|
| 246 | 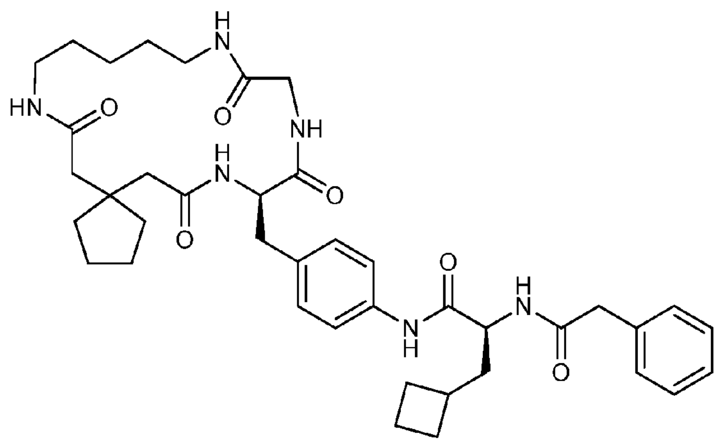 |
| 247 | 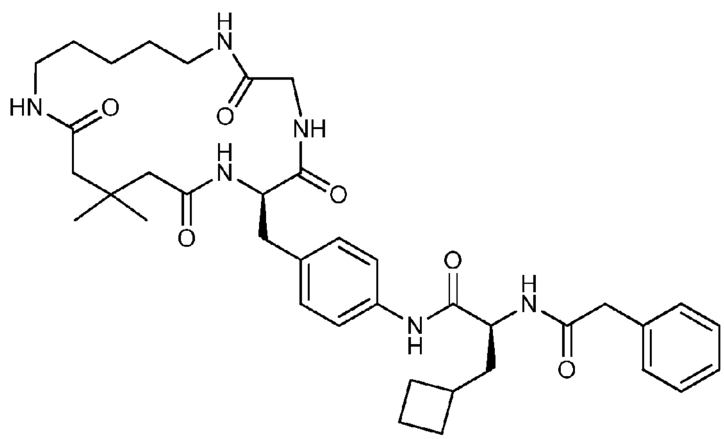 |

FIG. 12-65

| Compound No. | Structure |
|---|---|
| 248 | (chemical structure) |
| 249 | (chemical structure) |

| Compound No. | Structure |
|---|---|
| 250 | 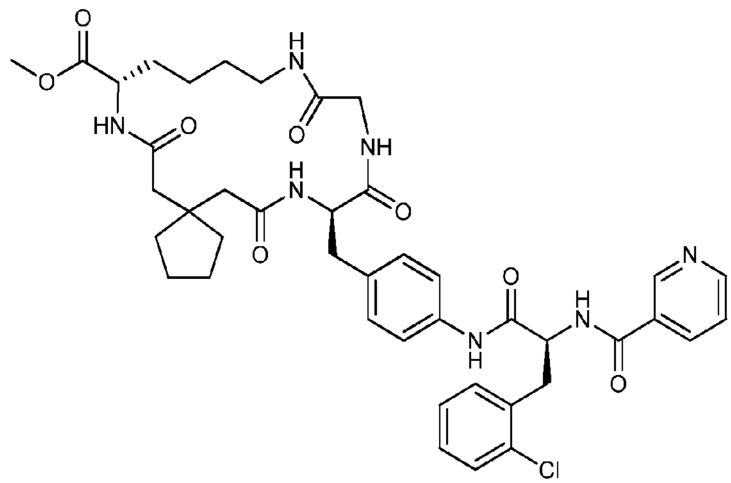 |
| 251 | 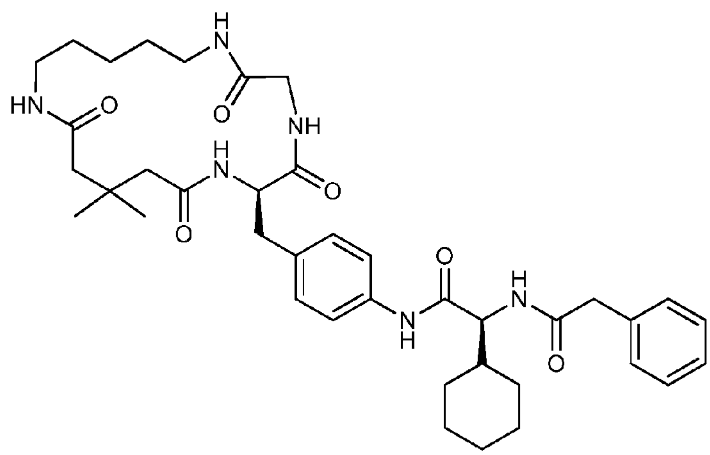 |

| Compound No. | Structure |
|---|---|
| 252 | 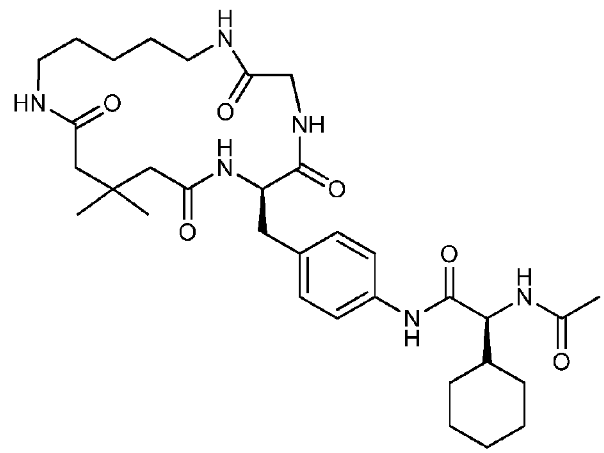 |
| 253 | 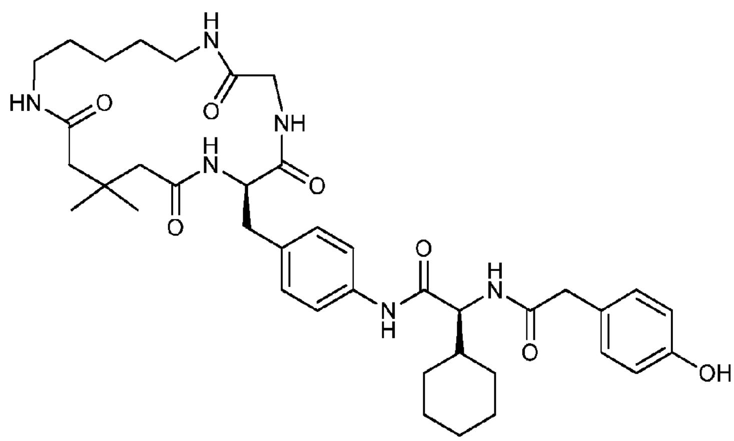 |

| Compound No. | Structure |
|---|---|
| 254 | 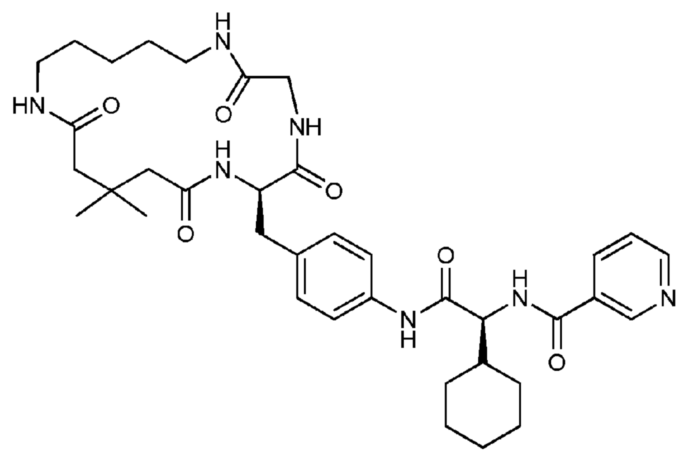 |
| 255 | 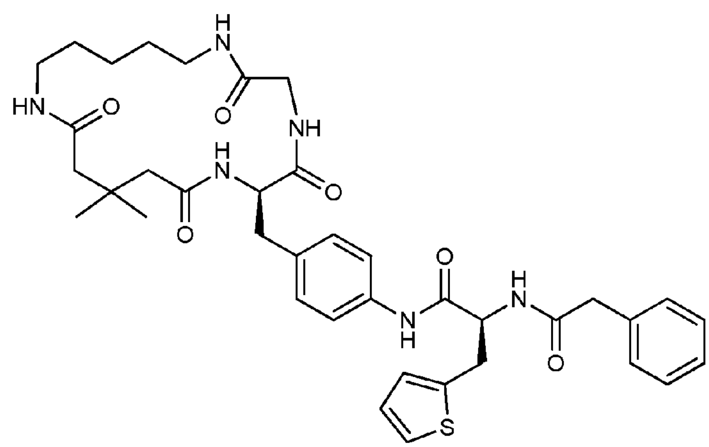 |

FIG. 12-69

| Compound No. | Structure |
|---|---|
| 256 | 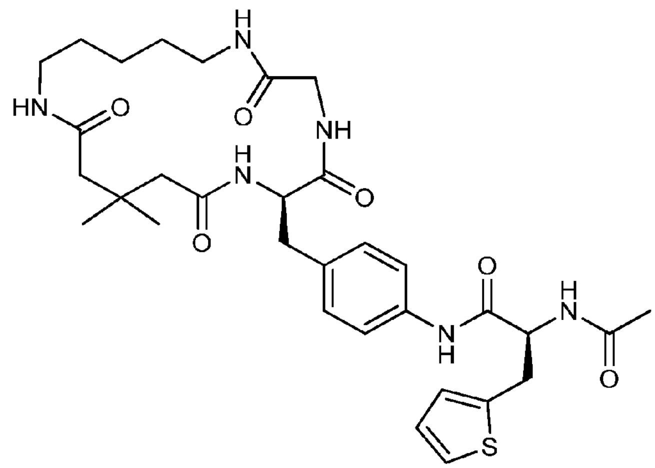 |
| 257 | 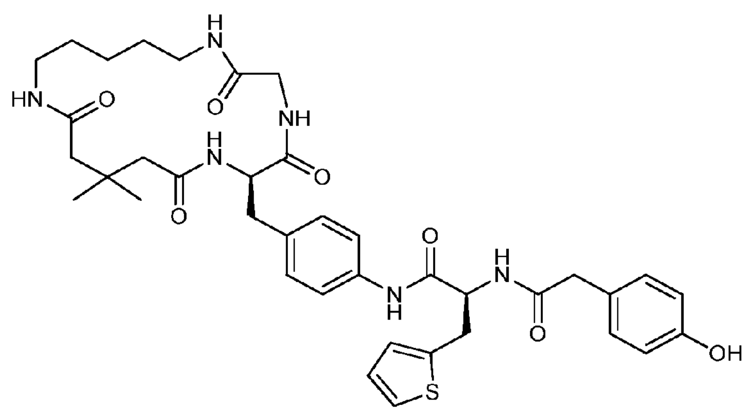 |

| Compound No. | Structure |
|---|---|
| 258 | 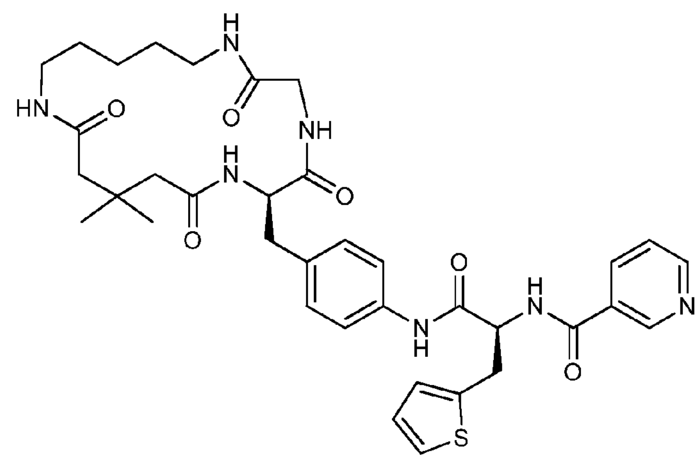 |
| 259 | 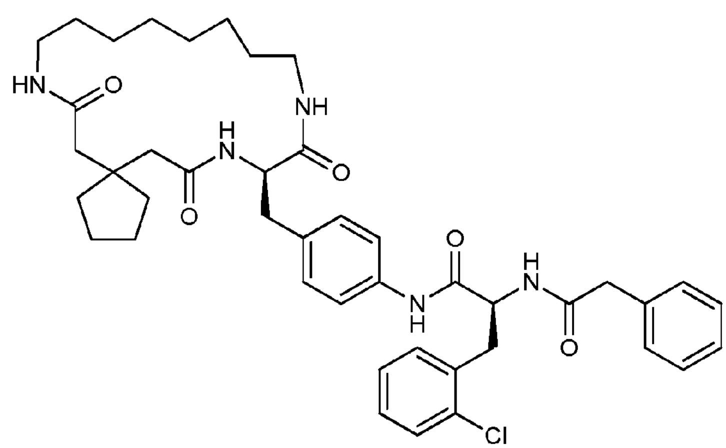 |

| Compound No. | Structure |
|---|---|
| 260 | 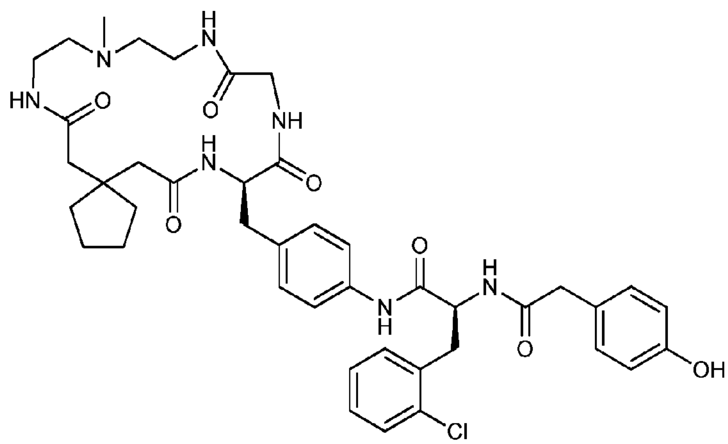 |
| 261 | 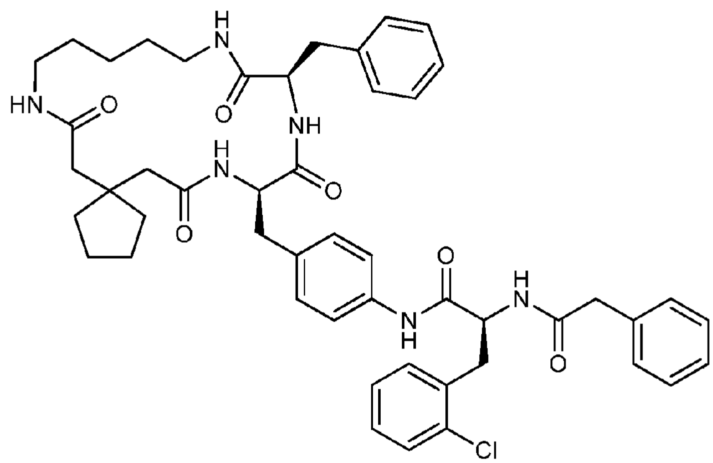 |

| Compound No. | Structure |
|---|---|
| 262 | 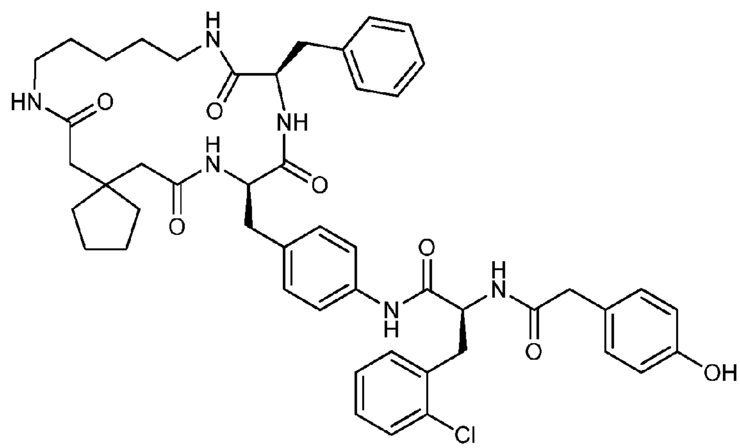 |
| 263 | 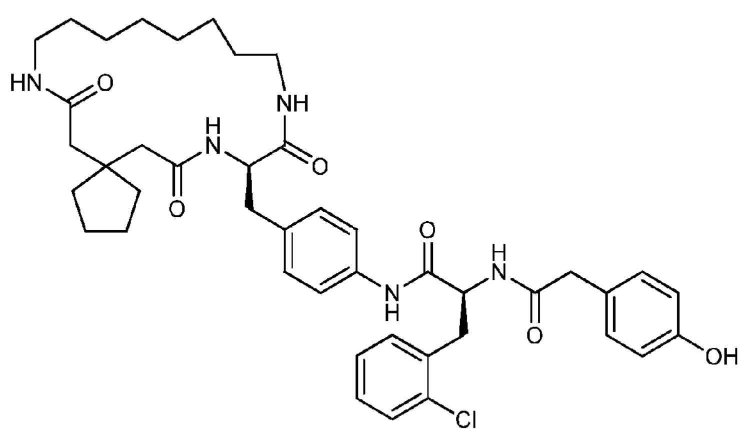 |

FIG. 12-73

| Compound No. | Structure |
|---|---|
| 264 | 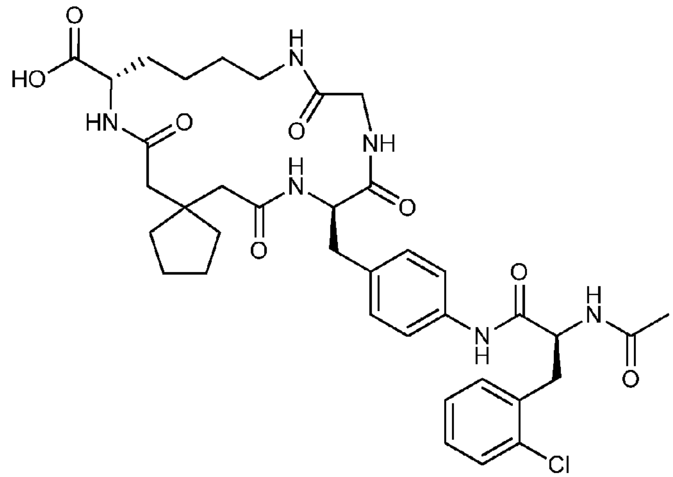 |
| 265 | 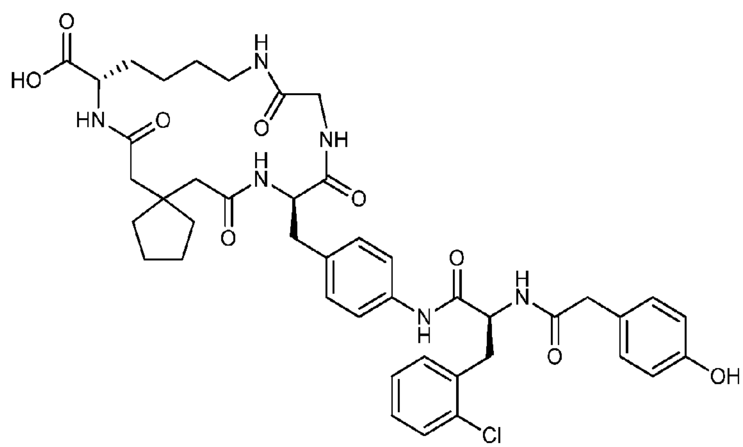 |

FIG. 12-74

| Compound No. | Structure |
|---|---|
| 266 | 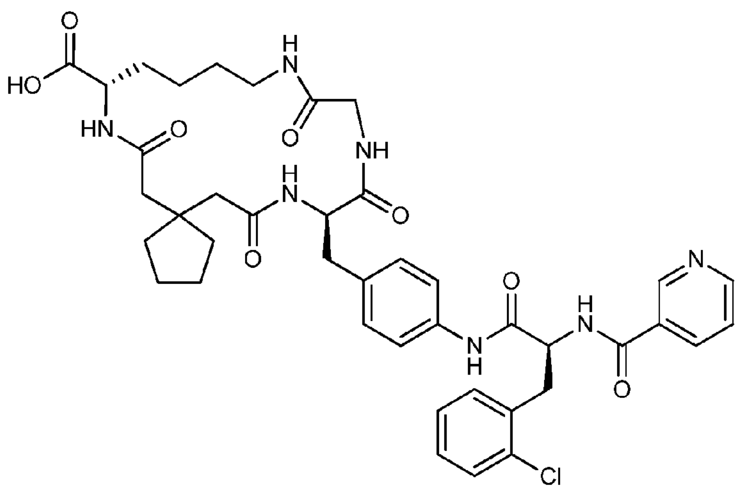 |
| 267 | 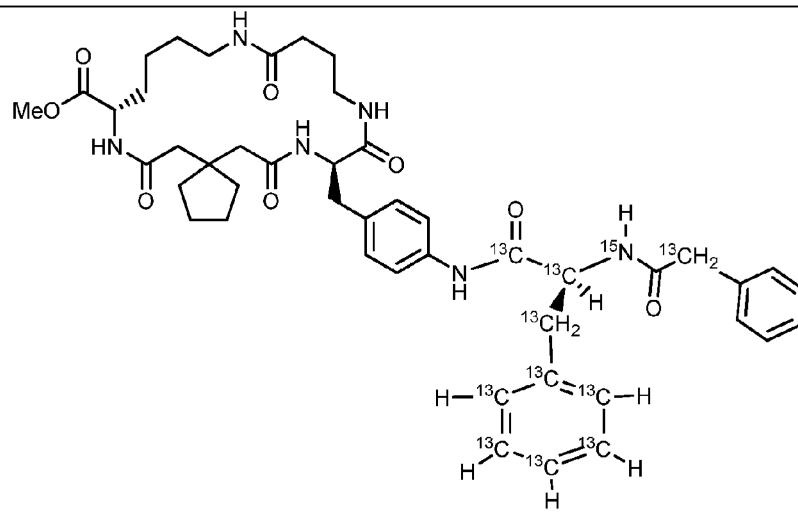 |

| Compound No. | Structure |
|---|---|
| 268 | 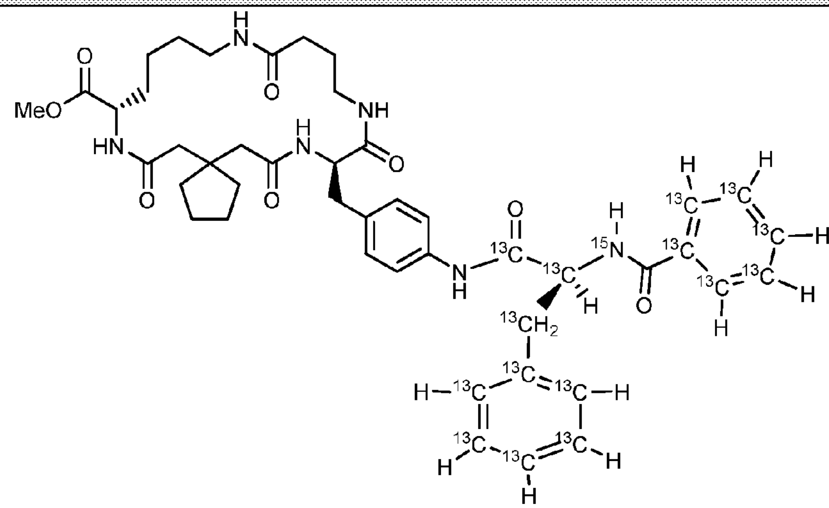 |
| 269 | 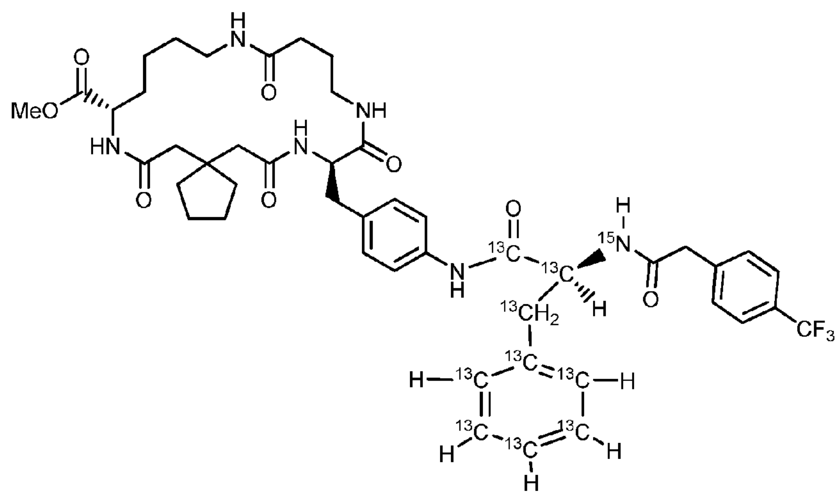 |

FIG. 12-76

| Compound No. | Structure |
|---|---|
| 270 | |
| 270 | |

FIG. 12-77

| Compound No. | Structure |
|---|---|
| 271 | 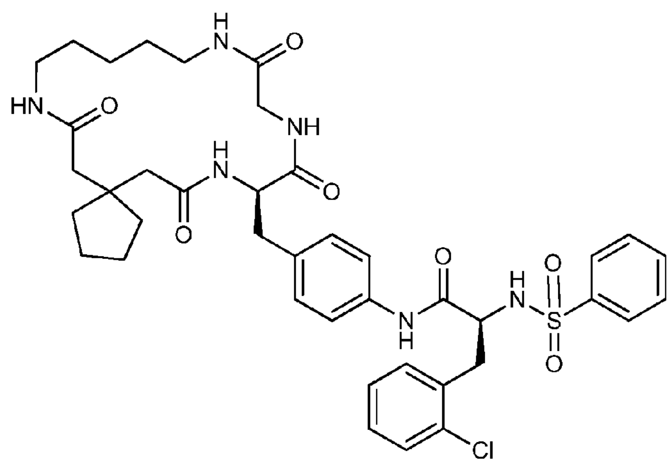 |
| 272 | 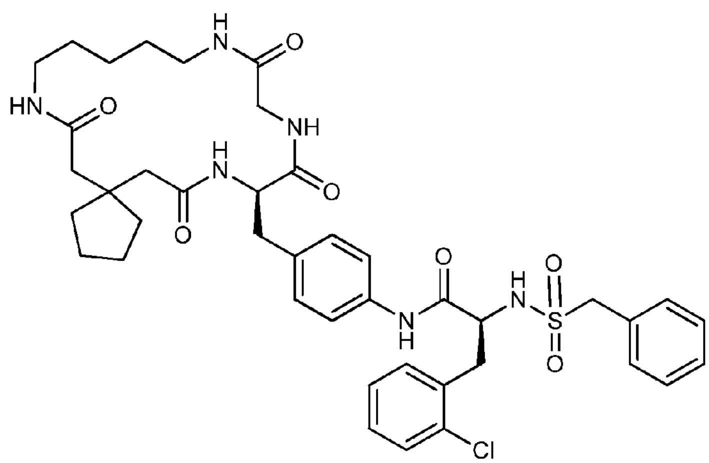 |

FIG. 12-78

| Compound No. | Structure |
|---|---|
| 273 | 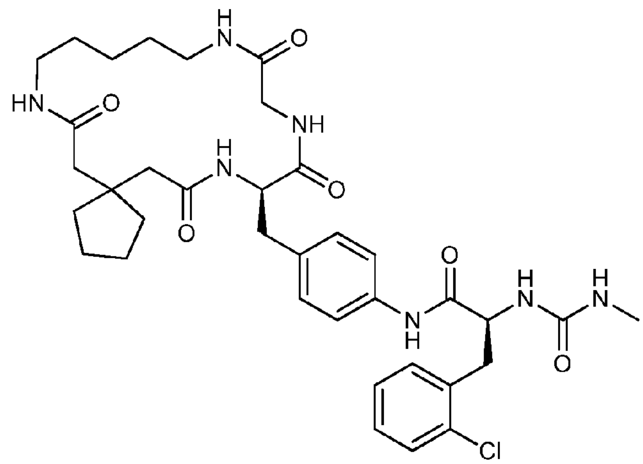 |
| 274 | 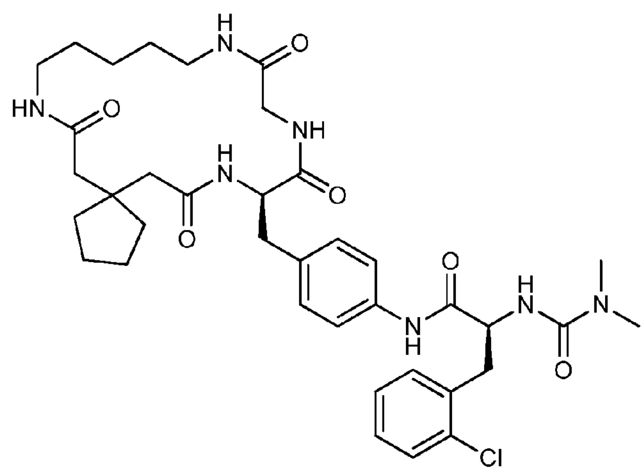 |

FIG. 12-79
| Compound No. | Structure |
|---|---|
| 275 | 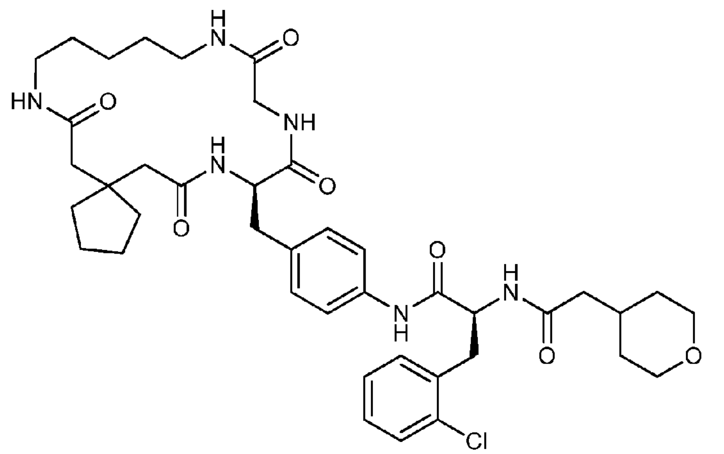 |
| 276 | 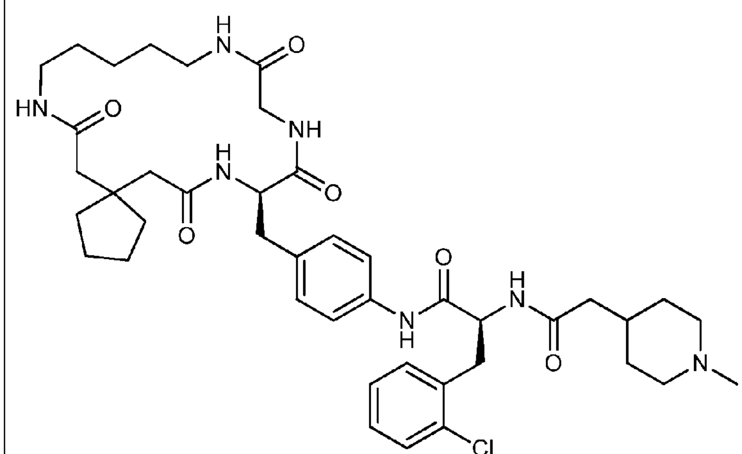 |
| 277 | 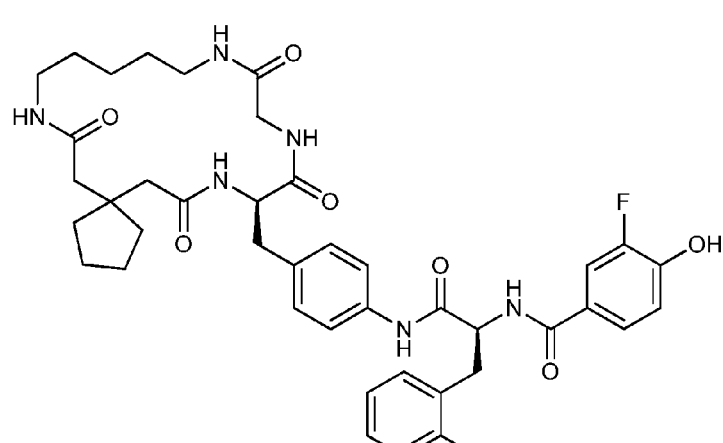 |

FIG. 12-80

| Compound No. | Structure |
|---|---|
| 278 | 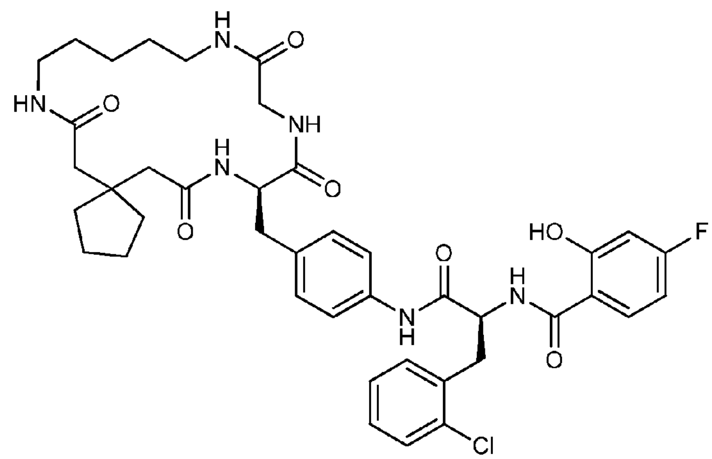 |
| 279 | 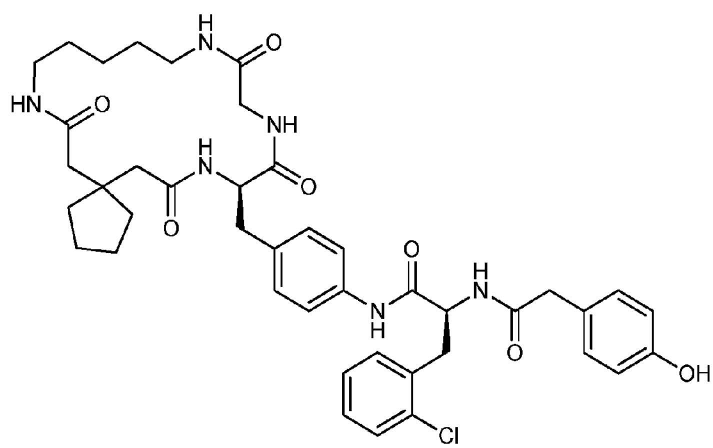 |

| Compound No. | Structure |
|---|---|
| 280 | 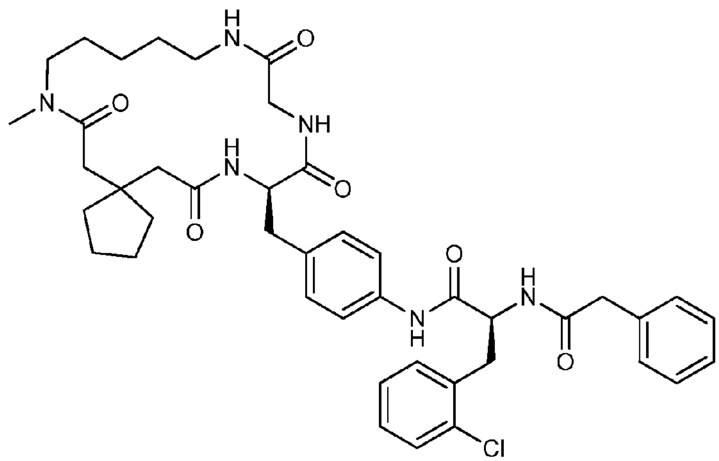 |
| 281 | 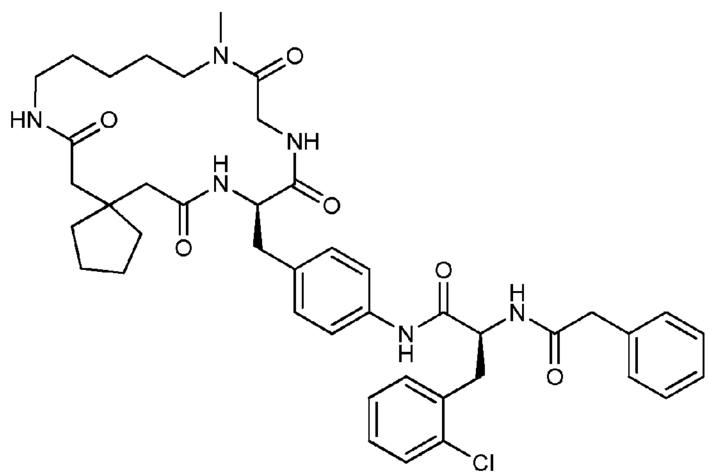 |

| Compound No. | Structure |
|---|---|
| 282 | 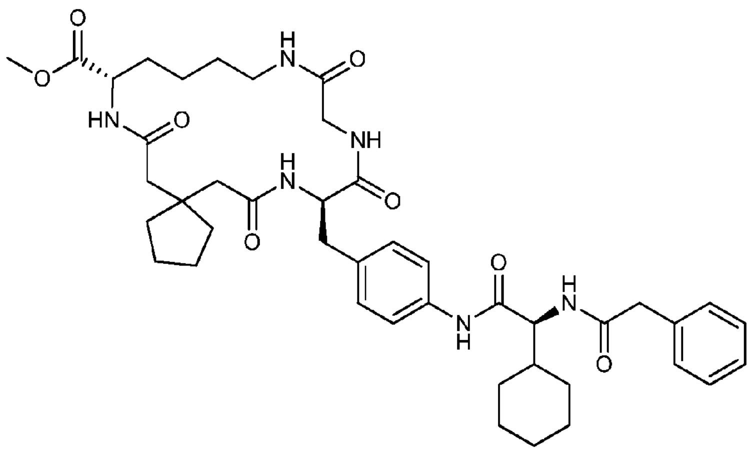 |
| 283 | 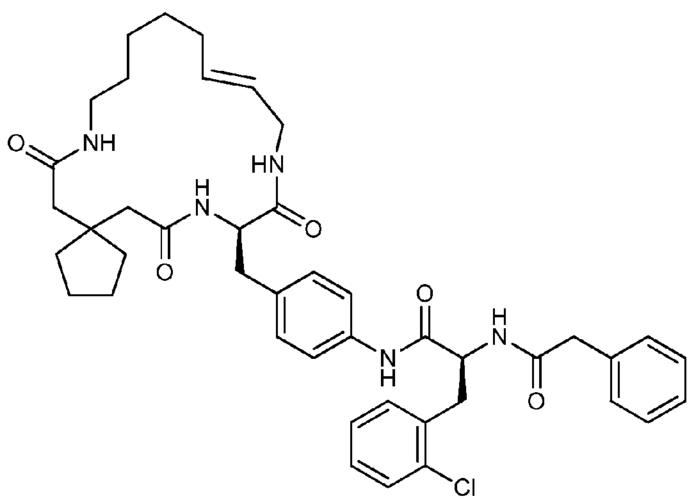 |

| Compound No. | Structure |
|---|---|
| 284 | 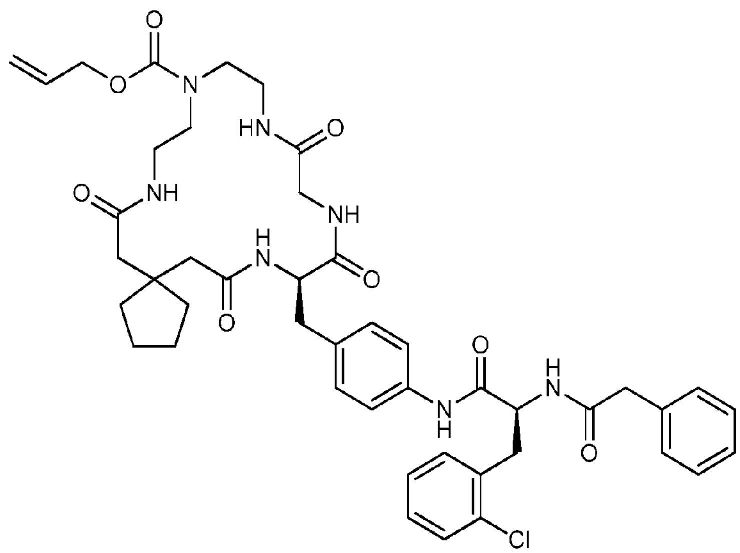 |
| 285 | 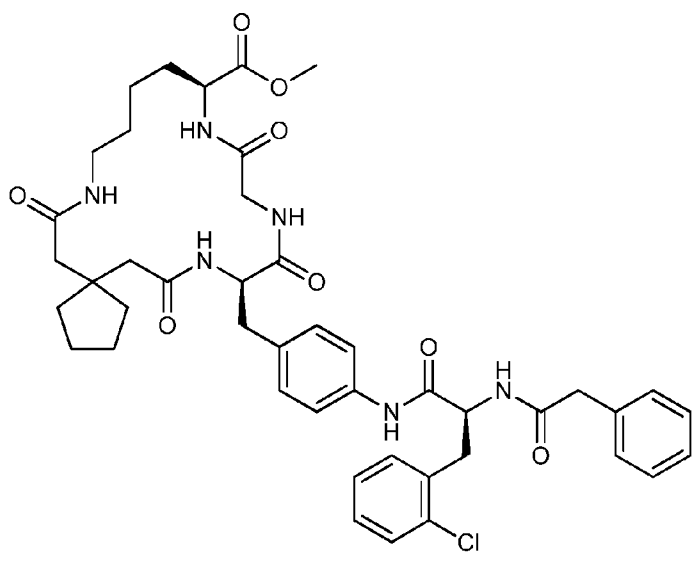 |

FIG. 12-84

| Compound No. | Structure |
|---|---|
| 286 | 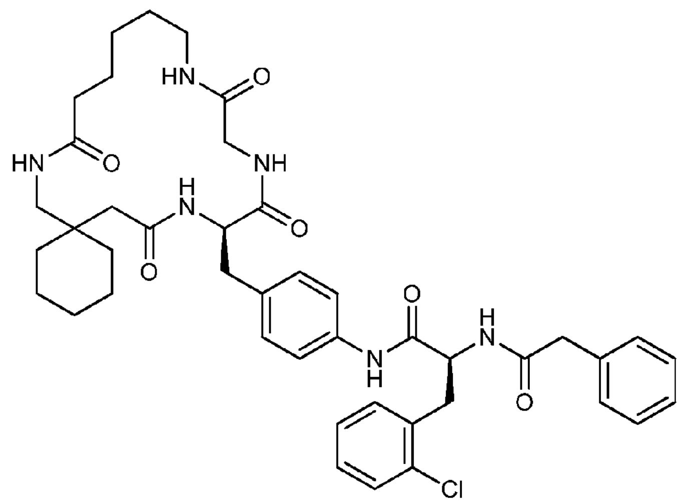 |
| 288 | 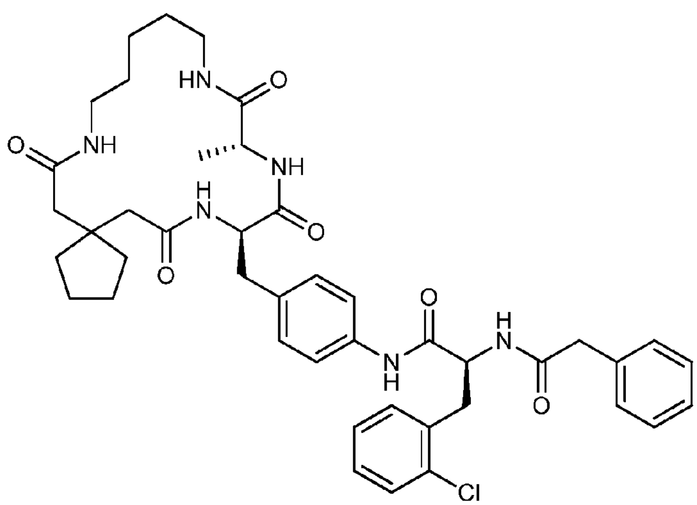 |

FIG. 12-85

| Compound No. | Structure |
|---|---|
| 289 | 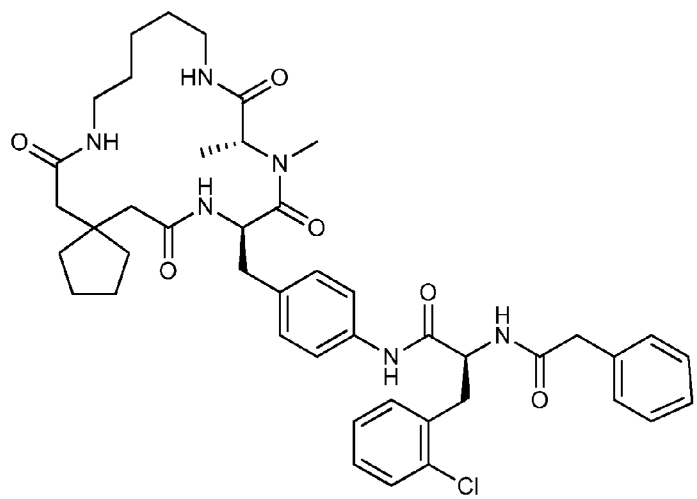 |
| 290 | 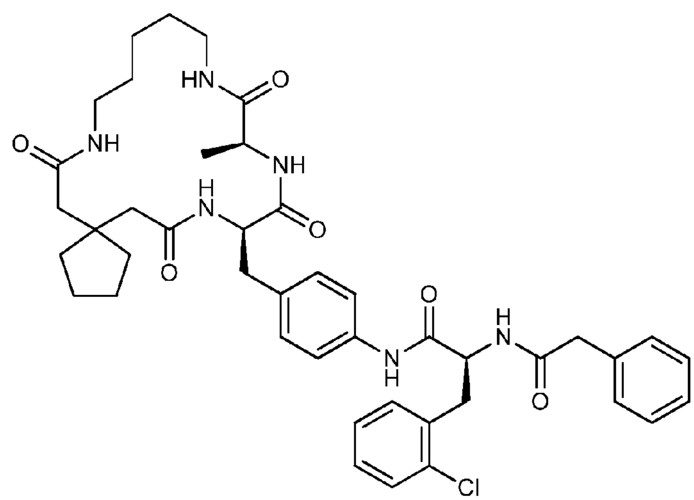 |

| Compound No. | Structure |
|---|---|
| 291 | 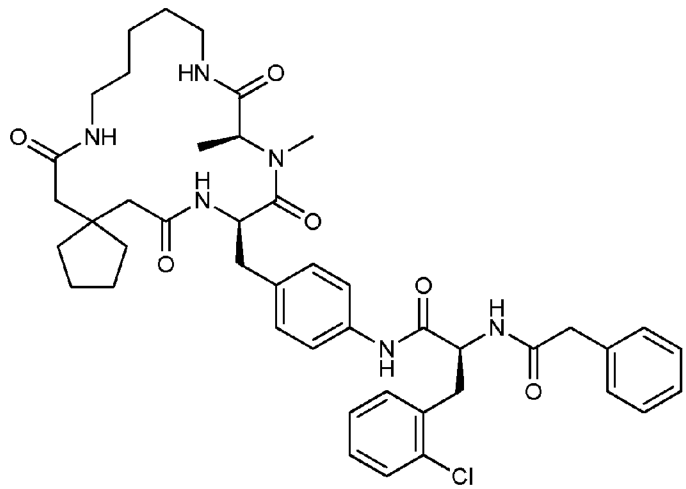 |
| 292 | 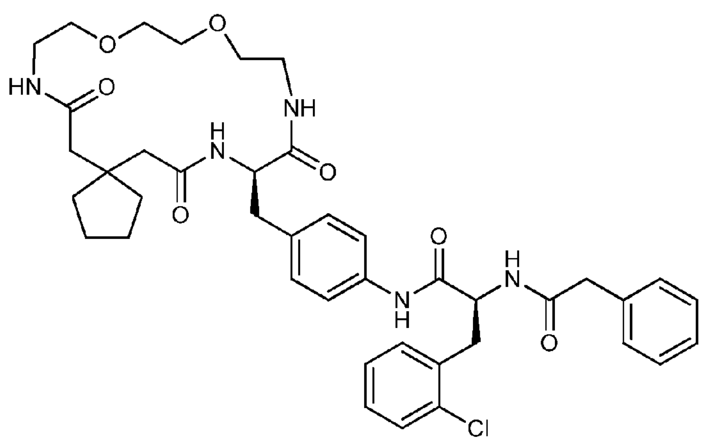 |

| Compound No. | Structure |
|---|---|
| 293 | 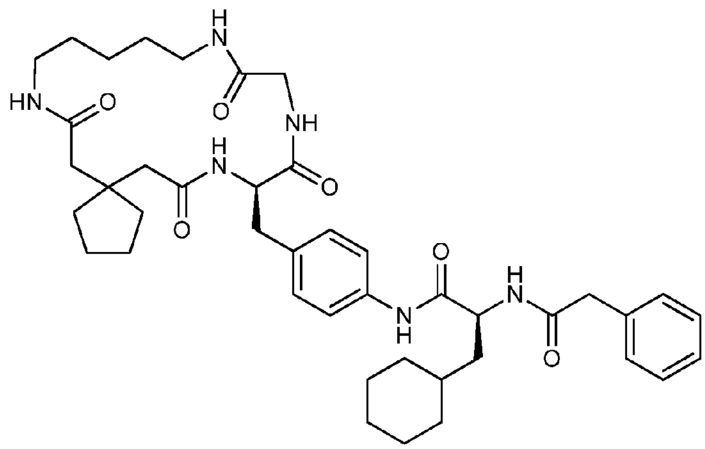 |
| 294 | 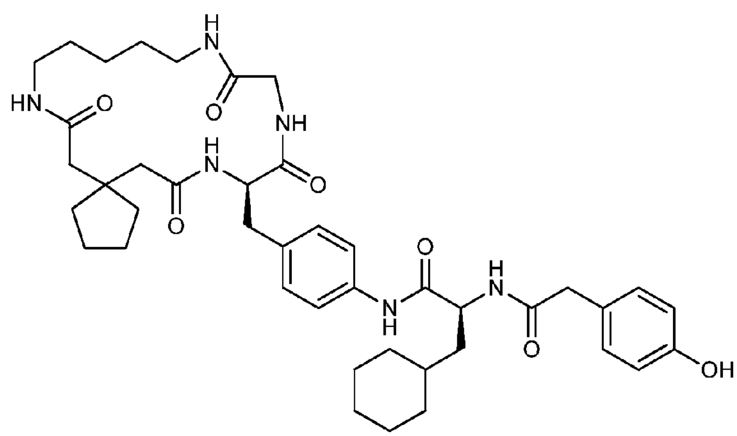 |

| Compound No. | Structure |
|---|---|
| 295 | 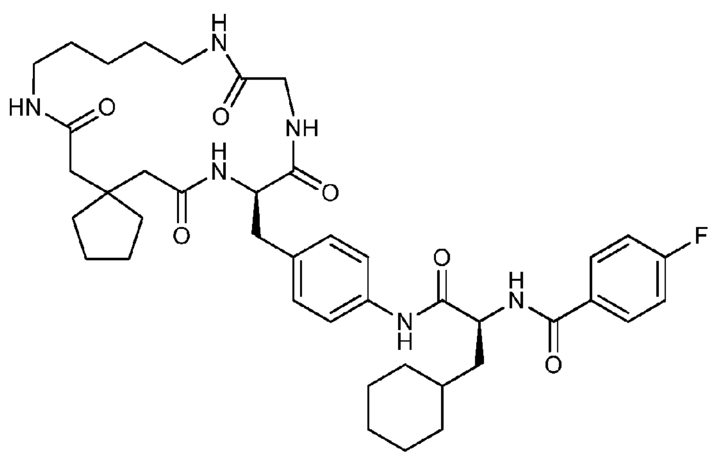 |
| 296 | 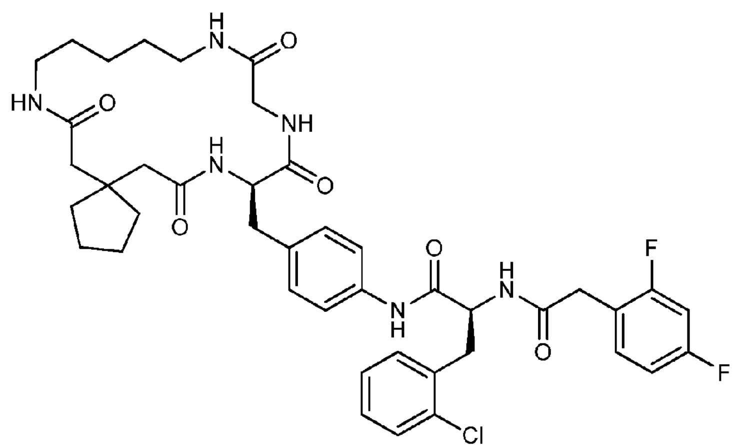 |

FIG. 12-89

| Compound No. | Structure |
|---|---|
| 297 | 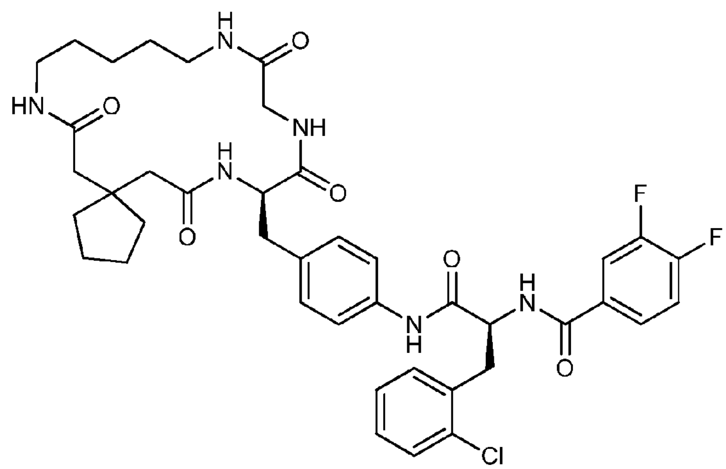 |
| 298 | 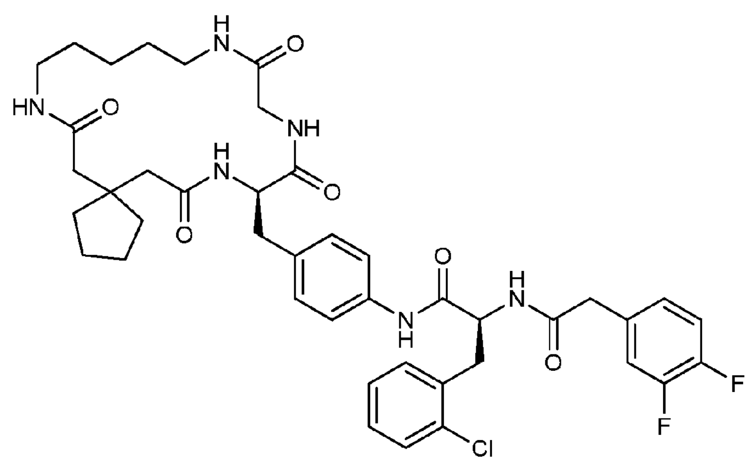 |

| Compound No. | Structure |
|---|---|
| 299 | 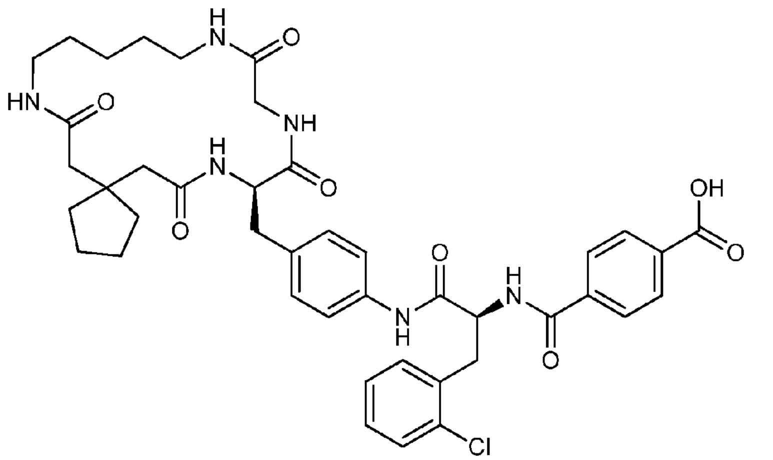 |
| 300 | 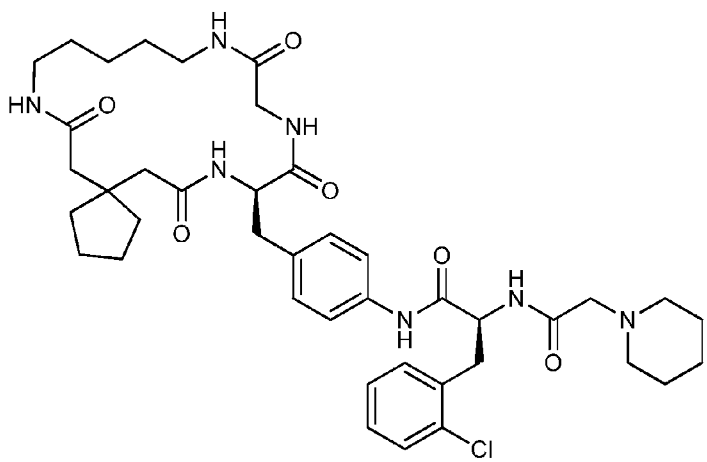 |

| Compound No. | Structure |
|---|---|
| 301 | 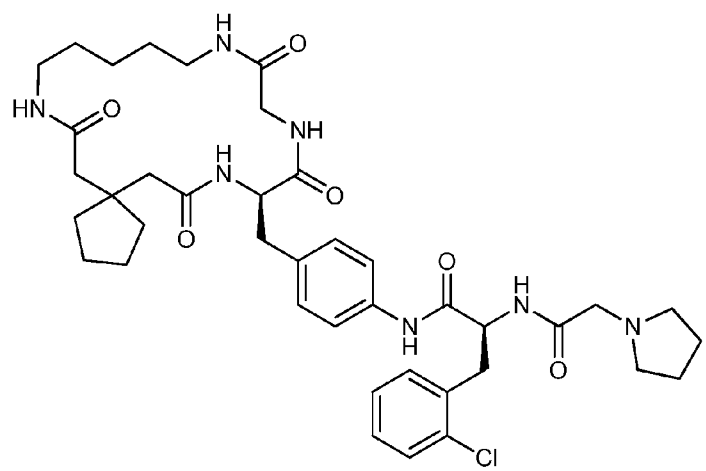 |
| 302 | 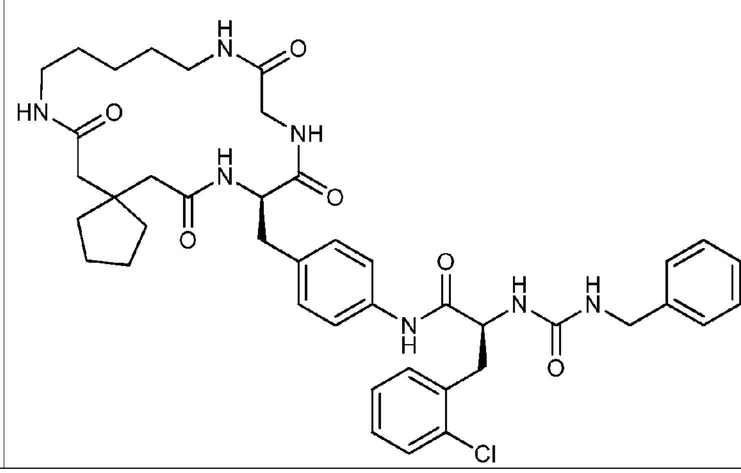 |

| Compound No. | Structure |
|---|---|
| 303 | 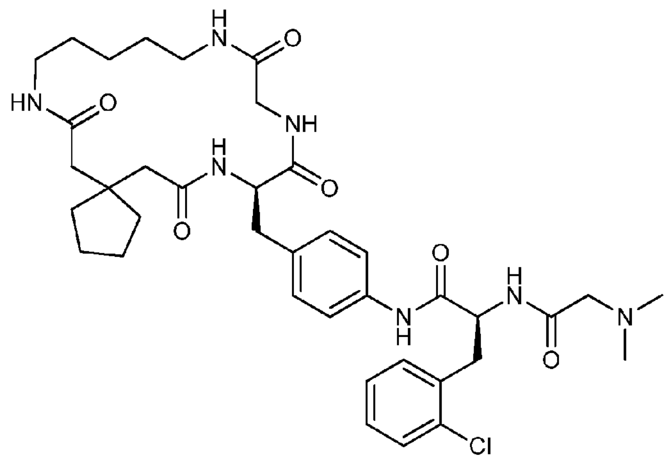 |
| 304 | 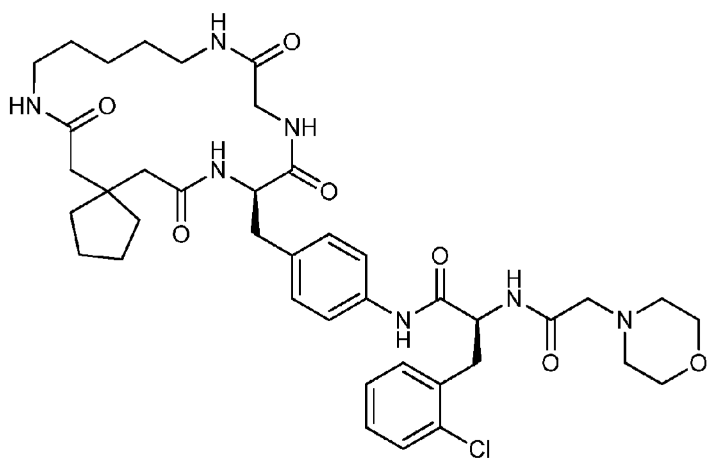 |

| Compound No. | Structure |
|---|---|
| 305 | 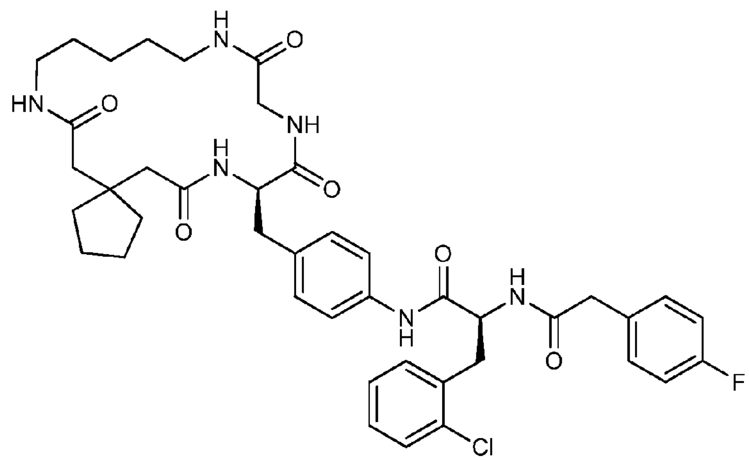 |
| 306 | 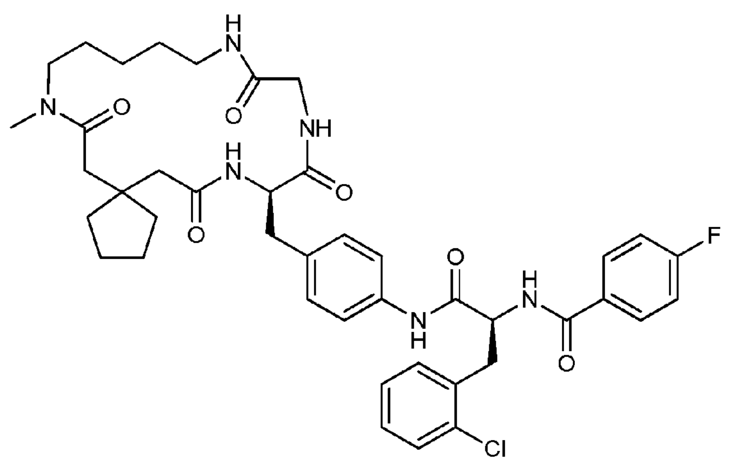 |

| Compound No. | Structure |
|---|---|
| 307 | 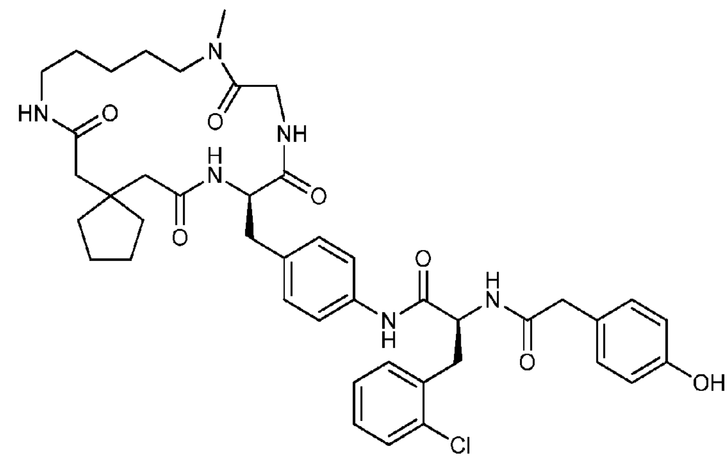 |
| 308 | 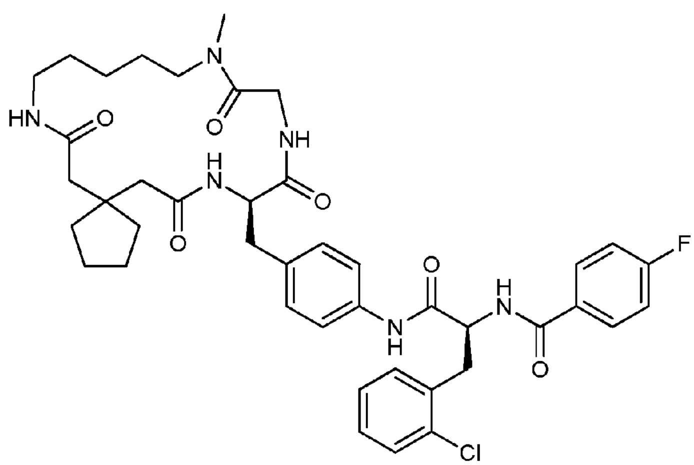 |

FIG. 12-95
| Compound No. | Structure |
|---|---|
| 309 | 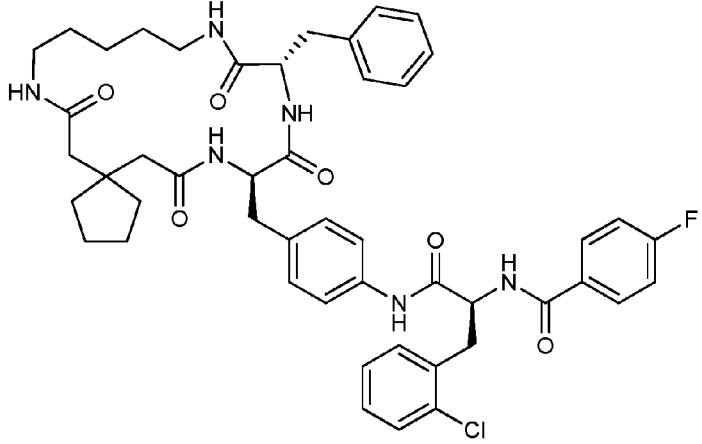 |
| 310 | 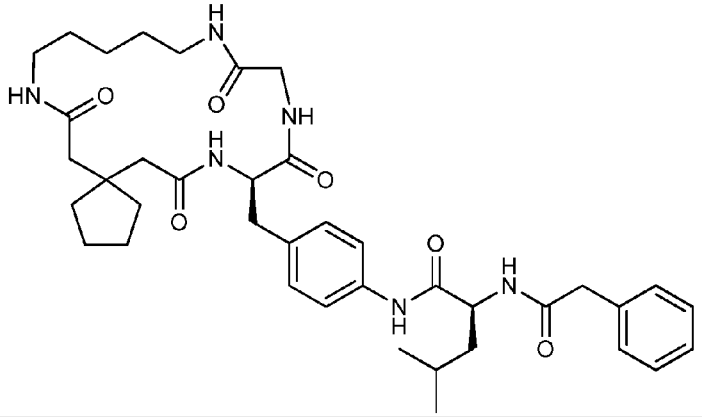 |
| 311 | 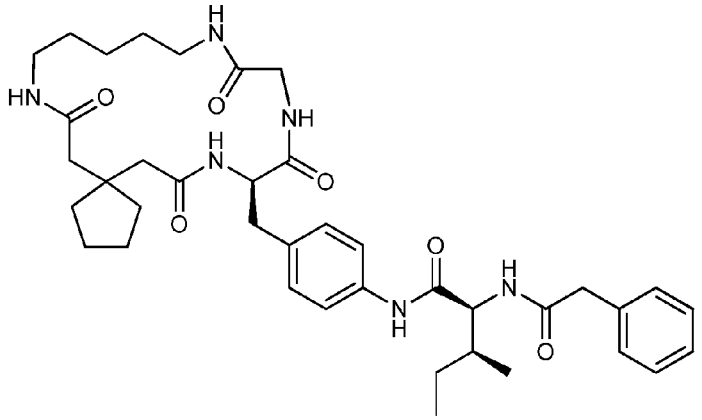 |

FIG. 12-96

| Compound No. | Structure |
|---|---|
| 312 | 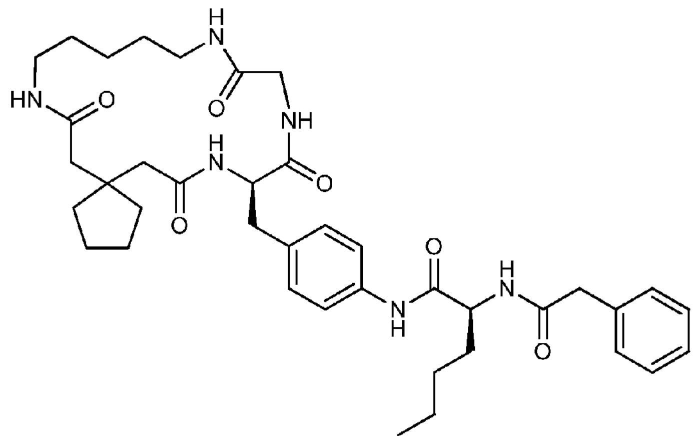 |
| 313 | 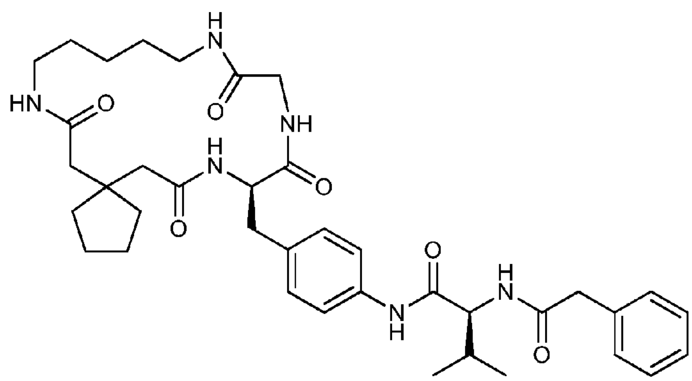 |
| 314 | 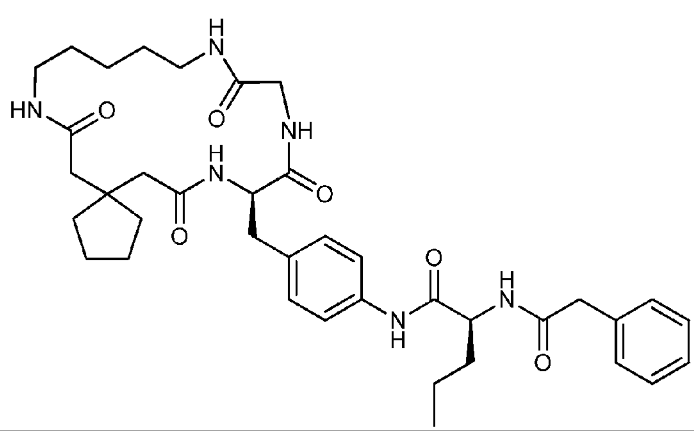 |

FIG. 12-97
| Compound No. | Structure |
|---|---|
| 315 | 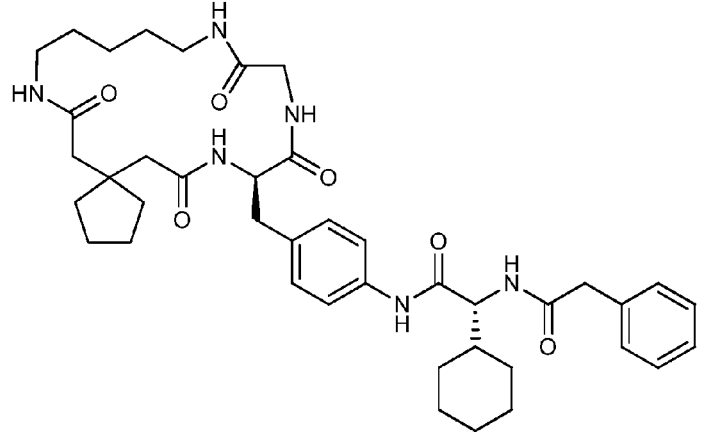 |
| 316 | 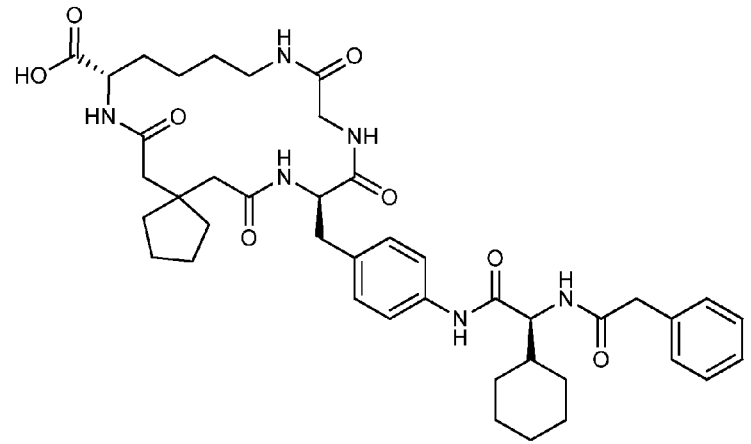 |
| 317 | 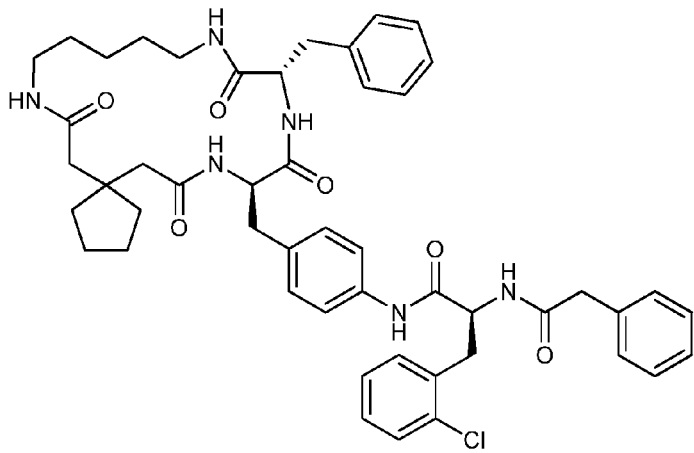 |

FIG. 12-98
| Compound No. | Structure |
|---|---|
| 318 | 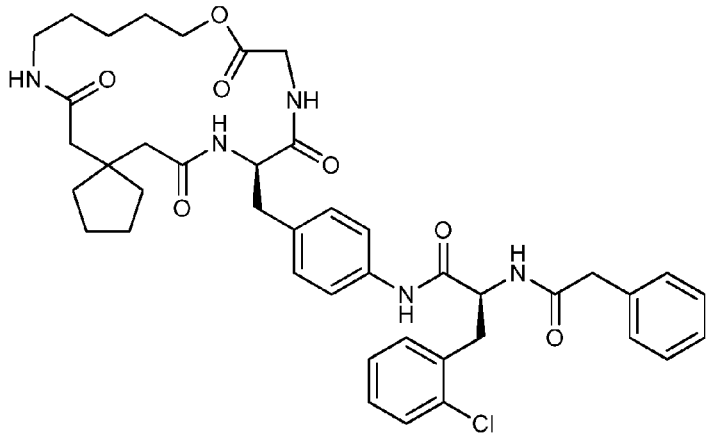 |
| 319 | 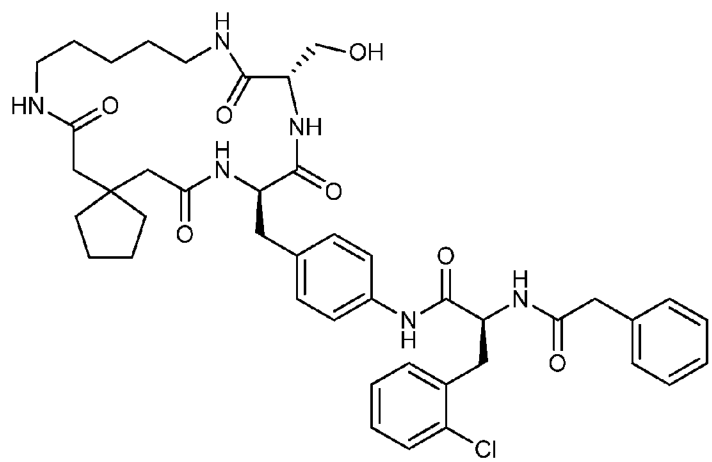 |
| 320 | 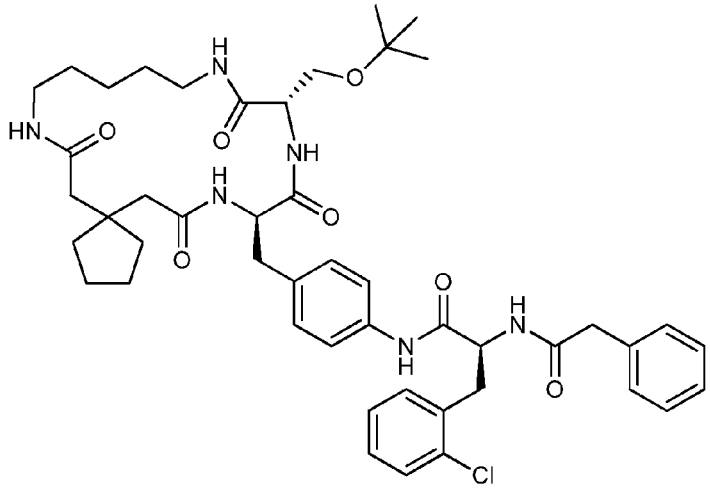 |

| Compound No. | Structure |
|---|---|
| 321 | 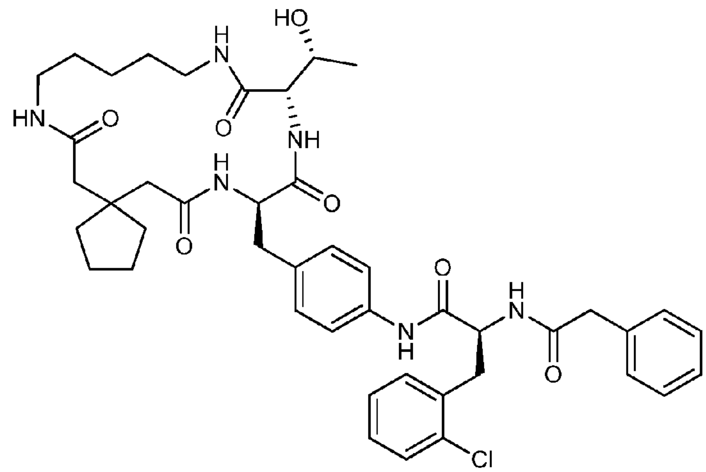 |
| 322 | 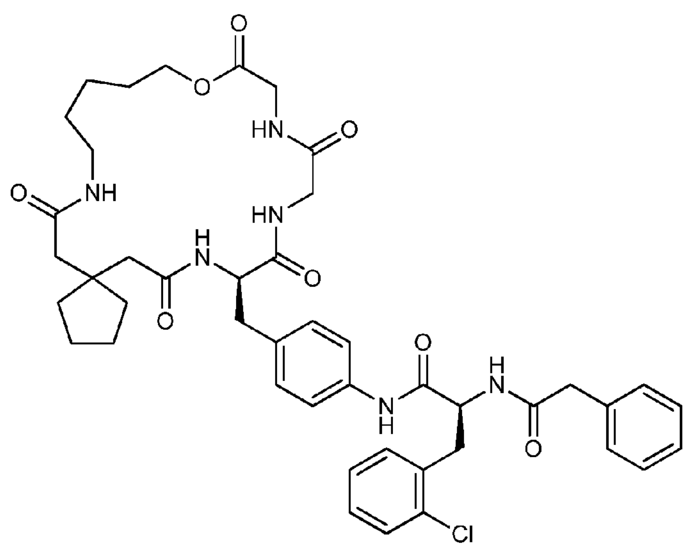 |

| Compound No. | Structure |
|---|---|
| 323 | 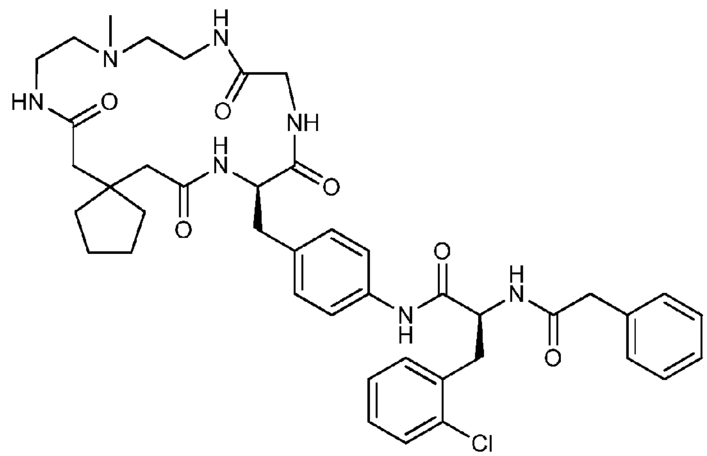 |
| 324 | 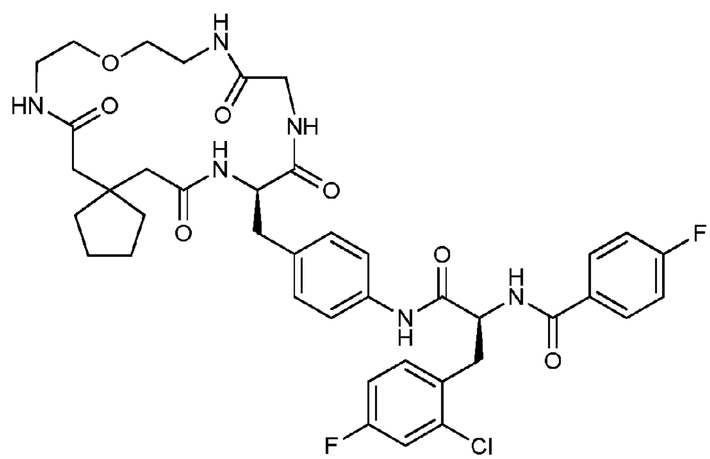 |

| Compound No. | Structure |
|---|---|
| 325 | 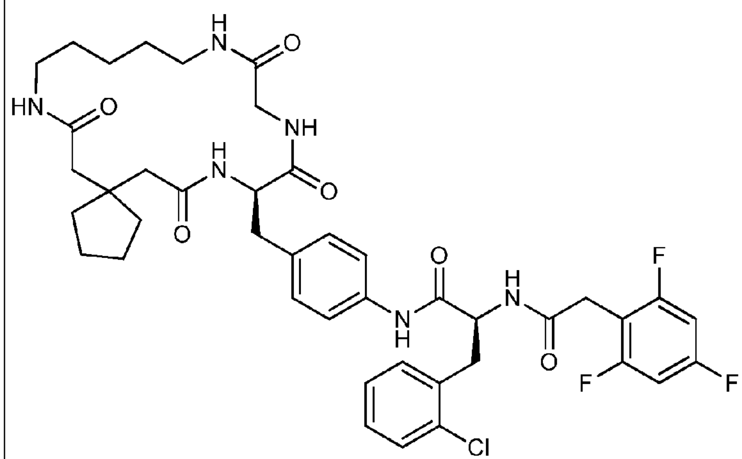 |
| 326 | 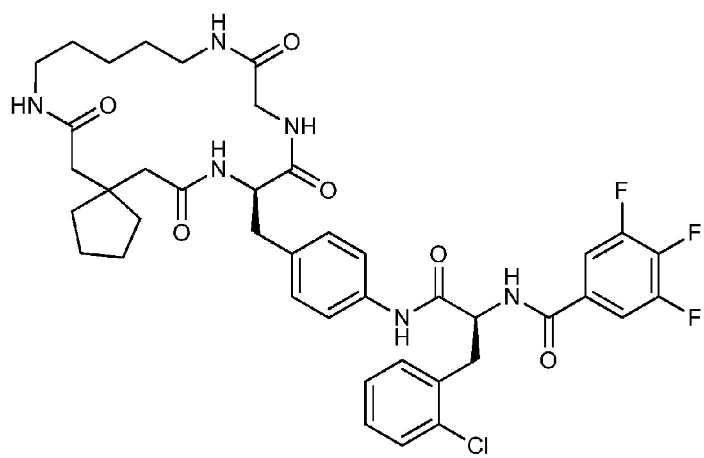 |

| Compound No. | Structure |
|---|---|
| 327 | 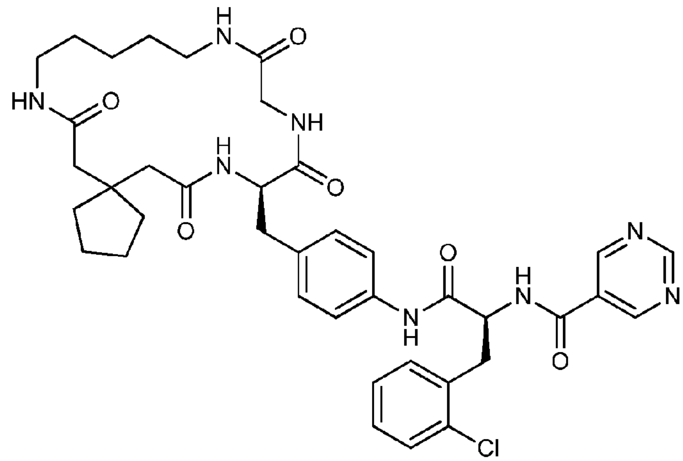 |
| 328 | 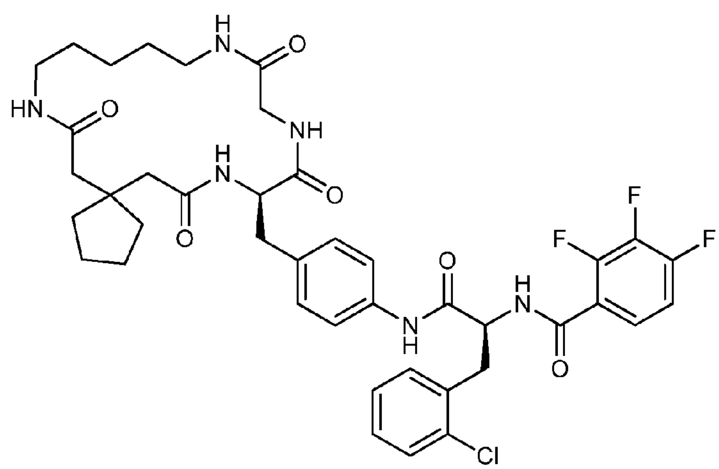 |

FIG. 12-103
| Compound No. | Structure |
|---|---|
| 329 | 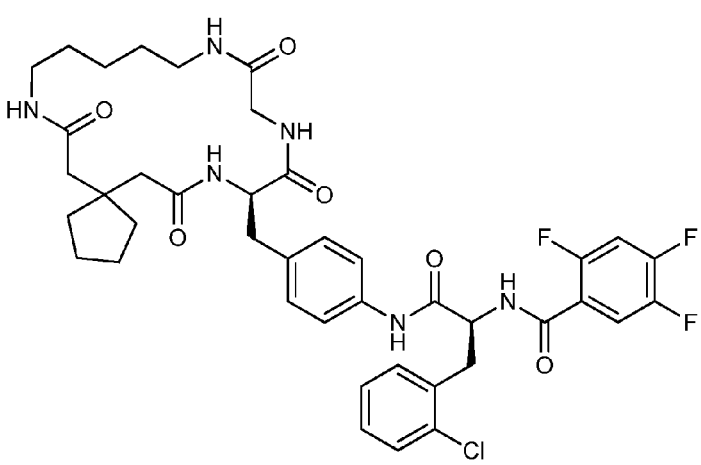 |
| 330 | 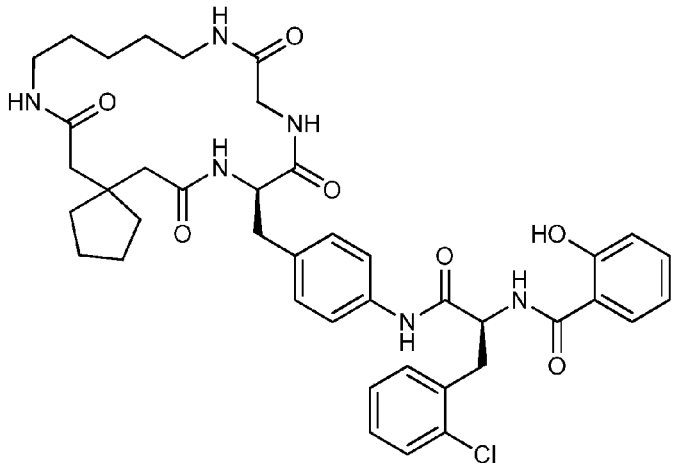 |
| 331 | 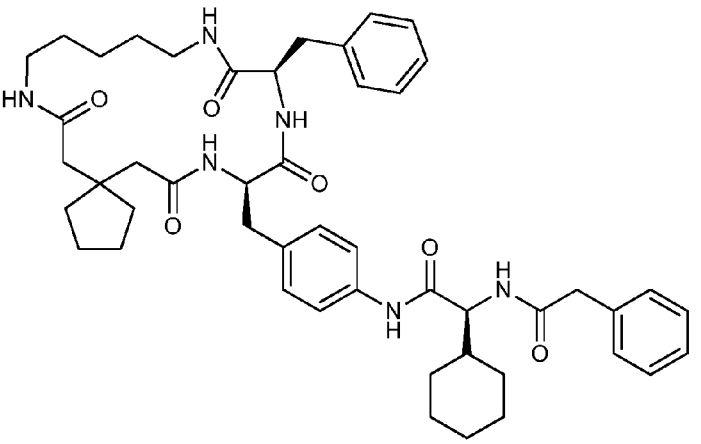 |

FIG. 12-104

| Compound No. | Structure |
|---|---|
| 332 | 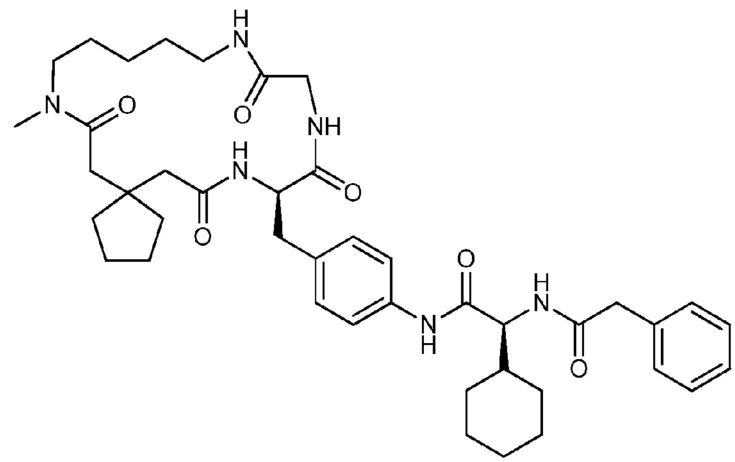 |
| 333 | 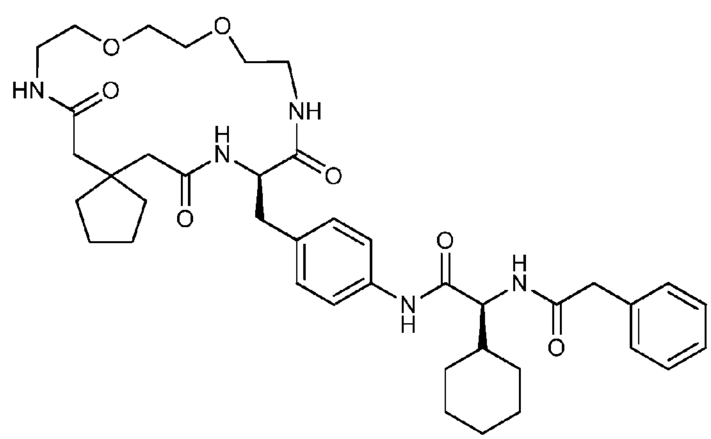 |
| 334 | 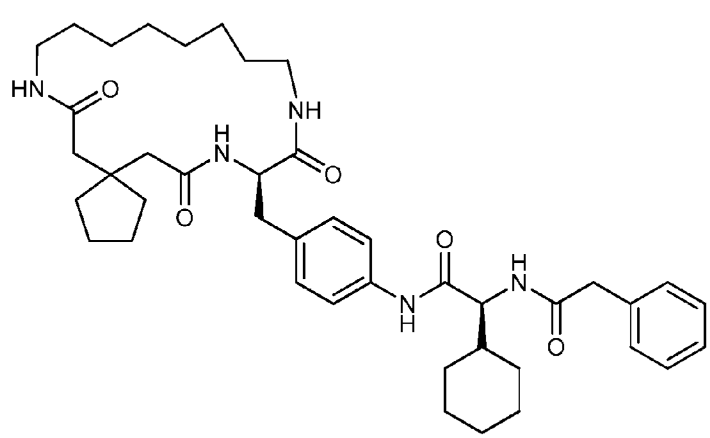 |

| Compound No. | Structure |
|---|---|
| 335 | 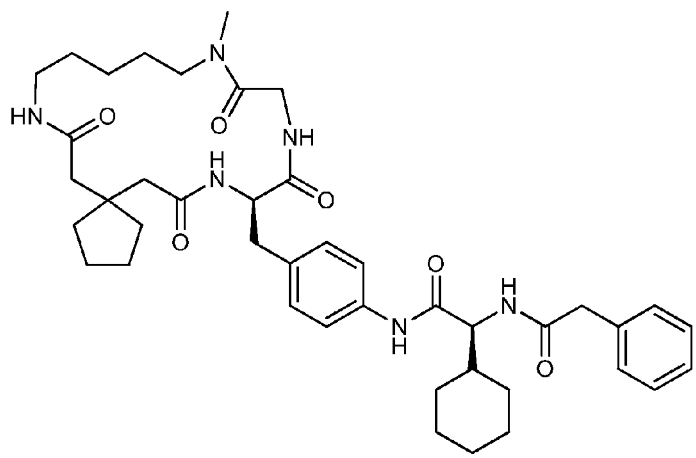 |
| 336 | 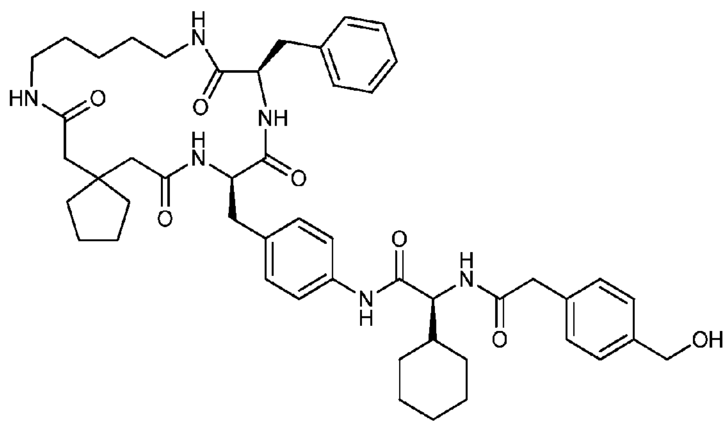 |

| Compound No. | Structure |
|---|---|
| 337 | 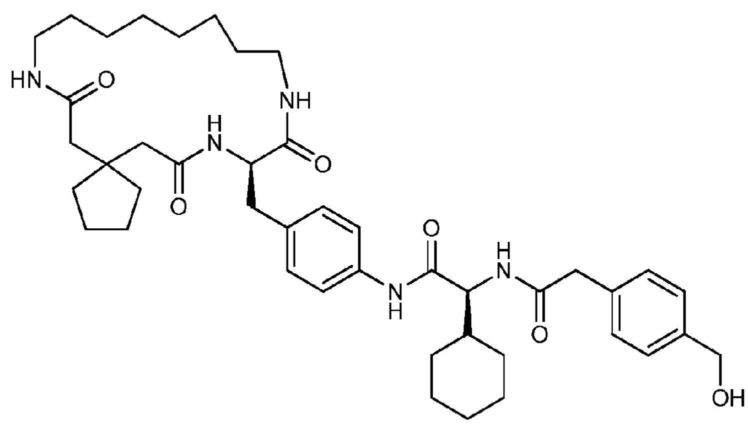 |
| 338 | 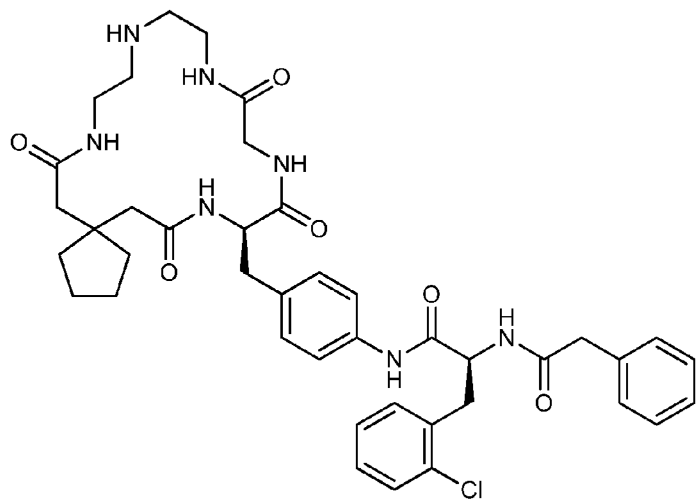 |

FIG. 12-107

| Compound No. | Structure |
|---|---|
| 339 | 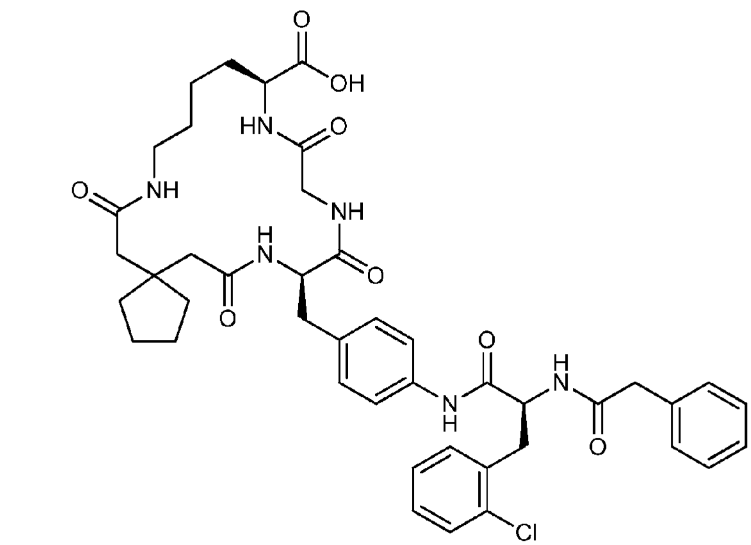 |
| 340 | 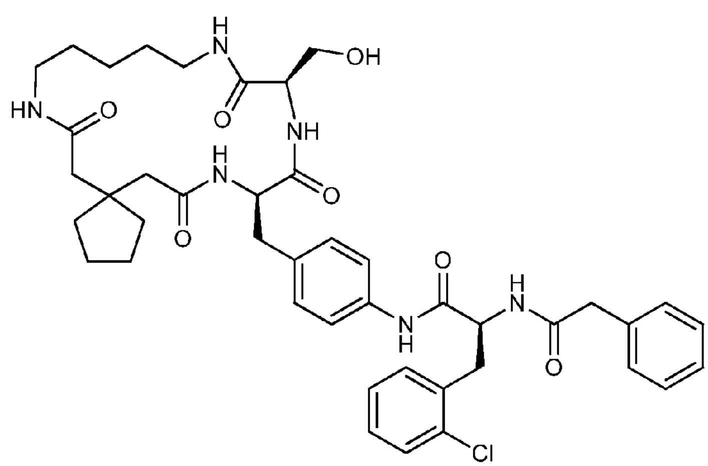 |

| Compound No. | Structure |
|---|---|
| 341 | 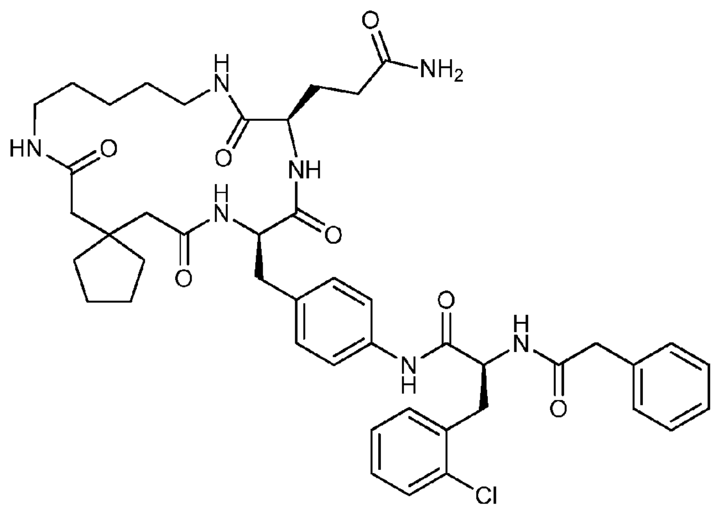 |
| 342 | 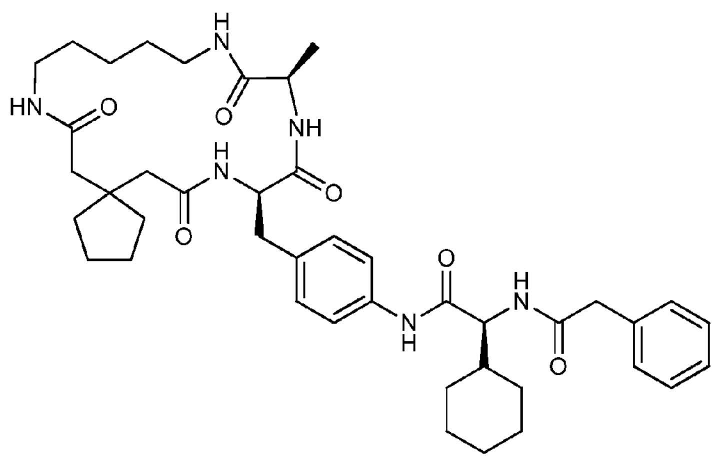 |

FIG. 12-109
| Compound No. | Structure |
|---|---|
| 343 | 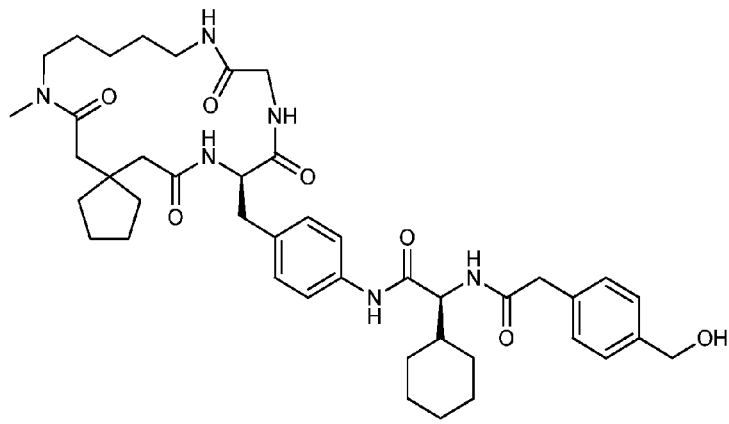 |
| 344 | 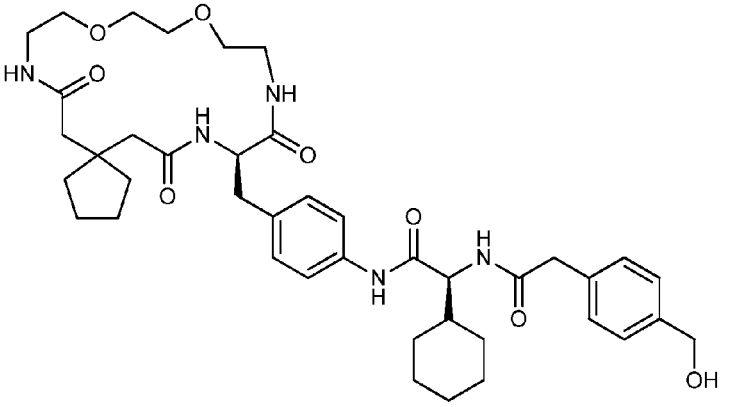 |
| 345 | 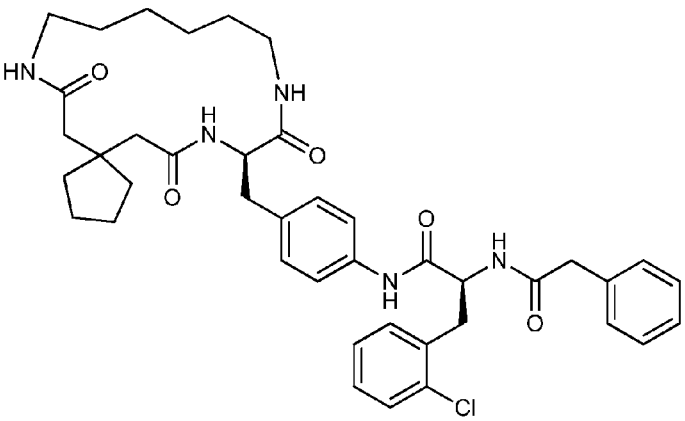 |

FIG. 12-110
| Compound No. | Structure |
|---|---|
| 346 | 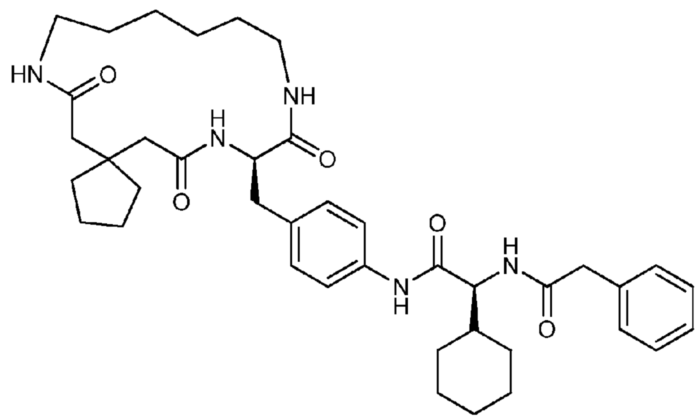 |
| 347 | 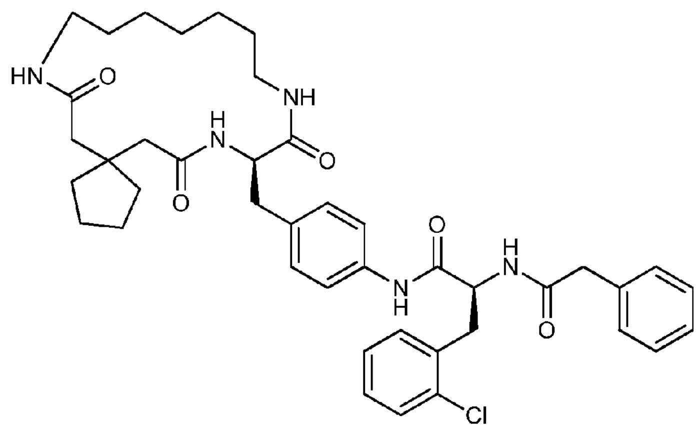 |
| 348 | 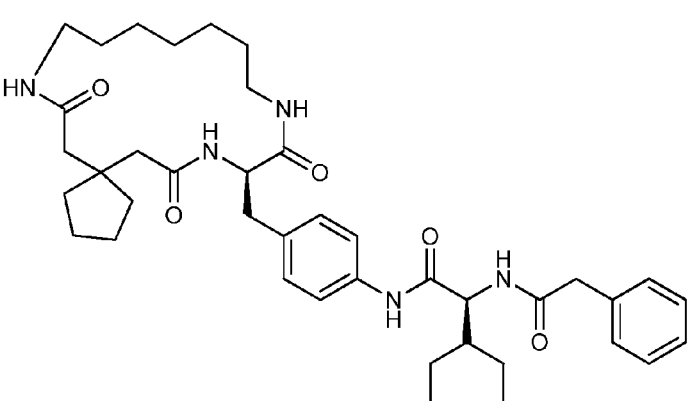 |

| Compound No. | Structure |
|---|---|
| 349 | 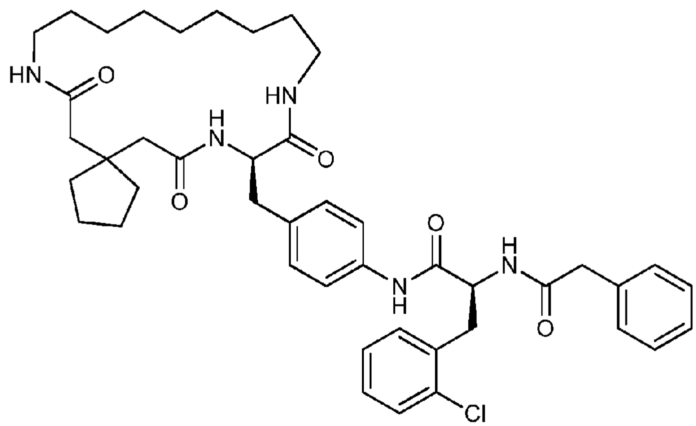 |
| 350 | 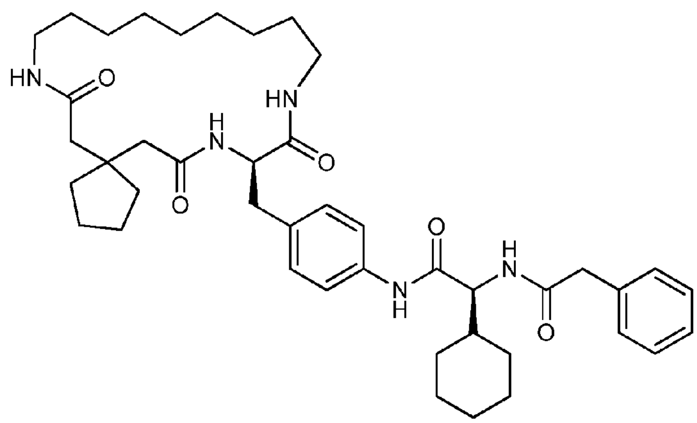 |

| Compound No. | Structure |
|---|---|
| 351 | 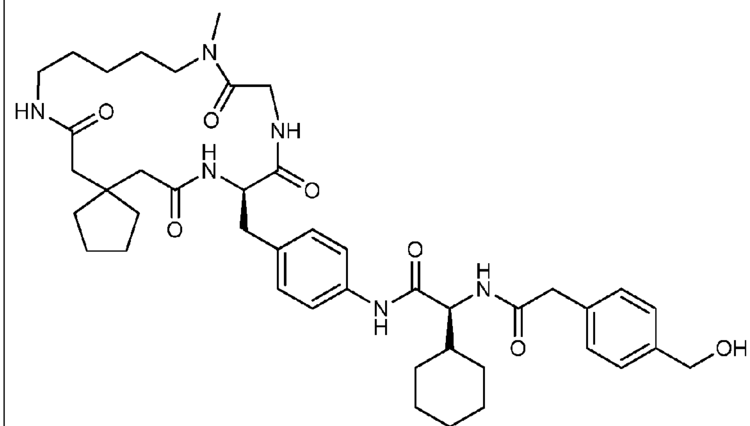 |
| 352 | 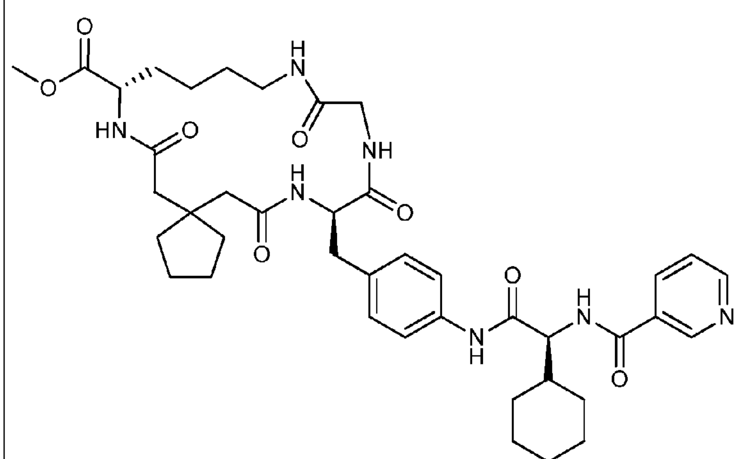 |

FIG. 12-113
| Compound No. | Structure |
|---|---|
| 353 | 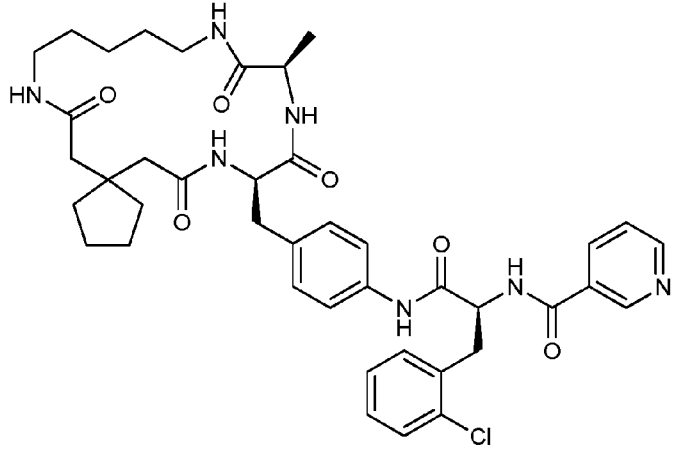 |
| 354 | 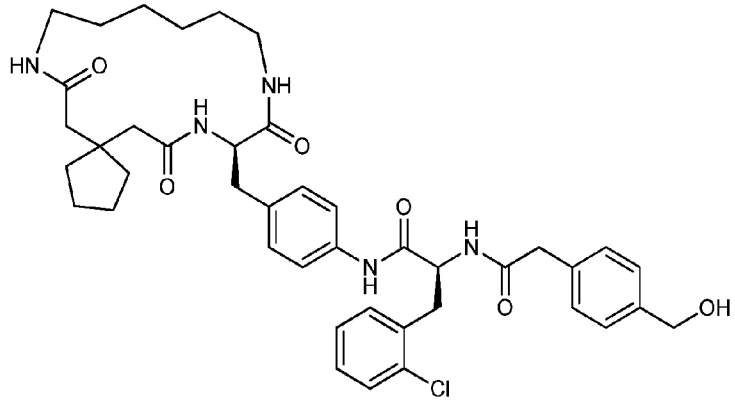 |
| 355 | 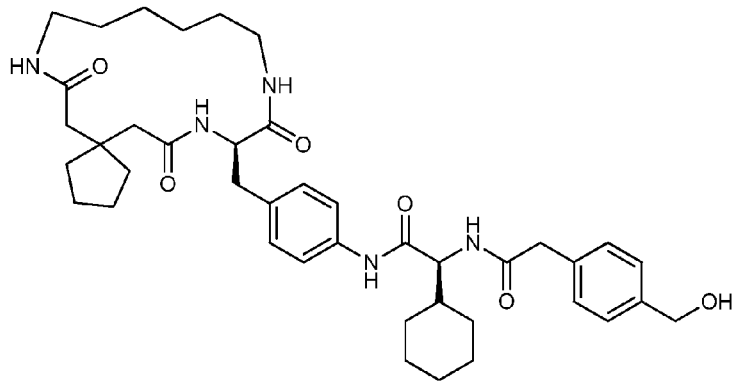 |

FIG. 12-114

| Compound No. | Structure |
|---|---|
| 356 | 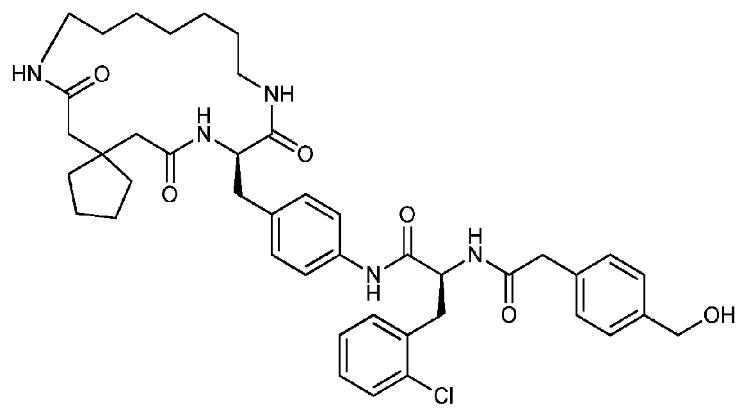 |
| 357 | 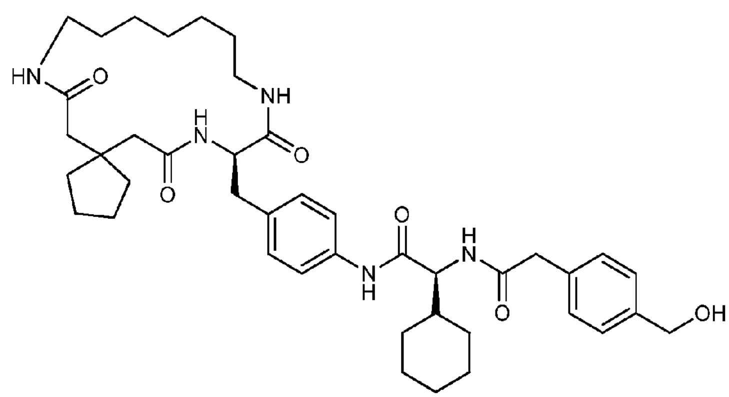 |
| 358 | 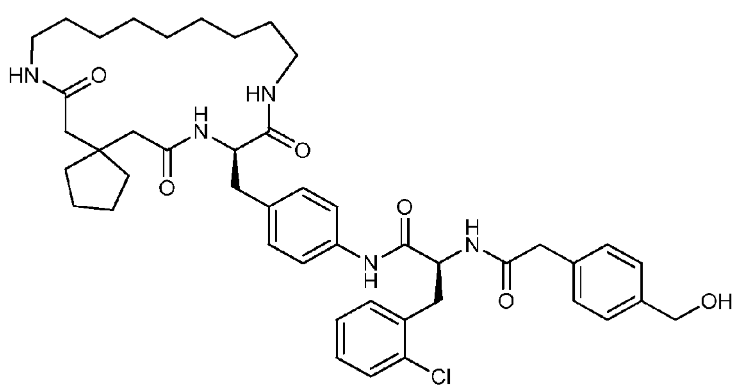 |

FIG. 12-115
| Compound No. | Structure |
|---|---|
| 359 | 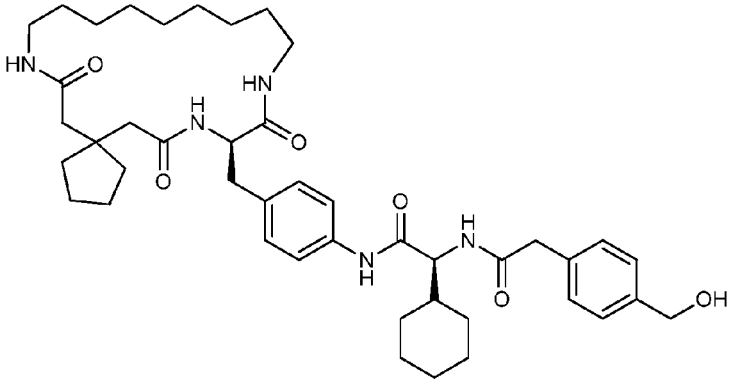 |
| 360 | 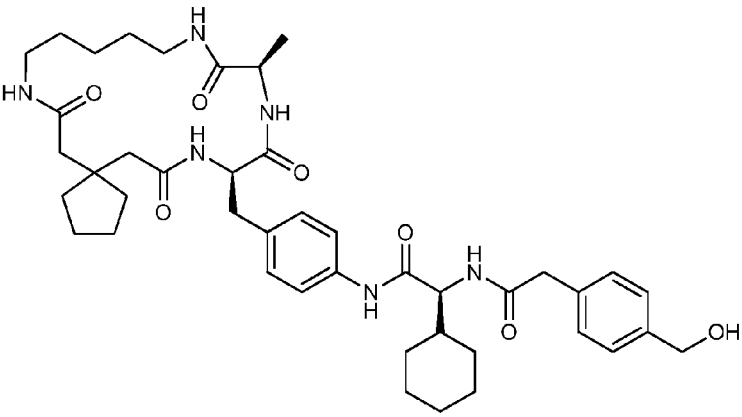 |
| 361 | 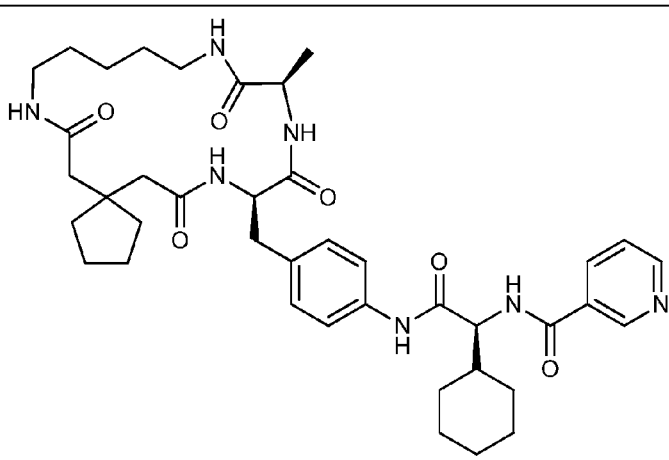 |

FIG. 12-116

| Compound No. | Structure |
|---|---|
| 362 | 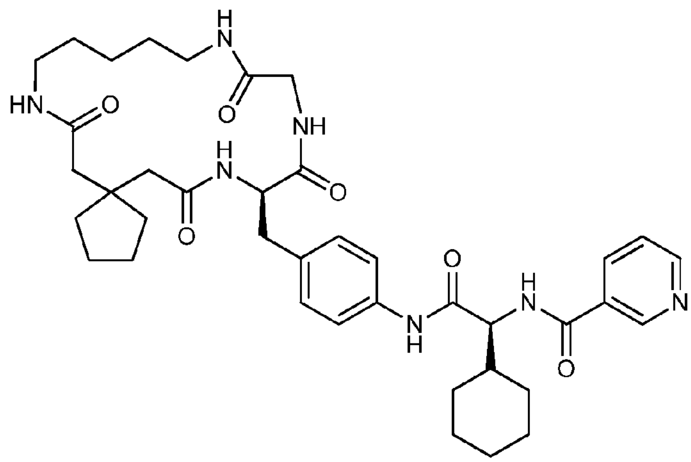 |
| 363 | 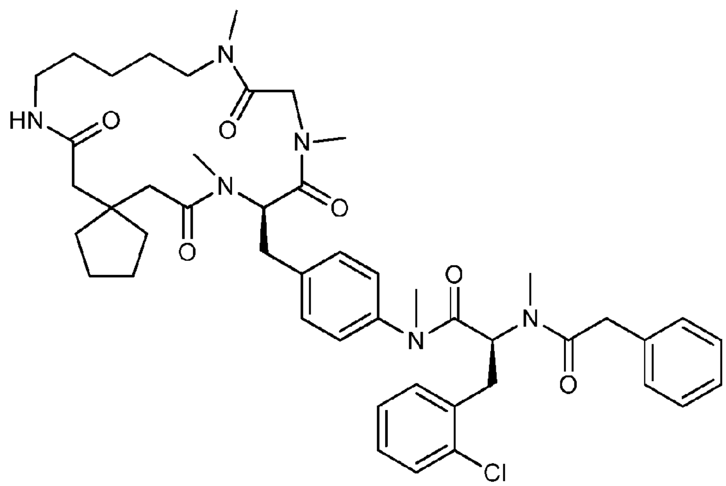 |

FIG. 12-117

| Compound No. | Structure |
|---|---|
| 364 | 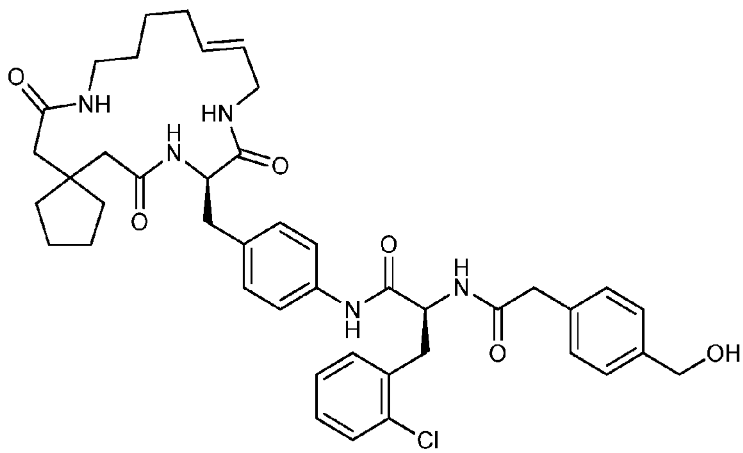 |
| 365 | 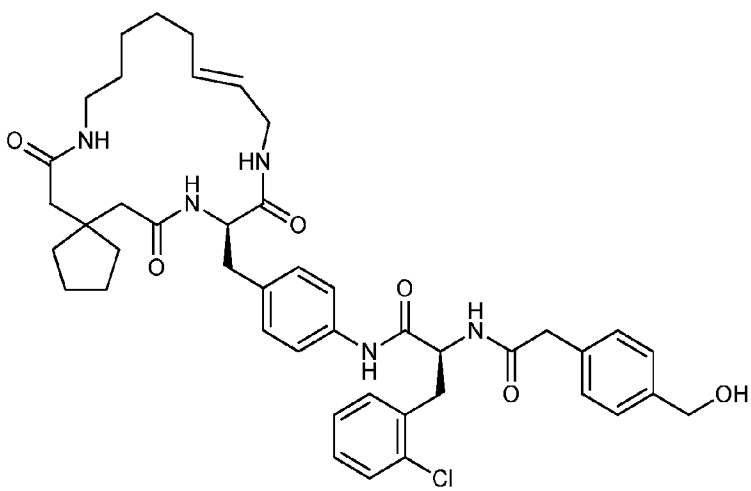 |
| 366 | 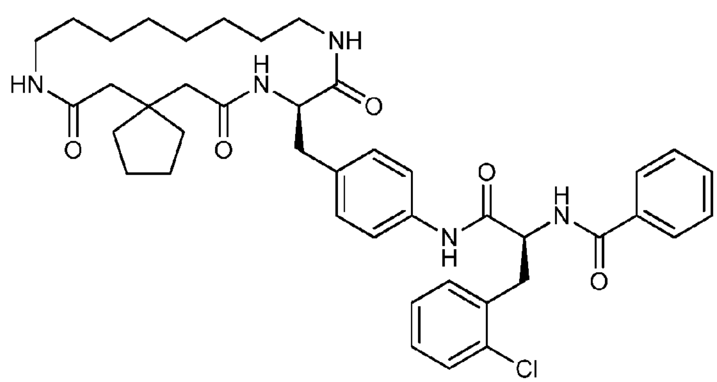 |

FIG. 12-118

| Compound No. | Structure |
|---|---|
| 367 | 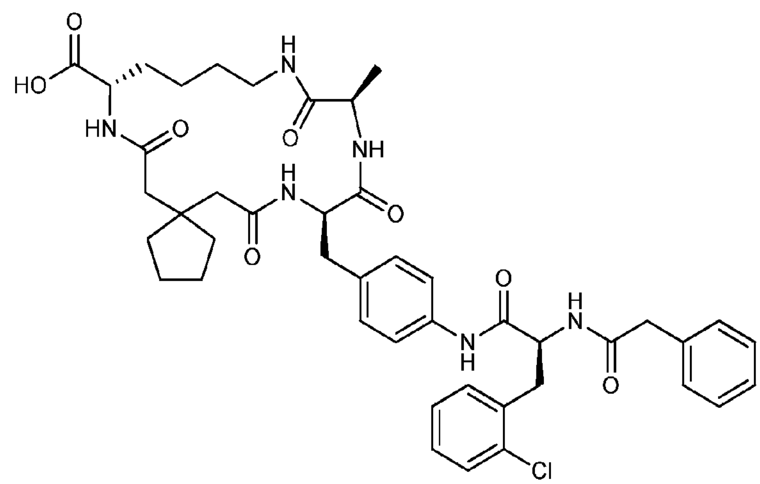 |
| 368 | 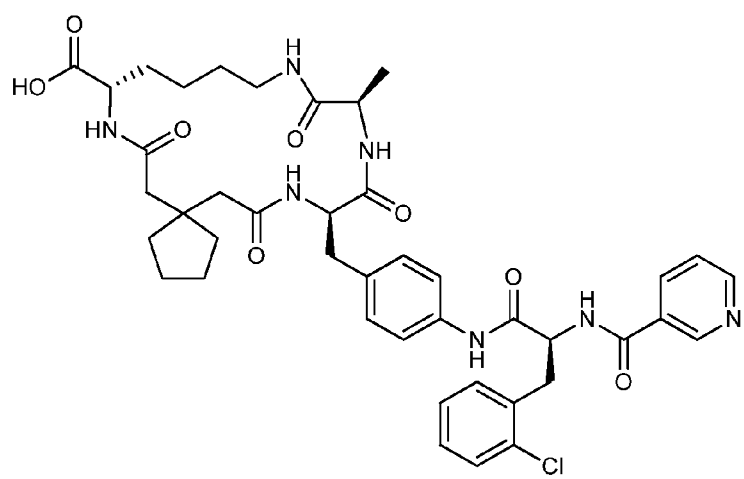 |

FIG. 12-119

| Compound No. | Structure |
|---|---|
| 369 | 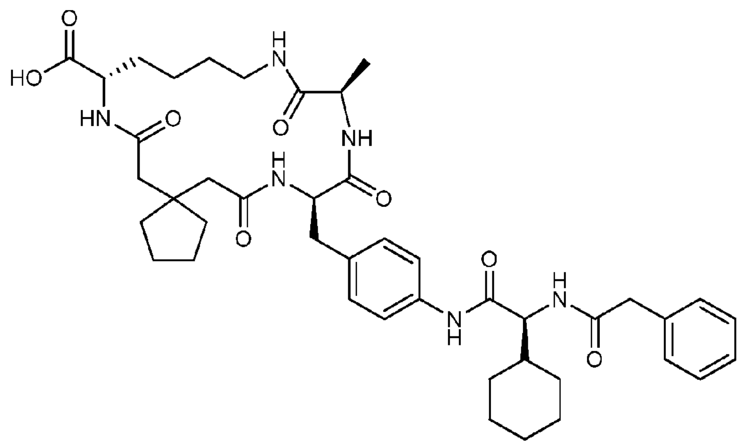 |
| 370 | 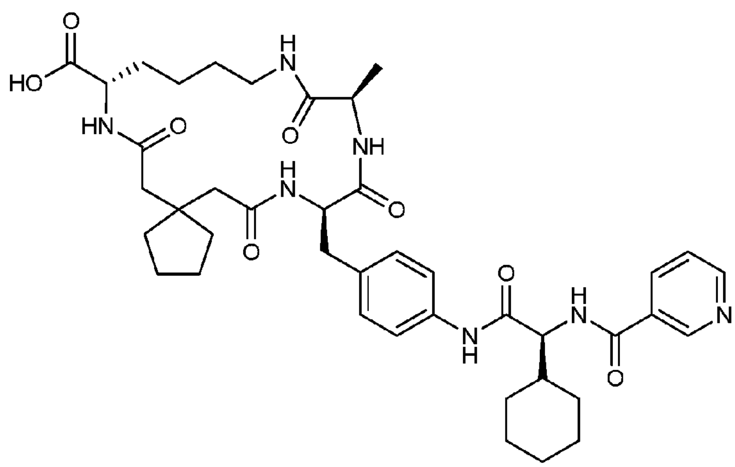 |

| Compound No. | Structure |
|---|---|
| 371 | 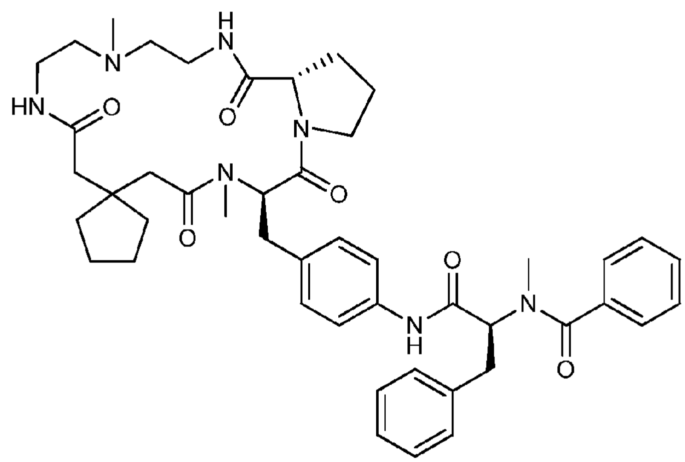 |
| 372 | 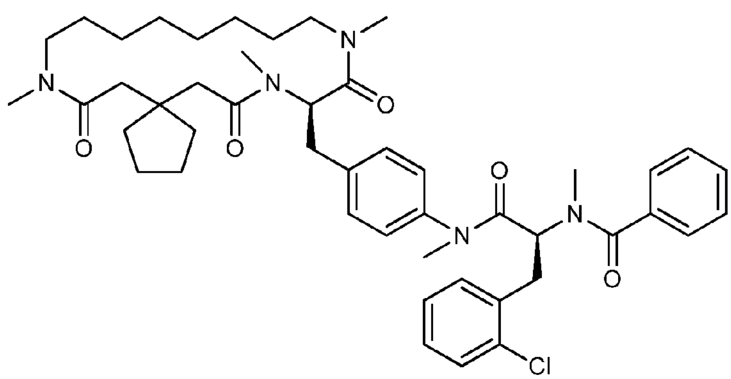 |

FIG. 12-121

| Compound No. | Structure |
|---|---|
| 373 | 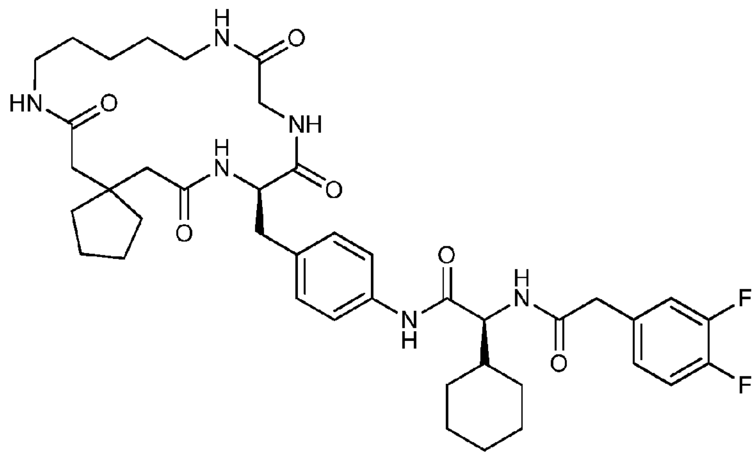 |
| 374 | 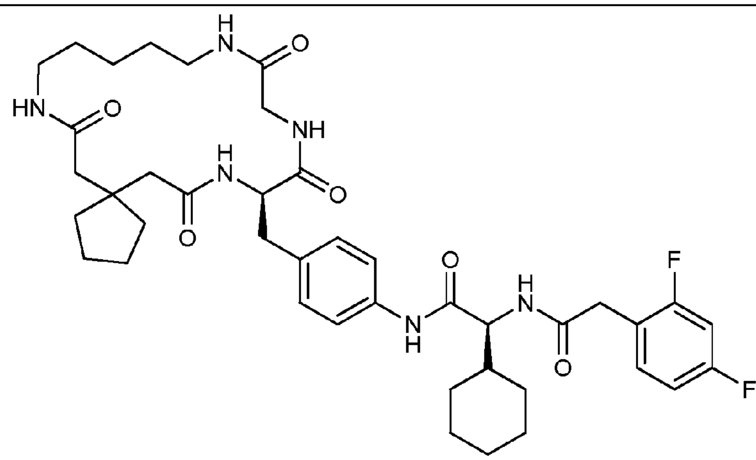 |

| Compound No. | Structure |
|---|---|
| 375 | 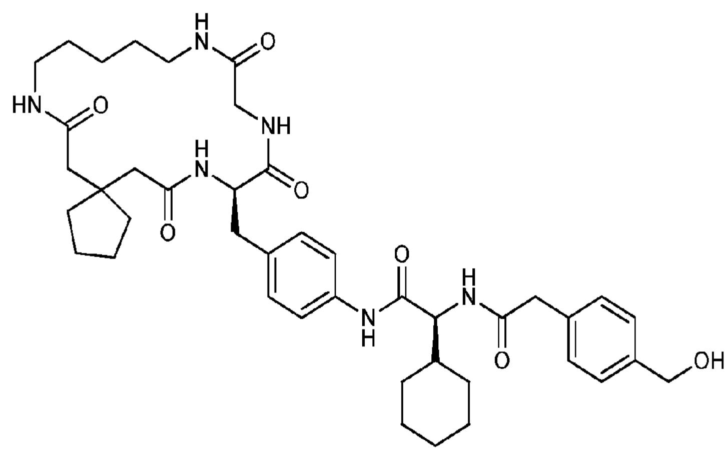 |
| 376 | 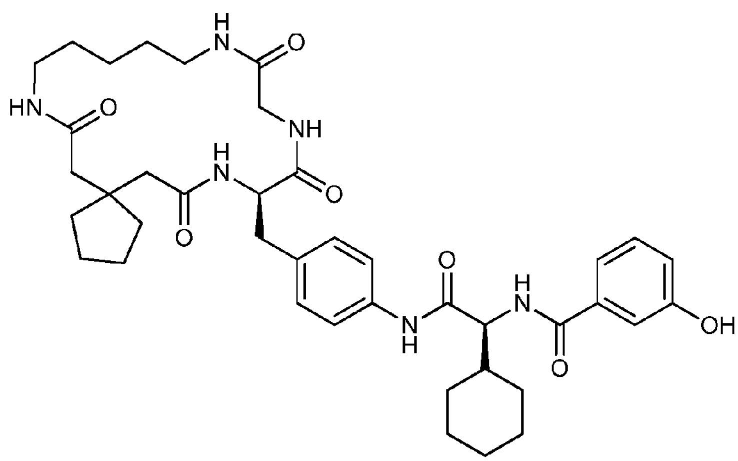 |

| Compound No. | Structure |
|---|---|
| 377 | 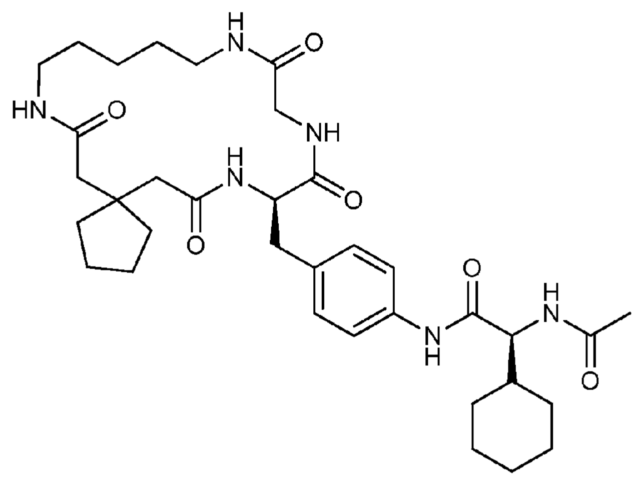 |
| 378 | 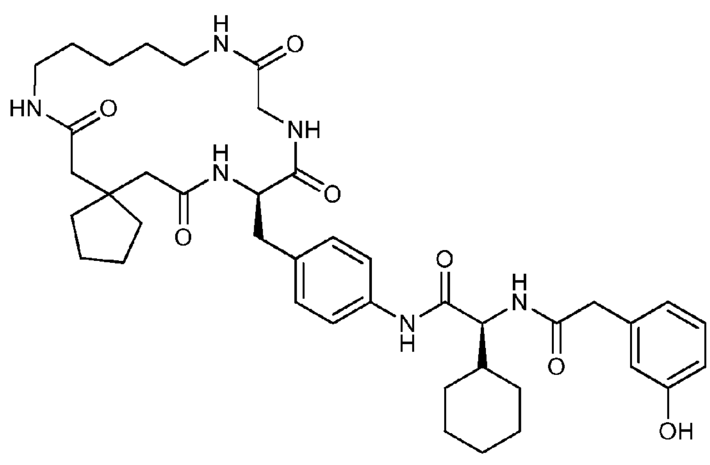 |

FIG. 12-124

| Compound No. | Structure |
|---|---|
| 379 | 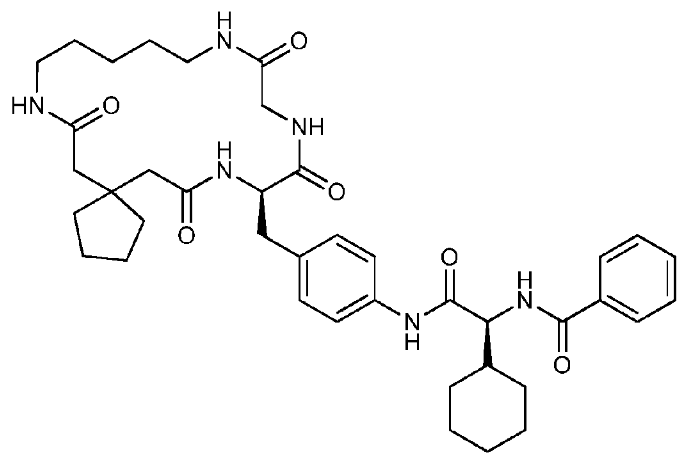 |
| 380 | 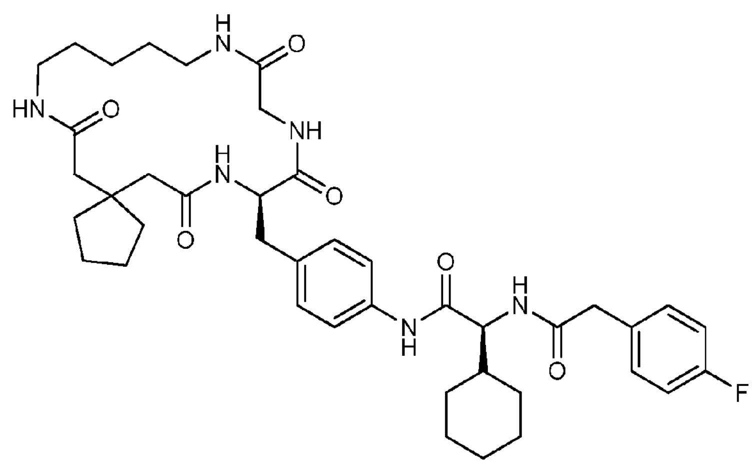 |

FIG. 12-125

| Compound No. | Structure |
|---|---|
| 381 | 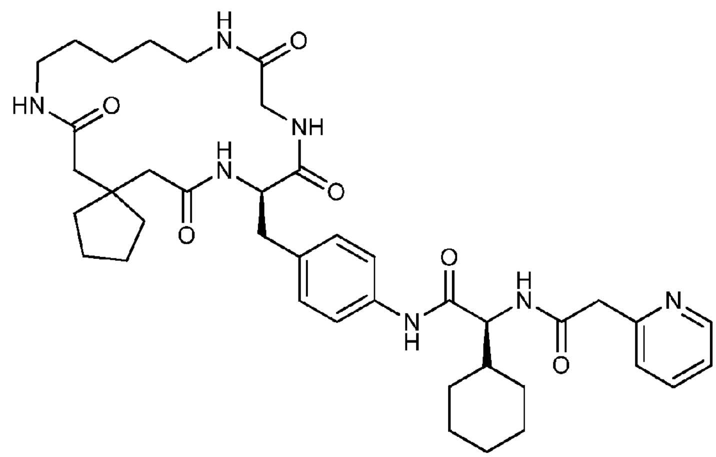 |
| 382 | 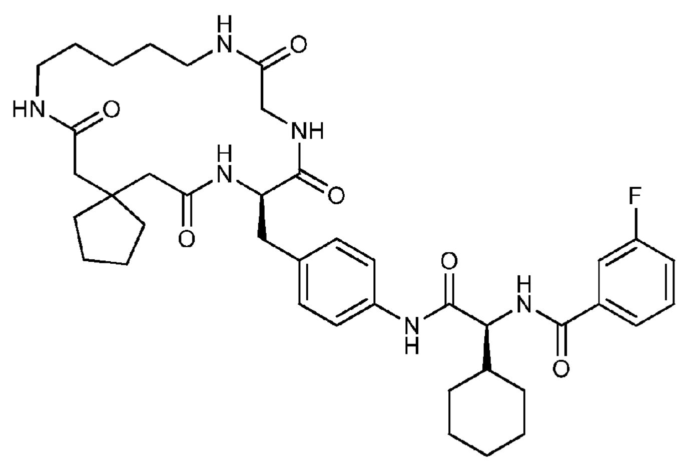 |

| Compound No. | Structure |
|---|---|
| 383 | 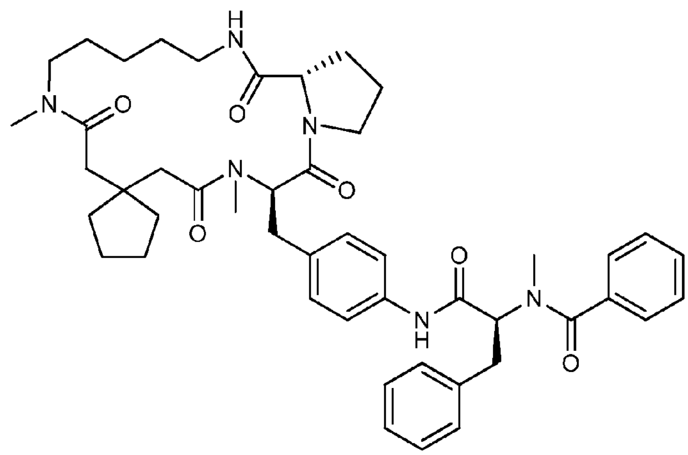 |
| 384 | 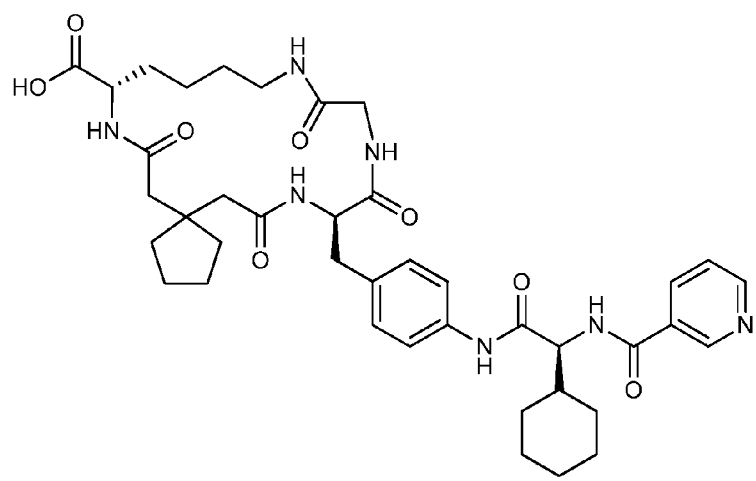 |

FIG. 12-127

| Compound No. | Structure |
|---|---|
| 385 | 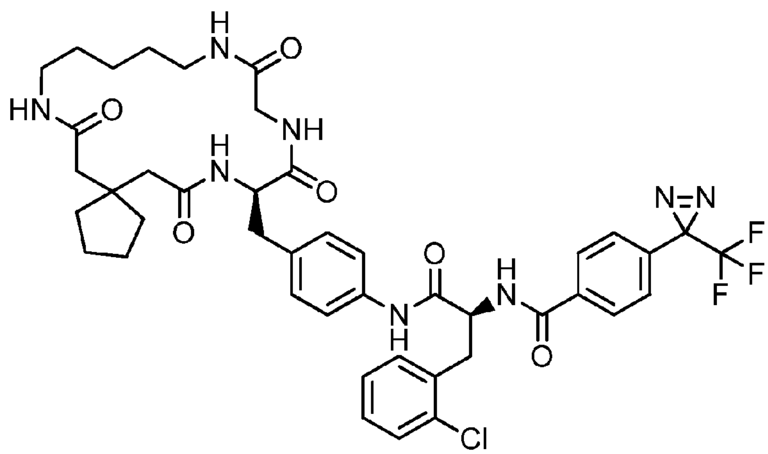 |
| 386 | 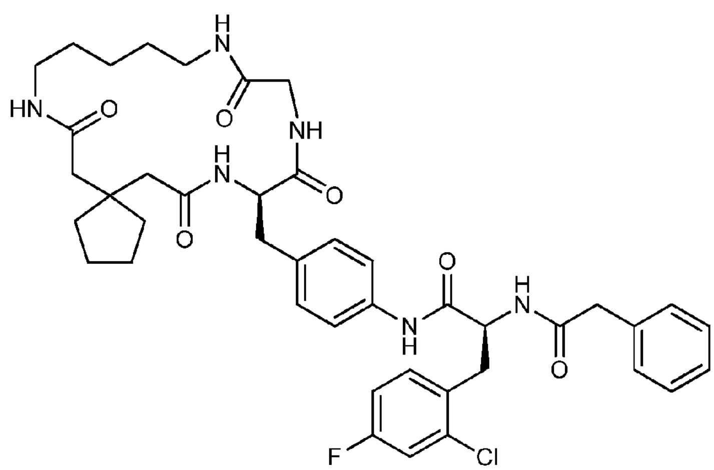 |

| Compound No. | Structure |
|---|---|
| 387 | 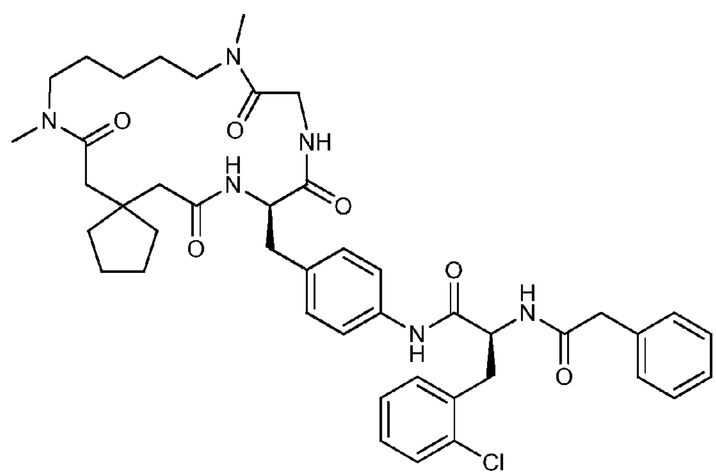 |
| 388 | 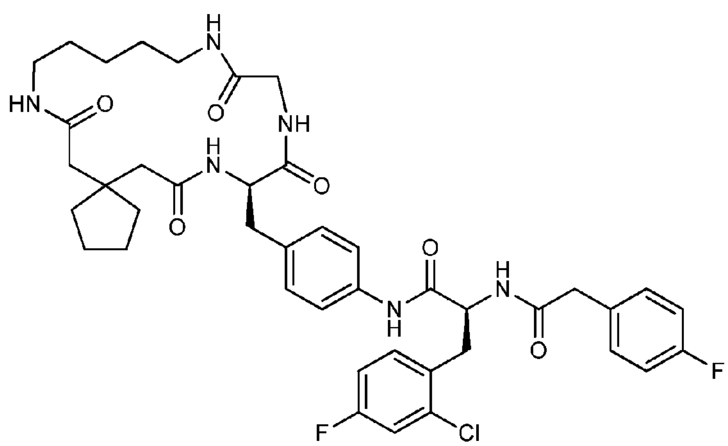 |

| Compound No. | Structure |
|---|---|
| 390 | 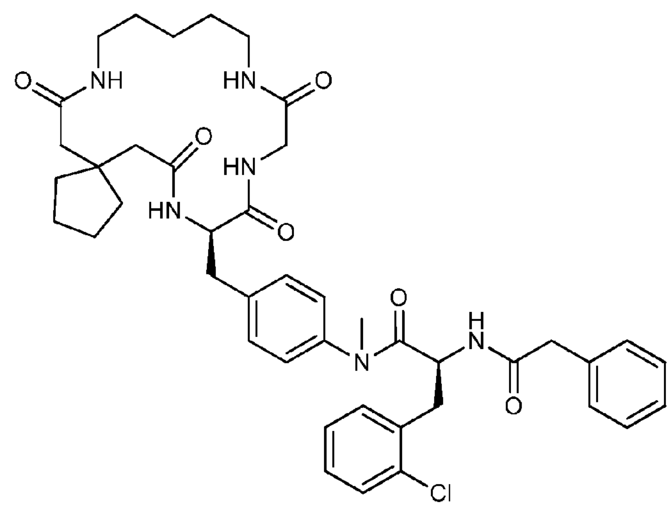 |
| 391 | 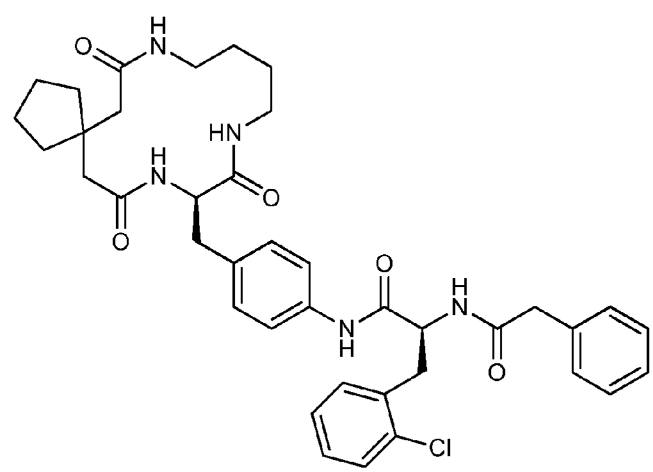 |

FIG. 12-130

| Compound No. | Structure |
|---|---|
| 392 | 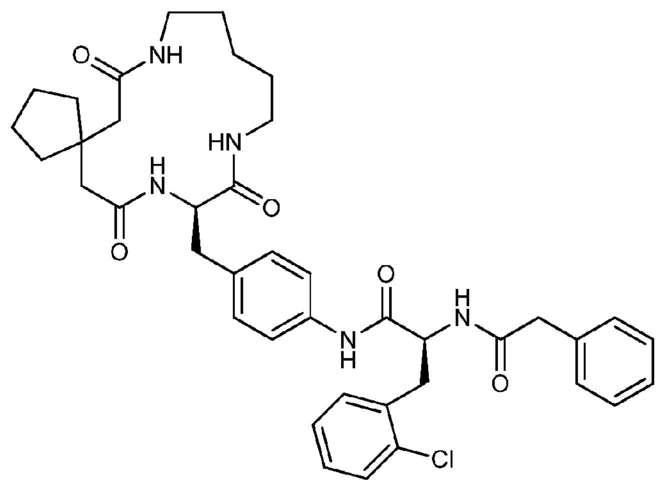 |
| 393 | 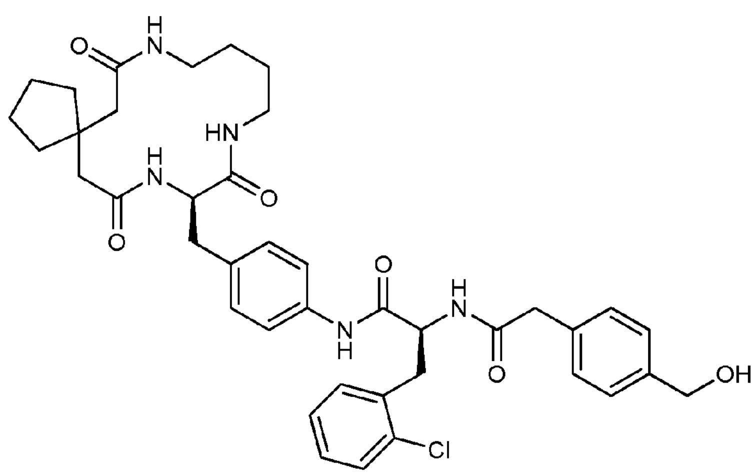 |

| Compound No. | Structure |
|---|---|
| 394 | 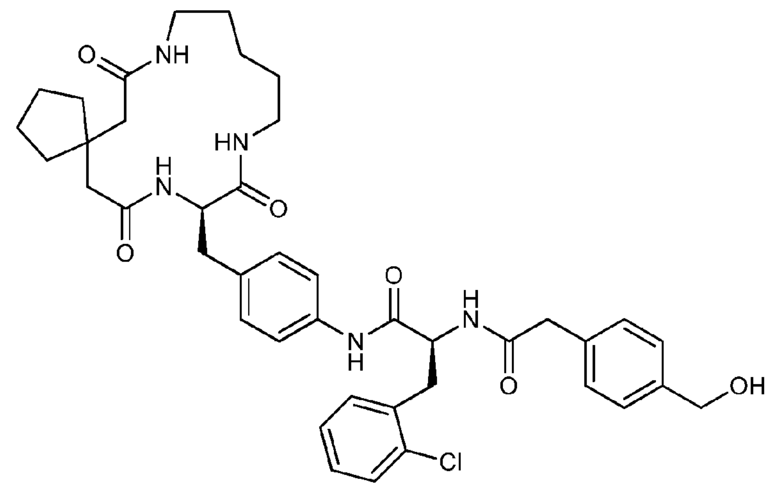 |
| 395 | 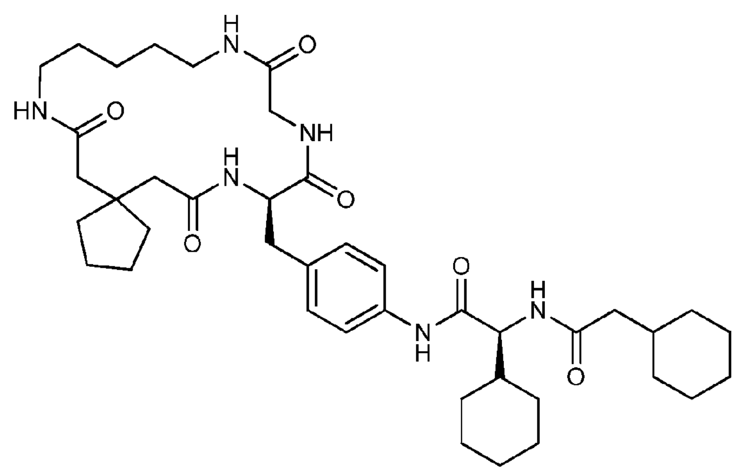 |

FIG. 12-132

| Compound No. | Structure |
|---|---|
| 396 | 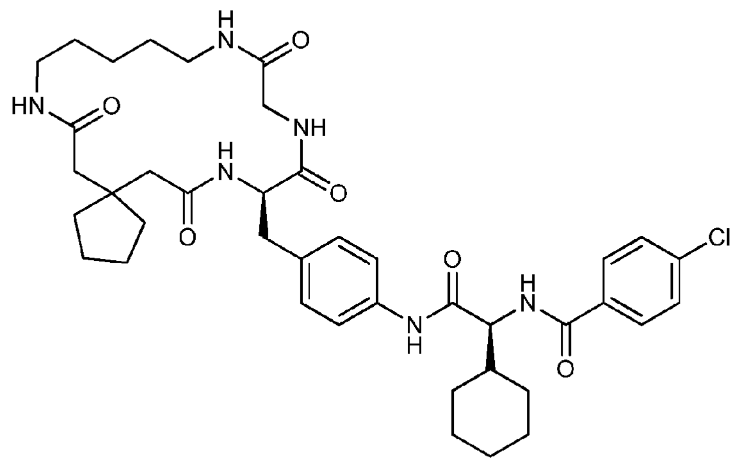 |
| 397 | 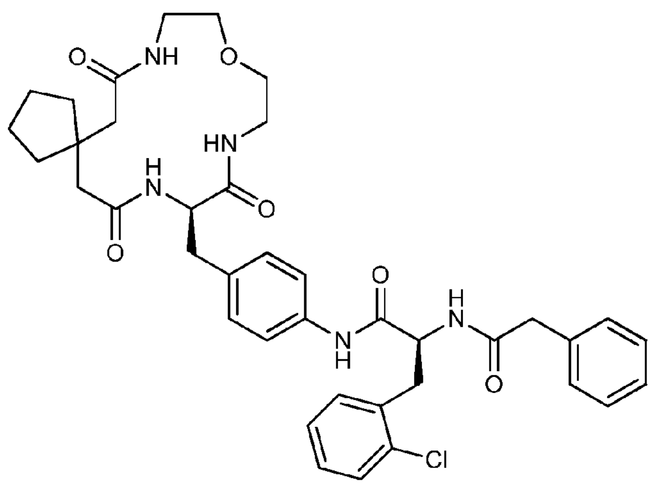 |

| Compound No. | Structure |
|---|---|
| 398 | 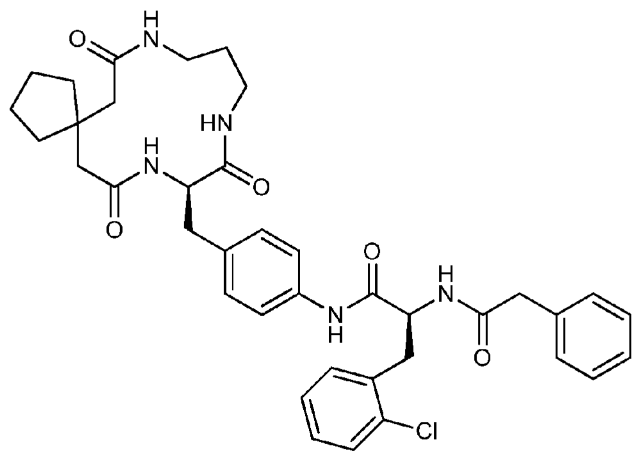 |
| 399 | 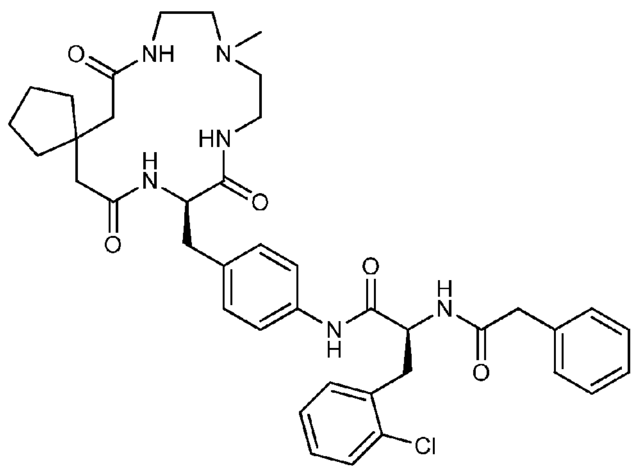 |

| Compound No. | Structure |
|---|---|
| 400 | 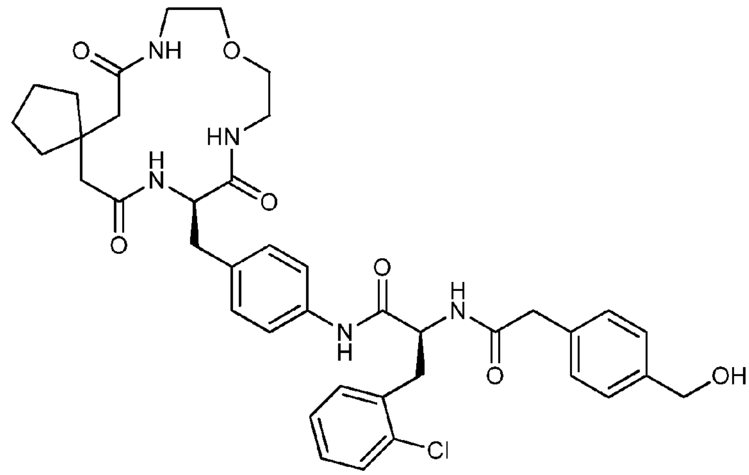 |
| 401 | 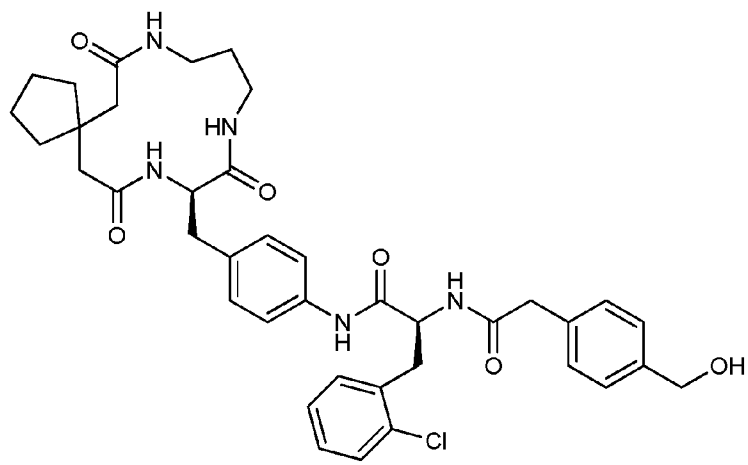 |

| Compound No. | Structure |
|---|---|
| 402 | 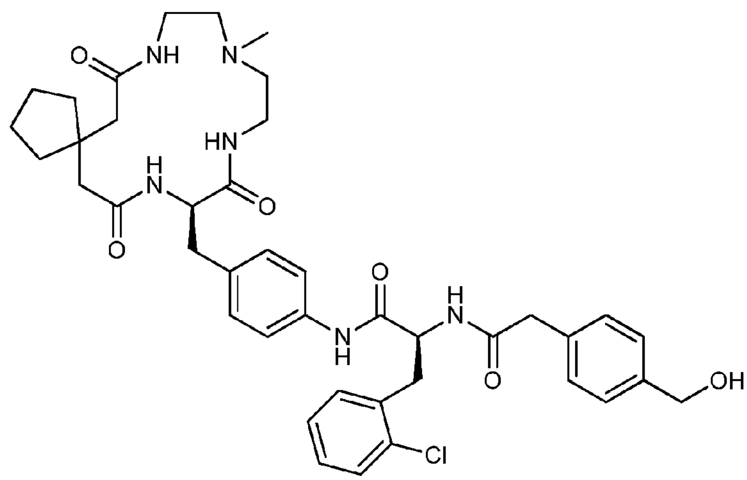 |
| 403 | 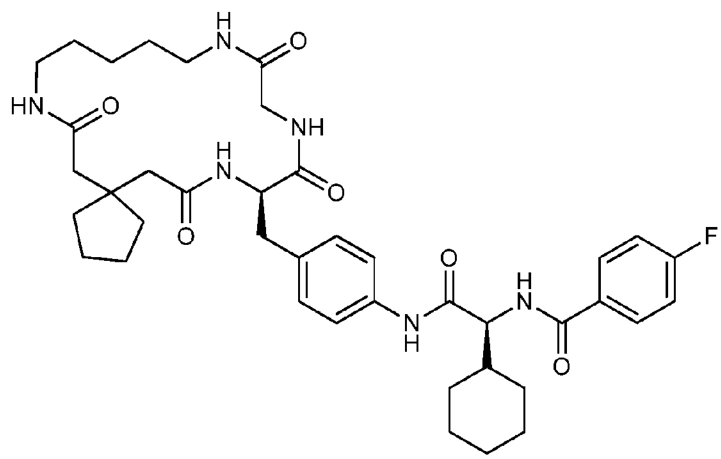 |

| Compound No. | Structure |
|---|---|
| 404 | 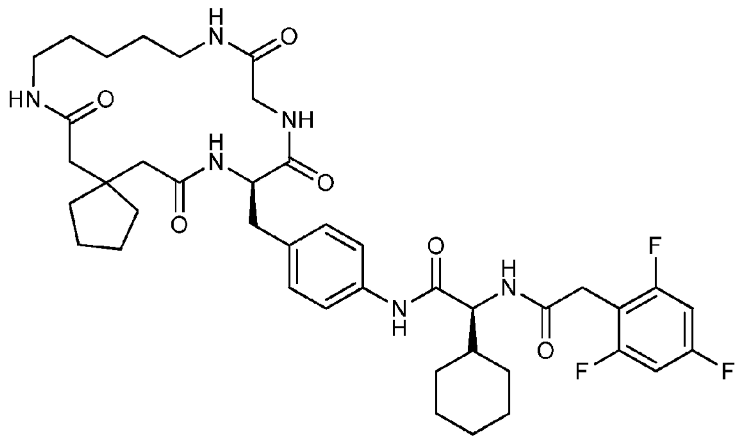 |
| 405 | 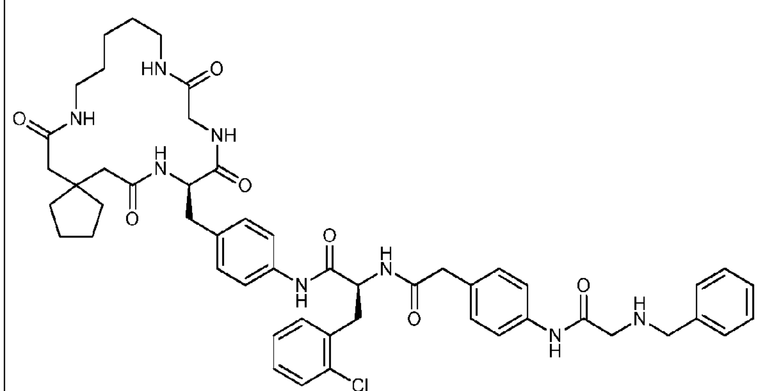 |

FIG. 12-137

| Compound No. | Structure |
|---|---|
| 406 | 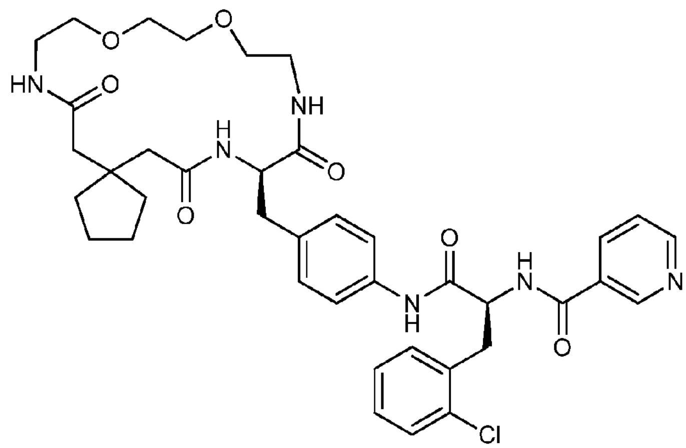 |
| 407 | 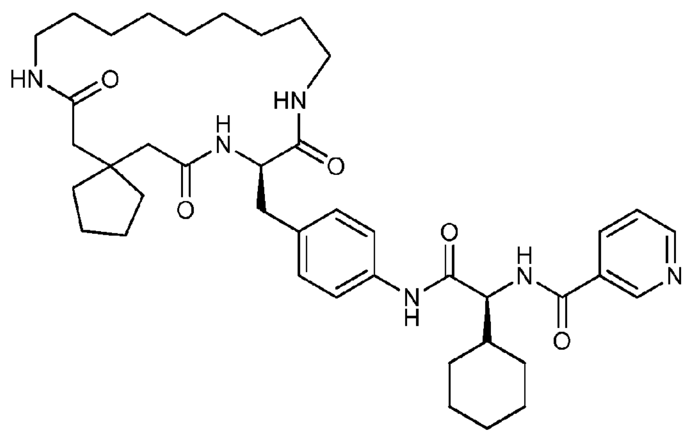 |

| Compound No. | Structure |
|---|---|
| 408 | 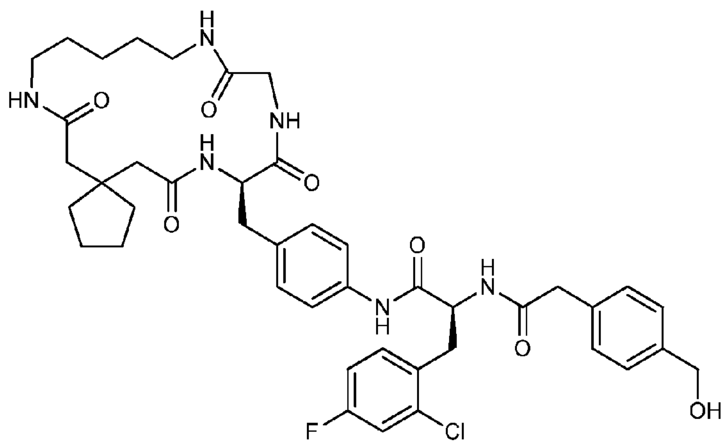 |
| 409 | 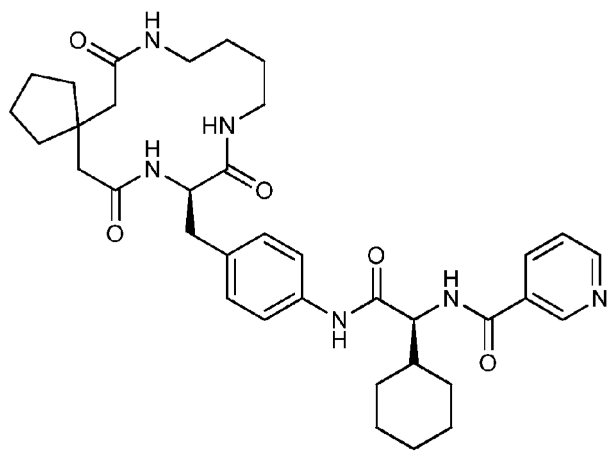 |

| Compound No. | Structure |
|---|---|
| 410 | 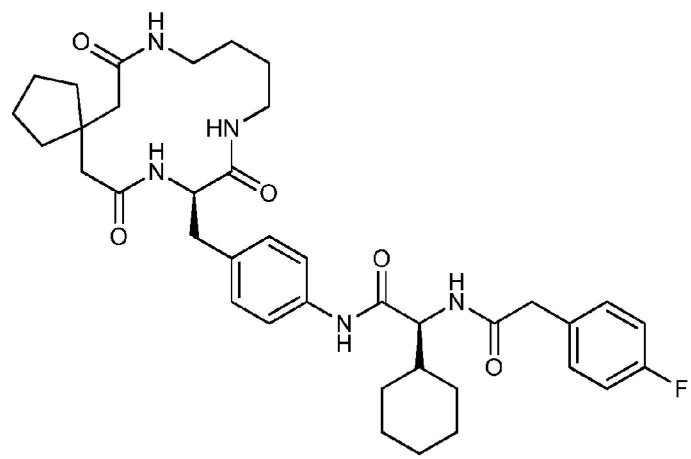 |
| 411 | 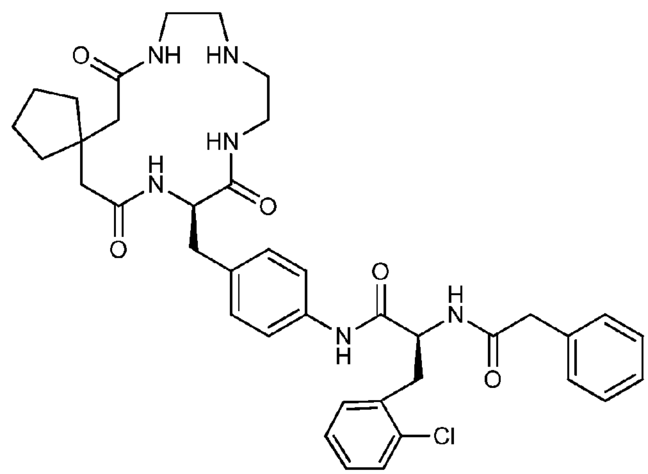 |

FIG. 12-140

| Compound No. | Structure |
|---|---|
| 412 | 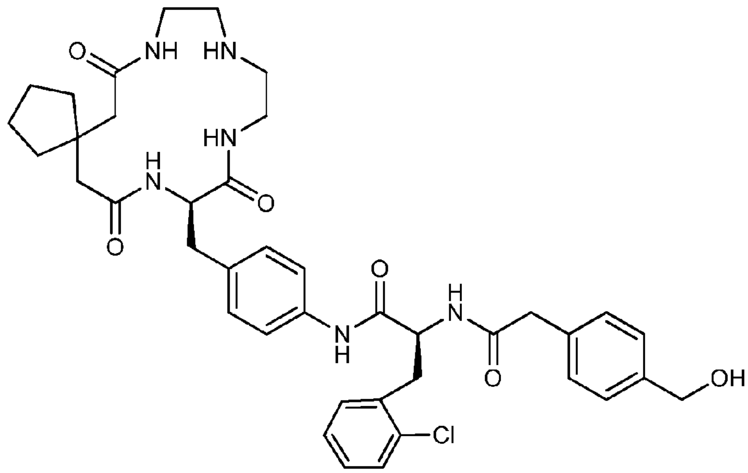 |
| 413 | 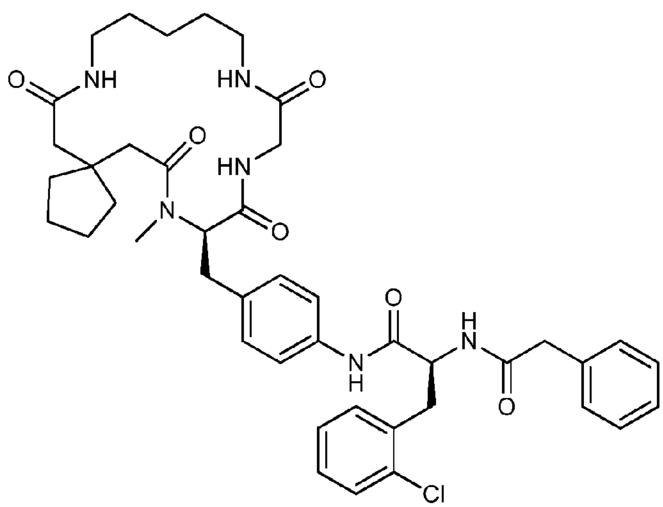 |

FIG. 12-141

| Compound No. | Structure |
|---|---|
| 414 | 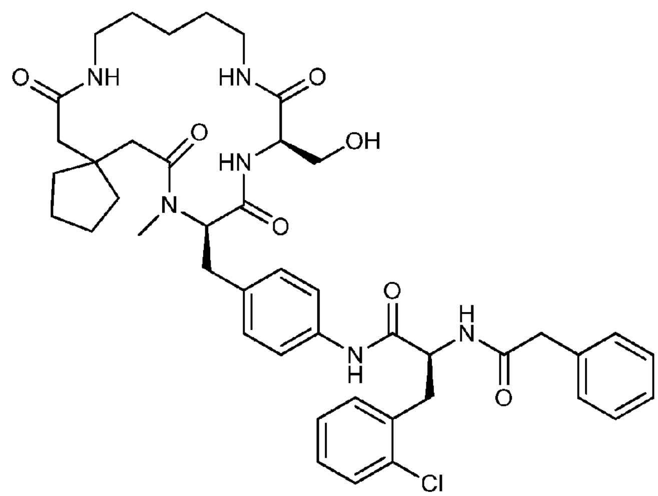 |
| 415 | 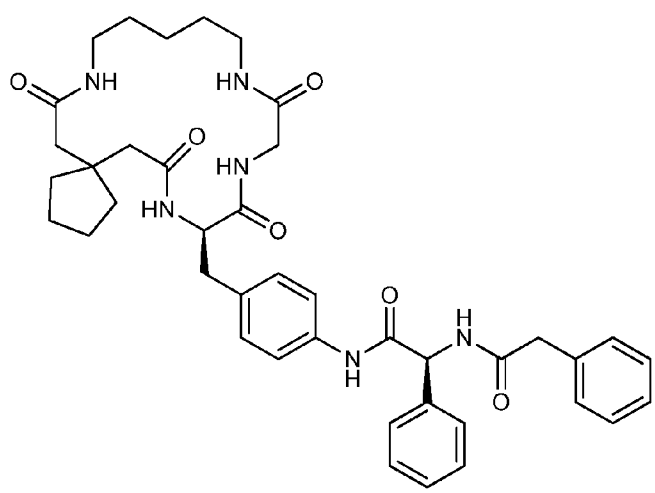 |

| Compound No. | Structure |
|---|---|
| 416 | 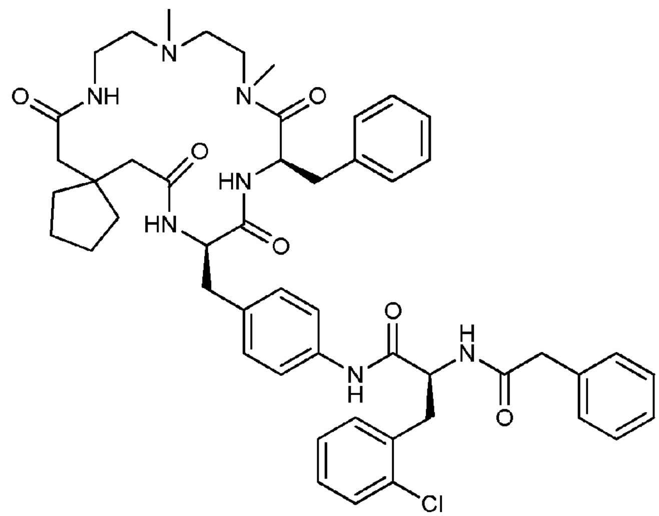 |
| 417 | 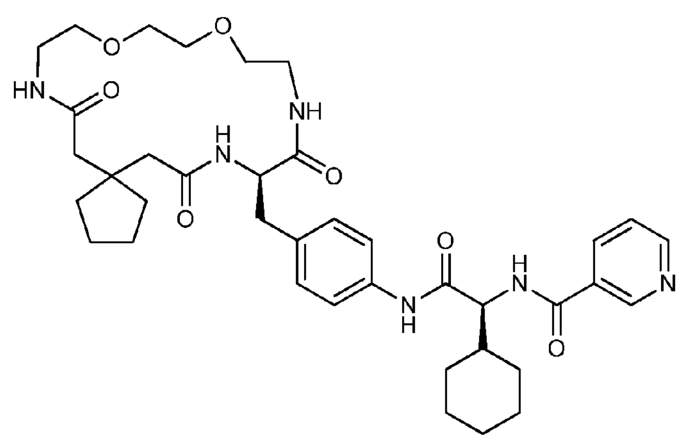 |

| Compound No. | Structure |
|---|---|
| 418 | 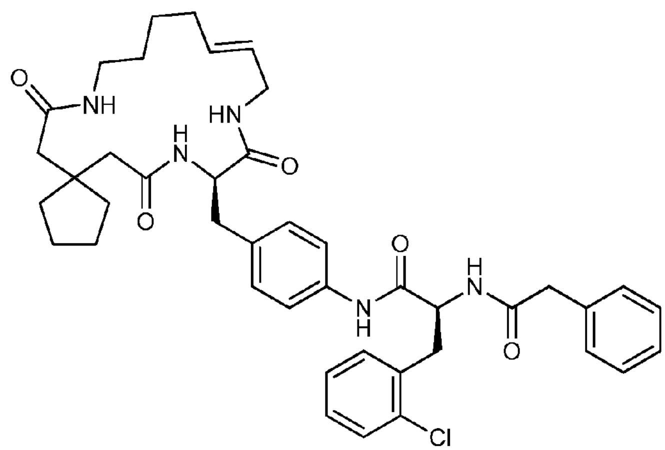 |
| 419 | 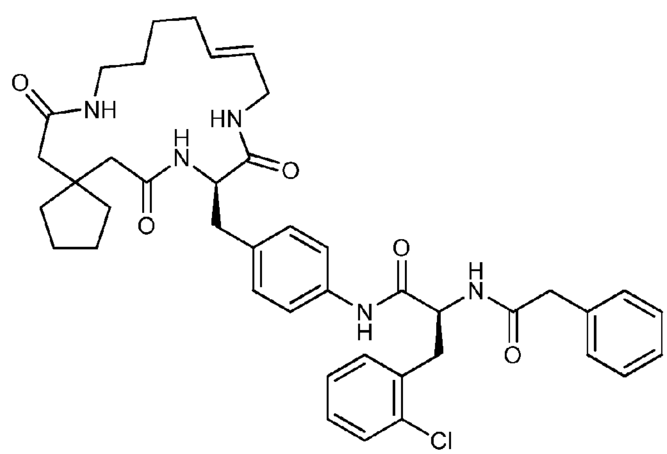 |

| Compound No. | Structure |
|---|---|
| 420 | 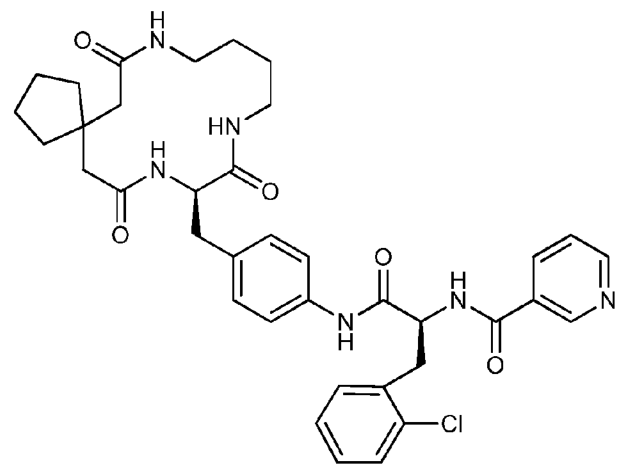 |
| 421 | 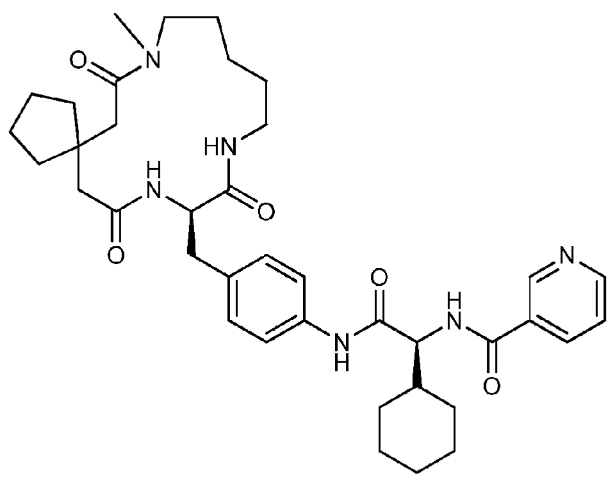 |

| Compound No. | Structure |
|---|---|
| 422 | 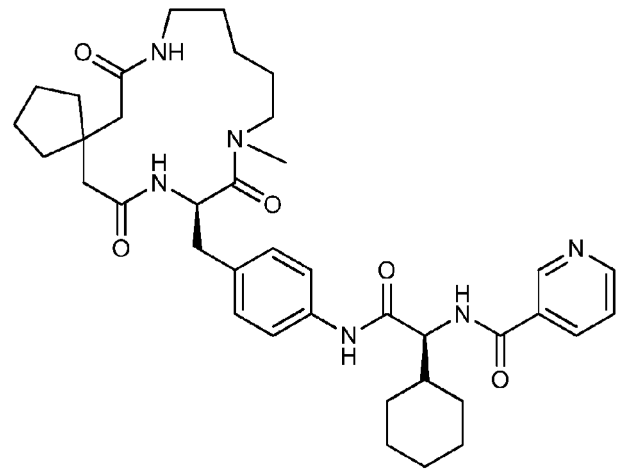 |
| 423 | 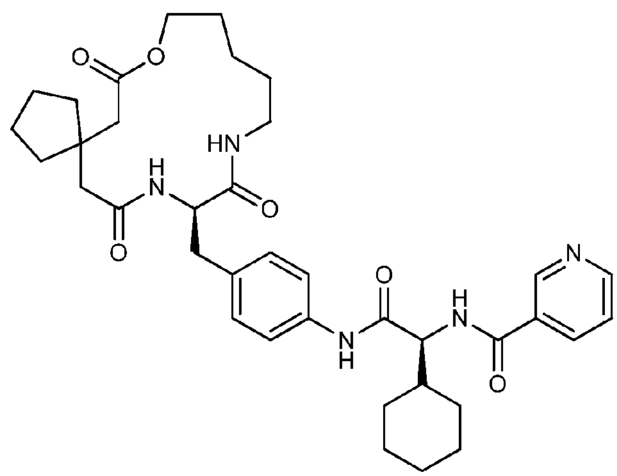 |

| Compound No. | Structure |
|---|---|
| 424 | 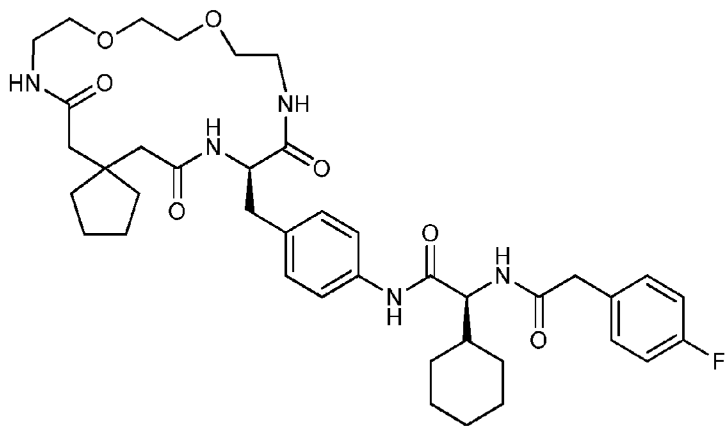 |
| 425 | 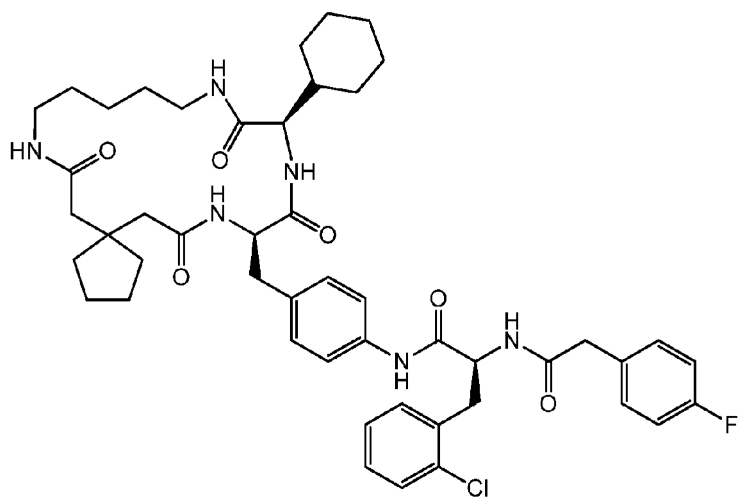 |

| Compound No. | Structure |
|---|---|
| 426 | 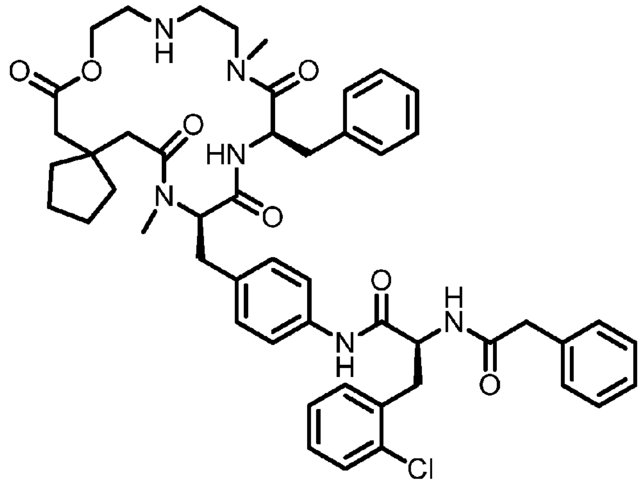 |
| 427 | 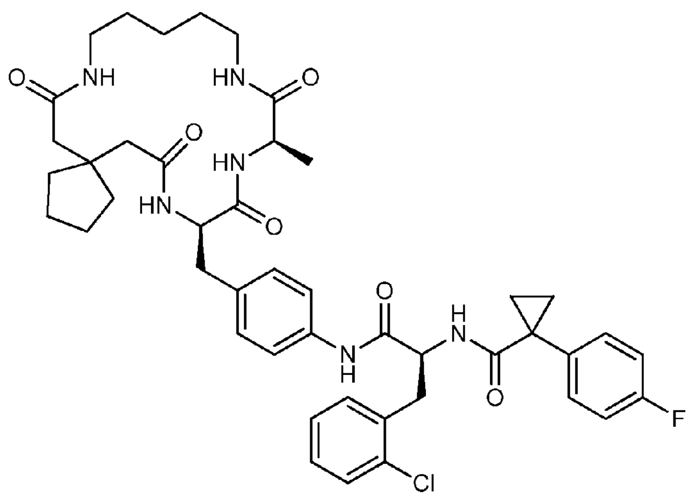 |

| Compound No. | Structure |
|---|---|
| 428 | 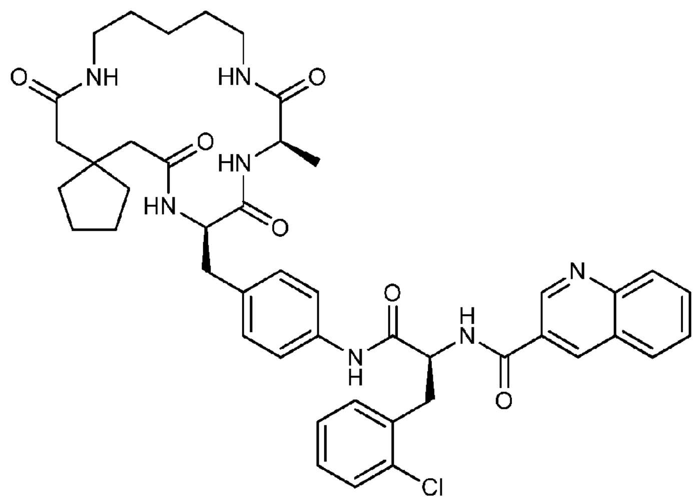 |
| 429 | 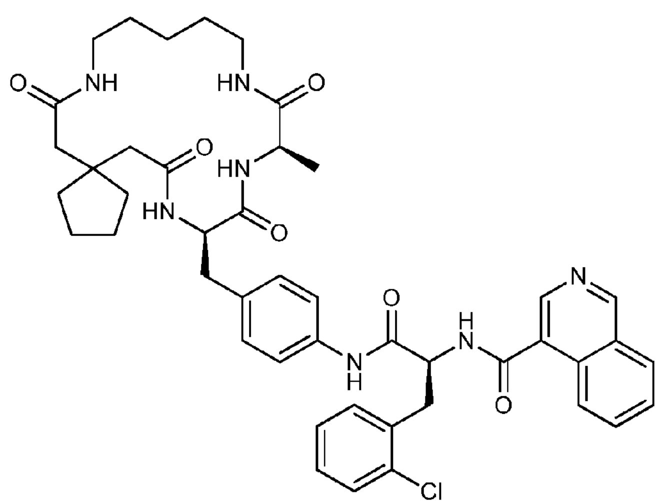 |

| Compound No. | Structure |
|---|---|
| 430 | 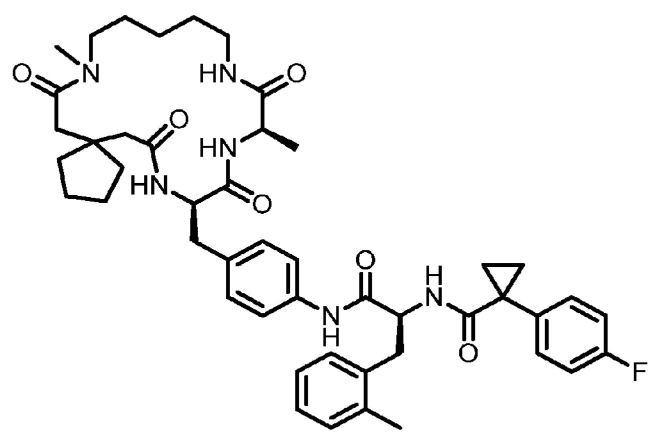 |
| 431 | 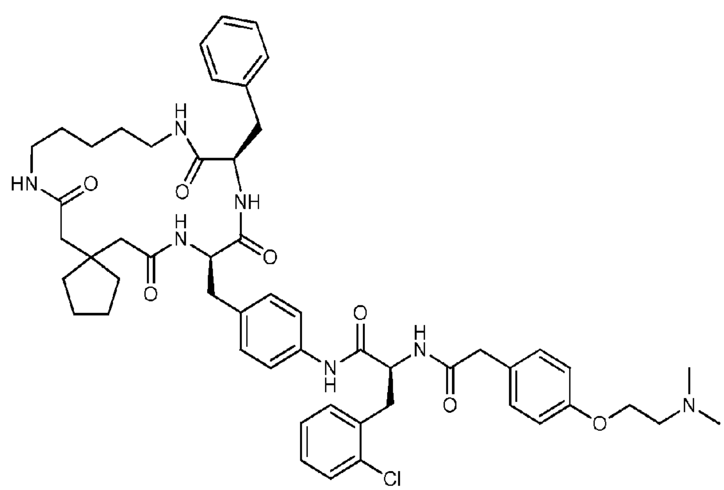 |

| Compound No. | Structure |
|---|---|
| 432 | 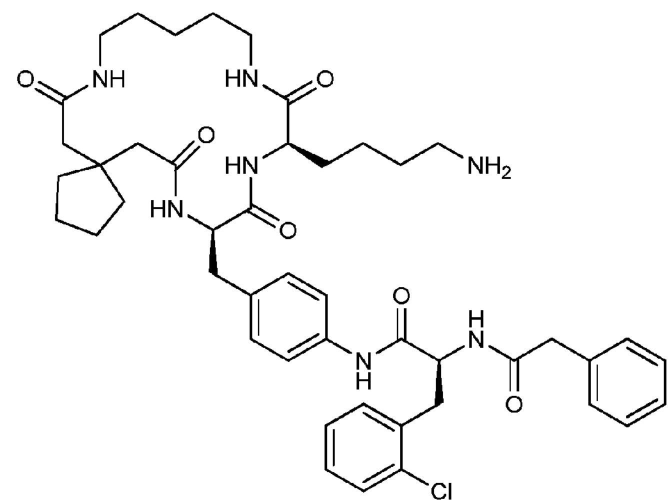 |
| 433 | 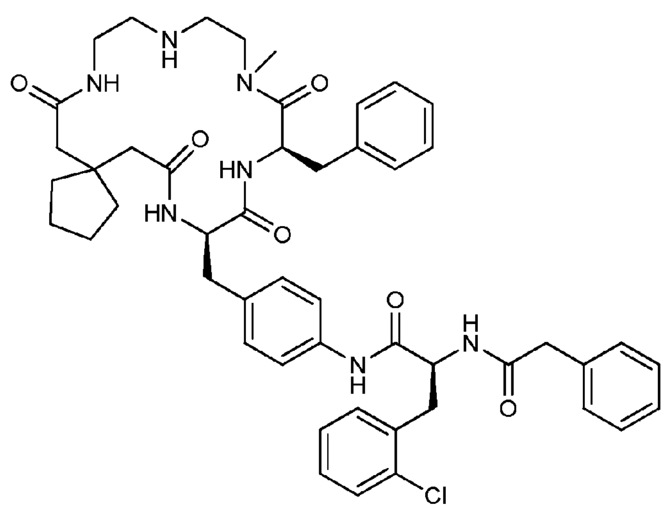 |

| Compound No. | Structure |
|---|---|
| 434 | 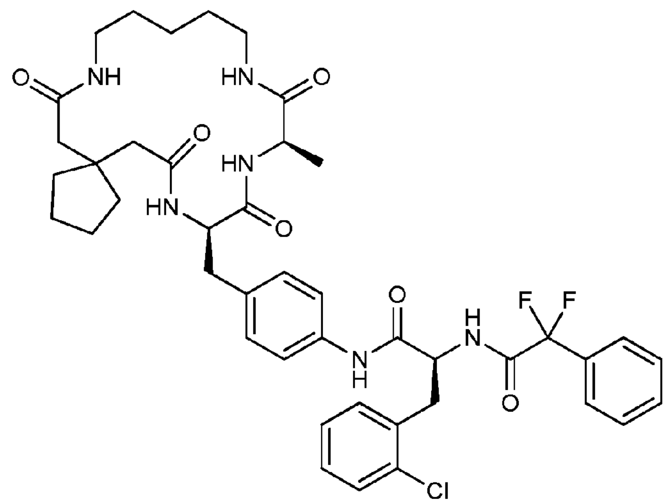 |
| 435 | 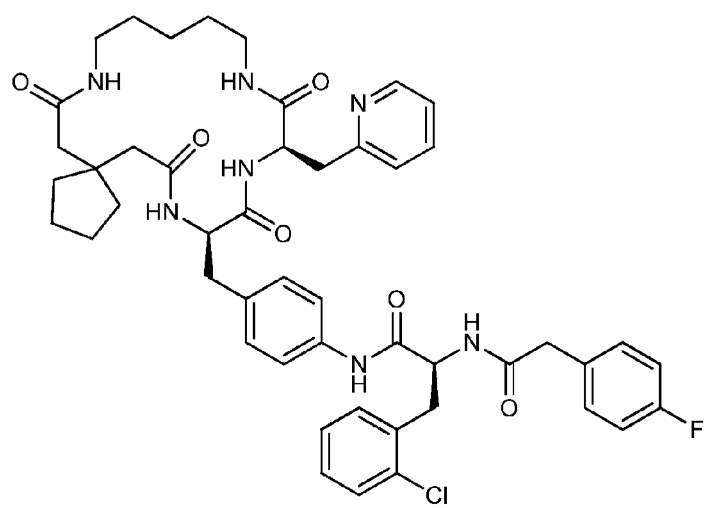 |

| Compound No. | Structure |
|---|---|
| 436 | 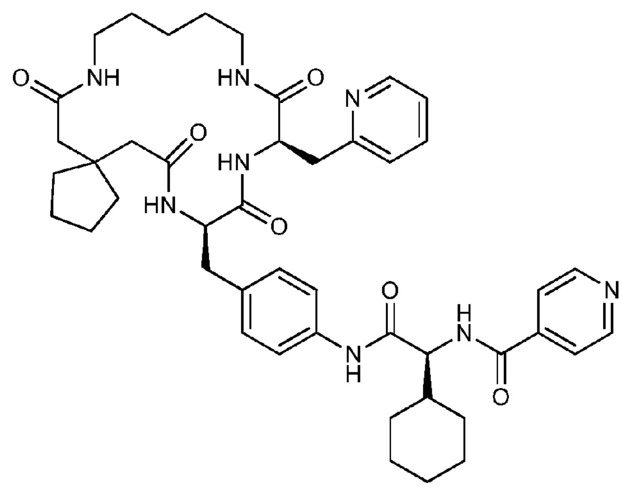 |
| 437 | 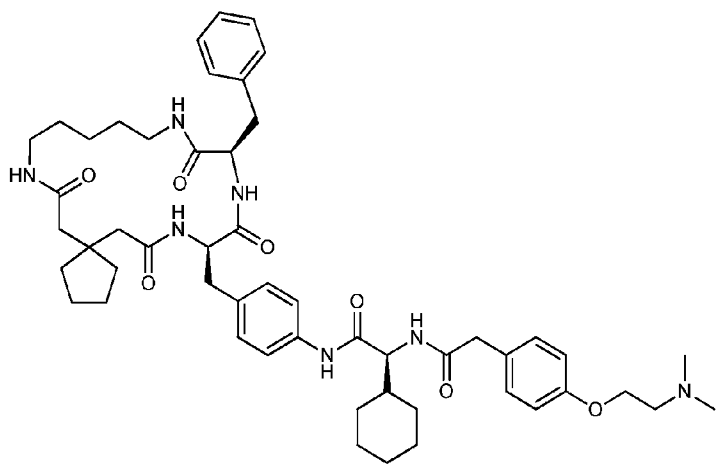 |

FIG. 12-153

| Compound No. | Structure |
|---|---|
| 438 | 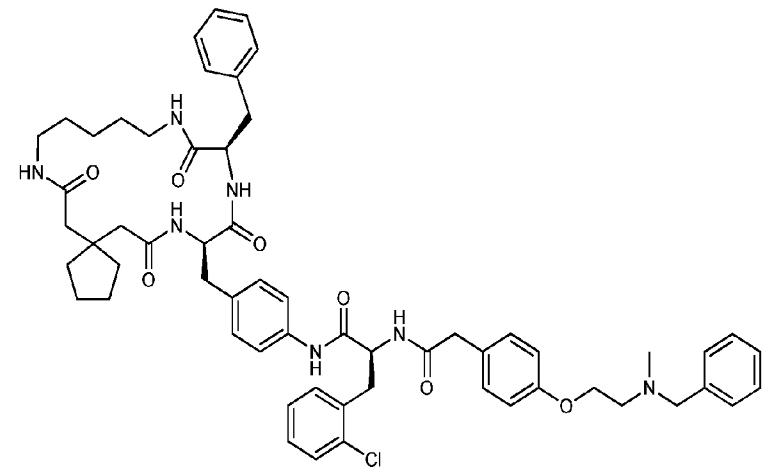 |
| 439 | 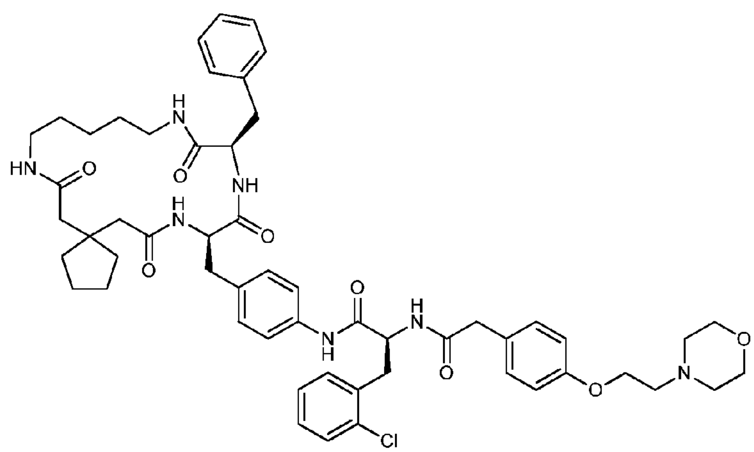 |
| 440 | 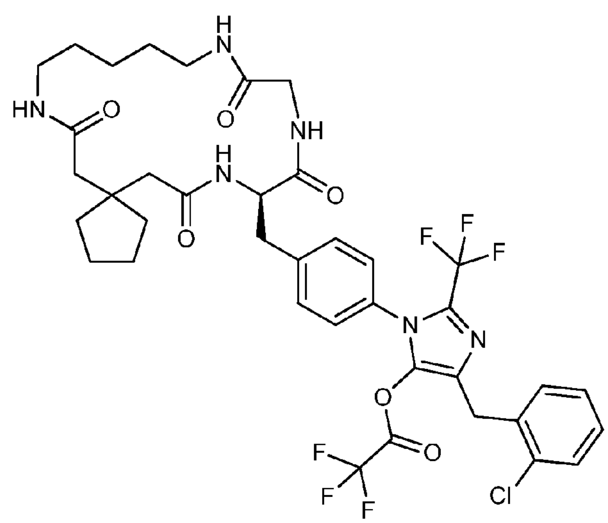 |

| Compound No. | Structure |
|---|---|
| 441 | 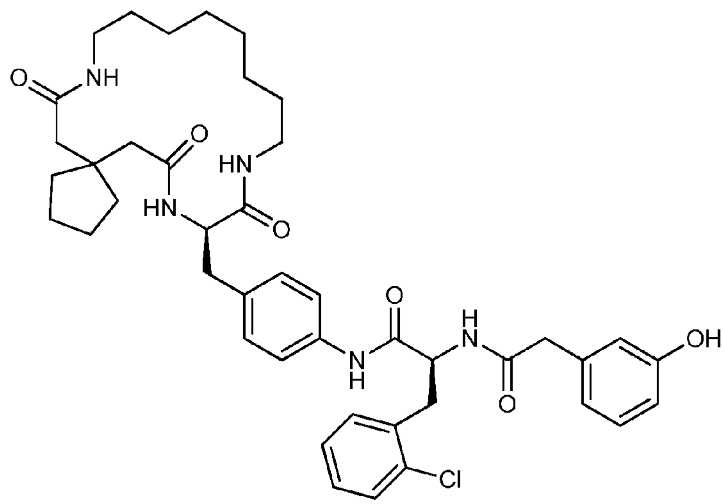 |
| 442 | 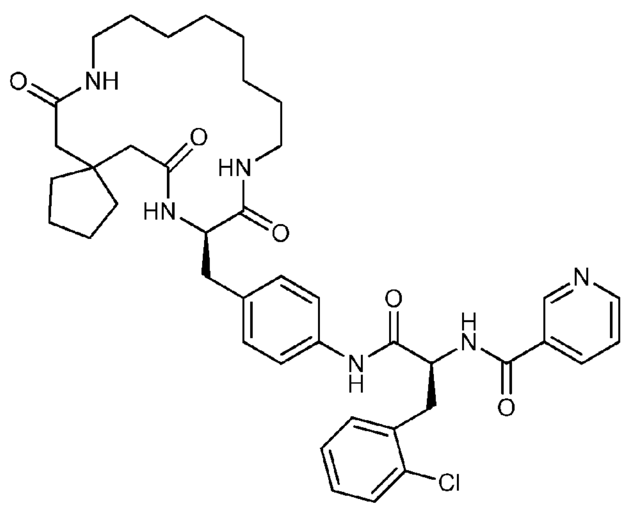 |

| Compound No. | Structure |
|---|---|
| 443 | 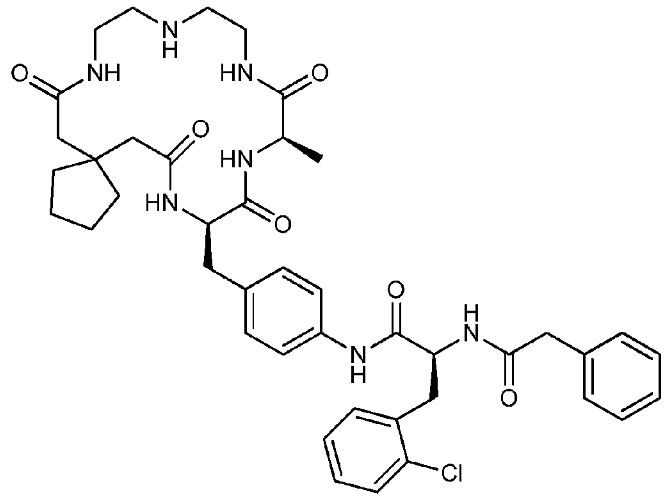 |
| 444 | 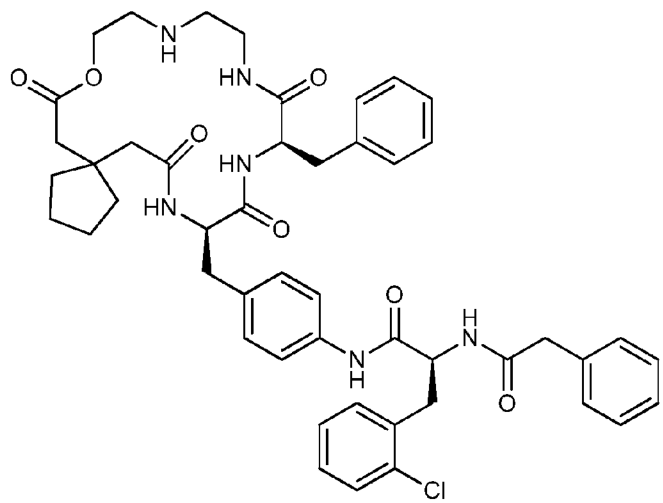 |

| Compound No. | Structure |
|---|---|
| 445 | 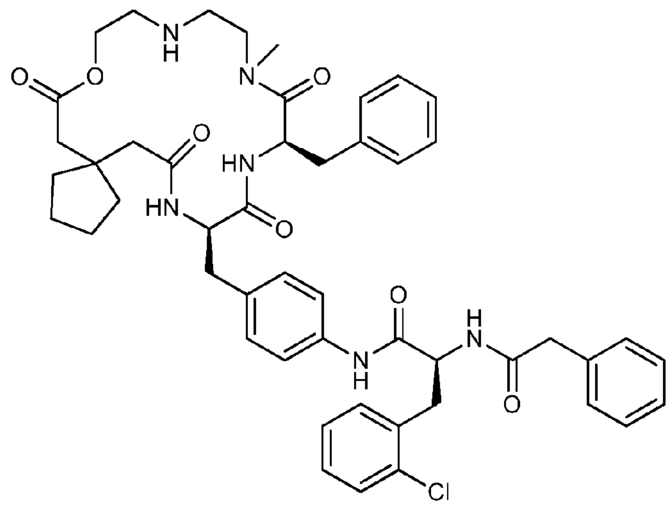 |
| 446 | 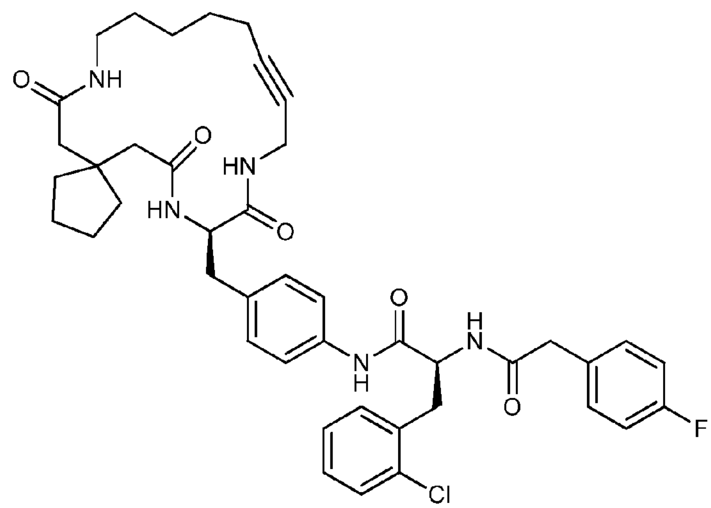 |

| Compound No. | Structure |
|---|---|
| 447 | 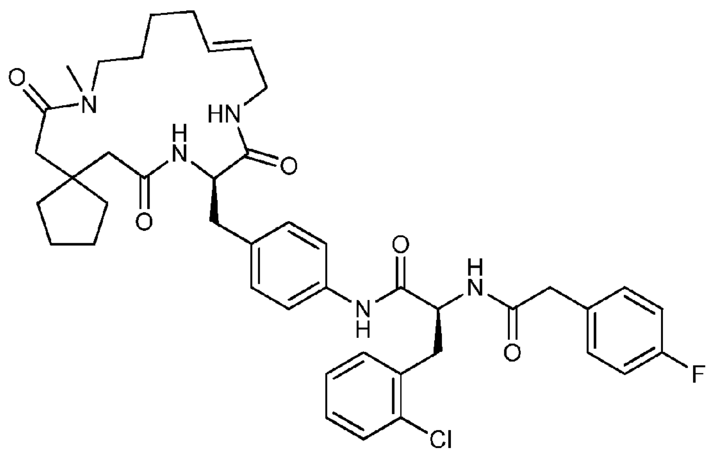 |
| 448 | 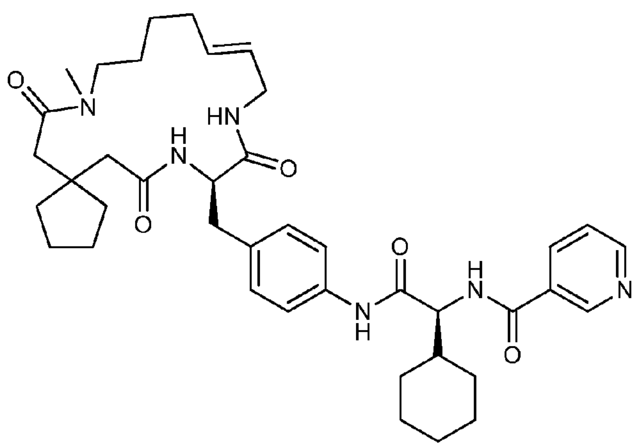 |

| Compound No. | Structure |
|---|---|
| 449 | 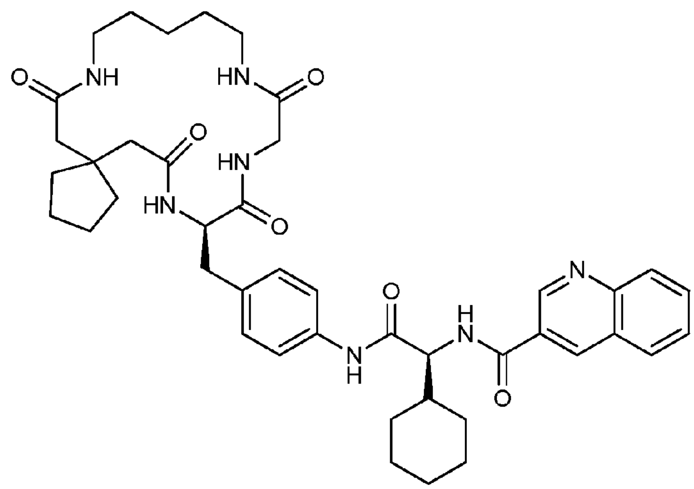 |
| 450 | 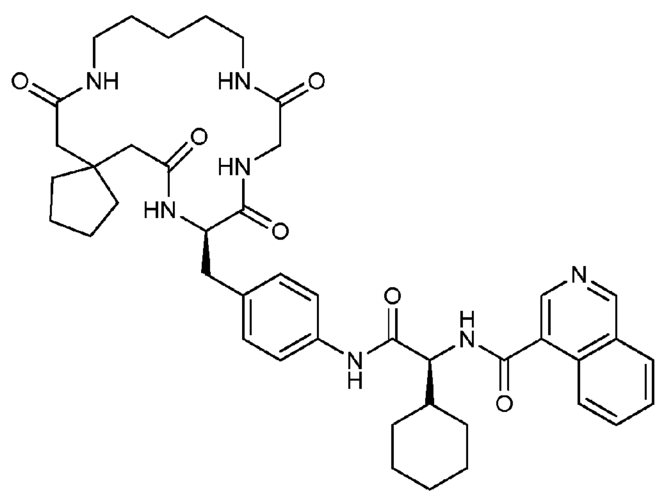 |

| Compound No. | Structure |
|---|---|
| 451 | 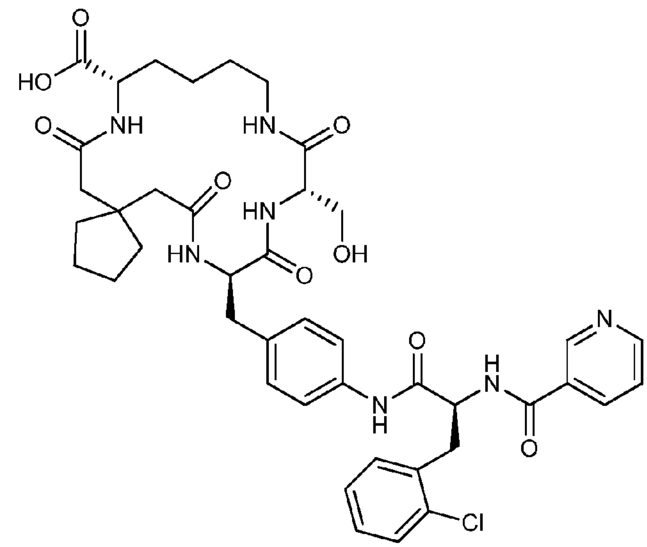 |
| 452 | 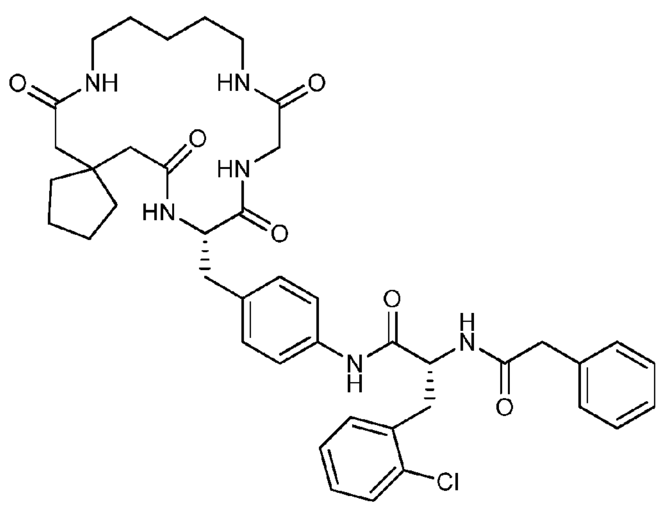 |

FIG. 12-160

| Compound No. | Structure |
|---|---|
| 453 | 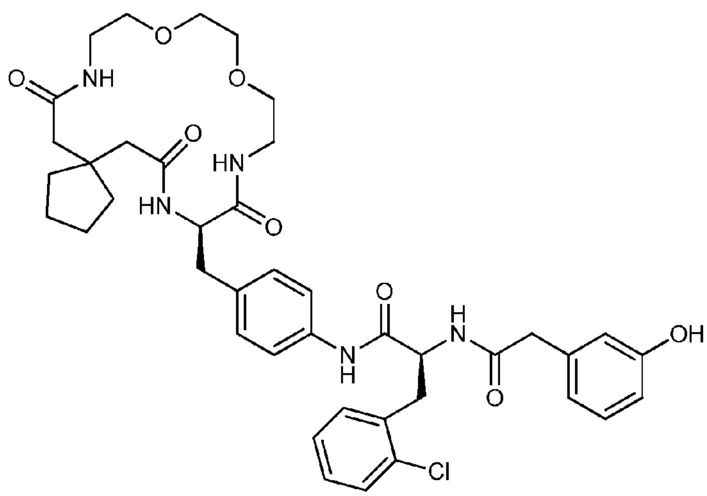 |
| 454 | 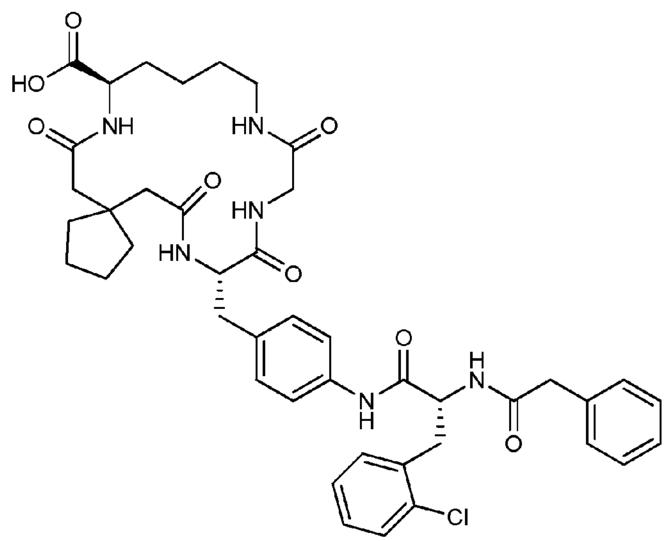 |

| Compound No. | Structure |
|---|---|
| 455 | 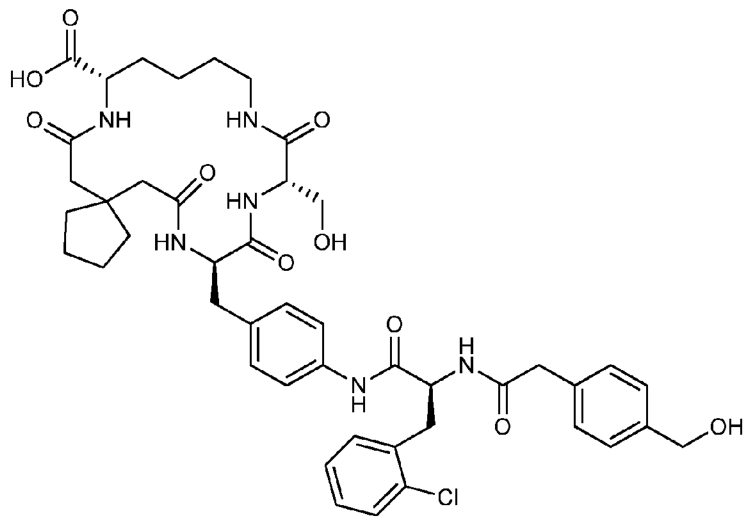 |
| 456 | 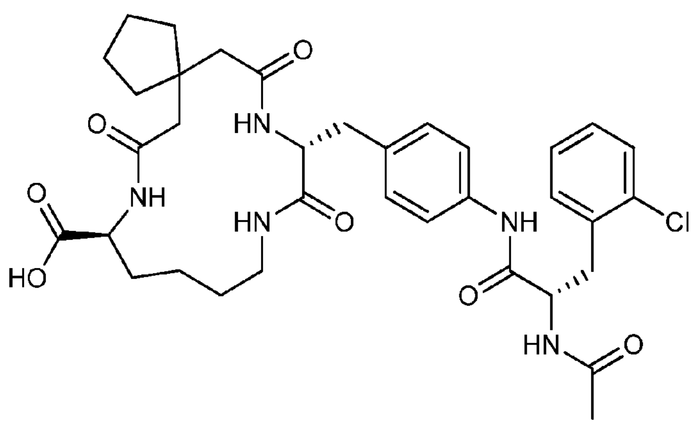 |

FIG. 12-162

| Compound No. | Structure |
|---|---|
| 457 | 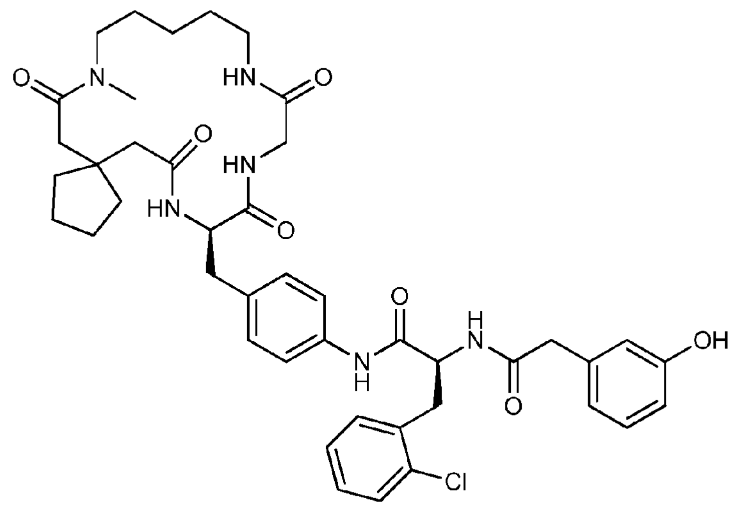 |
| 458 | 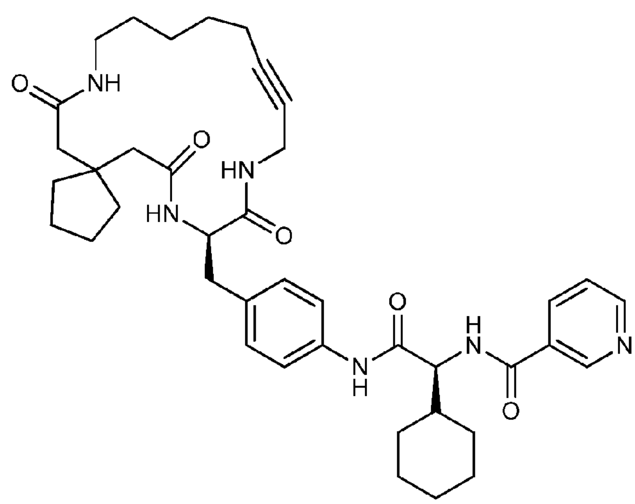 |

| Compound No. | Structure |
|---|---|
| 459 | 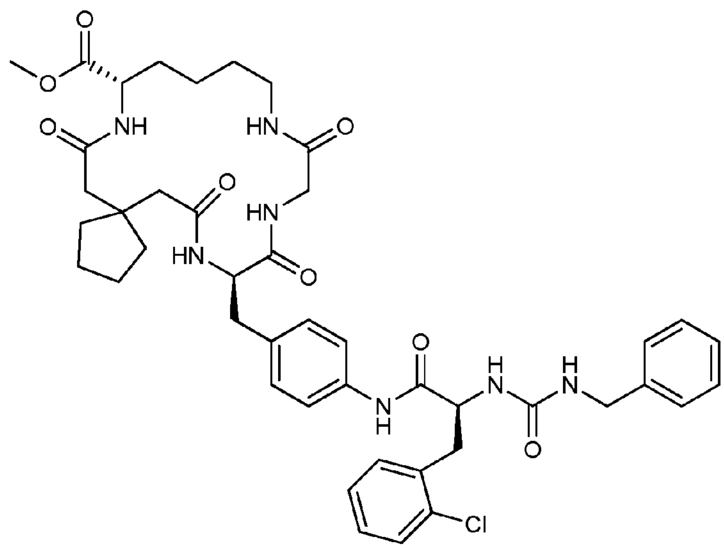 |
| 460 | 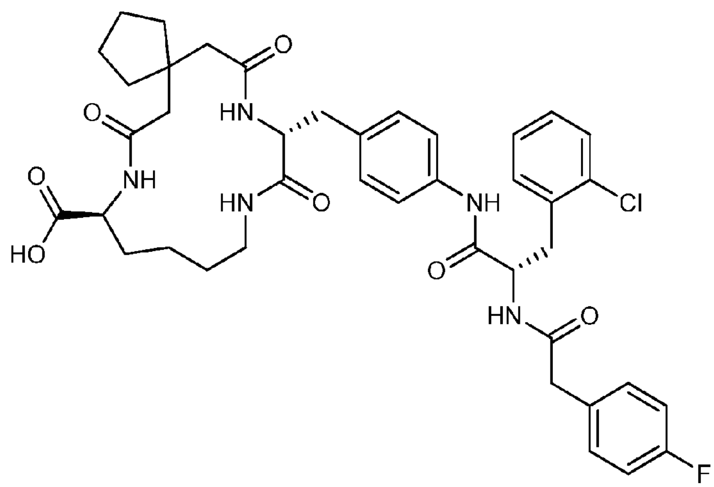 |

FIG. 12-164

| Compound No. | Structure |
|---|---|
| 461 | 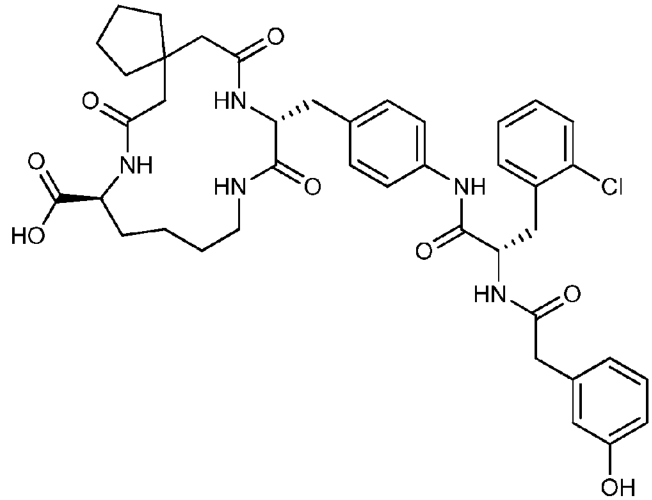 |
| 462 | 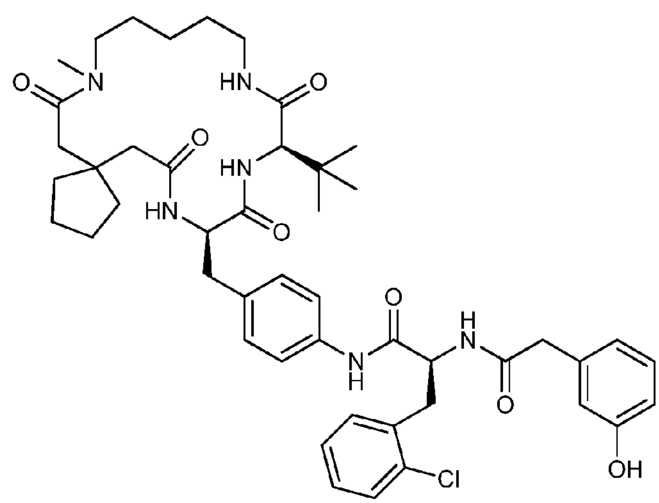 |

| Compound No. | Structure |
|---|---|
| 463 | 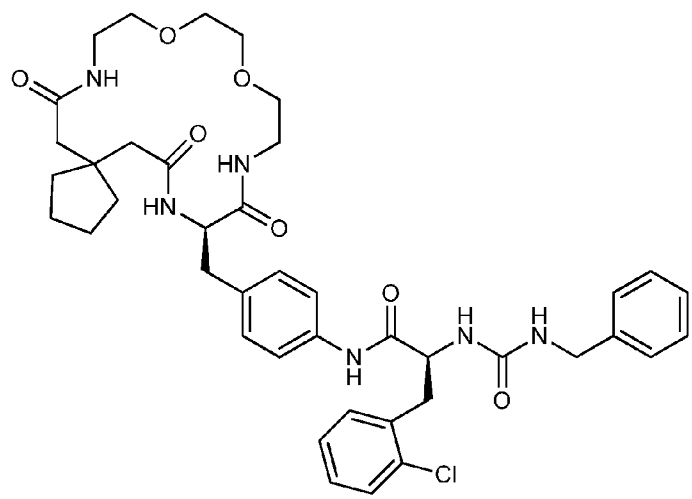 |
| 464 | 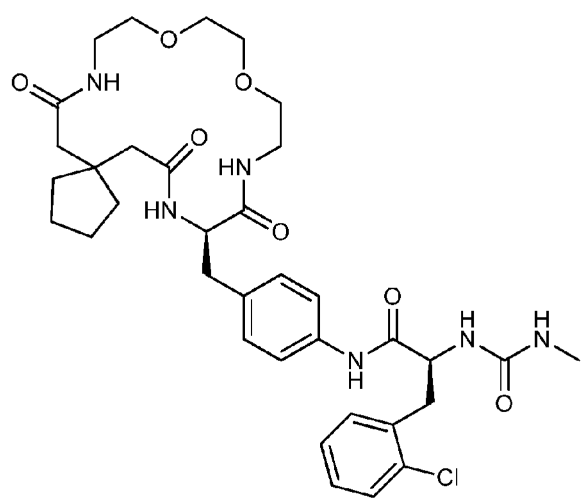 |

| Compound No. | Structure |
|---|---|
| 465 | 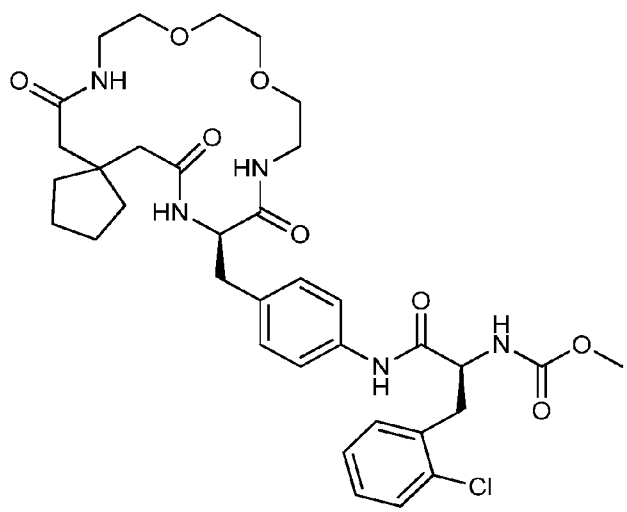 |
| 466 | 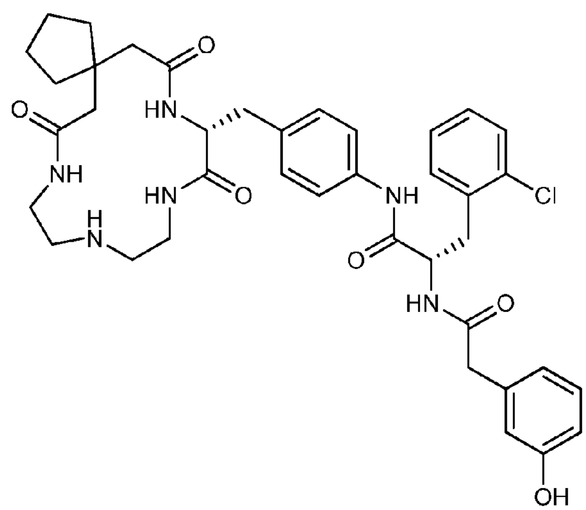 |

FIG. 12-167

| Compound No. | Structure |
|---|---|
| 467 | 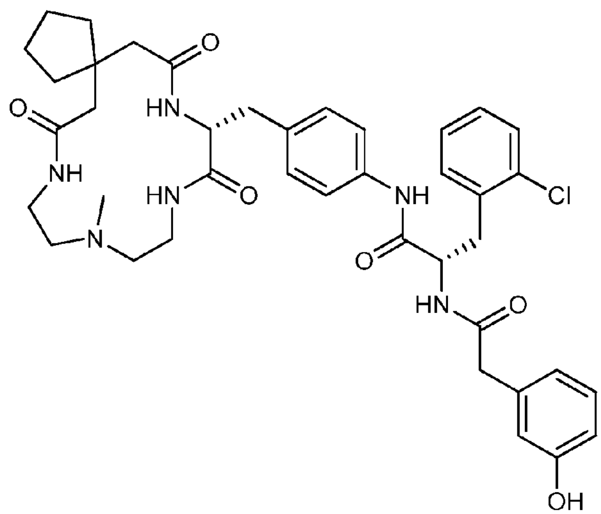 |
| 468 | 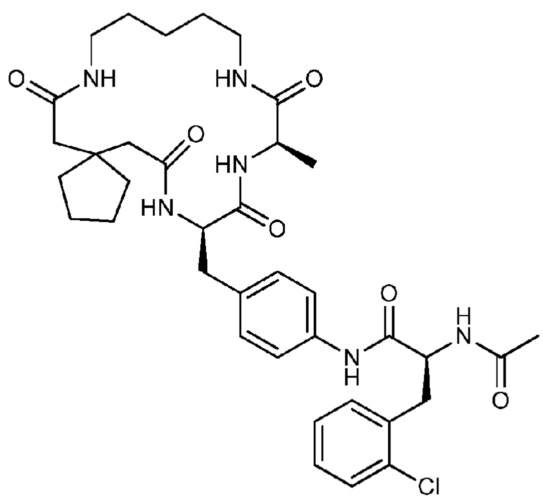 |

FIG. 12-168

| Compound No. | Structure |
|---|---|
| 469 | 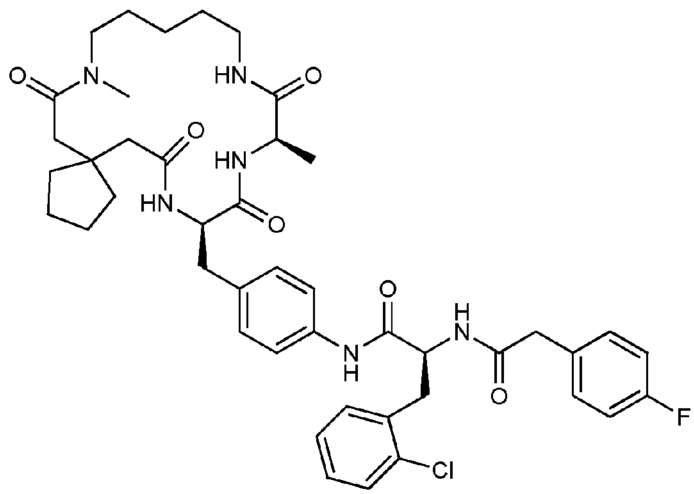 |
| 470 | 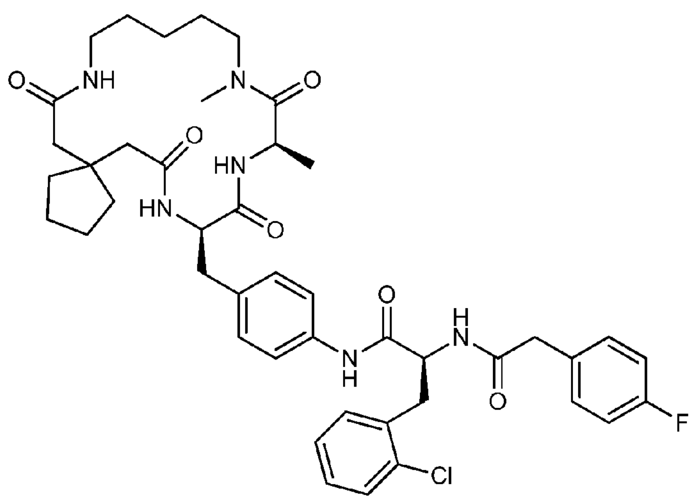 |

FIG. 12-169

| Compound No. | Structure |
|---|---|
| 471 | 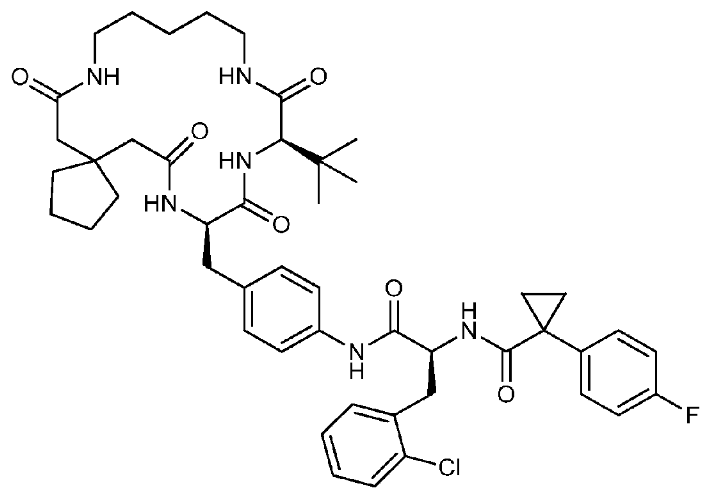 |
| 472 | 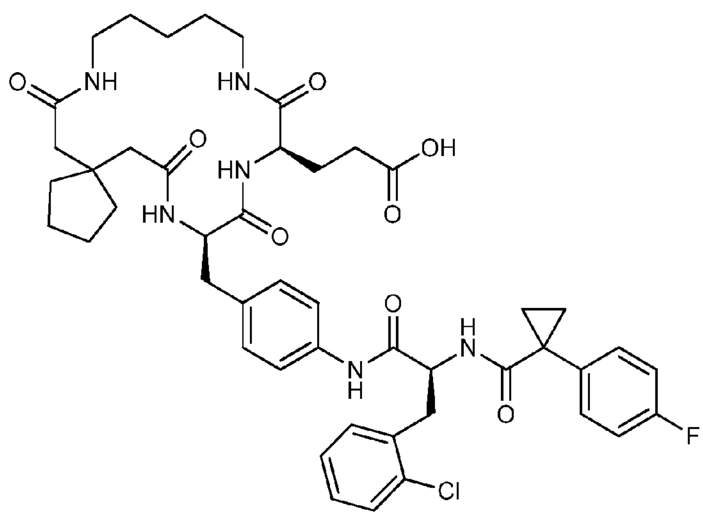 |

| Compound No. | Structure |
|---|---|
| 473 | 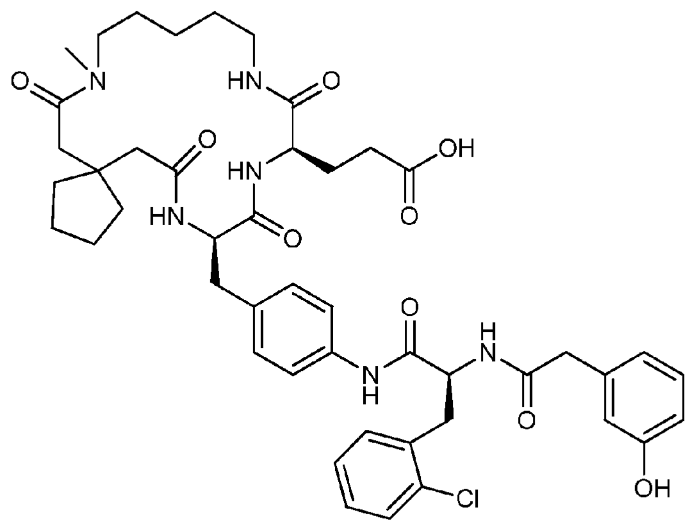 |
| 474 | 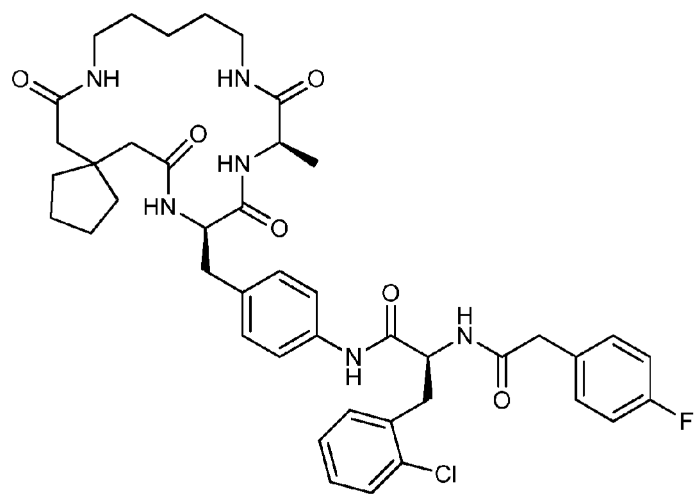 |

FIG. 12-171

| Compound No. | Structure |
|---|---|
| 475 | 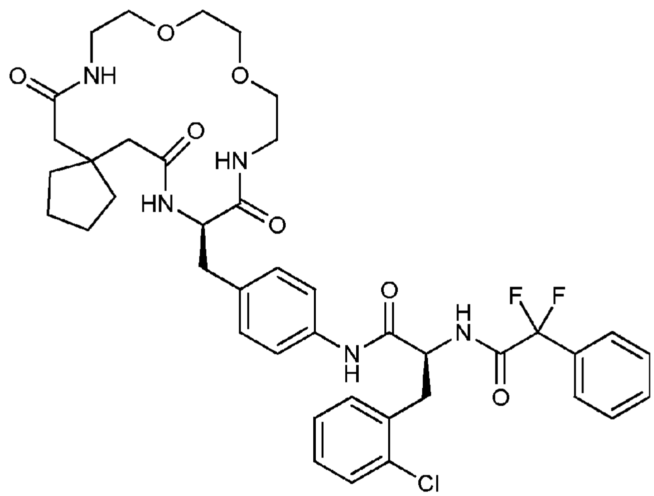 |
| 476 | 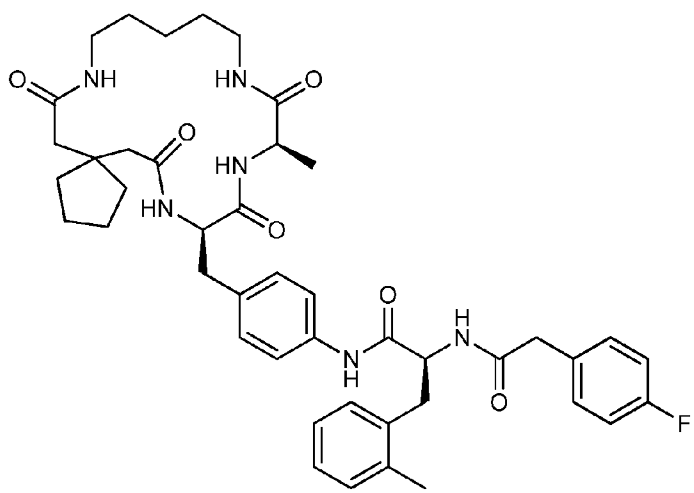 |

| Compound No. | Structure |
|---|---|
| 477 | 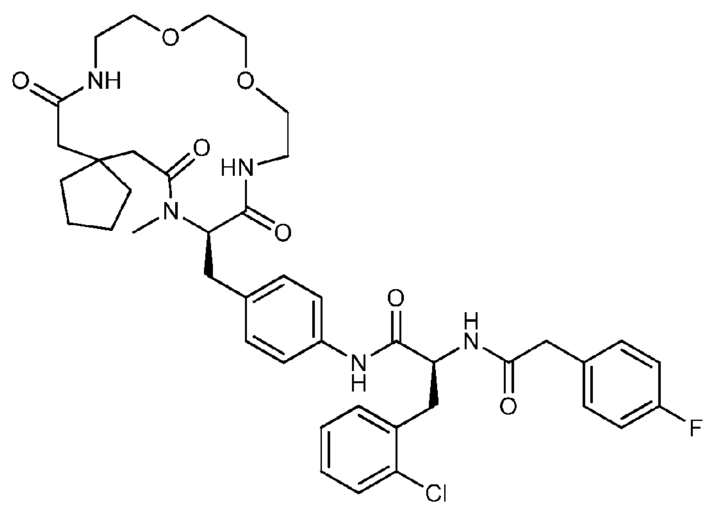 |
| 478 | 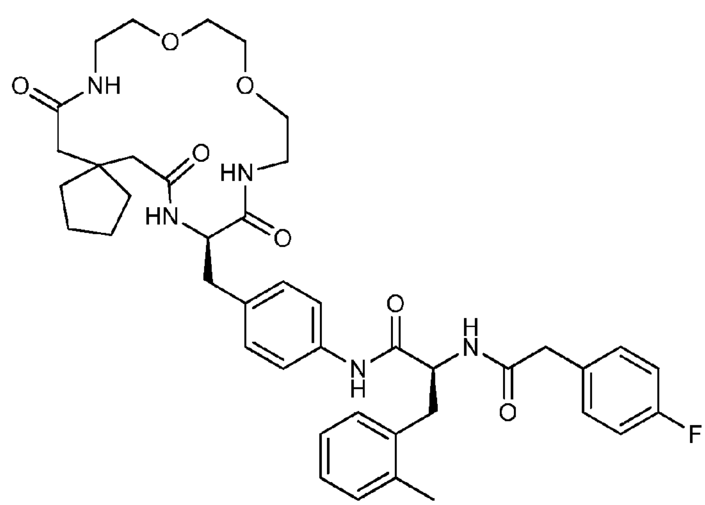 |

FIG. 12-173

| Compound No. | Structure |
|---|---|
| 479 | 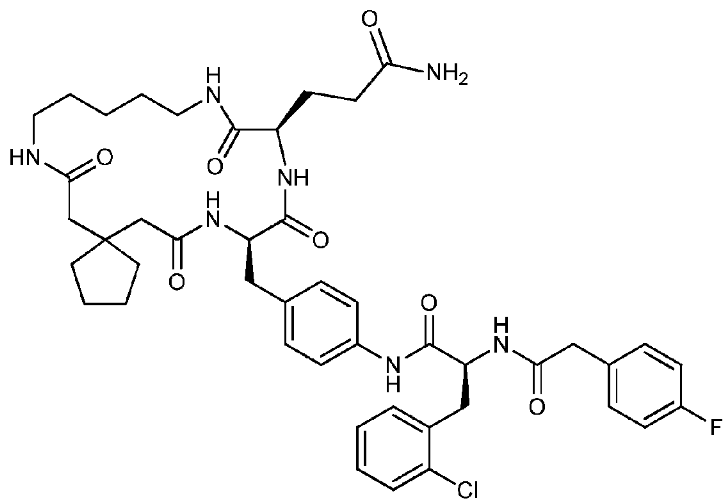 |
| 480 | 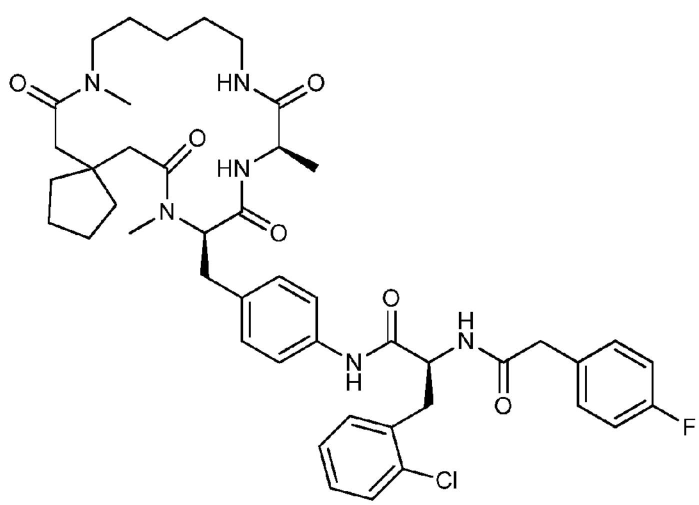 |

FIG. 12-174

| Compound No. | Structure |
|---|---|
| 481 | 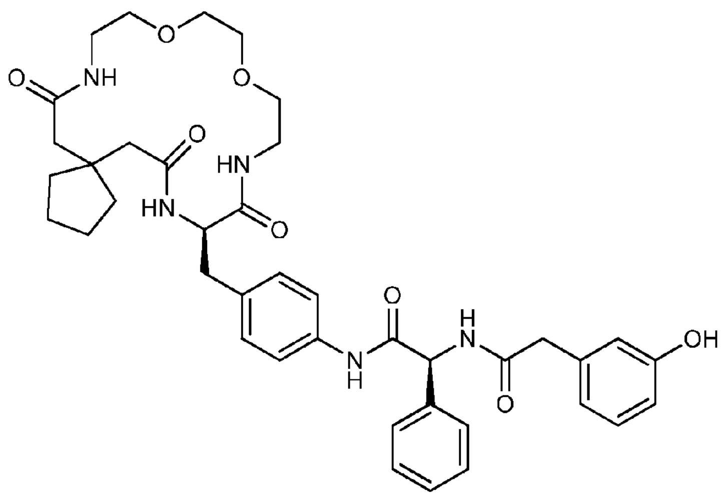 |
| 482 | 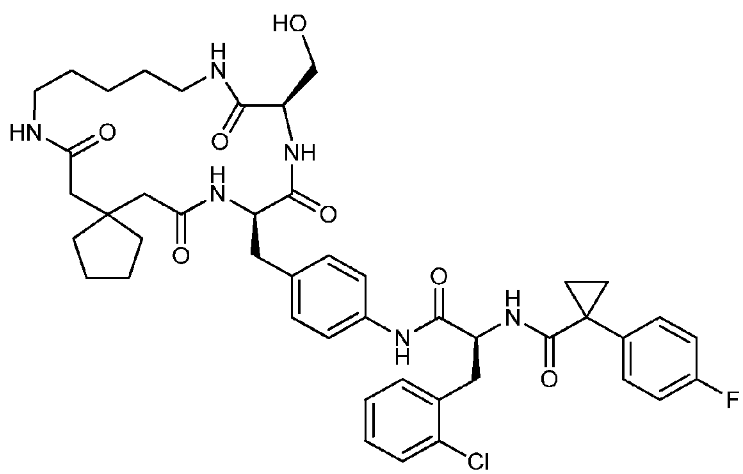 |

FIG. 12-175

| Compound No. | Structure |
|---|---|
| 483 | 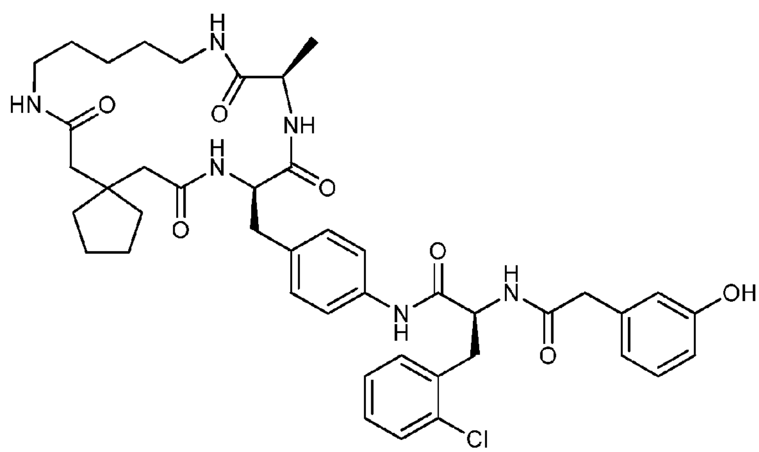 |
| 484 | 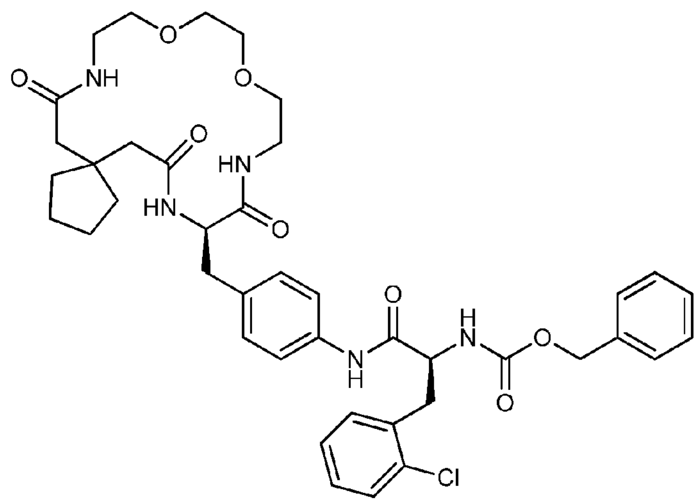 |

FIG. 12-176

| Compound No. | Structure |
|---|---|
| 485 | 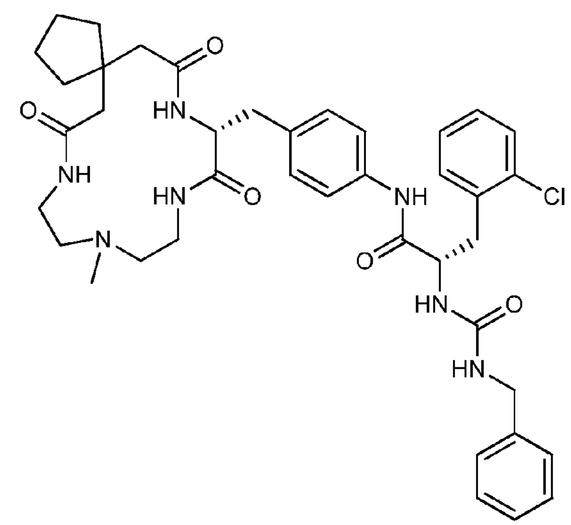 |
| 486 | 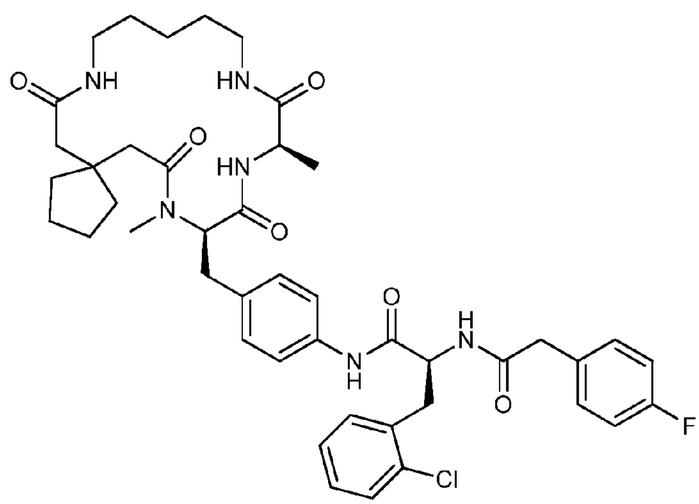 |

| Compound No. | Structure |
|---|---|
| 487 | 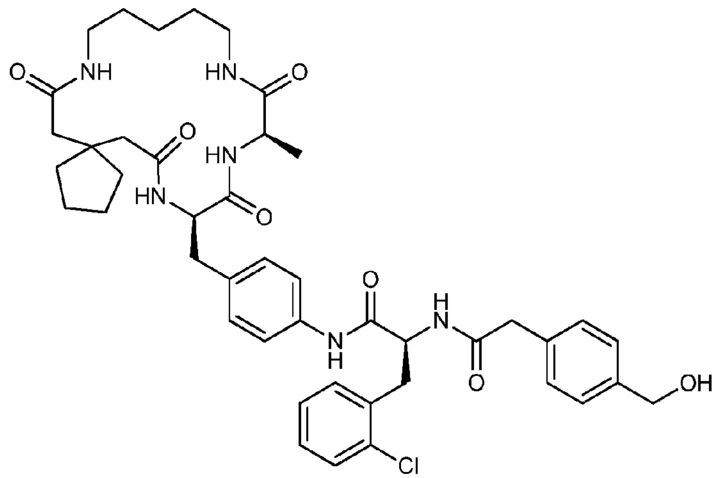 |
| 488 | 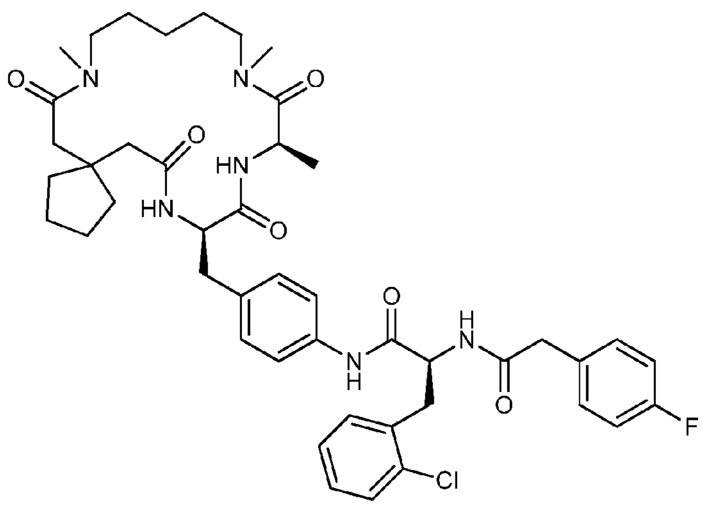 |

| Compound No. | Structure |
|---|---|
| 489 | 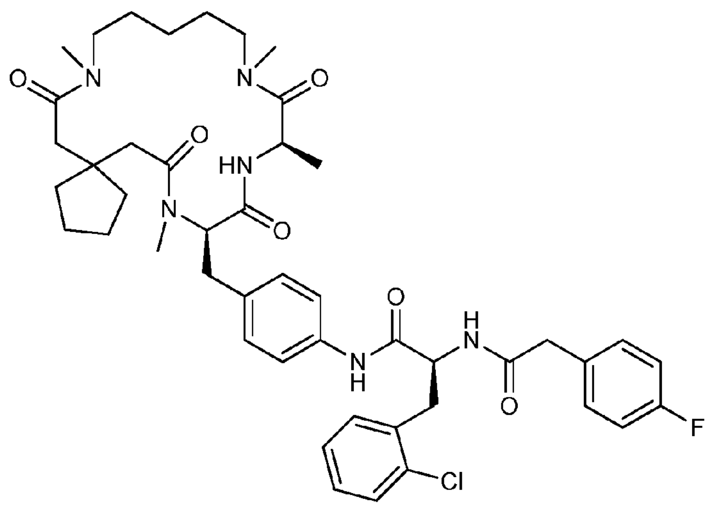 |
| 490 | 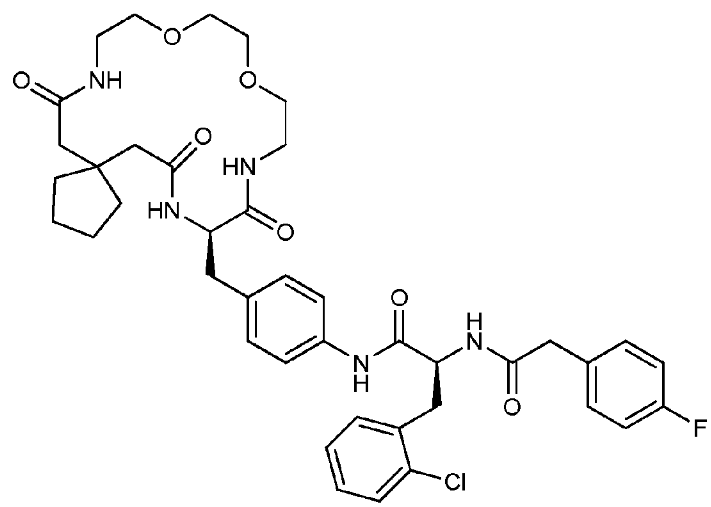 |

| Compound No. | Structure |
|---|---|
| 491 | 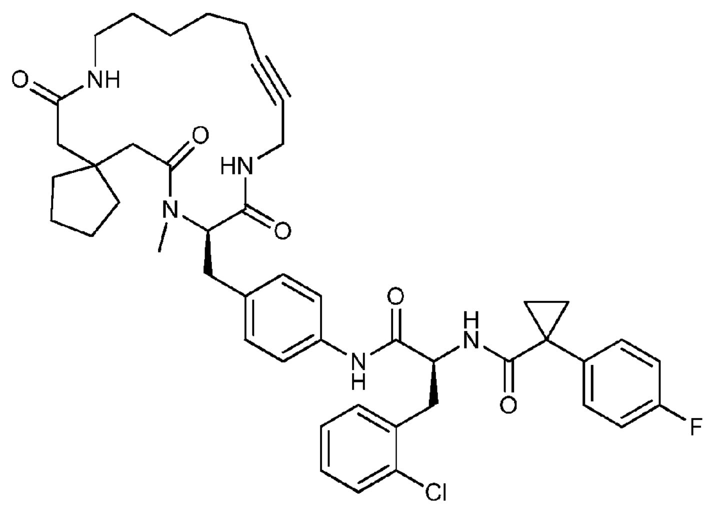 |
| 492 | 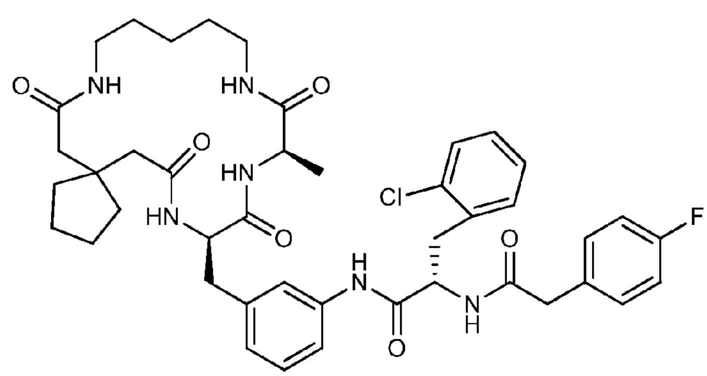 |

| Compound No. | Structure |
|---|---|
| 493 | 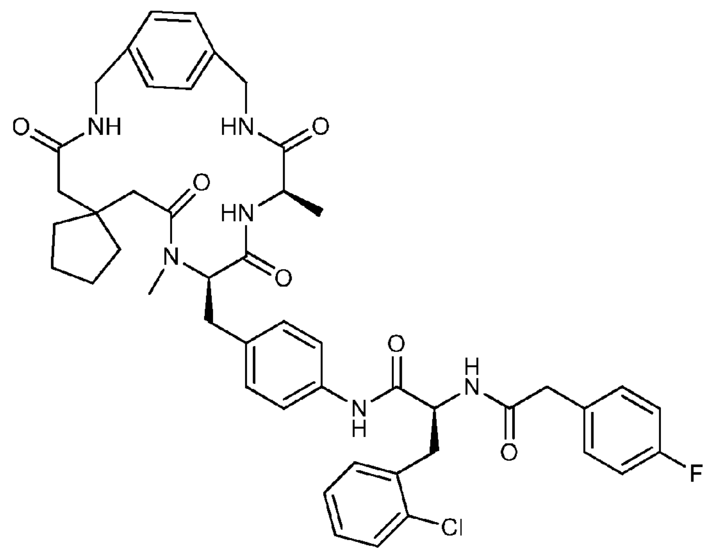 |
| 494 | 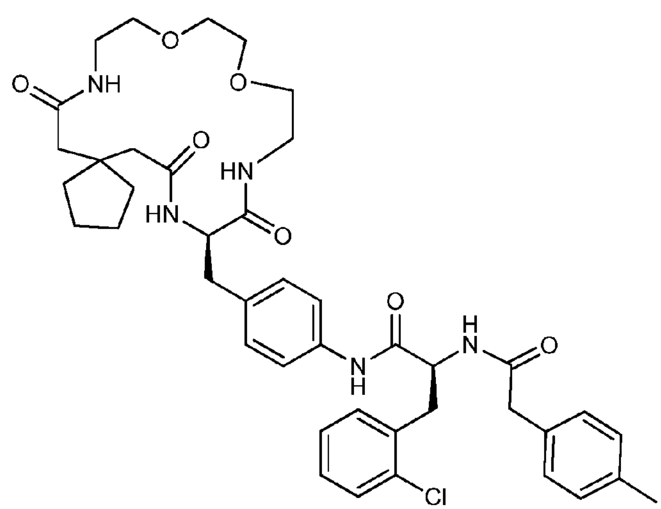 |

FIG. 12-181

| Compound No. | Structure |
|---|---|
| 495 | 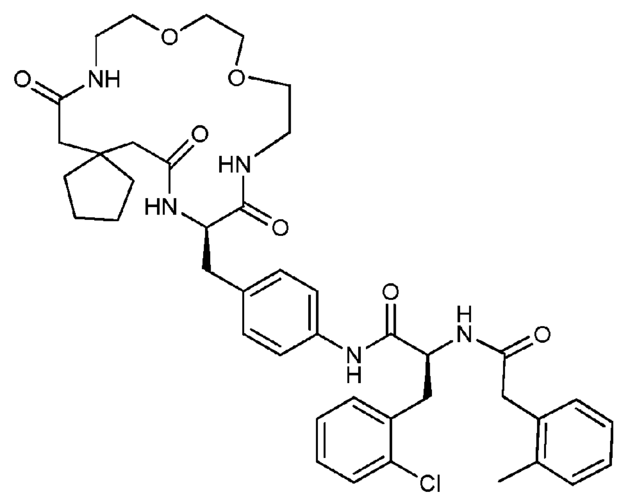 |
| 496 | 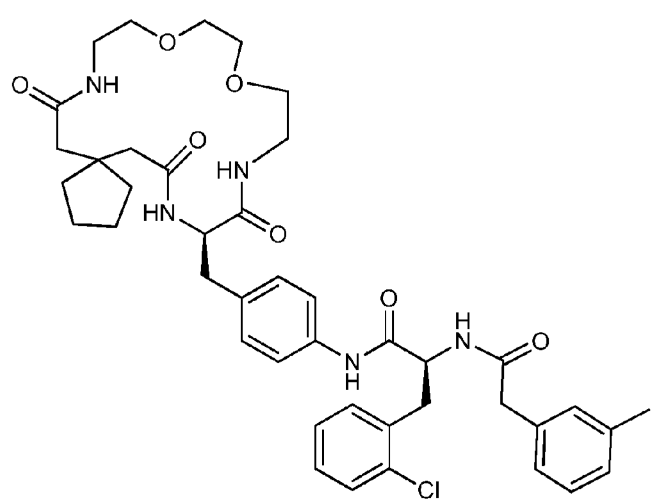 |

| Compound No. | Structure |
|---|---|
| 497 | 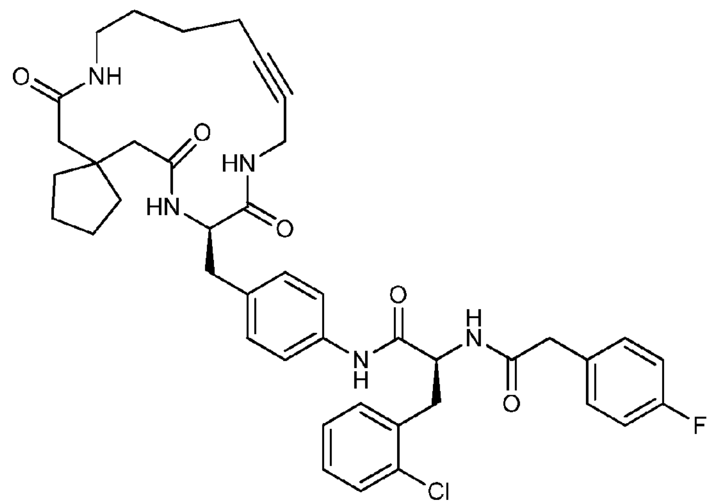 |
| 498 | 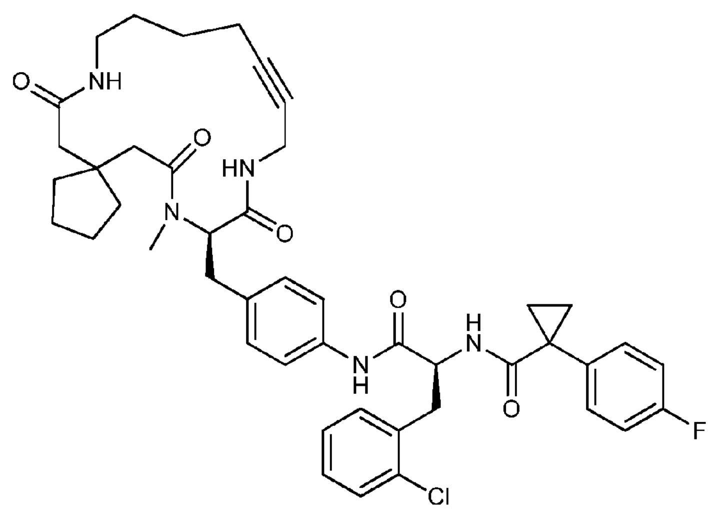 |

| Compound No. | Structure |
|---|---|
| 499 | 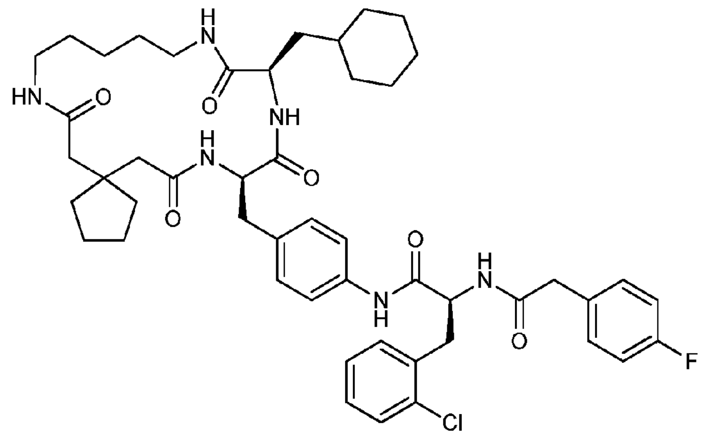 |
| 500 | 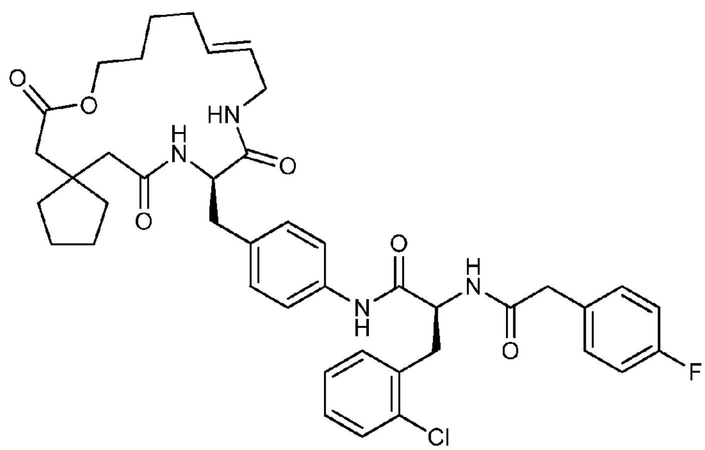 |

| Compound No. | Structure |
|---|---|
| 501 | 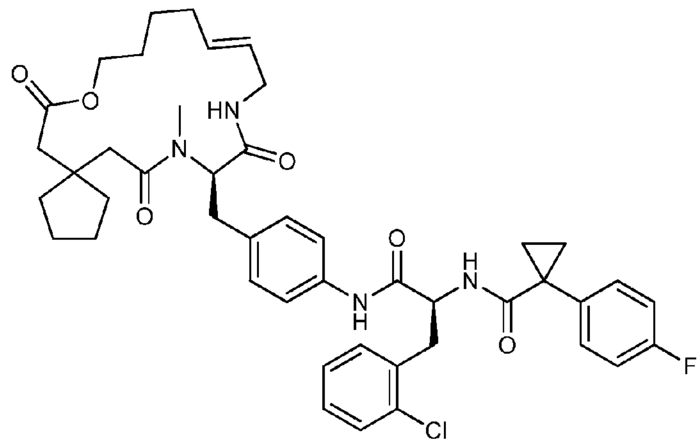 |
| 502 | 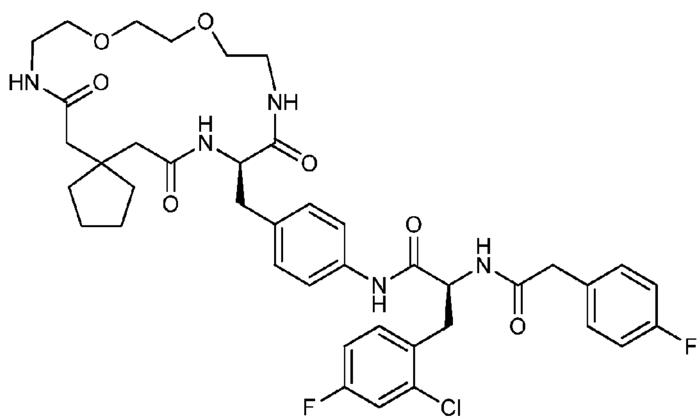 |

| Compound No. | Structure |
|---|---|
| 503 | 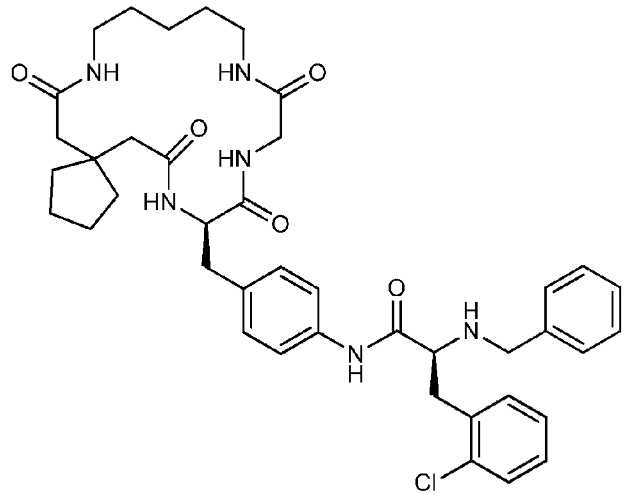 |
| 504 | 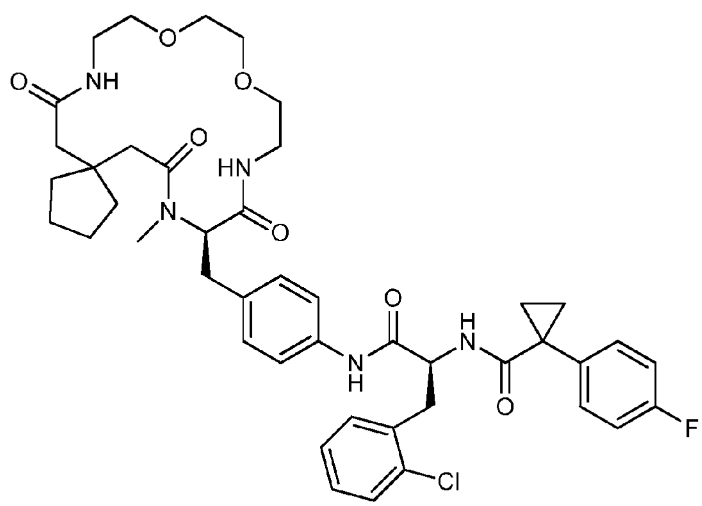 |

FIG. 12-186

| Compound No. | Structure |
|---|---|
| 505 | 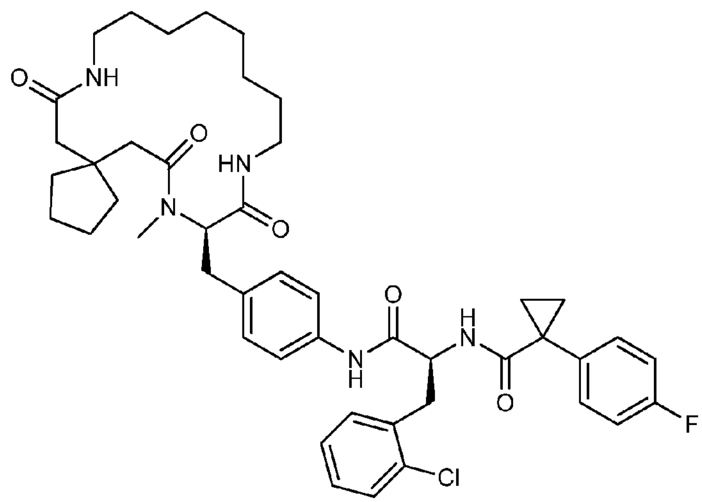 |
| 506 | 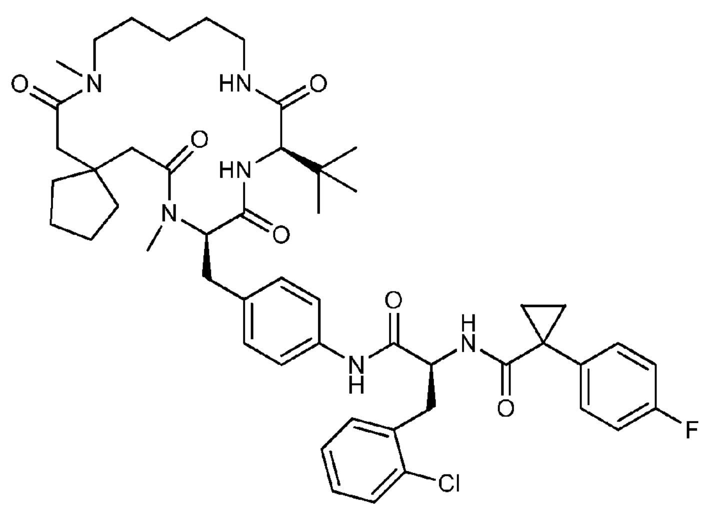 |

| Compound No. | Structure |
|---|---|
| 507 | 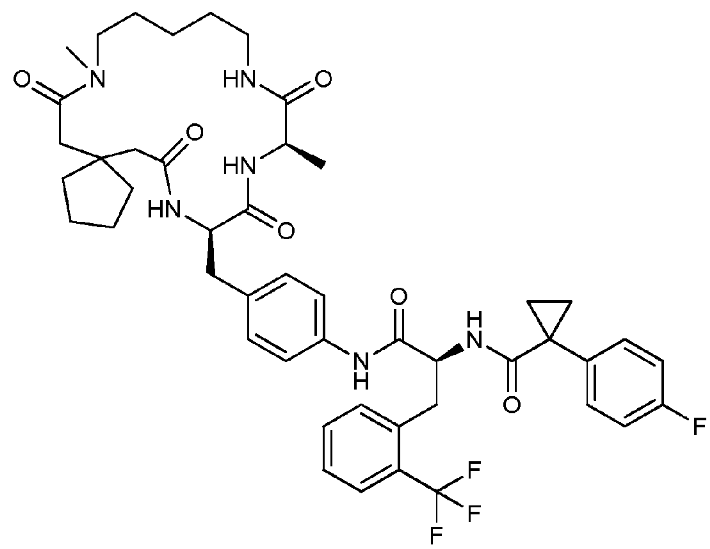 |
| 508 | 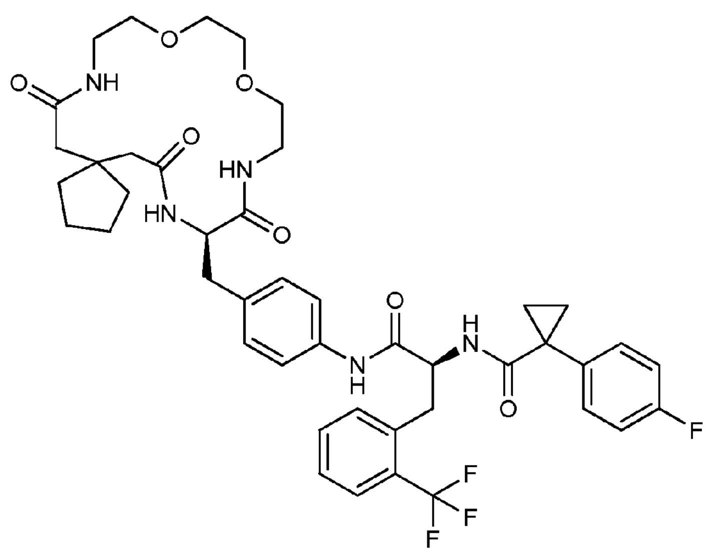 |

FIG. 12-188

| Compound No. | Structure |
|---|---|
| 509 | 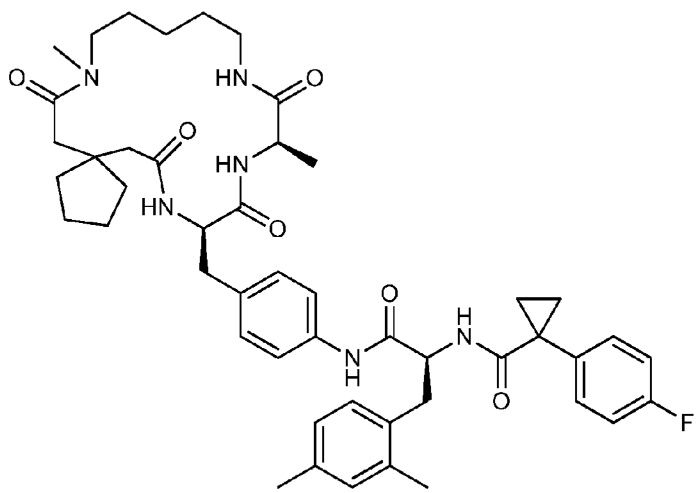 |
| 510 | 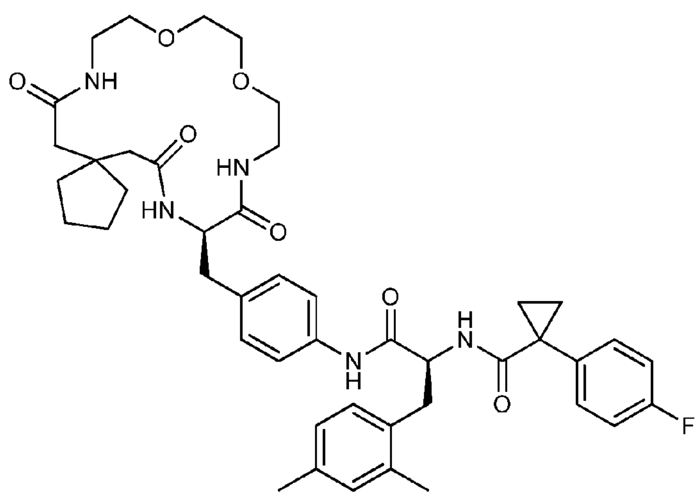 |

FIG. 12-189

| Compound No. | Structure |
|---|---|
| 511 | 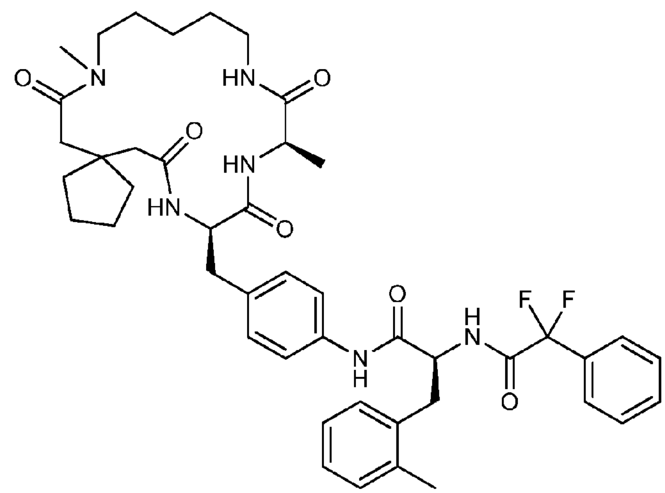 |
| 512 | 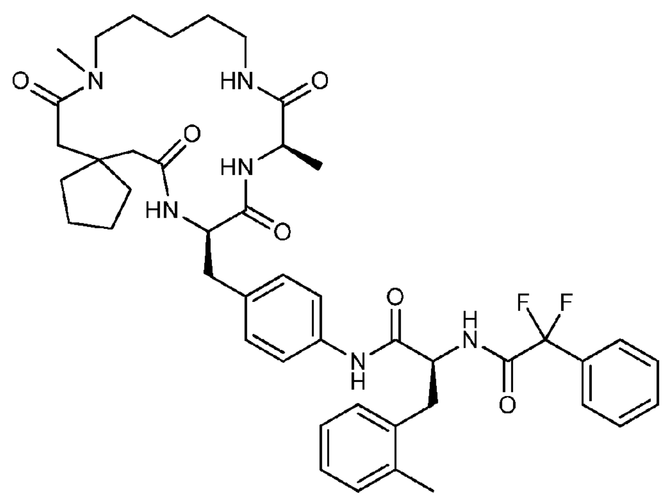 |

| Compound No. | Structure |
|---|---|
| 513 | 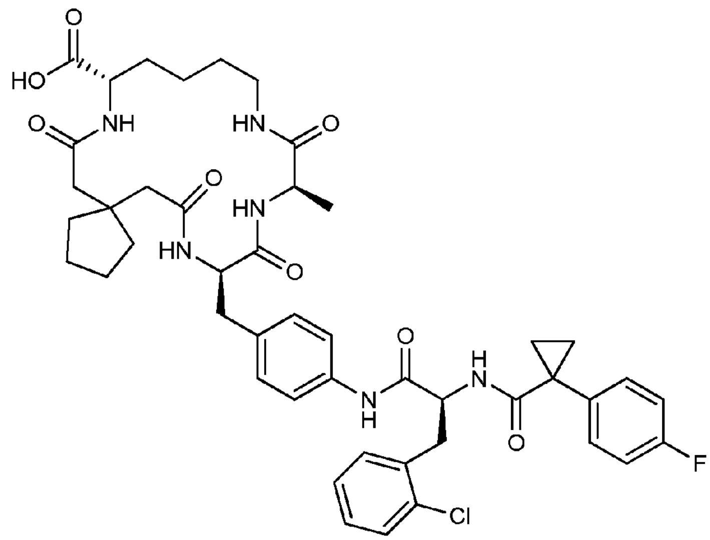 |
| 514 | 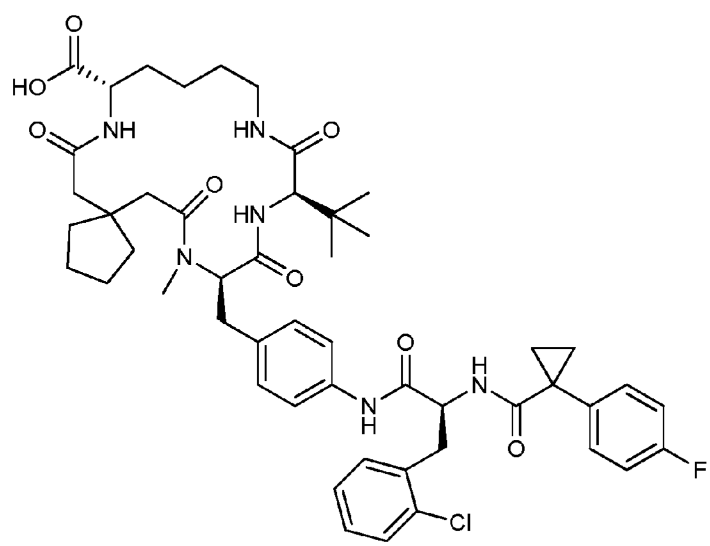 |

| Compound No. | Structure |
|---|---|
| 515 | 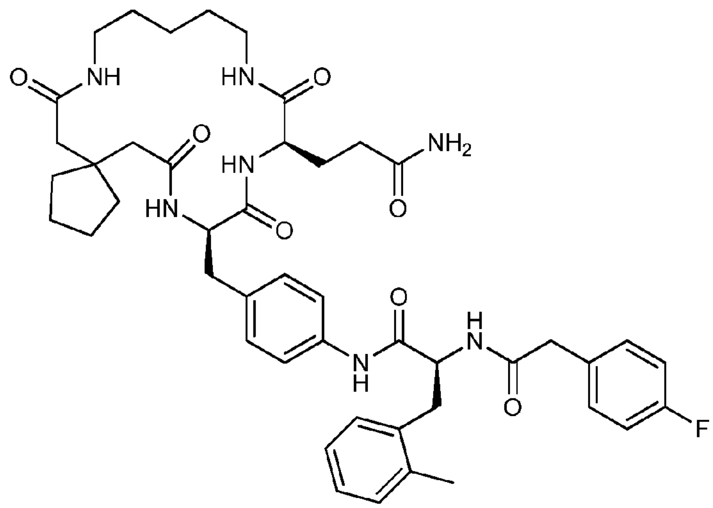 |
| 516 | 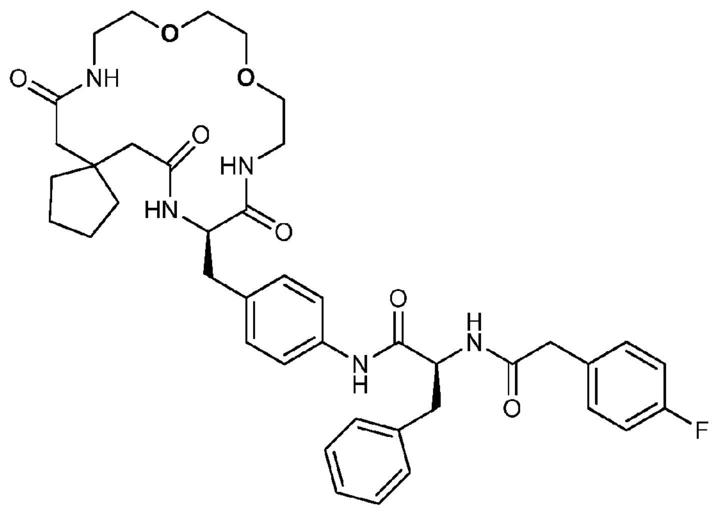 |

| Compound No. | Structure |
|---|---|
| 518 | 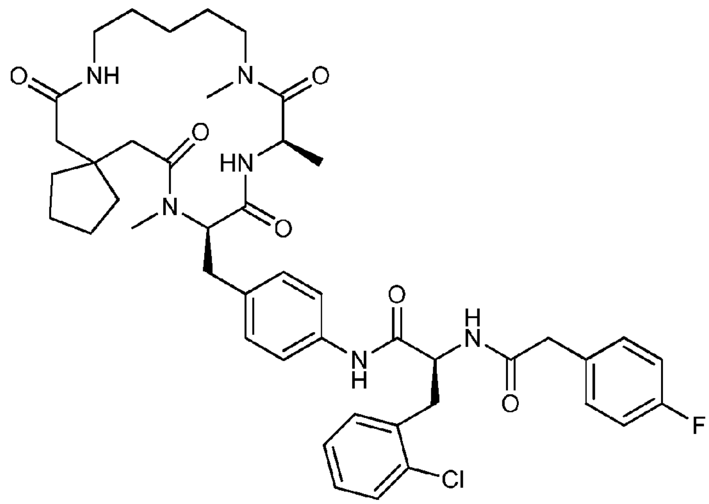 |
| 519 | 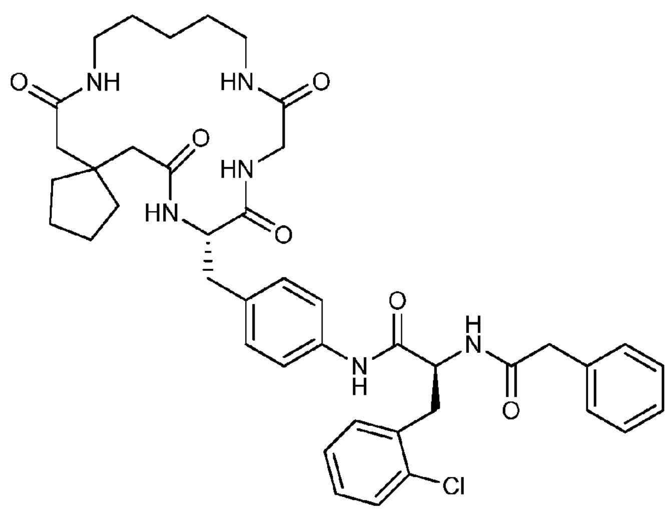 |

| Compound No. | Structure |
|---|---|
| 520 | 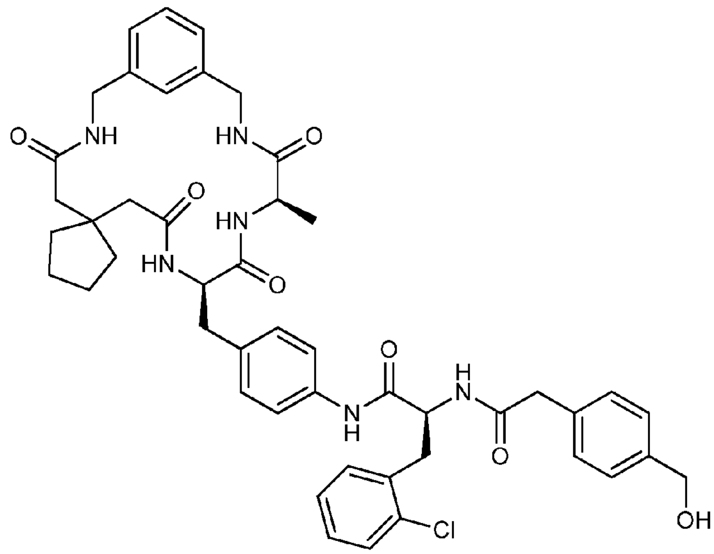 |
| 521 | 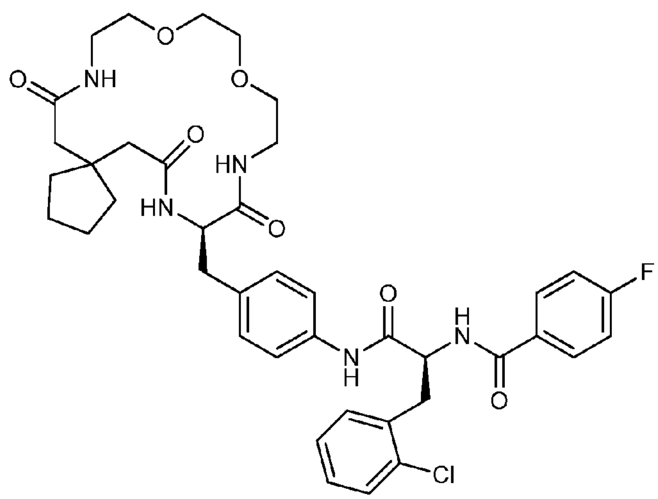 |

| Compound No. | Structure |
|---|---|
| 522 | 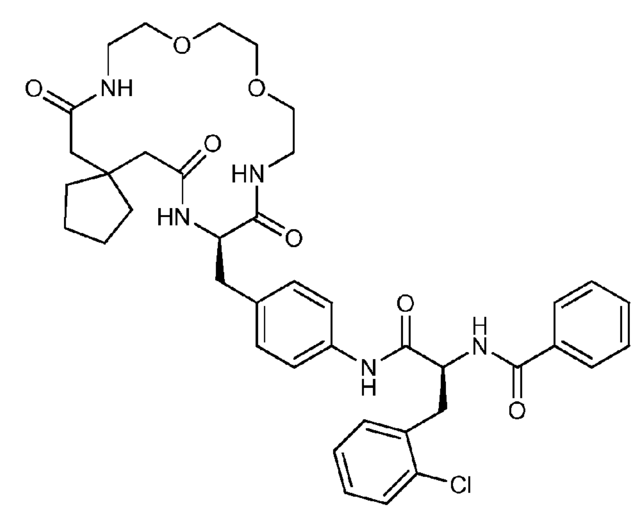 |
| 523 | 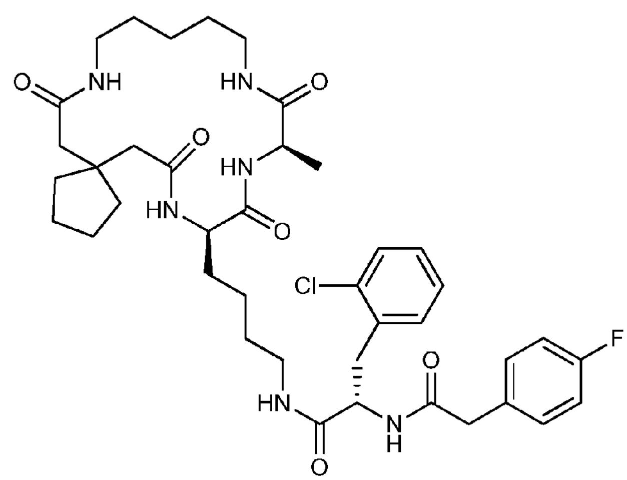 |

| Compound No. | Structure |
|---|---|
| 524 | 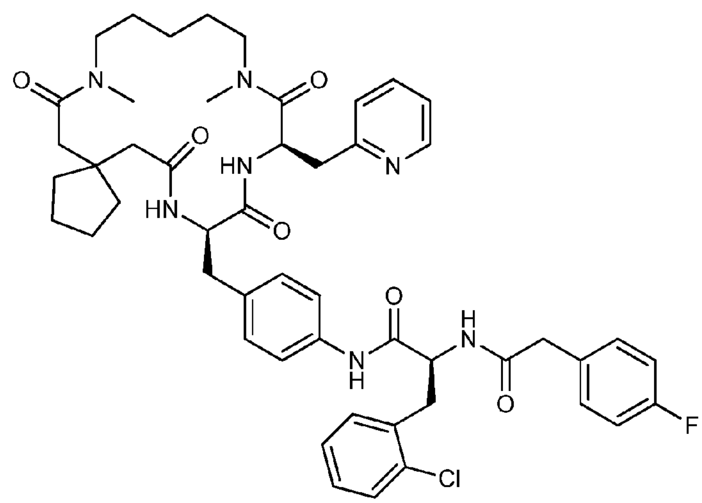 |
| 525 | 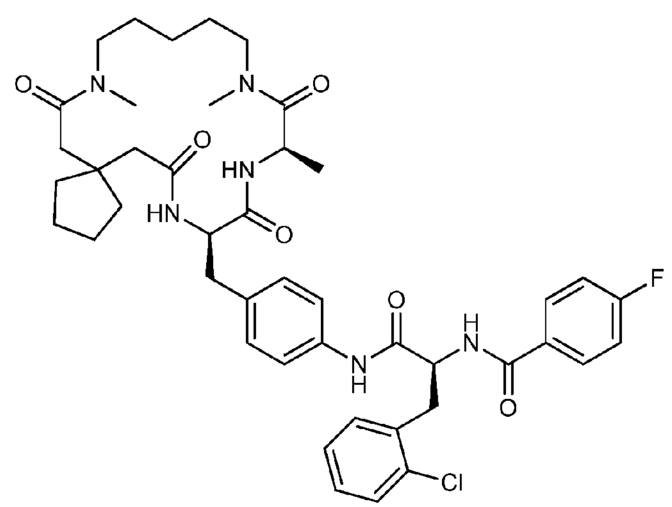 |

| Compound No. | Structure |
|---|---|
| 526 | 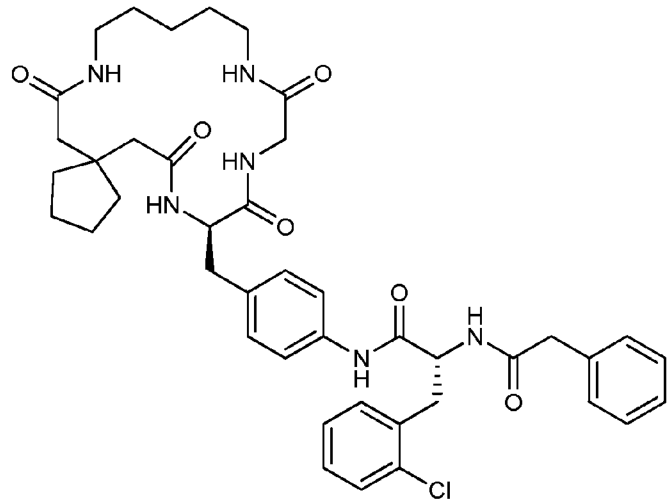 |
| 527 | 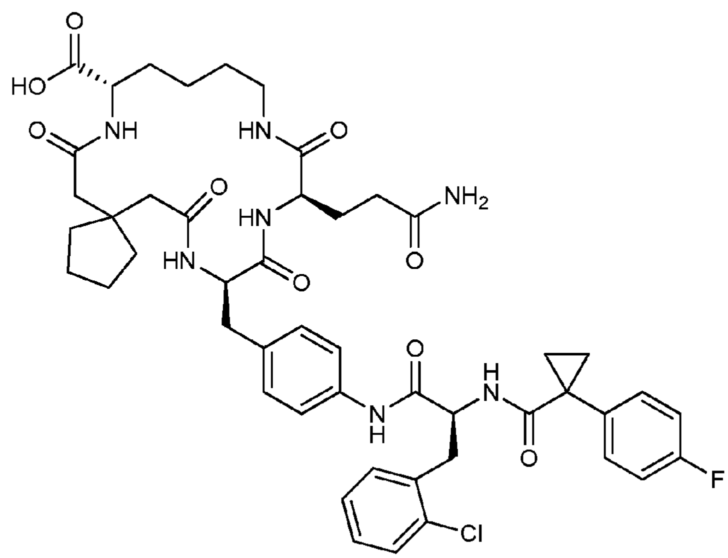 |

| Compound No. | Structure |
|---|---|
| 528 | 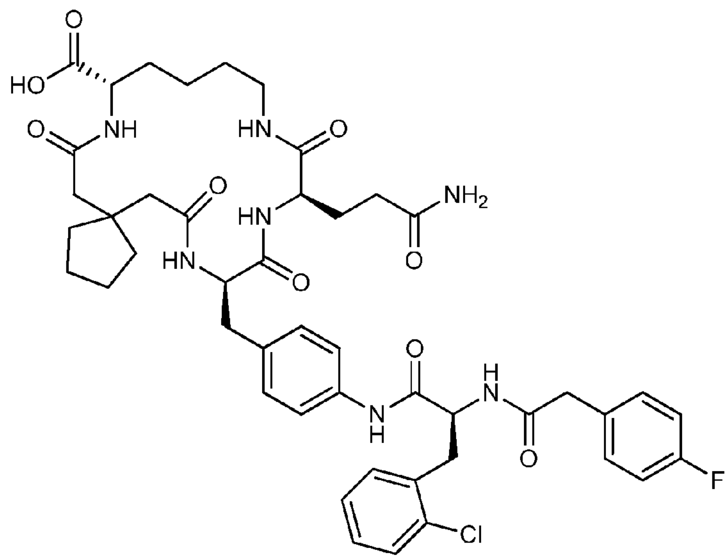 |
| 529 | 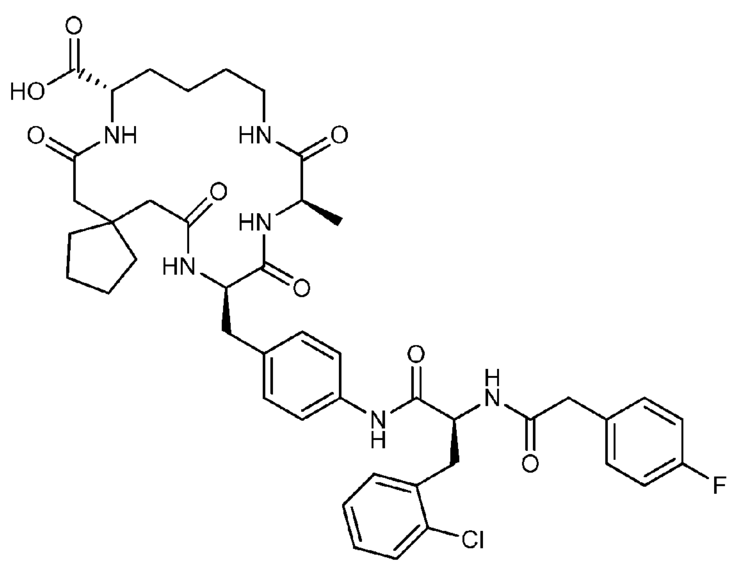 |

| Compound No. | Structure |
|---|---|
| 530 | 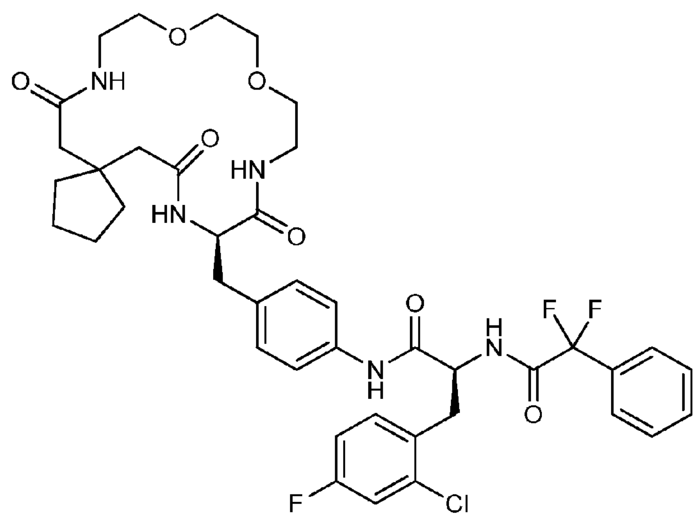 |
| 531 | 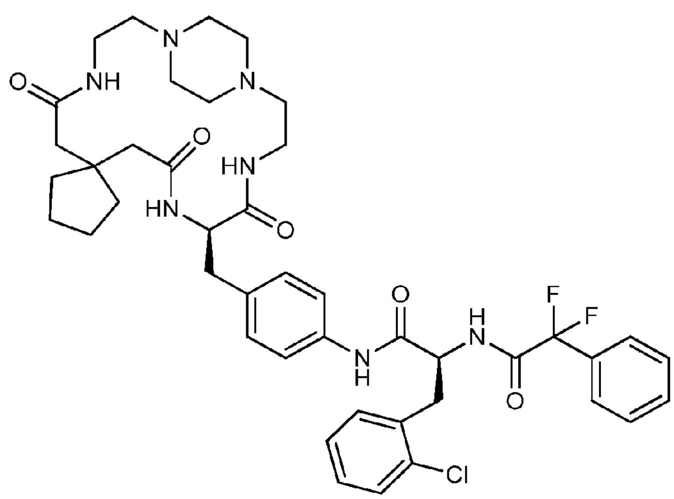 |

| Compound No. | Structure |
|---|---|
| 532 | 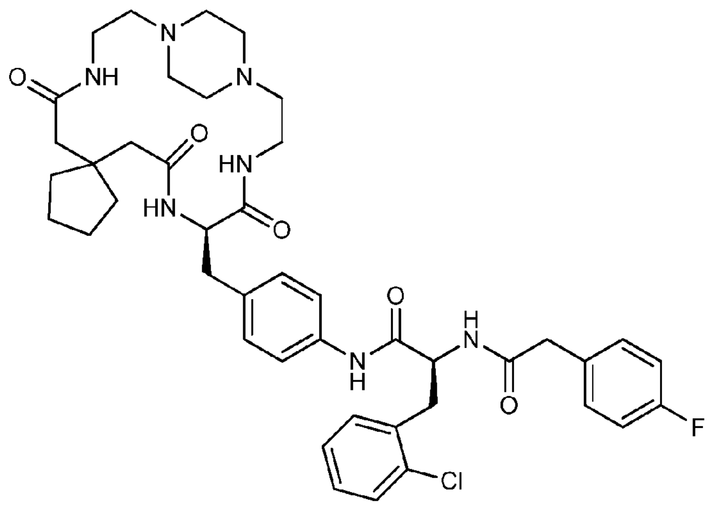 |
| 533 | 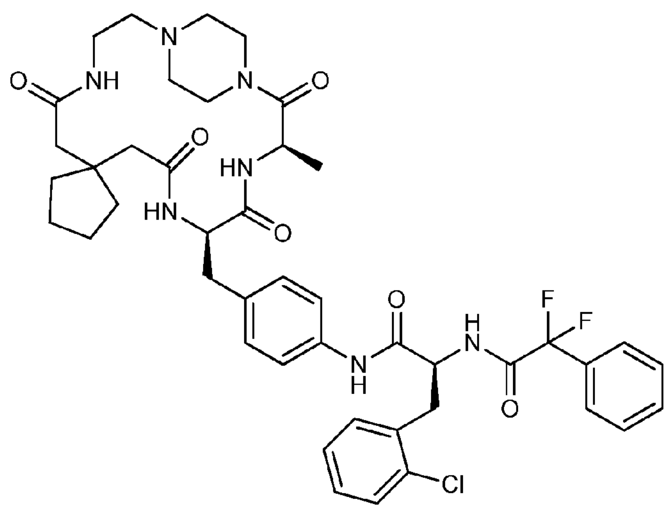 |

| Compound No. | Structure |
|---|---|
| 534 | 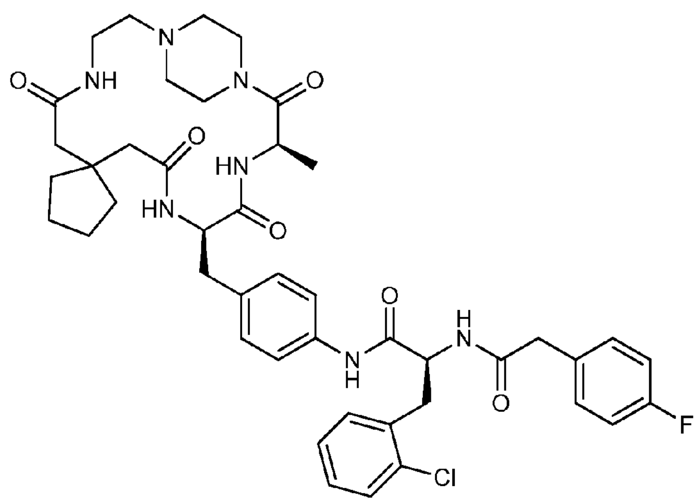 |
| 535 | 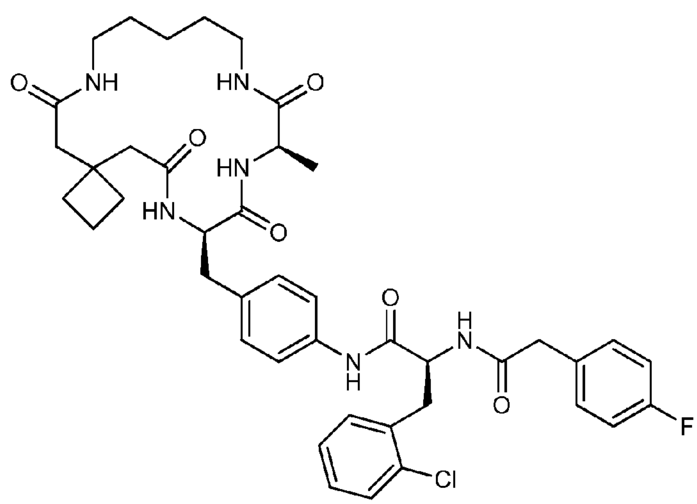 |

| Compound No. | Structure |
|---|---|
| 536 | 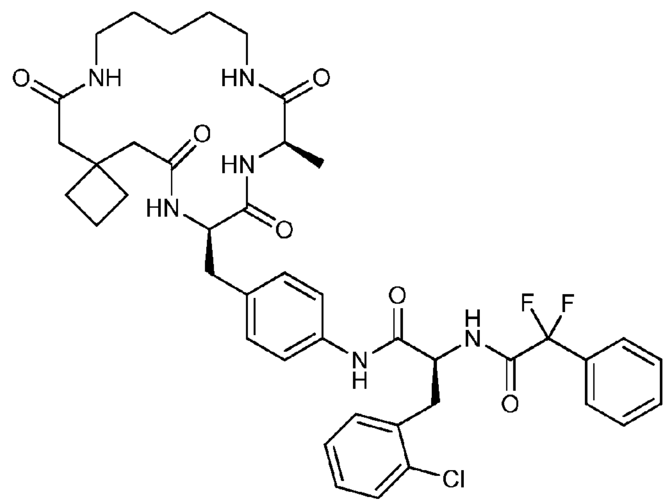 |
| 537 | 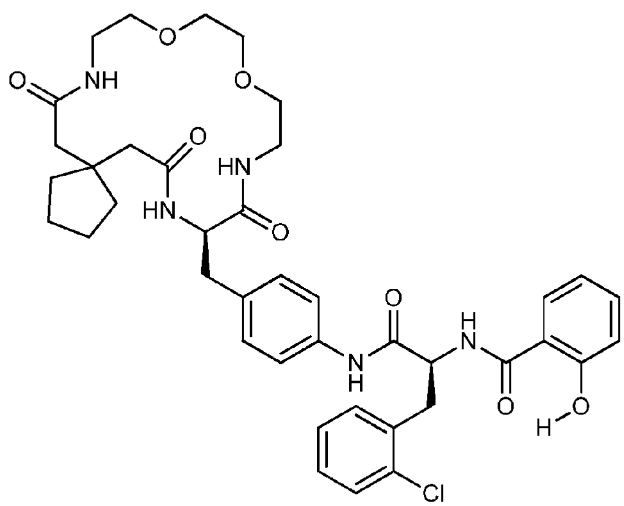 |

FIG. 12-202

| Compound No. | Structure |
|---|---|
| 538 | 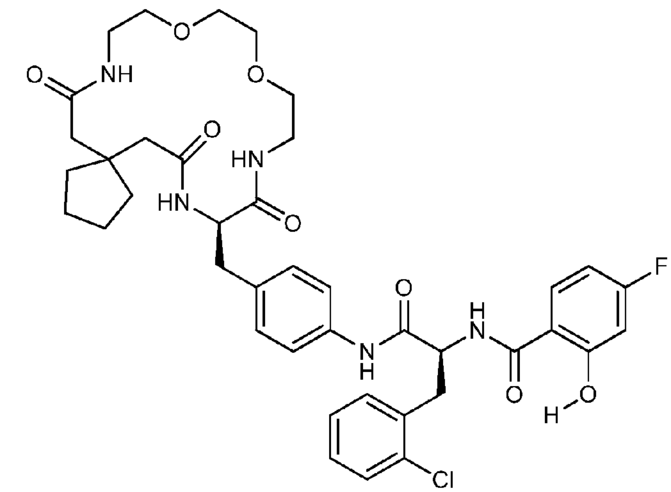 |
| 539 | 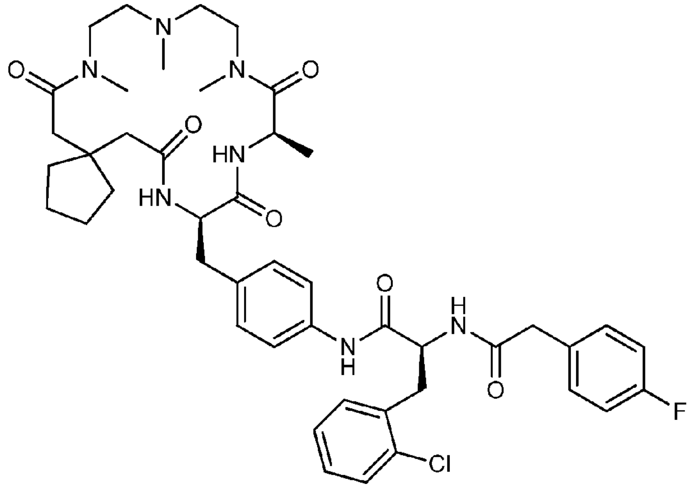 |

FIG. 12-203

| Compound No. | Structure |
|---|---|
| 540 | 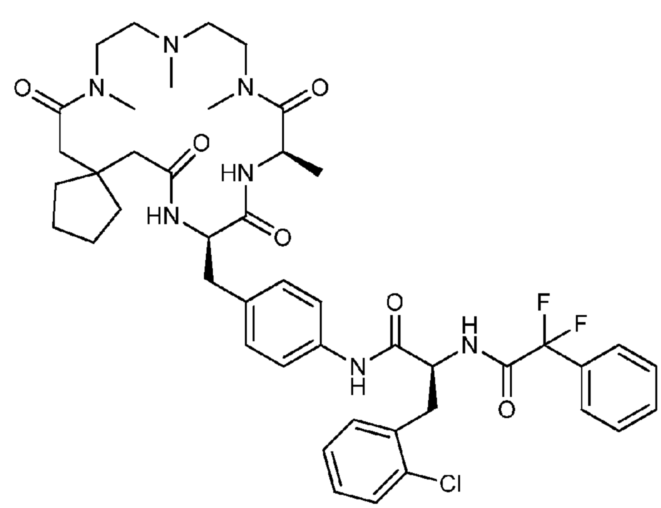 |
| 541 | 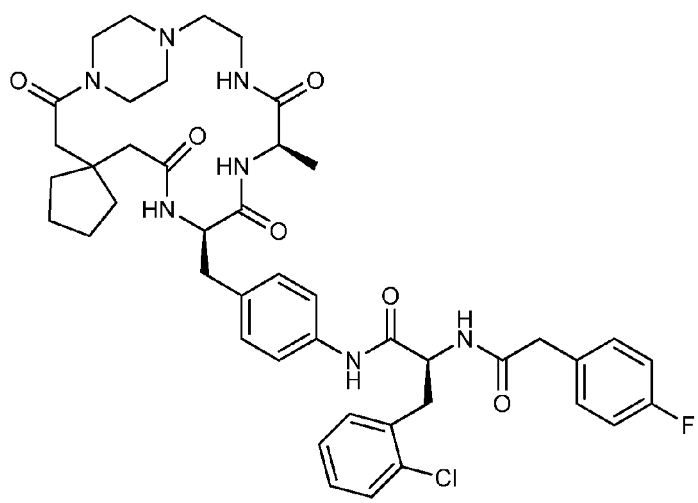 |

| Compound No. | Structure |
|---|---|
| 542 | 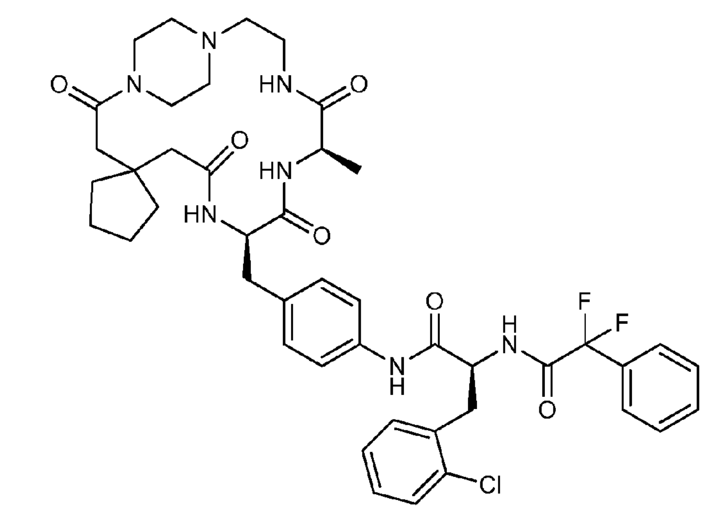 |
| 543 | 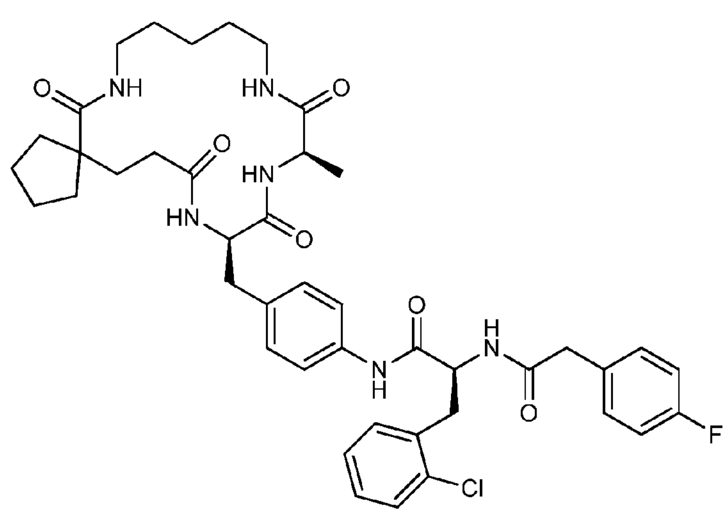 |

| Compound No. | Structure |
|---|---|
| 544 | 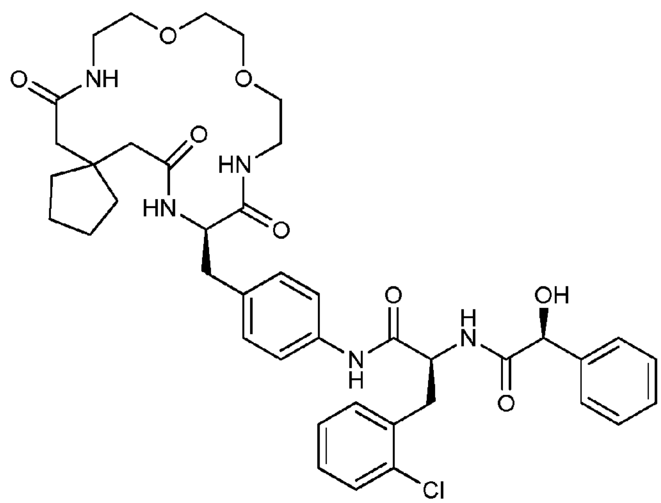 |
| 545 | 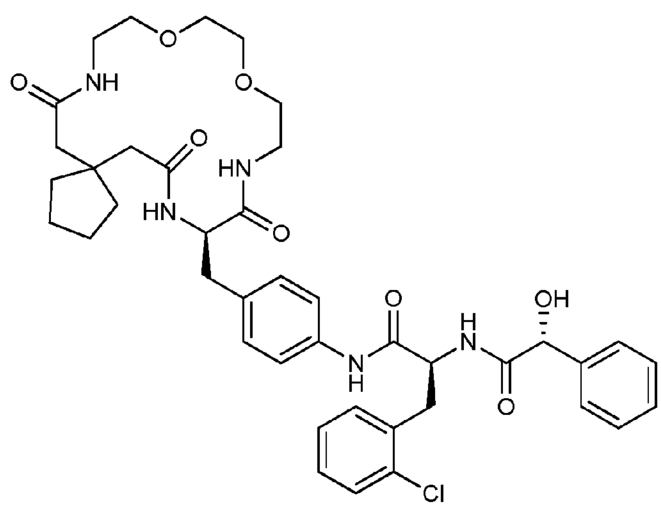 |

FIG. 12-206

| Compound No. | Structure |
|---|---|
| 546 | 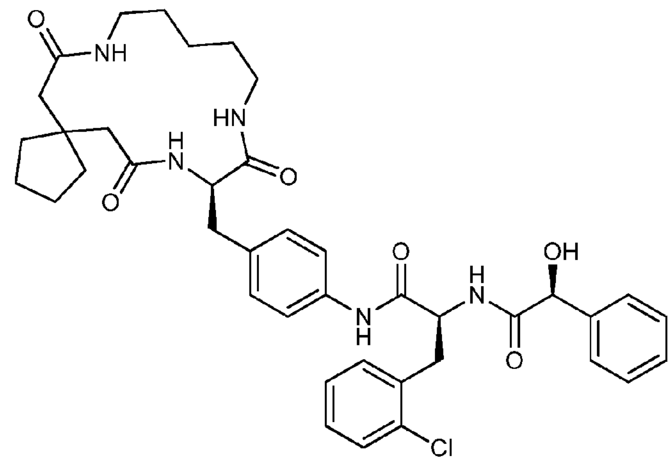 |
| 547 | 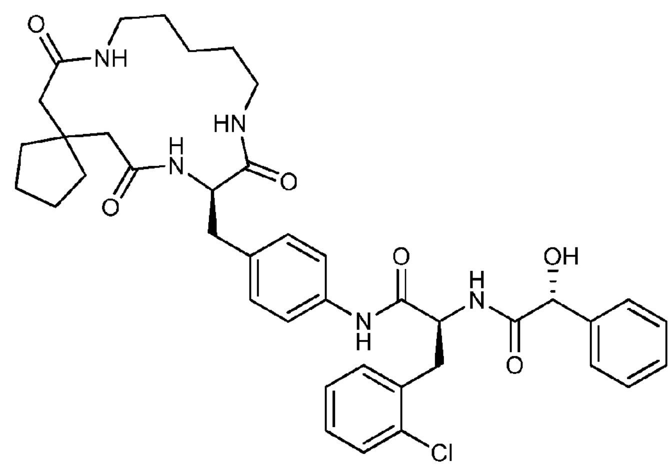 |

FIG. 12-207

| Compound No. | Structure |
|---|---|
| 548 | 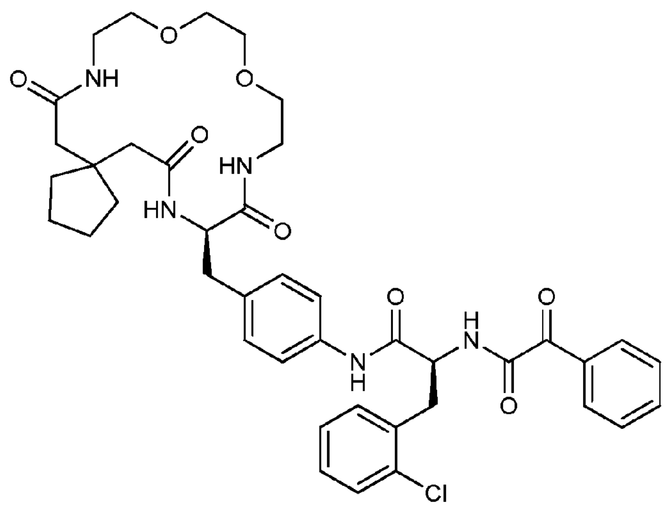 |
| 549 | 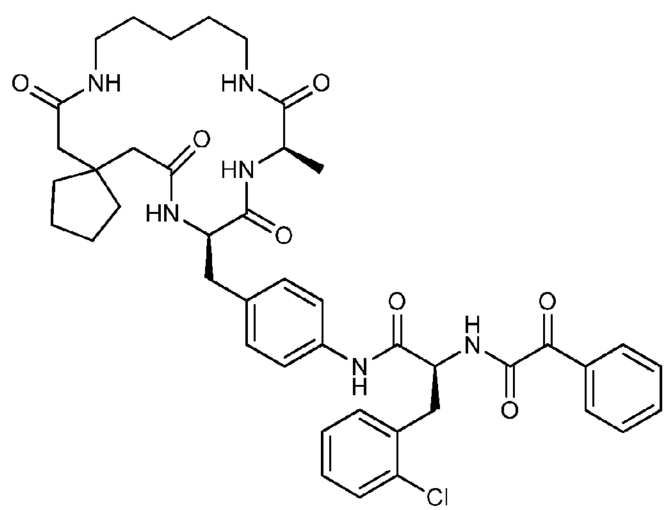 |

FIG. 12-208

| Compound No. | Structure |
|---|---|
| 550 | 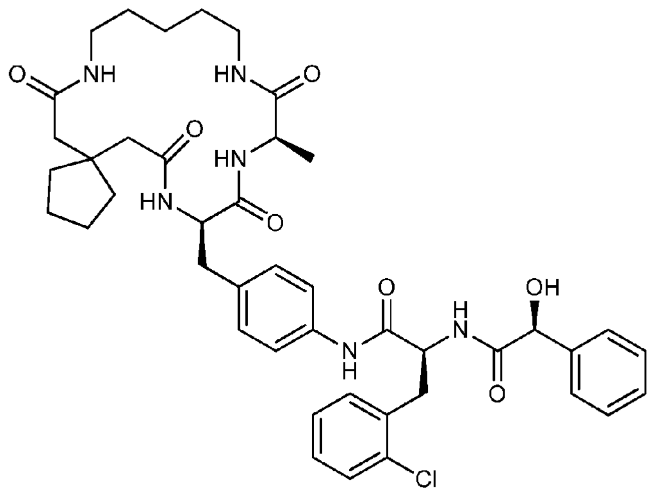 |
| 551 | 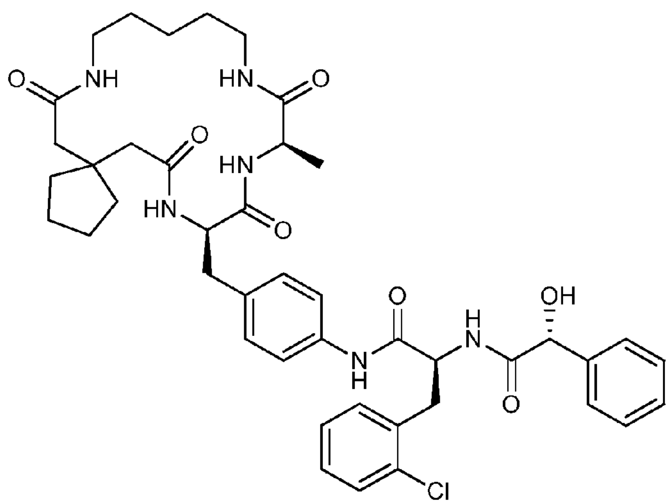 |

| Compound No. | Structure |
|---|---|
| 552 | 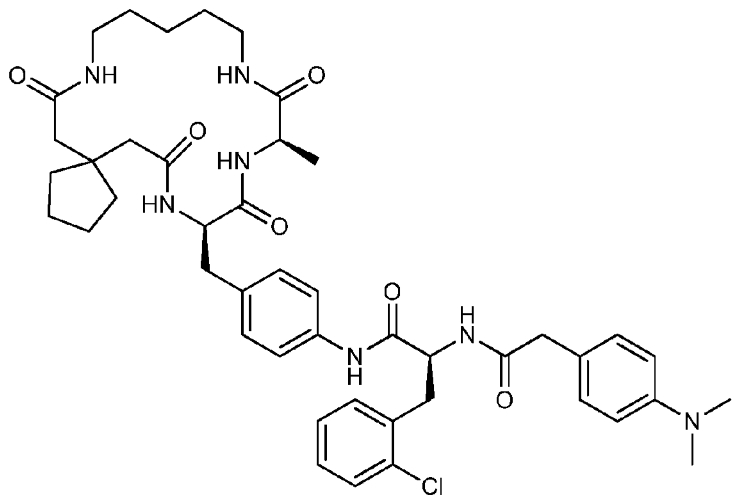 |
| 553 | 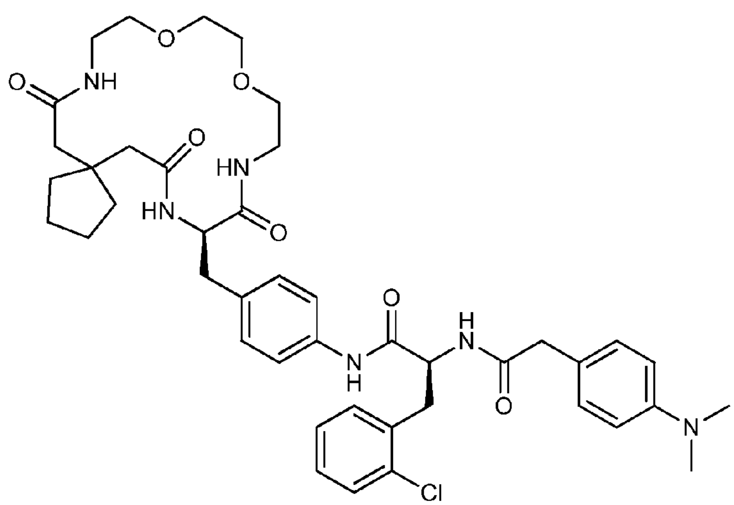 |

| Compound No. | Structure |
|---|---|
| 554 | 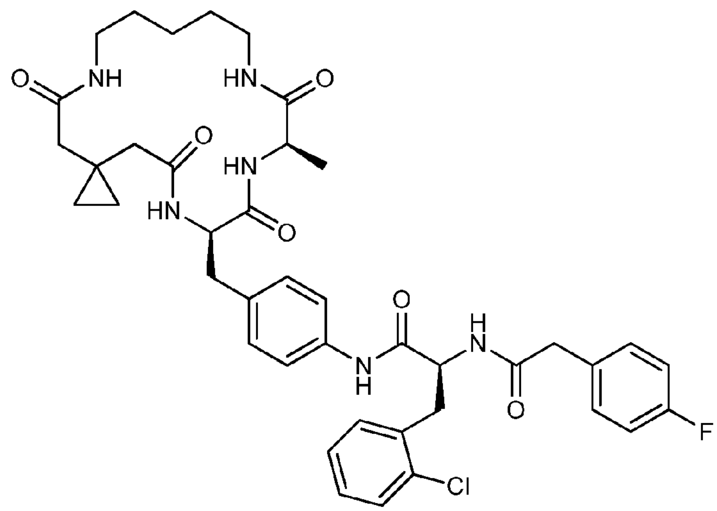 |
| 555 | 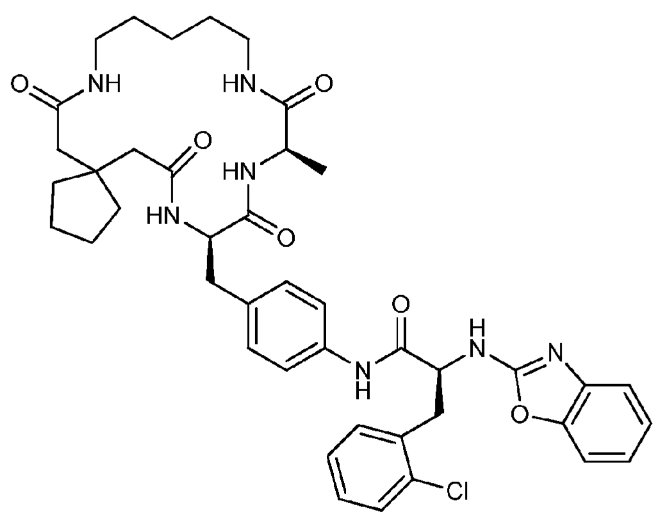 |

| Compound No. | Structure |
|---|---|
| 556 | 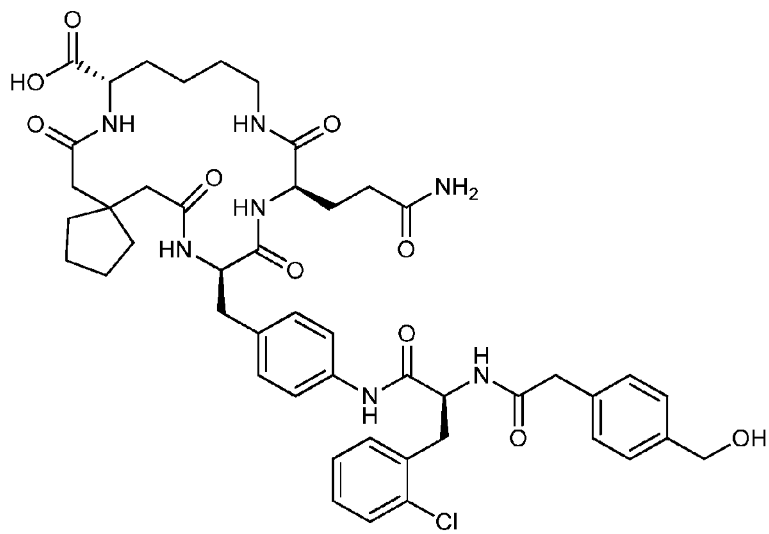 |
| 557 | 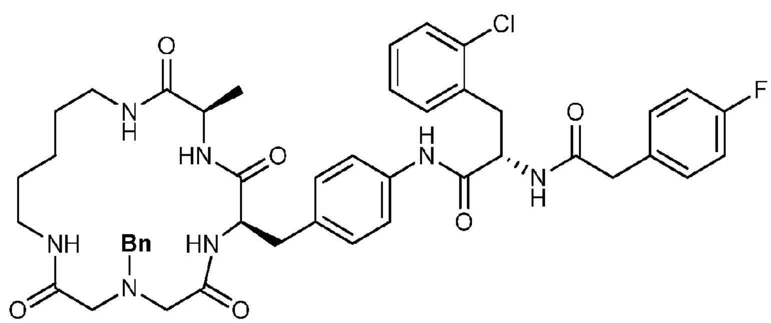 |

| Compound No. | Structure |
|---|---|
| 558 | 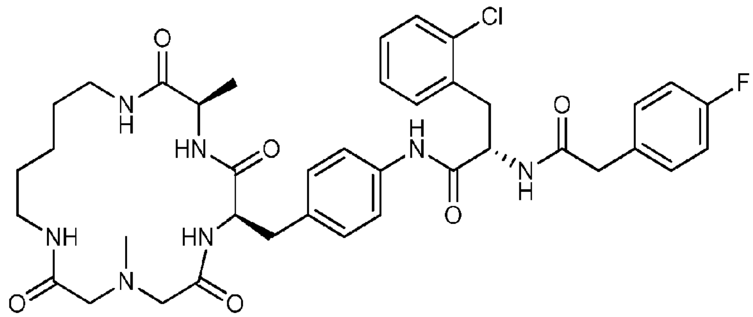 |
| 559 | 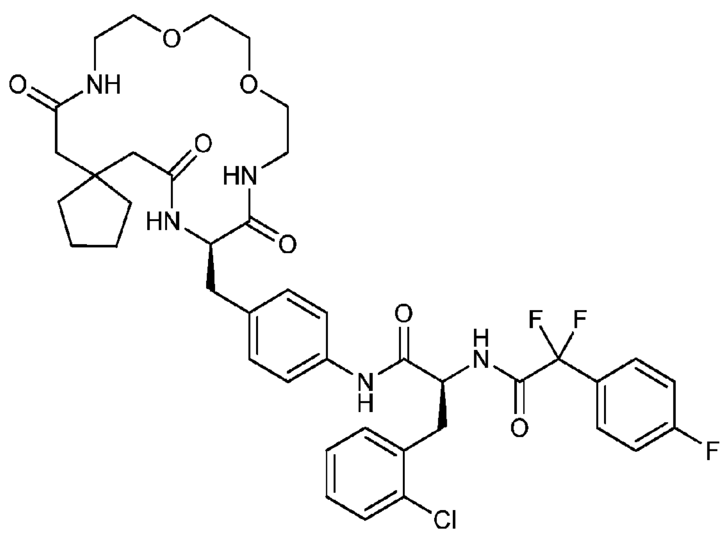 |

| Compound No. | Structure |
|---|---|
| 560 | 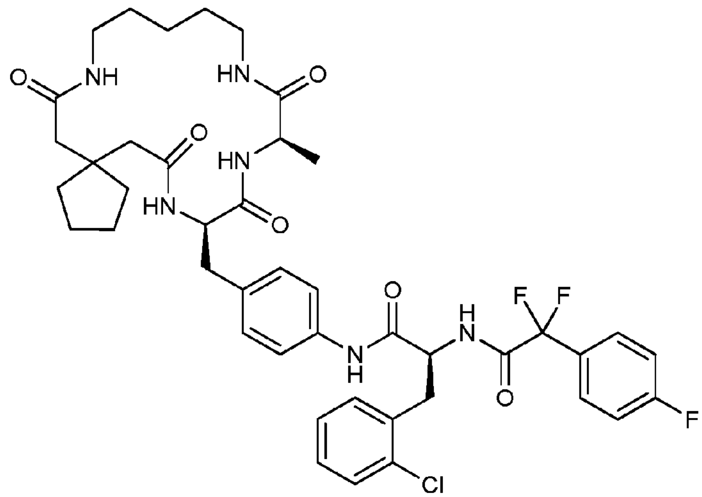 |
| 561 | 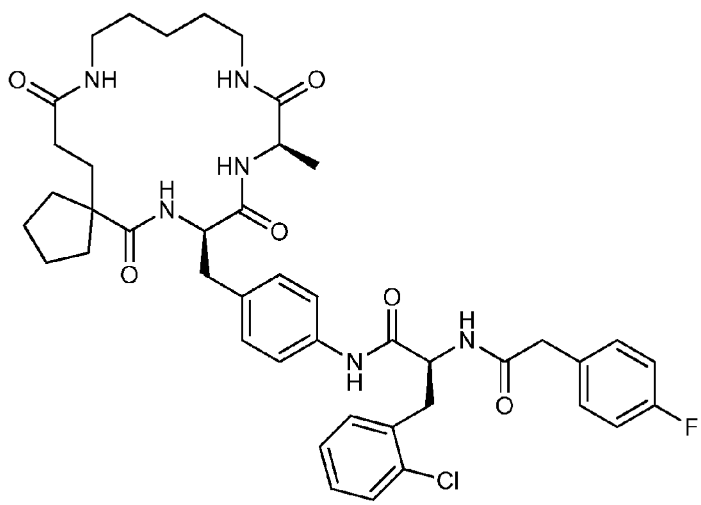 |

| Compound No. | Structure |
|---|---|
| 562 | 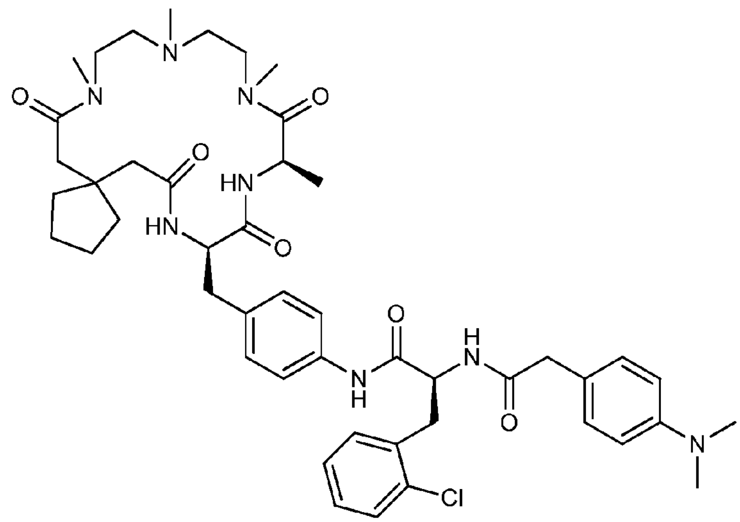 |
| 563 | 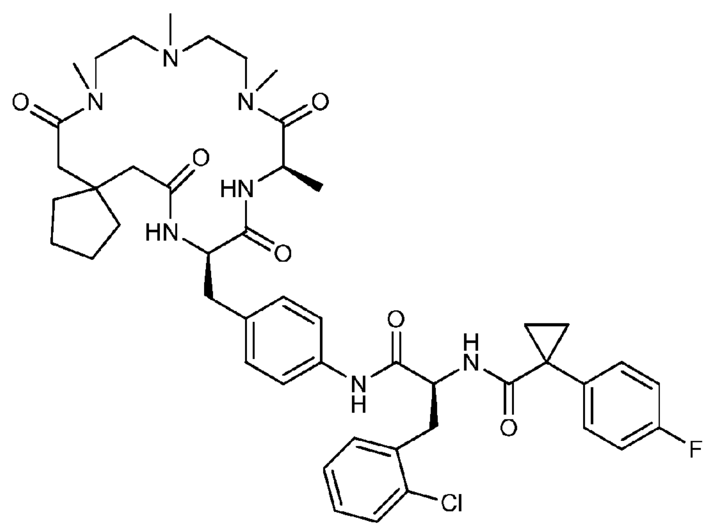 |

FIG. 12-215

| Compound No. | Structure |
|---|---|
| 564 | 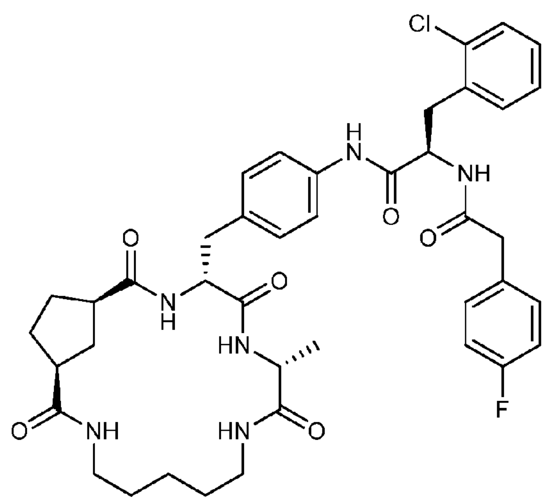 |
| 565 | 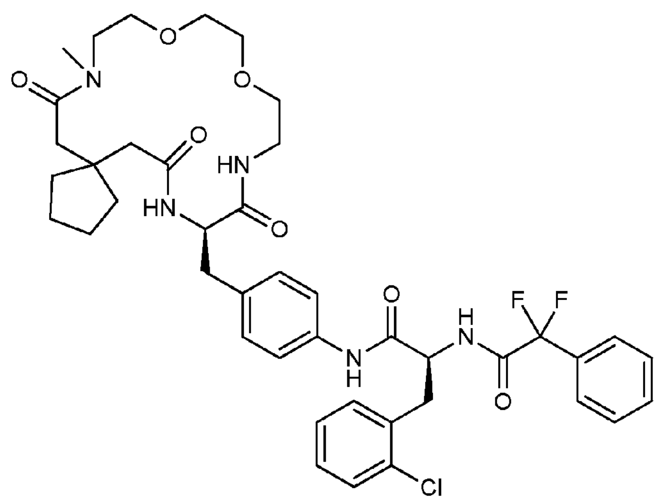 |

| Compound No. | Structure |
|---|---|
| 566 | 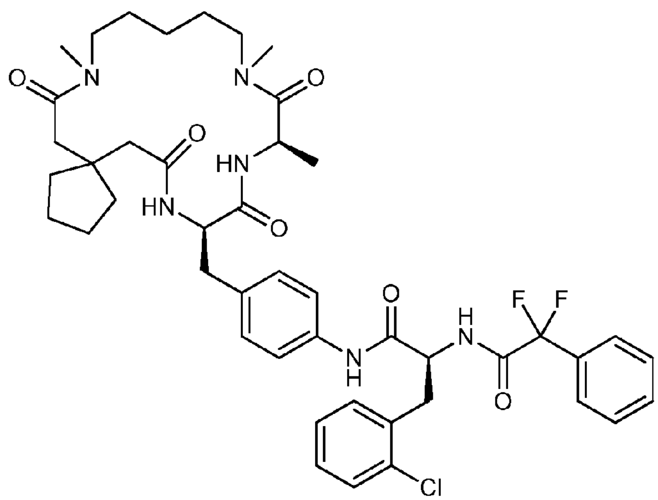 |
| 567 | 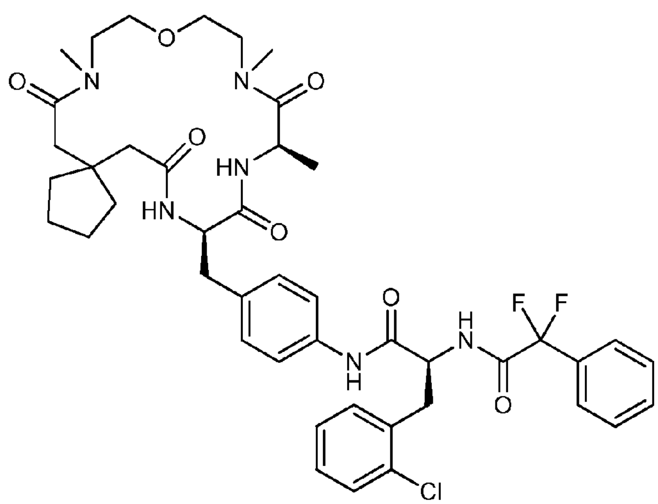 |

| Compound No. | Structure |
|---|---|
| 568 | 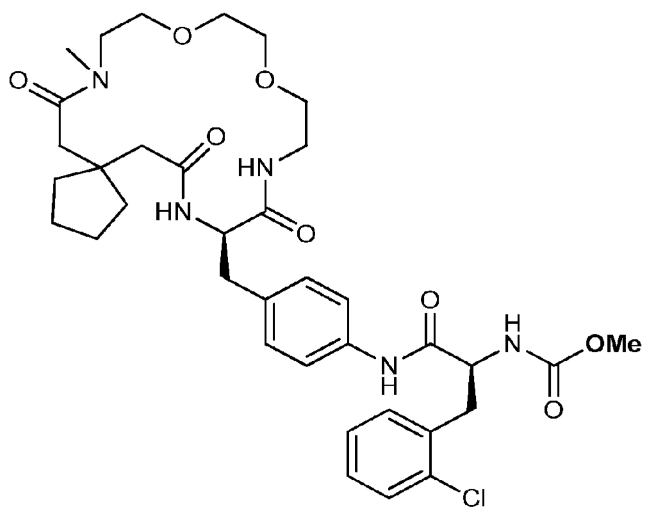 |
| 569 | 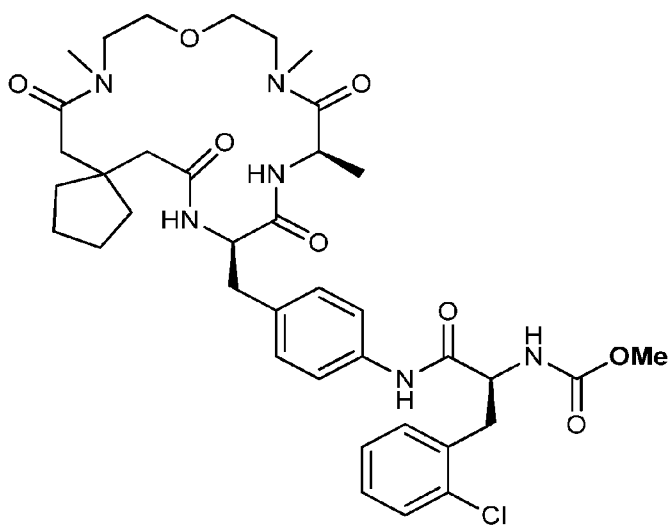 |

FIG. 12-218

| Compound No. | Structure |
|---|---|
| 570 | 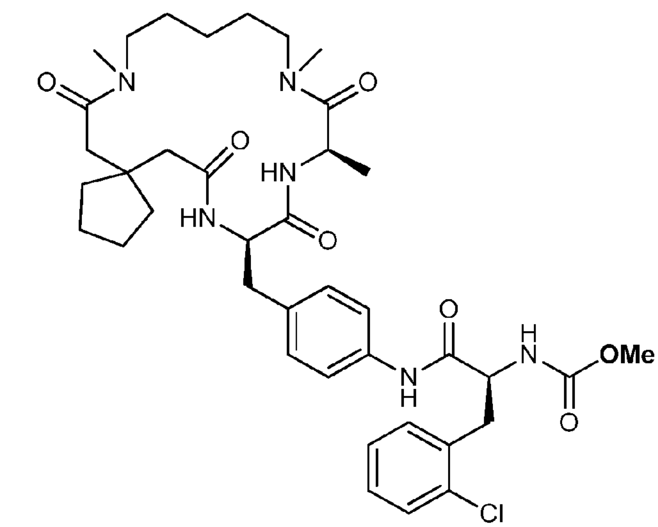 |
| 571 | 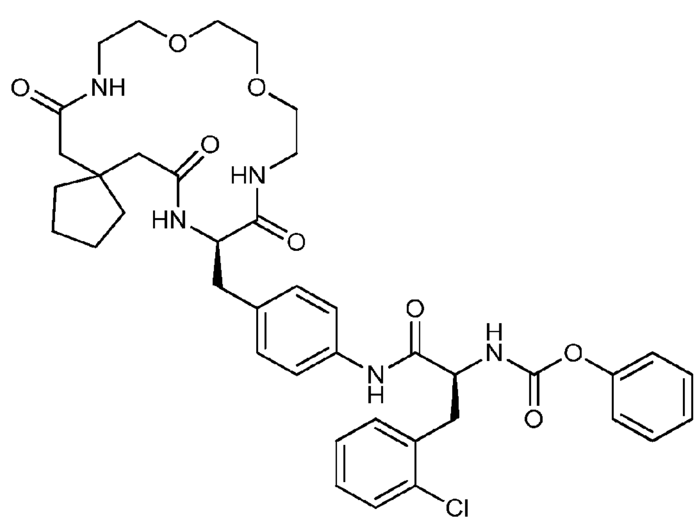 |

| Compound No. | Structure |
|---|---|
| 572 | 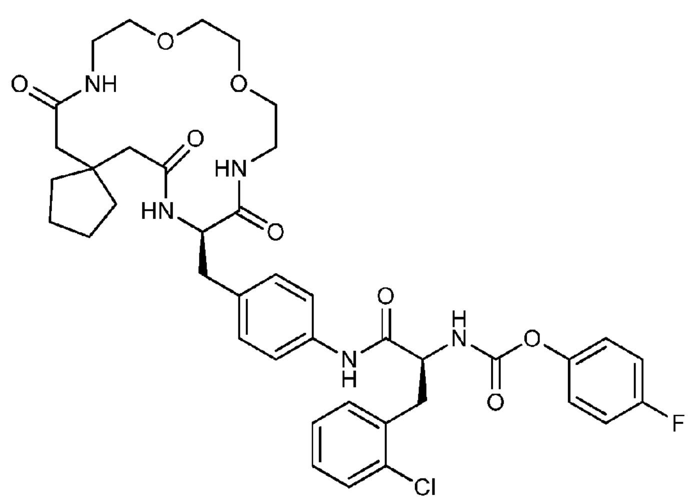 |
| 573 | 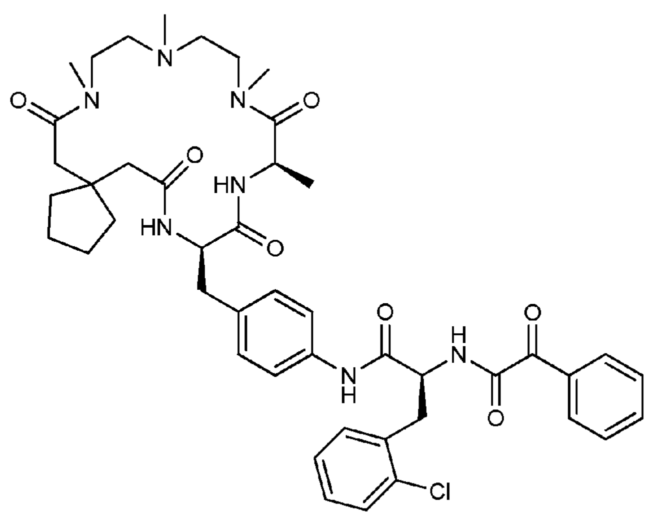 |

| Compound No. | Structure |
|---|---|
| 574 | 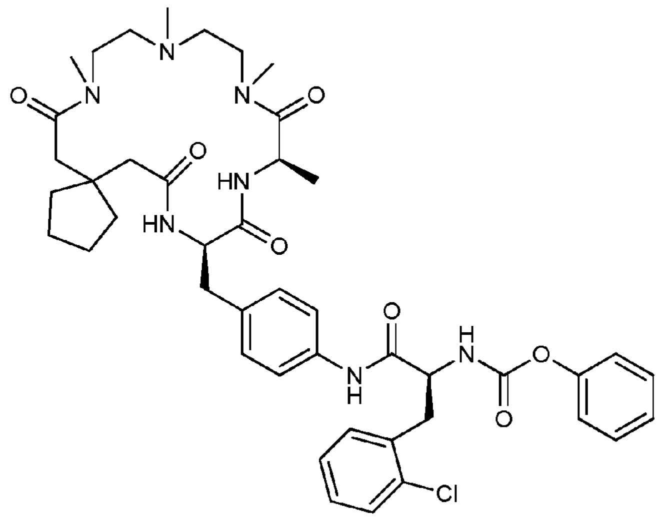 |
| 575 | 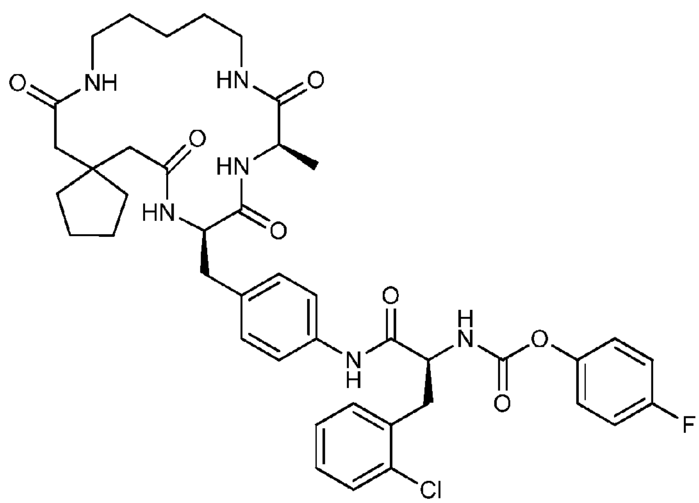 |

| Compound No. | Structure |
|---|---|
| 576 | 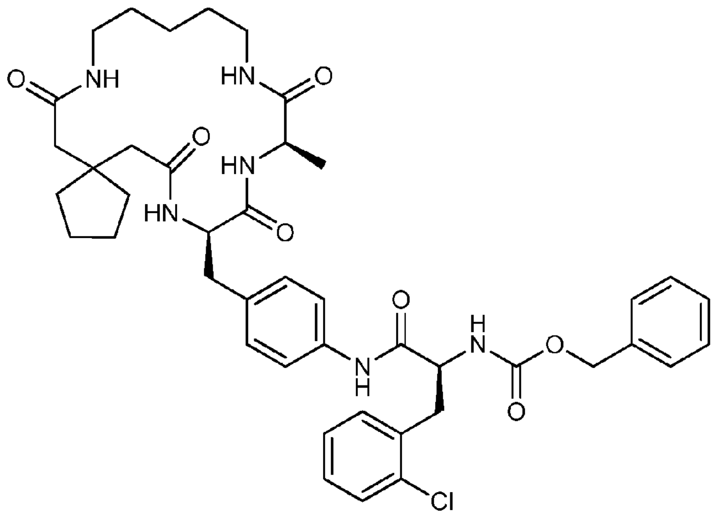 |
| 577 | 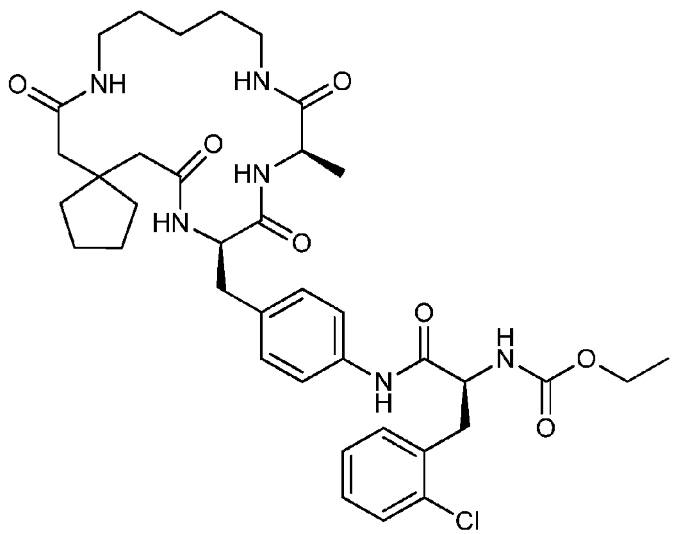 |

FIG. 12-222

| Compound No. | Structure |
|---|---|
| 578 | 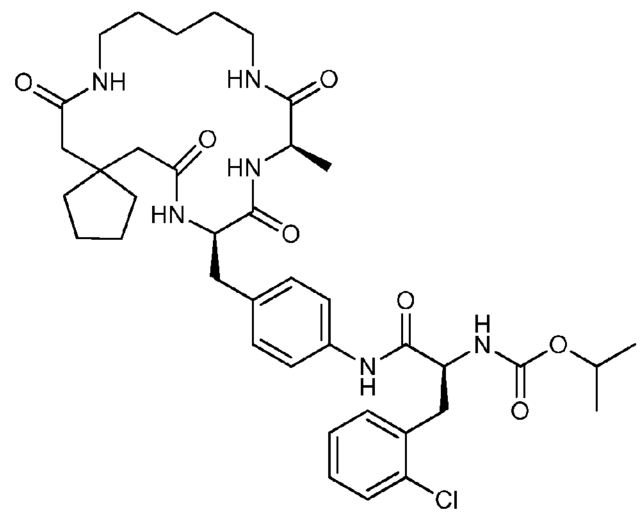 |
| 579 | 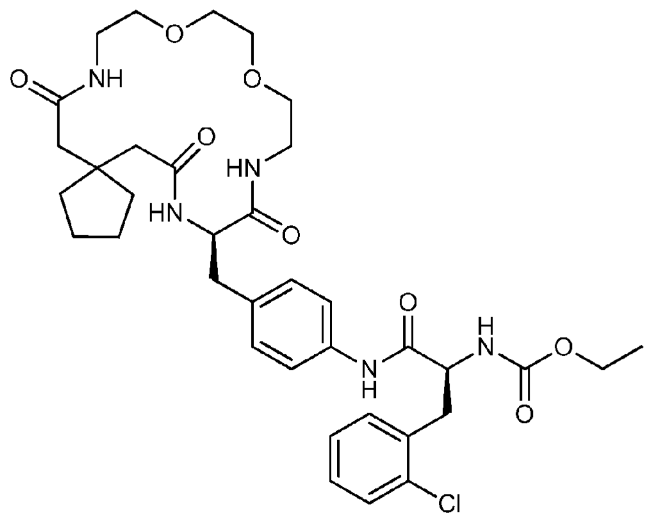 |

FIG. 12-223

| Compound No. | Structure |
|---|---|
| 580 | 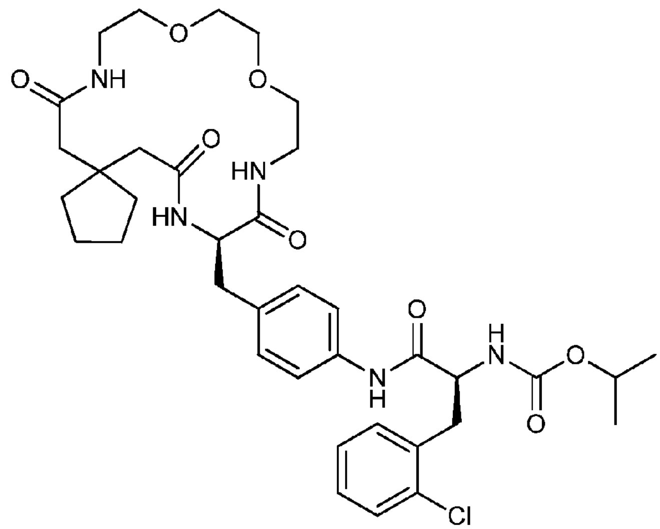 |
| 581 | 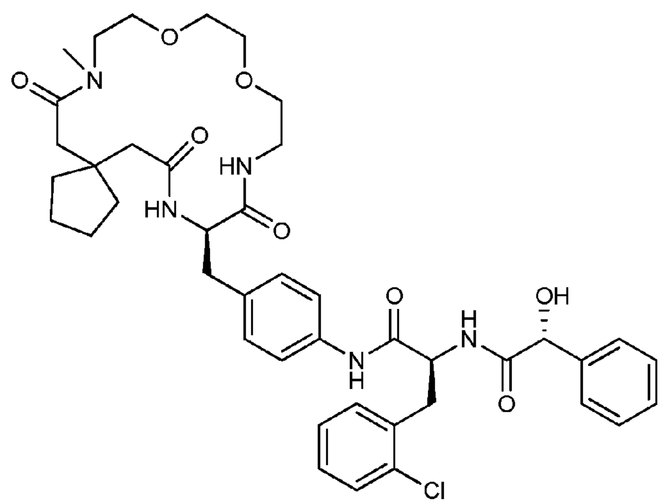 |

| Compound No. | Structure |
|---|---|
| 582 | 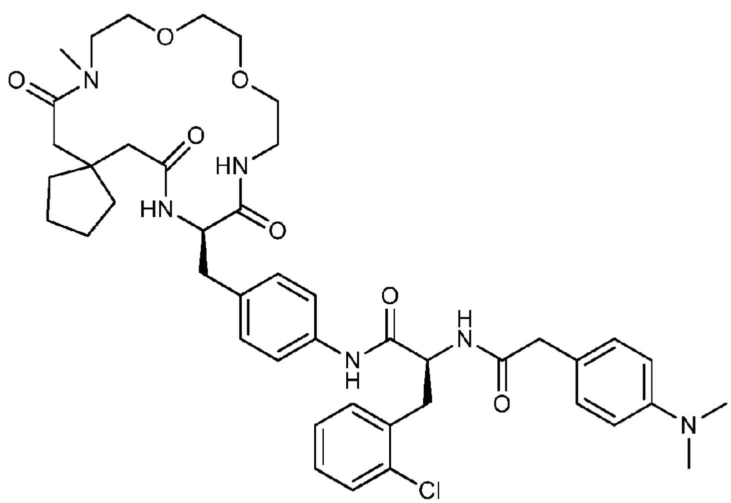 |
| 583 | 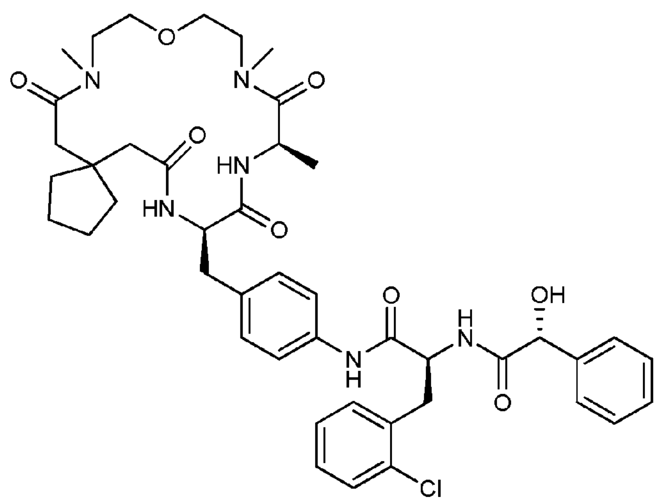 |

| Compound No. | Structure |
|---|---|
| 584 | 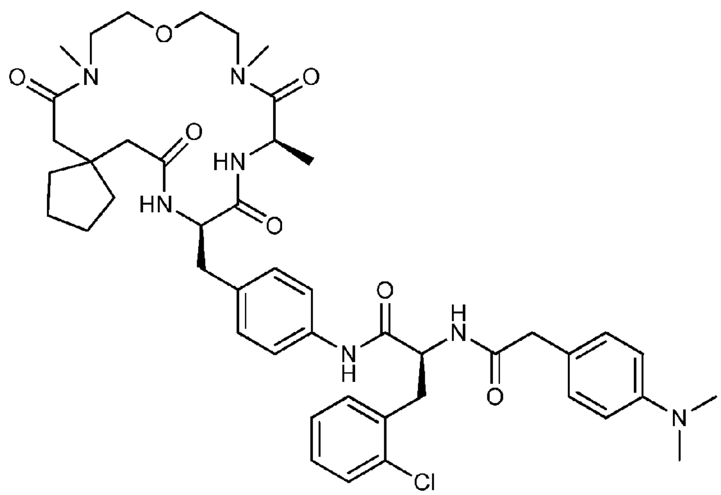 |
| 585 | 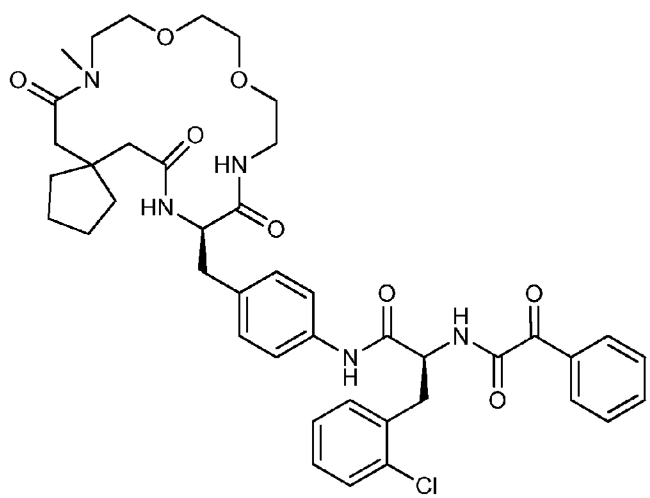 |

| Compound No. | Structure |
|---|---|
| 586 | 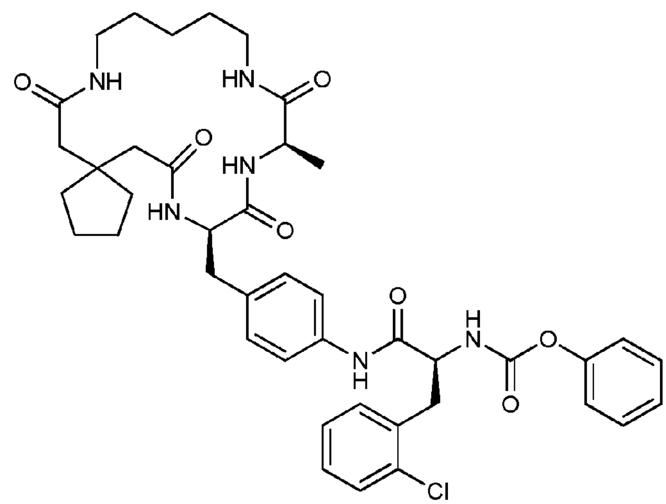 |
| 587 | 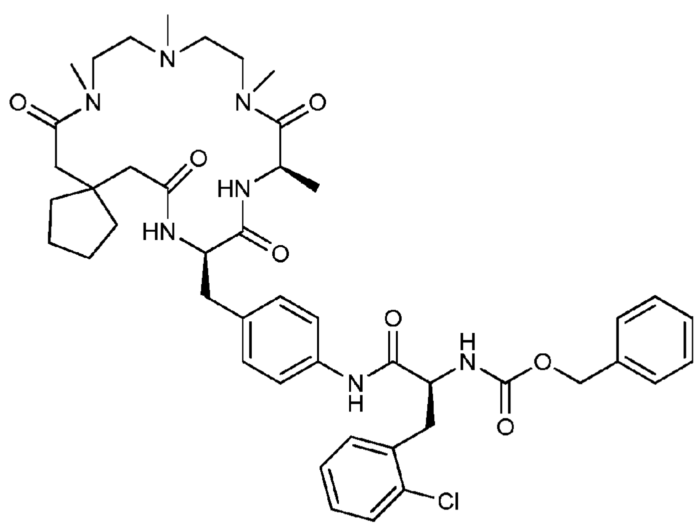 |

| Compound No. | Structure |
|---|---|
| 588 | 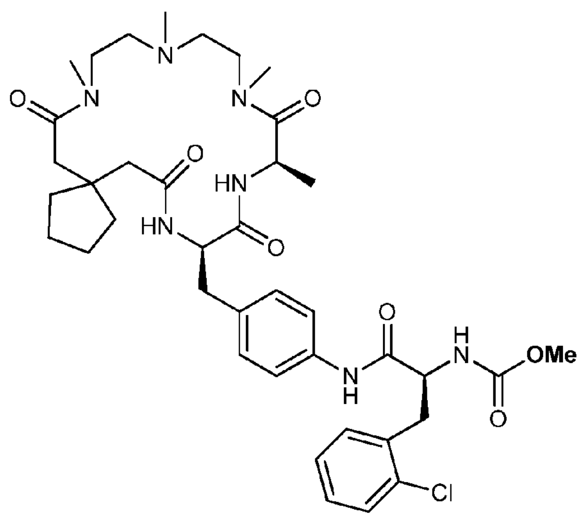 |
| 589 | 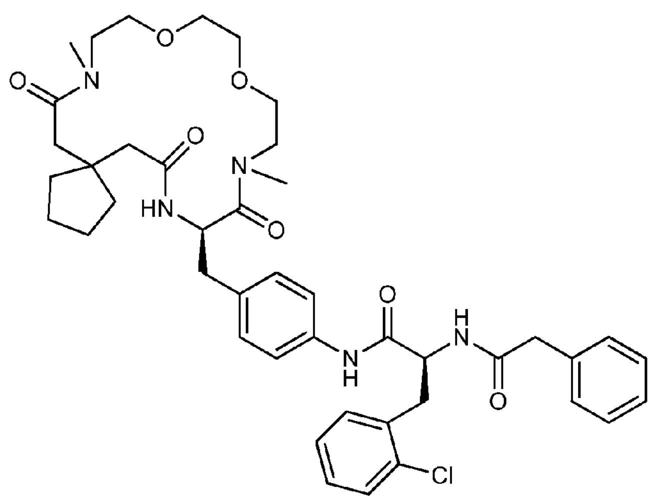 |

| Compound No. | Structure |
|---|---|
| 590 | 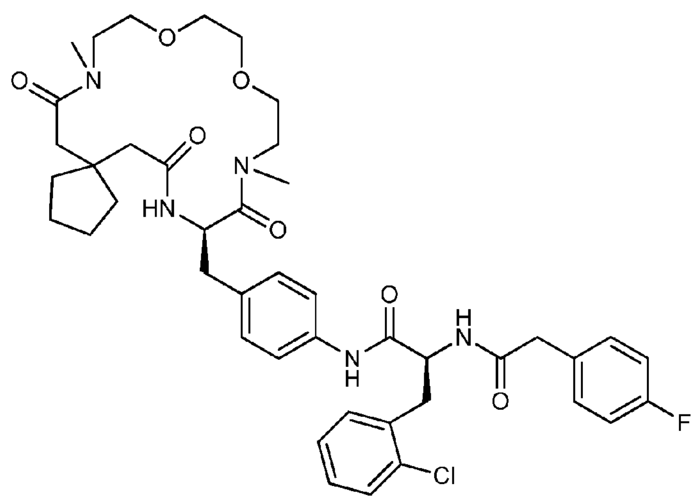 |
| 591 | 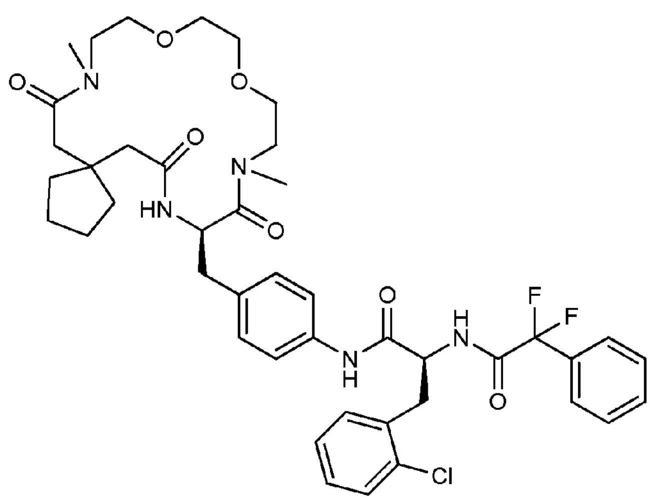 |

| Compound No. | Structure |
|---|---|
| 592 | 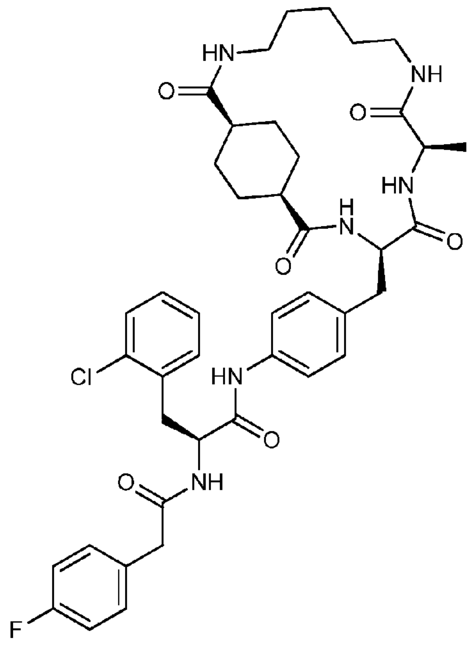 |
| 593 | 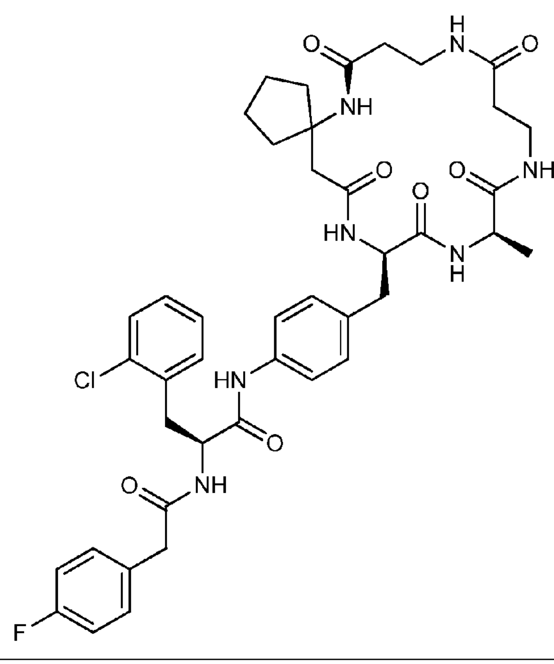 |

| Compound No. | Structure |
|---|---|
| 594 | 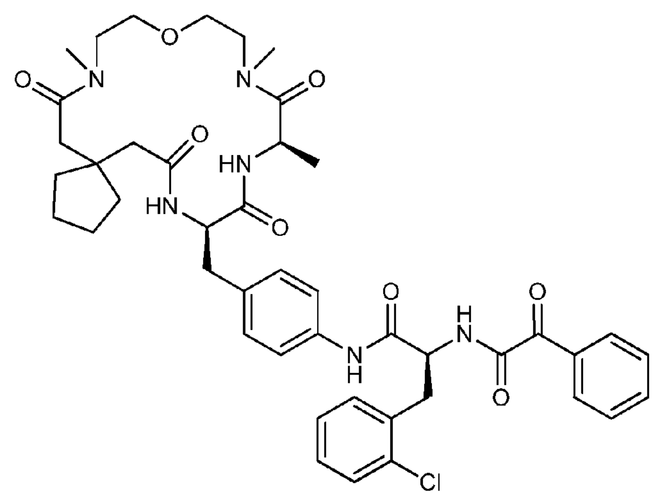 |
| 595 | 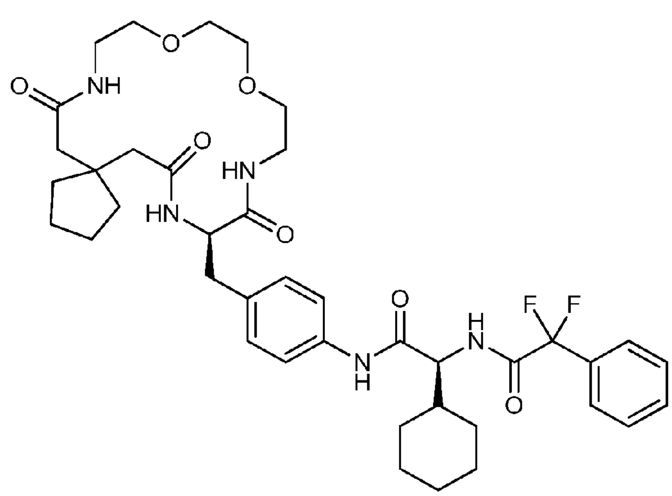 |

FIG. 12-231

| Compound No. | Structure |
|---|---|
| 596 | 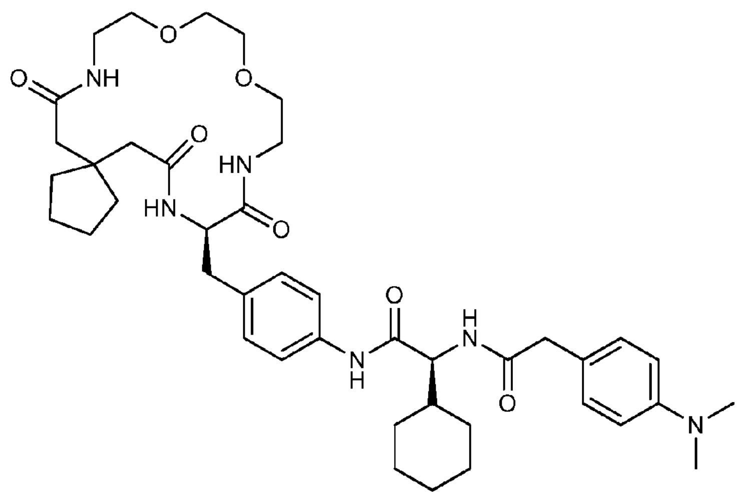 |
| 597 | 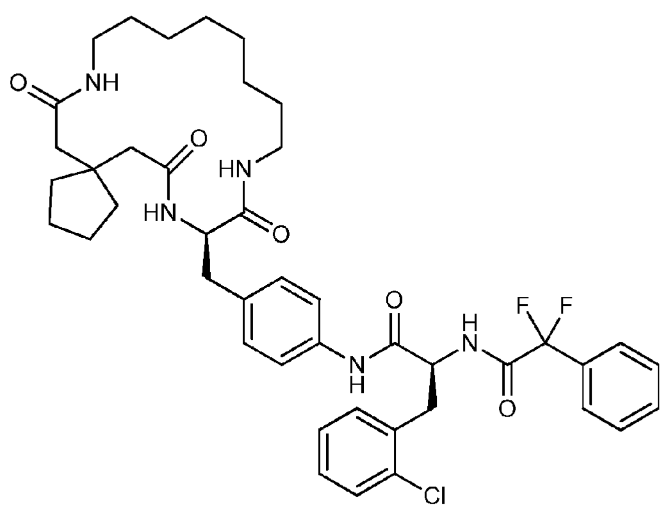 |

FIG. 12-232

| Compound No. | Structure |
|---|---|
| 598 | 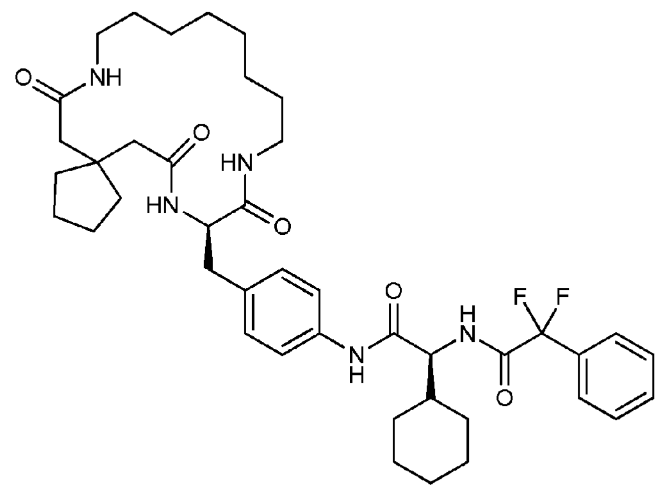 |
| 599 | 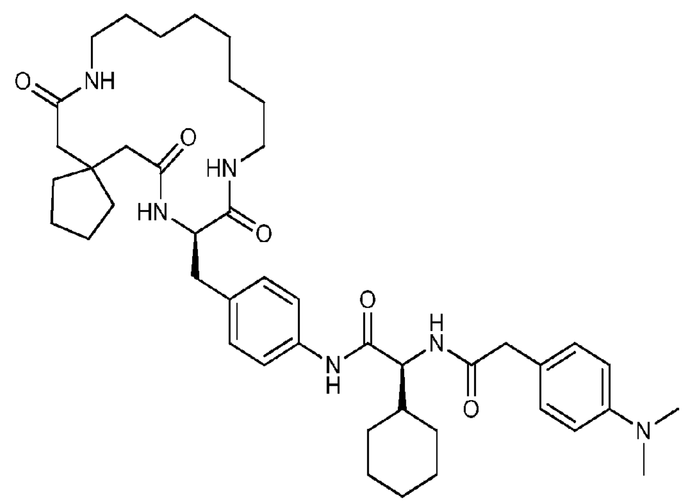 |

FIG. 12-233

| Compound No. | Structure |
|---|---|
| 600 | 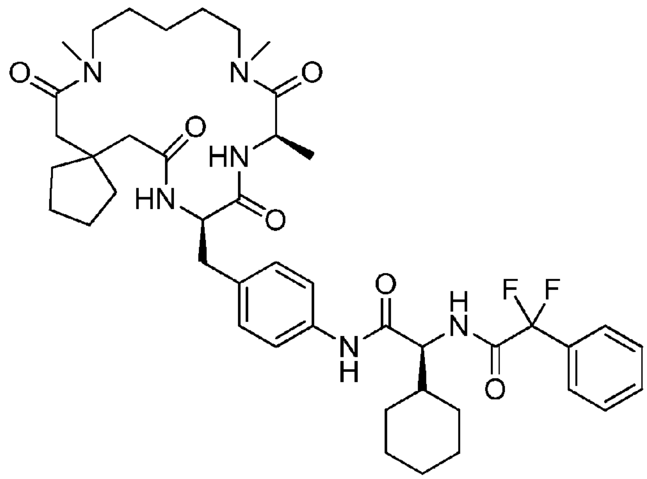 |
| 601 | 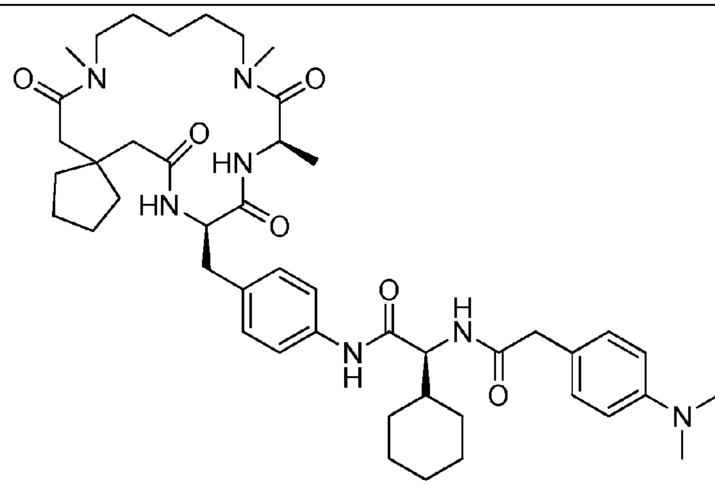 |

| Compound No. | Structure |
|---|---|
| 602 | 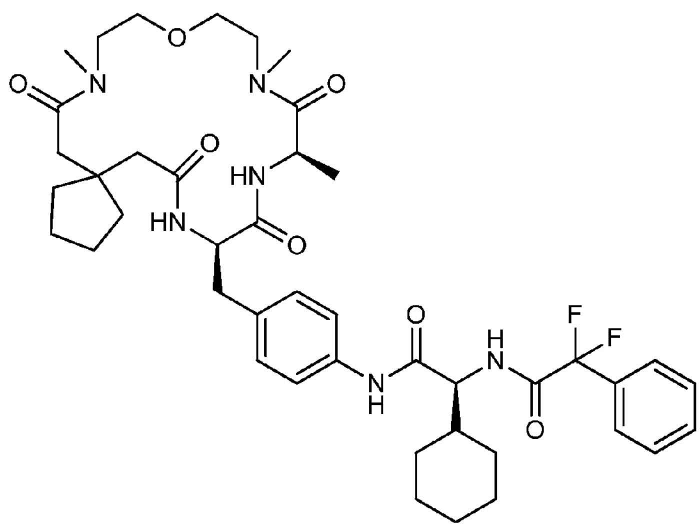 |
| 603 | 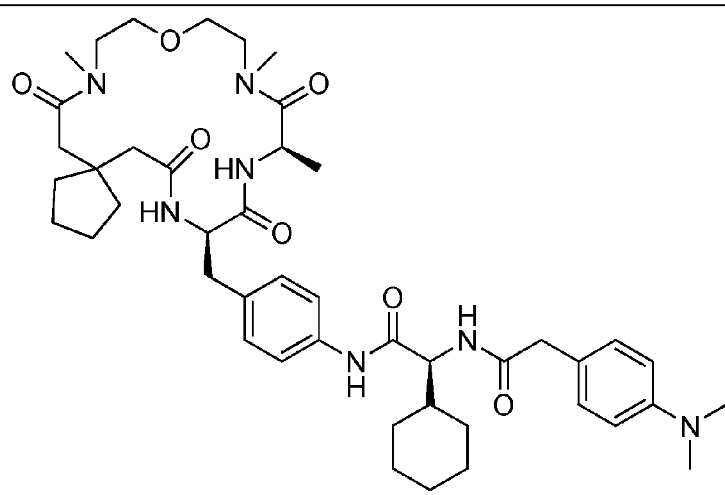 |

| Compound No. | Structure |
|---|---|
| 604 | 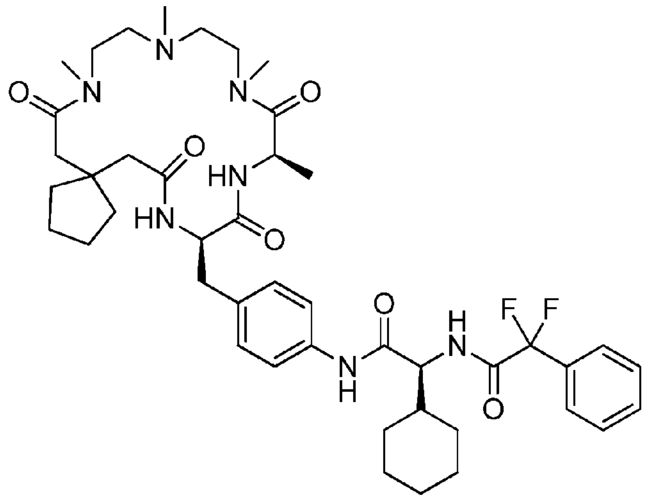 |
| 605 | 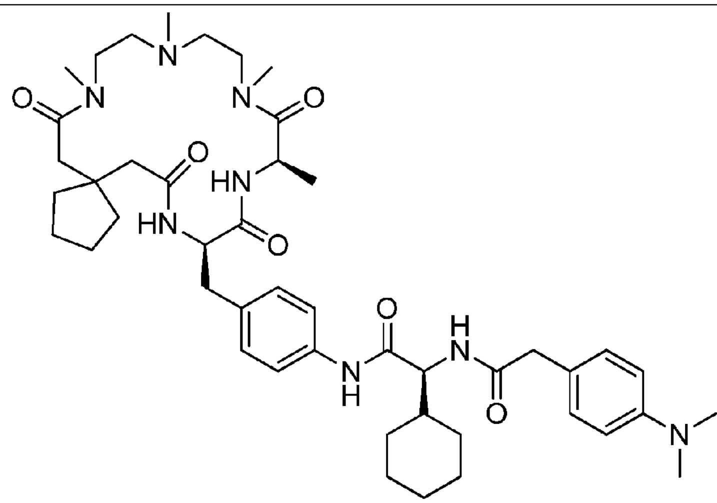 |

| Compound No. | Structure |
|---|---|
| 606 | 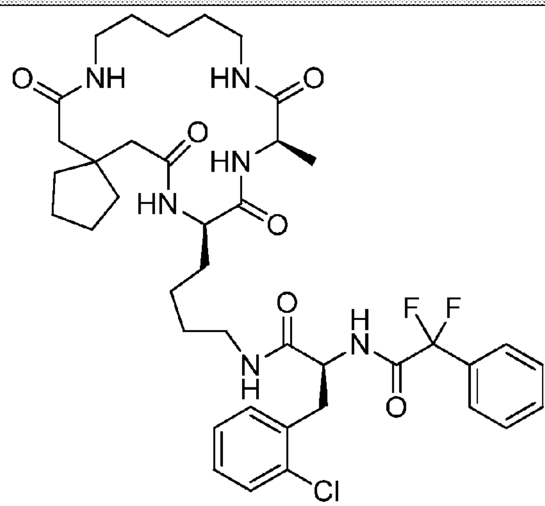 |
| 607 | 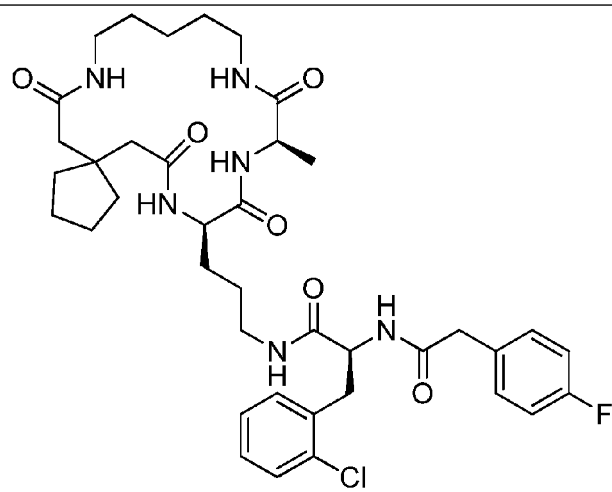 |

| Compound No. | Structure |
|---|---|
| 608 | 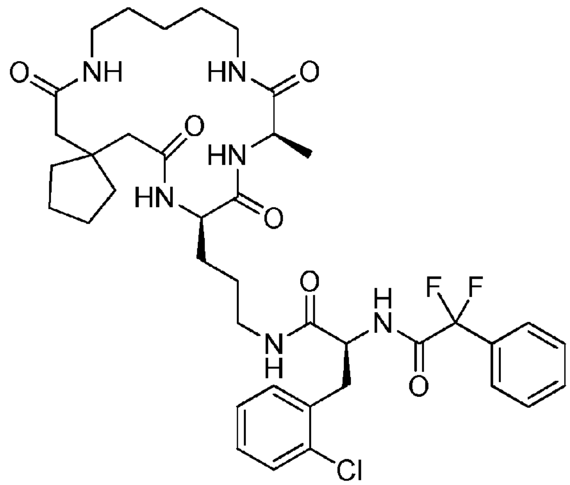 |
| 609 | 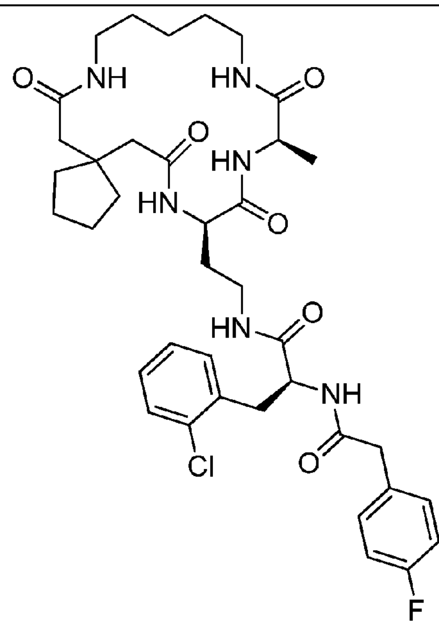 |

| Compound No. | Structure |
|---|---|
| 610 | 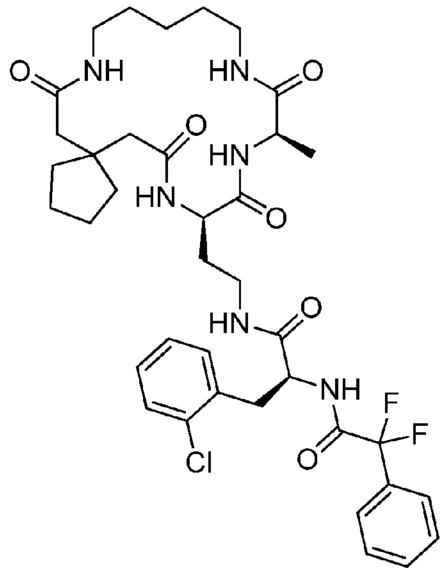 |
| 611 | 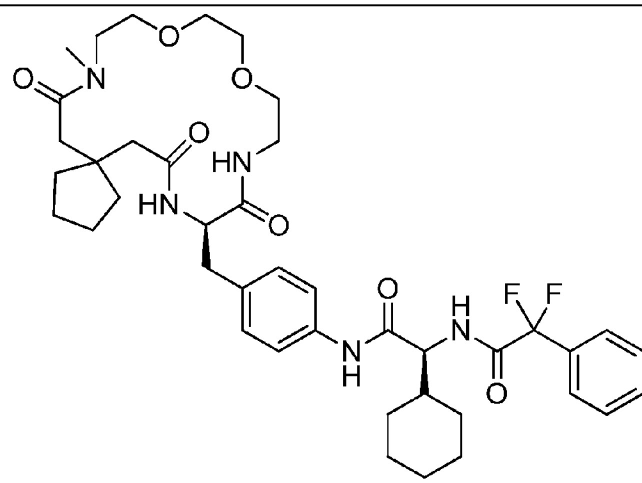 |

FIG. 12-239

| Compound No. | Structure |
|---|---|
| 612 | 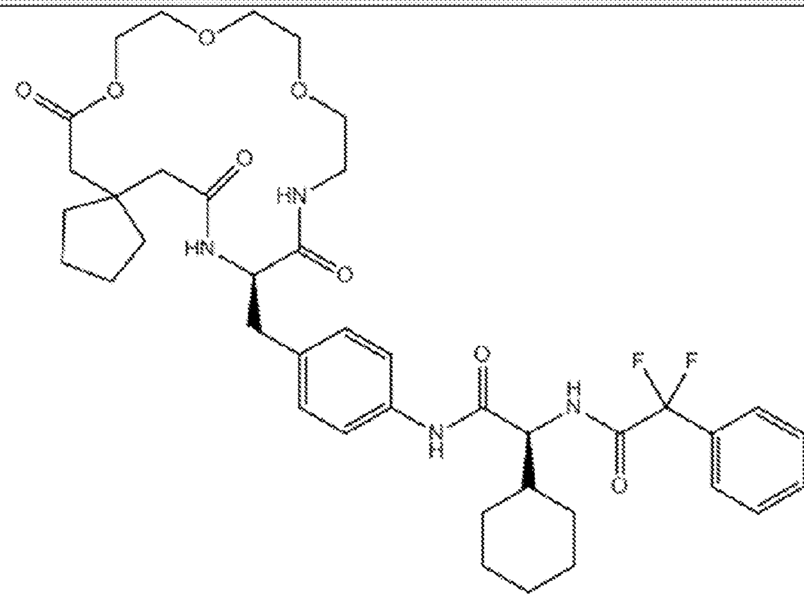 |
| 613 | 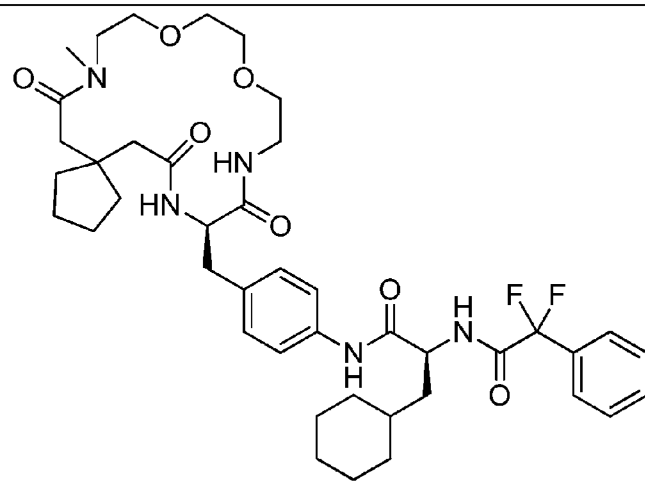 |

| Compound No. | Structure |
|---|---|
| 614 | 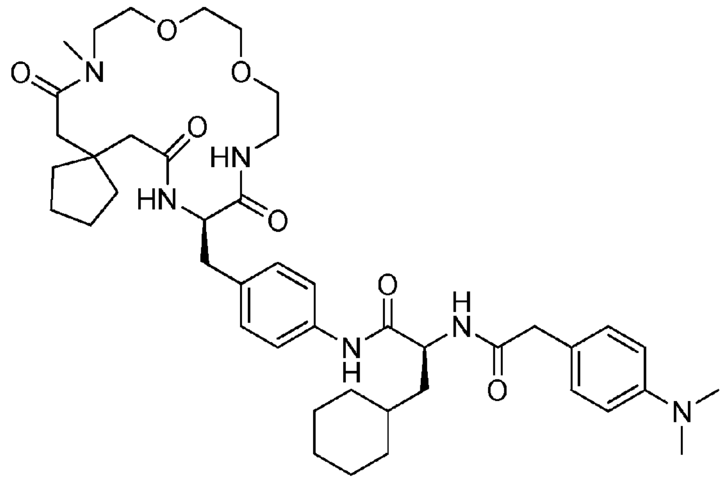 |
| 615 | 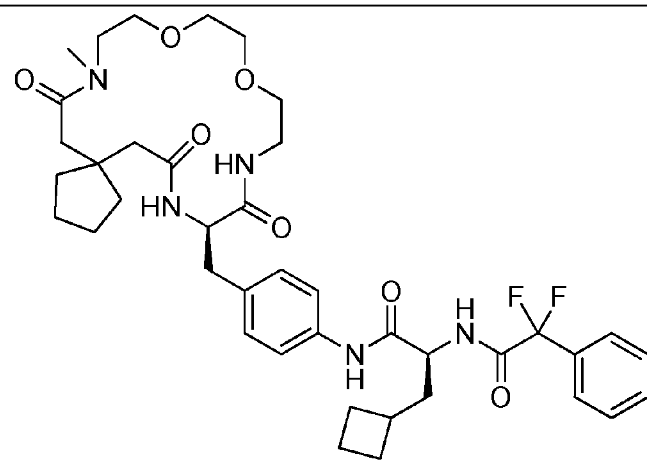 |

| Compound No. | Structure |
|---|---|
| 616 | 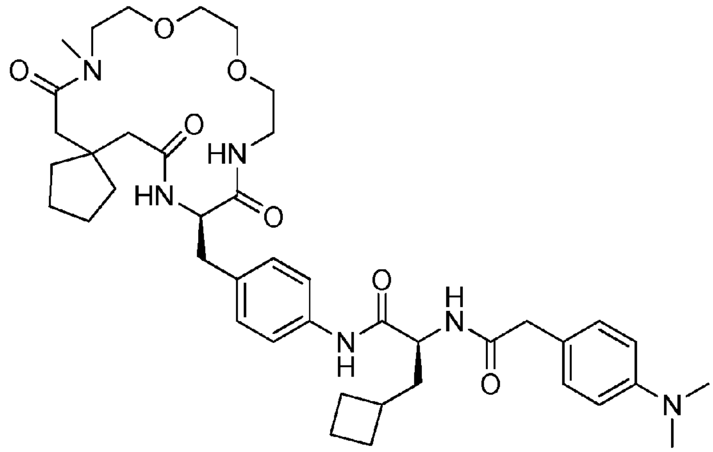 |
| 617 | 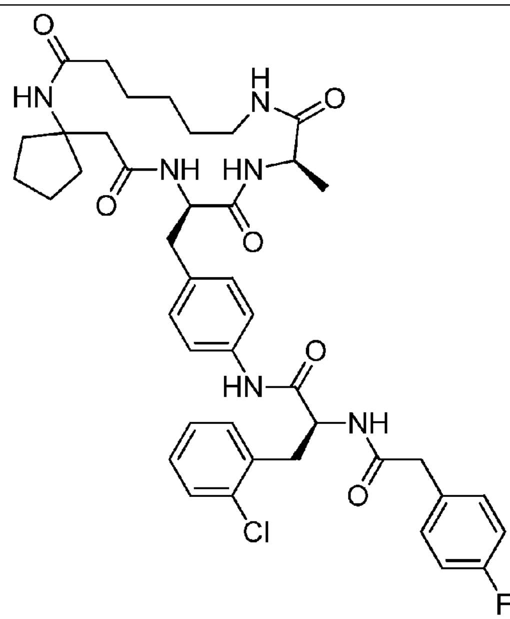 |

FIG. 12-242

| Compound No. | Structure |
|---|---|
| 618 | 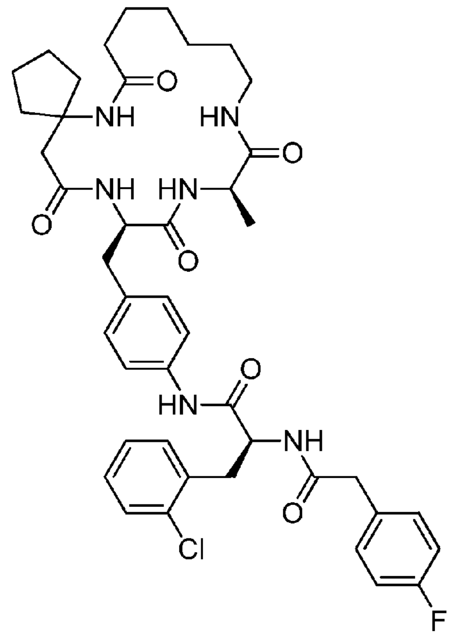 |
| 619 | 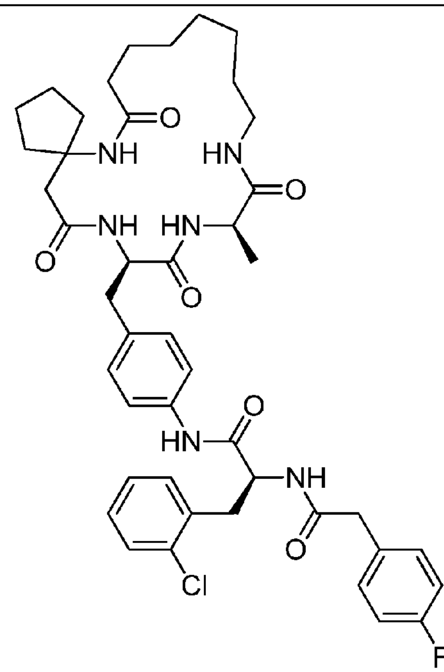 |

| Compound No. | Structure |
|---|---|
| 620 | 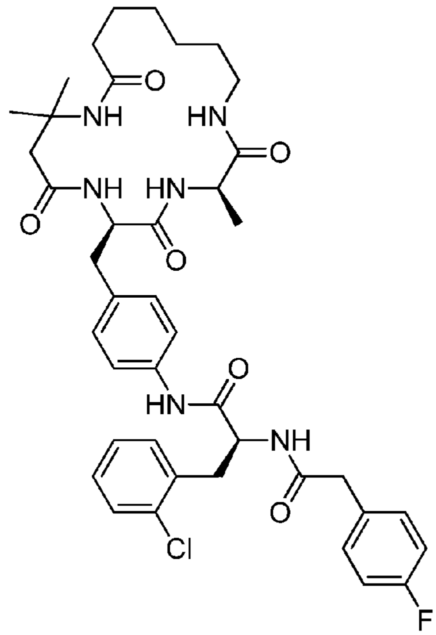 |
| 621 | 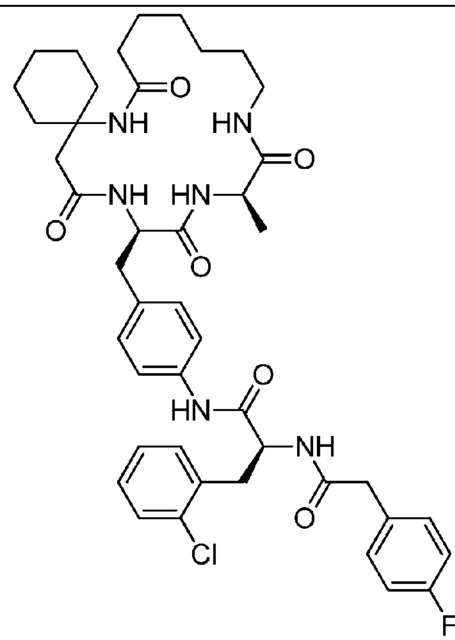 |

| Compound No. | Structure |
|---|---|
| 622 | 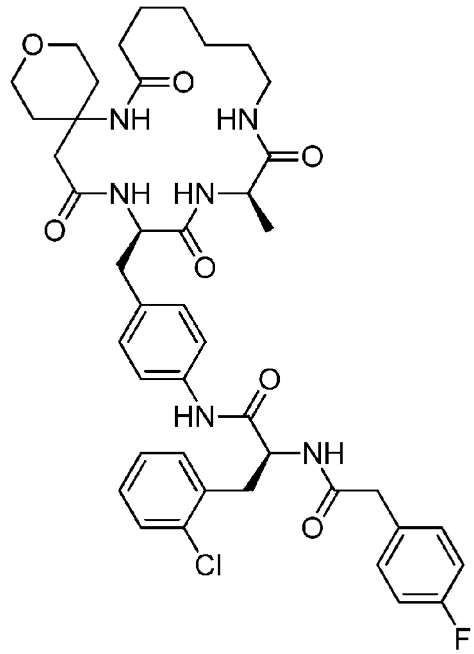 |
| 623 | 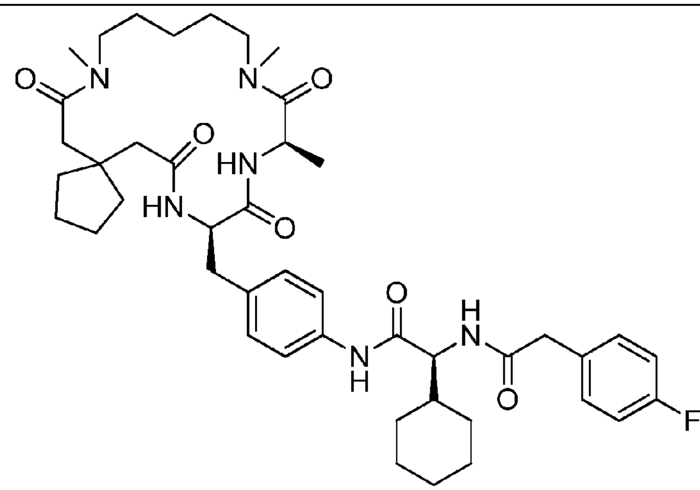 |

| Compound No. | Structure |
|---|---|
| 624 | 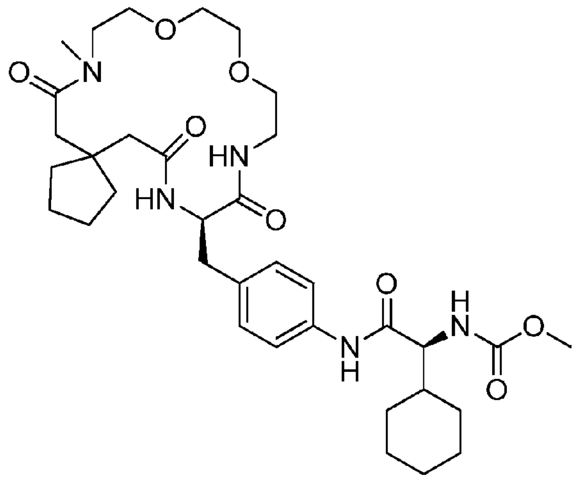 |
| 625 | 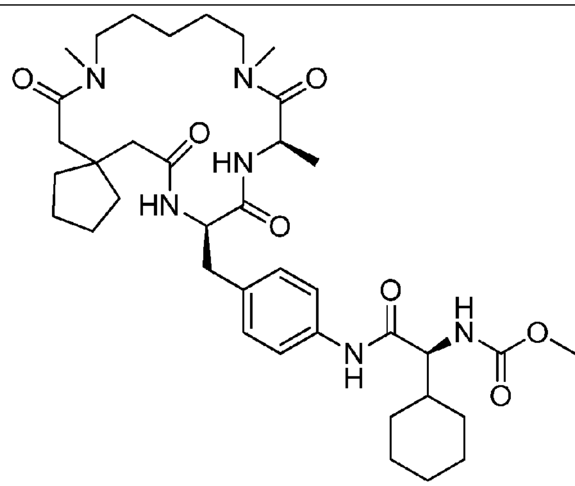 |

| Compound No. | Structure |
|---|---|
| 626 | 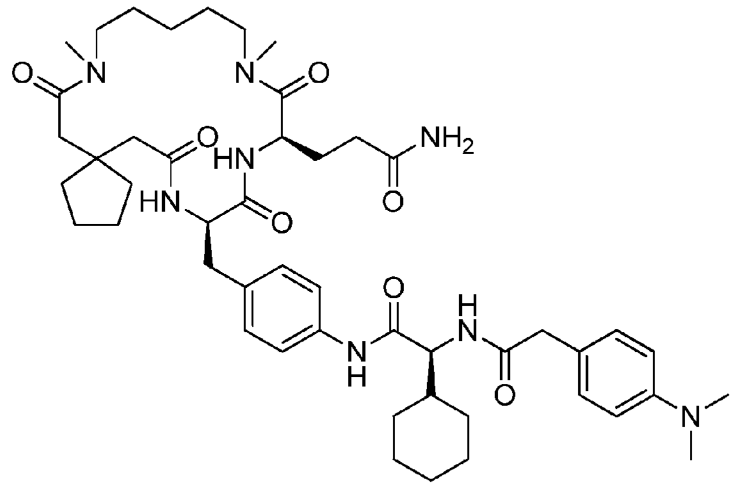 |
| 627 | 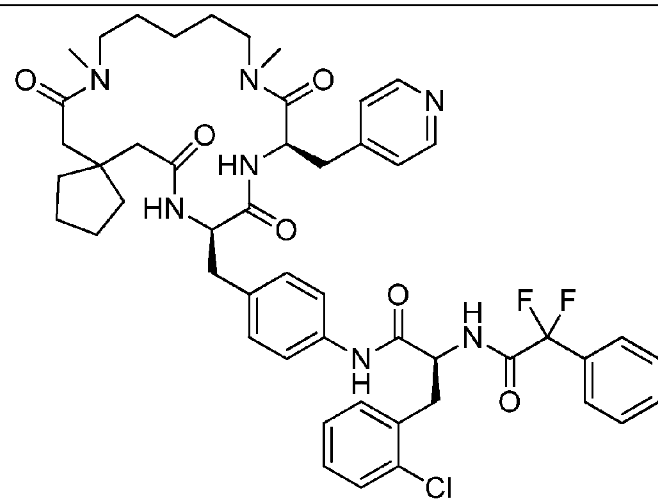 |

| Compound No. | Structure |
|---|---|
| 628 | 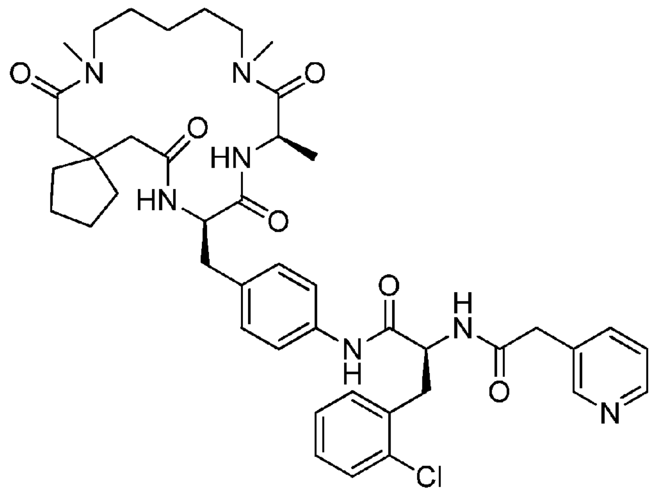 |
| 629 | 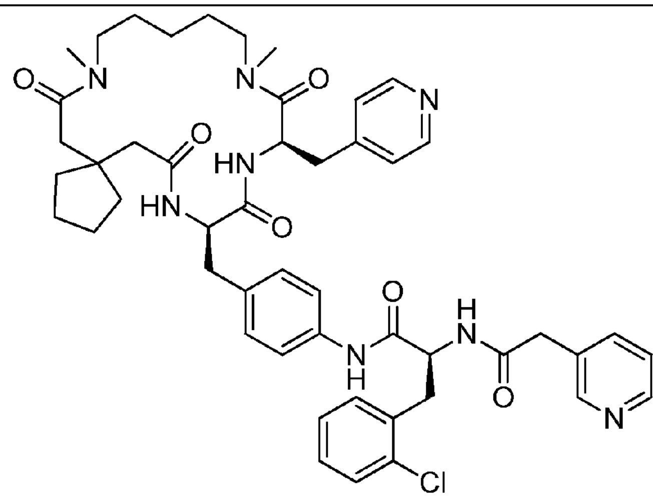 |

FIG. 12-248

| Compound No. | Structure |
|---|---|
| 630 | 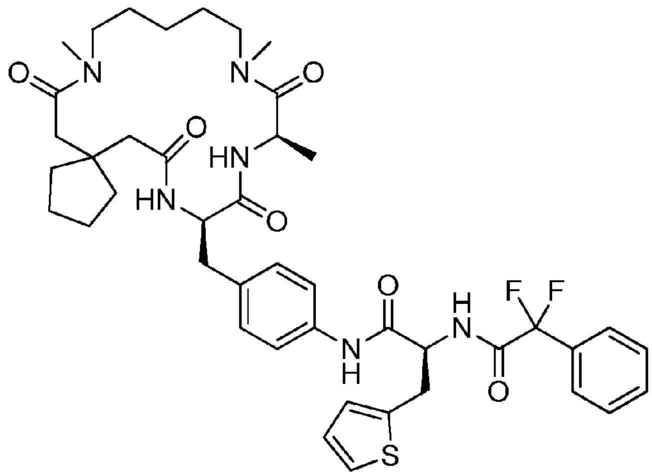 |
| 631 | 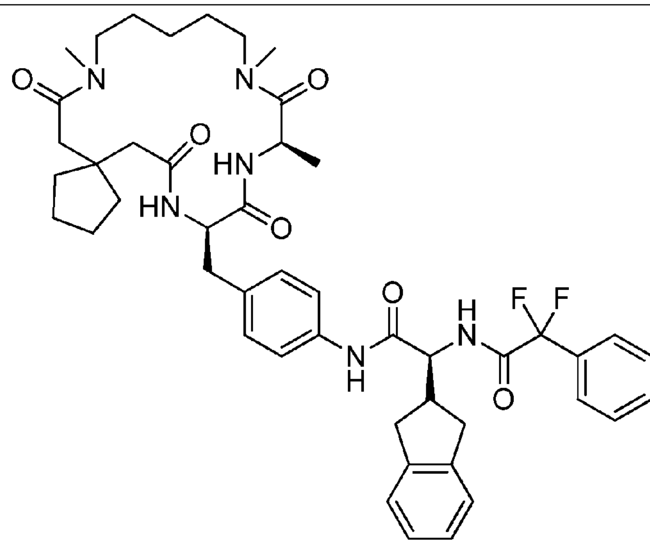 |

| Compound No. | Structure |
|---|---|
| 632 | 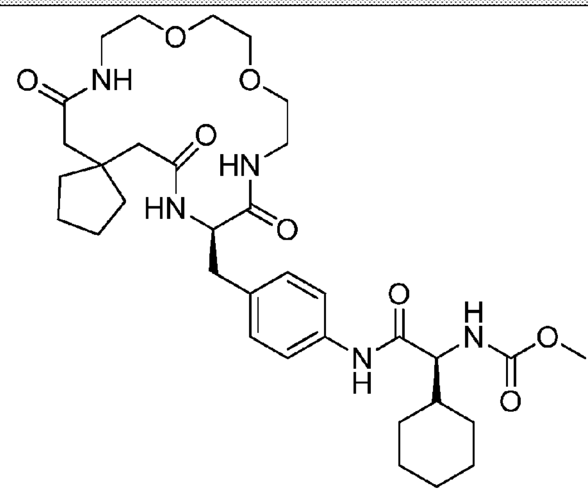 |
| 633 | 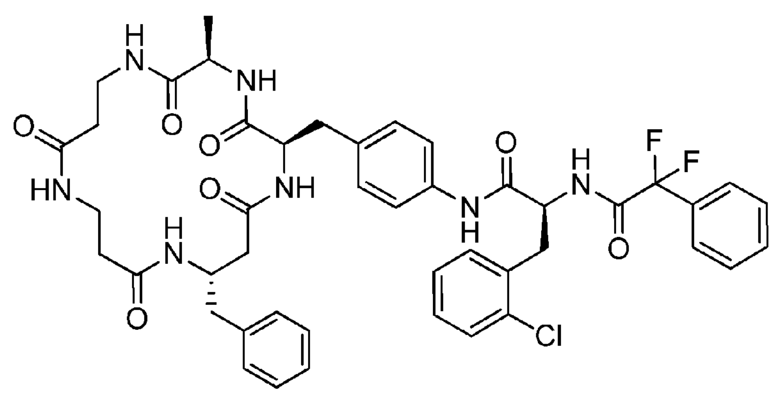 |

FIG. 12-250

| Compound No. | Structure |
|---|---|
| 634 | 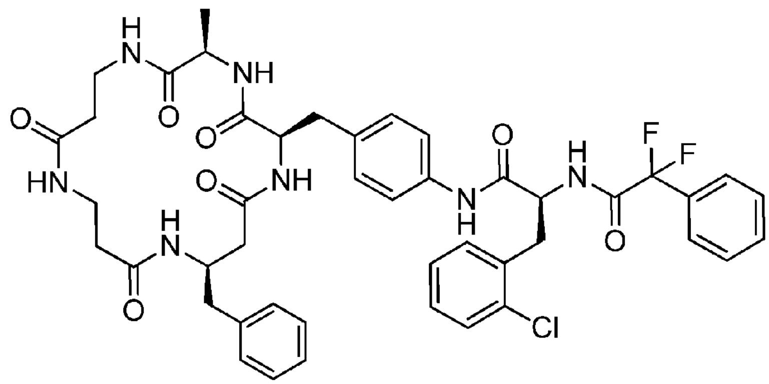 |
| 635 | 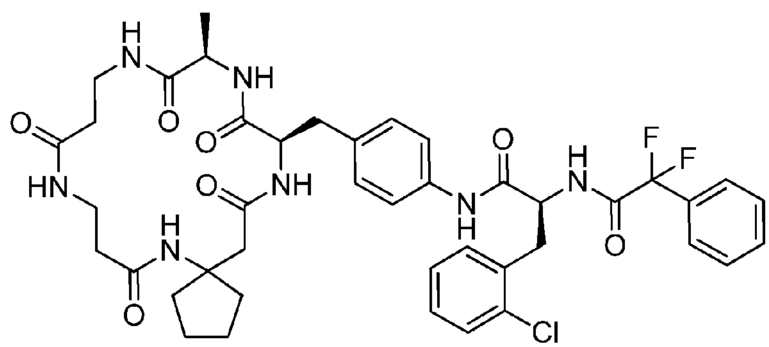 |
| 636 | 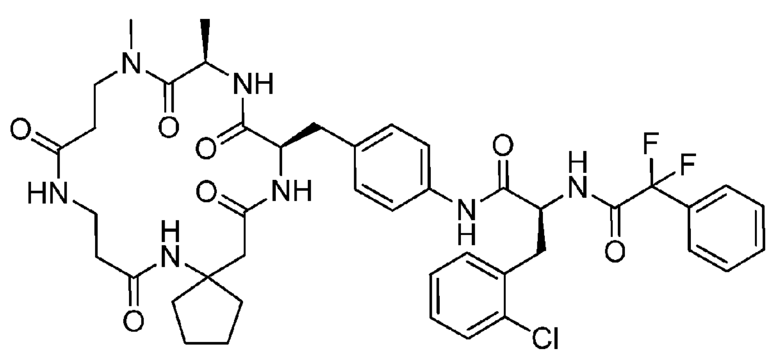 |

| Compound No. | Structure |
|---|---|
| 637 | 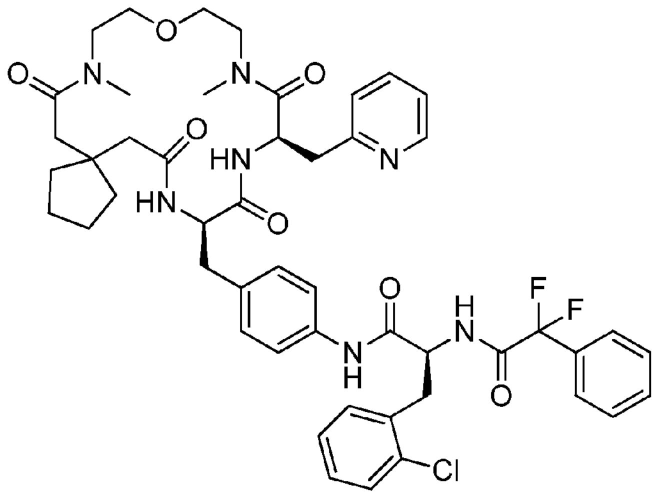 |
| 638 | 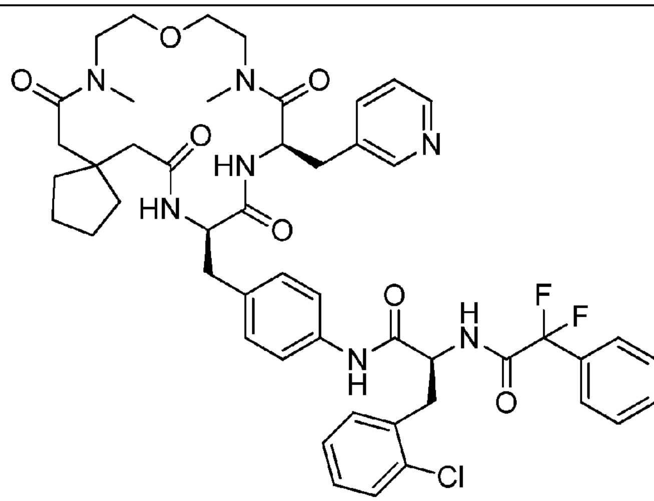 |

| Compound No. | Structure |
|---|---|
| 639 | 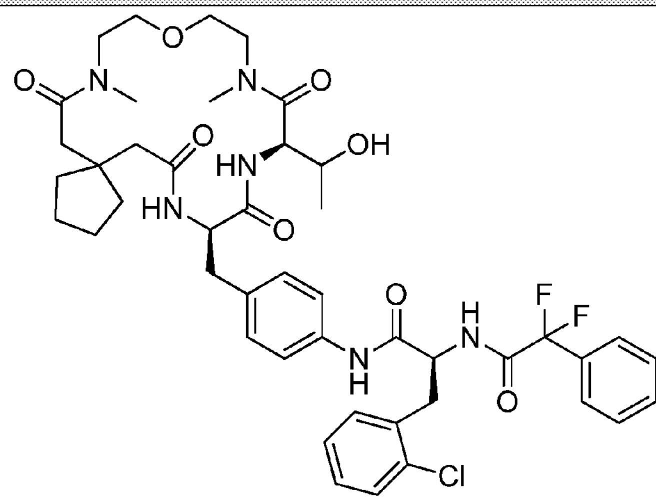 |
| 640 | 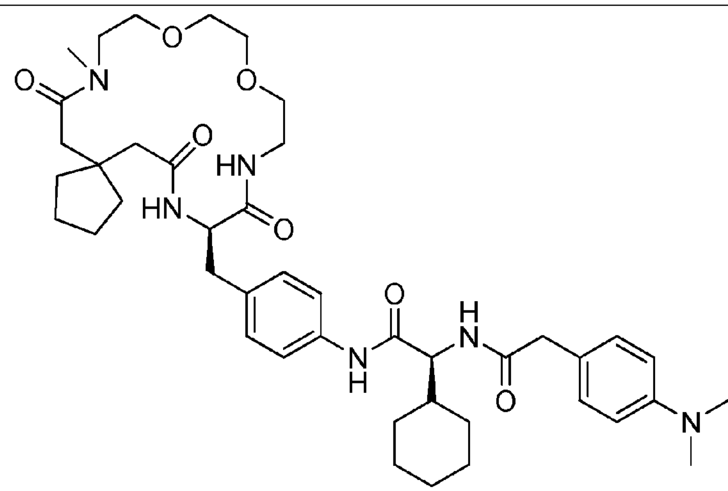 |

| Compound No. | Structure |
|---|---|
| 641 | 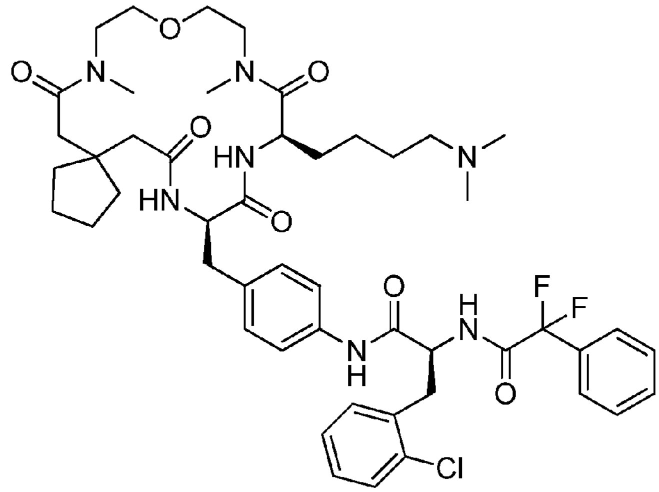 |
| 642 | 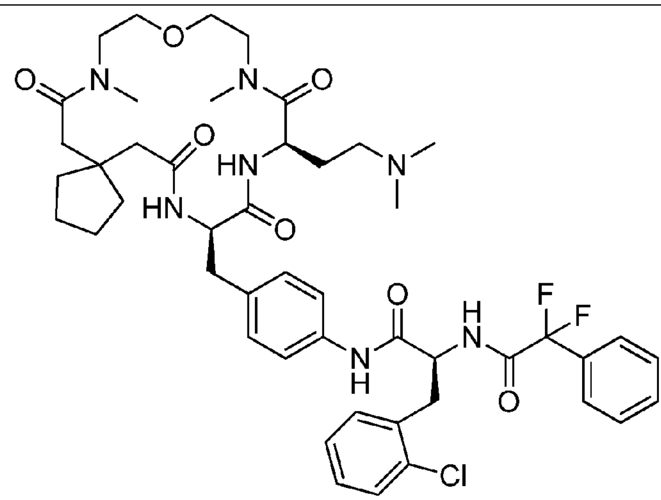 |

| Compound No. | Structure |
|---|---|
| 643 | 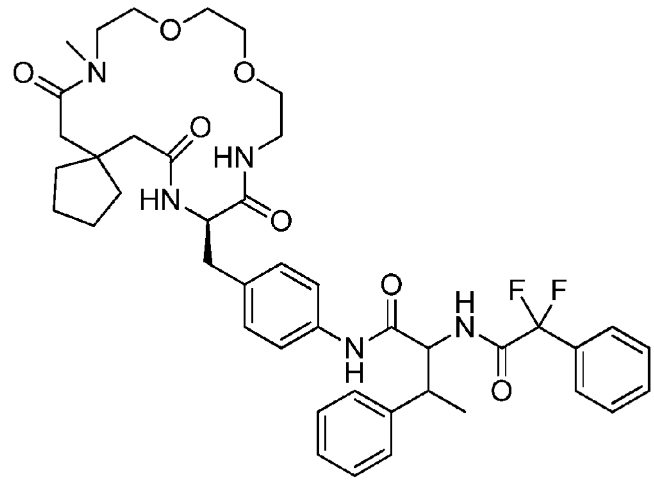 |
| 644 | 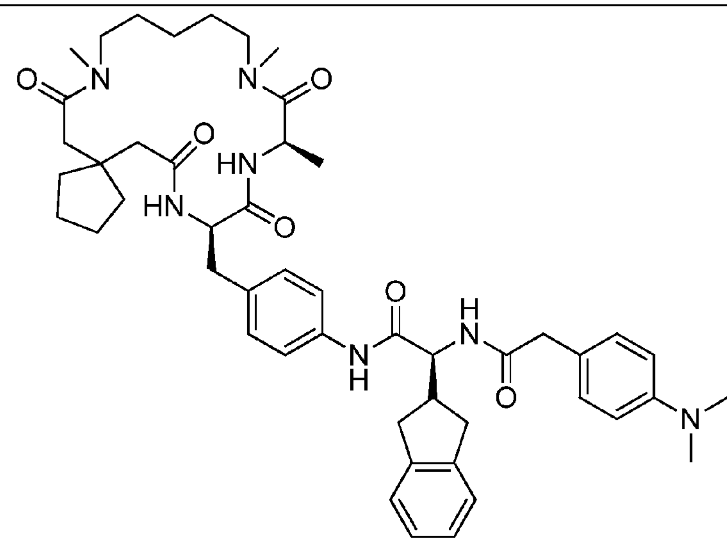 |

FIG. 12-255

| Compound No. | Structure |
|---|---|
| 645 | (chemical structure) |
| 646 | (chemical structure) |

FIG. 12-256

| Compound No. | Structure |
|---|---|
| 647 | 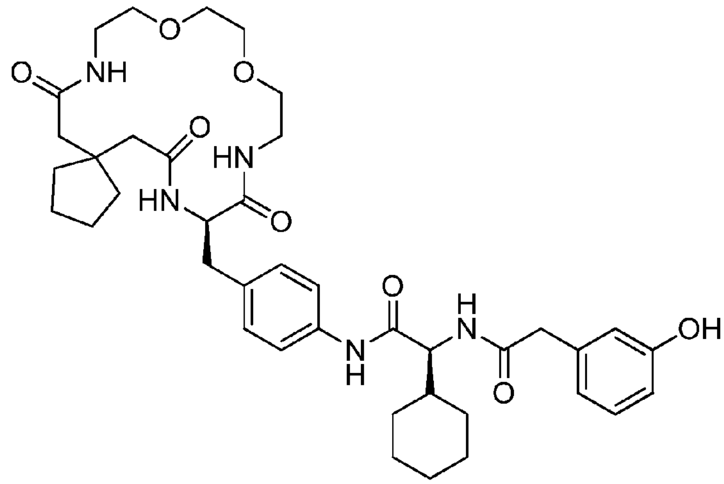 |
| 649 | 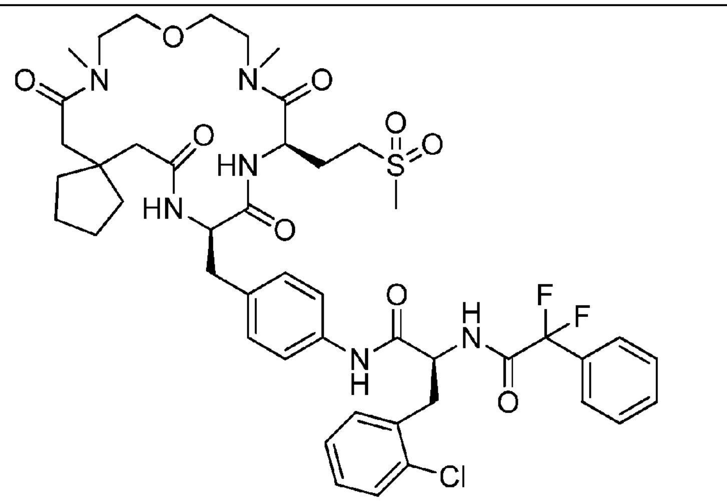 |

| Compound No. | Structure |
|---|---|
| 650 | 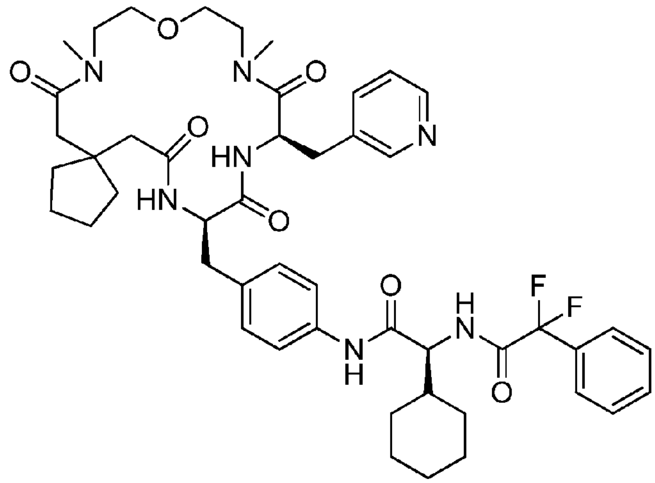 |
| 651 | 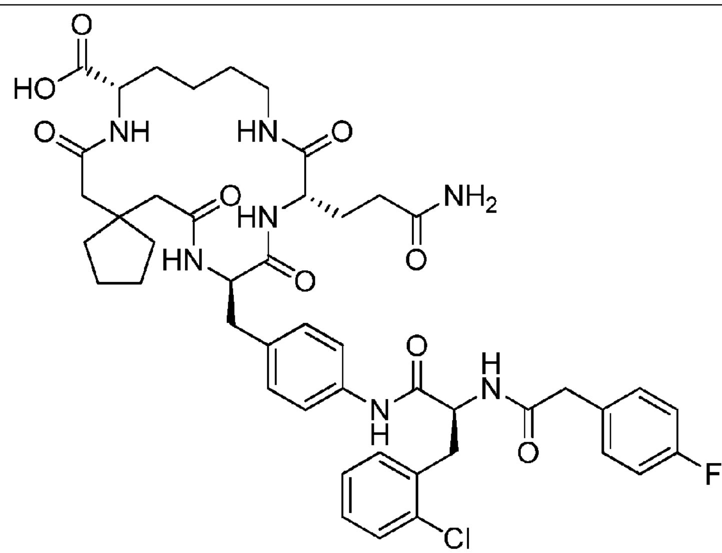 |

FIG. 12-258

| Compound No. | Structure |
|---|---|
| 652 | 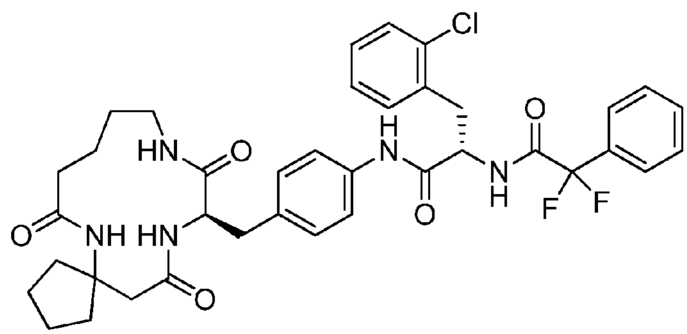 |
| 653 | 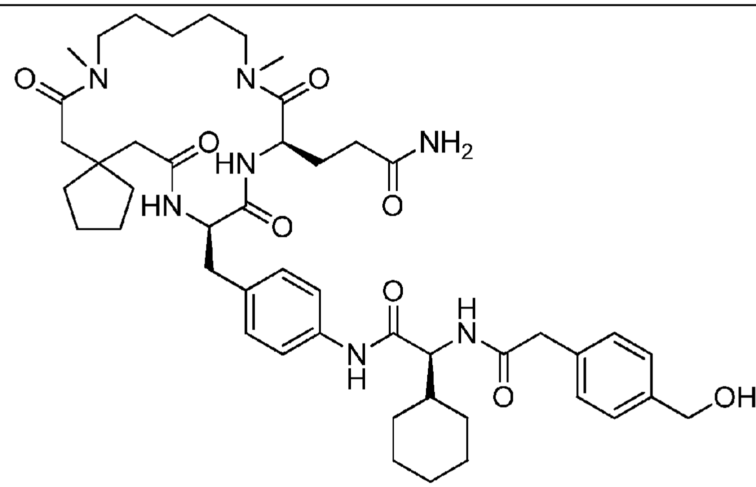 |

| Compound No. | Structure |
|---|---|
| 654 | 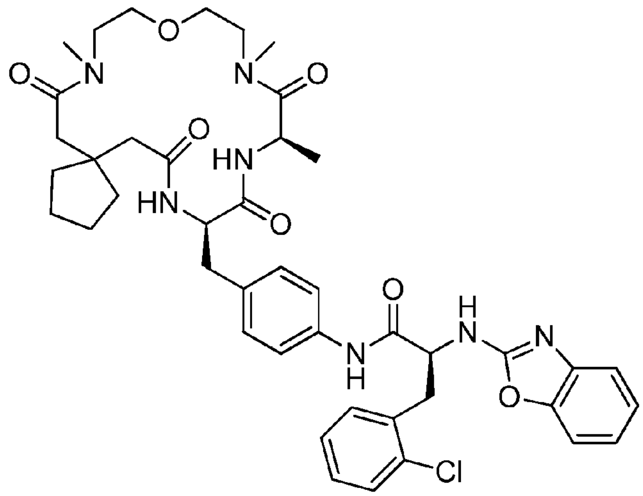 |
| 655 | 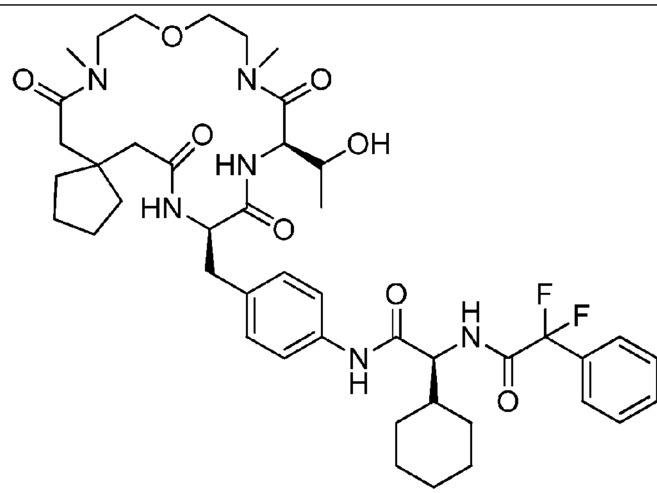 |

| Compound No. | Structure |
|---|---|
| 656 | 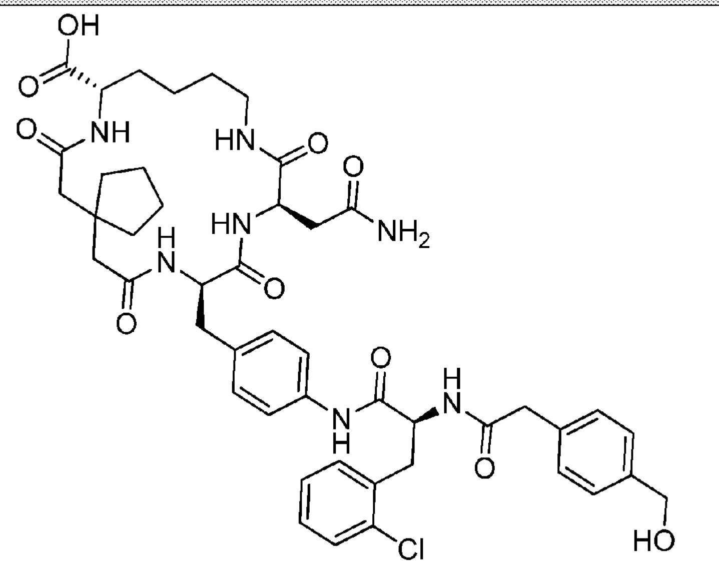 |
| 657 | 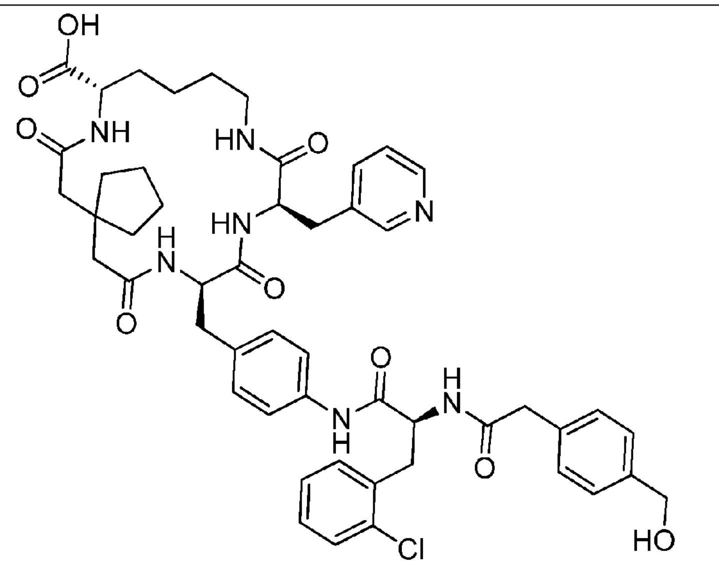 |

| Compound No. | Structure |
|---|---|
| 658 | 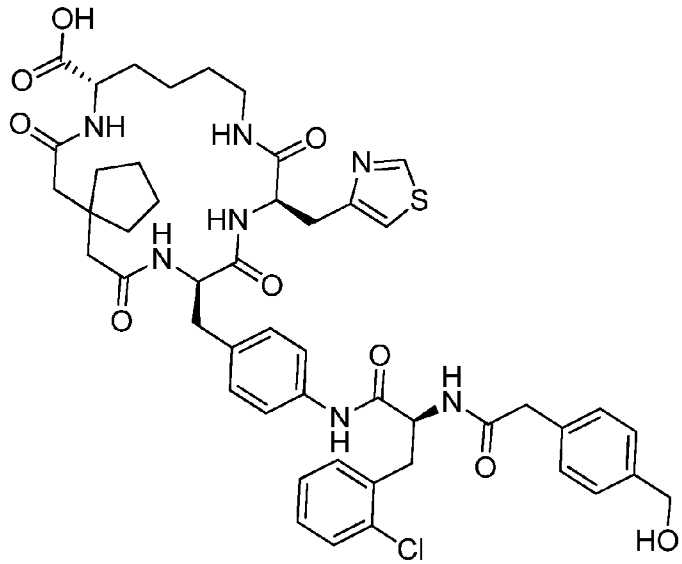 |
| 659 | 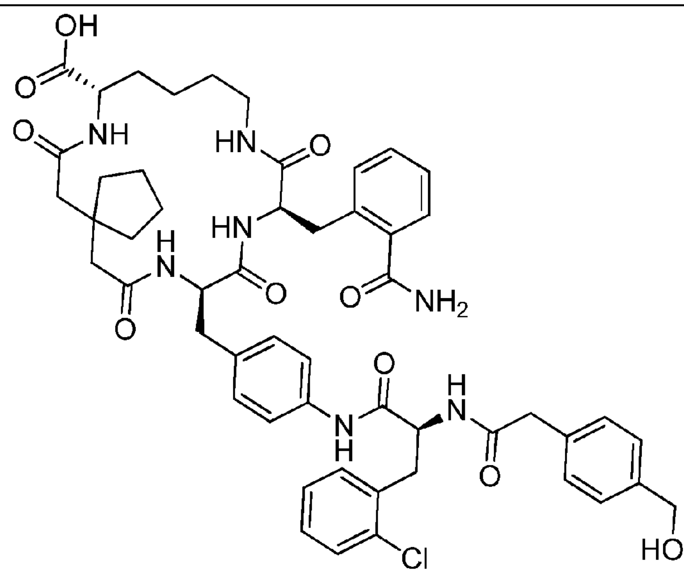 |

| Compound No. | Structure |
|---|---|
| 660 | 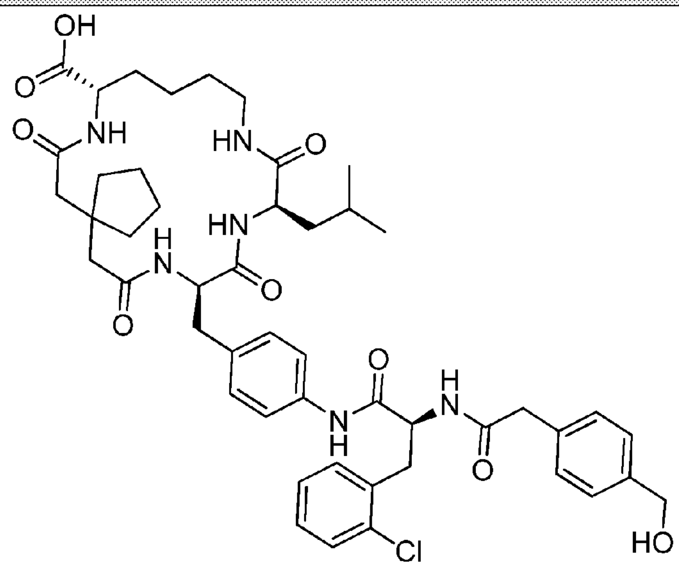 |
| 661 | 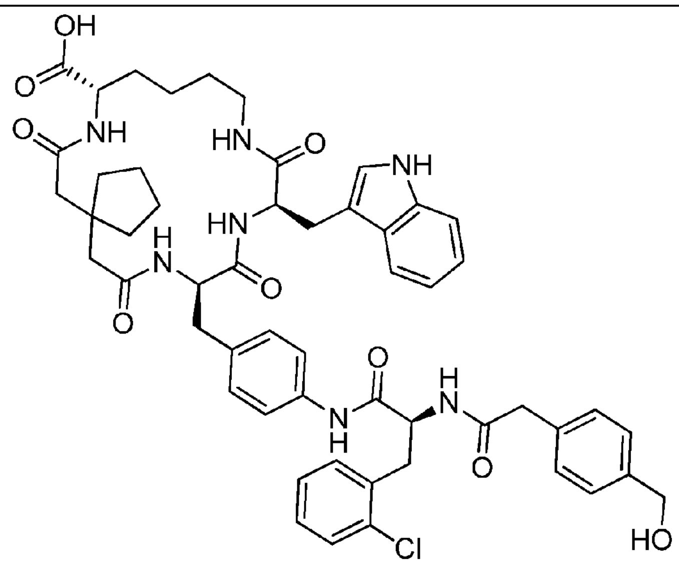 |

FIG. 12-263

| Compound No. | Structure |
|---|---|
| 662 | 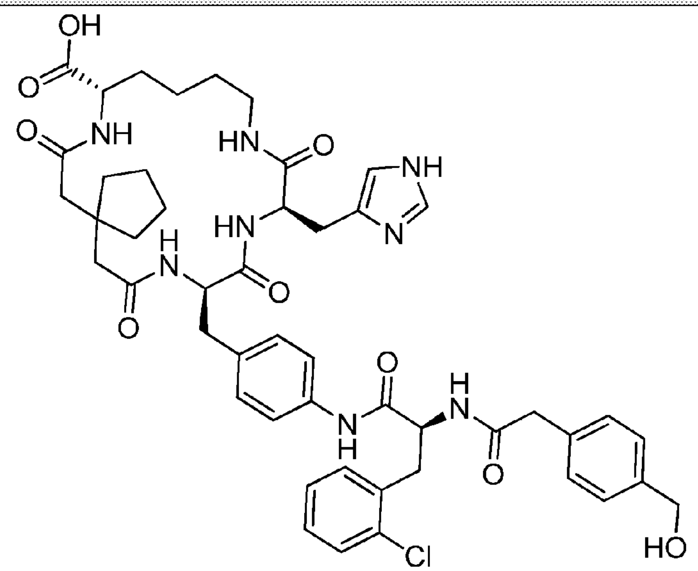 |
| 663 | 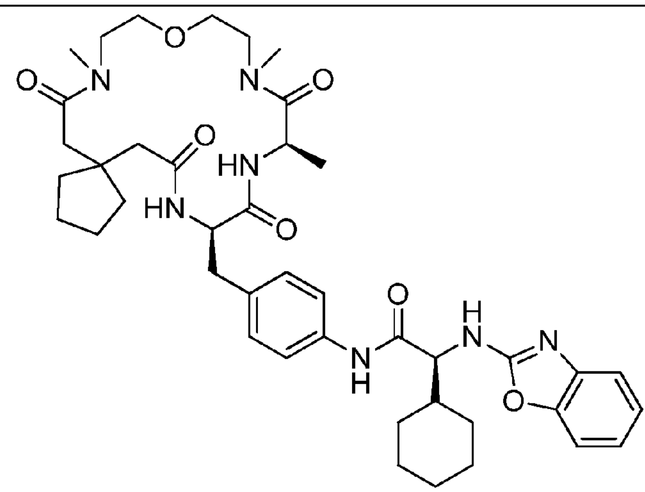 |

| Compound No. | Structure |
|---|---|
| 664 | 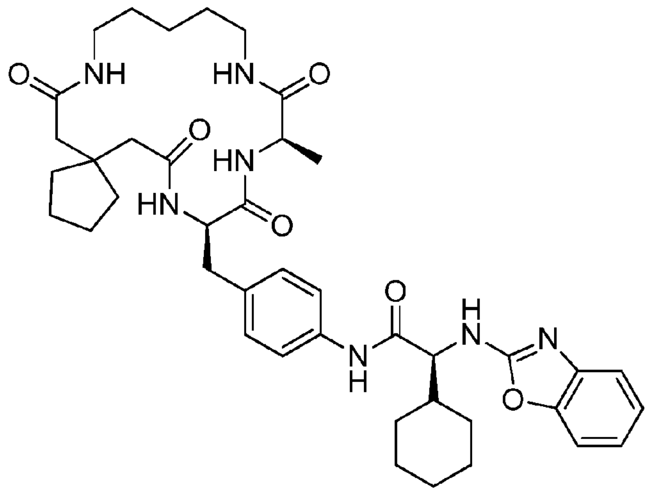 |
| 665 | 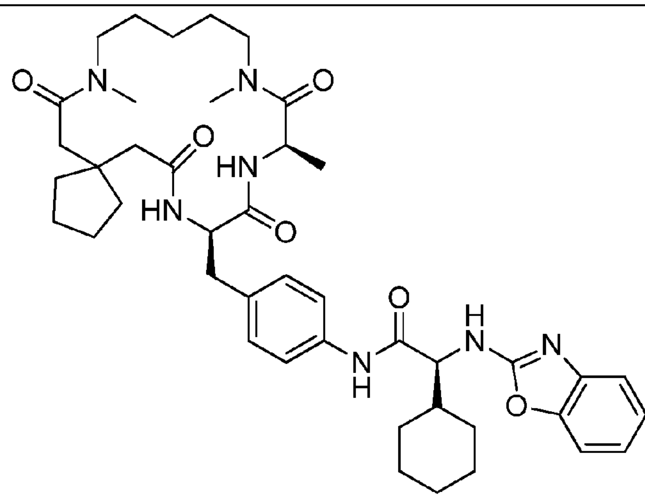 |

| Compound No. | Structure |
|---|---|
| 666 | 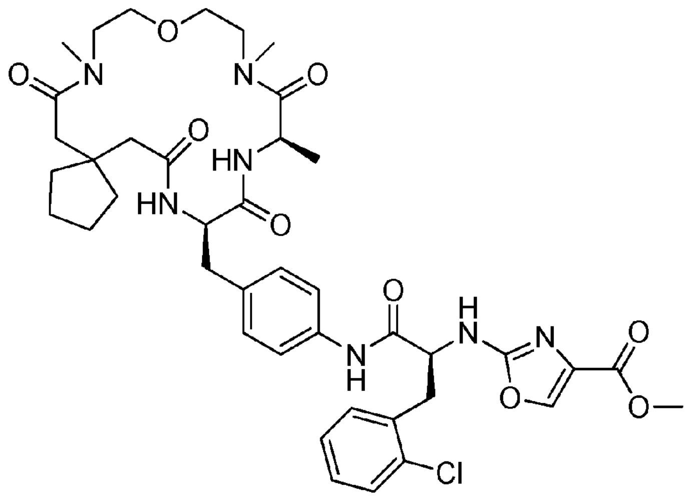 |
| 667 | 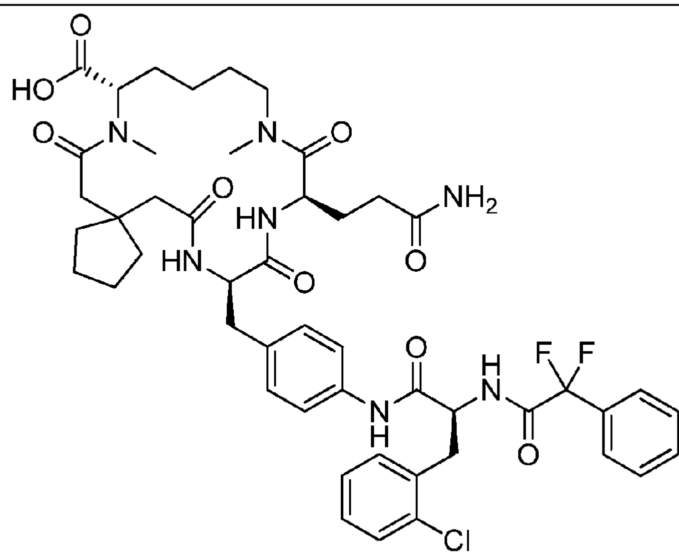 |

| Compound No. | Structure |
|---|---|
| 668 | 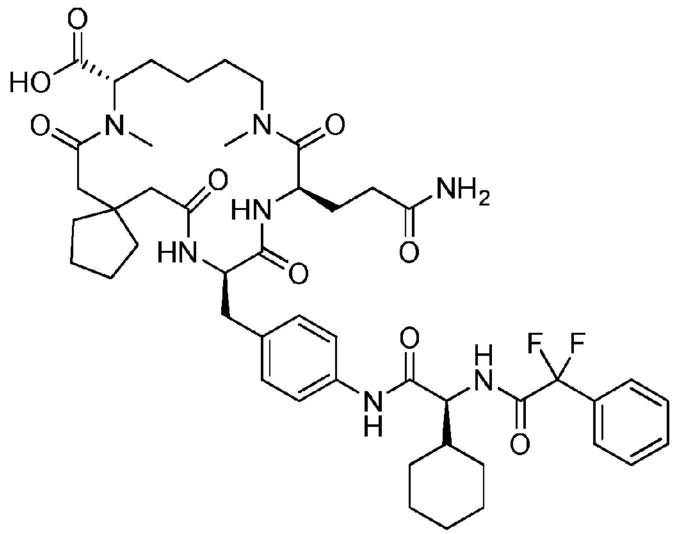 |
| 669 | 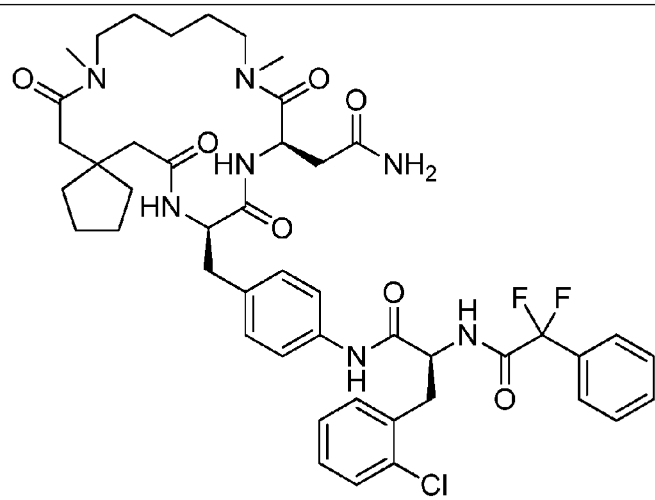 |

| Compound No. | Structure |
|---|---|
| 670 | 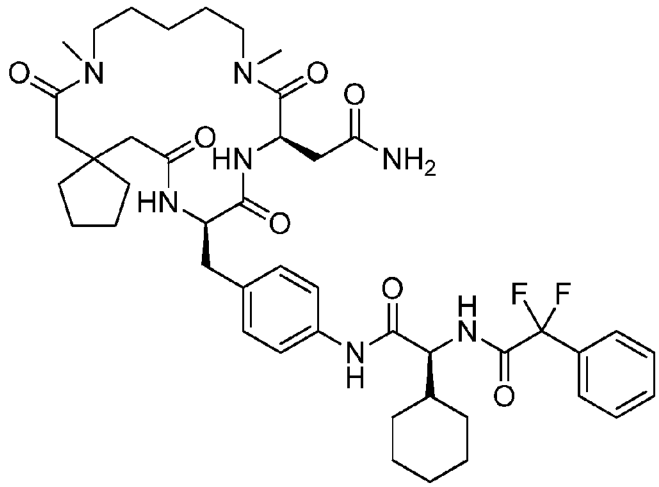 |
| 671 | 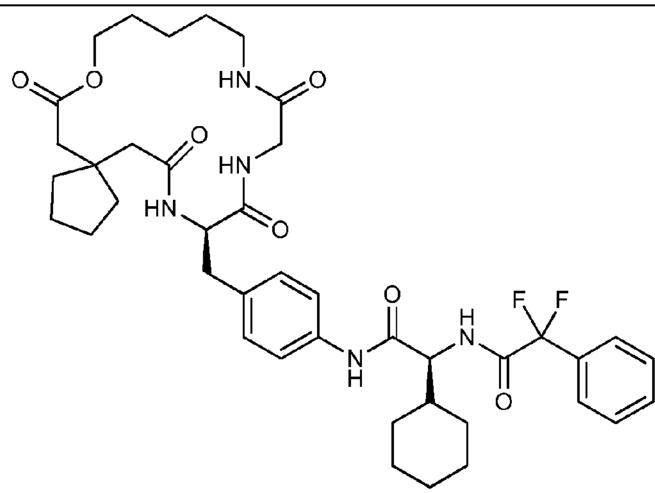 |

FIG. 12-268

| Compound No. | Structure |
|---|---|
| 672 | 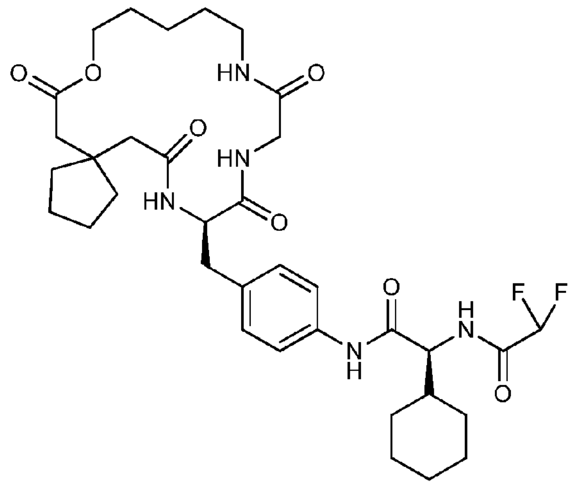 |
| 673 | 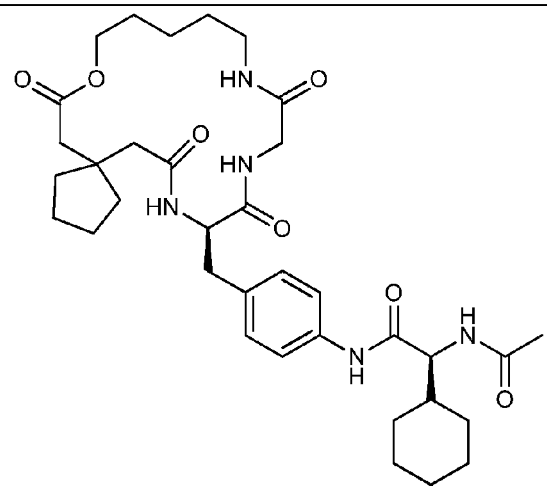 |

FIG. 12-269

| Compound No. | Structure |
|---|---|
| 674 | 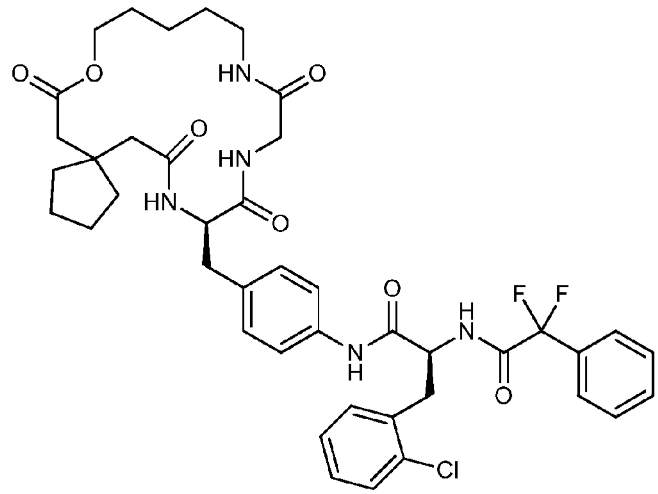 |
| 675 | 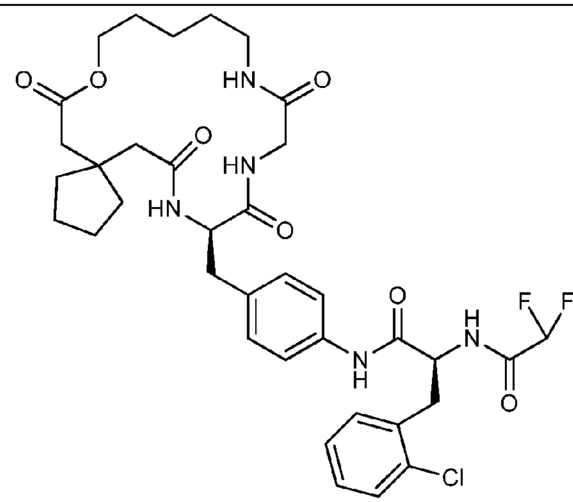 |

| Compound No. | Structure |
|---|---|
| 676 | 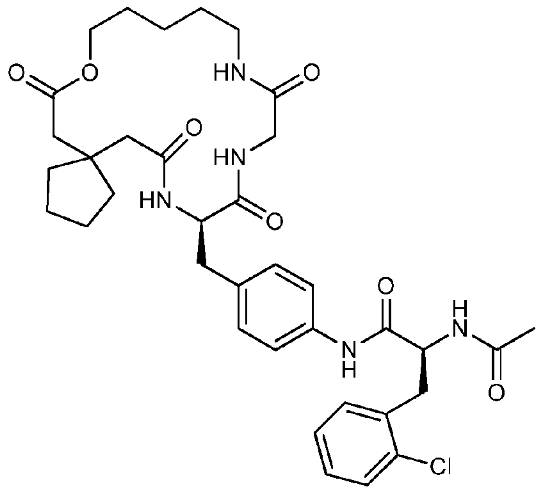 |
| 677 | 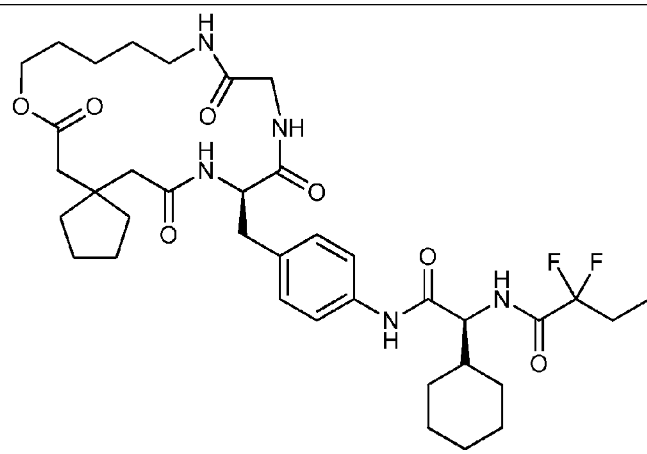 |

| Compound No. | Structure |
|---|---|
| 678 | 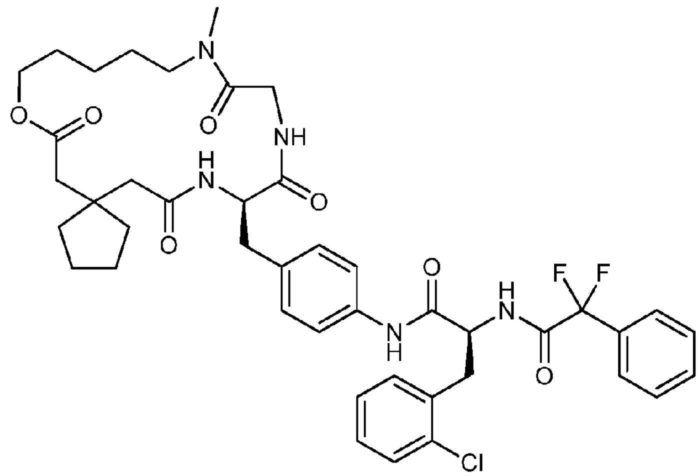 |
| 679 | 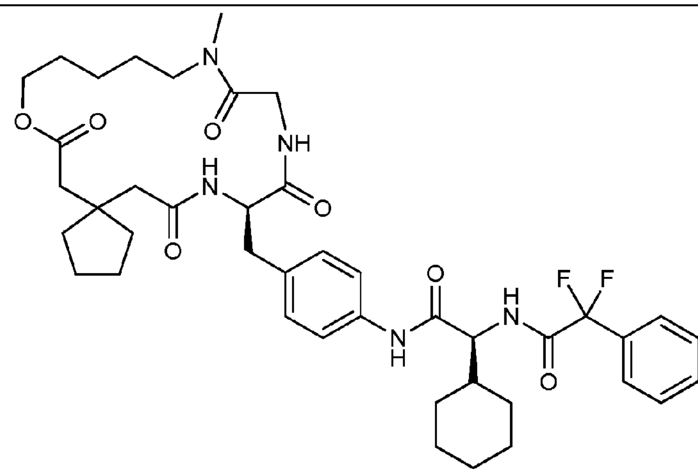 |

| Compound No. | Structure |
|---|---|
| 680 | 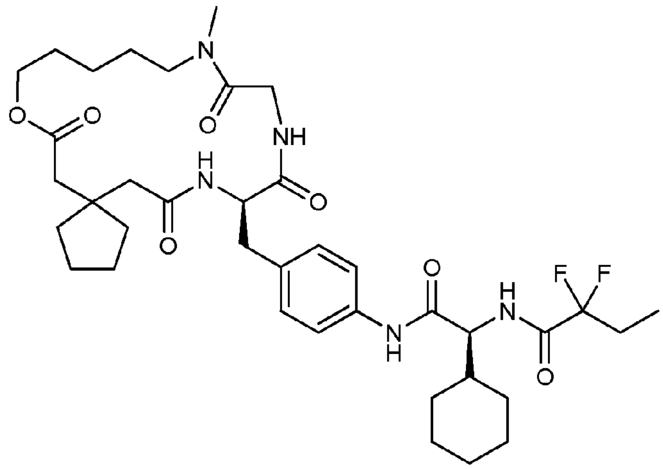 |
| 681 | 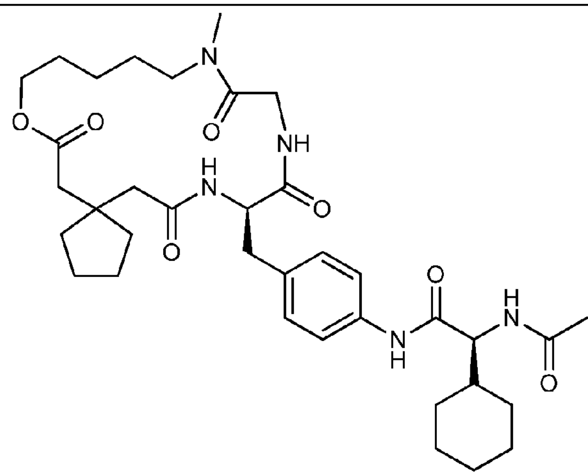 |

MACROCYCLIC COMPOUNDS FOR MODULATING IL-17

CROSS REFERENCE TO RELATED APPLICATIONS

This application is the national stage of International (PCT) Patent Application serial number PCT/US2013/024386, filed Feb. 1, 2013, which claims the benefit of and priority to U.S. Provisional Patent Application Ser. No. 61/593,993, filed Feb. 2, 2012, and U.S. Provisional Patent Application Ser. No. 61/725,878, filed Nov. 13, 2012, the contents of each of which are hereby incorporated by reference in their entirety.

FIELD OF THE INVENTION

The invention relates generally to macrocyclic compounds and their therapeutic use. More particularly, the invention relates to macrocyclic compounds that modulate the activity of IL-17 and/or are useful in the treatment of medical conditions, such as inflammatory diseases and other IL-17-associated disorders.

BACKGROUND OF THE INVENTION

Interleukin-17 ("IL-17"), also known as IL-17A and CTLA-8, is a pro-inflammatory cytokine that stimulates secretion of various other cytokines in a variety of cell types. For example, IL-17 can induce IL-6, IL-8, G-CSF, TNF-α, IL-1β, PGE2, and IFN-γ, as well as numerous chemokines and other effectors. See, e.g., Gaffen, S L, Arthritis Research & Therapy 6: 240-247 (2004).

IL-17 is expressed by TH17 cells, which are involved in the pathology of inflammation and autoimmunity. It is also expressed by CD8+ T cells, γδ cells, NK cells, NKT cells, macrophages and dendritic cells. IL-17 and Th17 are linked to pathogenesis of diverse autoimmune and inflammatory diseases, but are essential to host defense against many microbes, particularly extracellular bacteria and fungi. Human IL-17A is a glycoprotein with a molecular weight of 17,000 daltons (Spriggs et al., J Clin Immunol, 17: 366-369 (1997)). IL-17 can form homodimers or heterodimers with its family member, IL-17F. IL-17 binds to both IL-17 RA and IL-17 RC to mediate signaling. IL-17, signaling through its receptor, activates the NF-κB transcription factor, as well as various MAPKs. See, e.g., Gaffen, S L, Nature Rev Immunol, 9: 556-567 (2009).

IL-17 can act in cooperation with other inflammatory cytokines such as TNF-α, IFN-γ, and IL-1β to mediate pro-inflammatory effects. See, e.g., Gaffen, S L, Arthritis Research & Therapy 6: 240-247 (2004). Increased levels of IL-17 have been implicated in numerous diseases, including rheumatoid arthritis (RA), bone erosion, intraperitoneal abscesses, inflammatory bowel disease, allograft rejection, psoriasis, angiogenesis, atherosclerosis, asthma, and multiple sclerosis. See, e.g., Gaffen, S L, Arthritis Research & Therapy 6: 240-247 (2004); US Publication No 20080269467 A1, published Oct. 30, 2008. IL-17 was found in higher serum concentrations in patients with systemic lupus erythematosus (SLE) and was recently determined to act either alone or in synergy with B-cell activating factor (BAFF) to control B-cell survival, proliferation, and differentiation into immunoglobulin producing cells. Doreau et al., Nature Immunology 7:778-785 (2009). IL-17 has also been associated with ocular surface disorders, such as dry eye (PCT publication WO2010062858 and WO2011163452). IL-17 has also been implicated in playing a role in ankylosing spondylitis (H. Appel et al., Arthritis Research and Therapy 2011, 13R95) and psoriatic arthritis (McInnes, I. et al. Arthritis & Rheumatism, 2011; Volume 63, Suppl. 10:779).

IL-17 and IL-17-producing TH17 cells have recently been implicated in certain cancers, Ji and Zhang, Cancer Immunol Immunother 59: 979-987 (2010). For example, IL-17-expressing TH17 cells were shown to be involved in multiple myeloma, Prabhala et al., Blood, online DOI 10.1182/blood-2009-10-246660, Apr. 15, 2010, and to correlate with poor prognosis in patients with hepatocellular carcinoma (HCC), Zhang et al., J Hepatology 50: 980-89 (2009). Also, IL-17 was found to be expressed by breast-cancer-associated macrophages, Zhu et al., Breast Cancer Research 10:R95 (2008). However, the role of IL-17 in cancer, in many cases, has been unclear. In particular, IL-17 and IL-17-producing TH17 cells have been identified as having both a positive and a negative role in tumor immunity, sometimes in the same type of cancer. For a review, see, Ji and Zhang, Cancer Immunol Immuother 59: 979-987 (2010).

It can be seen from above that modulation of IL-17 has important therapeutic implications. Although various antibodies to IL-17 have been described in the prior art, very few small molecule-type, specific modulators of IL-17 with oral bioavailability are known. Accordingly, there is a need for the development of small molecule-like modulators of IL-17.

SUMMARY

The present invention provides macrocyclic compounds, methods of modulating the activity of IL-17, and methods for treating various medical conditions using such compounds. In one aspect, the invention provides a compound represented by Formula I:

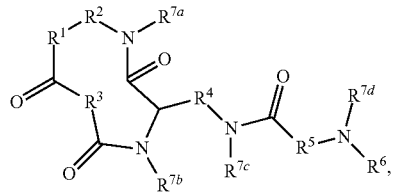

including pharmaceutically acceptable salts thereof, wherein the variables are as defined in the detailed description.

In another aspect, the invention provides a method of treating a patient suffering from or susceptible to a medical condition that is mediated directly or indirectly by IL-17. A number of medical conditions can be treated. The method comprises administering to the patient a therapeutically effective amount of a composition comprising a macrocyclic compound described herein. For example, the compounds described herein may be used to treat or prevent inflammatory diseases and conditions, proliferative diseases (e.g., cancer), autoimmune diseases and other disease described herein.

In another aspect, the invention provides a method of treating a patient suffering from a disease or condition associated with elevated levels of IL-17 comprising the steps of: a) determining whether the patient has an elevated level of IL-17; and b) if the patient does have an elevated level of IL-17, administering to the patient an effective amount of a compound of Formula I for a time sufficient to treat the disease or condition.

In still another aspect, the invention provides a method of treating a patient suffering from a disease or condition associated with elevated levels of IL-17 comprising the steps of: a) determining whether the patient has an elevated level of one or more IL-17-induced chemokine or effector; and b) if the patient does have an elevated level of the one or more IL-17 chemokine or effector, administering to the patient an effective amount of a compound of Formula I for a time sufficient to treat the disease or condition. In certain aspects, the IL-17 chemokine or effector is one or more of IL-6, IL-8, G-CSF, TNF-α, IL-1β, PGE2, and IFN-γ.

The foregoing and other aspects and embodiments of the invention may be more fully understood by reference to the following detailed description and claims.

DETAILED DESCRIPTION OF THE INVENTION

Figure 1:
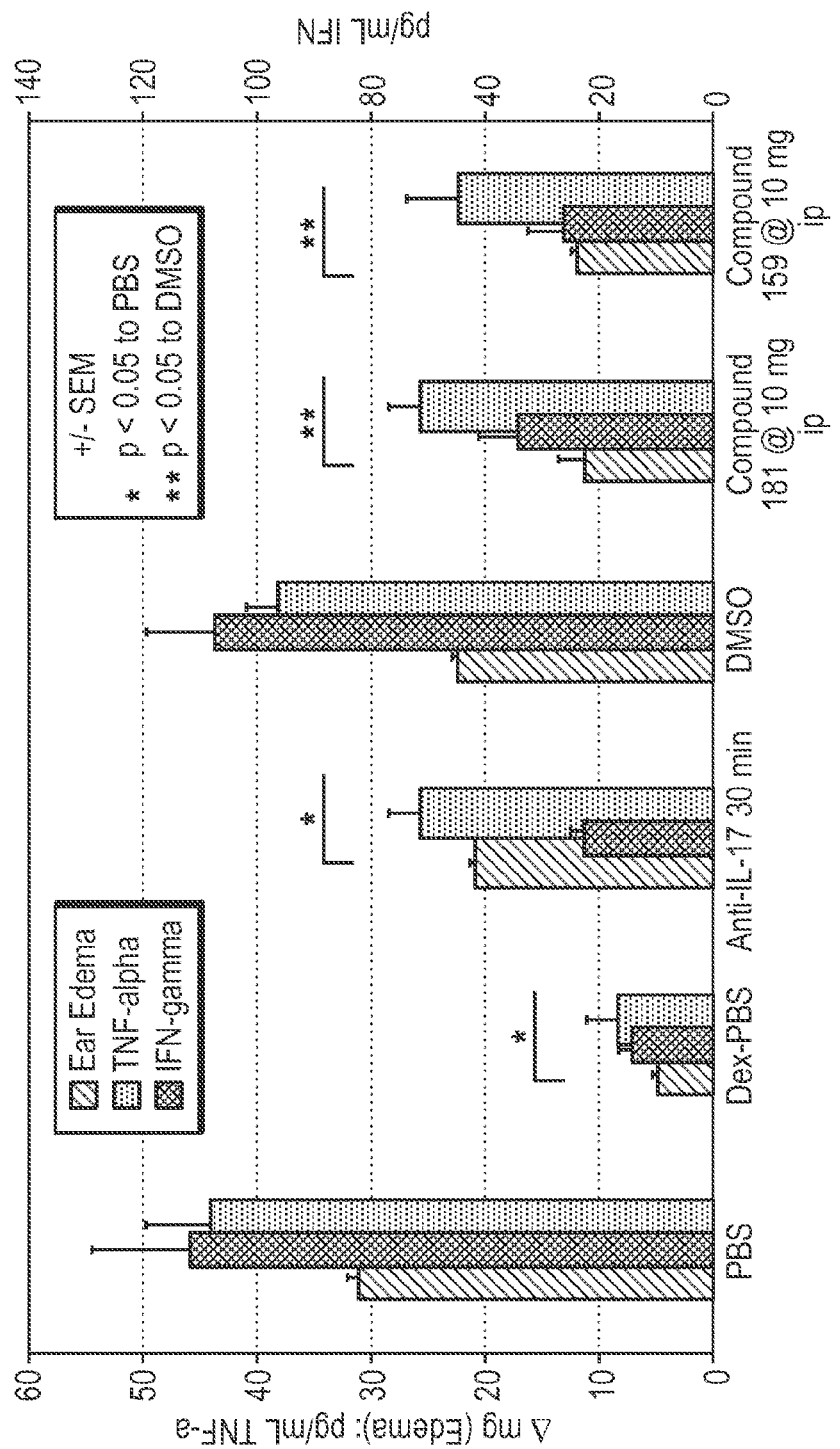
FIG. 1 depicts the effect of two intraperitoneally dosed exemplary compounds of the invention (i.e., compound nos. 159 and 181) on edema, TNF-α, and IFN-γ in a murine delayed hypersensitivity assay, as compared to an IL-17 antibody and vehicle controls.

The present invention provides macrocyclic compounds, methods of modulating the activity of IL-17, and methods for treating various medical conditions, especially inflammatory conditions and diseases, using such compounds. The practice of the present invention employs, unless otherwise indicated, conventional techniques of organic chemistry, pharmacology, and biochemistry. For example, procedures for synthesizing organic compounds are described in the literature, such as "Comprehensive Organic Synthesis" (BM Trost & I Fleming, eds., 1991-1992). Various aspects of the invention are set forth below in sections; however, aspects of the invention described in one particular section are not to be limited to any particular section. Further, when a variable is not accompanied by a definition, the previous definition of the variable controls.

I. DEFINITIONS

To facilitate an understanding of the present invention, a number of terms and phrases are defined below.

The term "alkyl" is art-recognized and refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The terms "alkenyl" and "alkynyl" are art-recognized and refer to unsaturated aliphatic groups analogous in length and possible substitution to the alkyls described above, but that contain at least one double or triple bond, respectively.

The term "cycloalkyl" is art-recognized and refers to a monovalent fully saturated cyclic, bicyclic, or bridged cyclic (e.g., adamantyl)hydrocarbon group of 3-10, 3-8, 4-8, or 4-6 carbons, referred to herein, e.g., as "$C_{4-8}$ cycloalkyl," derived from a cycloalkane. Exemplary cycloalkyl groups include, but are not limited to, cyclohexane, cyclopentane, cyclobutane, and cyclopropane.

The term "alkylene" refers to the diradical of an alkyl group.

The term "$C_0$ alkylene" as used herein means a bond. Thus, a moiety defined herein as "—($C_0$-$C_6$ alkylene)-aryl" includes both -aryl (i.e., $C_0$ alkylene-aryl) and —($C_1$-$C_6$ alkylene)-aryl.

The terms "alkenylene" and "alkynylene" refer to the diradicals of an alkenyl and an alkynyl group, respectively.

The term "methylene unit" refers to a divalent —$CH_2$— group present in an alkyl or alkylene moiety.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "carbocyclyl", as used herein, means a monocyclic, bicyclic or polycyclic hydrocarbon ring system, wherein each ring is either completely saturated or contains one or more units of unsaturation, but where no ring is aromatic. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like).

The term "aryl" is art-recognized and refers to a monocyclic, bicyclic or polycyclic hydrocarbon ring system, wherein at least one ring is aromatic. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like.

The term "arylene" refers to the diradical of an aryl group.

The term "1,4-phenylene" refers to a diradical of phenyl having the formula:

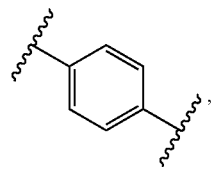

wherein each "⌇" represents a connection to the rest of the compound.

The term "heteroaryl" is art-recognized and refers to monocyclic, bicyclic or polycyclic ring system wherein at least one ring is both aromatic and comprises a heteroatom; and wherein no other rings are heterocyclyl (as defined below). In certain instances, a ring which is aromatic and comprises a heteroatom contains 1, 2, 3, or 4 ring heteroatoms in such ring. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

The term "heterocyclyl" refers to monocyclic, bicyclic and polycyclic ring systems where at least one ring is saturated or partially unsaturated (but not aromatic) and comprises a heteroatom. A heterocyclic ring can be attached to its pendant group at any heteroatom or carbon atom that results in a stable structure and any of the ring atoms can be optionally substituted. Representative heterocyclyls include ring systems in which (i) every ring is non-aromatic and at least one ring comprises a heteroatom, e.g., tetrahydrofuranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine.

The term "saturated heterocyclyl" refers to a heterocyclyl wherein every ring is saturated, e.g., tetrahydrofuran, tetrahydro-2H-pyran, pyrrolidine, piperidine and piperazine.

The terms "amine" and "amino" are art-recognized and refer to both unsubstituted and substituted amines, e.g., a moiety that may be represented by the general formula:

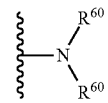

wherein each $R^{60}$ independently represent hydrogen or alkyl.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. The term "alkenyloxy" is art-recognized and refers to an alkenyl group, as defined above, having an oxygen radical attached thereto.

In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group (such as an alkyl, alkenyl, alkynyl, alkylene, alkenylene, alkynylene or the carbon atom of a carbocyclyl, aryl, heterocyclyl or heteroaryl) are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-4}Ph$ which may be substituted with $R°$; —CH=CHPh, which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°C(O)R°$; —$N(R°)N(R°)C(O)NR°_2$; —$N(R°)N(R°C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$—, $SC(S)SR°$; —$(CH_2)_{0-4}SC(O)R°$; —$(CH_2)_{0-4}C(O)NR°_2$; —$C(S)NR°_2$; —$C(S)SR°$; —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)RO_2$; —$OP(O)RO_2$; —$OP(O)(OR°)_2$; —$SiR°_3$; —$(C_{1-4}$ straight or branched) alkylene)-$N(R°)_2$; or —$(C_{1-4}$ straight or branched) alkylene)

C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•_2$, —NO$_2$, —SiR$^•_3$, —OSiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(C(R*)$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rt are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "moiety" refers to a portion of a compound of this invention comprising at least one hydrogen atom and at least one carbon atom.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivatizing with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium) hydroxides, ammonia, and compounds of formula $NW_4^+$ hydroxide, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

II. MACROCYCLIC COMPOUNDS

In one aspect, the invention provides a compound represented by Formula I:

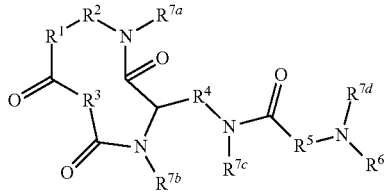

(I)

or a pharmaceutically acceptable salt thereof, wherein:
$R^1$ is selected from —O— and —N(($C_0$-$C_3$ alkylene)-Q)-, wherein
  Q is selected from hydrogen, —N($R^{2e}$), —OH, —O—$C_1$-$C_4$ alkyl, aryl, heteroaryl, carbocyclyl, and heterocyclyl;
  the alkylene portion of $R^1$, if present, is optionally substituted; and
  when the —C(O)— group adjacent to $R^1$ is bound directly to an —N($R^{2h}$)— in $R^3$, $R^1$ is additionally selected from —$CH_2$—;
$R^2$ is an optionally substituted $C_3$-$C_{12}$ alkylene, optionally substituted $C_3$-$C_{12}$ alkenylene, or optionally substituted $C_3$-$C_{12}$ alkynylene, wherein:

up to three methylene units of $R^2$ are optionally and independently replaced with —O—, —N($R^c$)—, —S—, —S(O)—, or —S(O)$_2$—, wherein
  $R^c$ is selected from hydrogen, $C_1$-$C_4$ alkyl, —C(O)—$C_1$-$C_3$ alkyl, —C(O)—($C_1$-$C_3$ alkylene)-aryl, —C(O)—($C_1$-$C_3$ alkylene)-heteroaryl, —C(O)—O—$C_1$-$C_3$ alkyl, —C(O)—O—$C_1$-$C_3$ alkenyl, —S(O)$_2$—$C_1$-$C_3$ alkyl, —S(O)$_2$—($C_1$-$C_3$ alkylene)-aryl, and —S(O)$_2$—($C_1$-$C_3$ alkylene)-heteroaryl; or
  when $R^1$ is —N(($C_0$-$C_3$ alkylene)-Q)-, $R^c$ is optionally taken together with $R^1$ and any intervening atoms to form a heterocyclyl;
  any two substituents bound to a common carbon atom in $R^2$ are optionally taken together to form =O, carbocyclyl, or heterocyclyl;
  any two substituents bound to different carbon atoms in $R^2$ are optionally taken together with any intervening atoms to form an aryl, heteroaryl, carbocyclyl, or heterocyclyl;
  any two $R^c$ are optionally taken together with the nitrogen atoms to which they are bound and any intervening atoms to form a heterocyclyl; and
  any substituent bound to a carbon atom in $R^2$ is optionally taken together with any one $R^c$ or with $R^{7a}$ and any intervening atoms to form heteroaryl or heterocyclyl;
$R^3$ is —[C($R^d$)($R^d$)]$_p$-[N($R^{7h}$)]$_{0\text{-}1}$—[C($R^d$)($R^d$)]$_q$—, wherein:
  each $R^d$ is independently selected from hydrogen and a suitable alkylene substituent; and any two $R^d$ are optionally taken together with any intervening atoms to form aryl, heteroaryl, carbocyclyl, or heterocyclyl;
  p is 0, 1 or 2;
  q is 0, 1 or 2; and
  p+q is 2 or more;
$R^4$ is —[C($R^e$)($R^e$)]$_n$—Y—[C($R^e$)($R^e$)]$_m$—, wherein:
  each $R^e$ is independently selected from hydrogen and a suitable alkylene substituent;
  Y is selected from aryl, heteroaryl, carbocyclyl, heterocyclyl, and optionally substituted $C_1$-$C_3$ alkylene;
  each of n and m are independently selected from 0, 1, 2, 3, 4, 5, and 6; and n+m is 6 or less;
$R^5$ is $C_1$-$C_2$ alkylene substituted with one or more —($C_0$-$C_5$ alkylene)-$R^f$, wherein each $R^f$ is independently selected from —$CH_3$, —O—$C_1$-$C_3$ alkyl, aryl, heteroaryl, carbocyclyl, and heterocyclyl;
$R^6$ is selected from heteroaryl, —$CH_2$-aryl, —C(O)—$R^8$, —C(O)—O—$R^8$, —C(O)—C(O)—$R^8$, —S(O)—$R^8$, —S(O)$_2$—$R^8$, C(O)—N($R^{2f}$)—$R^8$, and —S(O)$_2$—N($R^{2f}$)—$R^8$;
each $R^{7a}$, $R^{7b}$, $R^{7c}$, $R^{7d}$, $R^{7e}$, $R^{7f}$, and $R^{7g}$ is independently selected from hydrogen and $C_1$-$C_4$ alkyl;
$R^{7h}$ is independently selected from hydrogen, $C_1$-$C_4$ alkyl, phenyl, and benzyl;
$R^8$ is selected from —($C_0$-$C_6$ alkylene)-aryl, —($C_0$-$C_6$ alkylene)-heteroaryl, —($C_0$-$C_6$ alkylene)-carbocyclyl, —($C_0$-$C_6$ alkylene)-heterocyclyl, and $C_1$-$C_6$ alkyl, wherein
  when $R^8$ is $C_1$-$C_6$ alkyl, up to two methylene units in the alkyl are optionally and independently replaced with —O—, —N($R^{7g}$)—, —S—, —S(O)—, or —S(O)$_2$—; and
  any alkyl or alkylene portion of $R^8$ is optionally substituted with an appropriate alkyl or alkylene substituent other than =O; or
$R^{7d}$ and $R^6$ are optionally taken together to form a heterocyclyl; and
  any aryl, heteroaryl, carbocyclyl, or heterocyclyl portion of the compound is optionally substituted.

It will be understood by those of skill in the art that the optional and independent replacement of up to three methylene units of R² with —O—, —N(R^c)—, —S—, —S(O)—, or —S(O)₂—, contemplated by the present invention only includes such replacements that result in a stable compound. Accordingly, compounds containing combinations of such replacements that are known to be unstable, e.g., —O—O—, —S(O)—S(O)₂—, —N(R^c)—N(R^c)—O—, and the like, are not to be considered within the scope of the invention. It will be understood by those of skill in the art that because the compounds of the invention are limited to compounds that are stable, compounds formed by the optional and independent replacement of up to three methylene units in R² with certain combinations of —O—, —S—, —S(O)—, —S(O)₂—, or —NR^c— are not within the scope of the present invention. For example, compounds wherein the R² moiety comprises an —O—, —S—, —S(O)—, —S(O)₂, or —N(R^c)—, adjacent to an —O—, —S—, —S(O)—, —S(O)₂, or —N(R^c)— are not within the scope of the present invention, except for an —S(O)₂— adjacent a —N(R^c)—. In addition, R² should not comprise —O—CH₂—O—, —N—CH₂—O—, or —O—CH₂—N—, wherein the —CH₂— portion thereof is optionally substituted, except when the —CH₂— portion is substituted to become —C(O)—.

In certain embodiments of Formula I, R¹ is selected from —O— and —N((C₀-C₃ alkylene)-Q)-, wherein Q is selected from hydrogen, —N(R^{7e}), —OH, —O—C₁-C₄ alkyl, aryl, heteroaryl, carbocyclyl, and heterocyclyl.

In certain embodiments of Formula I, R¹ is selected from —O—, —NH— and —N(C₁-C₃ alkyl-OH)—. In one aspect of these embodiments, R¹ is selected from —O—, —NH— and —N(CH₂CH₂OH)—.

In other embodiments of Formula I, R¹ is selected from —O—, —NH— and —N(CH₃)—.

In still other embodiments of Formula I, when the —C(O)— group adjacent to R¹ is bound directly to an —N(R^{7h})— in R³, R¹ is —CH₂—

In certain embodiments of Formula I, R² is an optionally substituted C₅-C₁₂ alkylene, optionally substituted C₅-C₁₂ alkenylene, or optionally substituted C₅-C₁₂ alkynylene, wherein:

up to three methylene units of R² are optionally and independently replaced with —O—, —N(R^c)—, —S—, —S(O)—, or —S(O)₂—, wherein R^c is selected from hydrogen, C₁-C₄ alkyl, C(O)—C₁-C₃ alkyl, C(O)—(C₁-C₃ alkylene)-aryl, C(O)—(C₁-C₃ alkylene)-heteroaryl, S(O)₂—C₁-C₃ alkyl, S(O)₂—(C₁-C₃ alkylene)-aryl, and S(O)₂—(C₁-C₃ alkylene)-heteroaryl;

any two substituents bound to a common carbon atom in R² are optionally taken together to form =O, carbocyclyl or heterocyclyl;

any two substituents bound to different carbon atoms in R² are optionally taken together with any intervening atoms to form aryl, heteroaryl, carbocyclyl or heterocyclyl;

any substituent bound to a carbon atom in R² and any one R^c are optionally taken together with any intervening atoms to form heteroaryl or heterocyclyl; and any substituent bound to two R^c are optionally taken together with any intervening atoms to form a heterocyclyl.

In certain embodiments of Formula I, R² is selected from *—CH(R¹⁰)—(CH₂)₂₋₄—NH—C(O)—(C(R¹¹)₂)₁₋₅—, *—CH(R¹⁰)—(CH₂)₄₋₈—, *—CH(R¹⁰)—(CH₂)₂₋₄-(1,4-phenylene)-NH—C(O)—(C(R¹¹)₂)₁₋₃—, and *—CH(R¹⁰)—(CH₂)₂₋₄-(1,4-phenylene)-; R¹⁰ is selected from hydrogen, —C(O)—O—C₁-C₄ alkyl, and —C(O)—OH; and each R¹¹ is independently selected from hydrogen, benzyl, C₁-C₄ alkyl and C₁-C₄ hydroxyalkyl, wherein no more than two R¹¹ are other than hydrogen; one methylene unit in a specified —(CH₂)₂₋₄ or —(CH₂)₄₋₈ portion of R² is optionally replaced with —N(H)— or —N(CH₃)—; and "*" represents a terminus of R² bound to R¹. In one aspect of these embodiments, R² is selected from *—CH(R¹⁰)—(CH₂)₂₋₄—NH—C(O)—(CH₂)₁₋₅—, *—CH(R¹⁰)—(CH₂)₄—, *—CH(R¹⁰)—(CH₂)₂₋₄—NH—C(O)—C((CH₃)₂)—, *—CH(R¹⁰)—(CH₂)₂₋₄—NH—C(O)—CH(CH₂OH)—, *—CH(R¹⁰)—CH₂-(1,4-phenylene)-NH—C(O)—(CH₂)₁₋₃—, *—CH(R¹⁰)—CH₂-(1,4-phenylene)-, —(CH₂)₈—, *—(CH₂)₂—N(CH₃)—(CH₂)₂—NH—C(O)—CH₂—, and *—(CH₂)₅—NH—C(O)—CH(benzyl)-; and R¹⁰ is selected from hydrogen, —C(O)—O—CH₃, and C(O)—OH.

The term "specified —(CH₂)₂₋₄— or —(CH₂)₄₋₈— portion of R²" as used in the preceding paragraph refers to those embodiments of R² comprising portions that are indicated as —(CH₂)₂₋₄— or —(CH₂)₄₋₈—. For example, when R² is —CH(R¹⁰)—(CH₂)₂₋₄—NH—C(O)—(CH₂)₁₋₅—, only the bolded portion is a "specified —(CH₂)₂₋₄— portion of R²."

In other embodiments of Formula I, R² is selected from *—CH(R¹⁰)—Z—, or *—CH(R¹⁰)—X—CH(R¹⁰)—N(R¹²)—C(O)—CH(R¹¹)—(CH₂)₀₋₂—, wherein:

X is selected from —CH₂—O—CH₂—, —CH₂—N(R¹³)—CH₂—, —CH₂—N(H)—C(O)—, —CH₂—, —(CH₂)₂—, and —(CH₂)₃—;

Z is selected from C₂-C₈ alkylene, C₂-C₈ alkenylene, or C₂-C₈ alkynylene, wherein up to 2 methylene units in Z are optionally and independently replaced with —O—, —NH— or —N(CH₃)—;

each R¹⁰ is independently selected from hydrogen, —C(O)OH, and —C(O)OCH₃, wherein at least one R¹⁰ is hydrogen;

R¹¹ is selected from hydrogen, (S)—CH₂OH, (S)—CH₃, (S)—C(CH₃)₃, (S)-benzyl, (R)-benzyl, (S)—CH₂-pyridinyl, (S)-cyclohexyl, (S)—CH₂-cyclohexyl, (S)—(CH₂)₂—COOH, (S)—(CH₂)₂—C(O)NH₂, and (S)—(CH₂)₄—NH₂;

R¹² is selected from hydrogen and —CH₃;

R¹³ is selected from hydrogen and —CH₃; or

R¹³ is optionally taken together with R¹² or the —N((C₀-C₃ alkylene)-Q) portion of R¹ to form a heterocyclyl.

In certain embodiments of Formula I, Z is selected from *—(CH₂)₃₋₉—, *—CH(COOH)—(CH₂)₂₋₈—, *—(CH₂)₂—O—(CH₂)₂—, *—(CH₂)₂—O—(CH₂)₂—O—(CH₂)₂—, *—(CH₂)₂—NH—(CH₂)₂—, *—(CH₂)₂—N(CH₃)—(CH₂)₂—, *—CH₂—C≡C—(CH₂)₄₋₅, and *—CH₂—CH=CH—(CH₂)₄₋₅.

In other embodiments of Formula I, R² is selected from *—(CH₂)₃₋₉—, *—CH(COOH)—(CH₂)₂₋₈—, *—(CH₂)₂—O—(CH₂)₂—, *—(CH₂)₂—O—(CH₂)₂—O—(CH₂)₂—, *—(CH₂)₂—NH—(CH₂)₂—, *—(CH₂)₂—N(CH₃)—(CH₂)₂—, *—CH₂—C≡C—(CH₂)₄₋₅, and *—CH₂—CH=CH—(CH₂)₄₋₅.

In other embodiments of Formula I, R² is selected from)*—CH(R¹⁰—Z— and *—C(H)(R¹⁰)—X—C(H)(R¹⁰)—N(R¹²)—C(O)—C(H)(R¹¹)—(CH₂)₀₋₂—, wherein:

X is selected from —CH₂—O—CH₂—, —CH₂—N(H)—CH₂—, —CH₂—N(CH₃)—CH₂—, —CH₂—, —(CH₂)₂—, and —(CH₂)₃—;

Z is selected from C₂-C₈ alkylene, C₂-C₈ alkenylene, or C₂-C₈ alkynylene, wherein up to 2 methylene units in Z are optionally and independently replaced with —O—, —N(H)— or —N(CH₃)—;

each R¹⁰ is independently selected from hydrogen and —(R)—COOH, wherein at least one R¹⁰ is hydrogen;

R¹¹ is selected from hydrogen, (S)—CH₂OH, (S)—CH₃, (S)—C(CH₃)₃, (S)-benzyl, (R)-benzyl, (S)—CH₂-pyridinyl, (S)-cyclohexyl, (S)—CH₂-cyclohexyl, (S)—(CH₂)₂—COOH, (S)—(CH₂)₂—C(O)NH₂, and (S)—(CH₂)₄—NH₂;

$R^{12}$ is selected from hydrogen and —$CH_3$; and
"*" represents a terminus of $R^2$ bound to $R^1$.
In certain embodiments, p+q is 2, 3, or 4. In other embodiments, p+q is 3.
In a more specific embodiment, the portion of the compound represented by —$R^1$-$R^2$ is selected from:
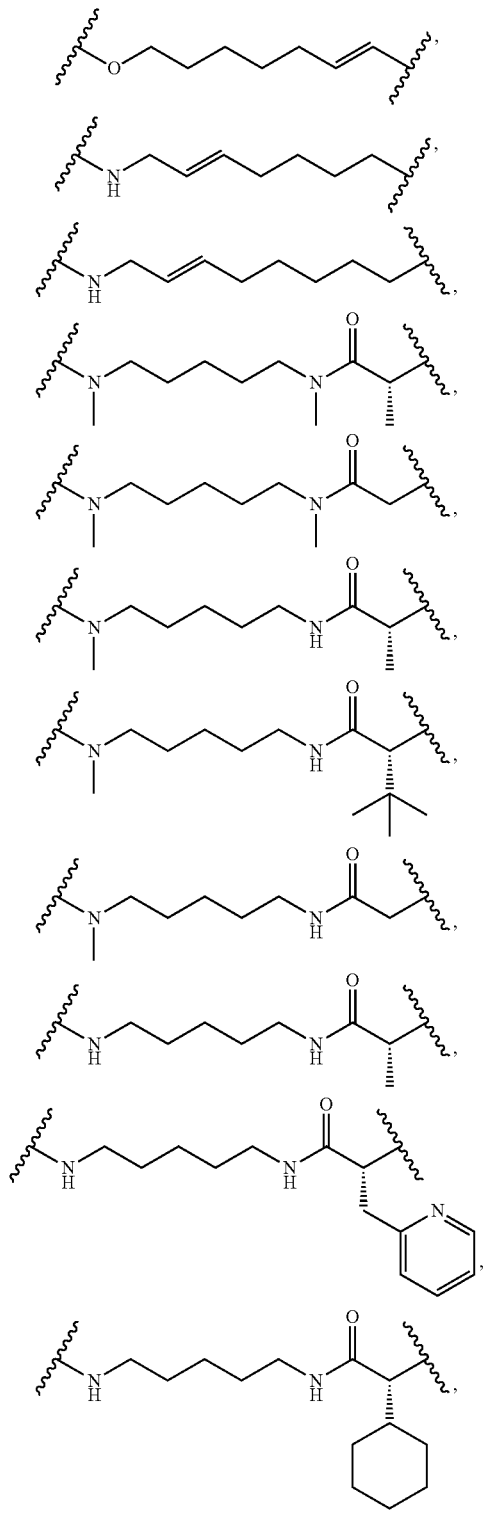
-continued
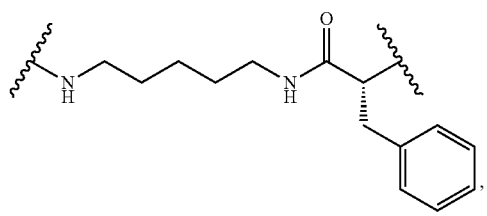
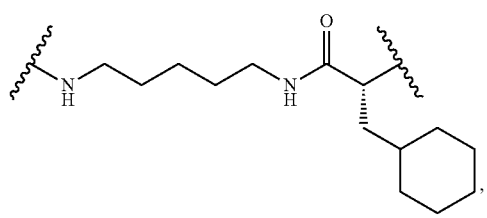
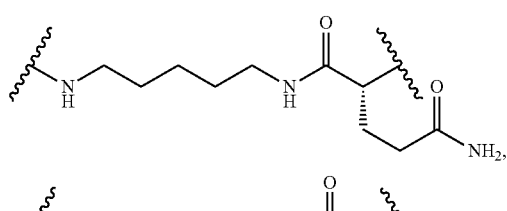
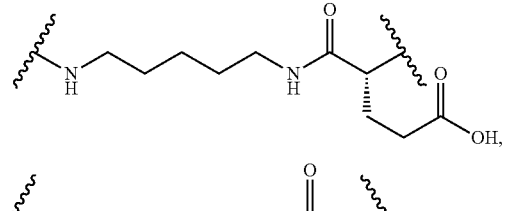
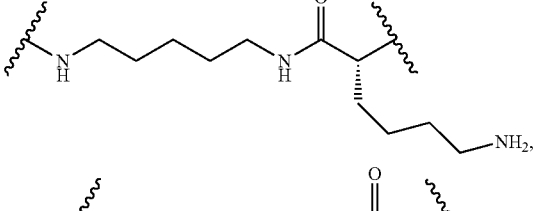
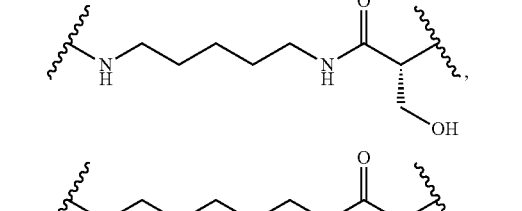
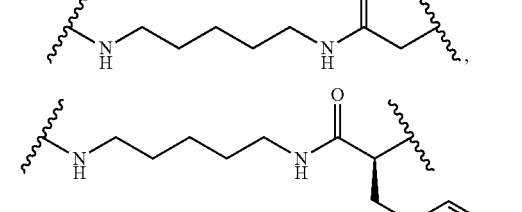
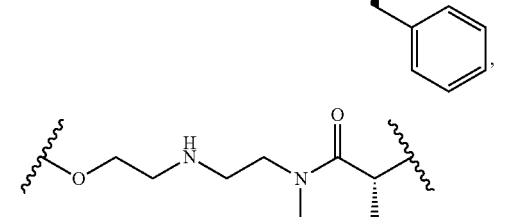
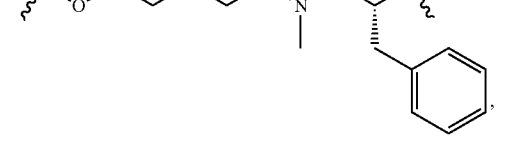

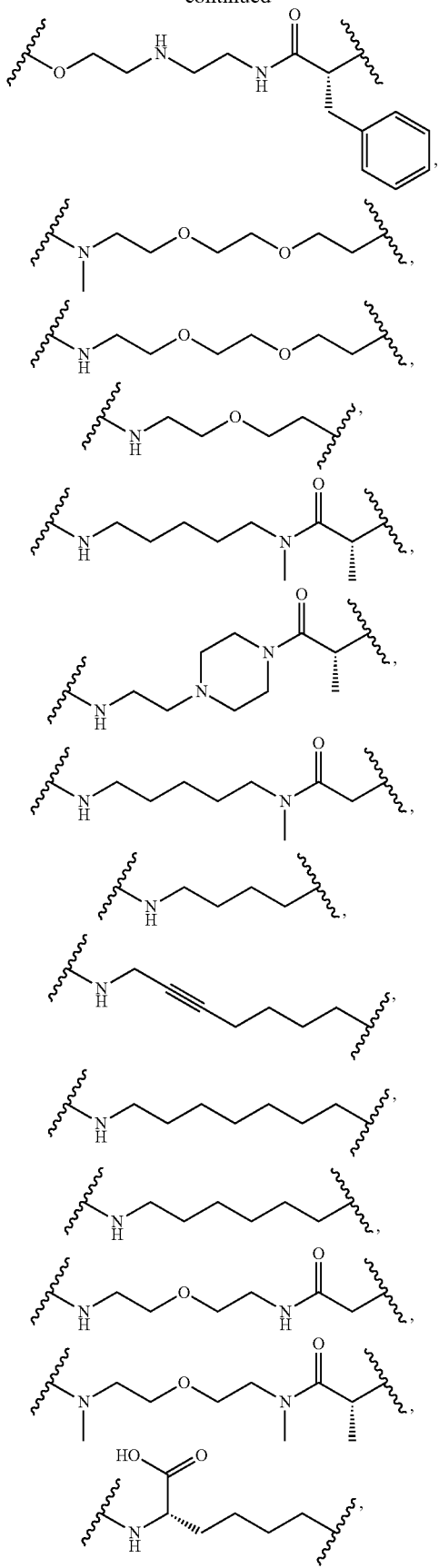
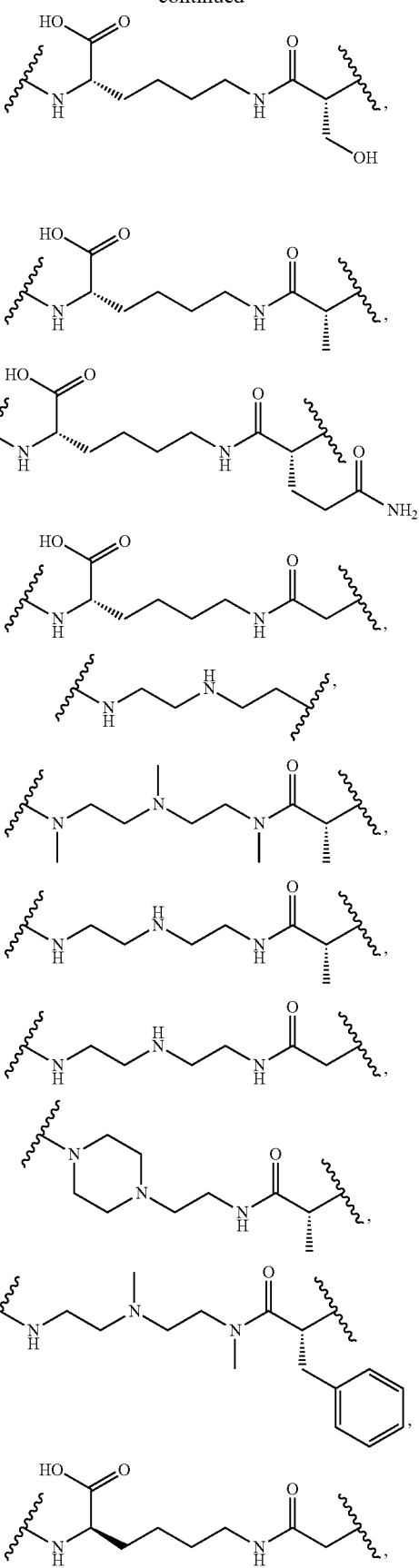

-continued
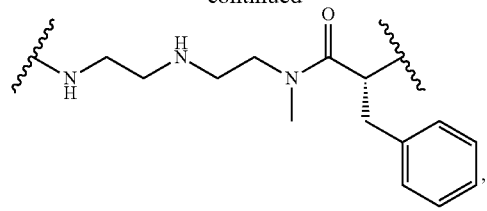
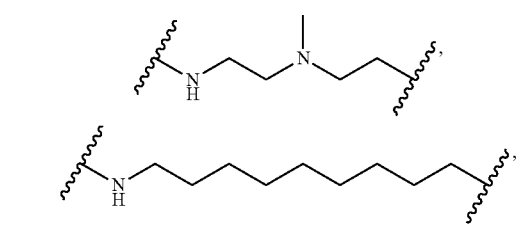
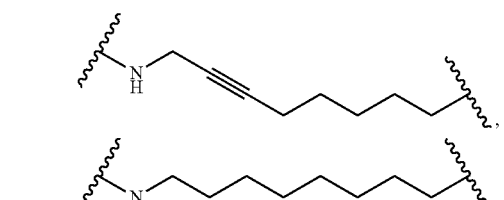
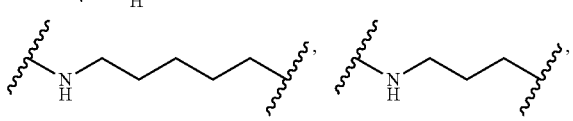
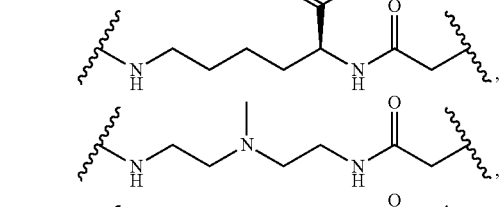
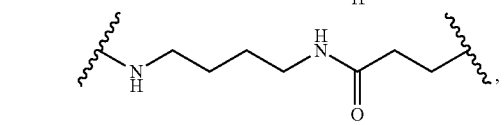
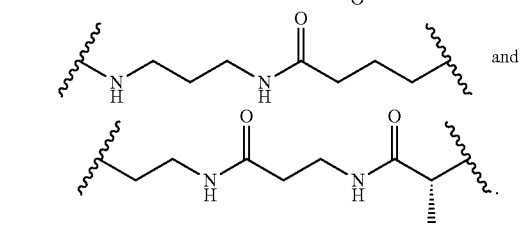
and
In certain other embodiments, the portion of the compound represented by —R¹-R² is selected from:
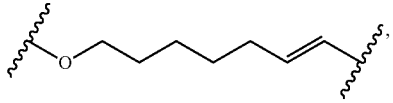
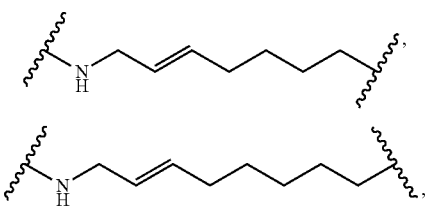
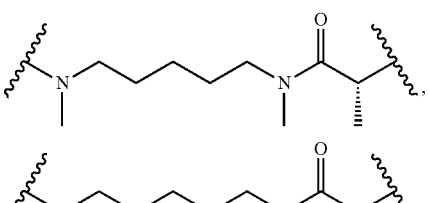
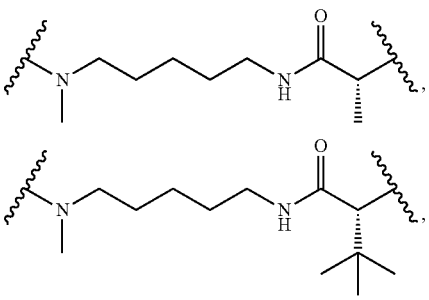
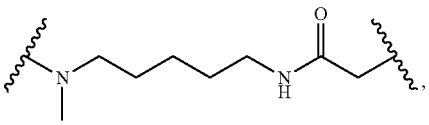
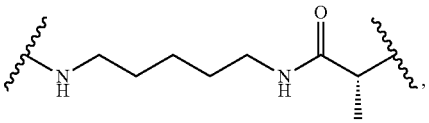
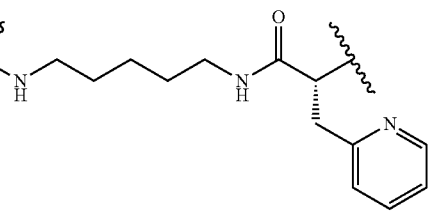
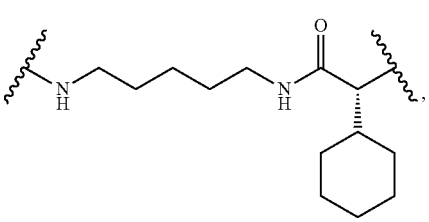

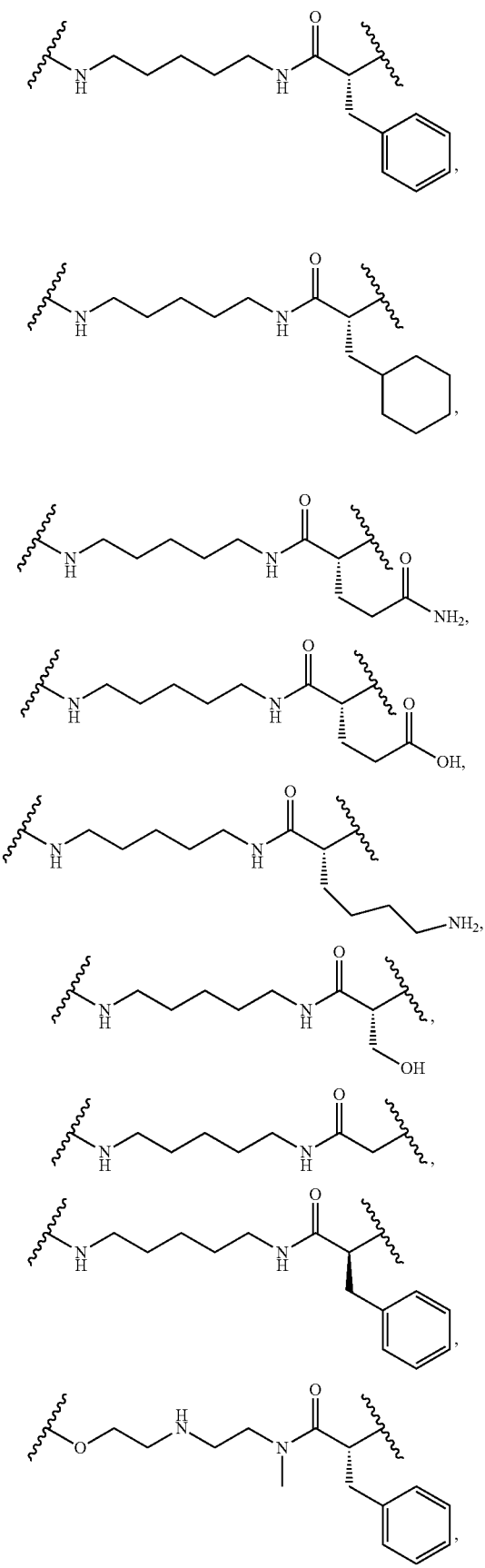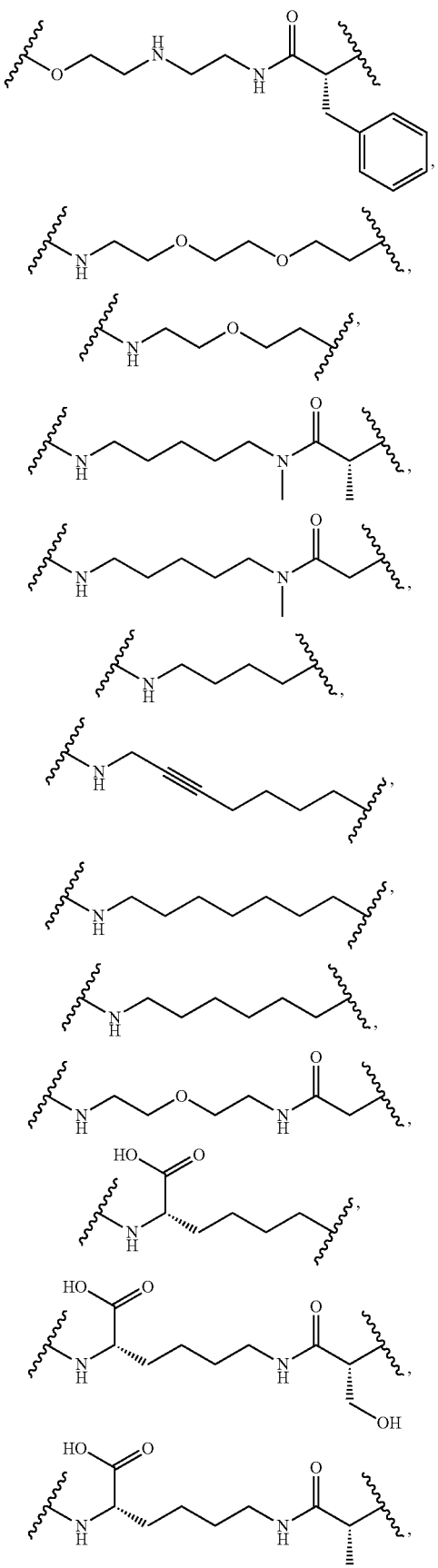

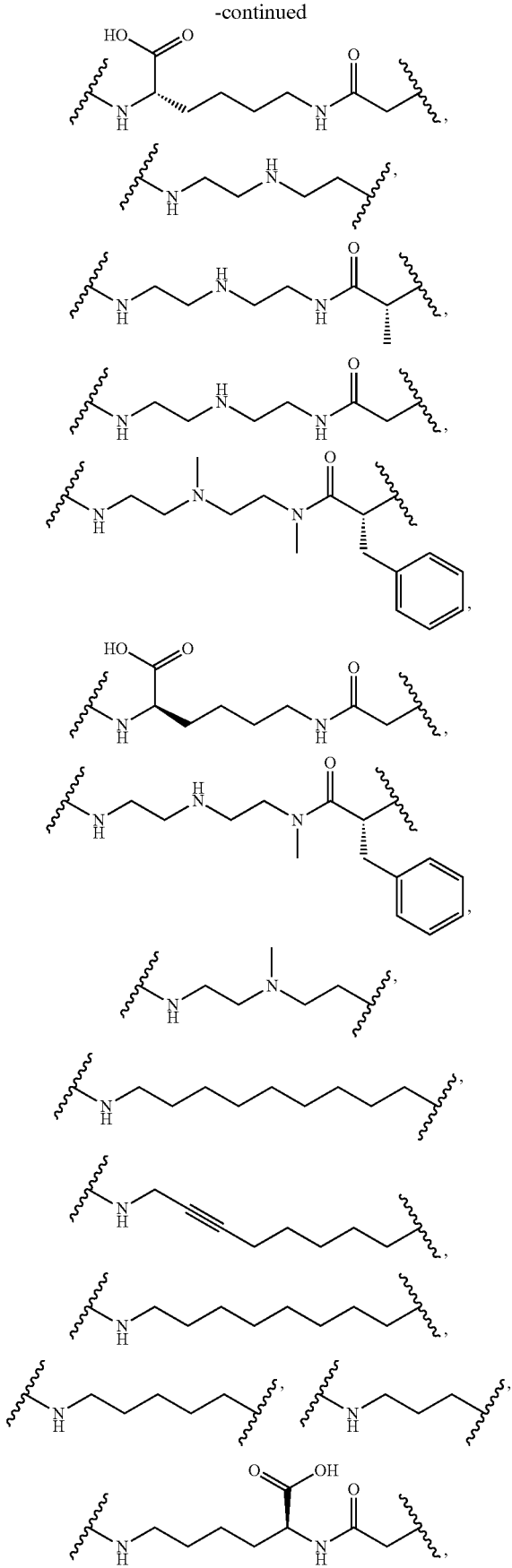
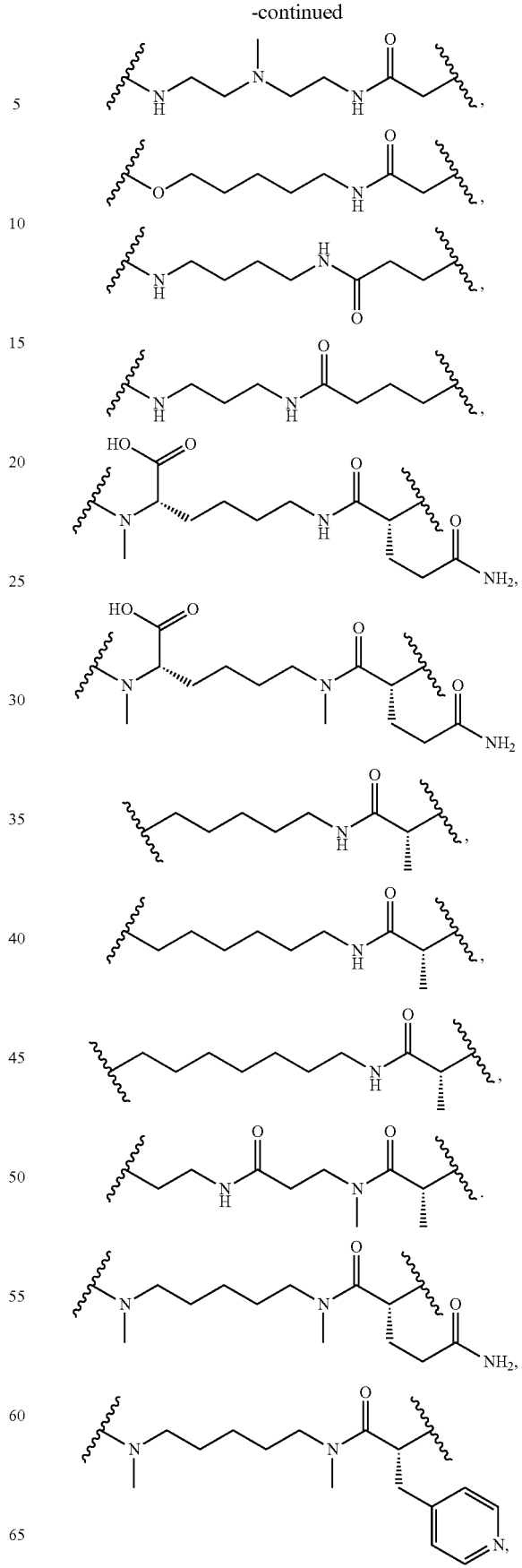

-continued
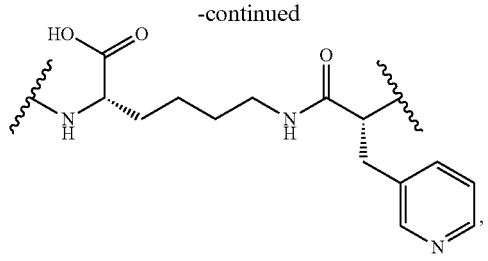
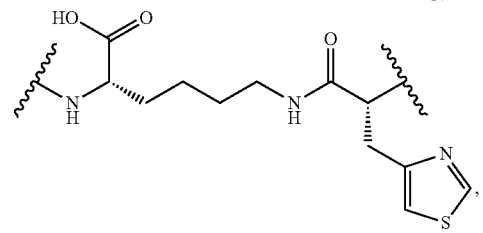
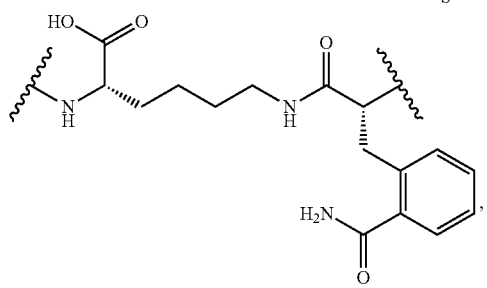
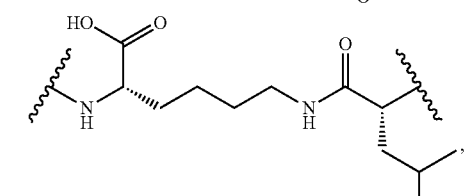
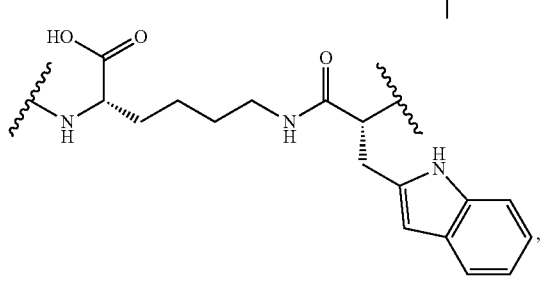
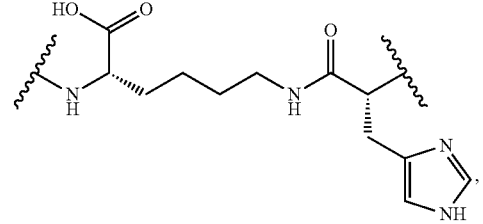
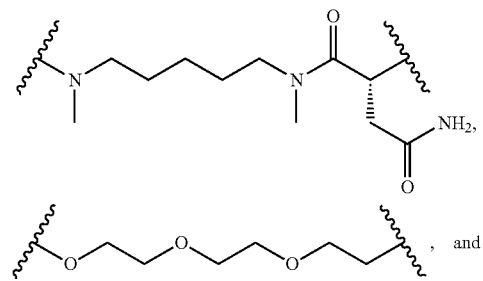
, and
-continued
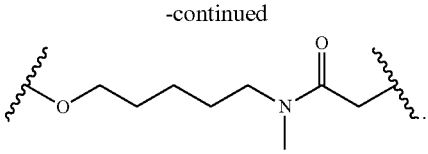
In certain other embodiments, the portion of the compound represented by —R$^1$-R$^2$ is selected from
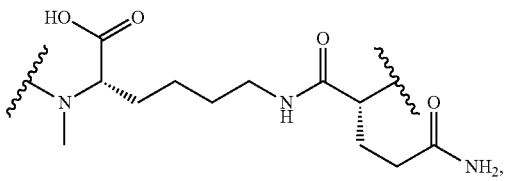
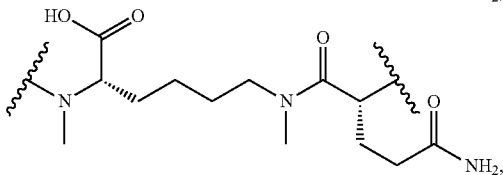
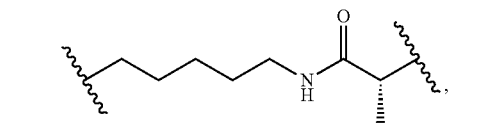
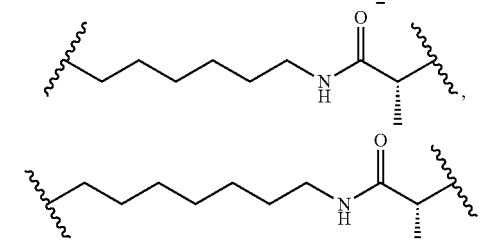
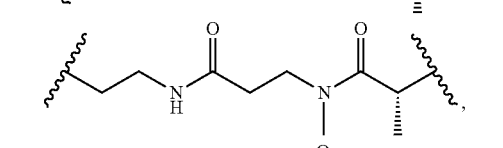
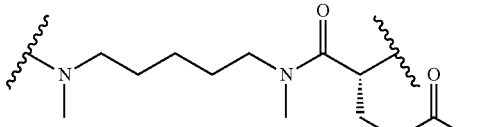
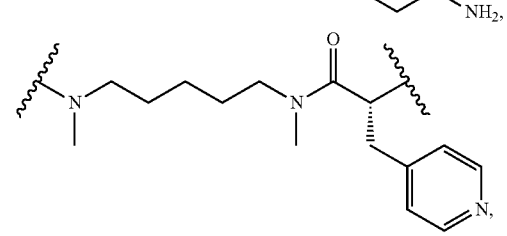
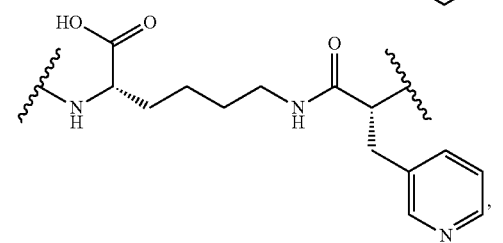

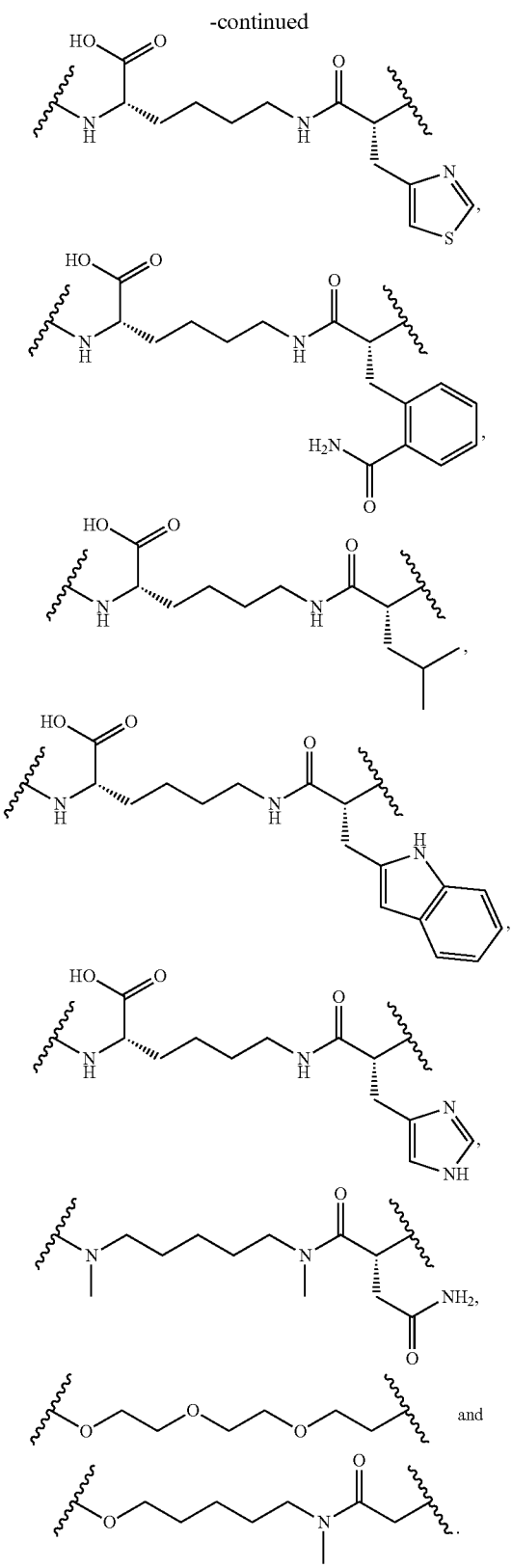

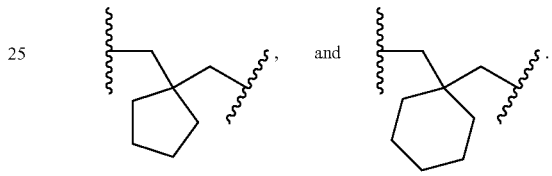

In certain embodiments of Formula I, $R^3$ is —[C($R^d$)($R^d_R$)]$_{2-4}$—, wherein:

each $R^d$ is independently selected from hydrogen and a suitable alkylene substituent; and any two $R^d$ are optionally taken together with any intervening atoms to form aryl, heteroaryl, carbocyclyl or heterocyclyl.

In certain embodiments of Formula I, $R^3$ is †—N($R^{7h}$)—[C($R^d$)($R^d$)]$_2$—, wherein:

each $R^d$ is independently selected from hydrogen and a suitable alkylene substituent;

any two $R^d$ are optionally taken together with any intervening atoms to form aryl, heteroaryl, carbocyclyl or heterocyclyl; and "†" represents a portion of $R^3$ bound to $R^1$.

In certain embodiments of Formula I, $R^3$ is —[C($R^d$)($R^d$)]—N($R^{7h}$)—[C($R^d$)($R^d$)]—, wherein: each $R^d$ is independently selected from hydrogen and a suitable alkylene substituent; and any two $R^d$ are optionally taken together with any intervening atoms to form aryl, heteroaryl, carbocyclyl or heterocyclyl.

In certain embodiments of Formula I, $R^3$ is selected from —(CH$_2$)$_3$—, —CH$_2$—C(CH$_3$)$_2$—CH$_2$—,

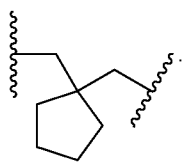 [SMILES: *CC1(C*)CCCC1]

In one aspect of these embodiments, $R^3$ is

In certain embodiments of Formula I, $R^3$ is selected from —CH$_2$—C(CH$_3$)$_2$—CH$_2$—, —CH$_2$—N(CH$_3$)—CH$_2$—,

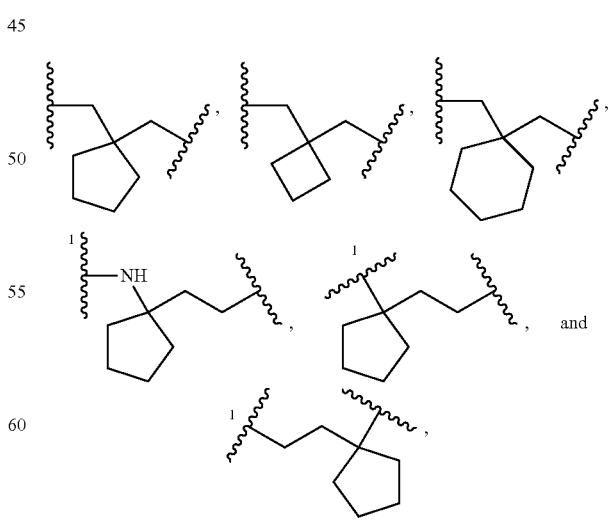

wherein "1" represents a portion of $R^3$ bound to the carbonyl moiety that is bound to $R^1$.

In certain embodiments of Formula I, $R^3$ is selected from —CH$_2$—C(CH$_3$)$_2$—CH$_2$—, —CH$_2$—N(CH$_3$)—CH$_2$,

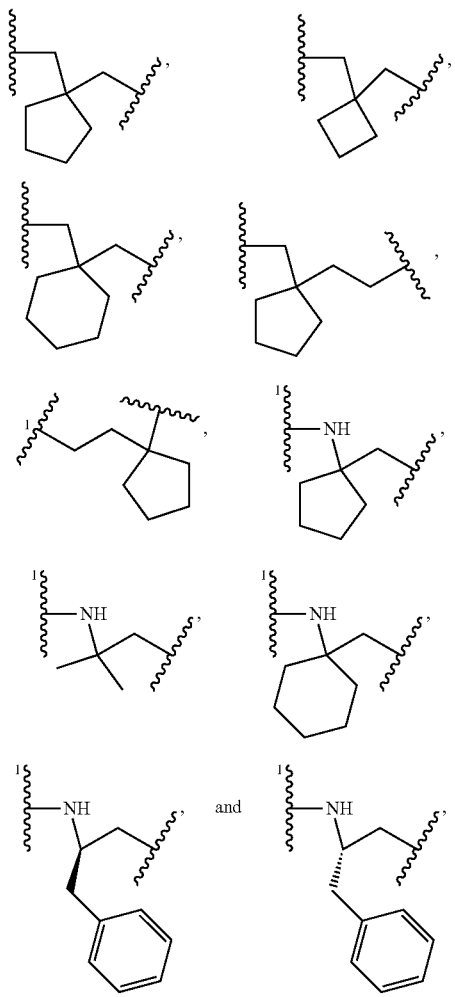

wherein "1" represents a portion of $R^3$ bound to the carbonyl moiety that is bound to $R^1$.

In certain other embodiments of Formula I, $R^3$ is selected from

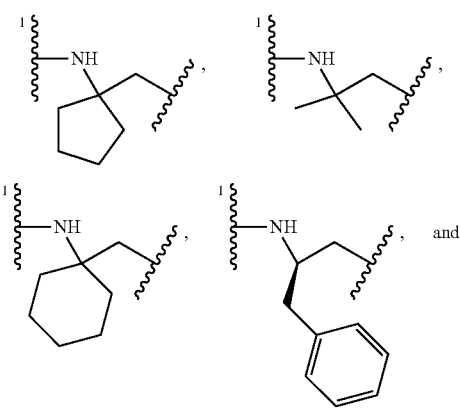

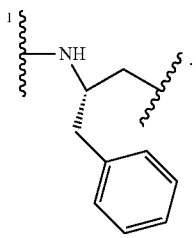

In certain embodiments of Formula I, each of n and m are independently selected from 0, 1, 2, 3; and n+m is 4 or less.

In certain embodiments of Formula I, $R^4$ is selected from —(CH$_2$)$_4$—, and —CH$_2$-(1,4-phenylene)-†, wherein "†" represents a portion of $R^4$ bound to N($R^7$). In a more specific aspect of these embodiments, $R^4$ is —CH$_2$-(1,4-phenylene)-†; and the stereochemistry of the carbon adjacent to $R^4$ is (S).

In certain embodiments of Formula I, $R^5$ is selected from —C(H)(C$_1$-C$_4$ alkyl)-, —C(H)(CH$_2$-aryl)-, —C(H)(CH$_2$-heteroaryl)-, —C(H)(CH$_2$-cycloalkyl)-, and —C(H)(cycloalkyl)-, wherein the aryl or heteroaryl is optionally substituted with up to two substituents independently selected from halo, C$_1$-C$_4$ alkyl, and phenyl. In one aspect of these embodiments, $R^5$ is selected from —C(H)(C(CH$_3$)$_3$)—, —C(H)(C(H)(CH$_2$CH$_3$)CH$_3$)—, —C(H)(C(CH$_2$CH$_3$)(CH$_3$))—, —C(H)(cyclohexyl)-, —C(H)(CH$_2$-furanyl)-, —C(H)(CH$_2$-phenyl)-, —C(H)(CH$_2$-biphenyl)-, —C(H)(CH$_2$-thiophenyl)-, —C(H)(CH$_2$-thiazolyl)-, —C(H)(CH$_2$-cyclobutyl)-, and —C(H)(CH$_2$-cyclopropyl)-, wherein any of the furanyl, phenyl, thiophenyl, or thiazolyl are optionally benzofused and optionally substituted with up to two substituents independently selected from fluoro, chloro, bromo, hydroxy and methyl.

In certain embodiments $R^5$ is —C(H)((R)-benzyl)- wherein a phenyl portion of the benzyl is optionally substituted with up to two substituents independently selected from bromo, chloro, fluoro, methyl, and —CF$_3$; or $R^5$ is selected from —C(H)(CH$_2$—(C$_4$-C$_6$ cycloalkyl))-, —C(H)(C$_4$-C$_6$ cycloalkyl)-, —C(H)(CH$_2$-thienyl)-, and —C(H)(CH$_2$-furanyl)-.

In certain other embodiments, $R^5$ is selected from —CH((R)-benzyl)-, wherein a phenyl portion of the benzyl is optionally substituted with up to two substituents independently selected from bromo, chloro, fluoro, methyl and —CF$_3$. In yet other embodiments, $R^5$ is —C(H)(CH$_2$—(C$_4$-C$_6$ cycloalkyl))-, —C(H)(C$_4$-C$_6$ cycloalkyl)-, —C(H)(CH$_2$-thienyl)-, or —C(H)(CH$_2$-furanyl)-.

In certain other embodiments, $R^5$ is —C(H)((R)-benzyl)- wherein a phenyl portion of the benzyl is optionally substituted with up to two substituents independently selected from bromo, chloro, fluoro, methyl, and —CF$_3$; or $R^5$ is selected from —C(H)(CH$_2$—(C$_4$-C$_6$ cycloalkyl))-, —C(H)(C$_4$-C$_6$ cycloalkyl)-, —C(H)(CH$_2$-thienyl)-, —C(H)(CH$_2$-furanyl)-, —C(H)(heterocyclyl)-, —C(H)(CH(CH$_3$)-(aryl))-, —C(H)(CH(CH$_3$)-(heteroaryl))-, —C(H)(CH(CH$_3$)-(heterocyclyl))-, —C(H)(CH(CH$_3$)-(carbocyclyl))-, and —C(H)(C$_3$-C$_4$ alkyl)-.

In a more specific embodiment, $R^5$ is selected from:
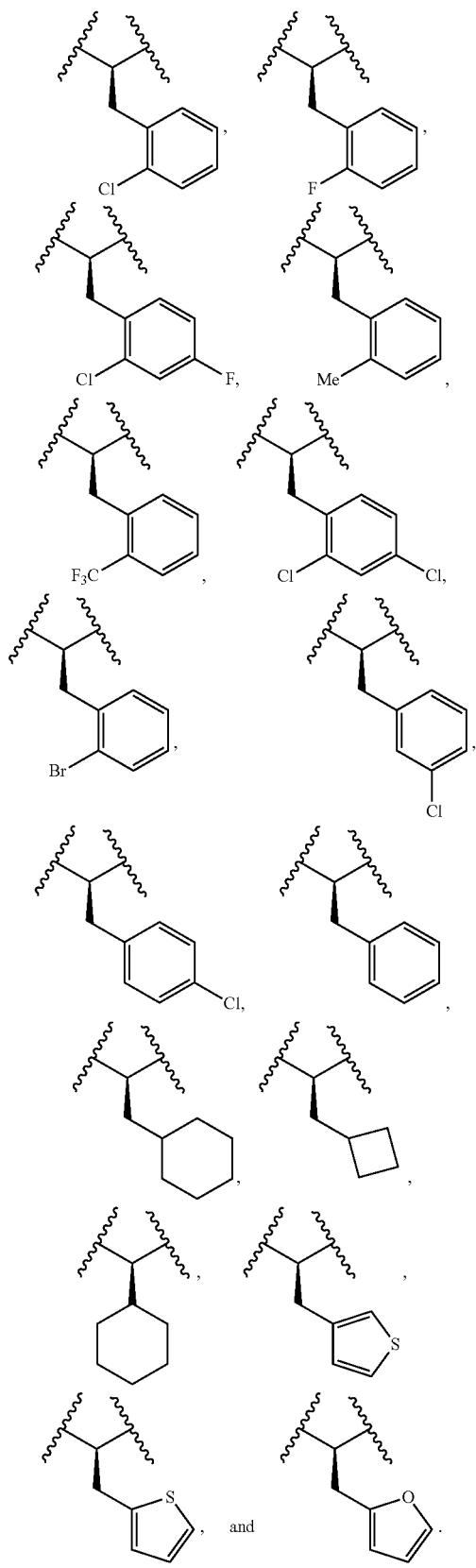
In another more specific embodiment, $R^5$ is selected from:
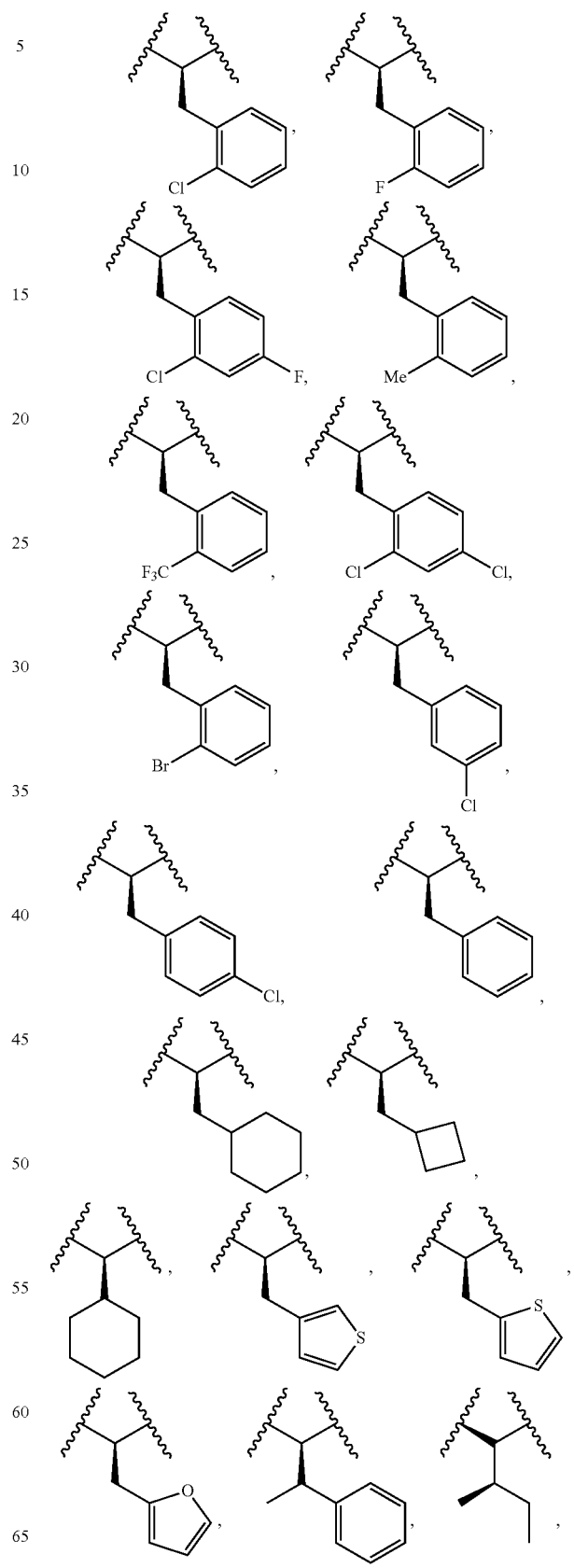

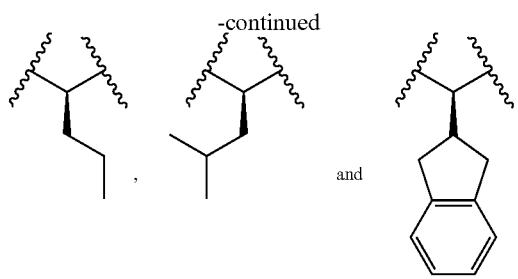

In certain other embodiments, $R^5$ is selected from —C(H)(heterocyclyl)-, —C(H)(CH(CH$_3$)(aryl))-, —C(H)(CH(CH$_3$)(heteroaryl))-, —C(H)(CH(CH$_3$)(heterocyclyl))-, —C(H)(CH(CH$_3$)(carbocyclyl))-, and —C(H)(C$_3$-C$_4$ alkyl)-. In In certain other embodiments, $R^5$ is selected from

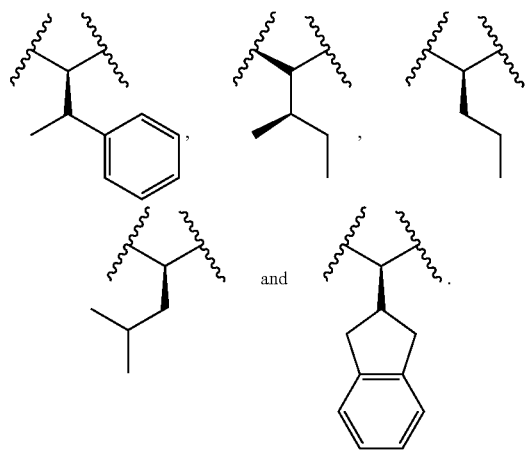

In certain embodiments of Formula I, $R^6$ is selected from heteroaryl, —C(O)—R$^8$, —C(O)—O—R$^8$, —C(O)—C(O)—R$^8$, —S(O)—R$^8$, —S(O)$_2$—R$^8$, C(O)—N(R$^{7f}$)—R$^8$, and —S(O)$_2$—N(R$^{7f}$)—R$^8$, wherein each R$^{7a}$, R$^{7b}$, R$^{7c}$, R$^{7d}$, R$^{7e}$, R$^{7f}$, R$^{7g}$ is independently selected from hydrogen and C$_1$-C$_4$ alkyl; and R$^8$ is as defined above.

In certain embodiments of Formula I, R$^6$ is —C(O)—[CH$_2$]$_{0-1}$—R$^9$; and R$^9$ is selected from aryl, heteroaryl, cycloalkyl, saturated heterocyclyl, and C$_1$-C$_4$ alkyl, wherein R$^9$ is optionally substituted with up to 2 substituents independently selected from halo, C$_1$-C$_4$ alkyl, C$_1$-C$_4$ haloalkyl, hydroxy, C$_1$-C$_4$ alkoxy, C$_1$-C$_4$ hydroxyalkyl. In one aspect of these embodiments, R$^9$ is selected from phenyl, pyridinyl, oxazolyl, pyrazinyl, pyrimidinyl, cyclobutyl, cyclopentyl, cyclohexyl, tetrahydropyranyl, —OCH$_3$, and C$_1$-C$_4$ alkyl, wherein any phenyl, pyridinyl, oxazolyl, pyrazinyl, or pyrimidinyl in R$^9$ is optionally substituted with up to 2 substituents independently selected from fluoro, chloro, CF$_3$, hydroxy, and —CH$_2$OH.

In alternate embodiments of Formula I, R$^6$ is —C(O)—[C(R$^{13}$)$_2$]$_{0-1}$—R$^{9a}$, wherein R$^{9a}$ is selected from aryl, heteroaryl, cycloalkyl, saturated heterocyclyl, C$_1$-C$_4$ alkyl, —O—C$_1$-C$_4$ alkyl, —NH—CH$_3$, —N(CH$_3$)$_2$, and —NH—CH$_2$-aryl, wherein any aryl, heteroaryl, cycloalkyl, or saturated heterocyclyl portion of R$^{9a}$ is optionally substituted with up to 2 substituents independently selected from halo, C$_1$-C$_4$ alkyl, C$_1$-C$_4$ haloalkyl, hydroxy, C$_1$-C$_4$ alkoxy, —O—(CH$_2$)$_2$-morpholin-4-yl, —N(C$_1$-C$_3$ alkyl)$_2$, an N-linked saturated heterocycle, —O—(CH$_2$)$_2$—N(R$^{14}$)—CH$_2$-phenyl, —NH—C(O)—CH$_2$—NH—CH$_2$-phenyl, and —O—(CH$_2$)$_2$—N(R$^{14}$)$_2$;

each R$^{13}$ is independently selected from hydrogen or fluoro, or two R$^{13}$ are taken together to form a C$_3$-C$_6$ cycloalkyl or =O; and each R$^{14}$ is independently hydrogen or —CH$_3$.

In certain embodiments, R$^{9a}$ is selected from phenyl, pyridyl, quinolinyl, isoquinolinyl, cyclohexyl, 3,3-difluorocyclopropyl, —CH$_3$, —C(CH$_3$)$_3$, —OCH$_3$, —N(CH$_3$)$_2$, —NH(CH$_3$), —NH-benzyl, wherein R$^{9a}$ is optionally substituted with up to 2 substituents independently selected from fluoro, chloro, methyl, methoxy, hydroxy, —O—(CH$_2$)$_2$-morpholin-4-yl, —O—(CH$_2$)$_2$—N(CH$_3$)—CH$_2$-phenyl, and —O—(CH$_2$)$_2$—N(CH$_3$)$_2$.

In certain embodiments, R$^6$ is —C(O)-benzyl or —C(O)-phenyl, wherein the benzyl and phenyl in R$^6$ are each optionally substituted with one or more substituents independently selected from the group consisting of halogen, hydroxyl, C$_1$-C$_4$ alkoxyl, and C$_1$-C$_4$ alkyl.

In certain embodiments, R$^6$ is selected from:

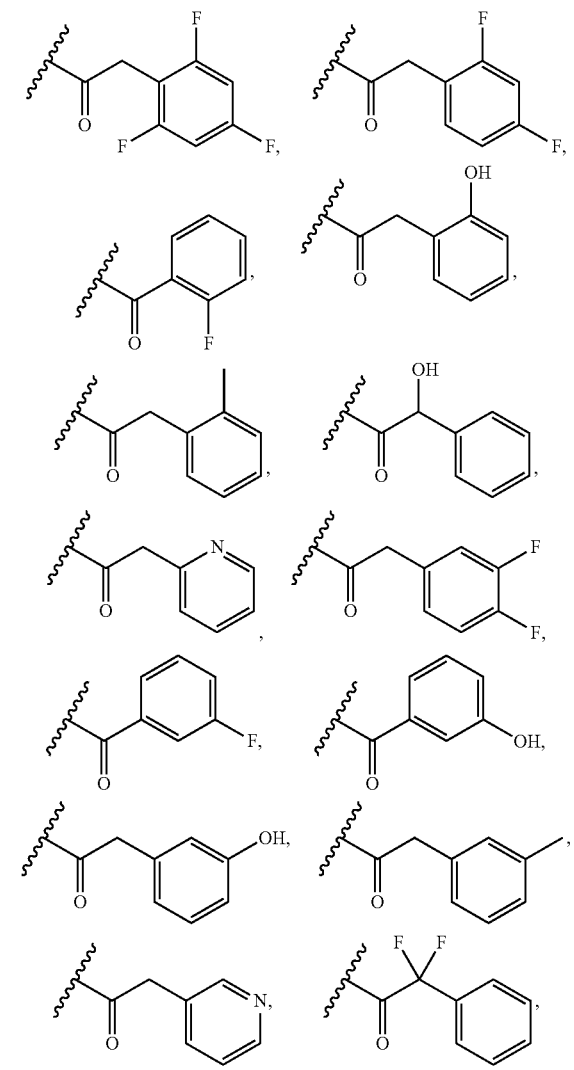

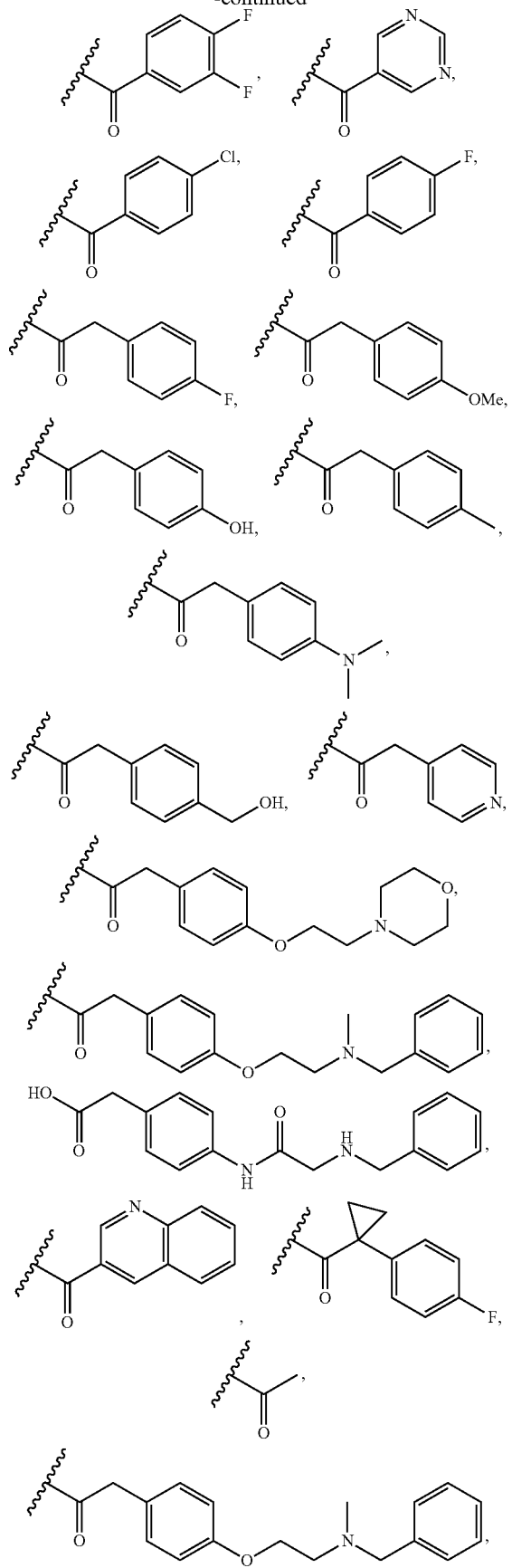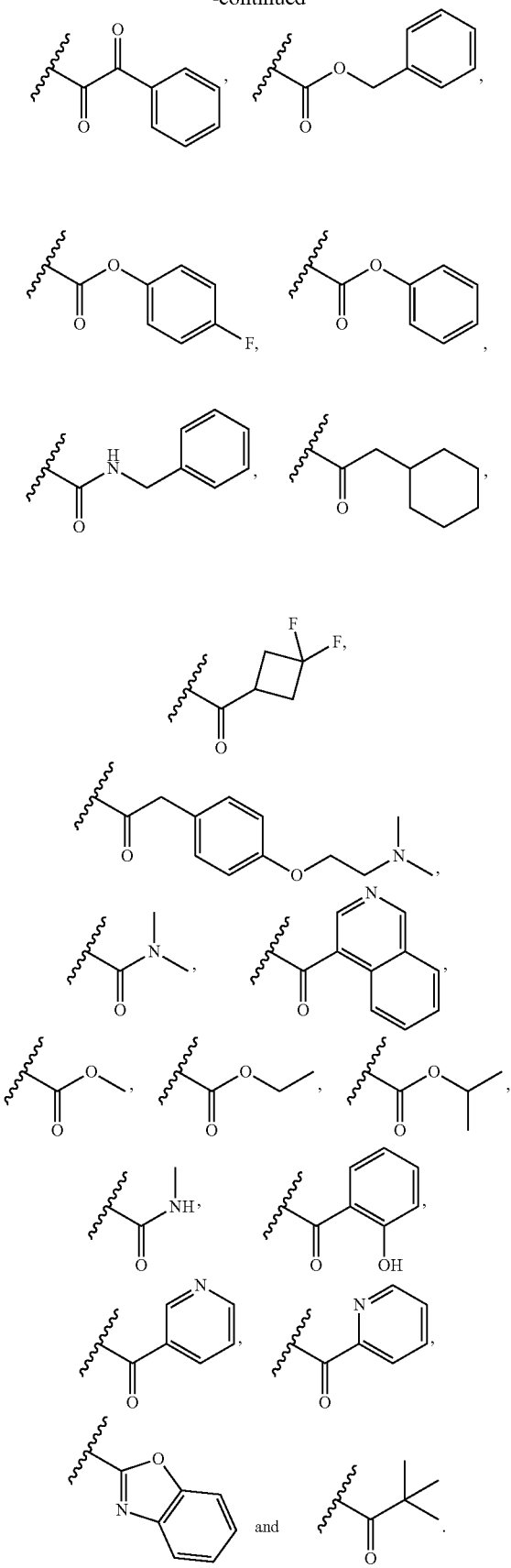

In certain embodiments, $R^6$ is selected from:
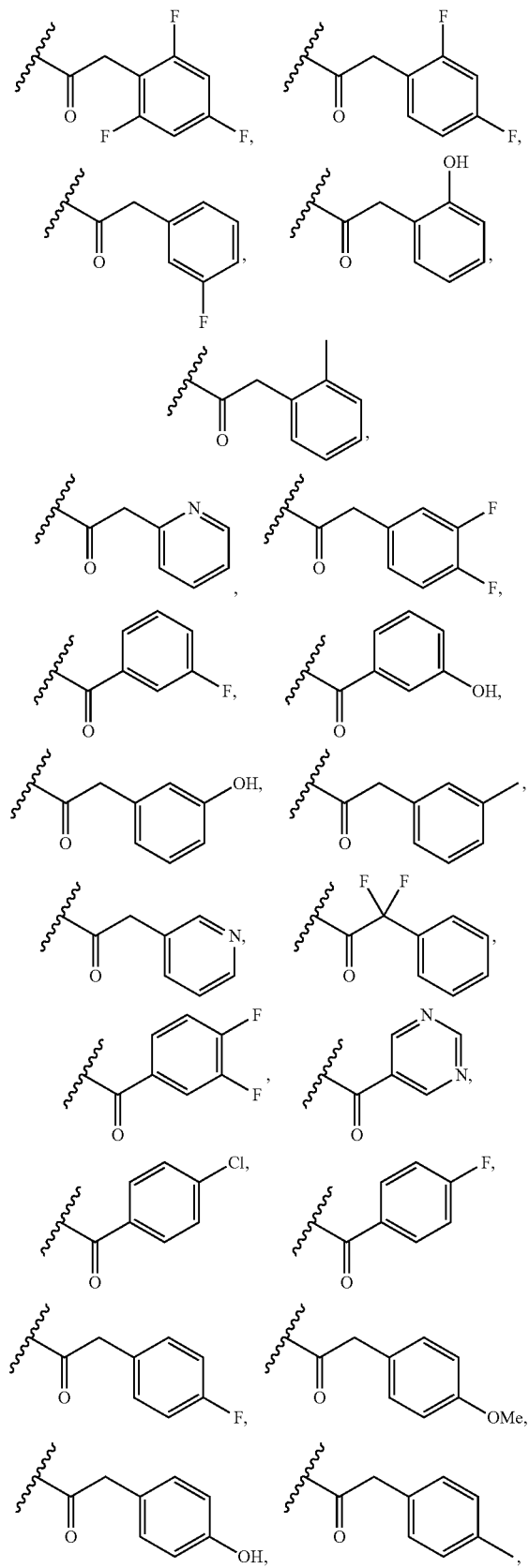
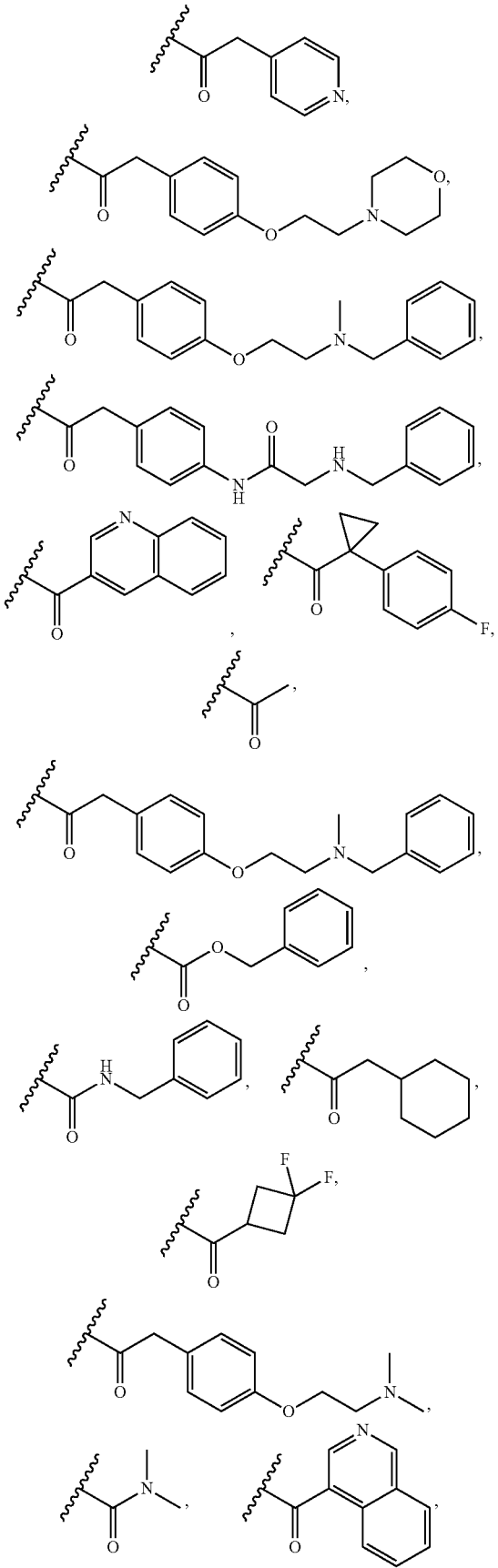

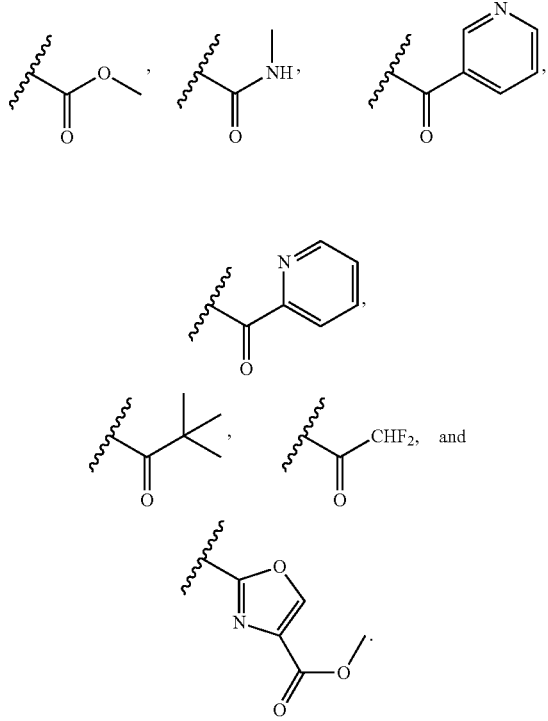

In certain other embodiments, $R^6$ is selected from

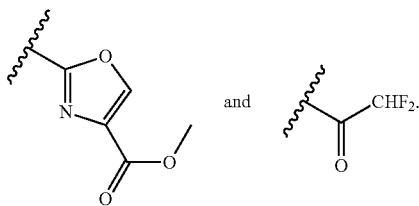

In certain embodiments of Formula I, $R^{7a}$, $R^{7b}$, $R^{7c}$, $R^{7d}$, $R^{7e}$, $R^{7f}$, $R^{7g}$ are independently selected from methyl and hydrogen.

Certain other embodiments relate to a compound of Formula I wherein rather than $R^{7d}$ and $R^6$ being optionally taken together to form a heterocyclyl, $R^{7d}$ and $R^8$ are optionally taken together to form a heterocyclyl.

The description above describes multiple embodiments relating to compounds of Formula I. The patent application specifically contemplates all combinations of the embodiments.

Figure 12:
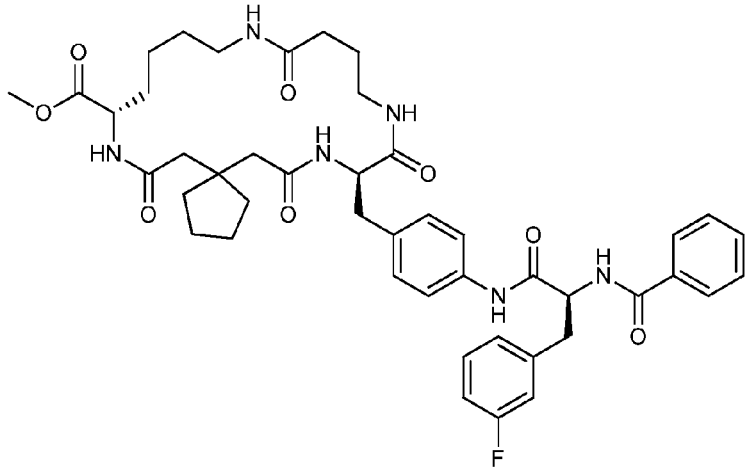
FIG. 12 is a table of exemplary compounds of the invention (Table 1).
Figure 6:
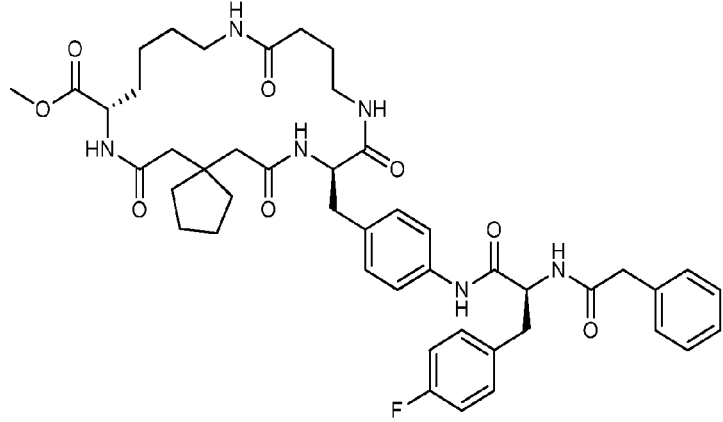
Figure 12:
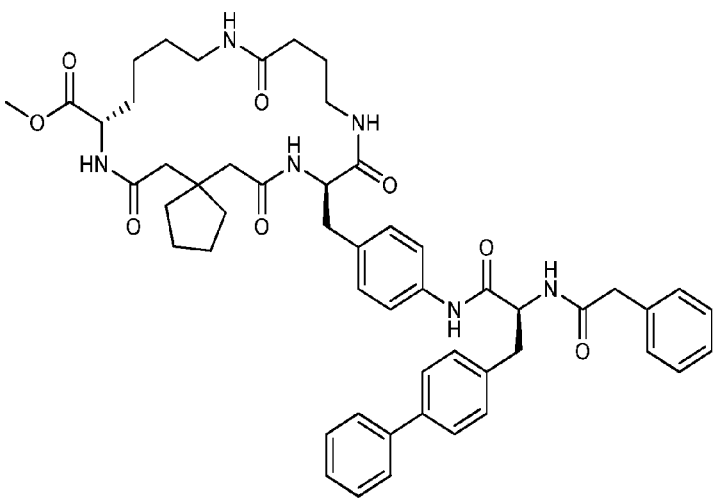
Figure 9:
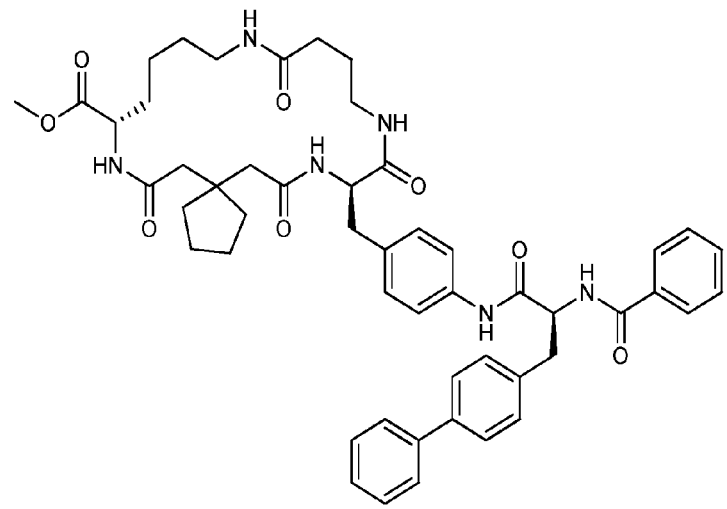
Figure 12:

Figure 64:

Figure 12:
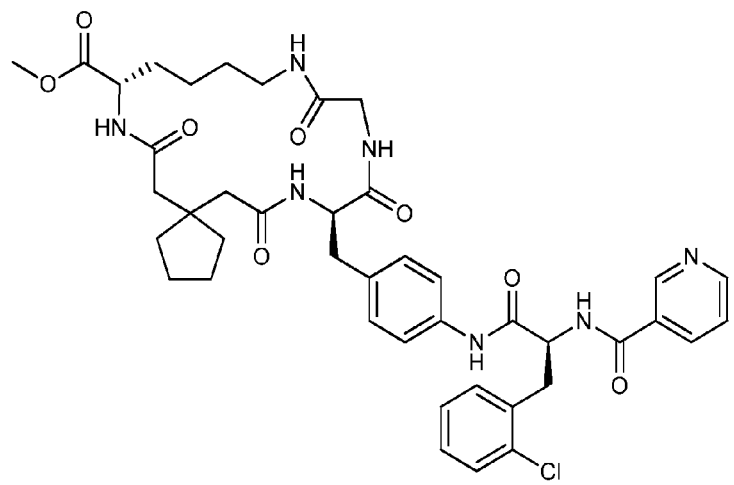
Figure 66:
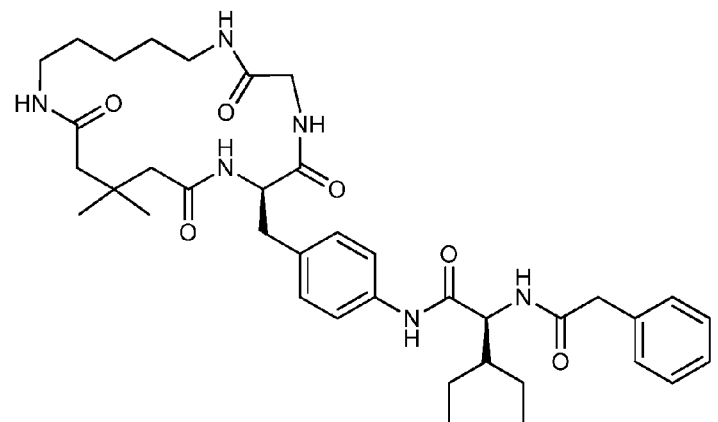
Figure 12:
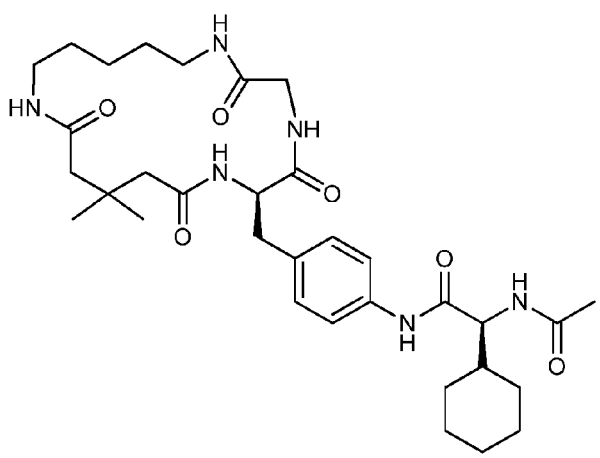
Figure 67:
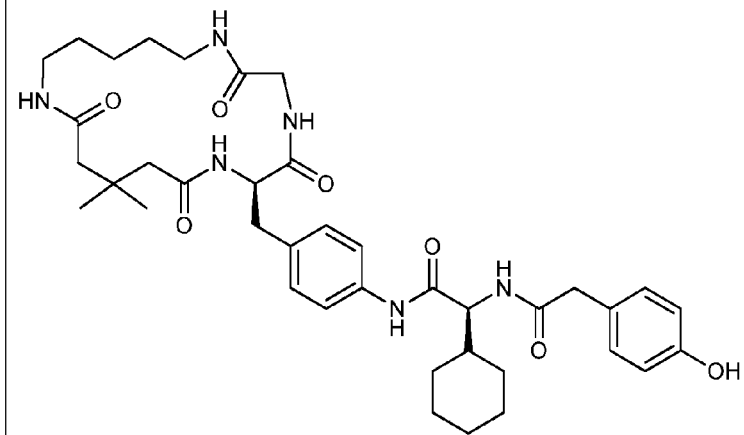
Figure 12:
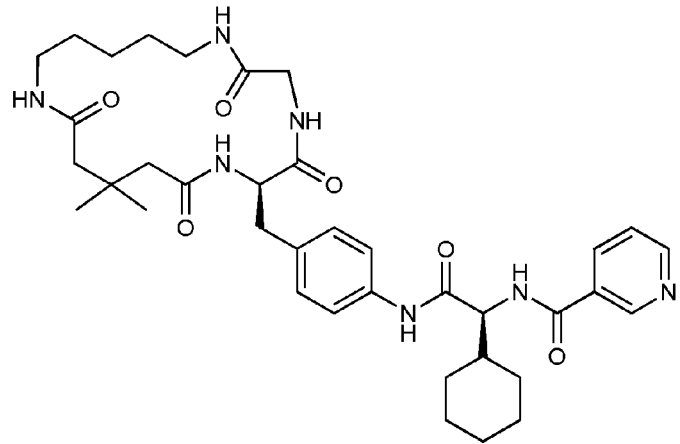
Figure 68:
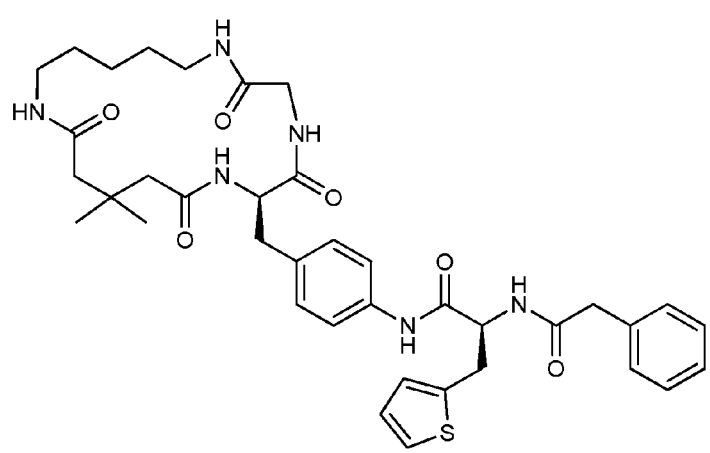
Figure 12:
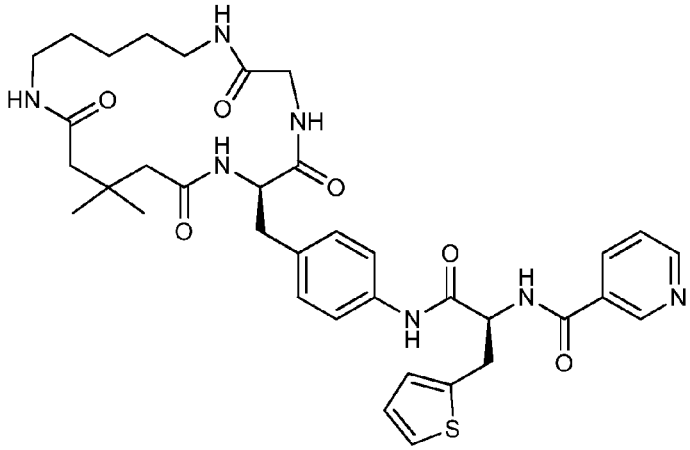
Figure 70:
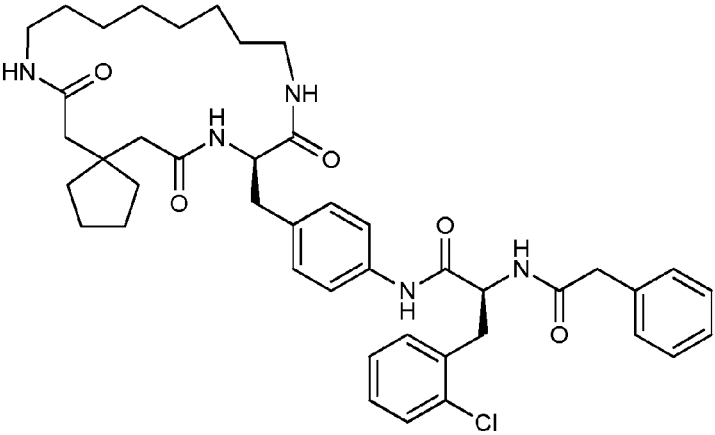
Figure 12:
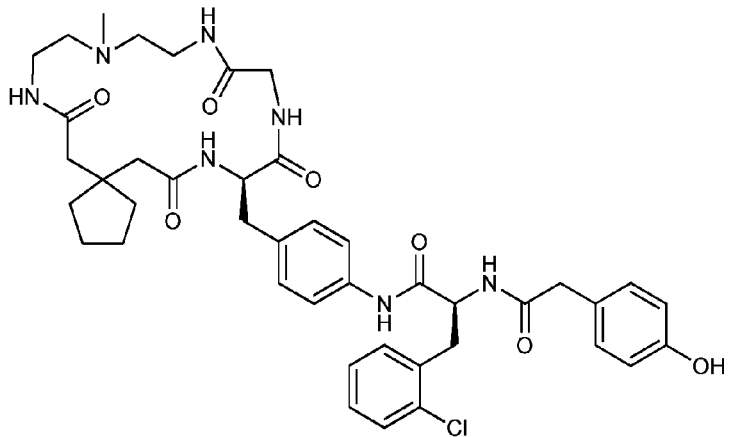
Figure 71:
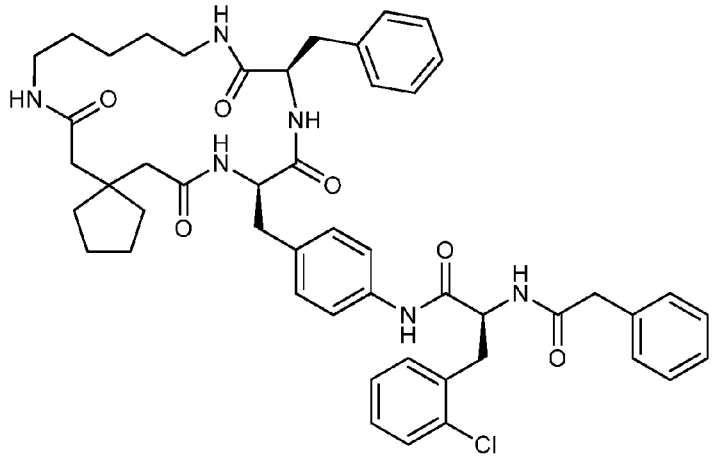
Figure 12:
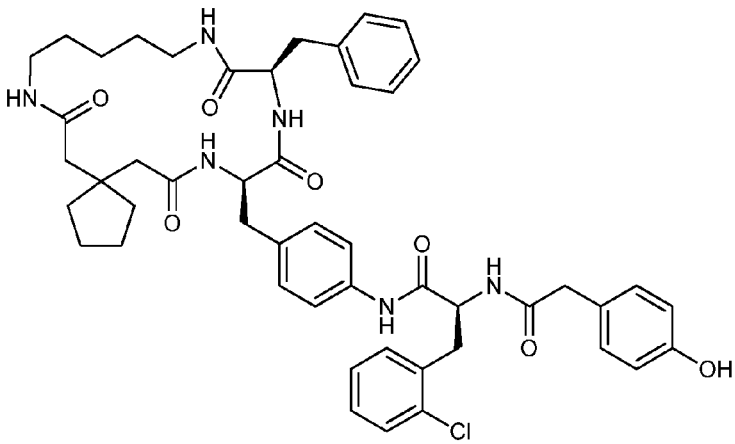
Figure 72:
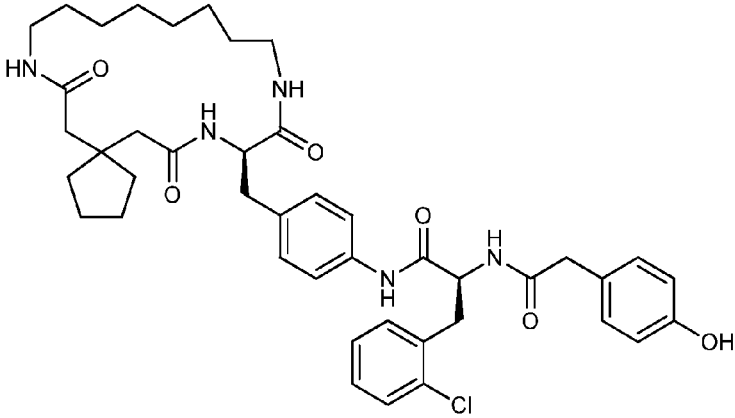
Figure 12:
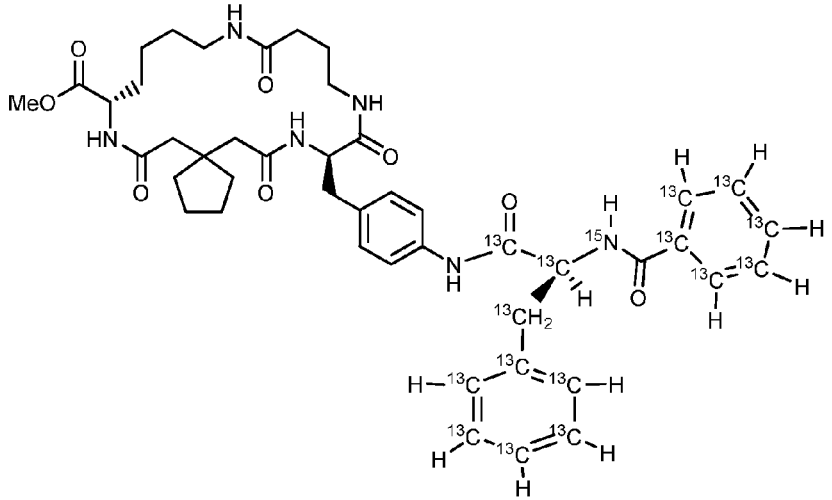
Figure 75:
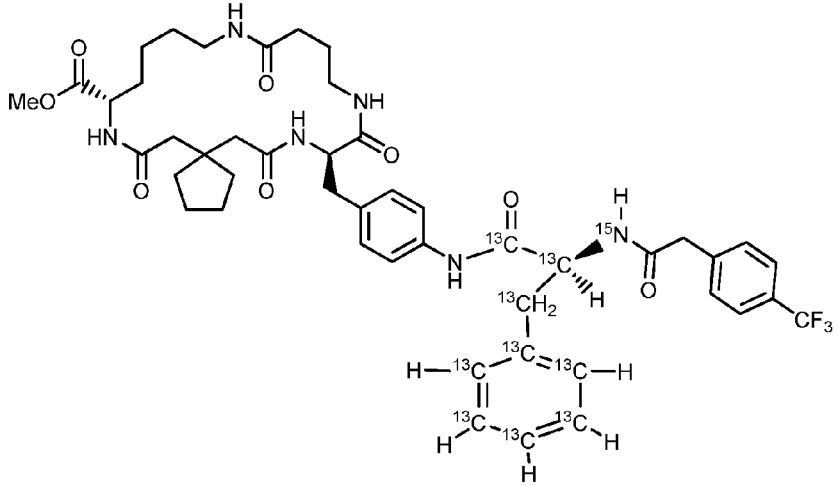
Figure 12:
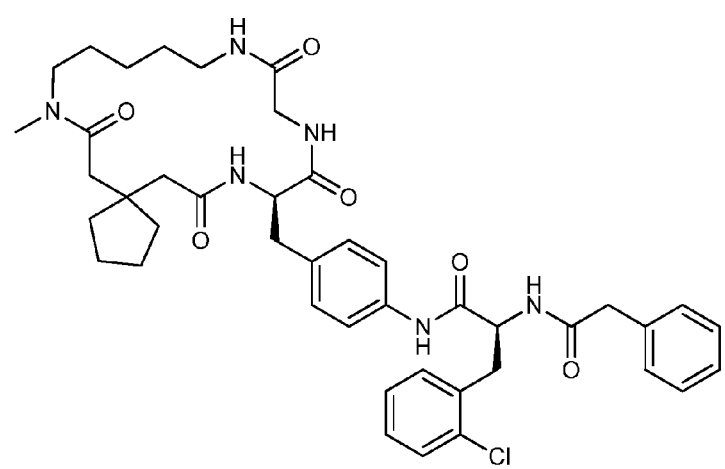
Figure 81:
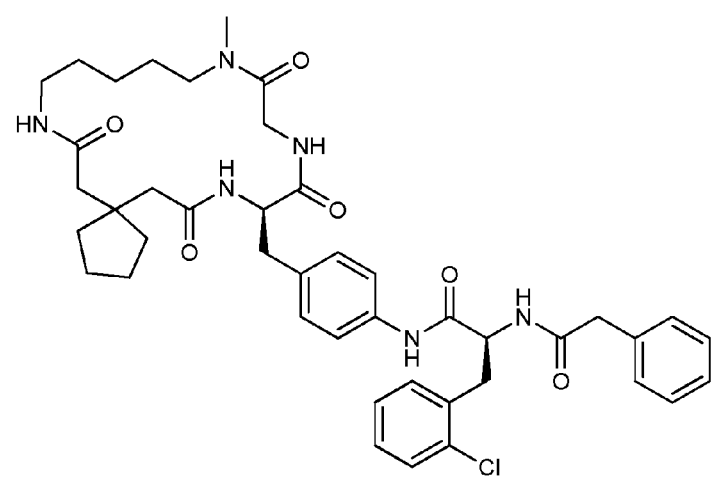
Figure 12:
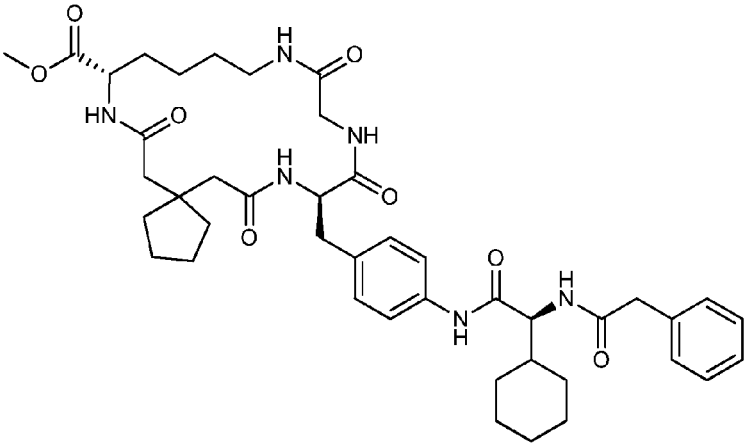
Figure 82:
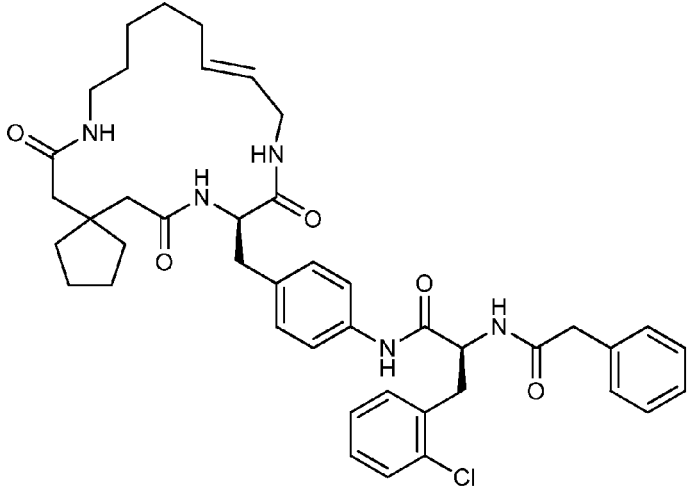
Figure 12:
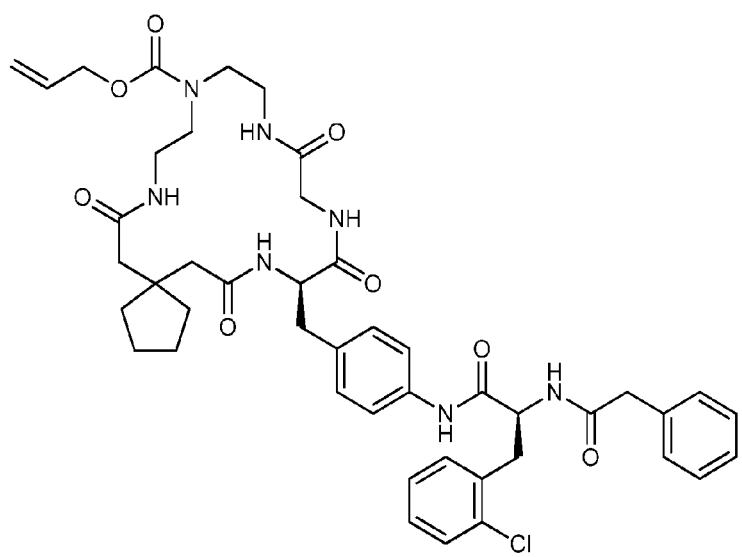
Figure 83:
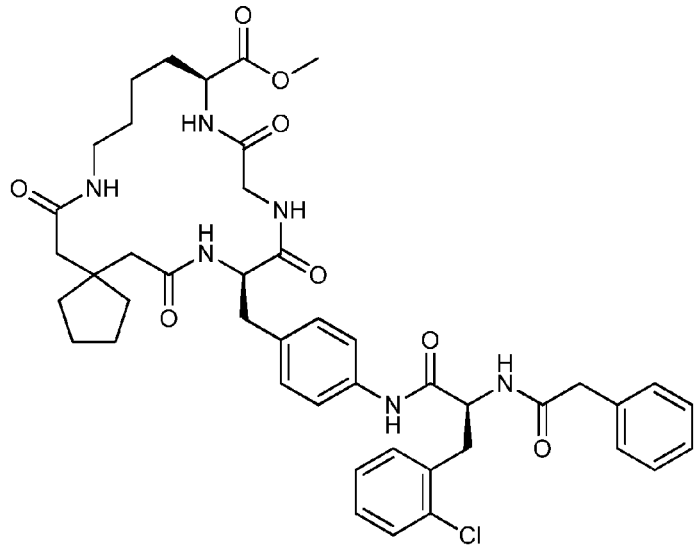
Figure 12:
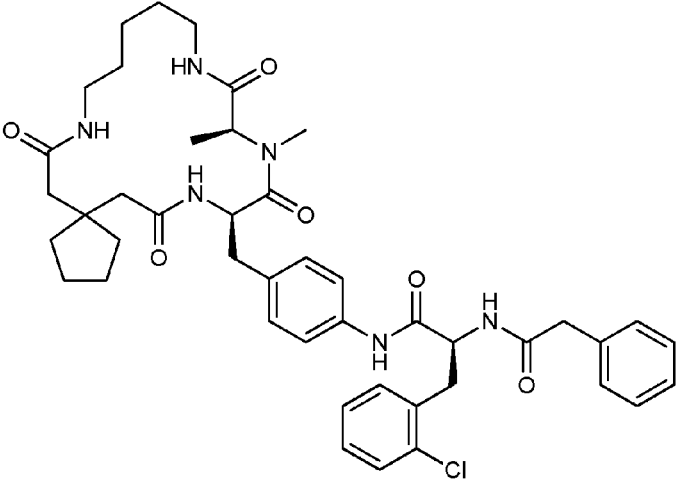
Figure 86:
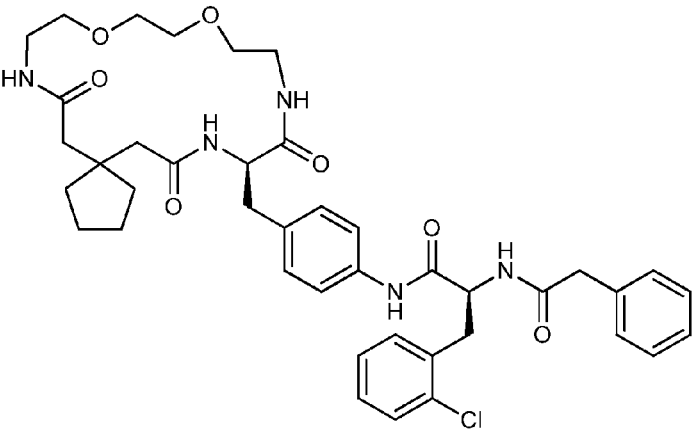
Figure 12:
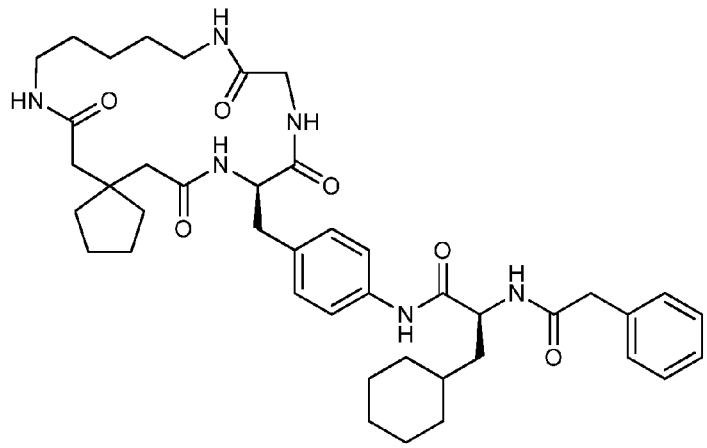
Figure 87:
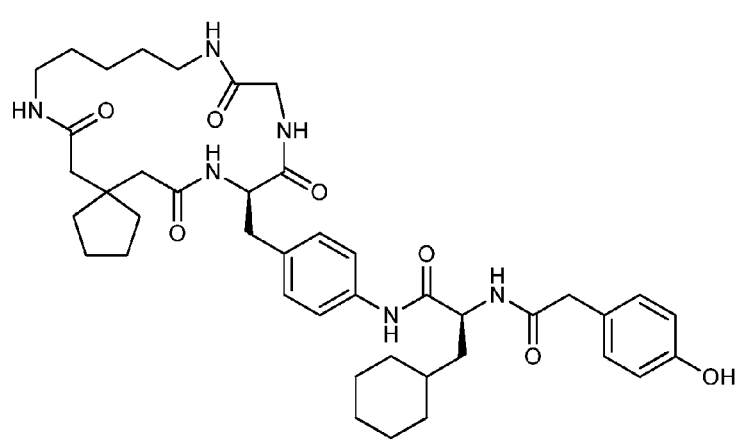
Figure 12:
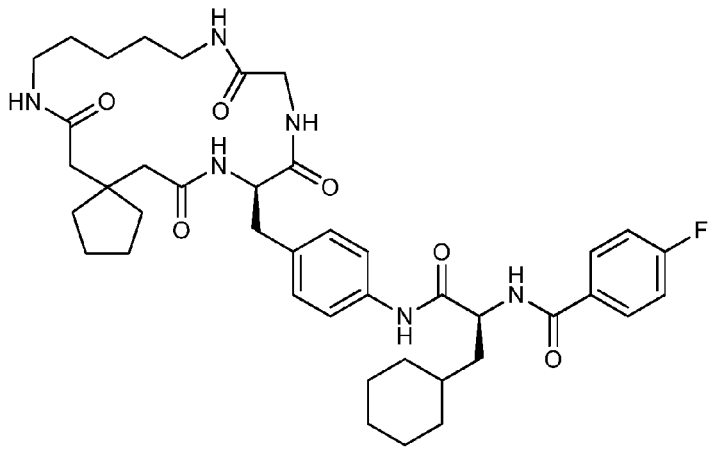
Figure 88:
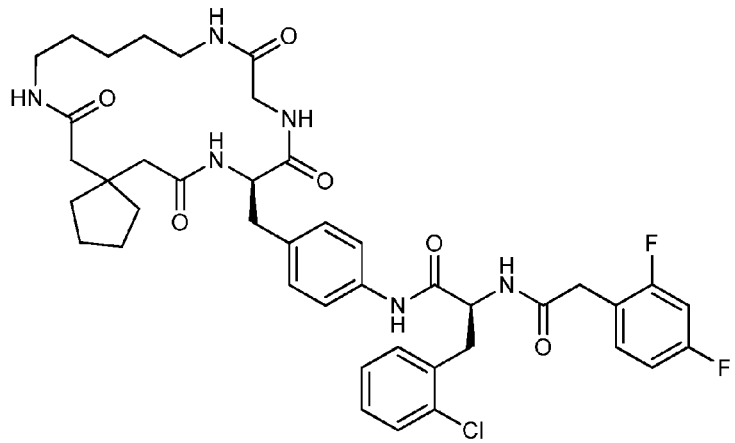
Figure 12:
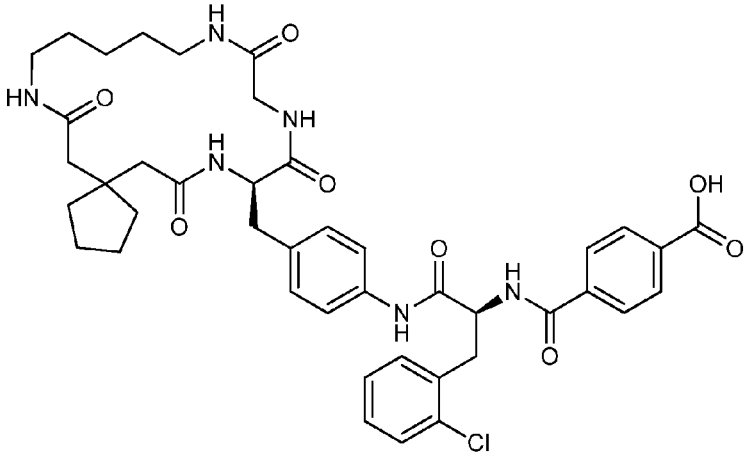
Figure 90:
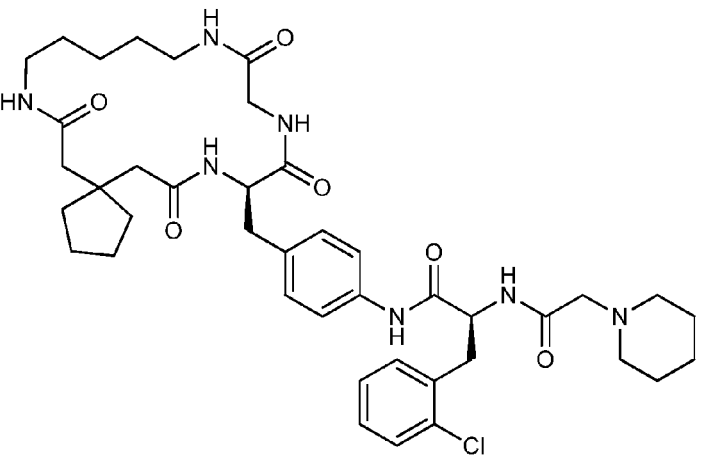
Figure 12:
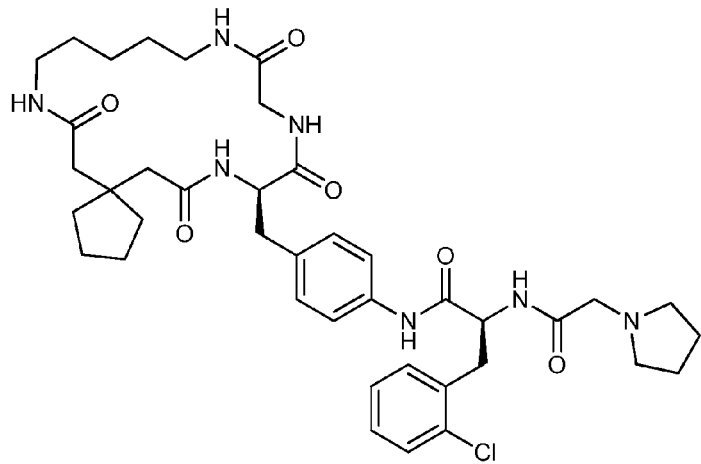
Figure 91:
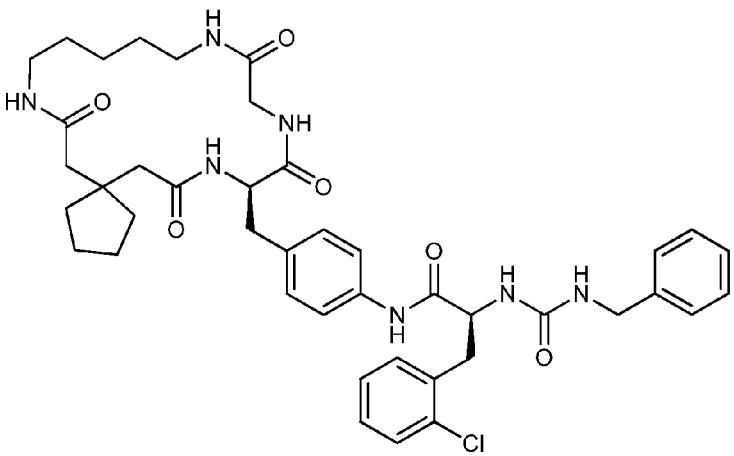
Figure 12:
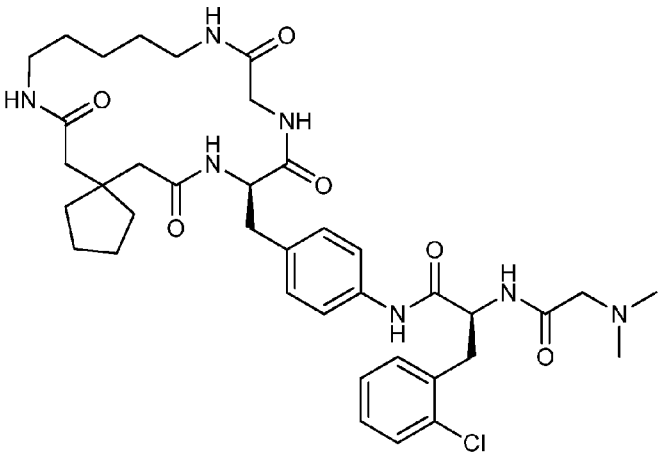
Figure 92:
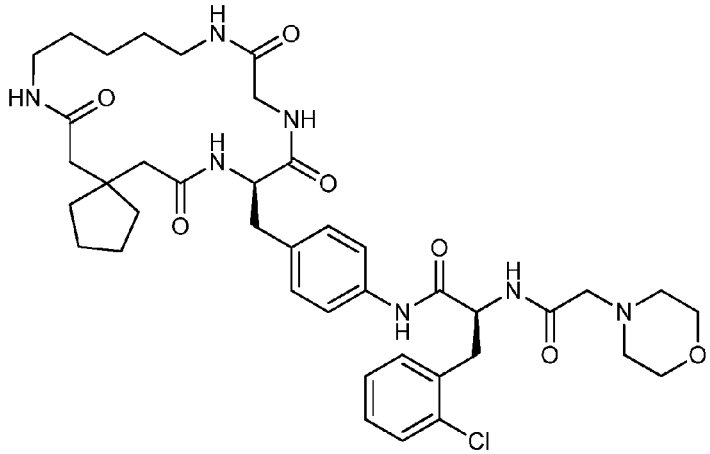
Figure 12:

Figure 93:

Figure 12:
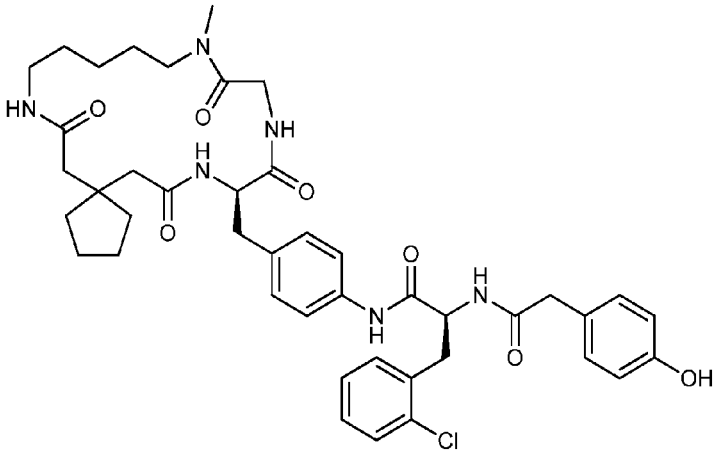
Figure 94:
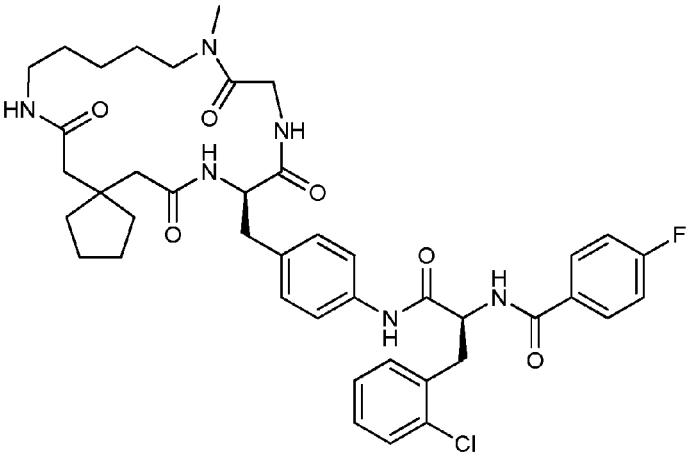
Figure 12:
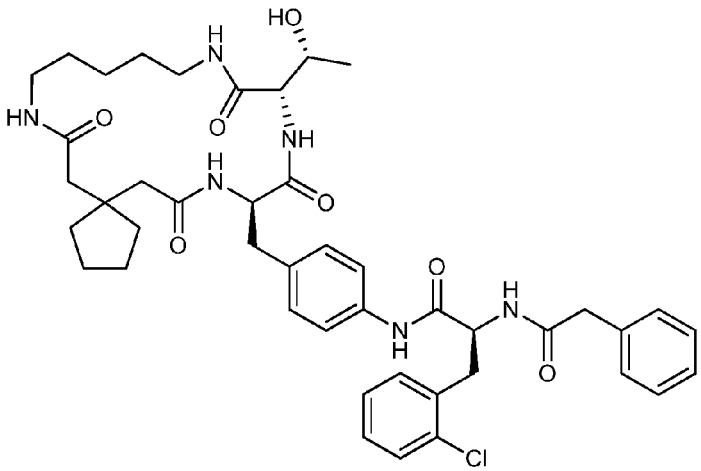
Figure 99:
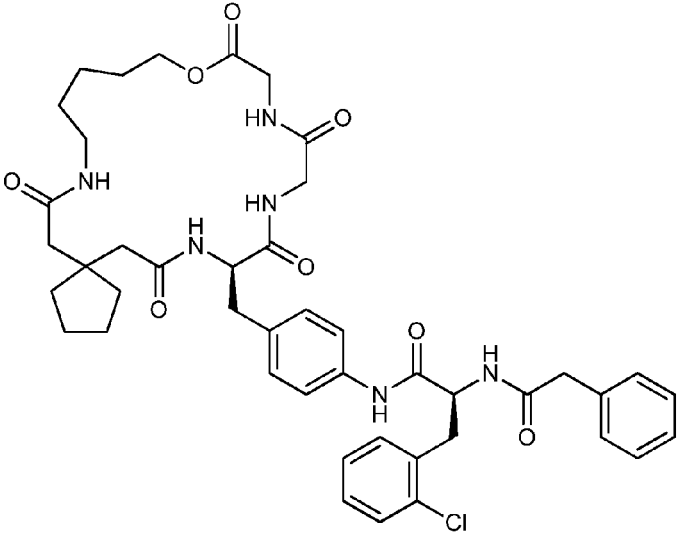
Figure 12:

Figure 100:

Figure 12:
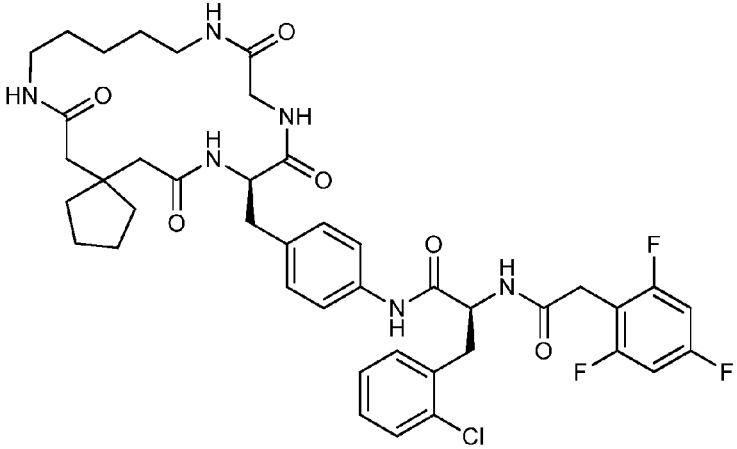
Figure 101:
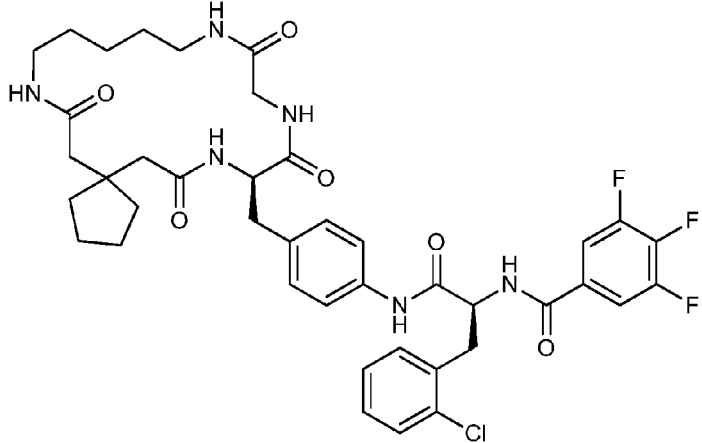
Figure 12:
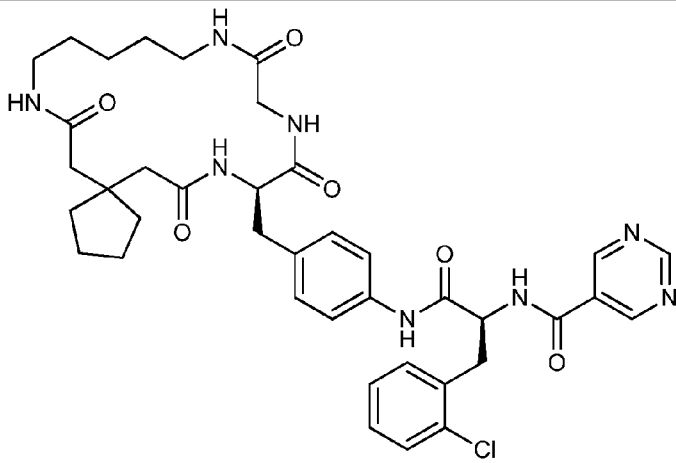
Figure 102:
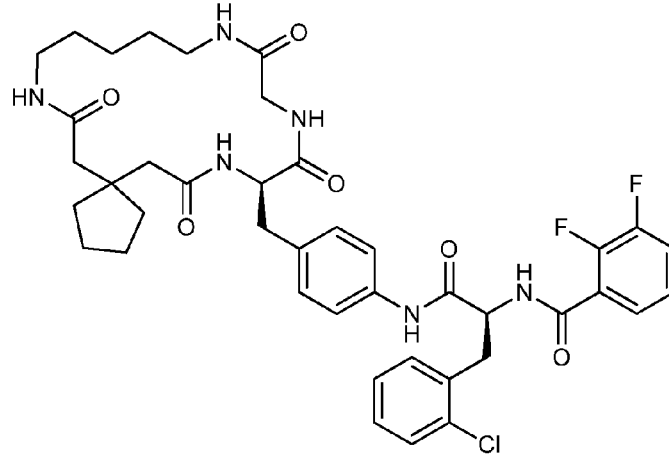
Figure 12:
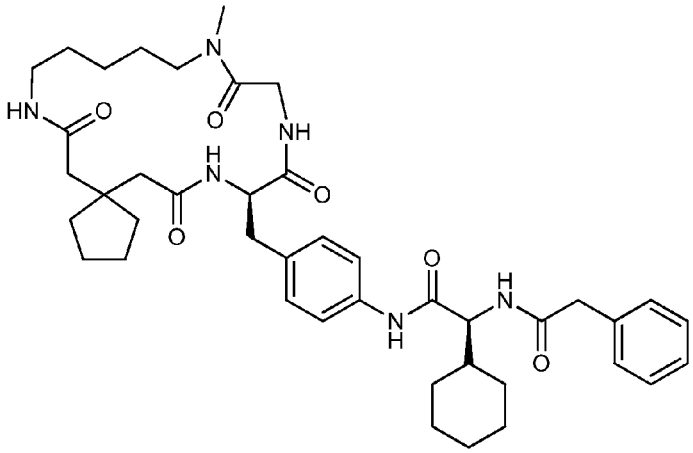
Figure 105:
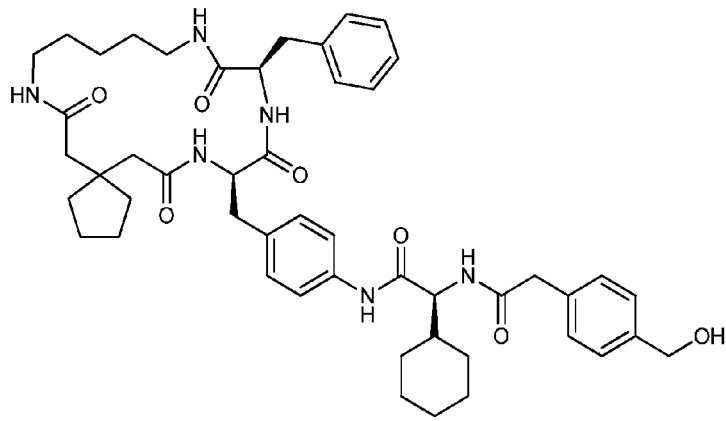
Figure 12:
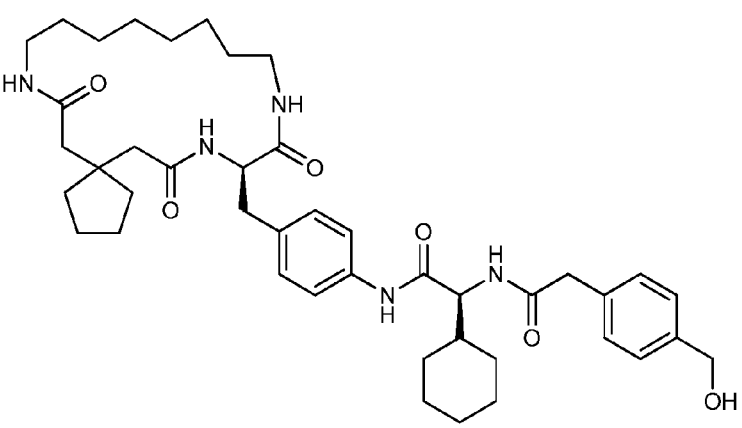
Figure 106:
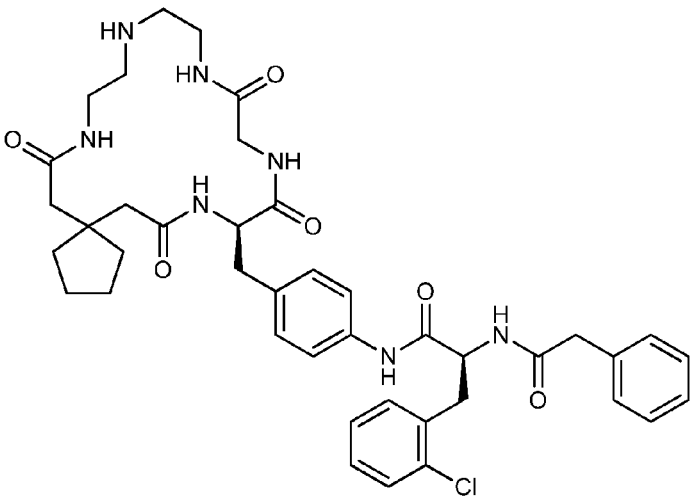
Figure 12:
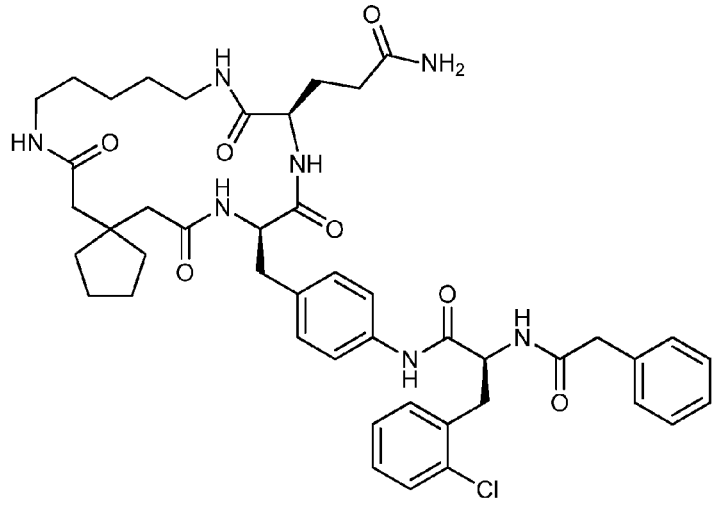
Figure 108:
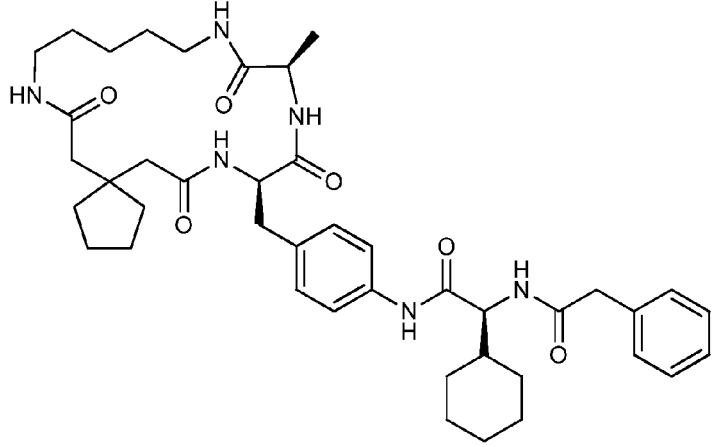
Figure 12:
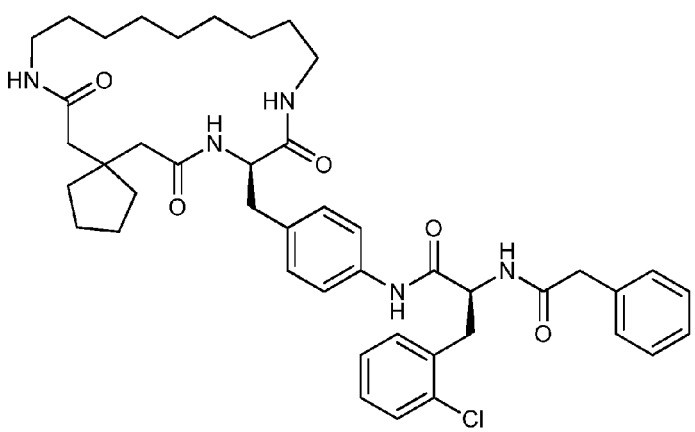
Figure 111:
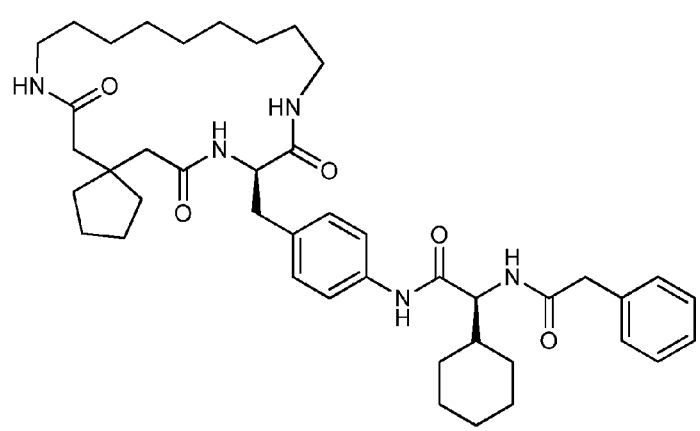
Figure 12:
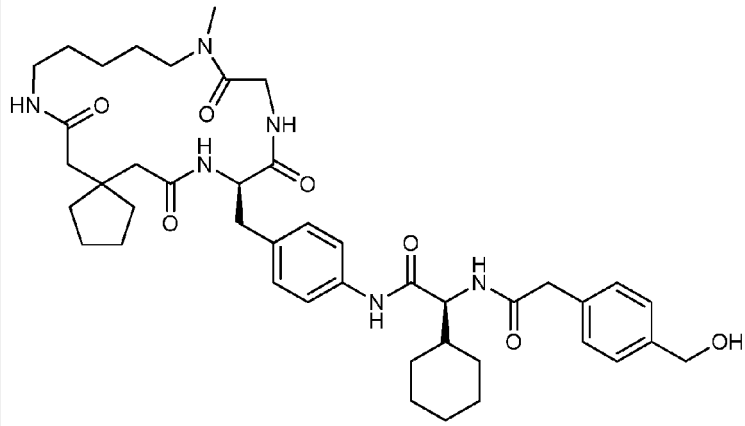
Figure 112:
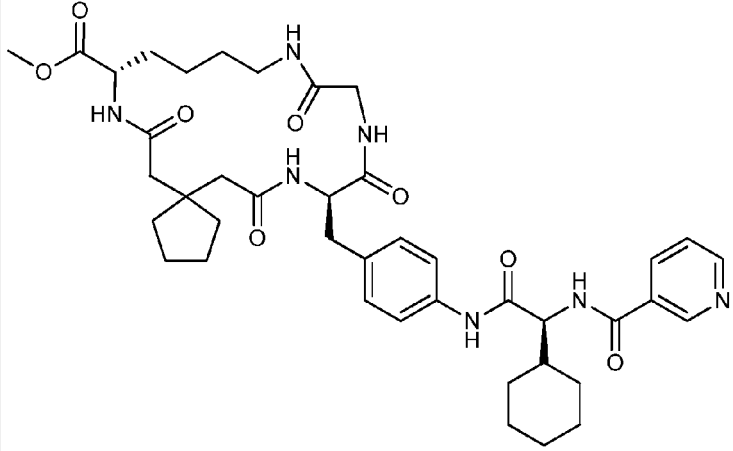
Figure 12:
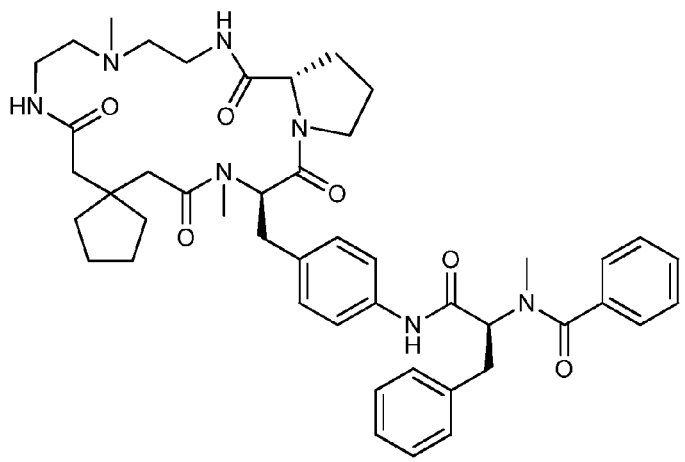
Figure 120:
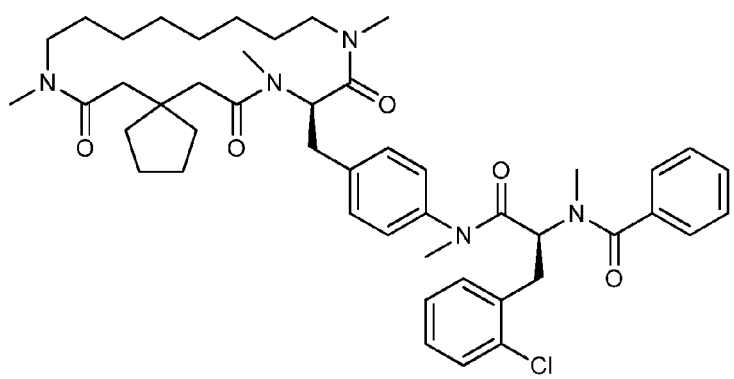
Figure 12:
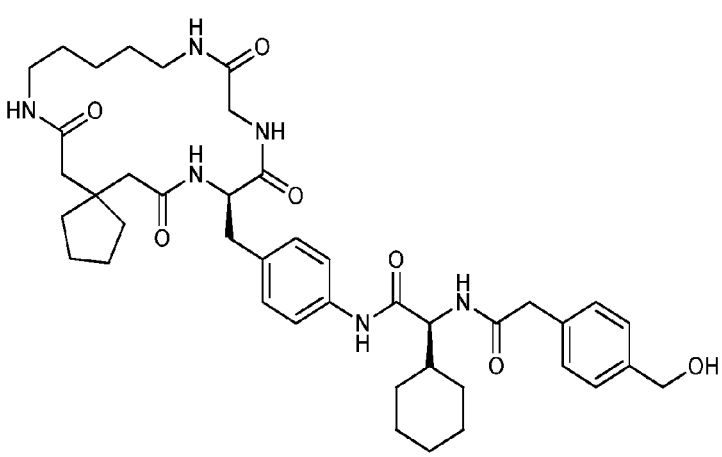
Figure 122:
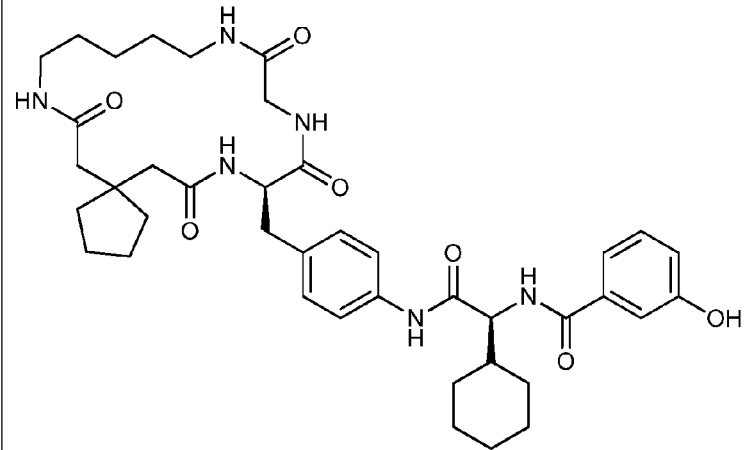
Figure 12:
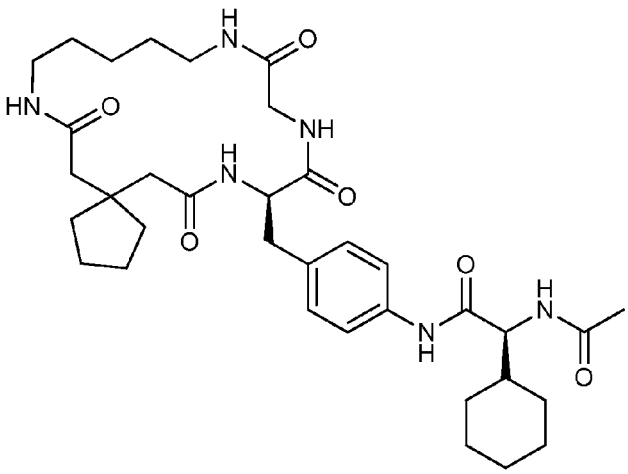
Figure 123:
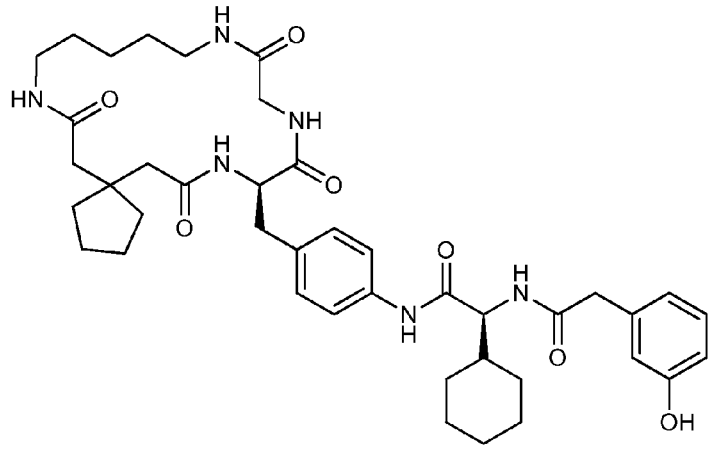
Figure 12:
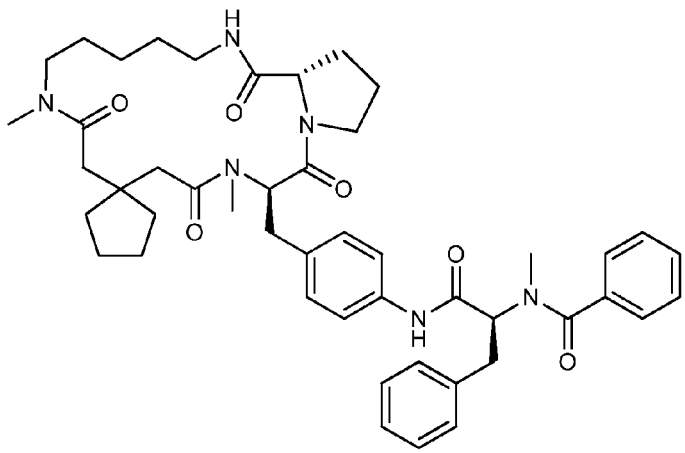
Figure 126:
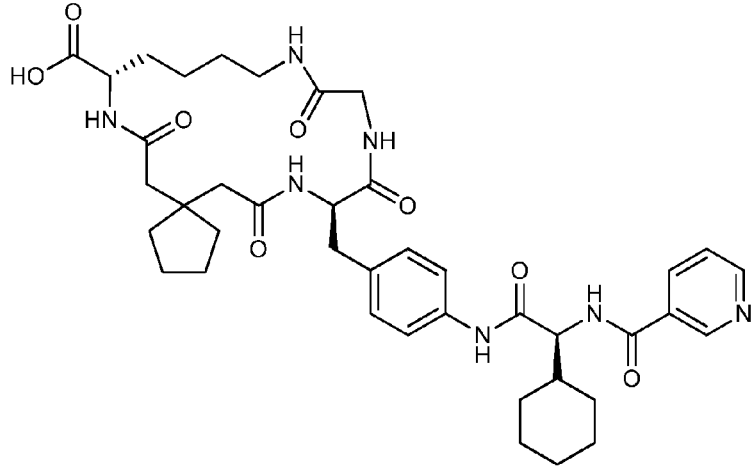
Figure 12:
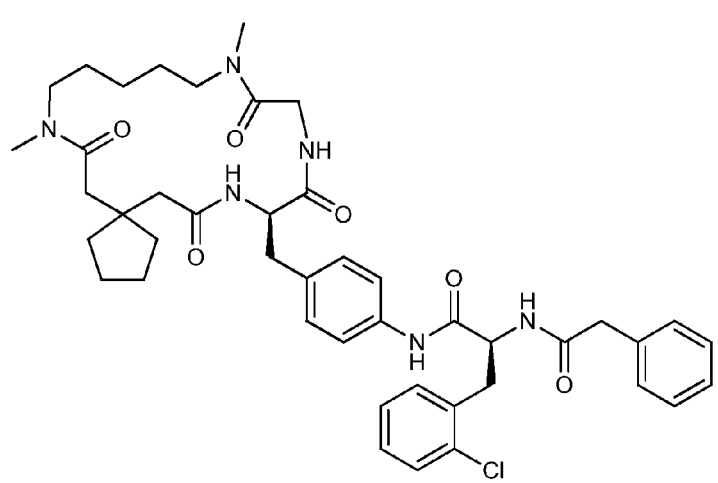
Figure 128:
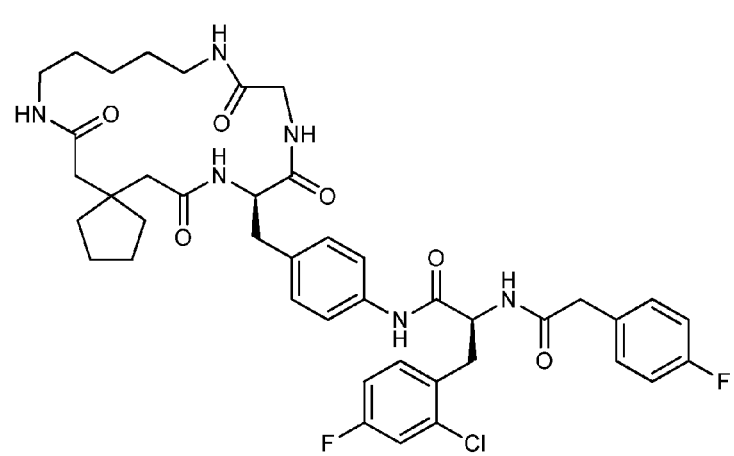
Figure 12:
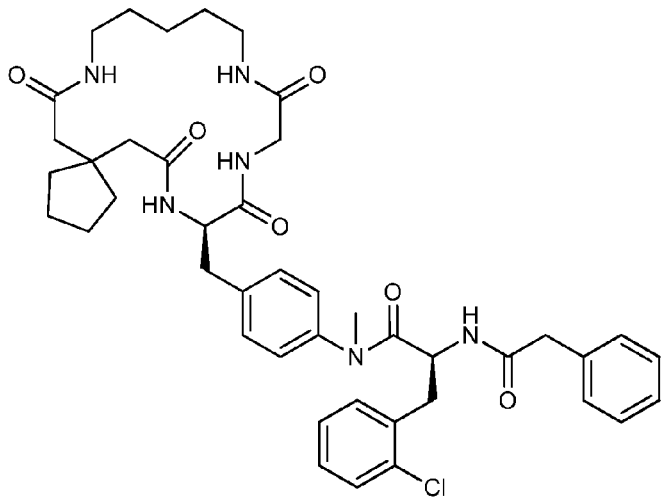
Figure 129:
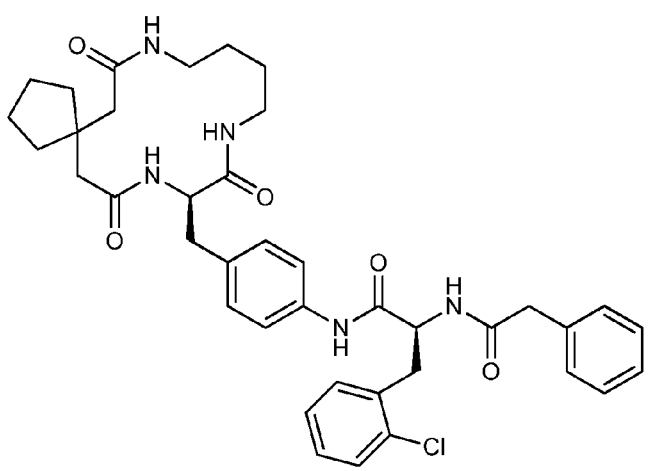
Figure 12:
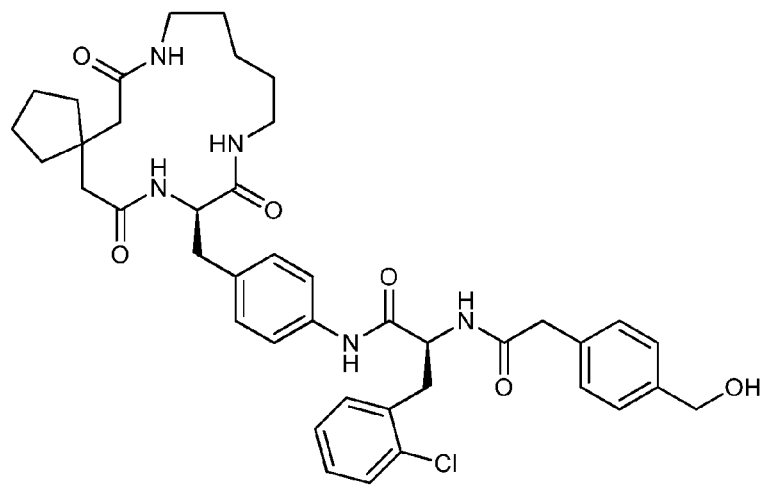
Figure 131:
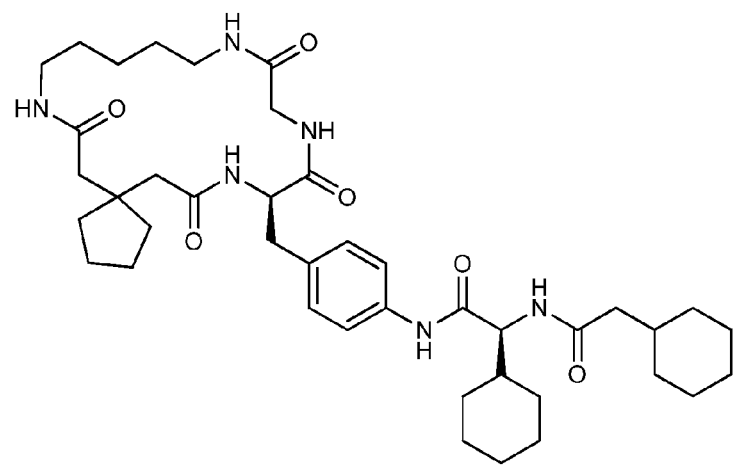
Figure 12:
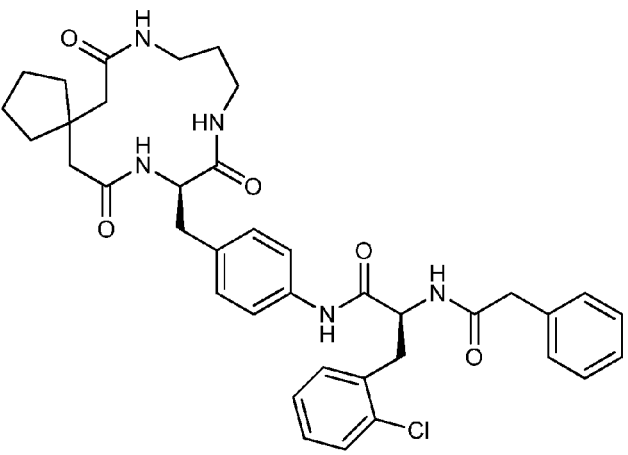
Figure 133:
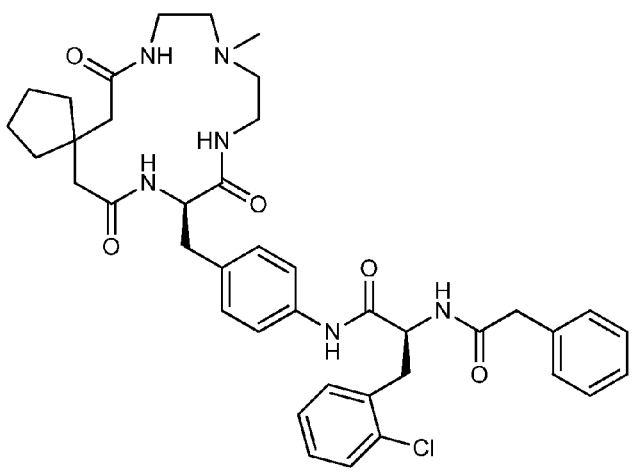
Figure 12:
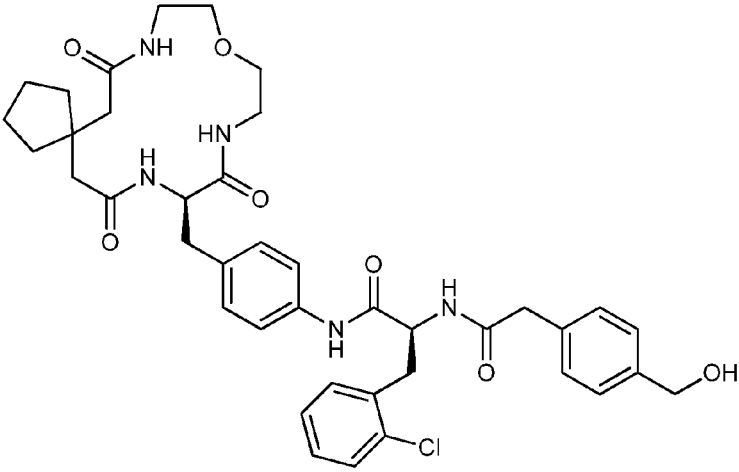
Figure 134:
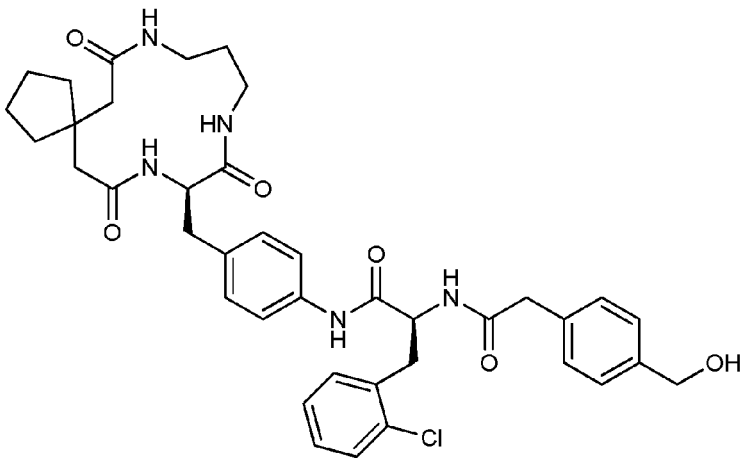
Figure 12:
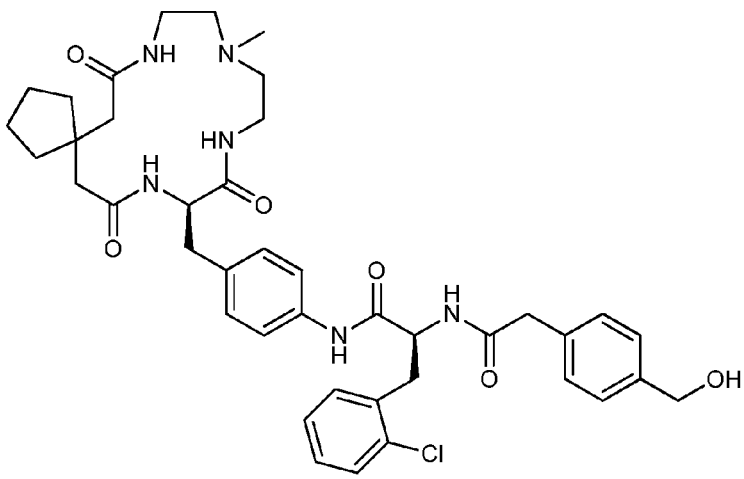
Figure 135:
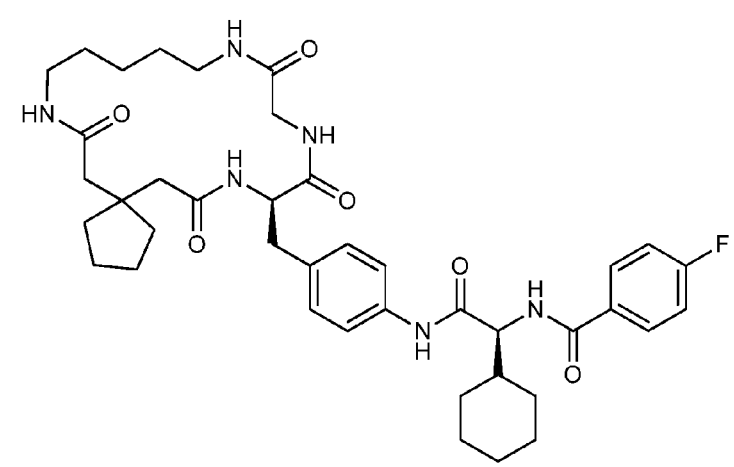
Figure 12:
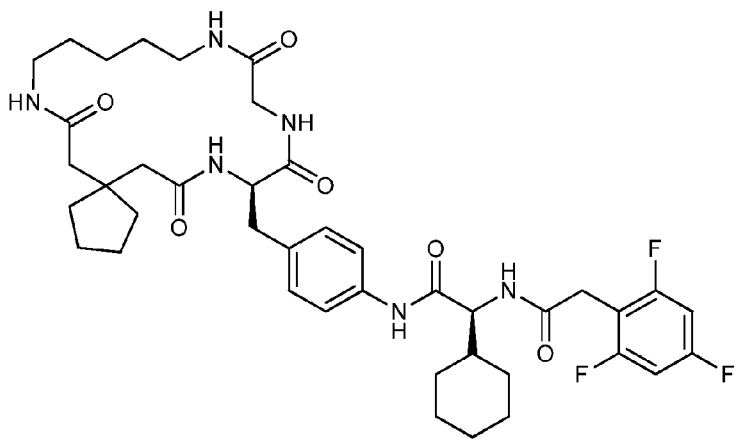
Figure 136:
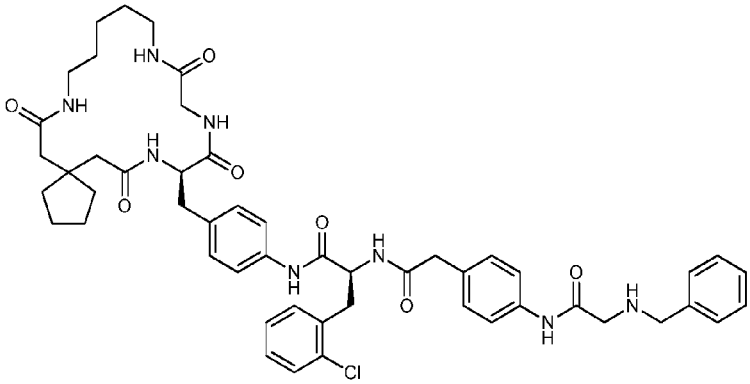
Figure 12:
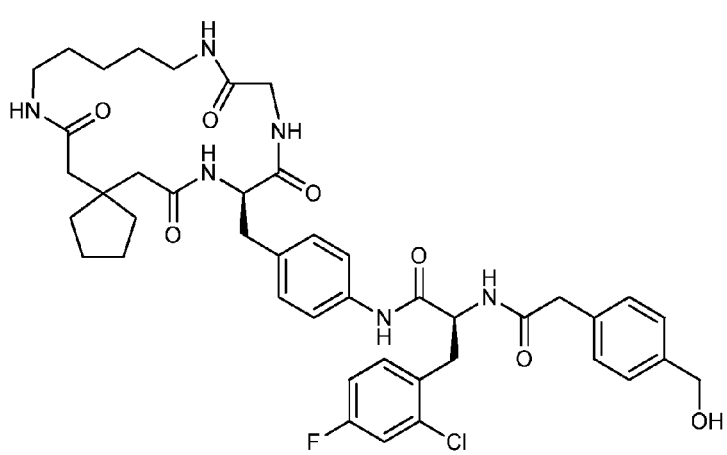
Figure 138:
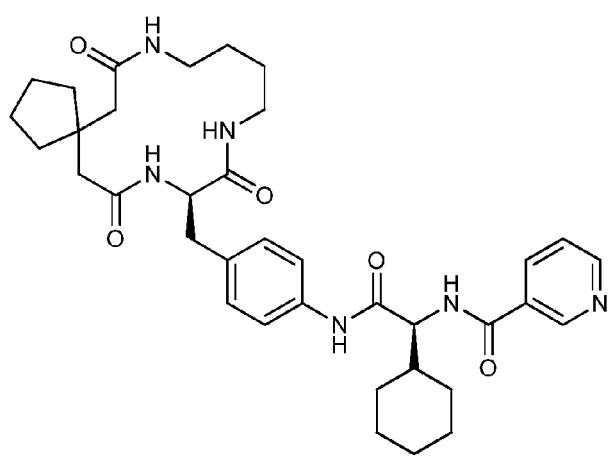
Figure 12:
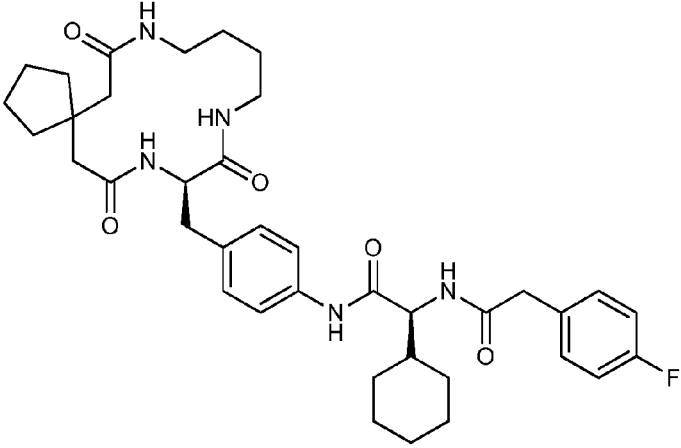
Figure 139:
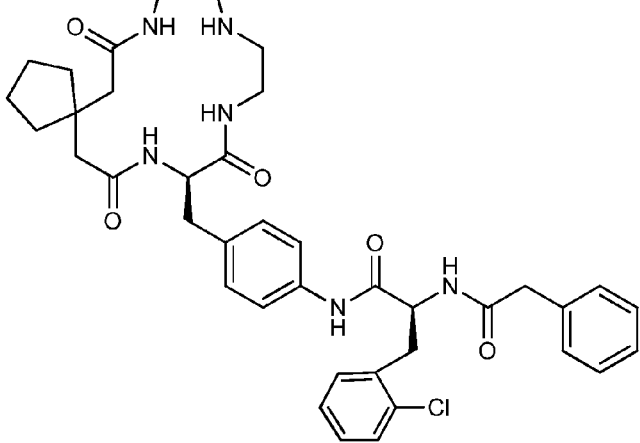
Figure 12:
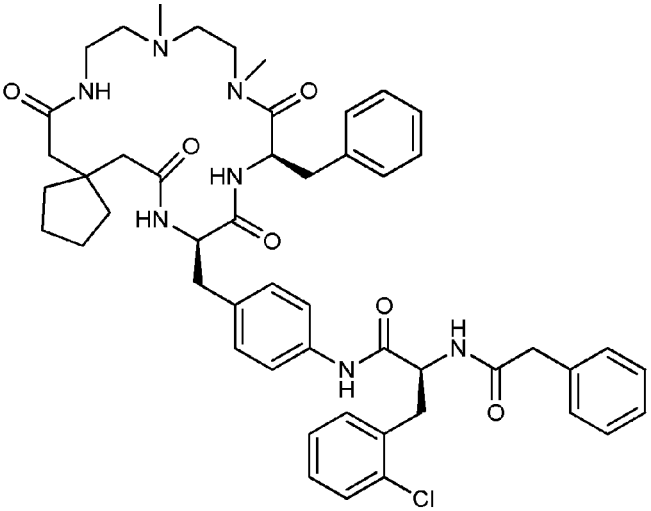
Figure 142:
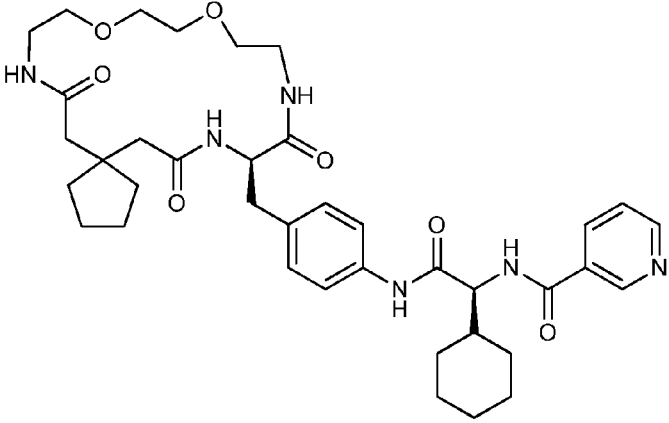
Figure 12:

Figure 143:

Figure 12:
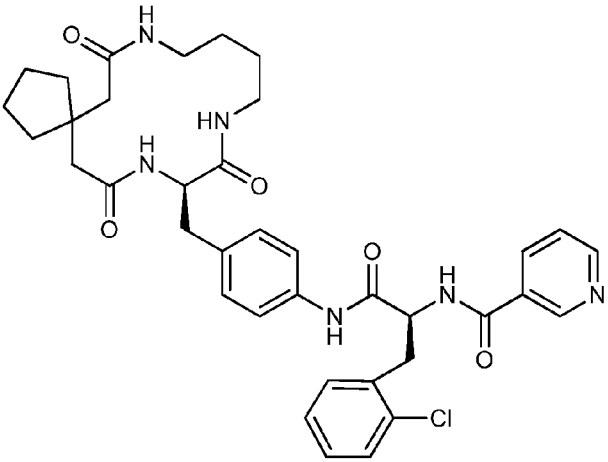
Figure 144:
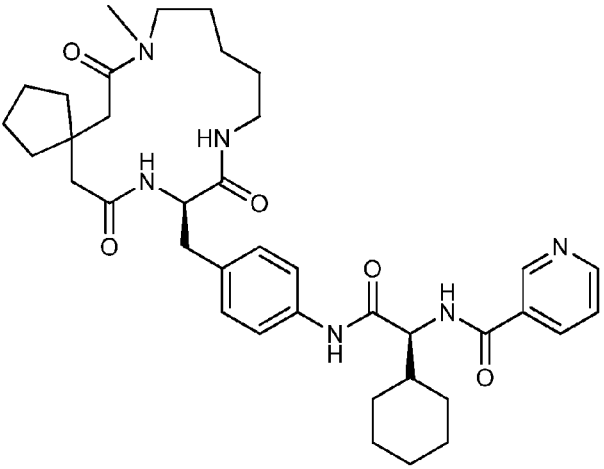
Figure 12:

Figure 145:

Figure 12:
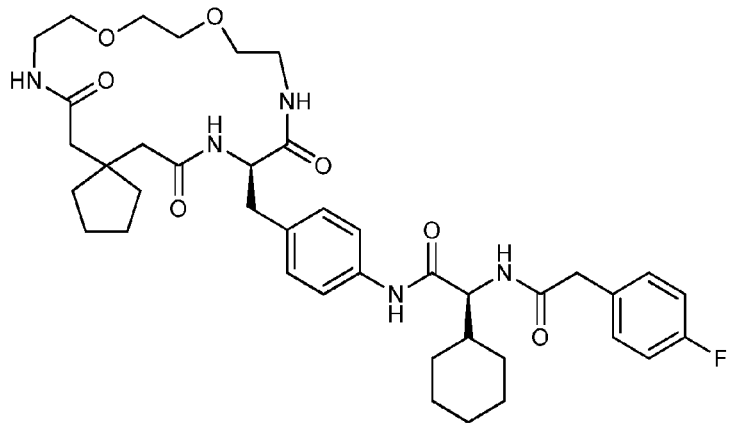
Figure 146:
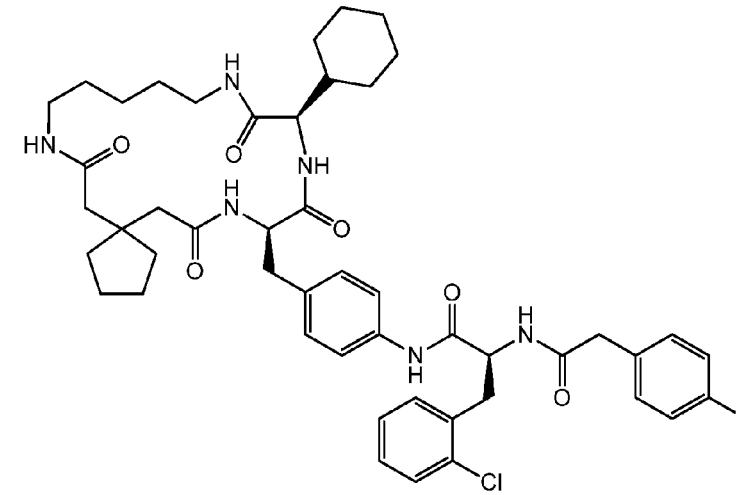
Figure 12:
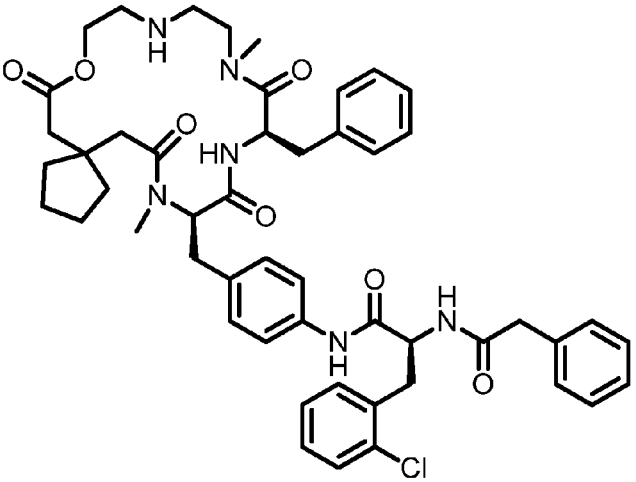
Figure 147:

Figure 12:
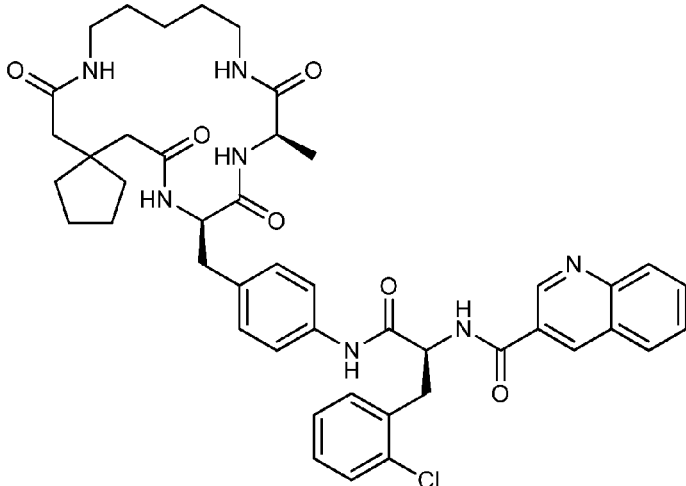
Figure 148:
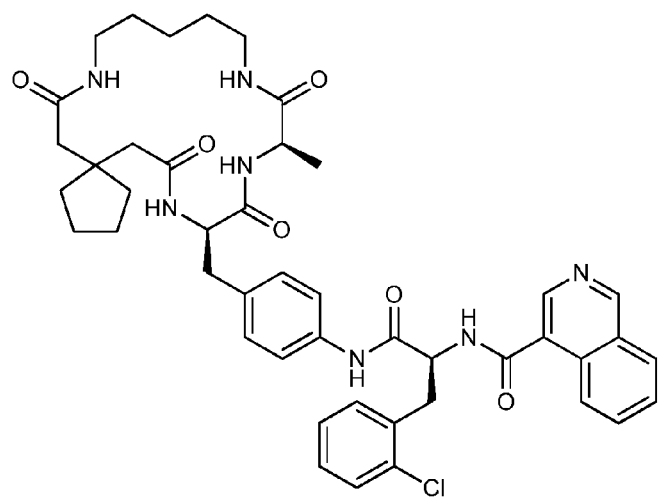
Figure 12:
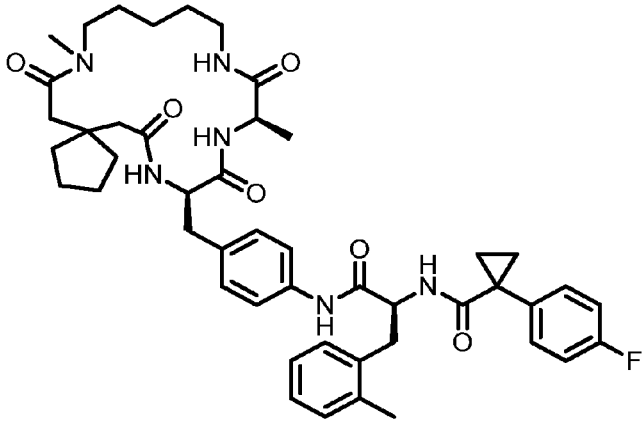
Figure 149:
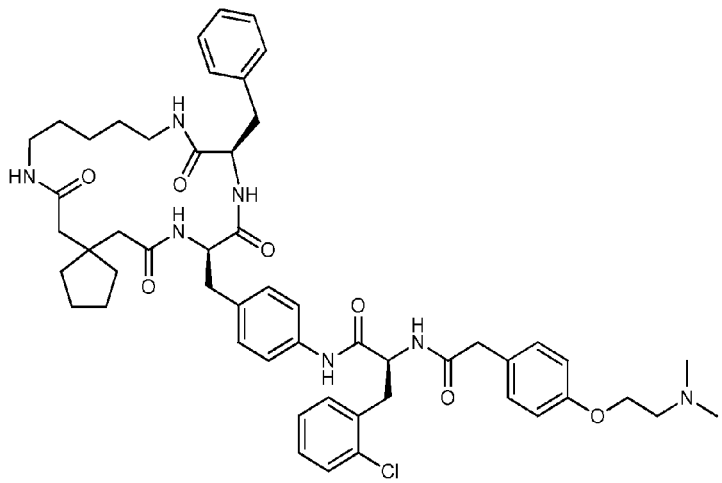
Figure 12:
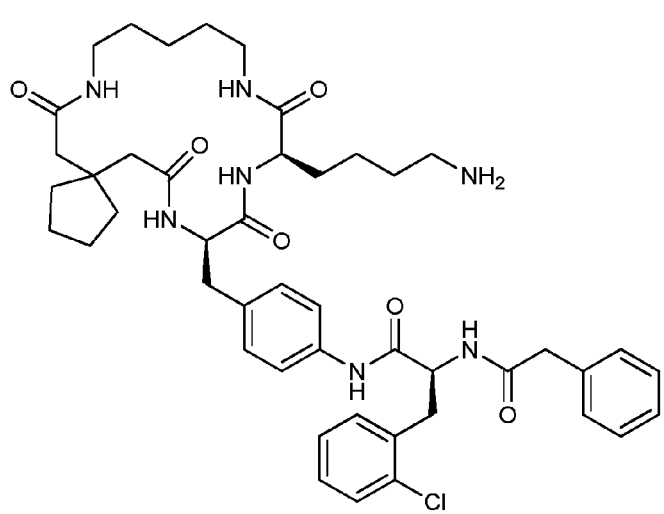
Figure 150:
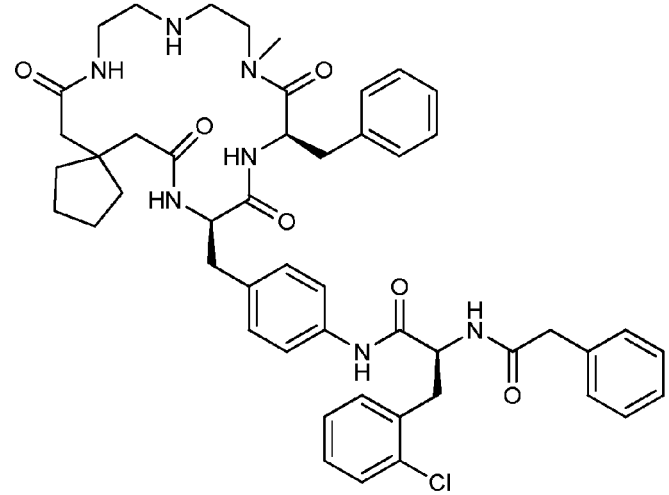
Figure 12:
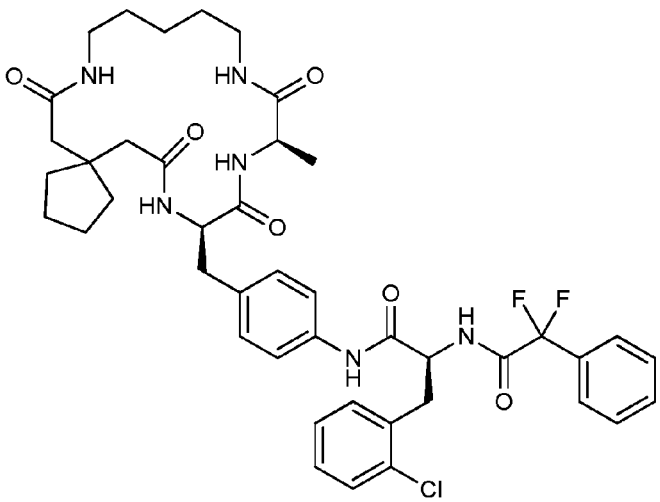
Figure 151:
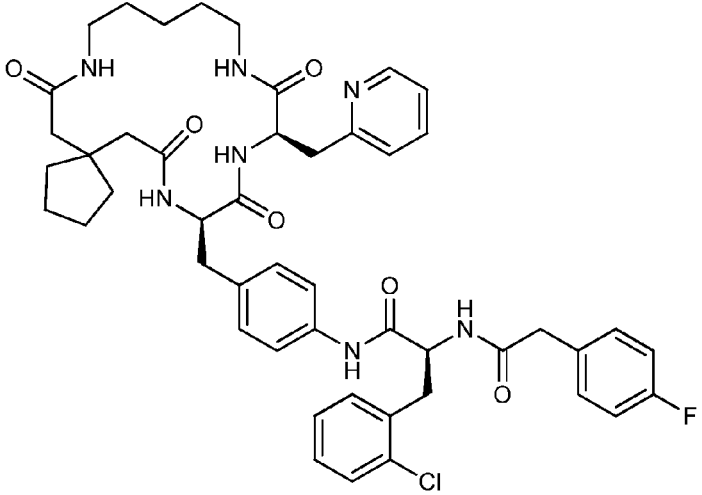
Figure 12:
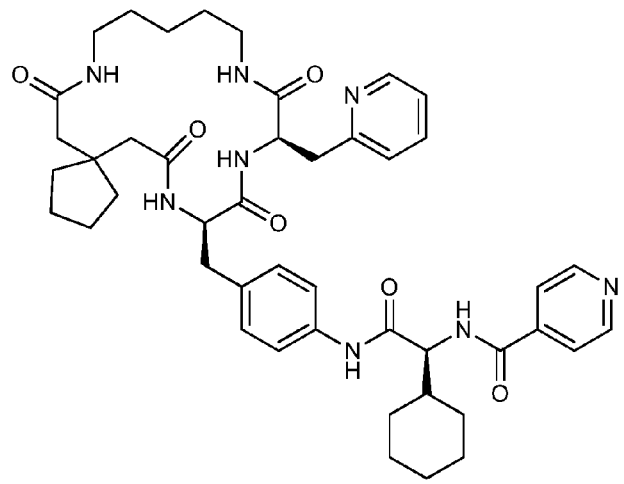
Figure 152:
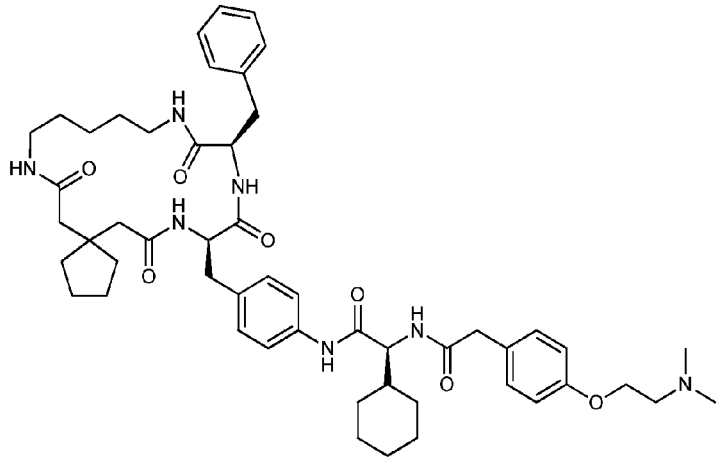
Figure 12:
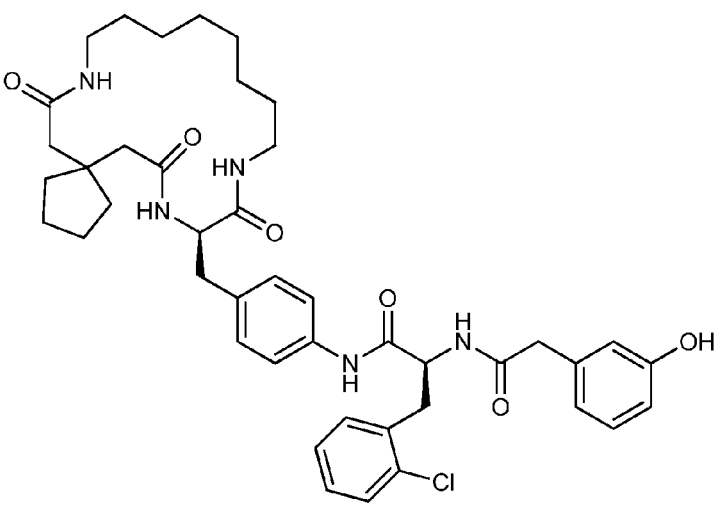
Figure 154:
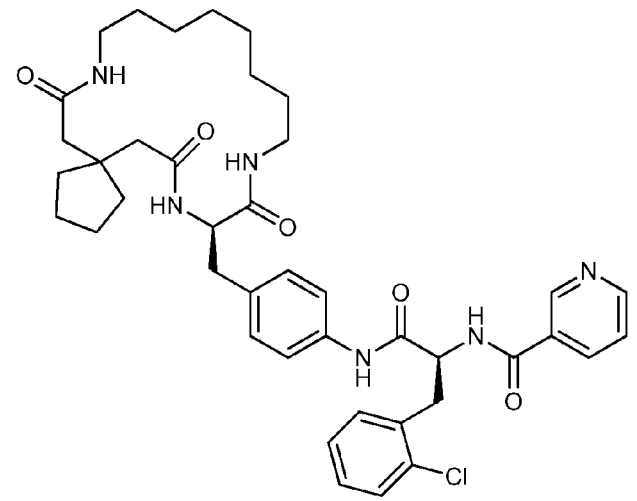
Figure 12:
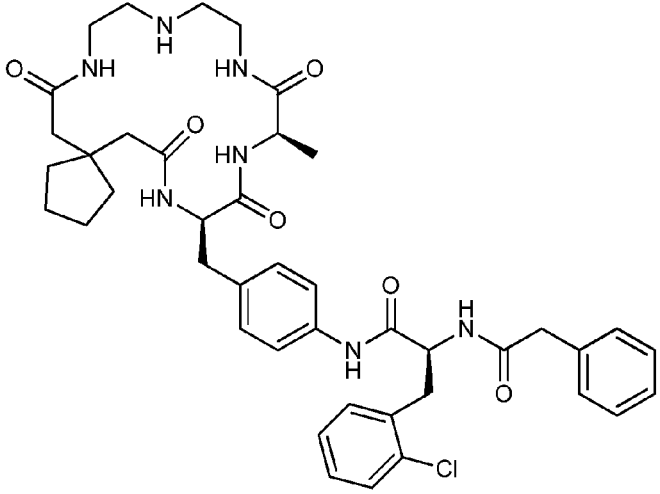
Figure 155:
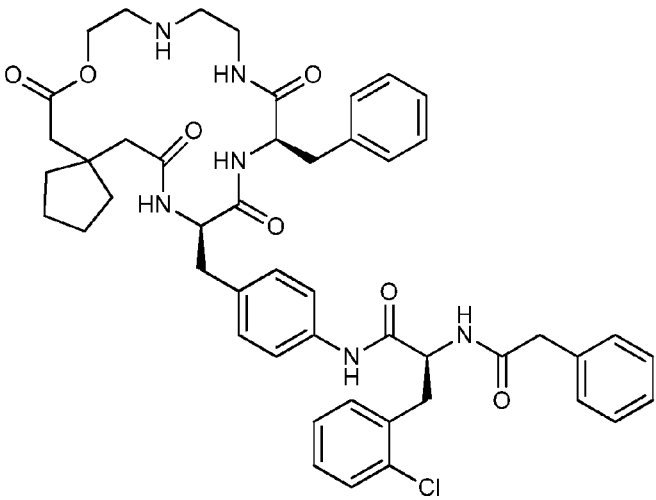
Figure 12:
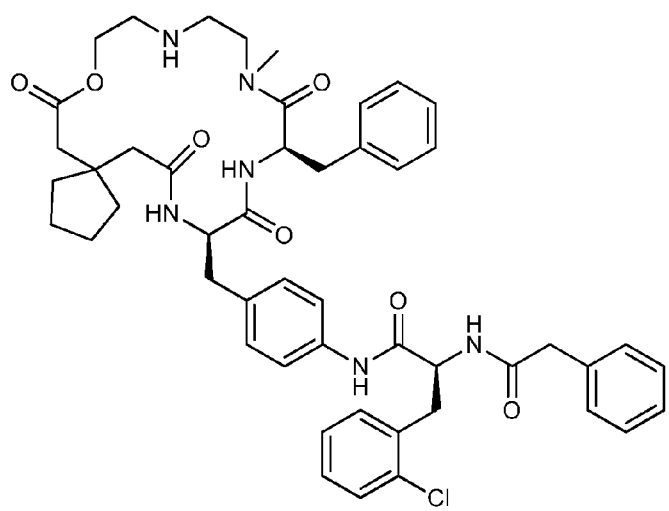
Figure 156:
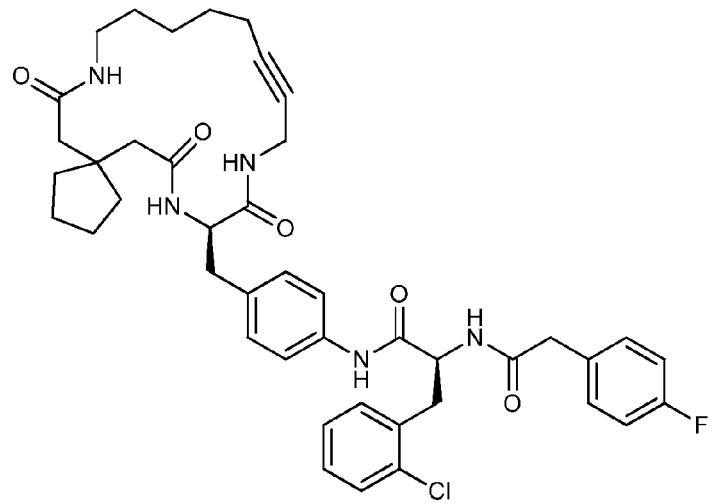
Figure 12:

Figure 157:

Figure 12:
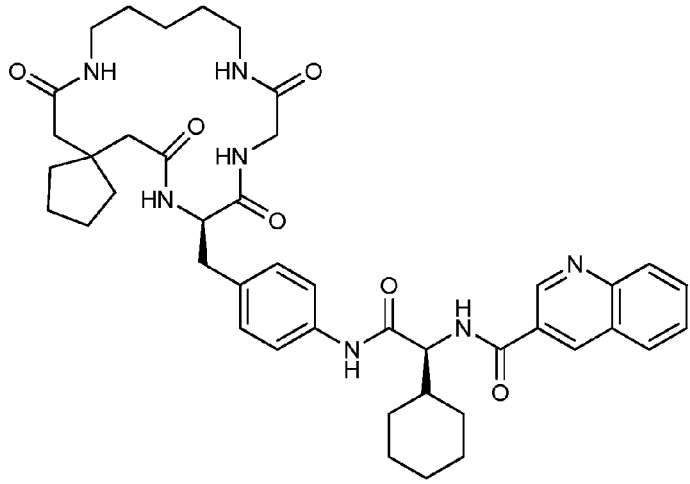
Figure 158:
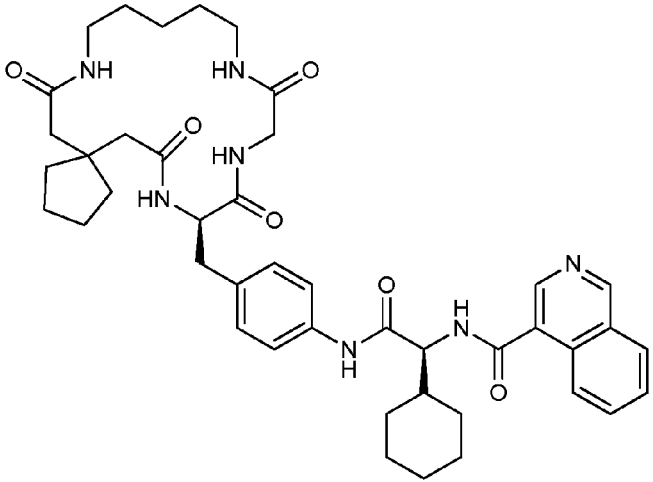
Figure 12:
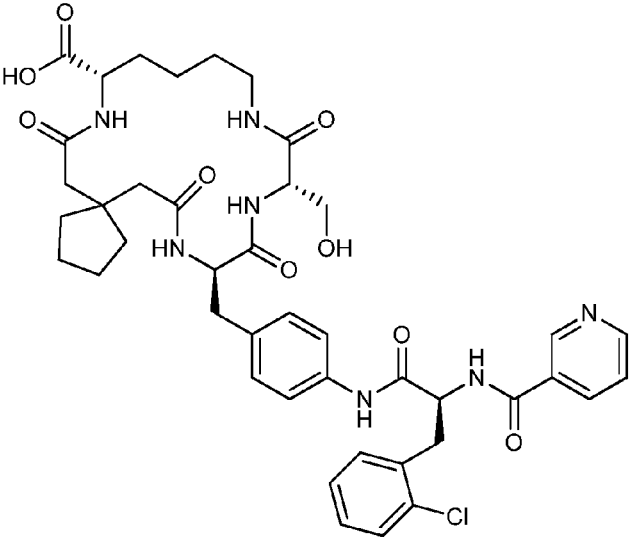
Figure 159:
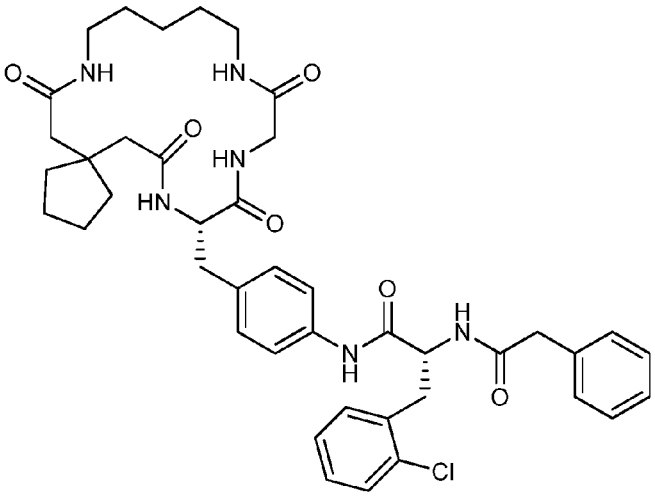
Figure 12:
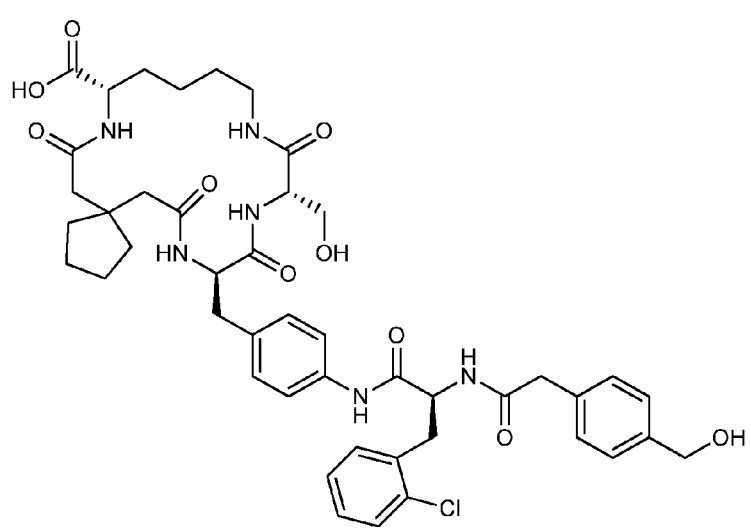
Figure 161:
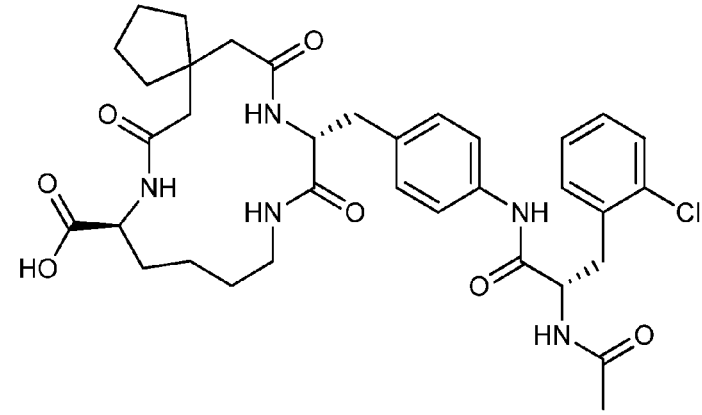
Figure 12:
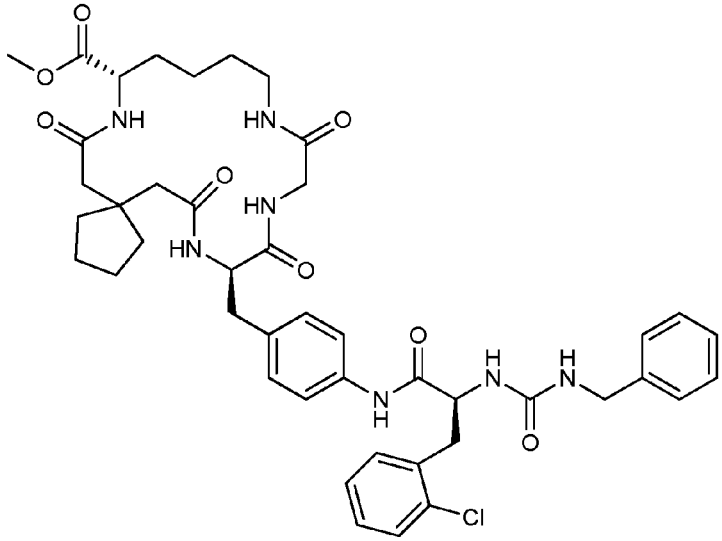
Figure 163:
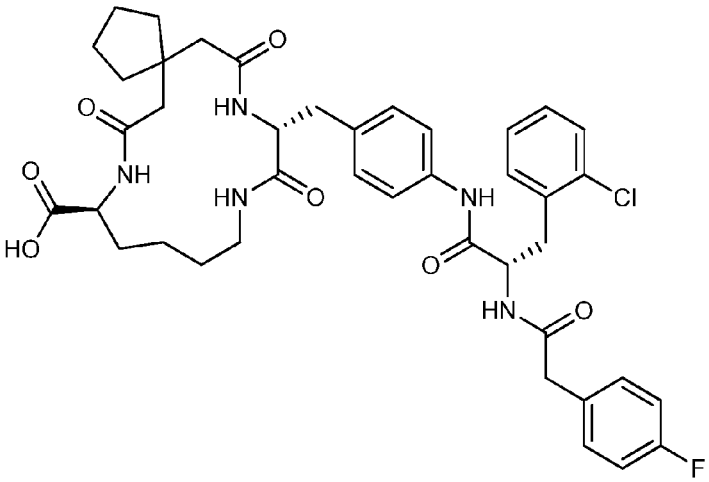
Figure 12:
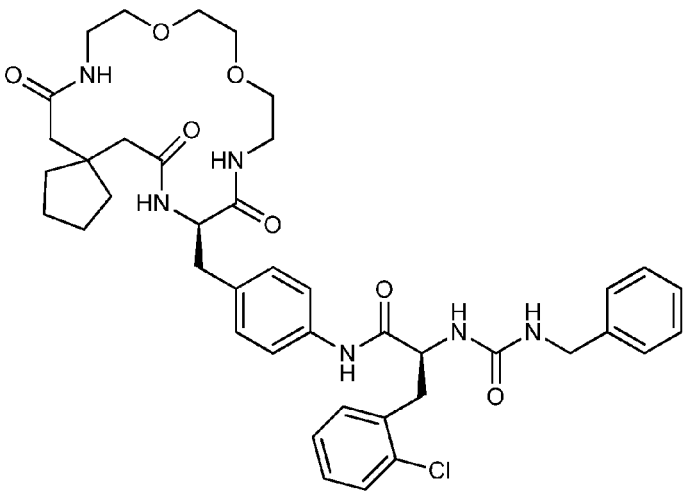
Figure 165:
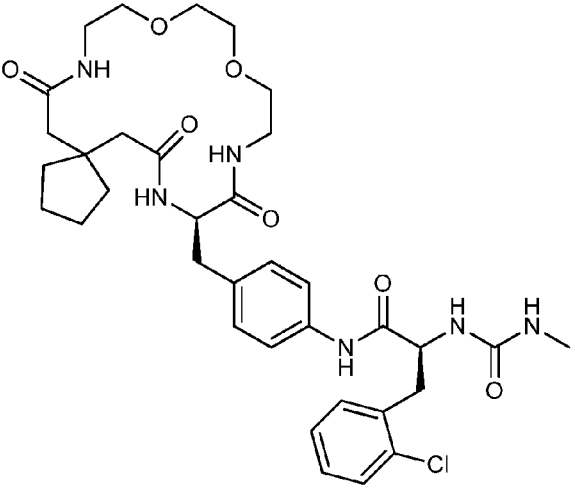
Figure 12:
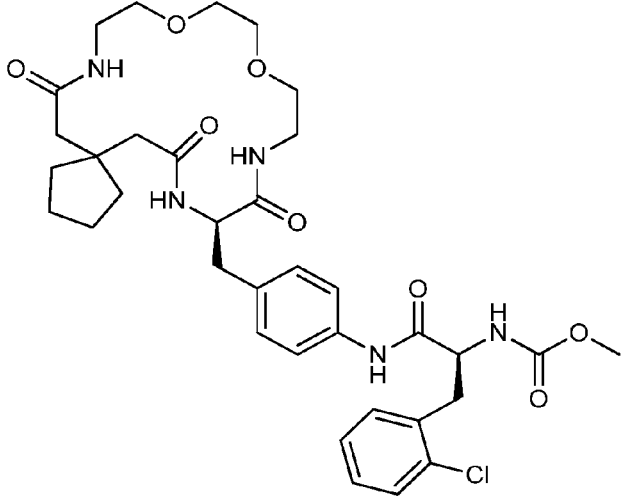
Figure 166:
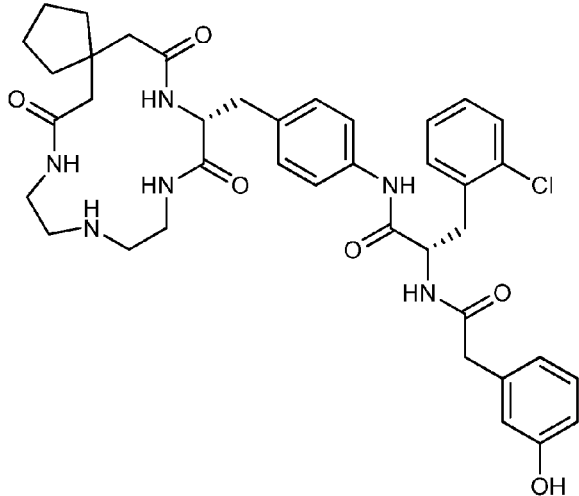
Figure 12:
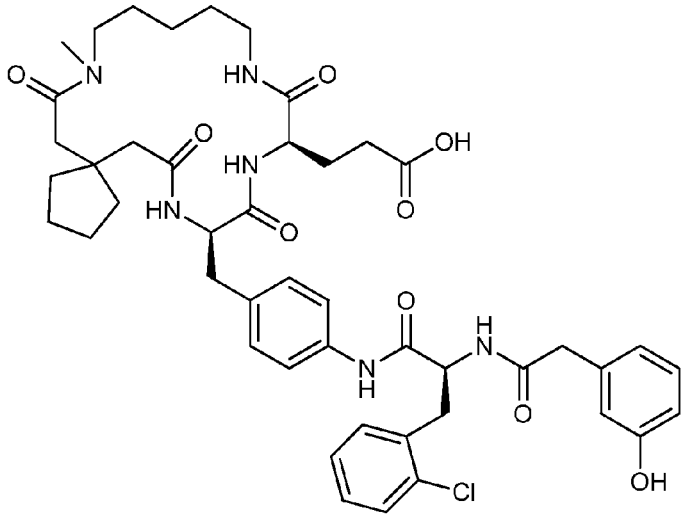
Figure 170:
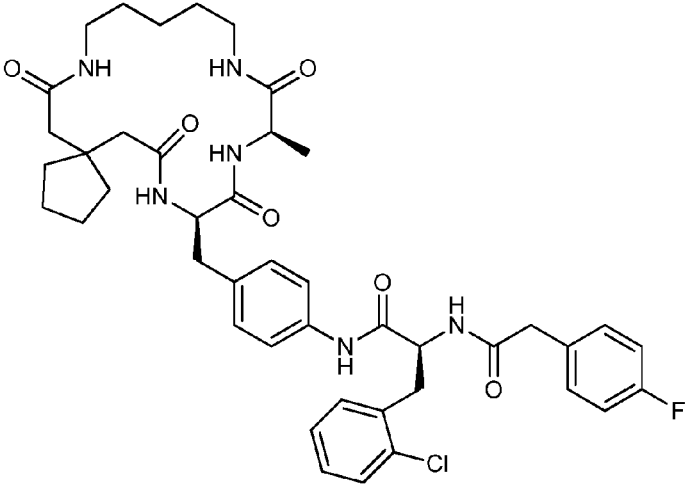
Figure 12:
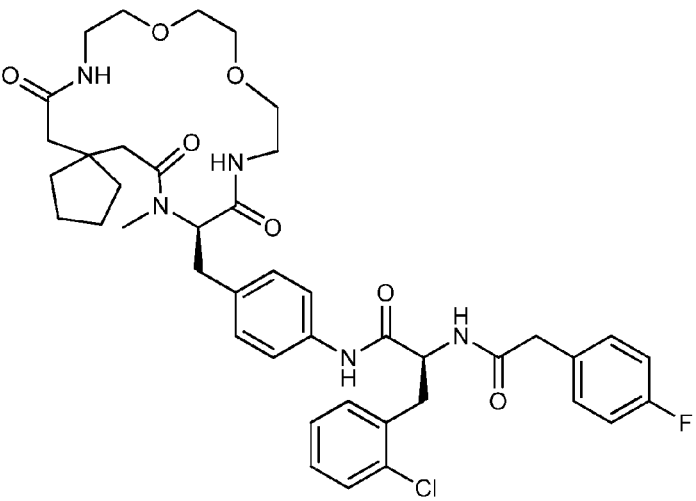
Figure 172:
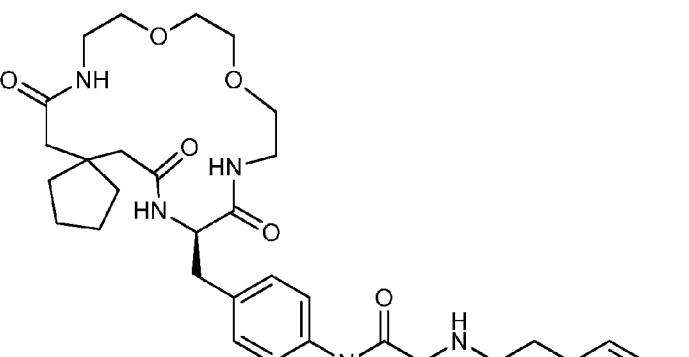
Figure 12:
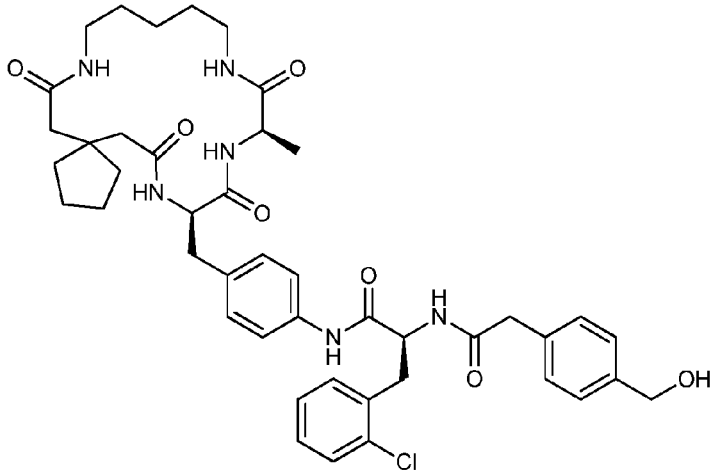
Figure 177:
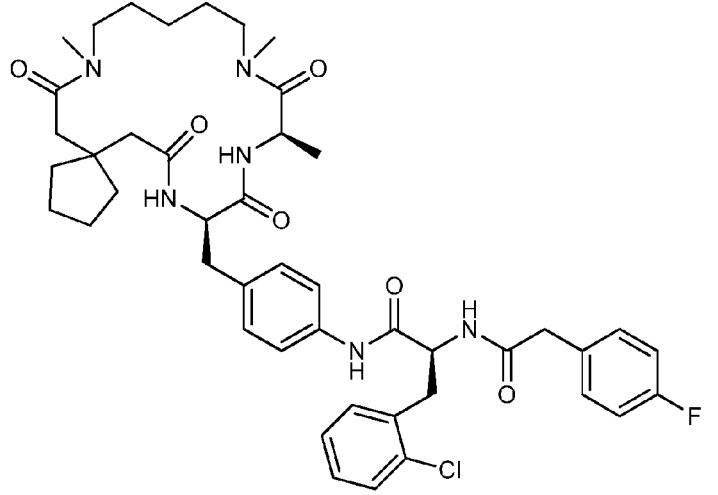
Figure 12:
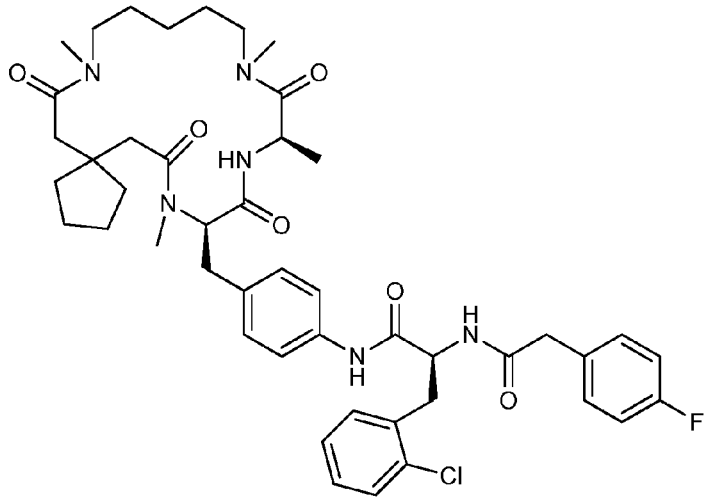
Figure 178:
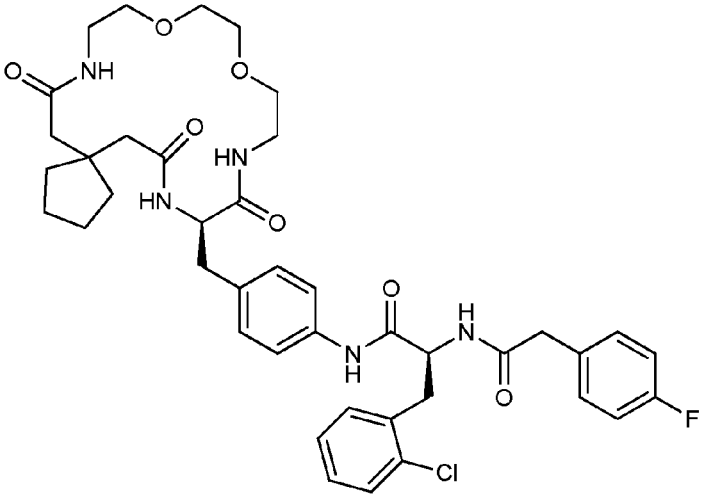
Figure 12:
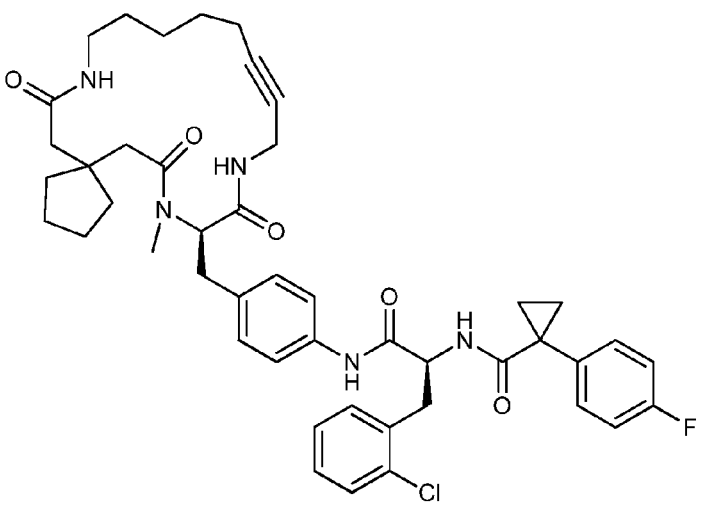
Figure 179:
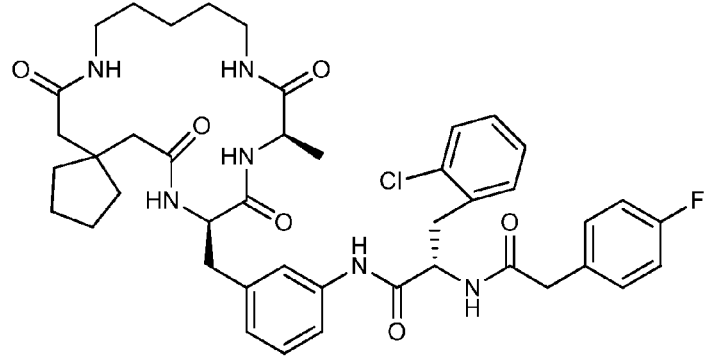
Figure 12:
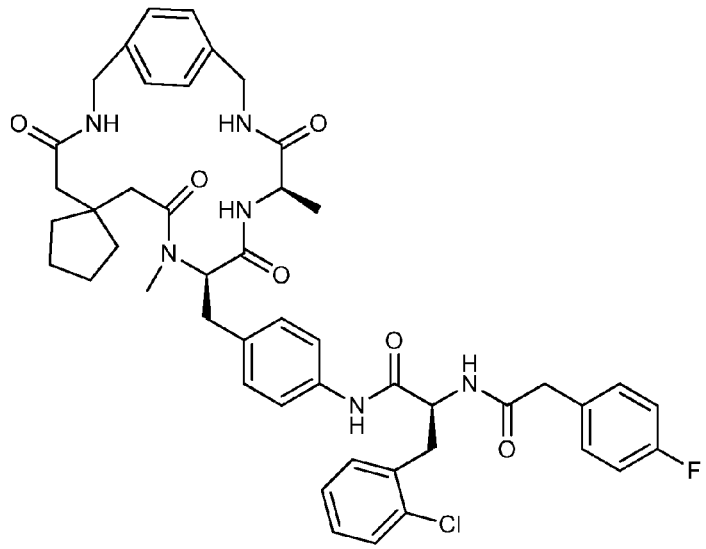
Figure 180:
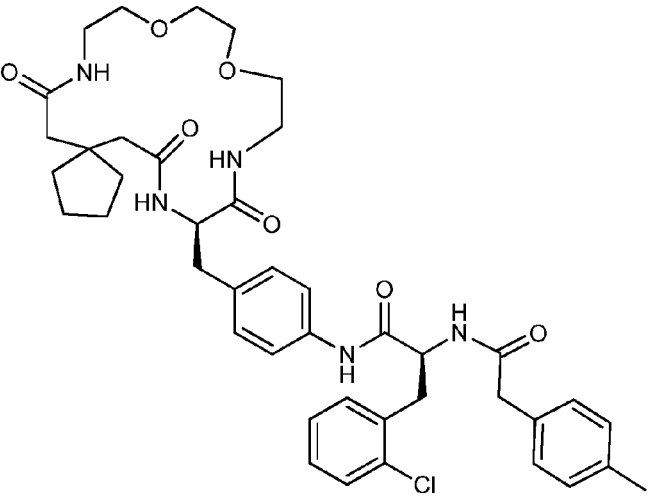
Figure 12:
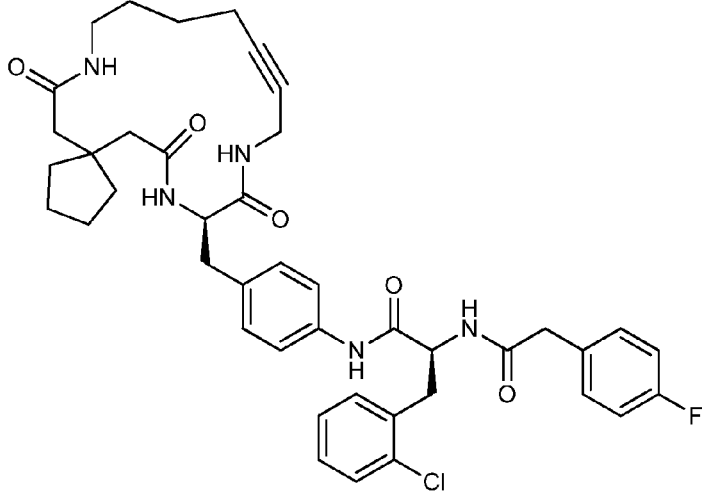
Figure 182:
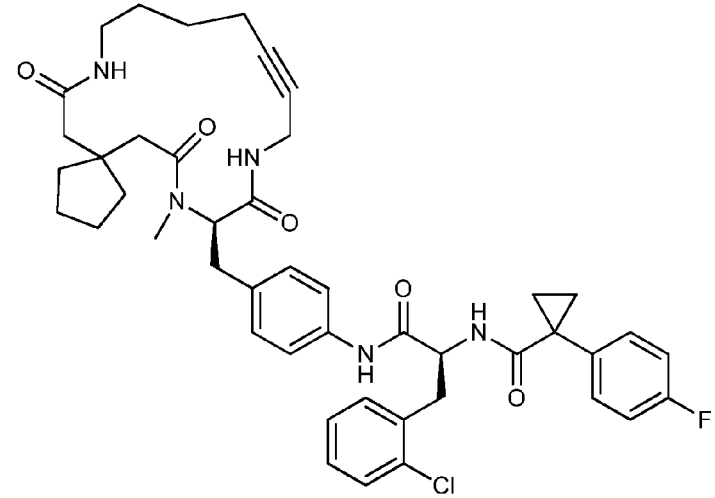
Figure 12:
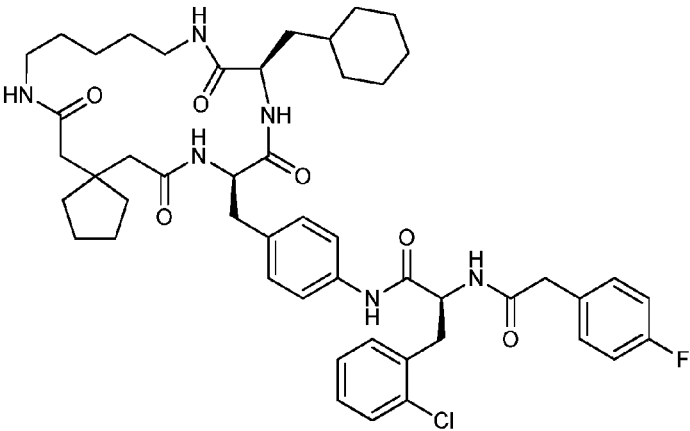
Figure 183:
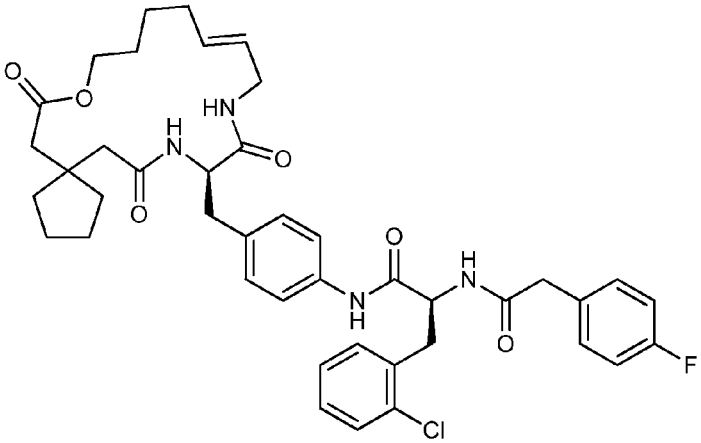
Figure 12:
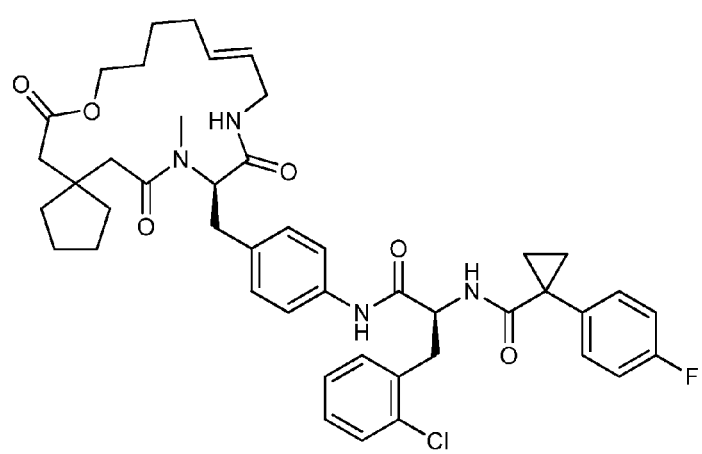
Figure 184:
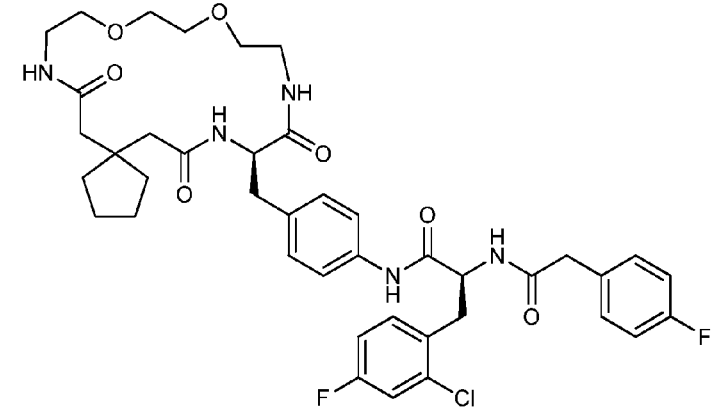
Figure 12:
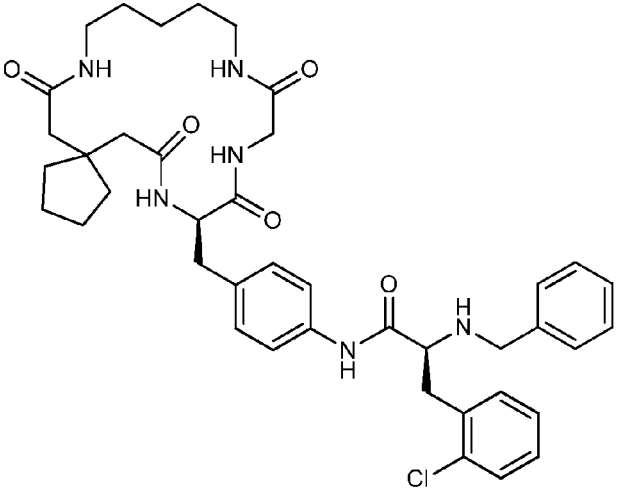
Figure 185:
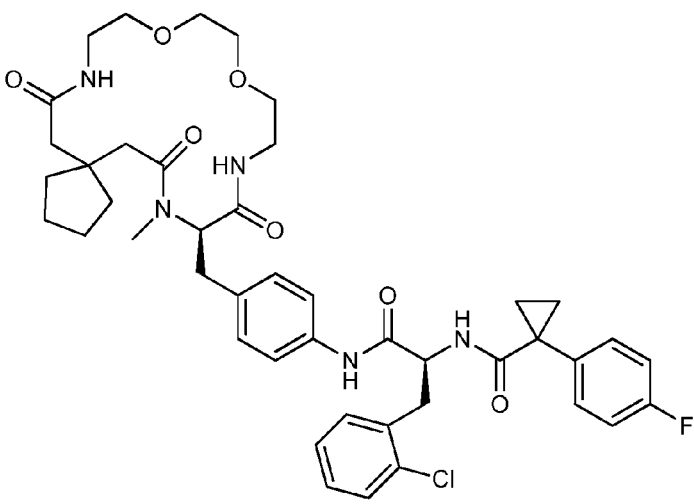
Figure 12:
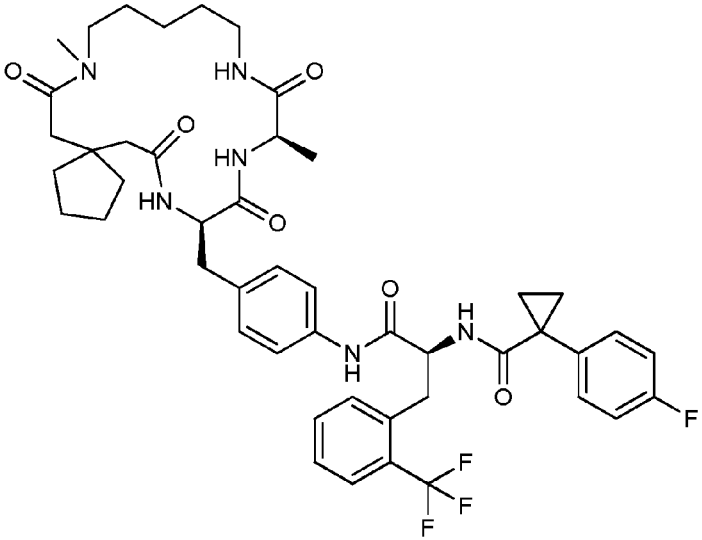
Figure 187:
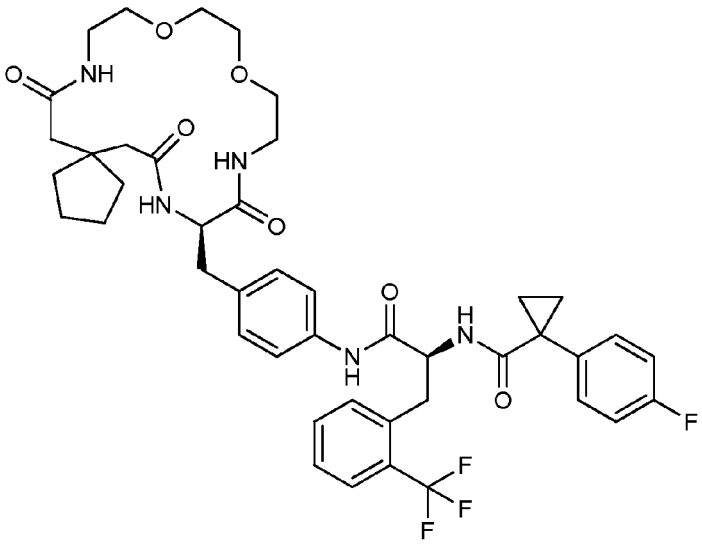
Figure 12:
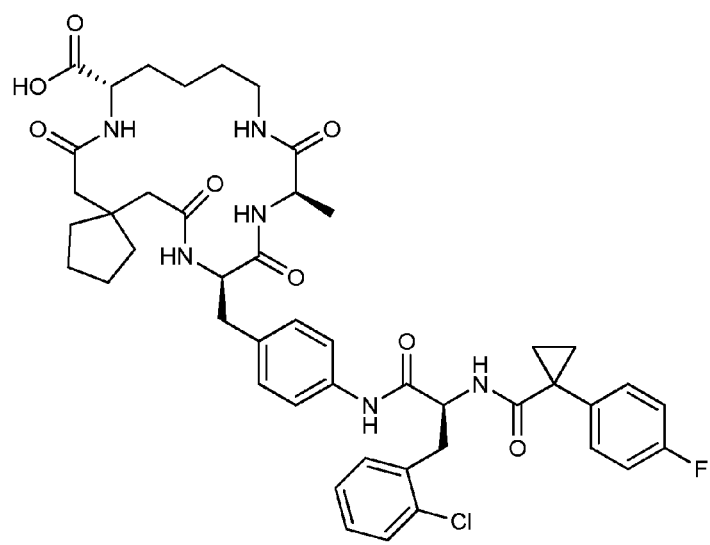
Figure 190:
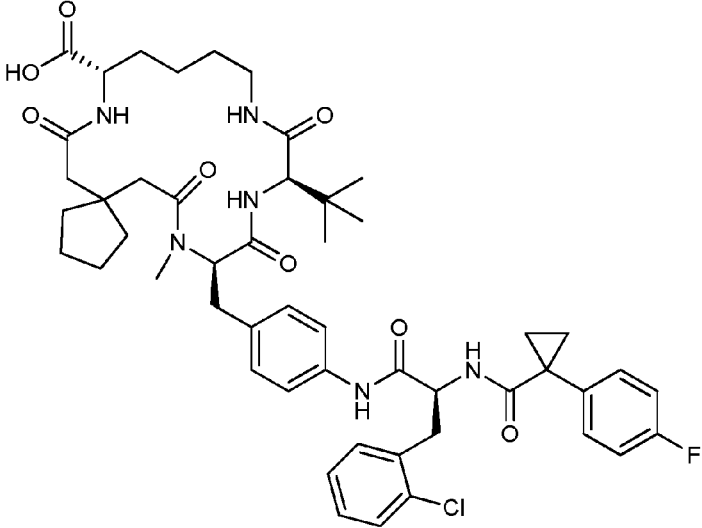
Figure 12:
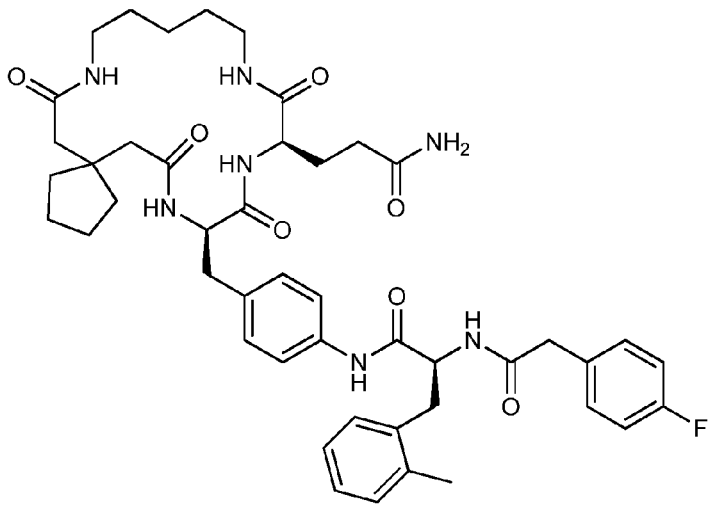
Figure 191:
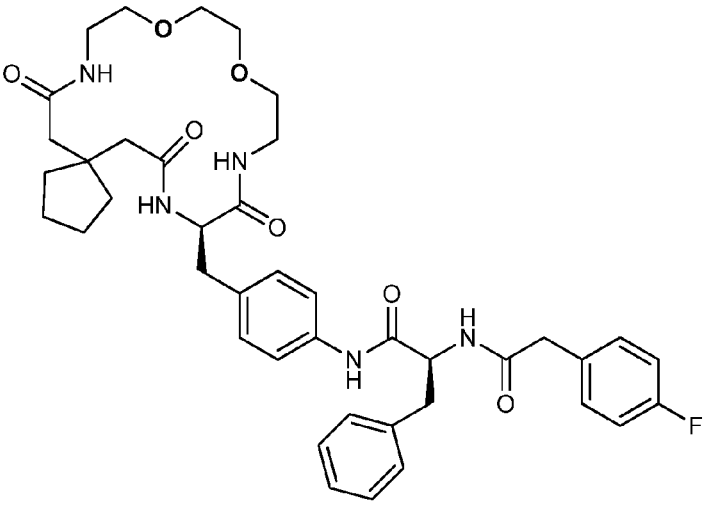
Figure 12:
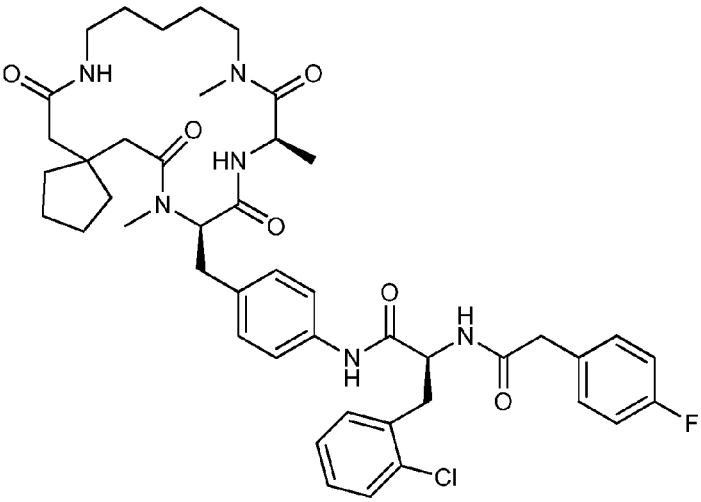
Figure 192:
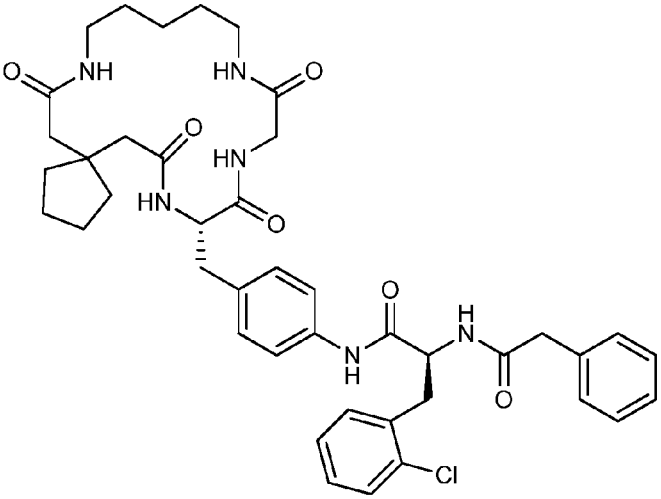
Figure 12:
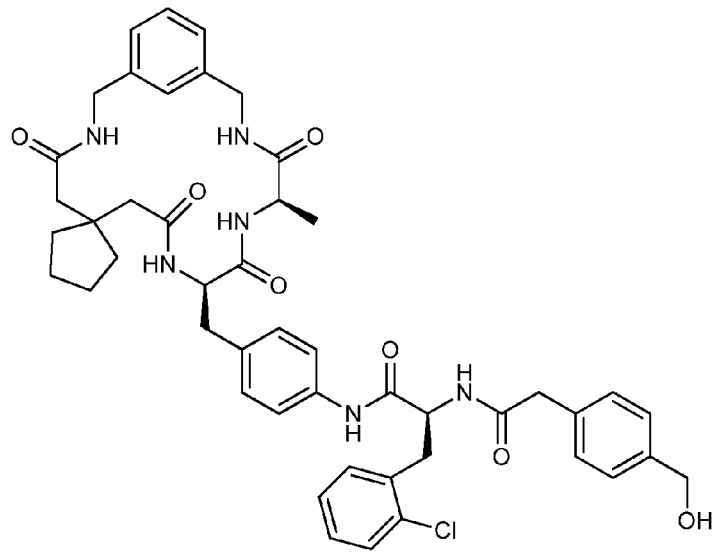
Figure 193:
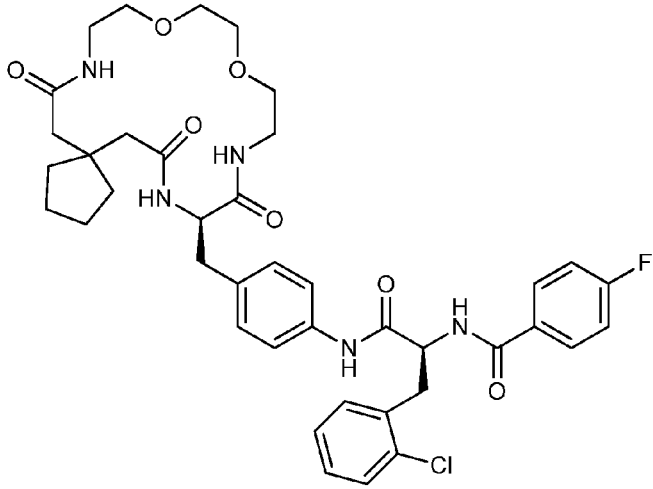
Figure 12:
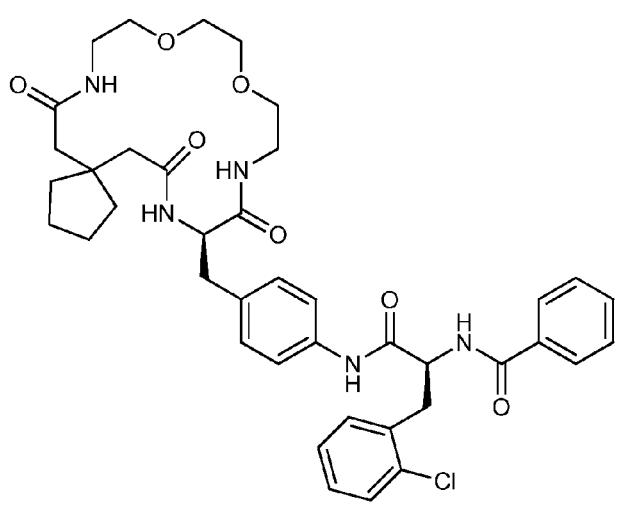
Figure 194:
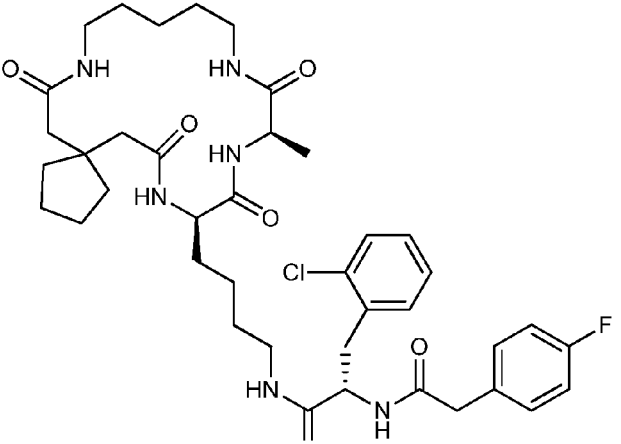
Figure 12:
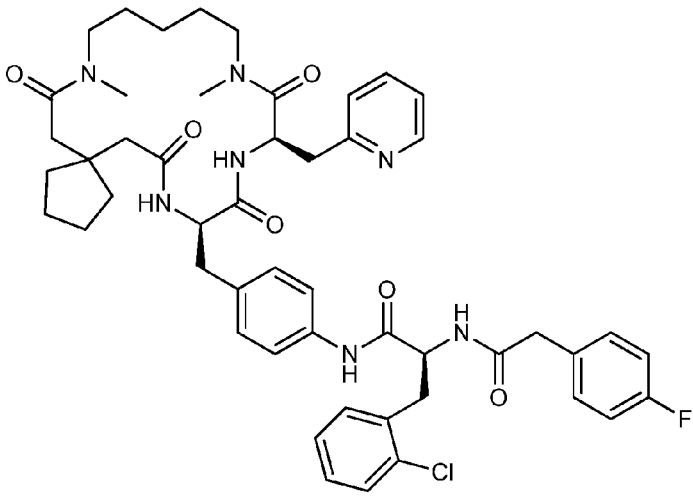
Figure 195:
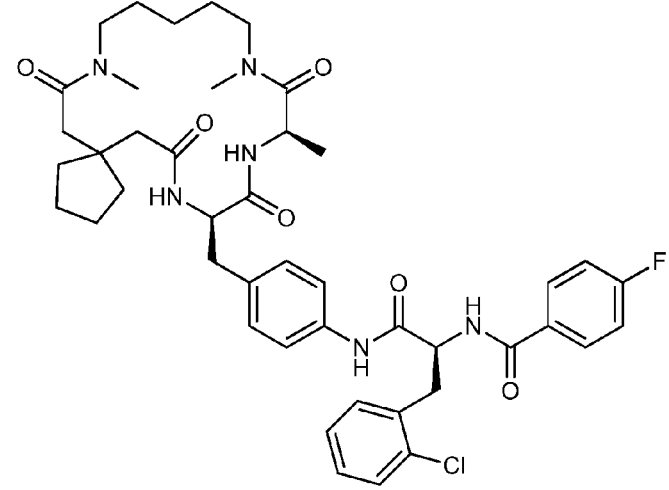
Figure 12:
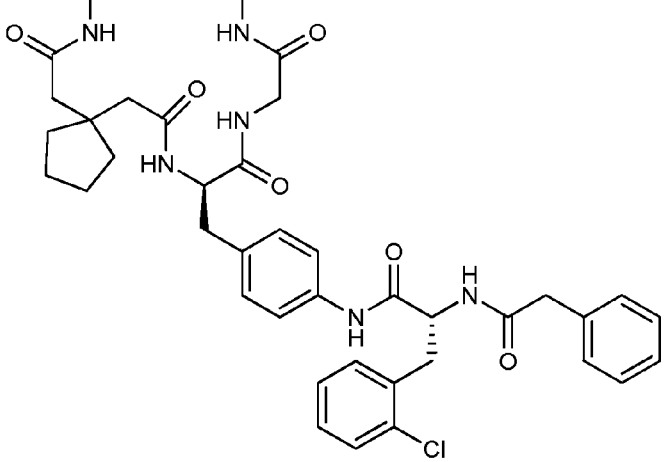
Figure 196:
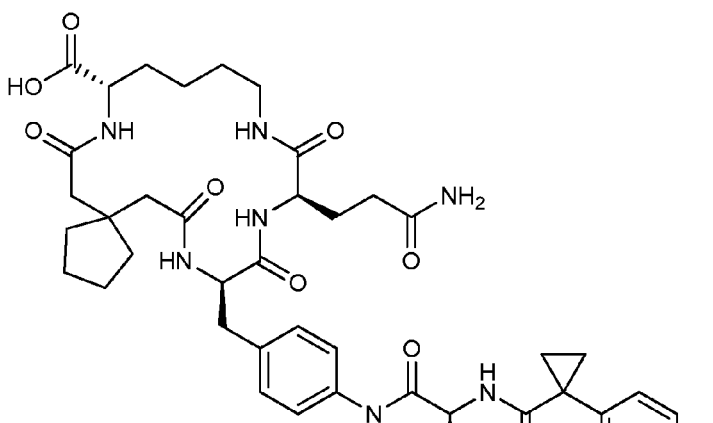
Figure 12:
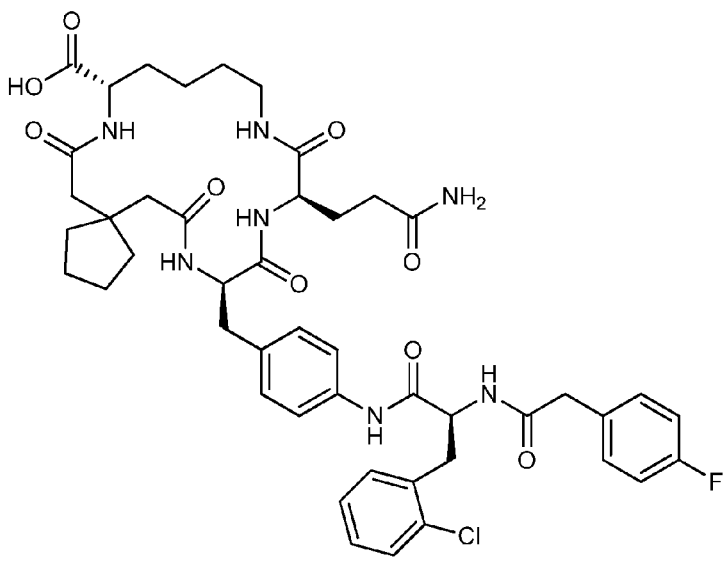
Figure 197:
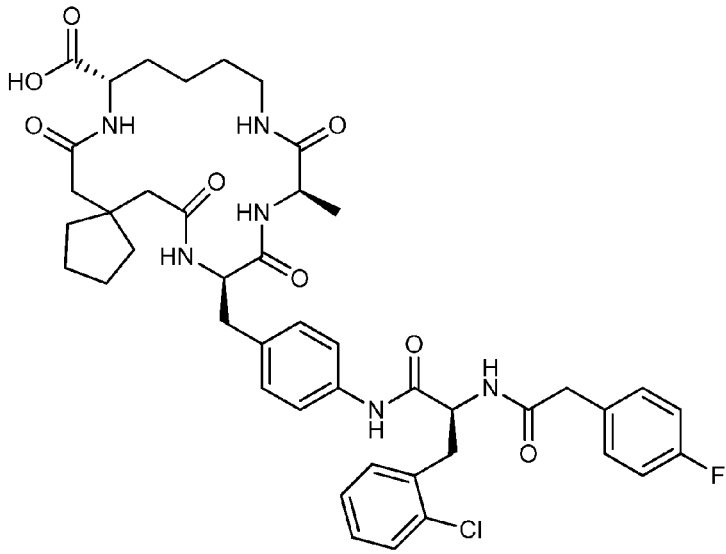
Figure 12:
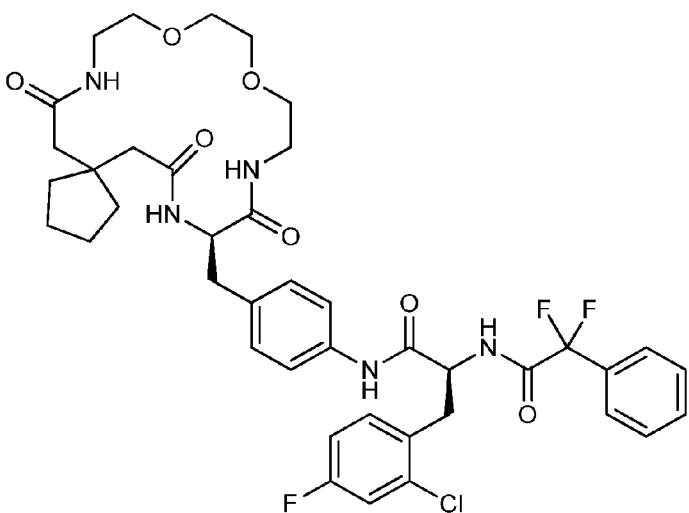
Figure 198:
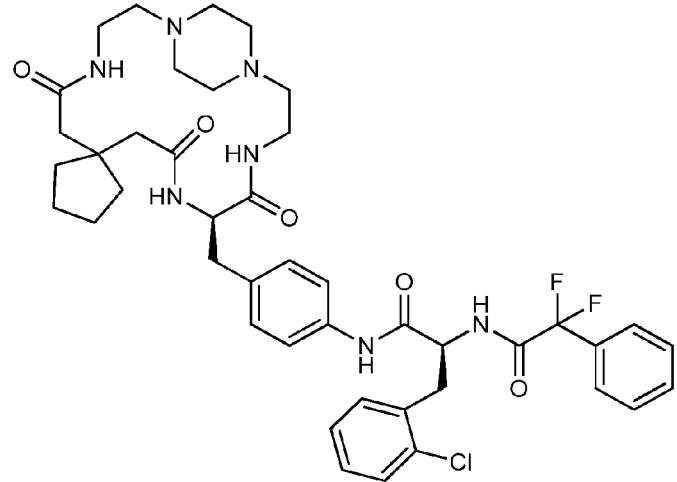
Figure 12:
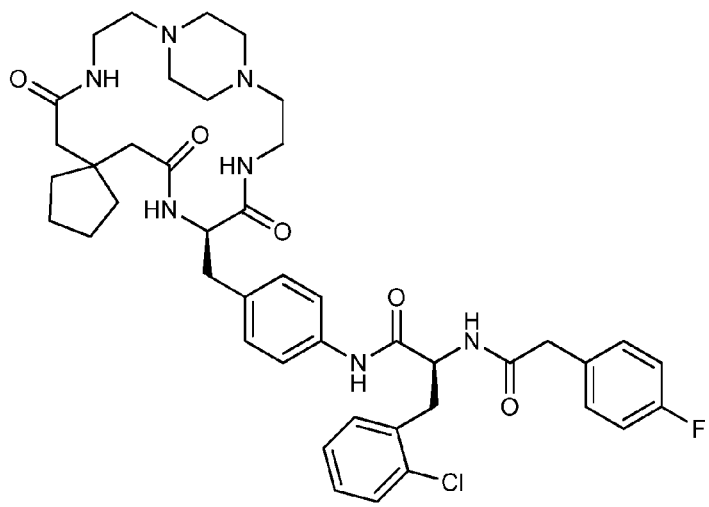
Figure 199:
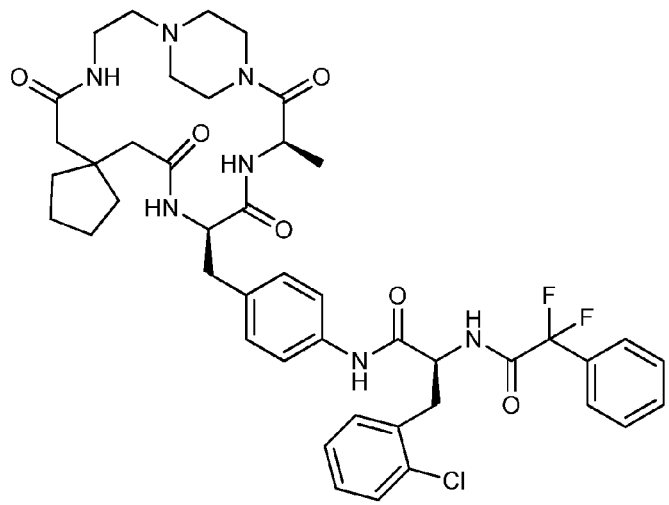
Figure 12:
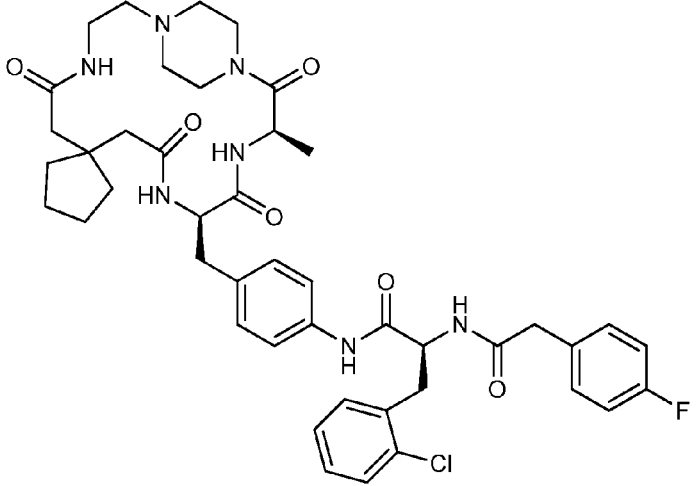
Figure 200:
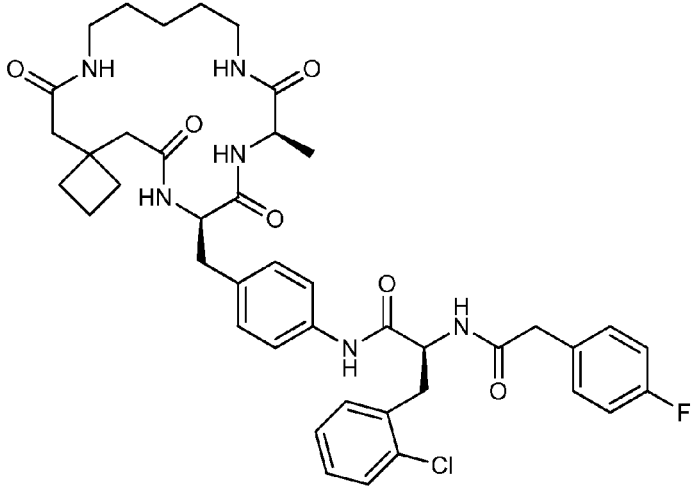
Figure 12:
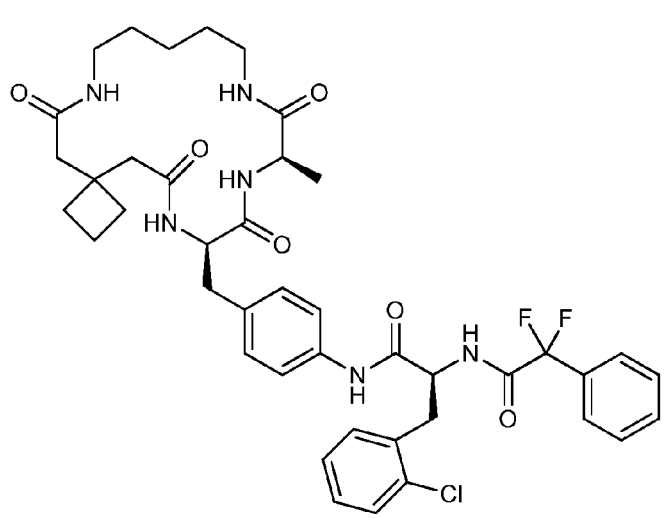
Figure 201:
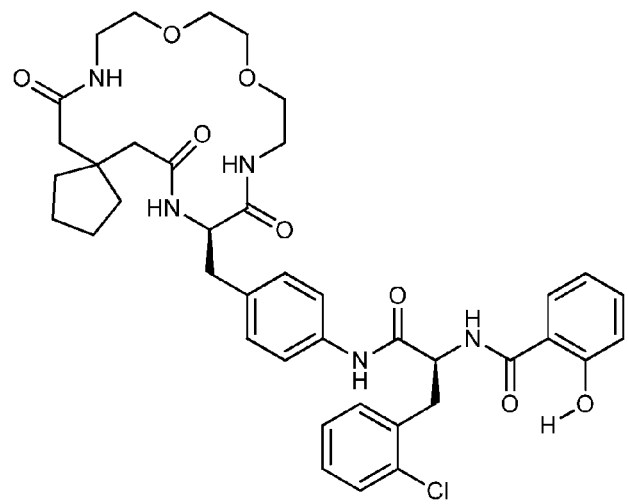
Figure 12:
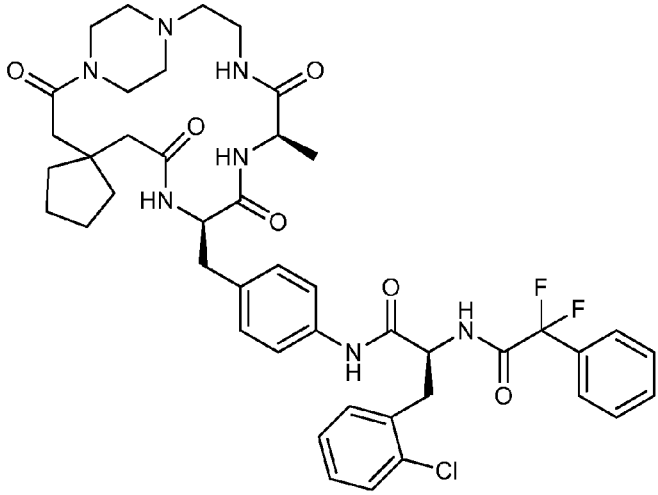
Figure 204:
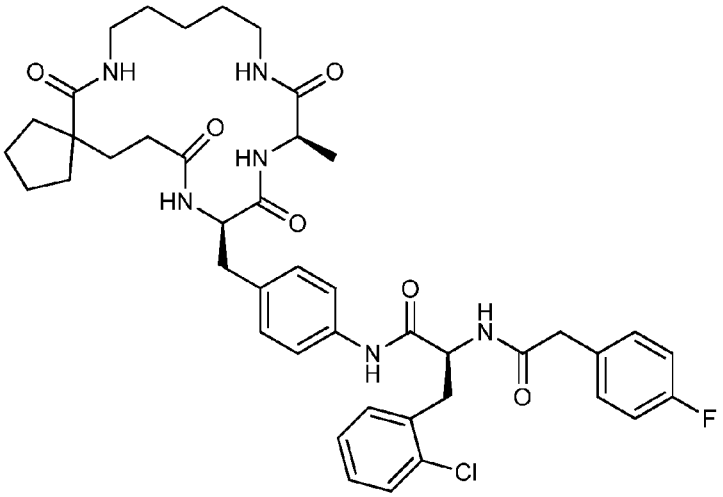
Figure 12:
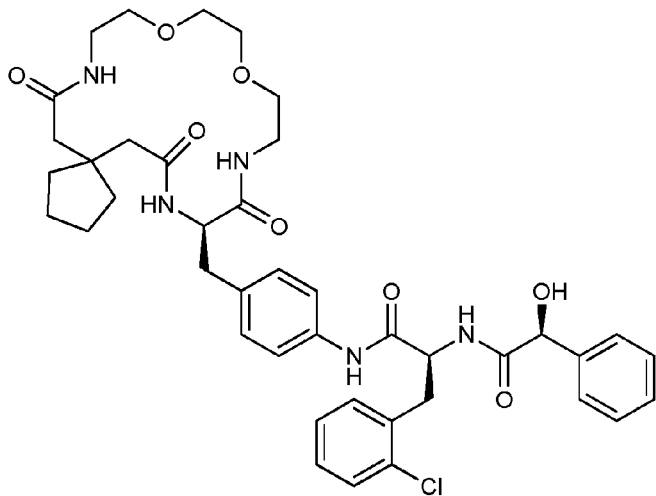
Figure 205:
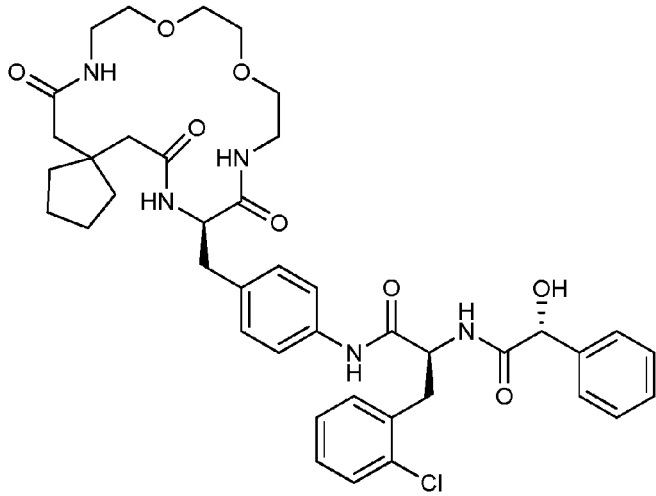
Figure 12:
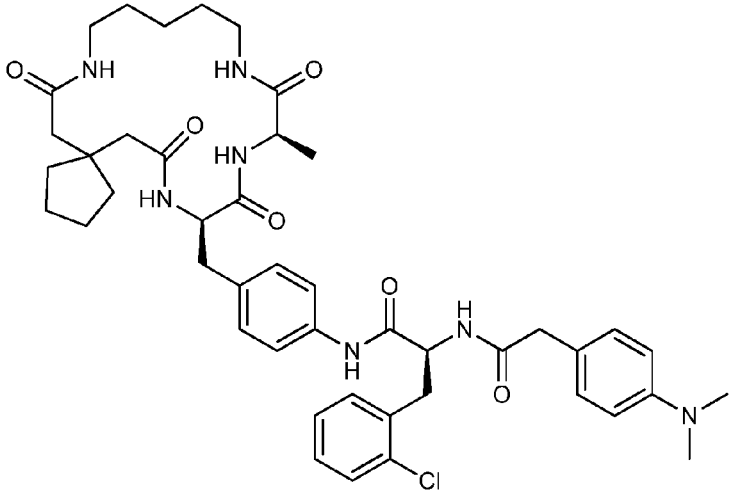
Figure 209:
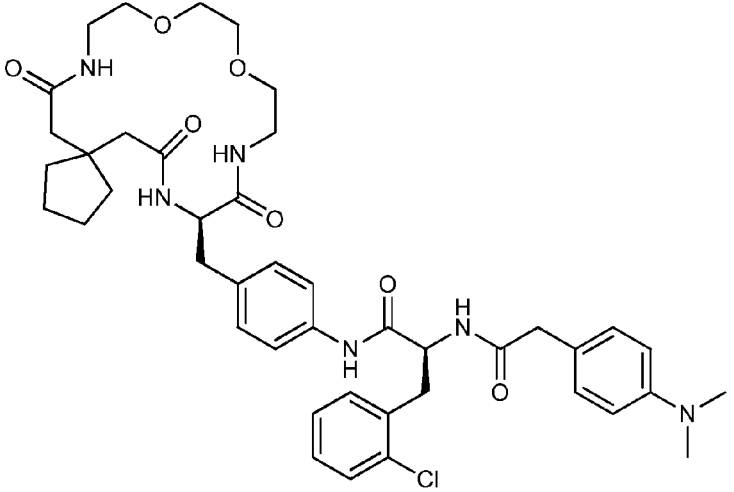
Figure 12:
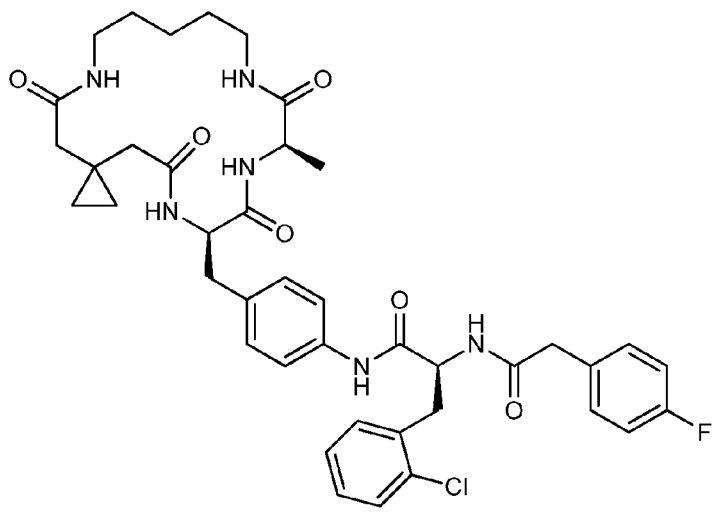
Figure 210:
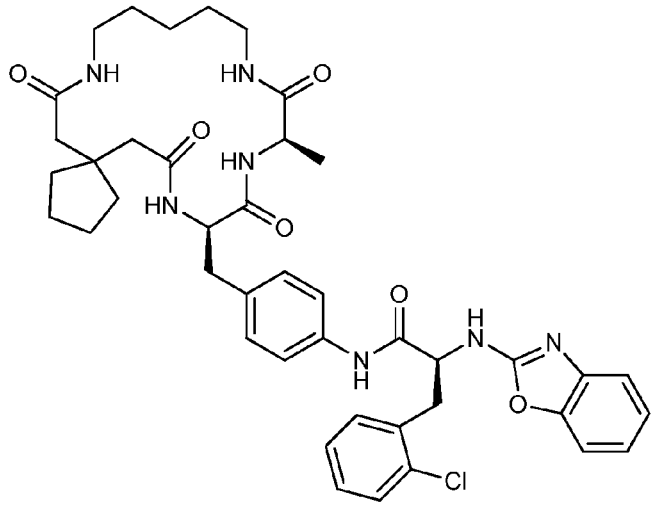
Figure 12:
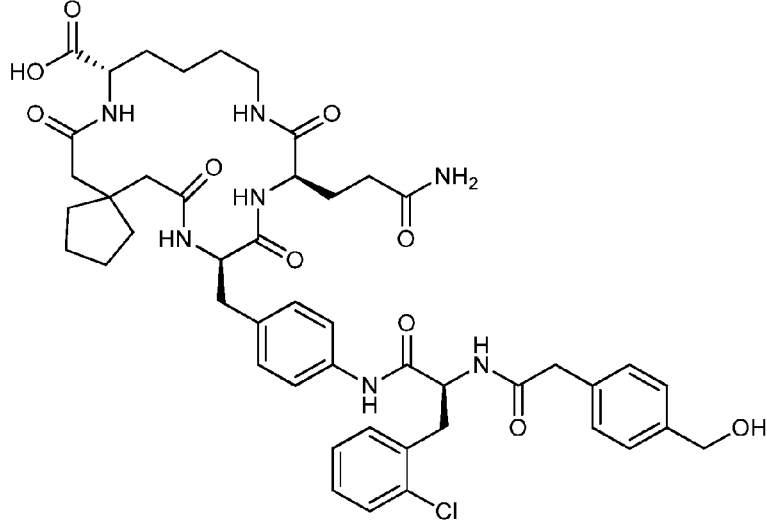
Figure 211:
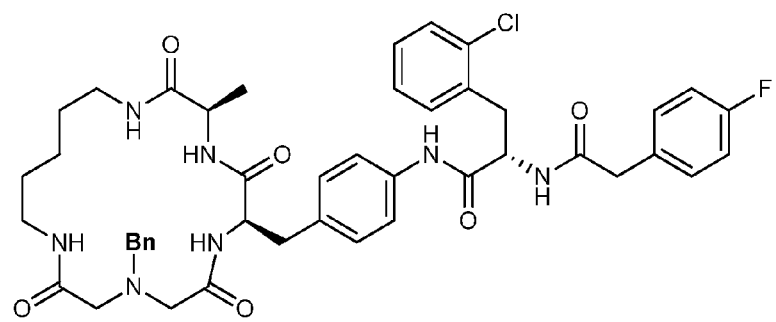
Figure 12:
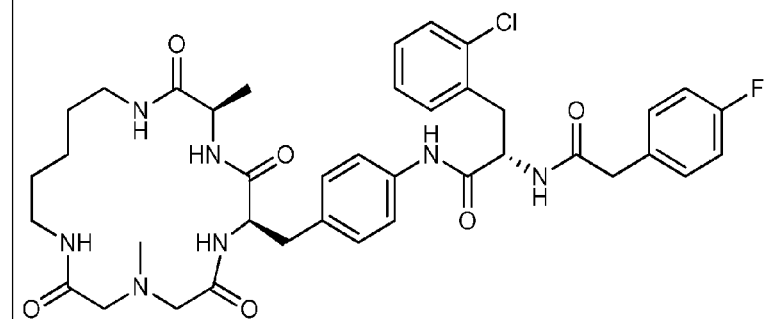
Figure 212:
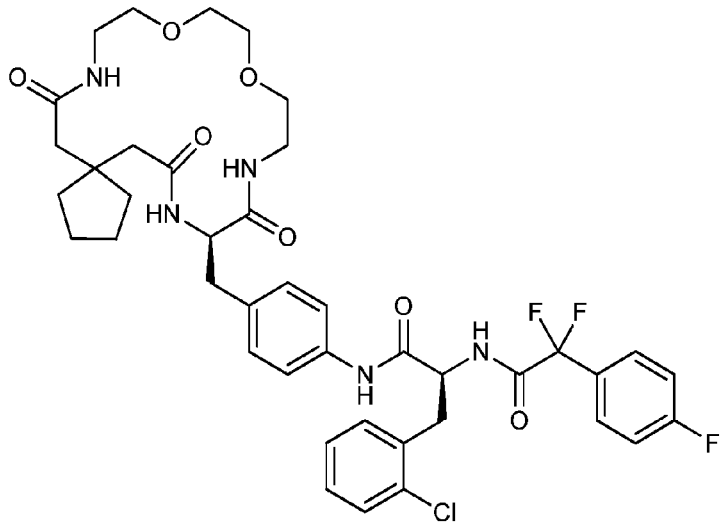
Figure 12:
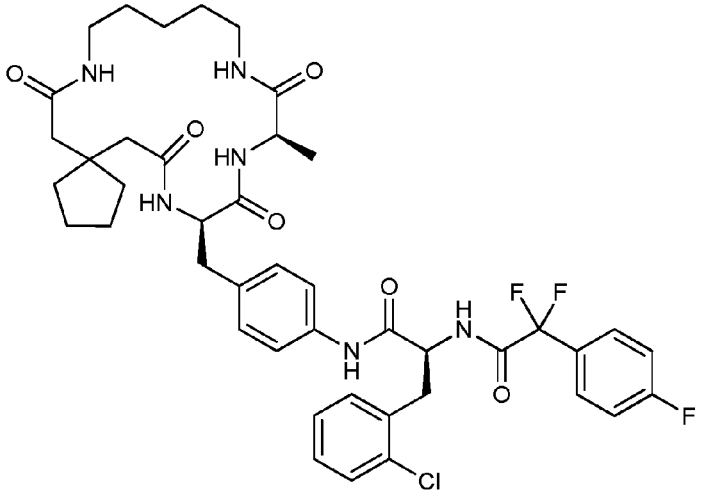
Figure 213:
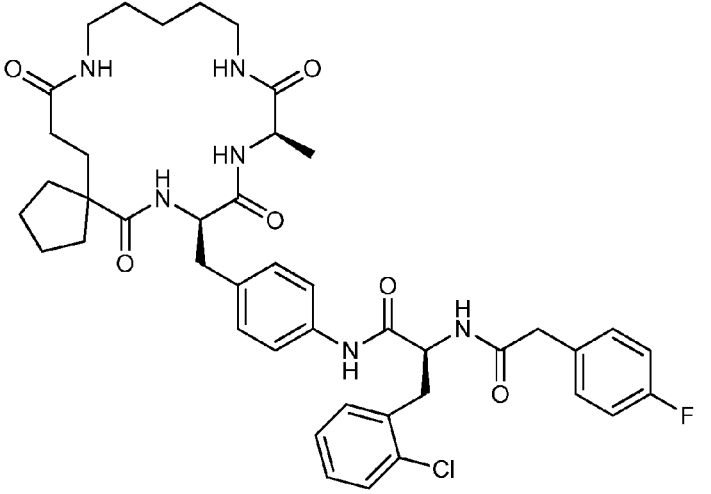
Figure 12:
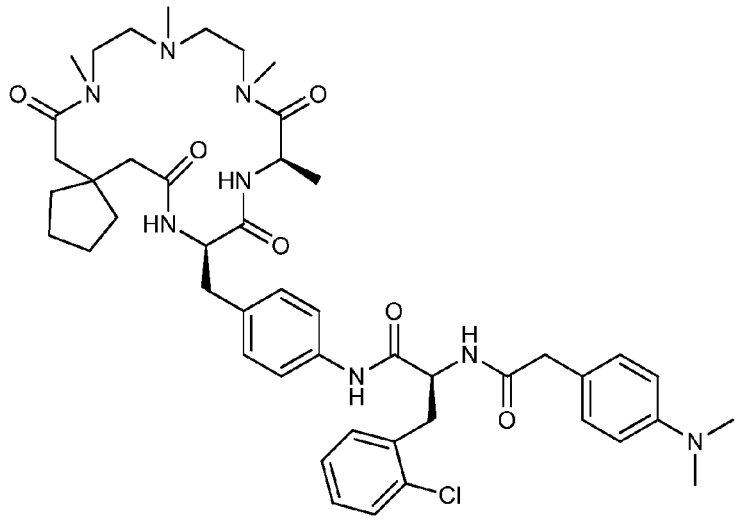
Figure 214:
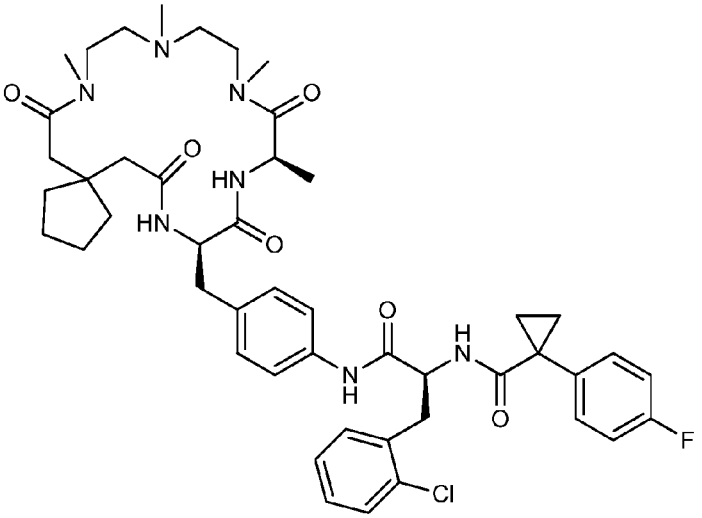
Figure 12:
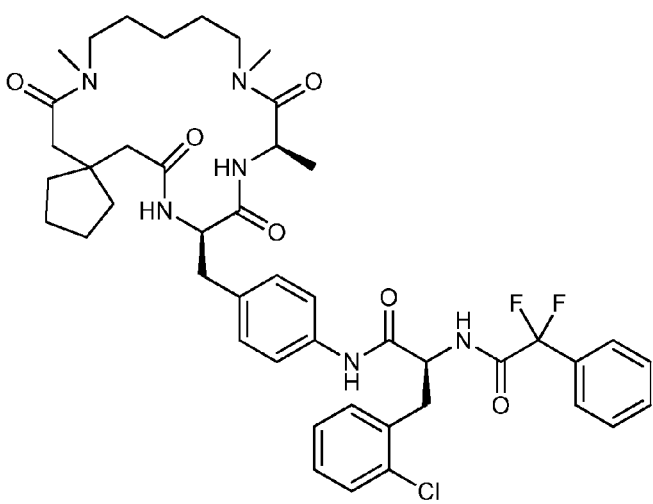
Figure 216:
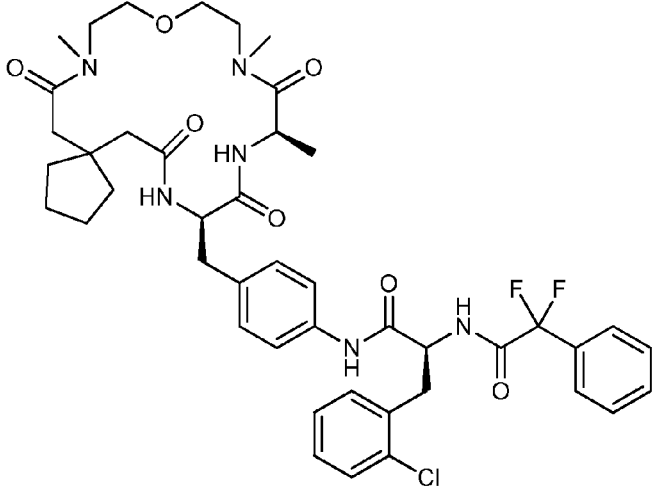
Figure 12:
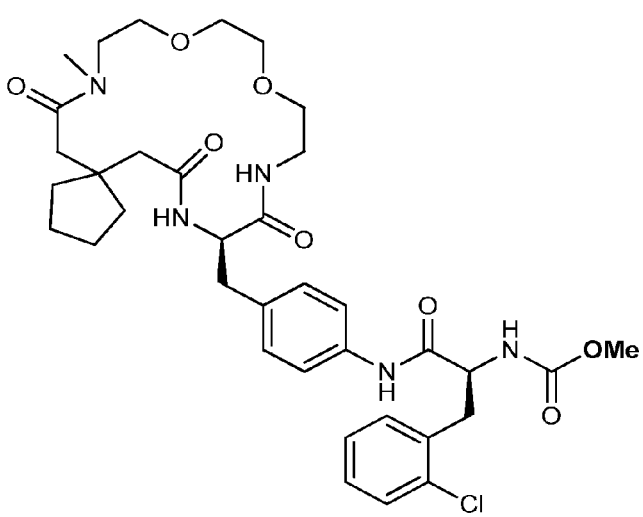
Figure 217:
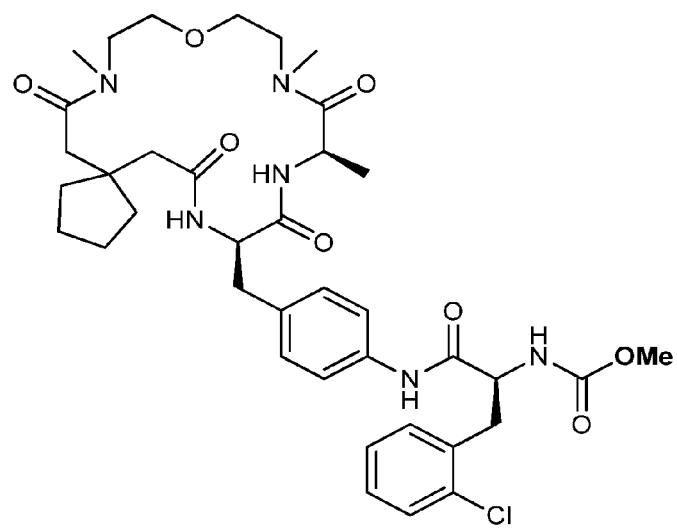
Figure 12:
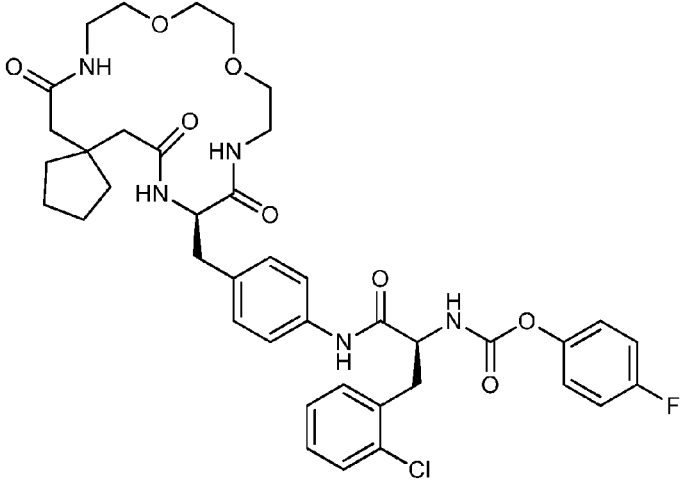
Figure 219:
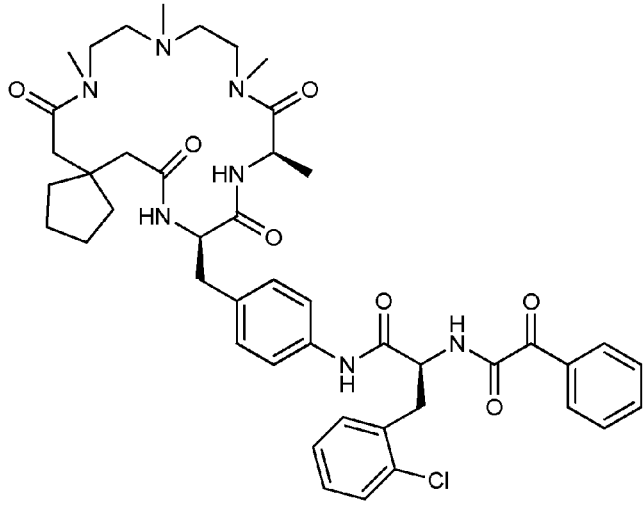
Figure 12:
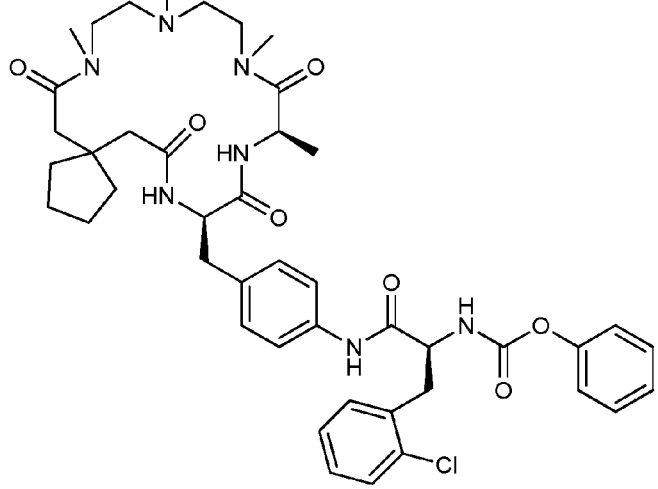
Figure 220:
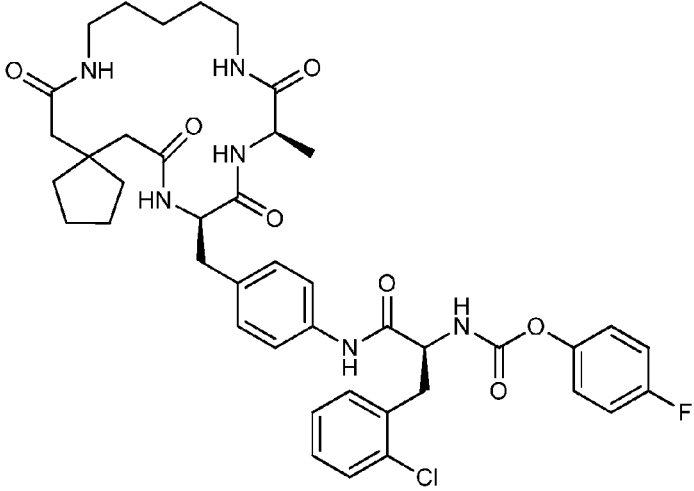
Figure 12:
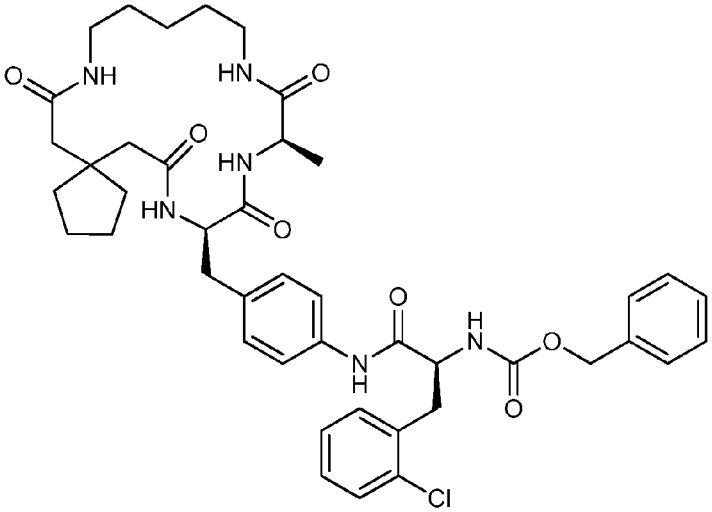
Figure 221:
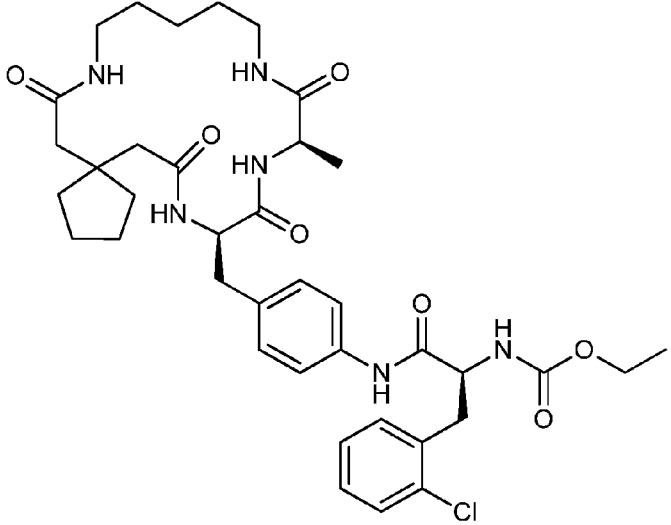
Figure 12:
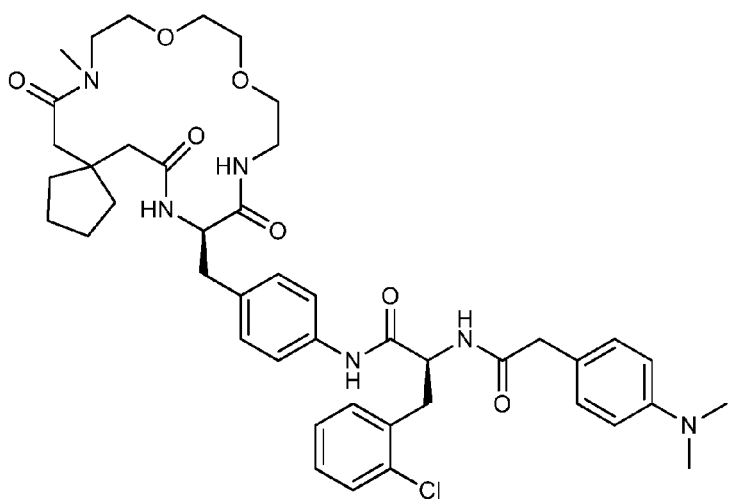
Figure 224:
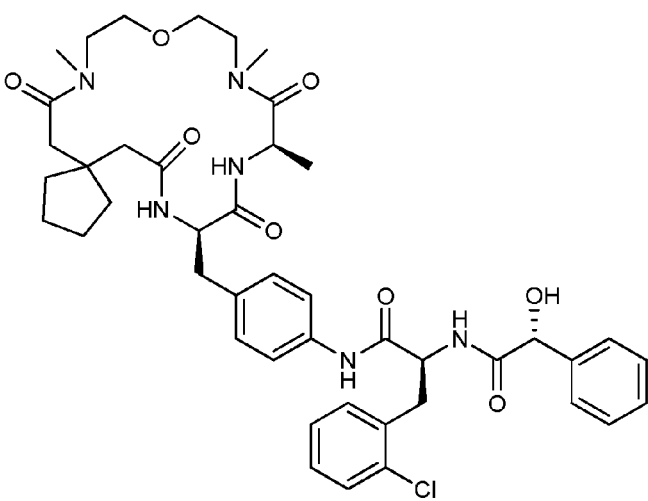
Figure 12:
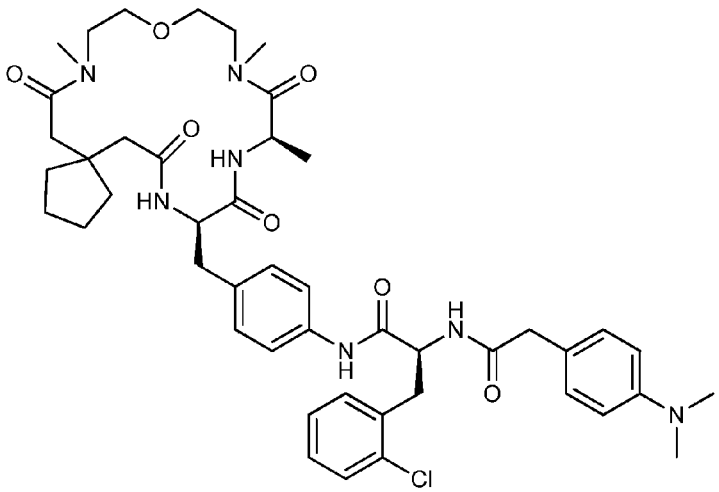
Figure 225:
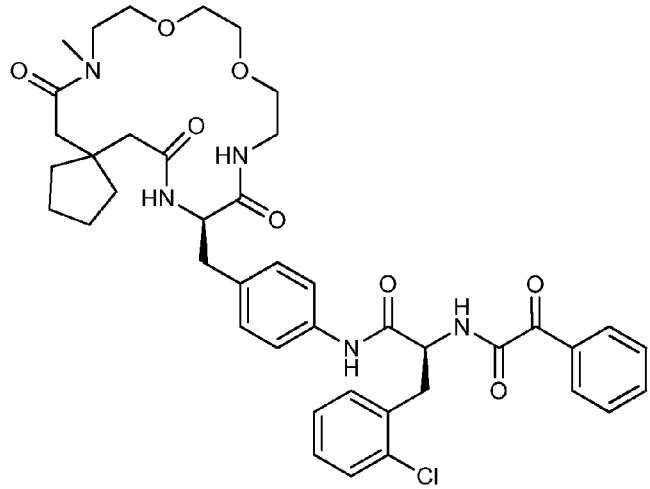
Figure 12:
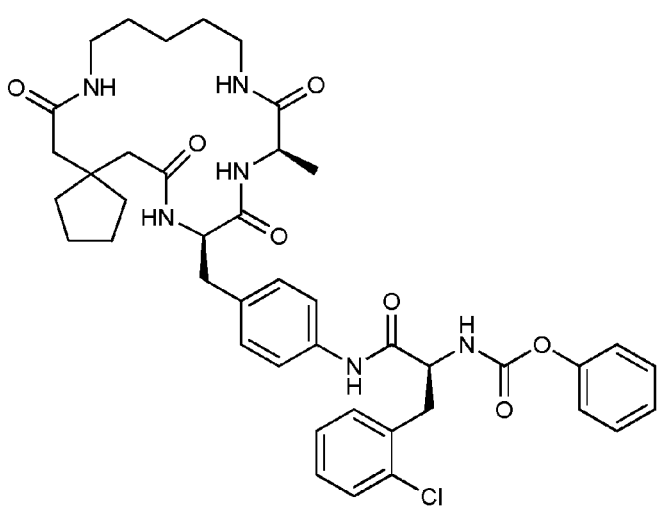
Figure 226:
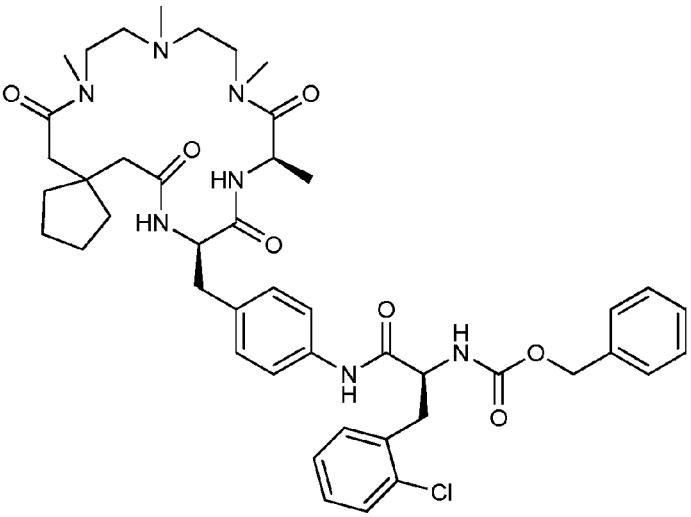
Figure 12:
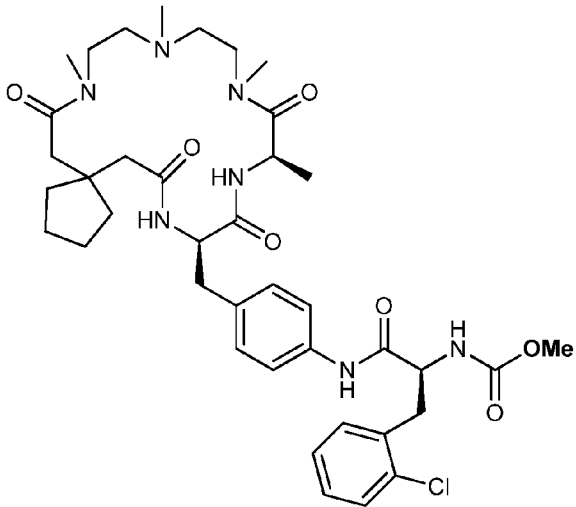
Figure 227:
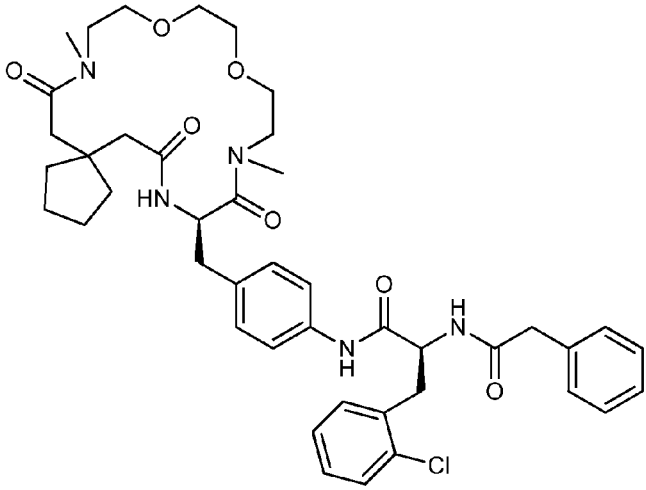
Figure 12:
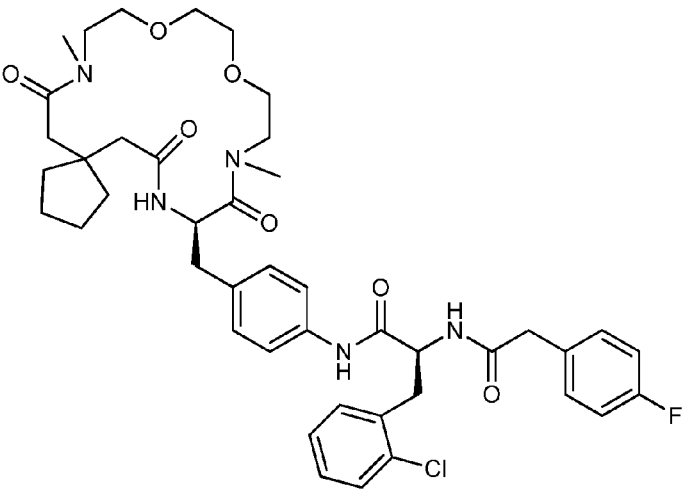
Figure 228:
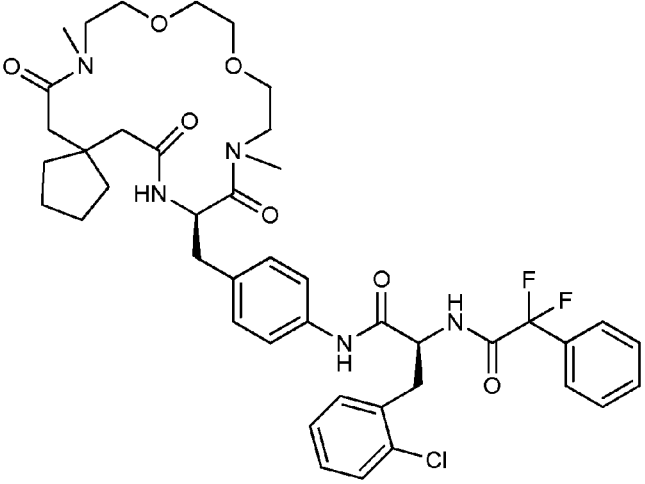
Figure 12:
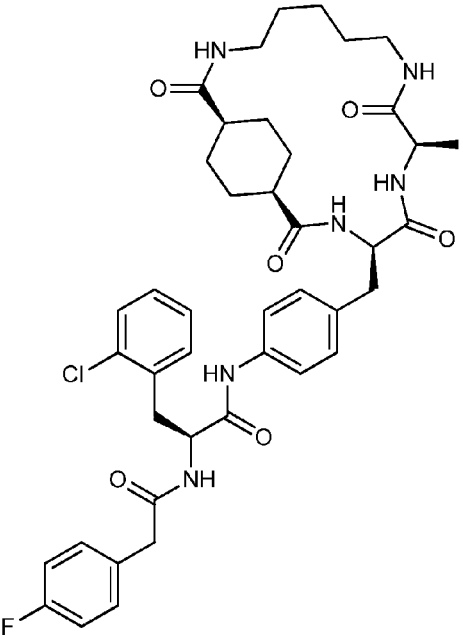
Figure 229:
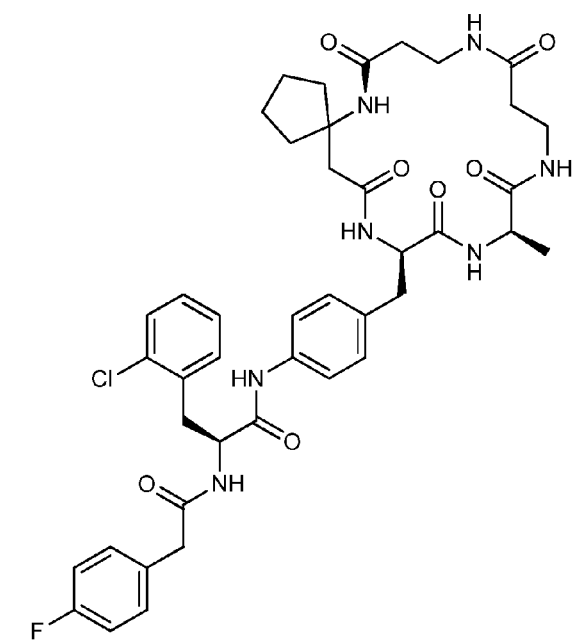
Figure 12:
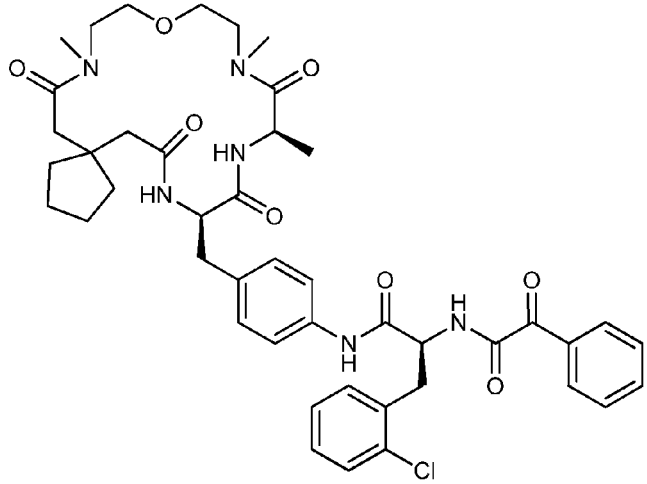
Figure 230:
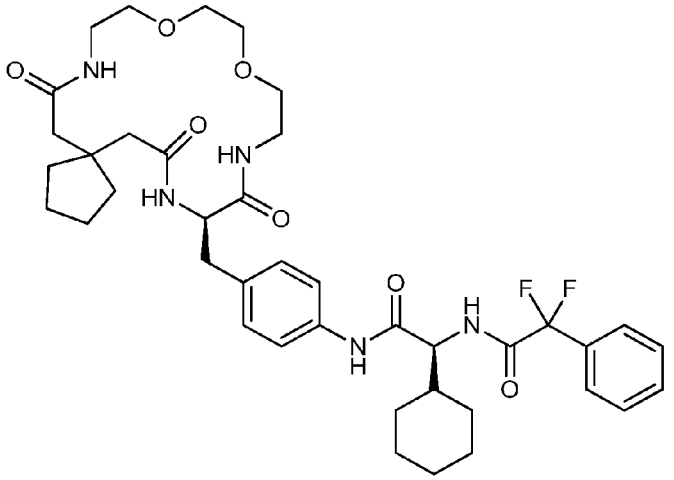
Figure 12:
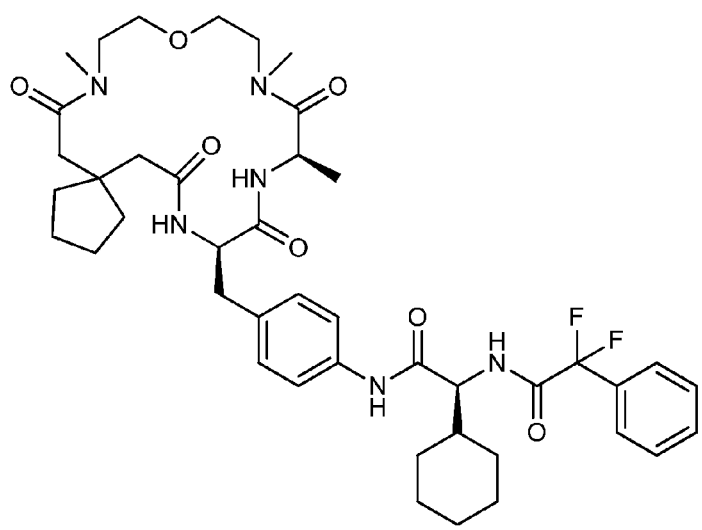
Figure 234:
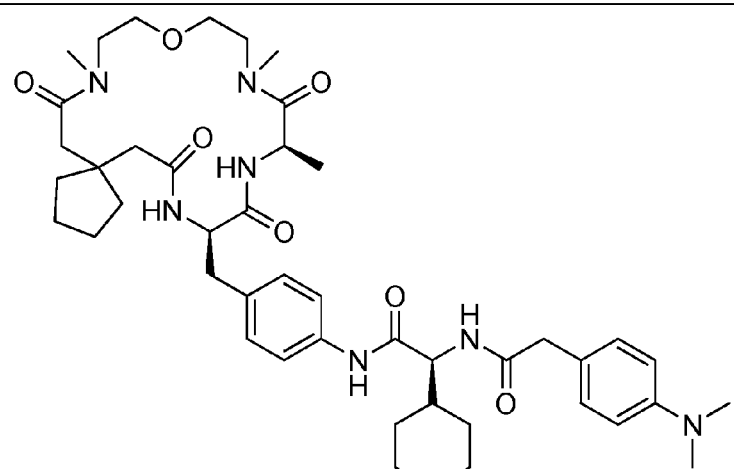
Figure 12:
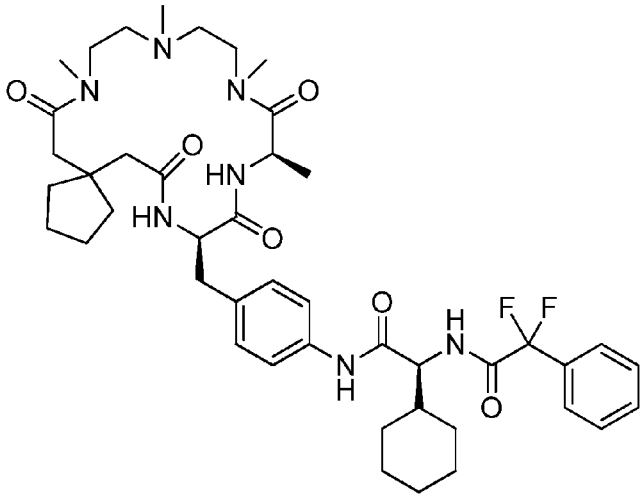
Figure 235:
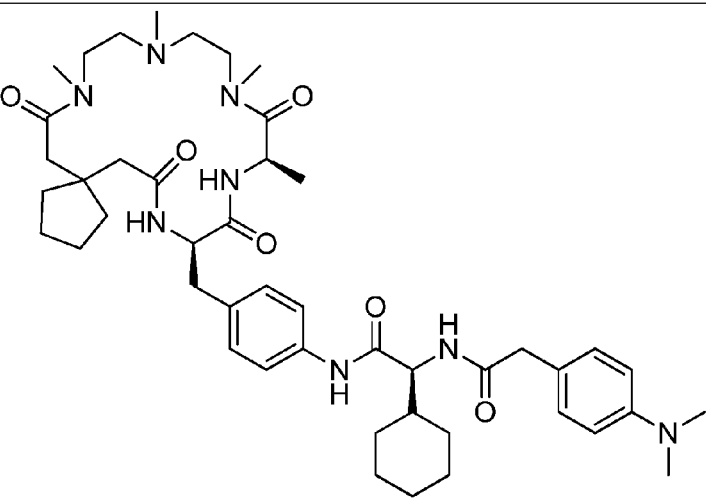
Figure 12:
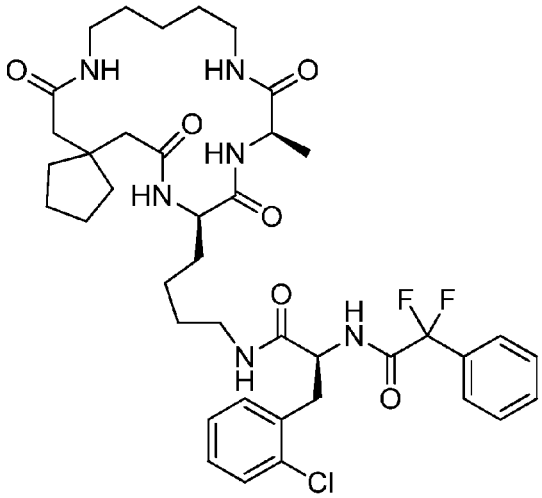
Figure 236:
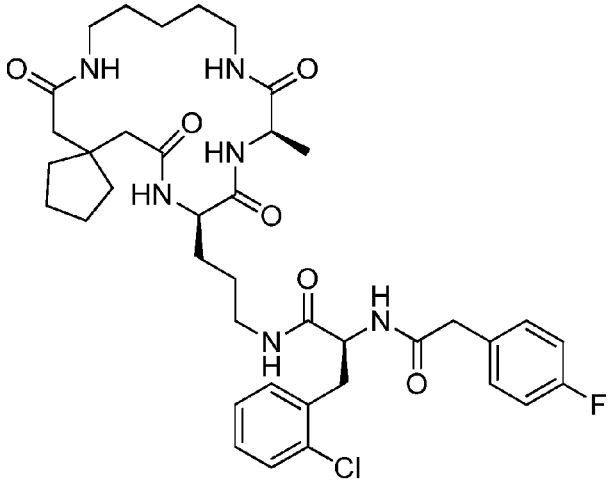
Figure 12:
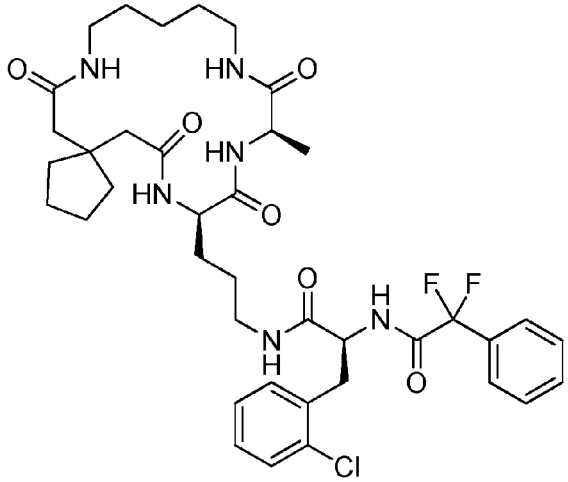
Figure 237:
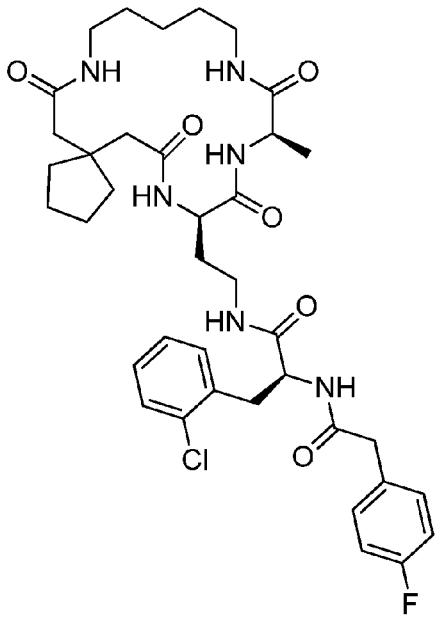
Figure 12:
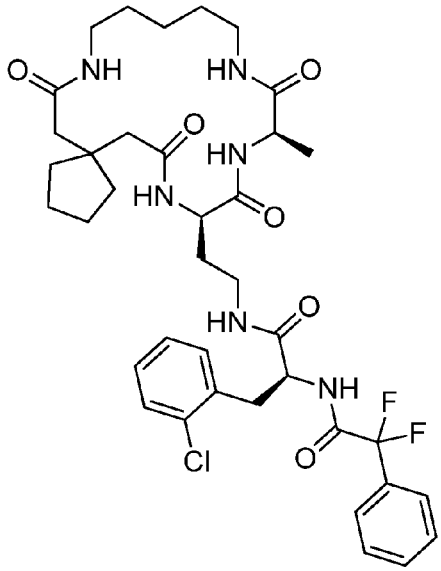
Figure 238:
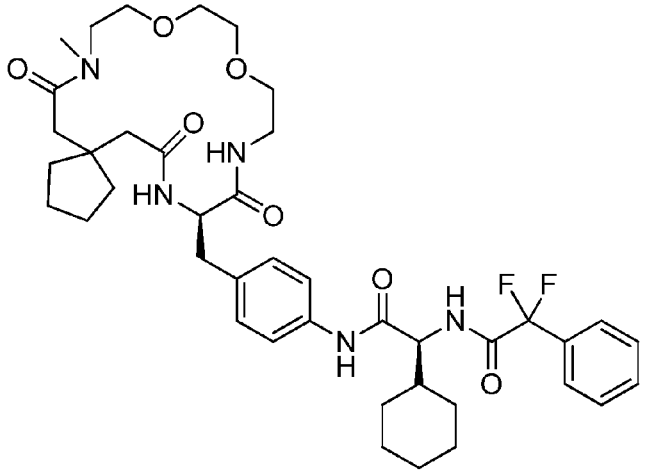
Figure 12:
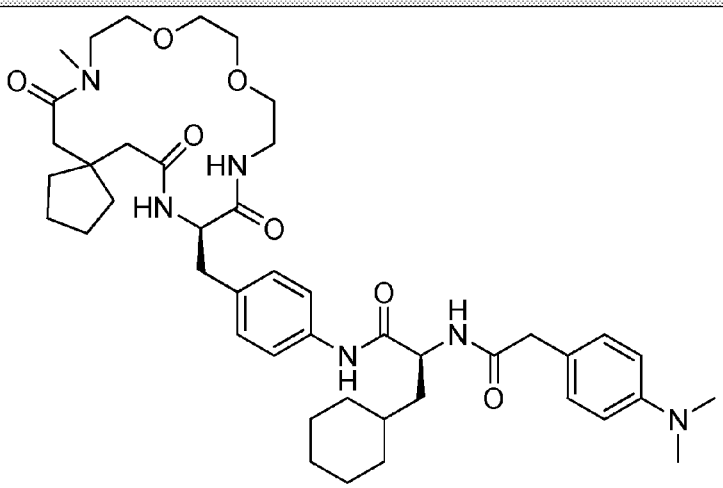
Figure 240:
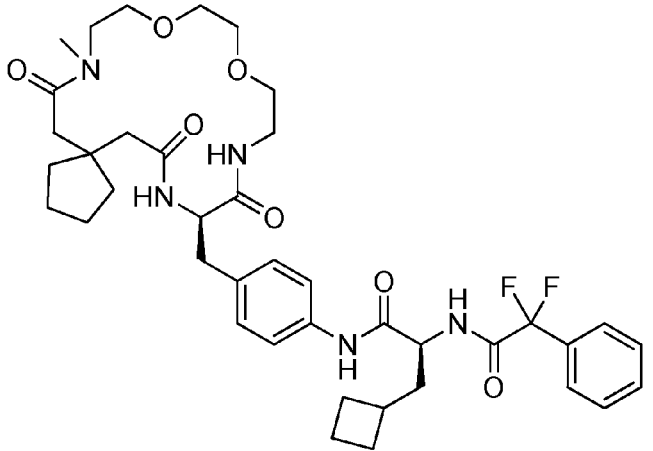
Figure 12:
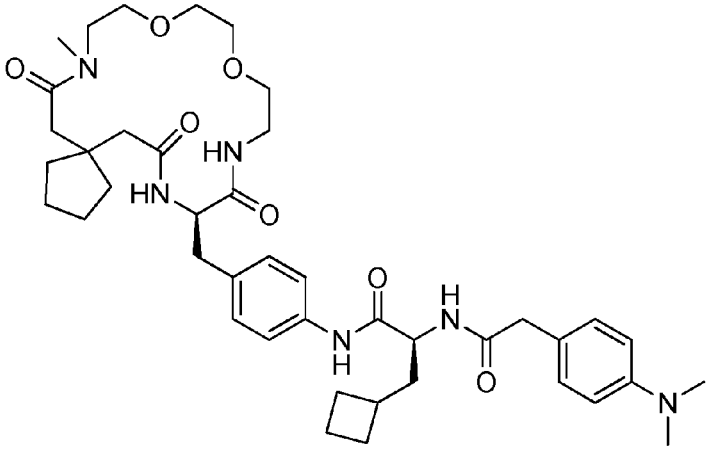
Figure 241:
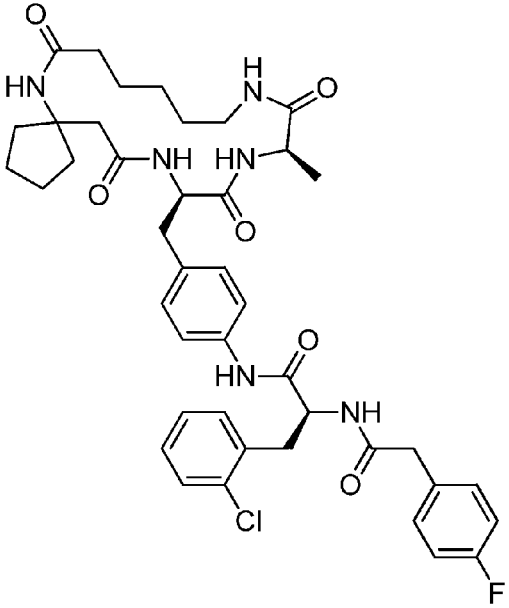
Figure 12:
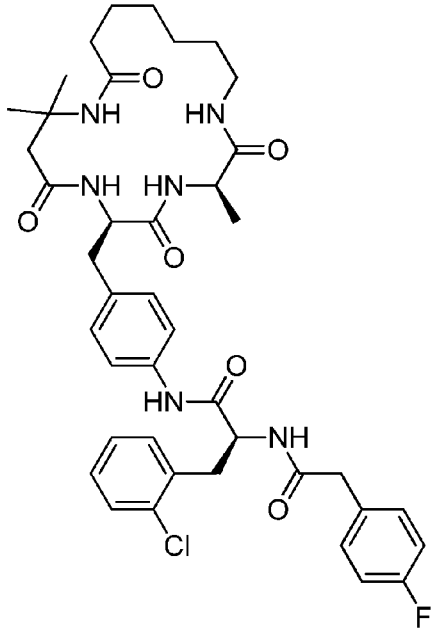
Figure 243:
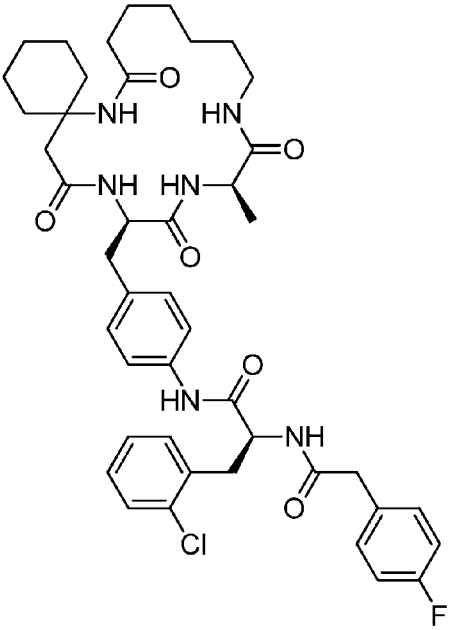
Figure 12:
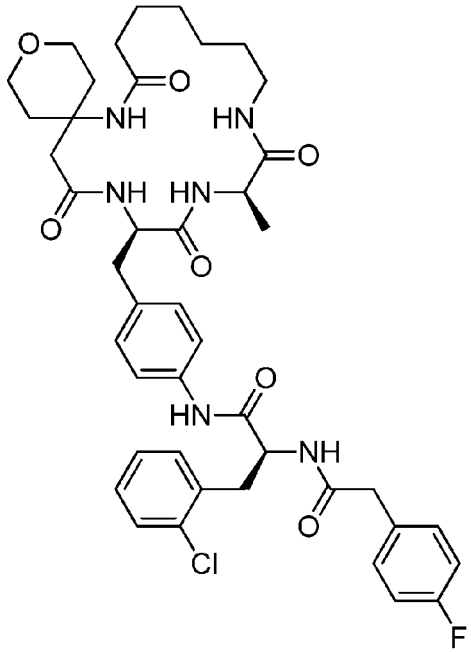
Figure 244:
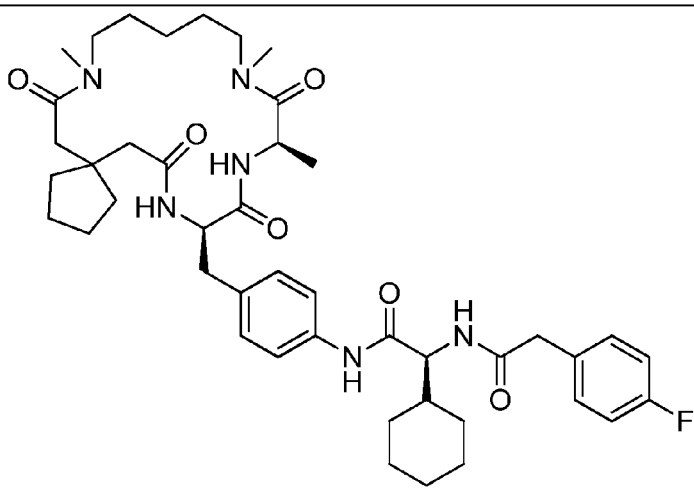
Figure 12:
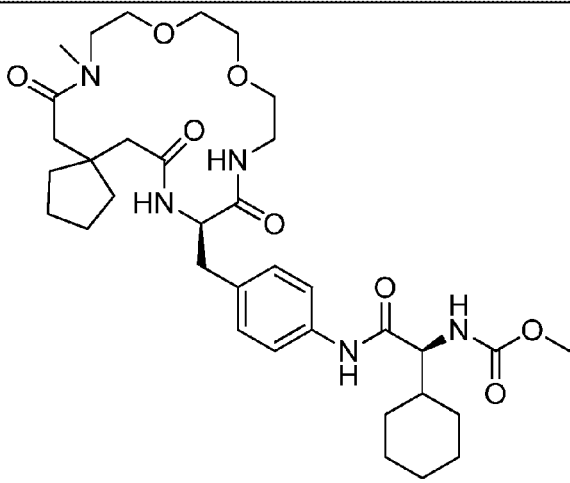
Figure 245:
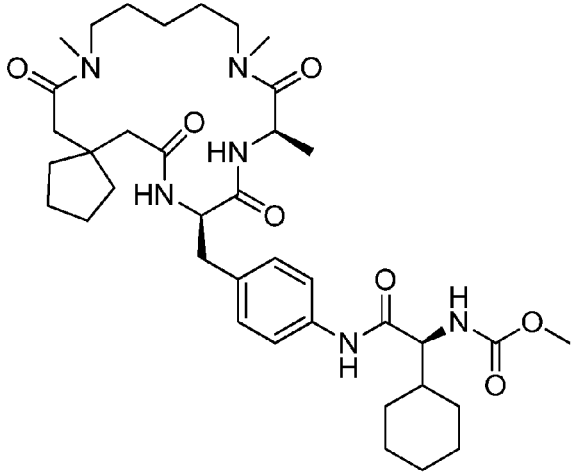
Figure 12:
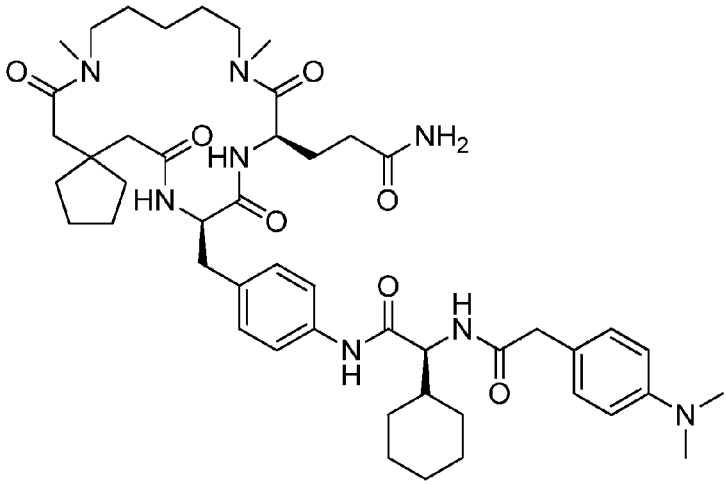
Figure 246:
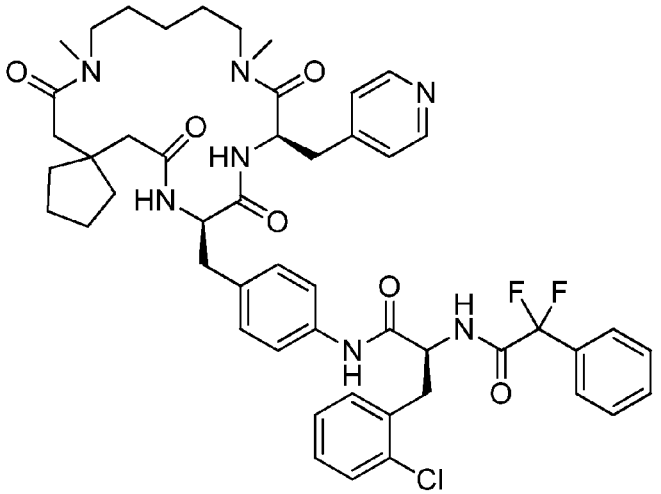
Figure 12:
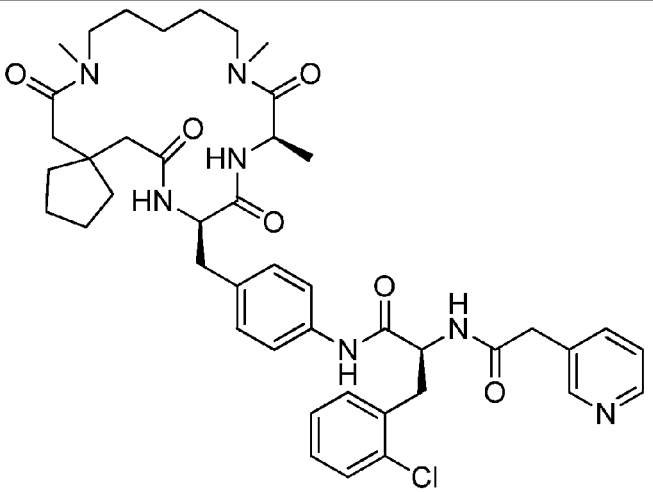
Figure 247:
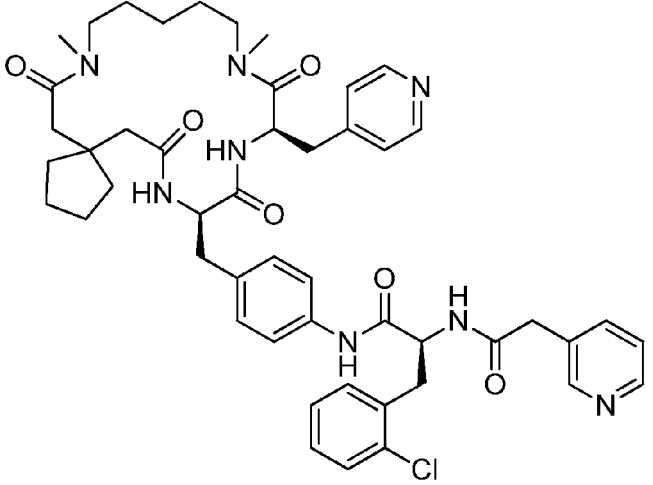
Figure 12:
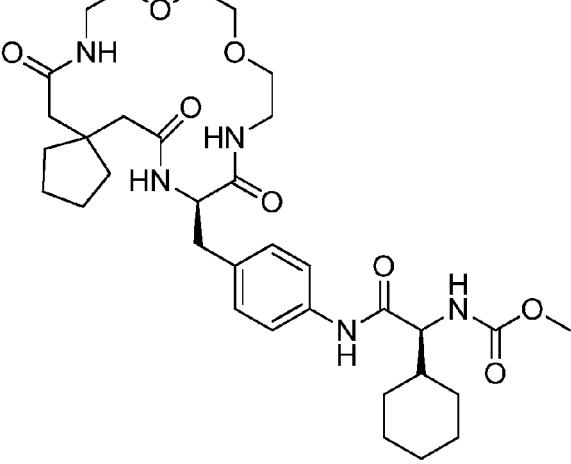
Figure 249:
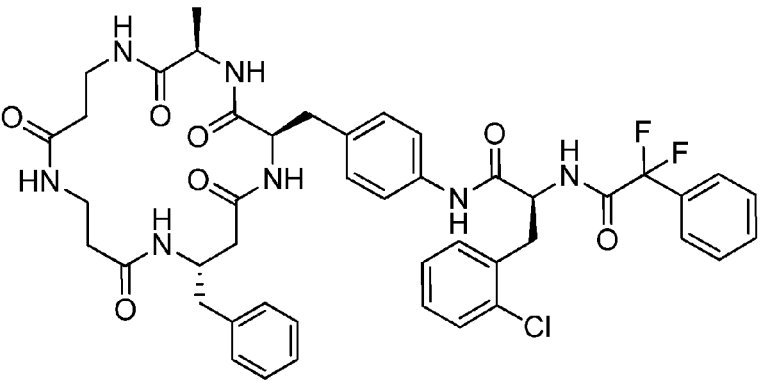
Figure 12:
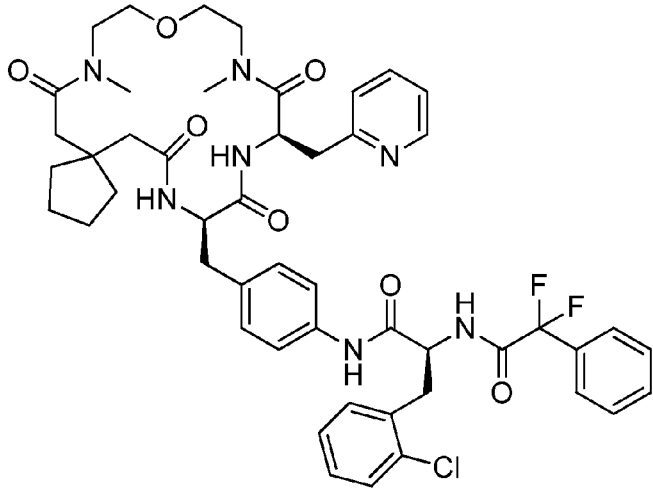
Figure 251:
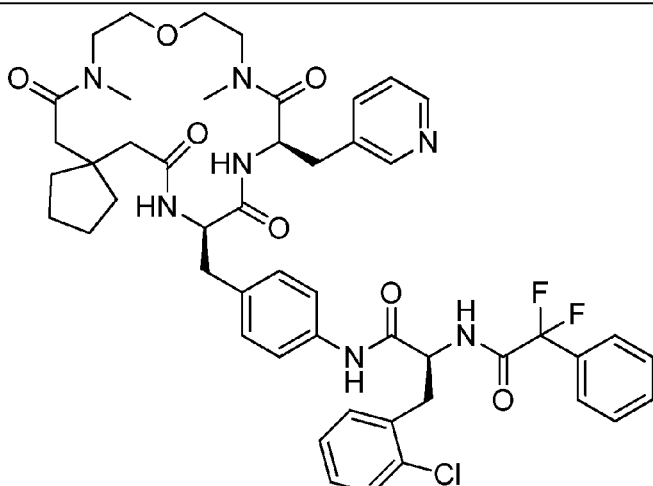
Figure 12:
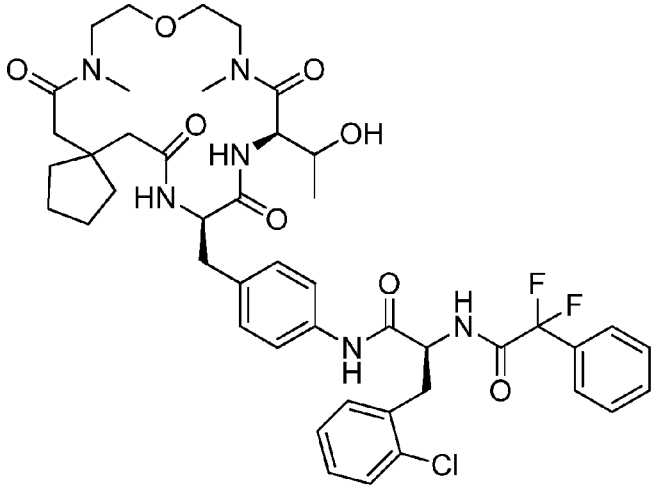
Figure 252:
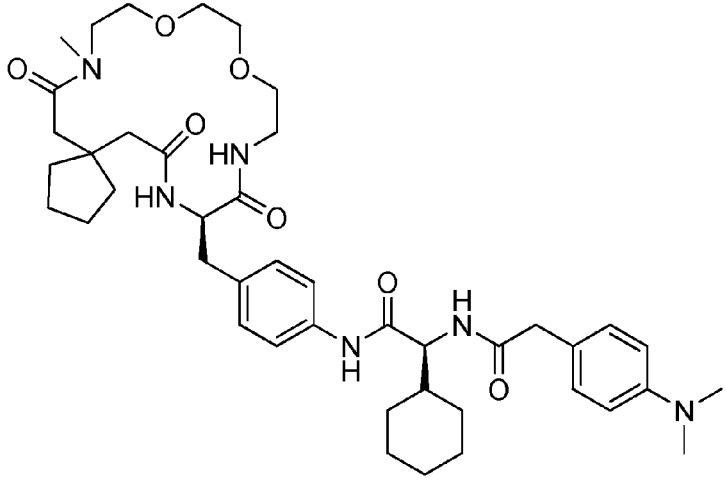
Figure 12:
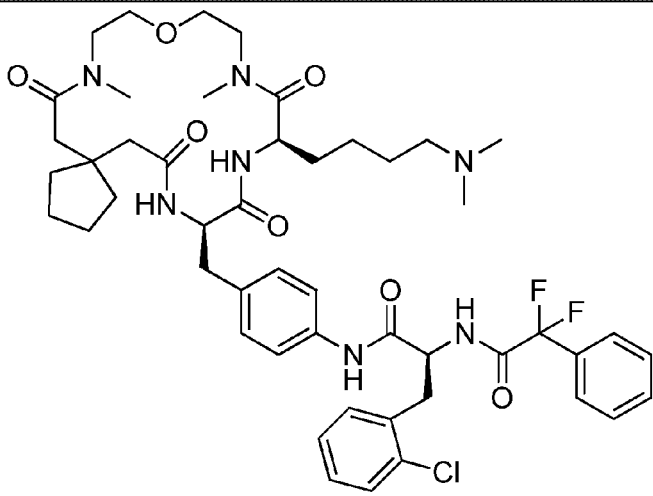
Figure 253:
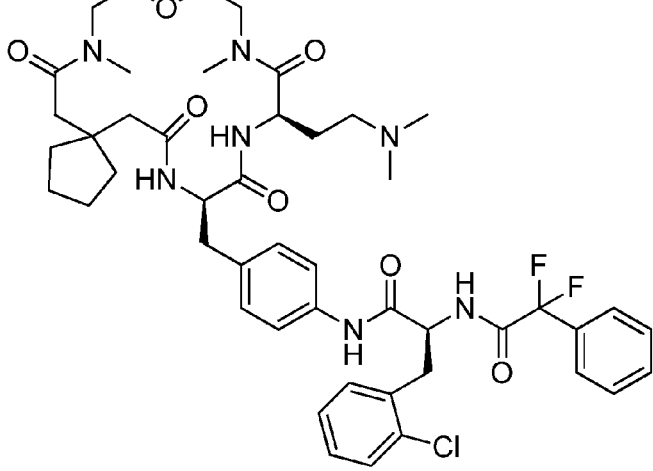
Figure 12:
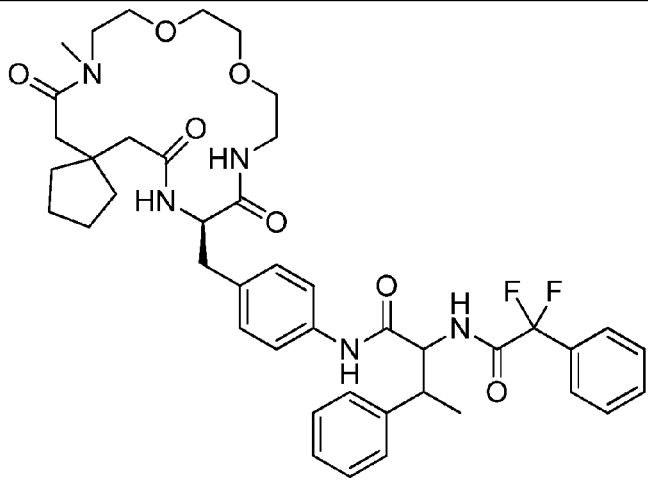
Figure 254:
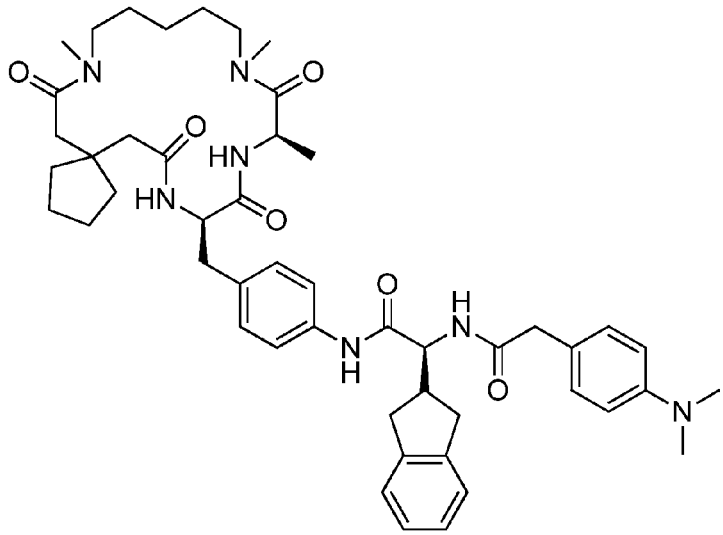
Figure 12:
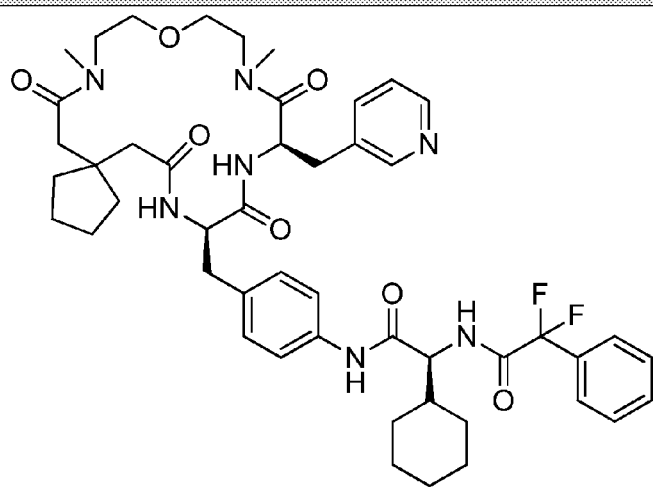
Figure 257:
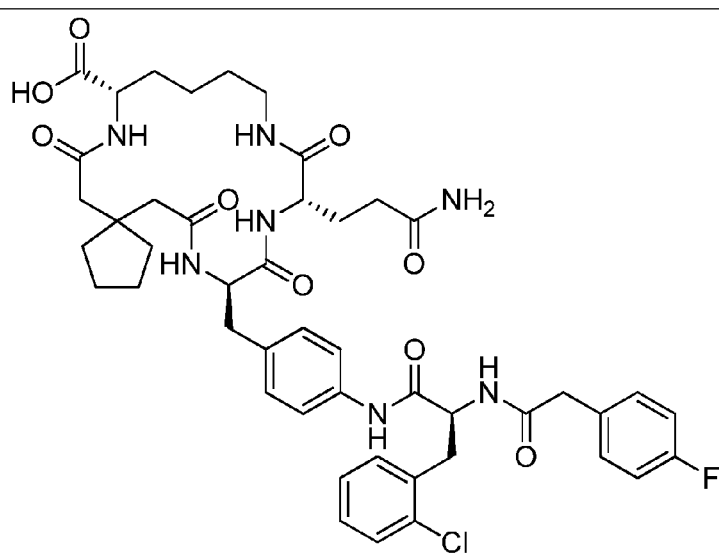
Figure 12:
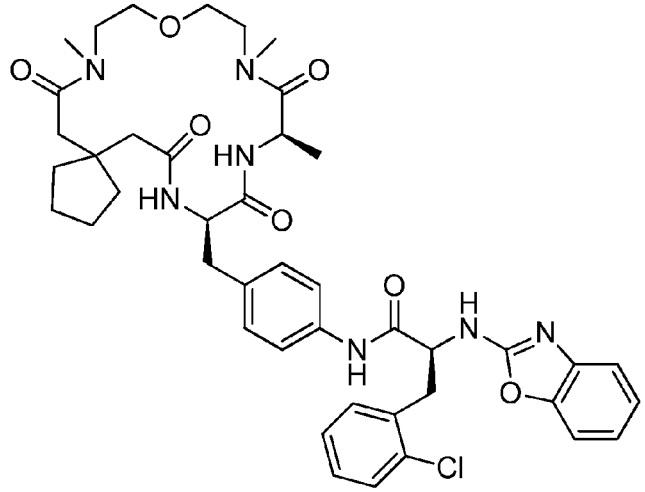
Figure 259:
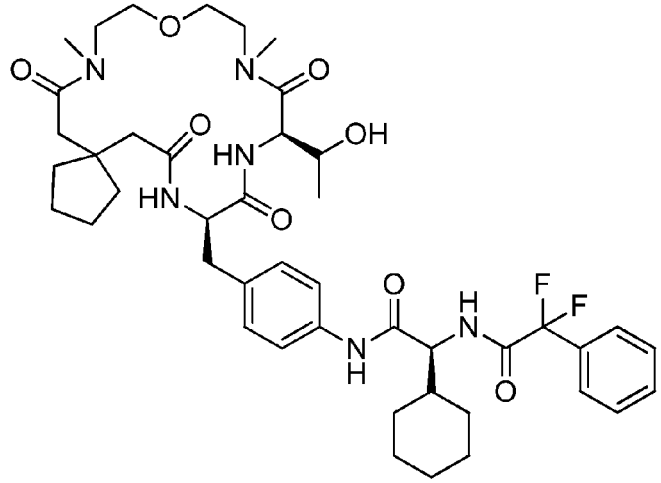
Figure 12:
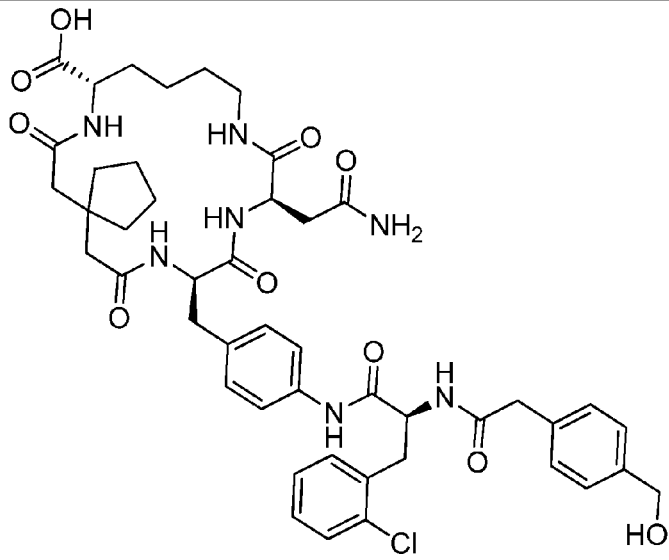
Figure 260:
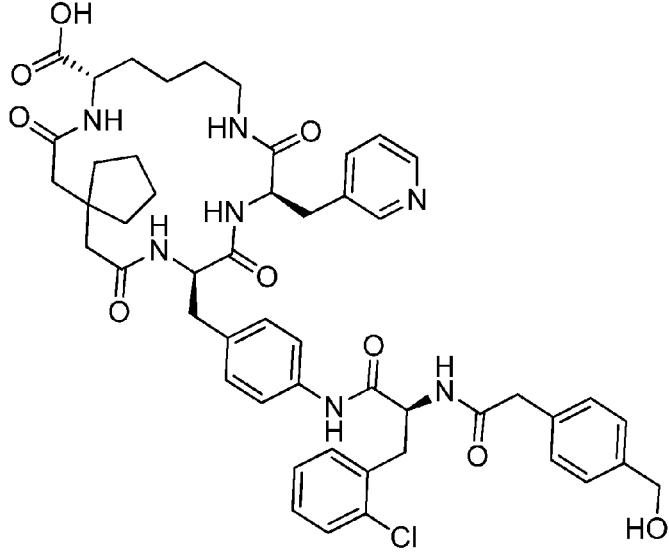
Figure 12:
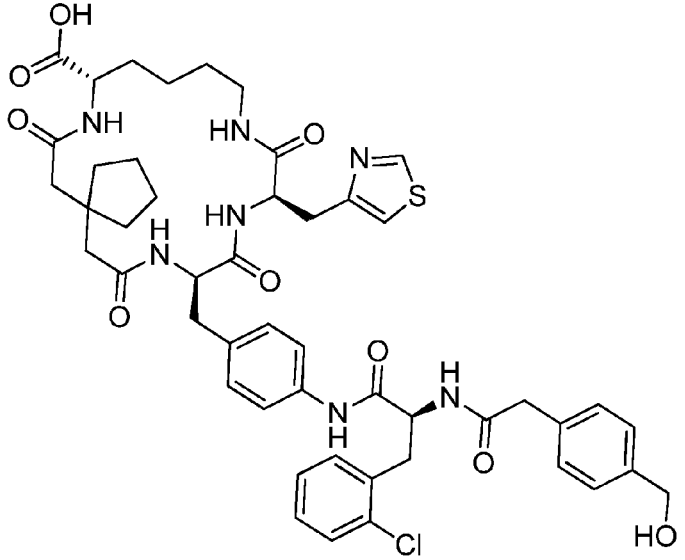
Figure 261:
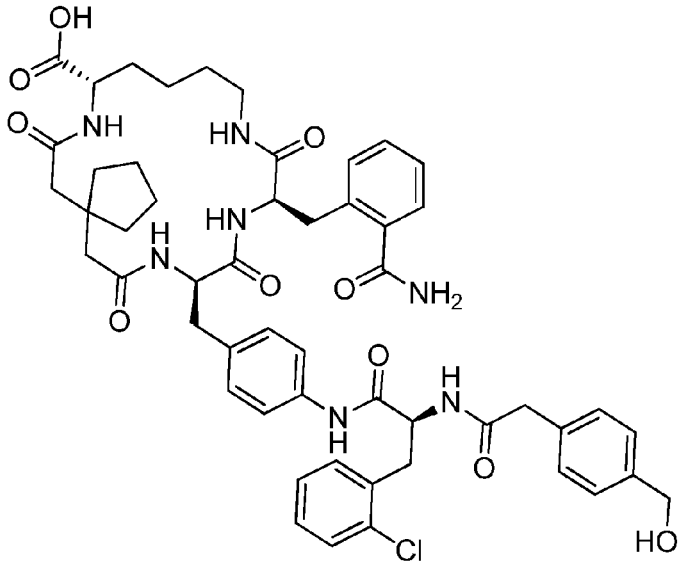
Figure 12:
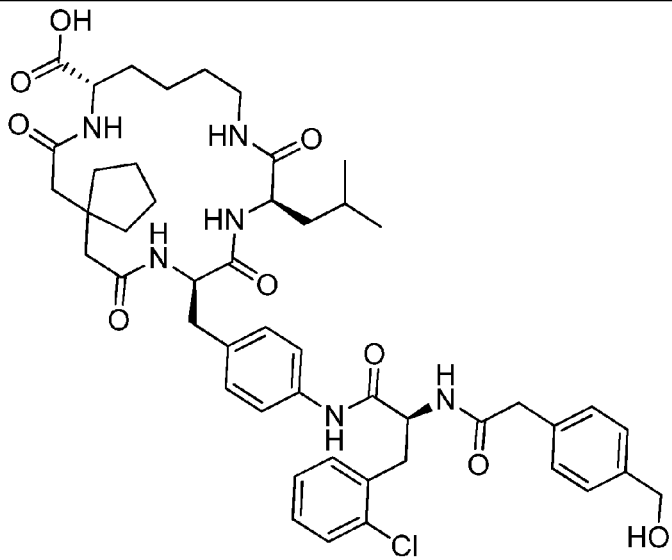
Figure 262:
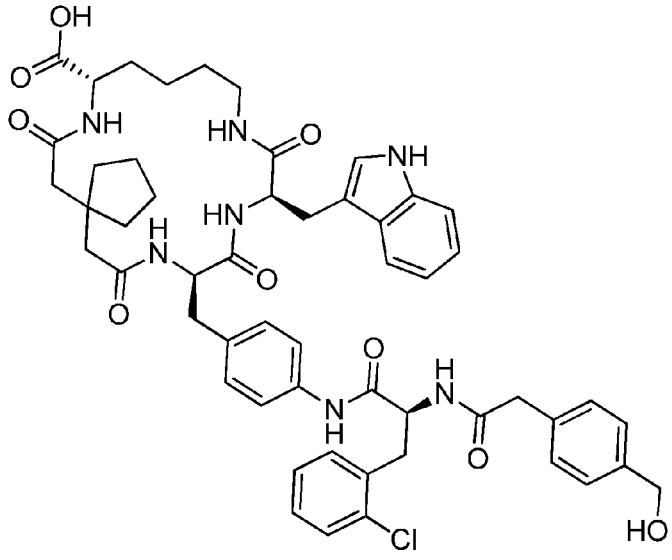
Figure 12:
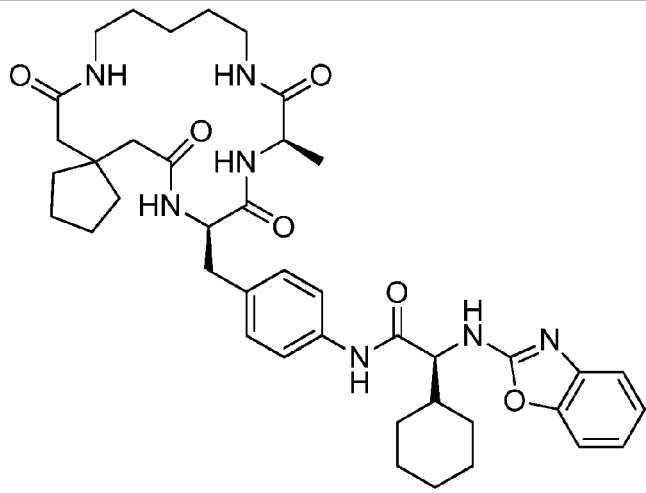
Figure 264:
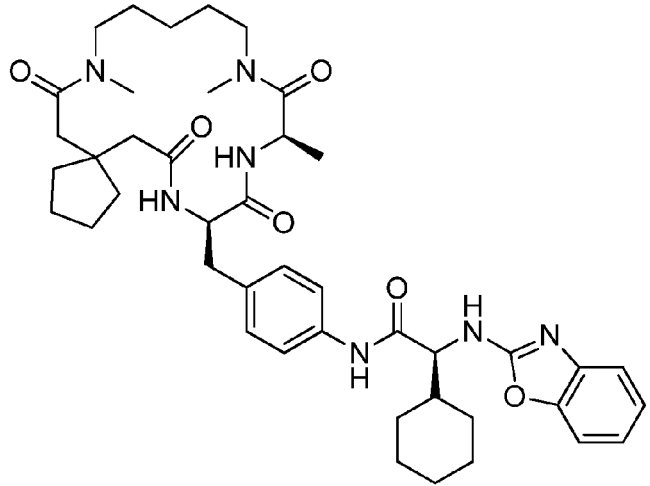
Figure 12:
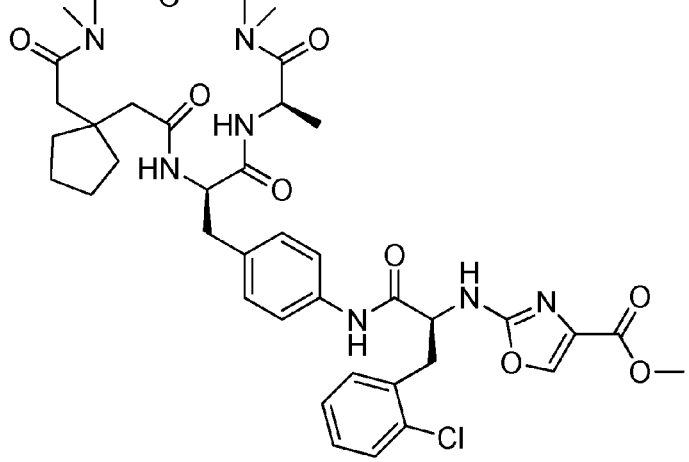
Figure 265:
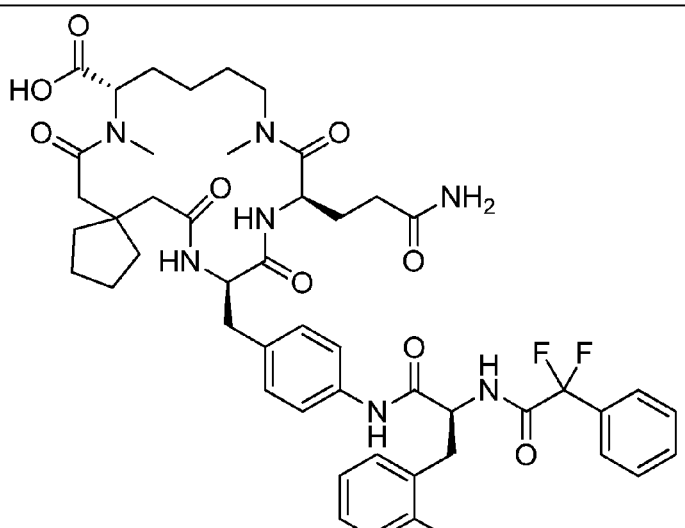
Figure 12:
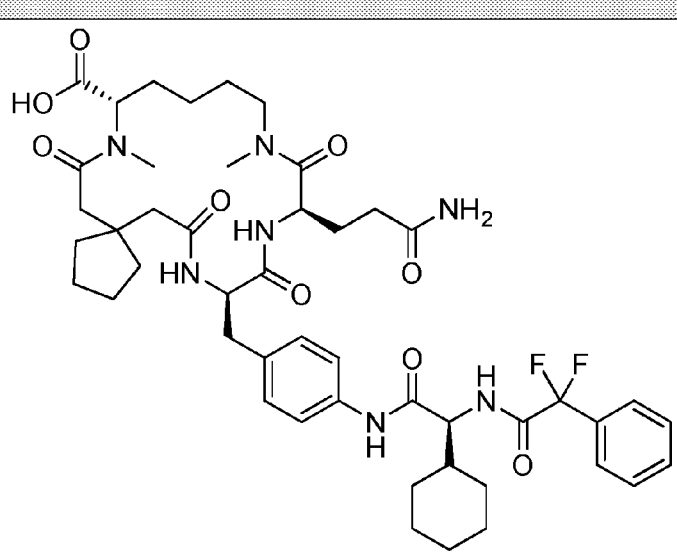
Figure 266:
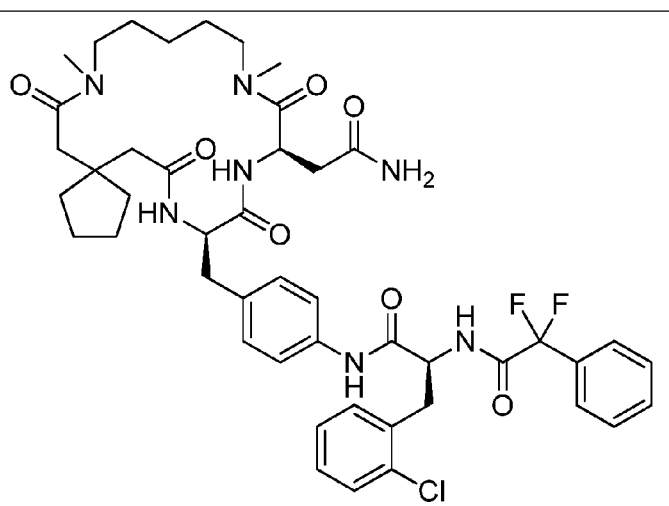
Figure 12:
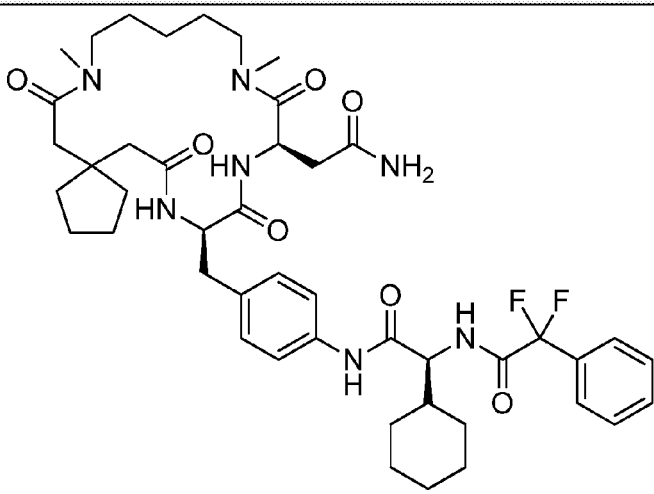
Figure 267:
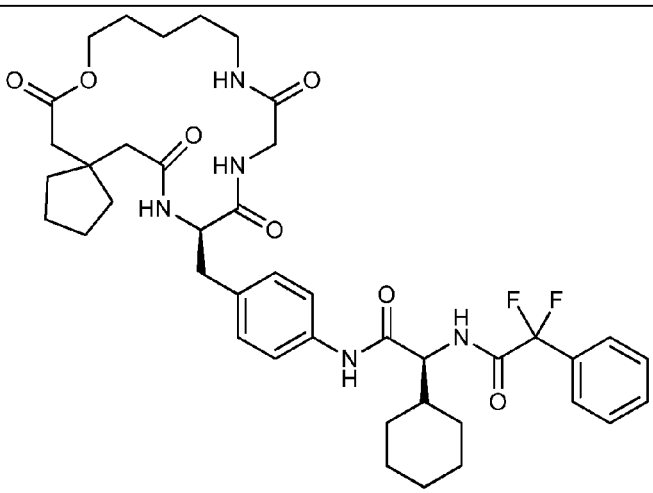
Figure 12:
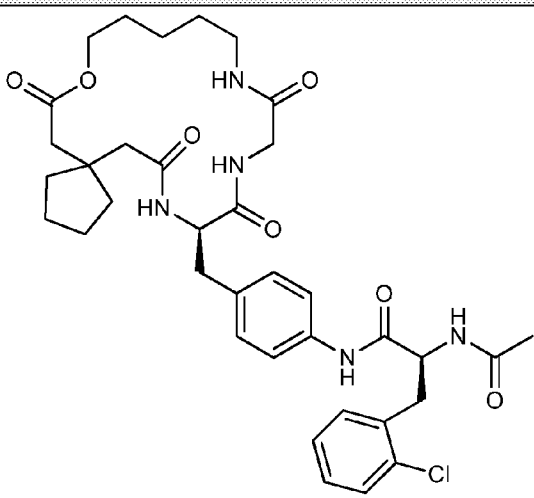
Figure 270:
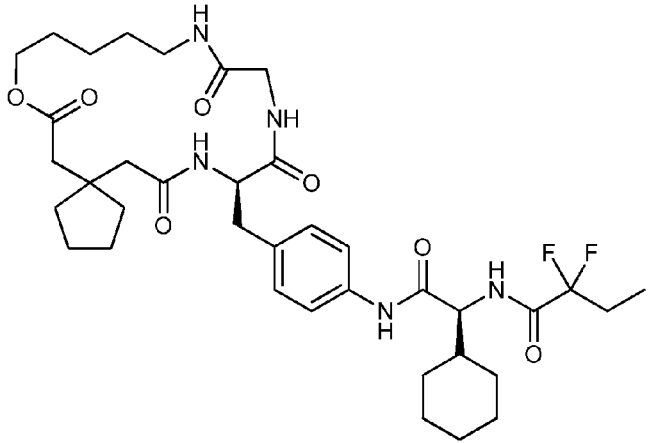
Figure 12:
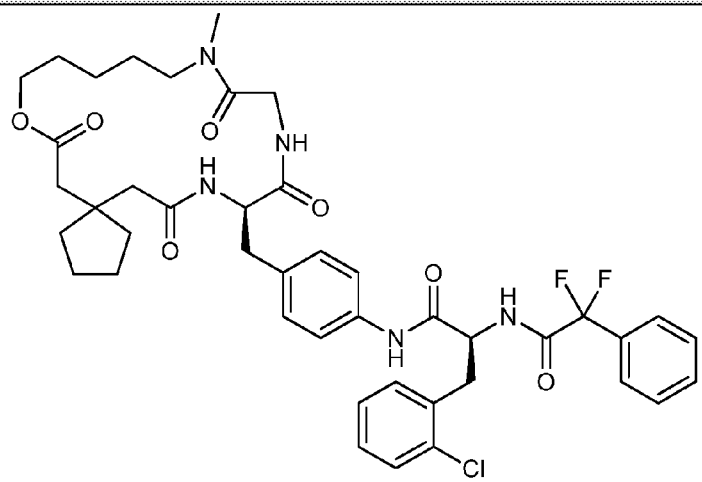
Figure 271:
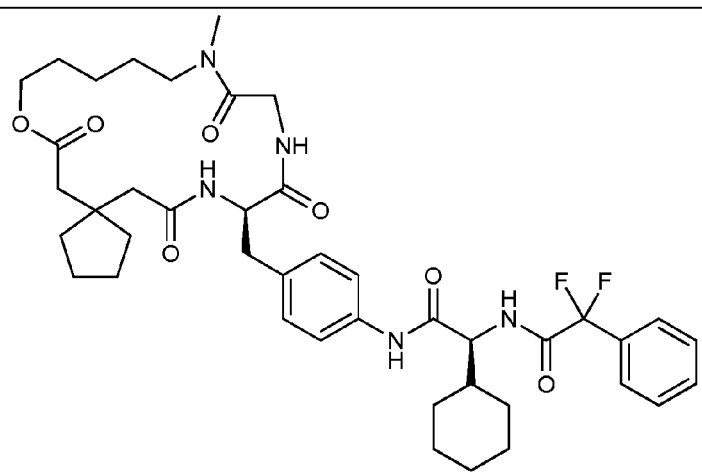
Figure 12:
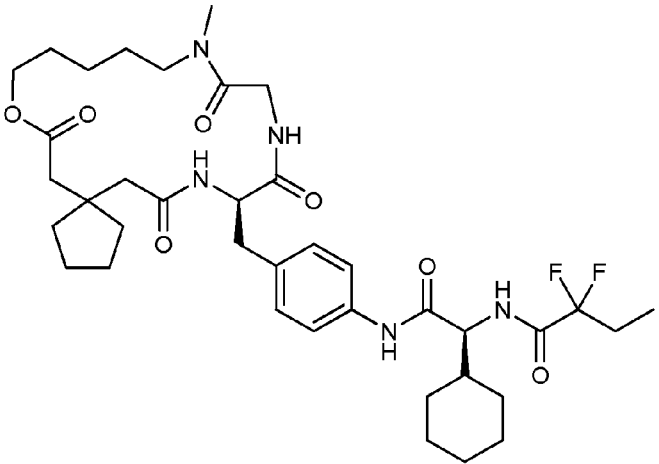
Figure 272:
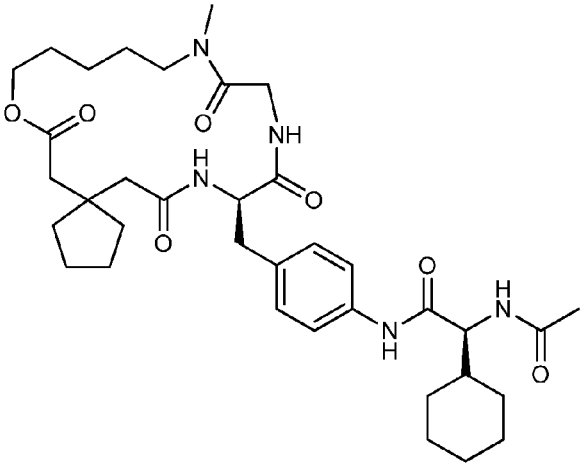

Exemplary specified compounds of Formula I are set forth in FIG. 12.

In one embodiment, the compound of Formula I is selected from any one of the compounds set forth in FIG. 12.

Any of the compounds of Formula I, may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like; N may be in any isotopic form, including $^{14}N$ and $^{15}N$.

In yet other embodiments, the invention provides a compound represented by Formula Ia:

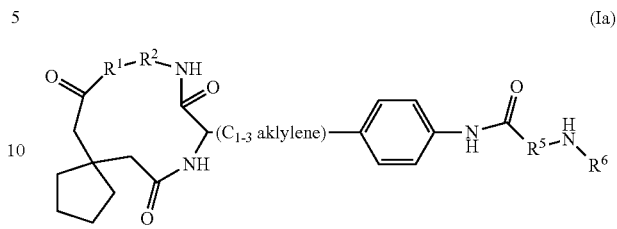

(Ia)

or a pharmaceutically acceptable salt thereof, wherein:
$R^1$ is —N(H)—;
$R^2$ is one of the following:
(a) -alkylene-N(H)C(O)-alkylene-ψ,
(b) —C(H)(CO$_2$H)-alkylene-N(H)C(O)-alkylene-ψ, or
(c) -alkylene-O-alkylene-O-alkylene-ψ; where ψ is a bond to the nitrogen atom in $R^1$;
$R^5$ is $C_1$-$C_2$ alkylene substituted with one —($C_1$-$C_5$ alkylene)-aryl that is optionally substituted with one or more substituents independently selected from the group consisting of halogen, $C_1$-$C_5$ alkyl, hydroxyl, and $C_1$-$C_3$ haloalkyl;
$R^6$ is —C(O)—$R^8$ or —C(O)—O—$R^8$;
$R^8$ is (a) $C_1$-$C_6$ alkyl or (b) —($C_1$-$C_3$ alkylene)-aryl optionally substituted with one or more substituents independently selected from the group consisting of halogen, $C_1$-$C_5$ alkyl, hydroxyl, and $C_1$-$C_3$ haloalkyl.

In certain embodiments, $R^2$ is -alkylene-N(H)C(O)-alkylene-ψ.

In certain embodiments, $R^5$ is

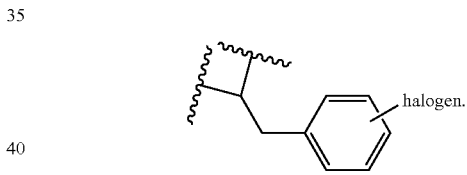

In certain embodiments, $R^6$ is —C(O)—$R^8$.

In certain embodiments, $R^8$—($C_1$-$C_3$ alkylene)-aryl optionally substituted with one or more substituents independently selected from the group consisting of halogen, $C_1$-$C_5$ alkyl, hydroxyl, and $C_1$-$C_3$ haloalkyl. In certain other embodiments, $R^8$ is benzyl optionally substituted with one or more substituents independently selected from the group consisting of halogen, $C_1$-$C_5$ alkyl, hydroxyl, and $C_1$-$C_3$ haloalkyl.

The description above describes multiple embodiments relating to compounds of Formula Ia. The patent application specifically contemplates all combinations of the embodiments. For example, the invention contemplates a compound of Formula Ia wherein $R^5$ is $C_1$-$C_2$ alkylene substituted with one —($C_1$-$C_5$ alkylene)-aryl that is optionally substituted with one or more substituents independently selected from the group consisting of halogen, $C_1$-$C_5$ alkyl, hydroxyl, and $C_1$-$C_3$ haloalkyl; and $R^6$ is —C(O)—O—$R^8$.

Unless otherwise indicated when a disclosed compound is named or depicted by a structure without specifying the stereochemistry and has one or more chiral centers, it is understood to represent all possible stereoisomers of the compound.

The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

A. Additional Exemplary Macrocyclic Compounds

An additional family of compounds of the invention is represented by Formula II:

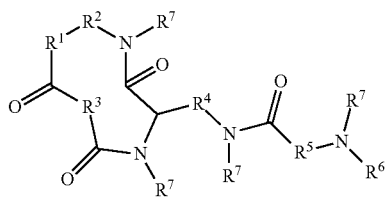

or a pharmaceutically acceptable salt thereof, wherein:

$R^1$ is selected from —O— and —N(($C_0$-$C_3$ alkylene)-Q)-, wherein Q is selected from hydrogen, —N($R^7$), —OH, —O—$C_1$-$C_4$ alkyl, aryl, heteroaryl, carbocyclyl, and heterocyclyl;

$R^2$ is $C_5$-$C_{12}$ alkylene, alkenylene or alkynylene, each of which is optionally substituted and wherein:

up to three methylene units of $R^2$ are optionally and independently replaced with —O—, —N($R^c$), —S—, —S(O)—, or —S(O)$_2$—, wherein $R^c$ is selected from hydrogen, $C_1$-$C_4$ alkyl, —C(O)—$C_1$-$C_3$ alkyl, —C(O)—($C_1$-$C_3$ alkylene)-aryl, —C(O)—($C_1$-$C_3$ alkylene)-heteroaryl, —S(O)$_2$—$C_1$-$C_3$ alkyl, —S(O)$_2$—($C_1$-$C_3$ alkylene)-aryl, and —S(O)$_2$—($C_1$-$C_3$ alkylene)-heteroaryl;

any two substituents bound to a common carbon atom in $R^2$ are optionally taken together to form =O, carbocyclyl or heterocyclyl;

any two substituents bound to different carbon atoms in $R^2$ are optionally taken together with any intervening atoms to form aryl, heteroaryl, carbocyclyl or heterocyclyl; and any substituent bound to a carbon atom in $R^2$ and any one $R^c$ are optionally taken together with any intervening atoms to form heteroaryl or heterocyclyl;

$R^3$ is optionally substituted —($C_2$-$C_4$ alkylene)-, wherein any two substituents on $R^3$ are optionally taken together with any intervening atoms to form aryl, heteroaryl, carbocyclyl or heterocyclyl;

$R^4$ is —($C_n$ alkylene)-Y—($C_m$ alkylene)-, wherein:

each alkylene portion of $R^4$ is optionally and independently substituted;

Y is selected from aryl, heteroaryl, carbocyclyl, heterocyclyl and optionally substituted $C_1$-$C_3$ alkylene;

each of n and m are independently selected from 0, 1, 2, 3, 4, 5 and 6; and n+m is 6 or less;

$R^5$ is $C_1$-$C_2$ alkylene substituted with one or more —($C_0$-$C_5$ alkylene)-$R^f$, wherein each $R^f$ is independently selected from —$CH_3$, —O—$C_1$-$C_3$ alkyl, aryl, heteroaryl, carbocyclyl, and heterocyclyl;

$R^6$ is selected from heteroaryl, —C(O)—$R^8$, —S(O)—$R^8$, —S(O)$_2$—$R^8$, —C(O)—N($R^7$)—$R^8$, and —S(O)$_2$—N($R^7$)—$R^8$;

each $R^7$ is independently selected from hydrogen and $C_1$-$C_4$ alkyl;

$R^8$ is selected from —($C_0$-$C_6$ alkylene)-aryl, —($C_0$-$C_6$ alkylene)-heteroaryl, —($C_0$-$C_6$ alkylene)-carbocyclyl, —($C_0$-$C_6$ alkylene)-heterocyclyl, and $C_1$-$C_6$ alkyl, wherein when $R^8$ is $C_1$-$C_6$ alkyl, up to two methylene units in the alkyl are optionally and independently replaced with —O—, —N($R^7$), —S—, —S(O)—, or —S(O)$_2$—; and any alkyl or alkylene portion of $R^8$ is optionally substituted with an appropriate alkyl or alkylene substituent other than =O; or $R^7$ and $R^8$ are optionally taken together to form a heterocyclyl; and any aryl, heteroaryl, carbocyclyl or heterocyclyl portion of the compound is optionally substituted.

It will be understood by those of skill in the art that because the compounds of the invention are limited to compounds that are stable, compounds formed by the optional and independent replacement of up to three methylene units in $R^2$ with certain combinations of —O—, —S—, —S(O)—, —S(O)$_2$—, or —N$R^c$— are not within the scope of the present invention. For example, compounds wherein the $R^2$ moiety comprises an —O—, —S—, —S(O)—, —S(O)$_2$, or —N($R^c$)—, adjacent to an —O—, —S—, —S(O)—, —S(O)$_2$, or —N($R^c$)— are not within the scope of the present invention, except for an —S(O)$_2$— adjacent a —N($R^c$)—. In addition, $R^2$ should not comprise —O—$CH_2$—O—, —N—$CH_2$—O—, or —O—$CH_2$—N—, wherein the —$CH_2$— portion thereof is optionally substituted, except when the —$CH_2$— portion is substituted to become —C(O)—.

In certain embodiments of Formula II, $R^1$ is selected from —O—, —NH— and —N($C_1$-$C_4$ alkyl-OH)—. In one aspect of these embodiments, $R^1$ is selected from —O—, —NH— and —N($CH_2CH_2OH$)—.

In certain embodiments of Formula II, $R^2$ is selected from *—C(H)($R^{10}$)—($CH_2$)$_{2-4}$—N(H)—C(O)—C($R^{11}$)$_2$)$_{1-5}$—, *—C(H)($R^{10}$)—($CH_2$)$_{4-8}$—, *—C(H)($R^{10}$)—($CH_2$)$_{2-4}$-(1,4-phenylene)-N(H)—C(O)—C($R^{11}$)$_2$)$_{1-3}$—, and *—C(H)($R^{10}$)—($CH_2$)$_{2-4}$-(1,4-phenylene)-; $R^{10}$ is selected from hydrogen, —C(O)—O—$C_1$-$C_4$ alkyl, and —C(O)—OH; and each $R^{11}$ is independently selected from hydrogen, benzyl, $C_1$-$C_4$ alkyl and $C_1$-$C_4$ hydroxyalkyl, wherein no more than two $R^{11}$ are other than hydrogen; one methylene unit in a specified —($CH_2$)$_{2-4}$ or —($CH_2$)$_{4-8}$ portion of $R^2$ is optionally replaced with —N($R^7$); and "*" represents a terminus of $R^2$ bound to $R^1$. In one aspect of these embodiments, $R^2$ is selected from *—C(H)($R^{10}$)—($CH_2$)$_{2-4}$—N(H)—C(O)—($CH_2$)$_{1-5}$—, *—C(H)($R^{10}$)—($CH_2$)$_4$—, *—C(H)($R^{10}$)—($CH_2$)$_{2-4}$—N(H)—C(O)—C(($CH_3$)$_2$)—, *—C(H)($R^{10}$)—($CH_2$)$_{2-4}$—N(H)—C(O)—C(H)($CH_2OH$)—, *—C(H)($R^{10}$)—$CH_2$-(1,4-phenylene)-N(H)—C(O)—($CH_2$)$_{1-3}$—, *—C(H)($R^{10}$)—$CH_2$-(1,4-phenylene)-, —($CH_2$)$_8$—, *—($CH_2$)$_2$—N($CH_3$)—($CH_2$)$_2$—N(H)—C(O)—$CH_2$—, and *—($CH_2$)$_5$—N(H)—C(O)—C(H)(benzyl)-; and $R^{10}$ is selected from hydrogen, —C(O)—O—$CH_3$, and C(O)—OH.

The term "specified —($CH_2$)$_{2-4}$— or —($CH_2$)$_{4-8}$— portion of $R^2$" as used in the preceding paragraph refers to the portion of those choices for $R^2$ that are indicated as —($CH_2$)$_{2-4}$— or —($CH_2$)$_{4-8}$—. For example, when $R^2$ is —C(H)($R^{10}$)—($CH_2$)$_{2-4}$—N(H)—C(O)—($CH_2$)$_{1-5}$—, only the bolded portion is a "specified —($CH_2$)$_{2-4}$— portion of $R^2$."

In certain embodiments of Formula II, $R^3$ is selected from —$(CH_2)_3$—, —$CH_2$—$C(CH_3)_2$—$CH_2$—,

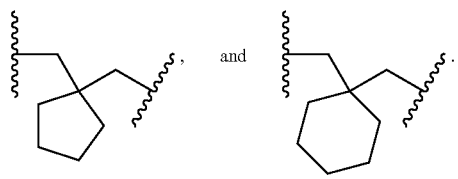 [SMILES: *CC1(C*)CCCC1 ; *CC1(C*)CCCCC1] and

In one aspect of these embodiments, $R^3$ is

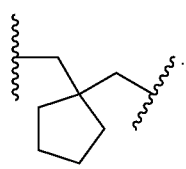

In certain embodiments of Formula II, $R^4$ is selected from —$(CH_2)_4$—*, and —$CH_2$-(1,4-phenylene)-*, wherein "*" represents a portion of $R^4$ bound to $N(R^7)$.

In certain embodiments of Formula II, $R^5$ is selected from —CH—($C_1$-$C_4$ alkyl), —CH—$CH_2$-aryl, —CH—$CH_2$-heteroaryl, —CH—$CH_2$-cycloalkyl, and —CH-cycloalkyl, wherein the aryl or heteroaryl is optionally substituted with up to two substituents independently selected from halo, $C_1$-$C_4$ alkyl, and phenyl. In one aspect of these embodiments, $R^5$ is selected from —CH—$C(CH_3)_3$, —CH—CH($CH_2CH_3$)—$CH_3$, —CH—cyclohexyl, —CH—$CH_2$-furanyl, —CH—$CH_2$-phenyl, —CH—$CH_2$-biphenyl, —CH—$CH_2$-thiophenyl, —CH—$CH_2$-thiazolyl, —CH—$CH_2$-cyclobutyl, and —CH—$CH_2$-cyclopropyl, wherein any of the furanyl, phenyl, thiophenyl or thiazolyl is optionally benzofused and optionally substituted with up to two substituents independently selected from fluoro, chloro, bromo, hydroxy and methyl.

In certain embodiments of Formula II, $R^6$ is —C(O)—$[CH_2]_{0-1}$—$R^9$; and $R^9$ is selected from aryl, heteroaryl, cycloalkyl, saturated heterocyclyl, and $C_1$-$C_4$ alkyl, wherein $R^9$ is optionally substituted with up to 2 substituents independently selected from halo, $C_1$-$C_4$ alkyl, $C_1$-$C_4$ haloalkyl, hydroxy, $C_1$-$C_4$ alkoxy, $C_1$-$C_4$ hydroxyalkyl. In one aspect of these embodiments, $R^9$ is selected from phenyl, pyridinyl, oxazolyl, pyrazinyl, pyrimidinyl, cyclobutyl, cyclopentyl, cyclohexyl, tetrahydropyranyl, —$OCH_3$, and $C_1$-$C_4$ alkyl, wherein any phenyl, pyridinyl, oxazolyl, pyrazinyl, or pyrimidinyl in $R^9$ is optionally substituted with up to 2 substituents independently selected from fluoro, chloro, $CF_3$, hydroxy, and —$CH_2OH$.

In certain embodiments of Formula II, each $R^7$ is independently selected from methyl and hydrogen.

In certain embodiments, the invention provides a compound of Formula IIa:

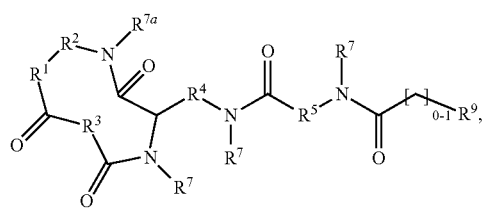

or a pharmaceutically acceptable salt thereof, wherein:

$R^1$ is selected from —O—, —NH— and —N($C_1$-$C_4$ alkyl-OH)—;

$R^2$ is selected from *—C(H)($R^{10}$)—$(CH_2)_{2-4}$—N(H)—C(O)—$(C(R^{11})_2)_{1-5}$—, *—C(H)($R^{10}$)—$(CH_2)_{4-8}$—, *—C(H)($R^{10}$)—$(CH_2)_{2-4}$-(1,4-phenylene)-N(H)—C(O)—$(C(R^{11})_2)_{1-3}$—, and *—C(H)($R^{10}$)—$(CH_2)_{2-4}$-(1,4-phenylene)-; wherein:

$R^{10}$ is selected from hydrogen, —C(O)—O—$C_1$-$C_4$ alkyl, and —C(O)—OH;

each $R^{11}$ is independently selected from hydrogen, benzyl, $C_1$-$C_4$ alkyl and $C_1$-$C_4$ hydroxyalkyl;

no more than two $R^{11}$ are other than hydrogen;

one methylene unit in a specified —$(CH_2)_{2-4}$ or —$(CH_2)_{4-8}$ portion of $R^2$ is optionally replaced with —$N(R^7)$; and "*" represents a terminus of $R^2$ bound to $R^1$;

$R^3$ is selected from —$(CH_2)_3$—, —$CH_2$—$C(CH_3)_2$—$CH_2$—,

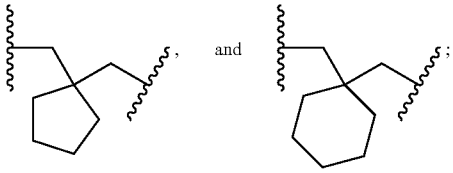 [SMILES: *CC1(C*)CCCC1 ; *CC1(C*)CCCCC1]

$R^4$ is selected from —$(CH_2)_4$—*, and —$CH_2$-(1,4-phenylene)-*

$R^5$ is selected from —CH—($C_1$-$C_4$ alkyl), —CH—$CH_2$-aryl, —CH—$CH_2$-heteroaryl, —CH—$CH_2$-cycloalkyl, and —CH-cycloalkyl, wherein the aryl or heteroaryl is optionally substituted with up to two substituents independently selected from halo, $C_1$-$C_4$ alkyl, and phenyl; and each $R^7$ is independently selected from hydrogen and $C_1$-$C_4$ alkyl;

$R^9$ is selected from aryl, heteroaryl, cycloalkyl, saturated heterocyclyl, and $C_1$-$C_4$ alkyl, wherein $R^9$ is optionally substituted with up to 2 substituents independently selected from halo, $C_1$-$C_4$ alkyl, $C_1$-$C_4$ haloalkyl, hydroxy, $C_1$-$C_4$ alkoxy, and $C_1$-$C_4$ hydroxyalkyl.

II. METHODS OF SYNTHESIZING COMPOUNDS OF THE INVENTION

The compounds of the present invention can be prepared using an iterative peptide coupling procedure as illustrated in following synthetic schemes. Exemplary general synthetic protocols are presented in Schemes 1 through 4. The schemes and accompanying description of synthetic procedures are given for the purpose of illustrating the invention, and should not be construed as limiting the scope or spirit of the invention.

Abbreviations as used herein include O-(7-azabenzotriazol-1-yl)-N,N,N',N'-tetramethyluronium hexafluorophosphate (HATU); diisopropylethylamine (DIPEA); dimethylformamide (DMF); 9-fluorenylmethoxycarbonyl (Fmoc); methanol (MeOH); methylene chloride (DCM); tert-butoxycarbonyl (Boc); tert-butyl (tBu); tetrahydrofuran (THF); trifluoroacetic acid (TFA); 1,8-diazobicyclo[5.4.0]-undec-7-ene (DBU); N-methylmorpholine (NMM); 1-hydroxy-7-azabenzotriazole (HOAt); phenyl (Ph); trifluoroacetic acid (TFA); triethylamine (Et$_3$N); petroleum ether (PE); ethyl acetate (EA); acetic acid (AcOH); diethyl ether (Et$_2$O); Boc anhydride ((Boc)$_2$O); dimethylsulfoxide (DMSO); diisopropylethylamine (DIEA); N-bromosuccinimide (NBS); trityl chloride (TrtCl); triphenyl phosphate (PPh$_3$); (9H-fluoren-9-yl)methyl (2,5-dioxopyrrolidin-1-yl) carbonate (Fmoc-Osu); room temperature (r.t. or RT); and thin-layer chromatography (TLC).

SCHEME 1.

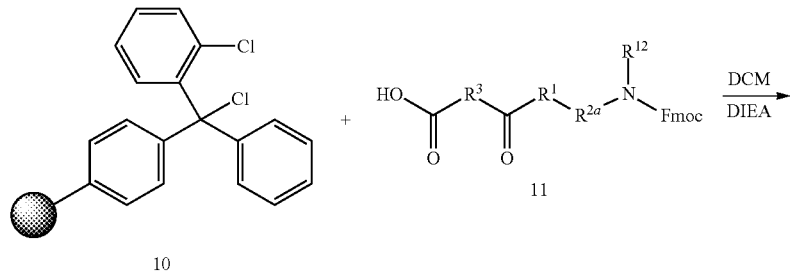

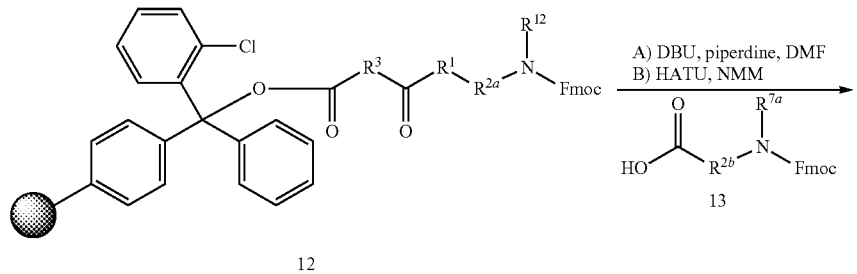

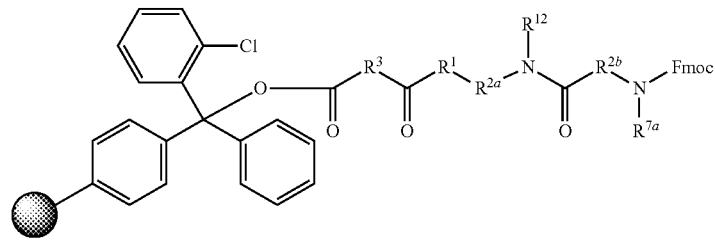

Scheme 1 depicts a general synthesis method for an intermediate to compounds of Formula I, wherein $R^2$ is *—CH($R^{10}$)—X—CH($R^{10}$)—N($R^{12}$)—C(O)—CH($R^{11}$)—(CH$_2$)$_{0-2}$—, as defined for Formula I. In Scheme 1, $R^{2a}$ represents the *—CH($R^{10}$)—X—CH($R^{10}$)— terminal portion of $R^2$, and $R^{2b}$ represents the —CH($R^{11}$)—(CH$_2$)$_{0-2}$- terminal portion of $R^2$. A 2-chloro-trityl chloride resin 10 is combined with an appropriate protected alkylamino acetic acid 11 in DCM to form resin 12. Resin 12 is then deprotected with DBU and piperidine in DMF and then coupled to a protected amino acid 13 using HATU and NMM to produce resin 14, which is further coupled according to Scheme 3, below.

SCHEME 2.

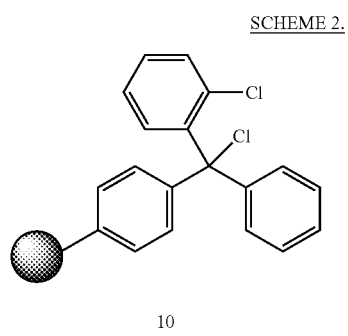

10

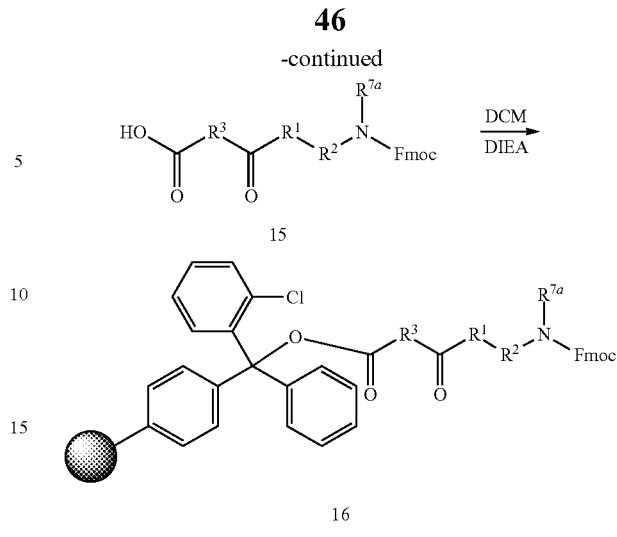

Scheme 2 depicts a general synthesis method for an intermediate to compounds of Formula I, wherein $R^2$ is *—CH($R^{10}$)—Z—. A 2-chloro-trityl chloride resin 10 is combined with an appropriate protected alkylamino acetic acid 15 in DCM to form resin 16, which is further coupled according to Scheme 3, below.

SCHEME 3.

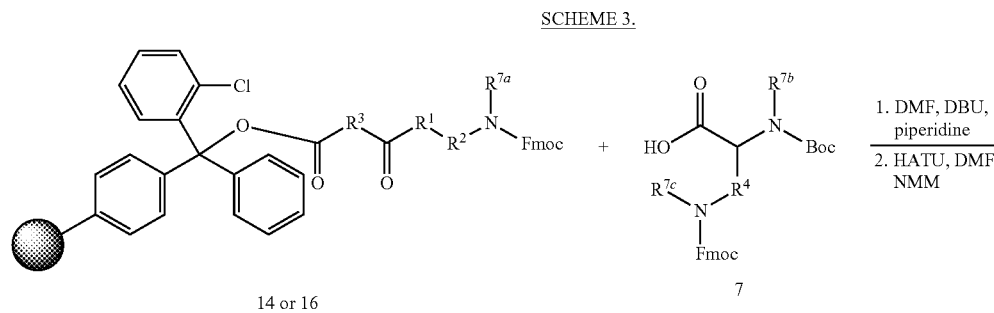

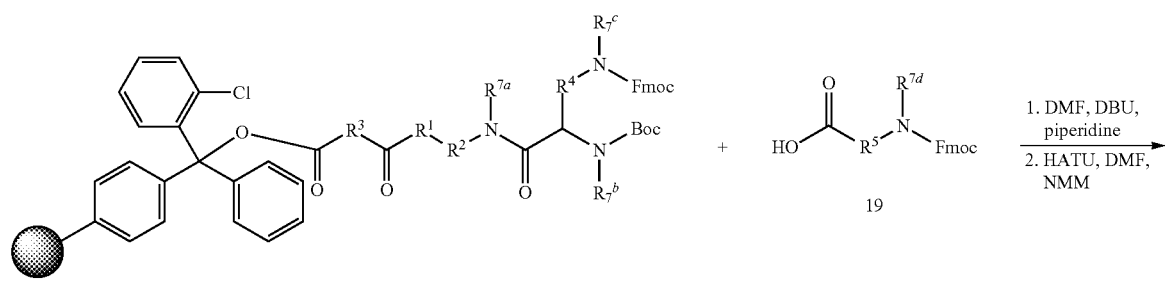

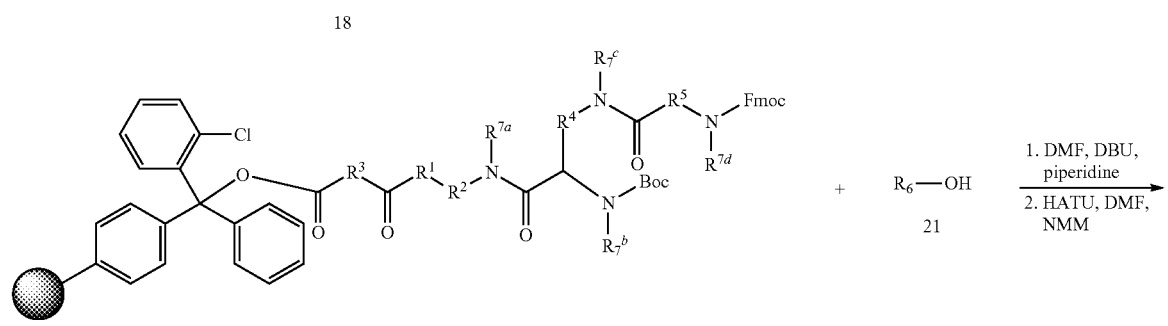

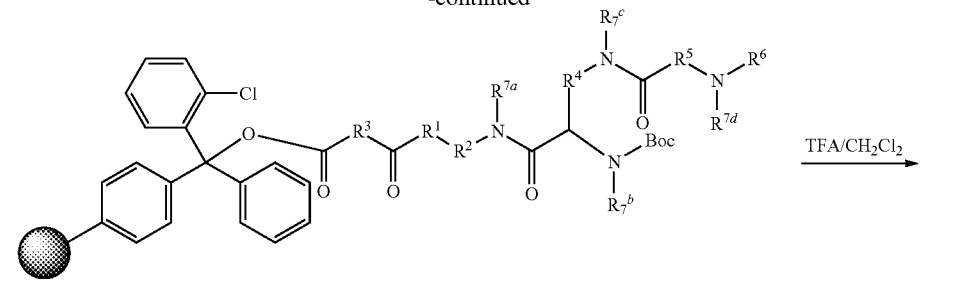

22

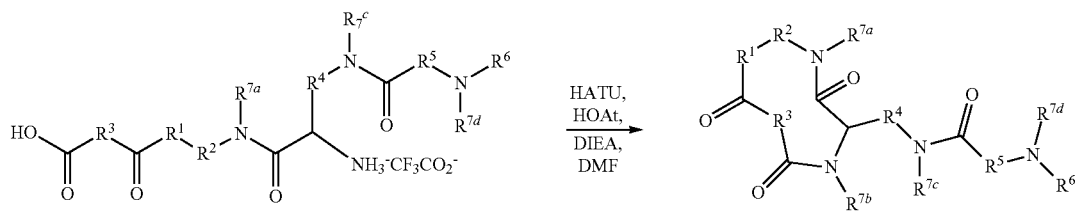

23

Formula I

Scheme 3 depicts a general synthesis for compounds of Formula I, starting with intermediate 14 from Scheme 1 or intermediate 16 from Scheme 2. The structures of intermediates 14 and 16 are shown in the scheme for convenience. Each $R^7$ depicted in Scheme 3 is independently selected from hydrogen and $C_1$-$C_4$ alkyl. Intermediate 14 or intermediate 16 is deprotected with DBU and piperidine in DMF and then coupled to the appropriate N,N'-orthogonally-protected diamino acid 17. The Fmoc group of 17 is removed again with DBU and piperidine in DMF and the resulting deprotected resin is coupled to amino acid 19. The deprotection/coupling process is repeated to add acid 21. Reaction of compound 22 with TFA/CH$_2$Cl$_2$ removes the Boc protecting group and hydrolyzes the ester bond to the resin to form intermediate 23, which is cyclized using HATU, HOAt, DIEA and DMF to form a compound of Formula I.

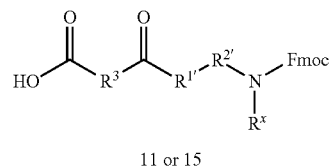

11 or 15

SCHEME 4C

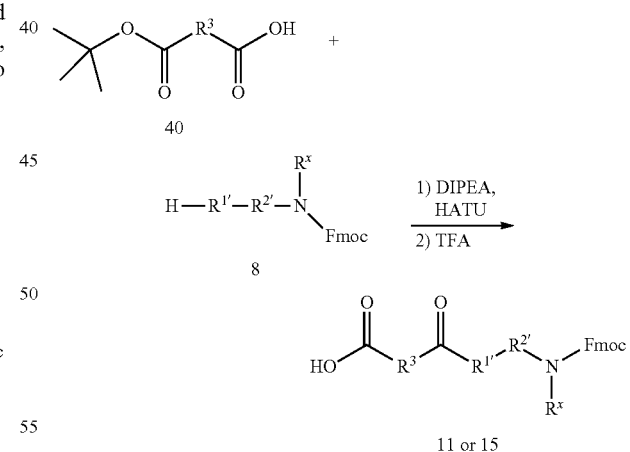

SCHEME 4A

SCHEME 4B

SCHEME 4D

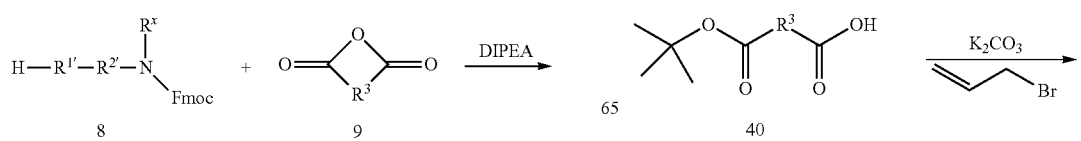

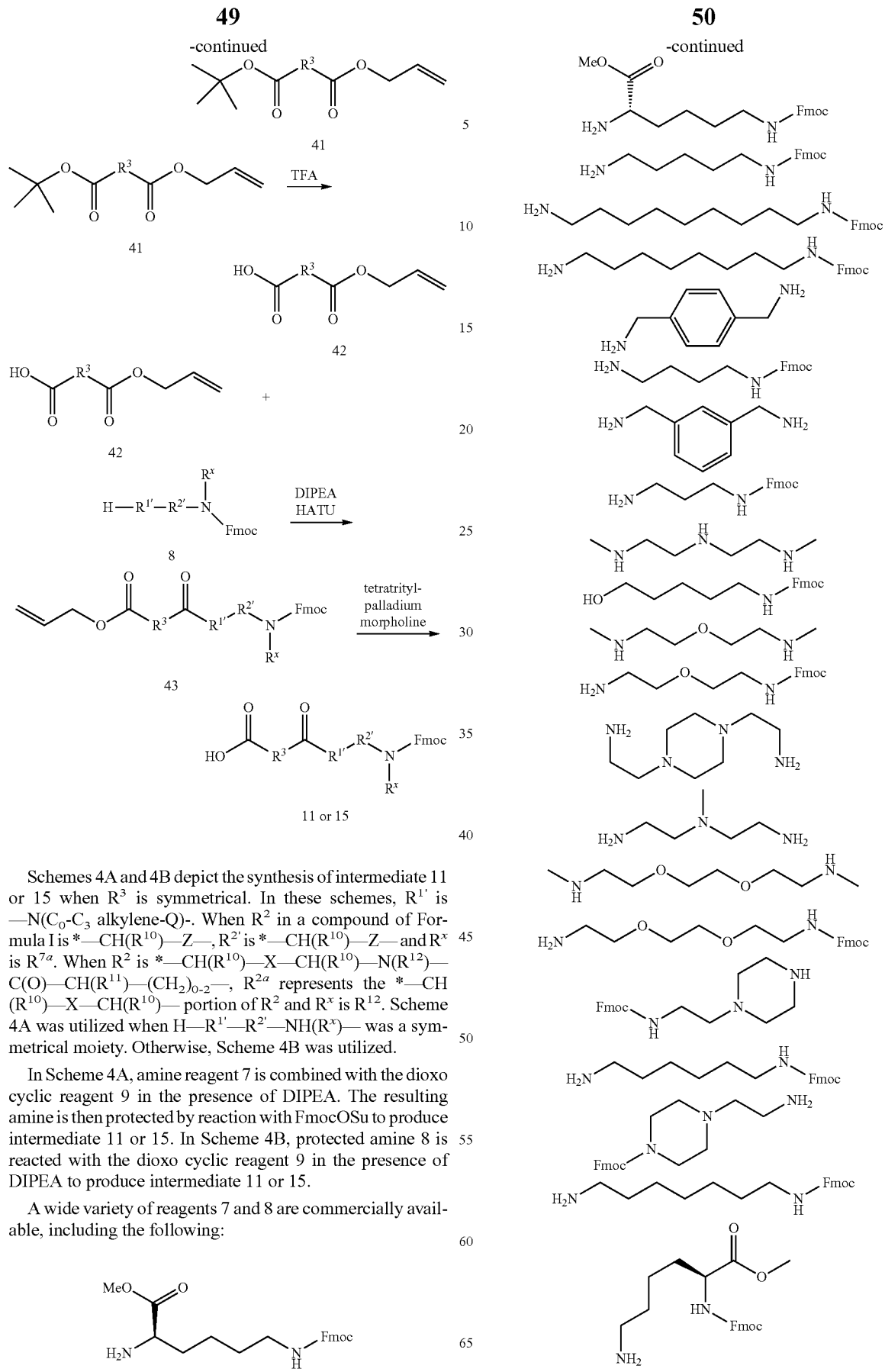

Schemes 4A and 4B depict the synthesis of intermediate 11 or 15 when $R^3$ is symmetrical. In these schemes, $R^{1'}$ is —$N(C_0$-$C_3$ alkylene-Q)-. When $R^2$ in a compound of Formula I is *—$CH(R^{10})$—Z—, $R^{2'}$ is *—$CH(R^{10})$—Z— and $R^x$ is $R^{7a}$. When $R^2$ is *—$CH(R^{10})$—X—$CH(R^{10})$—$N(R^{12})$—$C(O)$—$CH(R^{11})$—$(CH_2)_{0-2}$—, $R^{2a}$ represents the *—$CH(R^{10})$—X—$CH(R^{10})$— portion of $R^2$ and $R^x$ is $R^{12}$. Scheme 4A was utilized when H—$R^{1'}$—$R^{2'}$—$NH(R^x)$— was a symmetrical moiety. Otherwise, Scheme 4B was utilized.

In Scheme 4A, amine reagent 7 is combined with the dioxo cyclic reagent 9 in the presence of DIPEA. The resulting amine is then protected by reaction with FmocOSu to produce intermediate 11 or 15. In Scheme 4B, protected amine 8 is reacted with the dioxo cyclic reagent 9 in the presence of DIPEA to produce intermediate 11 or 15.

A wide variety of reagents 7 and 8 are commercially available, including the following:

-continued

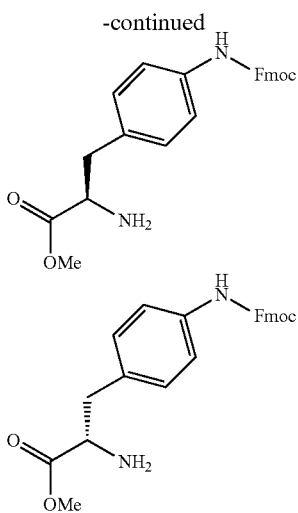

If additional or alternate protection of reactive groups in such commercially available reagents is required (Fmoc and/or Boc protection; Boc deprotection, methyl esterification), it may be achieved by standard protection protocols well known in the art.

Similarly, a variety of reagents 9 are commercially available including,

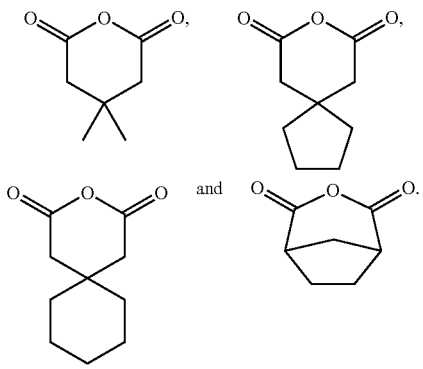

Schemes 4C and 4D depict the synthesis of intermediate 11 or 15 when $R^3$ is asymmetrical. In these schemes, $R^{1'}$ is —N($C_0$-$C_3$ alkylene-Q)-. When $R^2$ in a compound of Formula I is *—CH($R^{10}$)—Z—, $R^{2'}$ is *—CH($R^{10}$)—Z— and $R^x$ is $R^{7a}$. When $R^2$ is *—CH($R^{10}$)—X—CH($R^{10}$)—N($R^{12}$)—C(O)—CH($R^{11}$)—(CH$_2$)$_{0-2}$—, $R^{2a}$ represents the *—CH($R^{10}$)—X—CH($R^{10}$)— portion of $R^2$ and $R^x$ is $R^{12}$.

In Scheme 4C, protected amine 8 is reacted with carboxylic acid 40 in the presence of DIPEA and HATU, followed by treatment with TFA to produce intermediate 11 or 15.

In Scheme 4D, carboxylic acid 40 is converted to allyloxycarbonyl carboxylic acid 41 by reaction with 3-bromopropene and $K_2CO_3$. The allyloxycarbonyl carboxylic acid 41 is then reacted with TFA to produce 42, which is then reacted with amine 8 in the presence of DIPEA and HATU to produce allyl intermediate 43. Intermediate 43 is then converted to intermediate 11 or 15 by treatment with tetratritylpalladium and morpholine.

Different t-butyl protected carboxylic acids 40 can be synthesized by reacting an appropriate alkyl carboxylic acid or cycloalkyl carboxylic acid with tert-butyl acrylate. This is shown in more detail in the Examples.

Combinations of substituents and variables contemplated by the present invention are only those that result in the formation of compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

III. THERAPEUTIC APPLICATIONS

The compounds and pharmaceutical compositions of the present invention are useful in treating or preventing any disease or condition that is mediated directly or indirectly by IL-17. Such diseases include inflammatory diseases and conditions, proliferative diseases (e.g., cancer), autoimmune diseases and other disease described herein.

Increased levels of IL-17 (i.e., IL-17A) have been associated with several conditions including airway inflammation, rheumatoid arthritis (RA), osteoarthritis, bone erosion, intraperitoneal abscesses and adhesions, inflammatory bowel disorder (IBD), allograft rejection, psoriasis, psoriatic arthritis, ankylosing spondylitis, certain types of cancer, angiogenesis, atherosclerosis and multiple sclerosis (MS). Both IL-17 and IL-17R are upregulated in the synovial tissue of RA patients. IL-17 exerts its role in pathogenesis of RA through IL-1-β and TNF-α dependent and independent pathways. IL-17 stimulates secretion of other cytokines and chemokines, e.g., TNF-α, IL-1β, IL-6, IL-8 and Gro-α. IL-17 directly contributes to disease progression in RA. Injection of IL-17 into the mouse knee promotes joint destruction independently of IL-I β activity (Ann Rheum Dis 2000, 59:529-32). Anti-IL-1β antibody has no effect on IL-17 induced inflammation and joint damage (J Immunol 2001, 167:1004-1013). In an SCW-induced murine arthritis model, IL-17 induced inflammatory cell infiltration and proteoglycan depletion in wild-type and IL-1β knockout and TNF-α knockout mice. IL-17 knockout mice are phenotypically normal in the absence of antigenic challenge, but have markedly reduced arthritis following type II collagen immunization (J Immunol 2003, 171:6173-6177).

Increased levels of IL-17-secreting cells have also been observed in the facet joints of patients suffering from ankylosing spondylitis (H Appel et al., Arthritis Res Therap 2011, 13:R95).

Multiple sclerosis is an autoimmune disease characterized by central nervous system (CNS) inflammation with damage to the myelin sheath surrounding axons. A hallmark of MS is that T cells infiltrate into the CNS. Higher numbers of IL-17 mRNA-expressing blood mono-nuclear cells (MNC) are detected during MS clinical exacerbation compared to remission (Multiple Sclerosis, 5:101-104, 1999). Furthermore, experimental autoimmune encephalomyelitis ("EAE"), a preclinical animal model for MS is significantly suppressed in IL-17 knockout mice.

In one embodiment, the invention provides a method for the treatment or prevention of a condition including, but not limited to, airway inflammation, ankylosing spondylitis, asthma, RA (including juvenile RA), osteoarthritis, bone erosion, intraperitoneal abscesses and adhesions, IBD, Crohn's disease, allograft rejection, psoriasis, psoriatic arthritis, certain types of cancer, angiogenesis, atherosclerosis and MS, as well as other inflammatory disorders, conditions, diseases or states including without limit: erythematosus, response to allergen exposure, *Helicobacter pylori* associated gastritis, bronchial asthma, allograft rejection (e.g., renal), systemic lupus erythematosus and lupus nephritis. The method comprises the step of administering to a subject in need thereof an amount of a compound or composition of the invention effective to treat the condition.

In another embodiment, the invention provides a method for the treatment or prevention of a condition including, but not limited to, Behcet's disease, ulcerative colitis, Wegener's granulomatosis, sarcoidosis, systemic sclerosis, insulin-dependent diabetes mellitus, septic shock syndrome, Alzheimer's disease, an inflammatory eye disease, and uveitis.

In a more specific embodiment, a compound of the invention or a pharmaceutical composition comprising a compound of the invention may be useful for the treatment or prevention of a condition selected from RA, airway inflammation, MS, psoriasis, psoriatic arthritis, and ankylosing spondylitis. More specifically, the condition is RA.

The use of the compounds of the present invention for treating or preventing of at least one of the aforementioned disorders in which IL-17 activity is detrimental or which benefits for decreased levels of bioactive IL-17 is contemplated herein. Additionally, the use of a compound of the present invention for use in the manufacture of a medicament for the treatment of at least one of the aforementioned disorders is contemplated.

In another aspect, the invention provides a method of treating a patient suffering from a disease or condition associated with elevated levels of IL-17 comprising the steps of: a) determining whether the patient has an elevated level of IL-17; and b) if the patient does have an elevated level of IL-17, administering to the patient an effective amount of a compound of Formula I for a time sufficient to treat the disease or condition.

In still another aspect, the invention provides a method of treating a patient suffering from a disease or condition associated with elevated levels of IL-17 comprising the steps of: a) determining whether the patient has an elevated level of one or more IL-17-induced chemokine or effector; and b) if the patient does have an elevated level of the one or more IL-17 chemokine or effector, administering to the patient an effective amount of a compound of Formula I for a time sufficient to treat the disease or condition. In certain aspects the IL-17 chemokine or effector is one or more of IL-6, IL-8, G-CSF, TNF-α, IL-1β, PGE2, and IFN-γ.

Methods for determining the levels of IL-17 or any of its chemokines or effectors in a patient are well-known in the art. Typically, a tissue or biological fluid sample is obtained from the patient and is subject to ELISA with commercially available antibodies or kits (e.g., Quantikine IL-17 ELISA; R&D Systems, Abington, UK). Commercially available antibodies and kits are available for IL-6, IL-8, G-CSF, TNF-α, IL-1β, PGE2, and IFN-γ.

The invention also provides for combination therapy of a macrocyclic compound described herein and a second therapeutic agent. "Combination therapy" (or "co-therapy") includes the administration of a macrocyclic compound described herein and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

Combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Accordingly, in certain instances, the method further comprises administering a therapeutically effective amount of an anti-inflammatory agent. In certain instances, the anti-inflammatory agent is a salicylate, diclofenac, aceclofenac, acemetacin, alclofenac, bromfenac, etodolac, indometacin, nabumetone, oxametacin, proglumetacin, sulindac, tolmetin, piroxicam, droxicam, lornoxicam, meloxicam, tenoxicam, ibuprofen, alminoprofen, carprofen, dexibuprofen, dexketoprofen, fenbufen, fenoprofen, flunoxaprofen, flurbiprofen, ibuproxam, indoprofen, ketorolac, loxoprofen, naproxen, oxaprozin, pirprofen, suprofen, tiaprofenic acid, mefenamic acid, flufenamic acid, meclofenamic acid, tolfenamic acid, phenylbutazone, ampyrone, azapropazone, clofezone, kebuzone, metamizole, mofebutazone, oxyphenbutazone, phenazone, phenylbutazone, sulfinpyrazone, celecoxib, etoricoxib, lumiracoxib, parecoxib, rofecoxib, valdecoxib, prednisone, methylprednisolone, hydrocortisone, or budesonide.

In certain instances, the method further comprises administering a therapeutically effective amount of an agent for treating multiple sclerosis. In certain instances, the agent for treating multiple sclerosis is interferon beta-2, interferon beta-1, glatiramer, natalizumab, or mitoxantrone.

In certain instances, the method further comprises administering infliximab, etanercept, adalimumab, or certolizumab pegol.

In certain instances, the method is designed to treat rheumatoid arthritis and further comprises the step of administering to the patient in need thereof a therapeutically effective amount of an agent selected from the group consisting of a salicylate, diclofenac, aceclofenac, acemetacin, alclofenac, bromfenac, etodolac, indometacin, nabumetone, oxametacin, proglumetacin, sulindac, tolmetin, piroxicam, droxicam, lornoxicam, meloxicam, tenoxicam, ibuprofen, alminoprofen, carprofen, dexibuprofen, dexketoprofen, fenbufen, fenoprofen, flunoxaprofen, flurbiprofen, ibuproxam, indoprofen, ketorolac, loxoprofen, naproxen, oxaprozin, pirprofen, suprofen, tiaprofenic acid, mefenamic acid, flufenamic acid, meclofenamic acid, tolfenamic acid, phenylbutazone, ampyrone, azapropazone, clofezone, kebuzone, metamizole, mofebutazone, phenazone, sulfinpyrazone, celecoxib, etoricoxib, lumiracoxib, parecoxib, prednisone, methylprednisolone, hydrocortisone, and budesonide.

IV. PHARMACEUTICAL COMPOSITIONS AND DOSING

The invention also provides pharmaceutically acceptable compositions which comprise a therapeutically-effective amount of one or more of the macrocyclic compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and nonionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

EXAMPLES

The invention now being generally described, will be more readily understood by reference to the following examples, which are included merely for purposes of illustration of certain aspects and embodiments of the present invention, and are not intended to limit the invention.

Example 1

Synthesis of 2-(1-(2-(4-(((9H-fluoren-9-yl)methoxy) carbonylamino)pentylamino)-2-oxoethyl)cyclopentyl)acetic Acid (Intermediate 20)

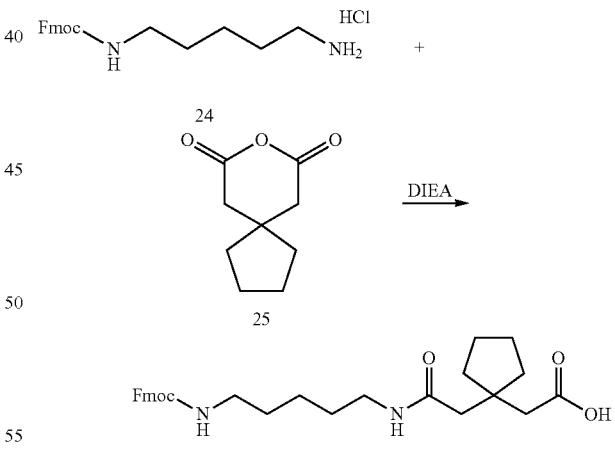

(9H-fluoren-9-yl)methyl (5-aminopentyl)carbamate hydrochloride (24; 3.2 g, 8.9 mmol) and N-ethyl-N-isopropylpropan-2-amine (8.7 mL, 49.5 mmol) were dissolved in DMF (40 mL) followed by addition of 8-oxaspiro[4.5]decane-7,9-dione (25; 5 g, 29.7 mmol). The mixture was agitated for 1 hr followed by evaporation of volatiles. The crude product was purified directly on a Biotage purification system using 45%-75% acetonitrile/water. After evaporation of volatiles and lyophilization, a white powder was isolated consistent with desired product 20 (1.5 g, 3.0 mmol, 34%).

Example 2

Synthesis of Compound 159

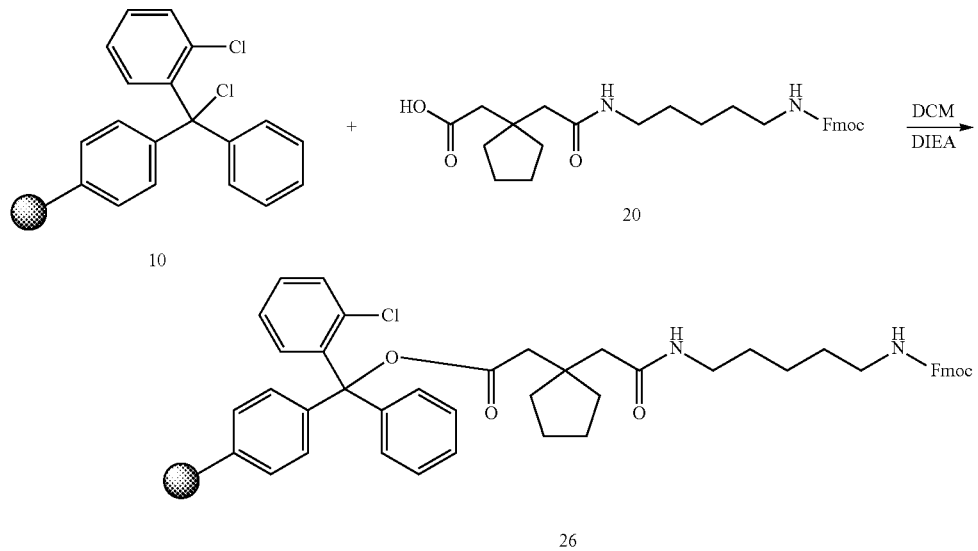

2-Chloro-trityl chloride resin (10; 0.58 g, 0.70 mmol) was swelled in DCM (5 mL) for 10 min, then filtered, and washed with DCM (5 mL). 2-(1-(2-(4-(((9H-fluoren-9-yl)methoxy)carbonylamino)butylamino)-2-oxoethyl)cyclopentyl)acetic acid (20; 0.335 g, 0.700 mmol) and N-ethyl-N-isopropylpropan-2-amine (0.610 mL, 3.50 mmol) was dissolved in DCM (30 mL). The resulting solution was added to the swelled resin and agitated for 2 hours. The resin was then washed with 85:10:5 DCM:MeOH:DIPEA (5 mL×3); DCM (5 mL×3), DMF (5 mL×3), and DCM (5 mL×3). After flushing with argon and drying under vacuum, resin 26 (0.99 g) was obtained.

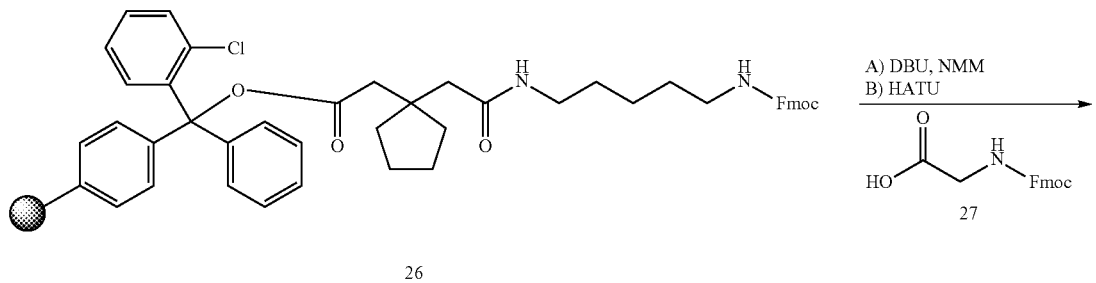

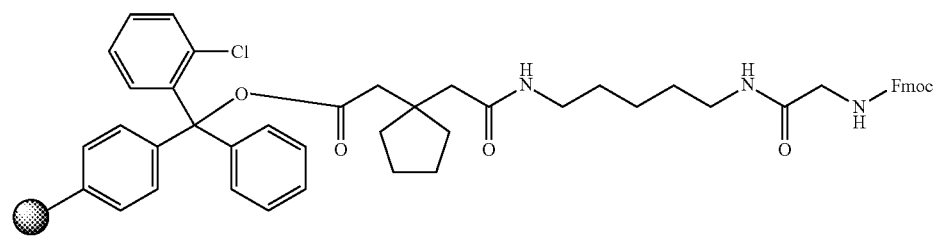

Resin 26 (0.075 mmol, 125 mg) was suspended in DMF (2 mL×5 min) and mixed with a stream of N₂ every 30 seconds. The Fmoc group was removed from the resin-supported building block by mixing the resin twice with a solution of 2% DBU, 2% piperidine in DMF (2 mL×5 min) while agitating with a stream of N₂ every 30 seconds. The resin was washed six times with DMF (2 mL×30 sec). Fmoc-glycine (27; 0.1 M solution in DMF, 2.5 mL, 3.3 equiv, 0.25 mmol), followed by HATU (0.2 M solution in DMF, 1.15 mL, 3.1 equiv, 0.23 mmol) and N-methyl morpholine (1.0 M in DMF, 0.5 mL, 6.7 equiv, 0.5 mmol) were added to the resin. The reaction mixture was agitated by a stream of nitrogen for 30 min. The reagents were drained from the reaction vessel, and the resin 28 was washed six times with DMF (2 mL×30 sec).

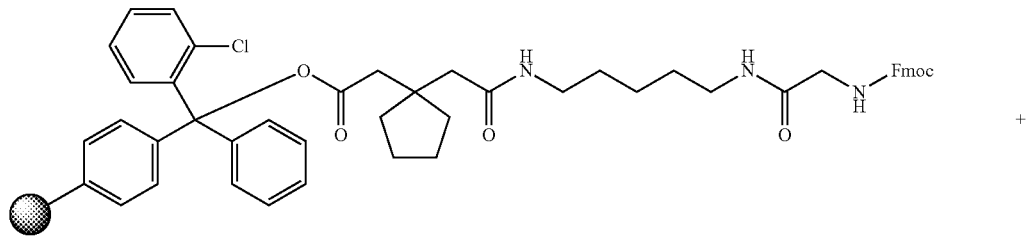

28

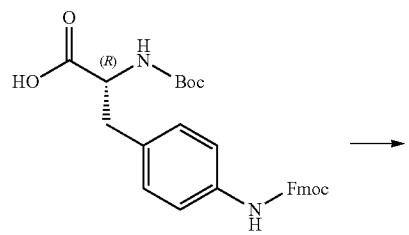

29

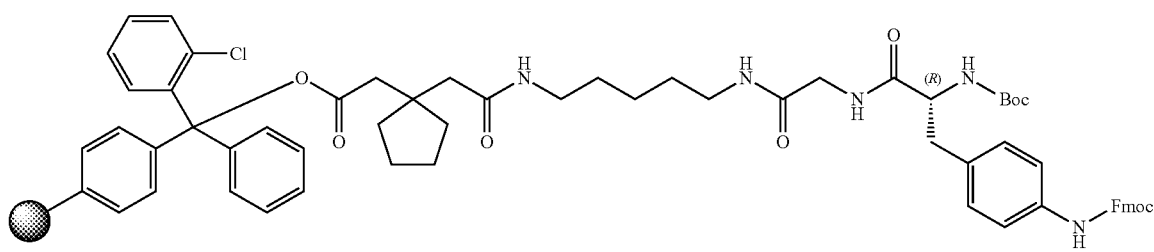

30

Resin 28 (0.075 mmol, 125 mg) was suspended in DMF (2 mL×5 min) and mixed with a stream of $N_2$ every 30 seconds. The Fmoc group was removed from the resin-supported building block by mixing the resin twice with a solution of 2% DBU, 2% piperidine in DMF (2 mL×5 min) while agitating with a stream of $N_2$ every 30 seconds. The resin was washed six times with DMF (2 mL×30 sec). (R)-3-(4-((((9H-fluoren-9-yl)methoxy)carbonyl)amino)-phenyl)-2-((tert-butoxycarbonyl)amino)propanoic acid 29; (0.1 M solution in DMF, 2.5 mL, 3.3 equiv, 0.25 mmol), followed by HATU (0.2M solution in DMF, 1.15 mL, 3.1 equiv, 0.23 mmol) and N-methyl morpholine (1.0 M in DMF, 0.5 mL, 6.7 equiv, 0.5 mmol) were added to the resin. The reaction mixture was agitated by a stream of nitrogen for 30 min. The reagents were drained from the reaction vessel, and the resin 30 was washed six times with DMF (2 mL×30 sec).

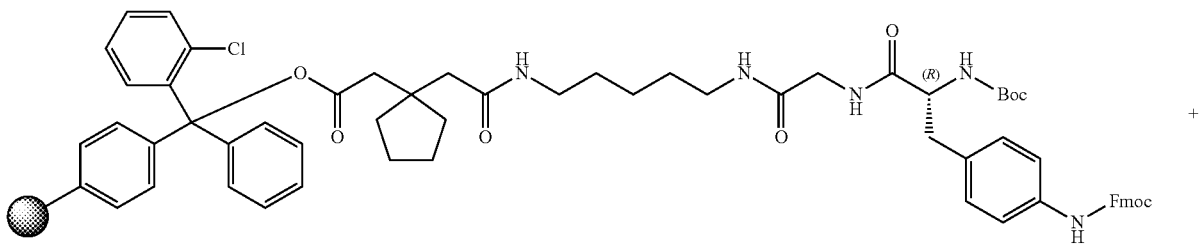

30

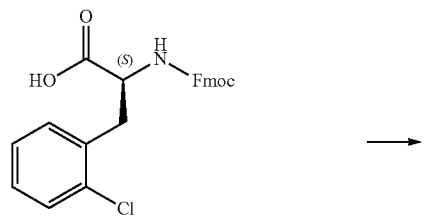

31

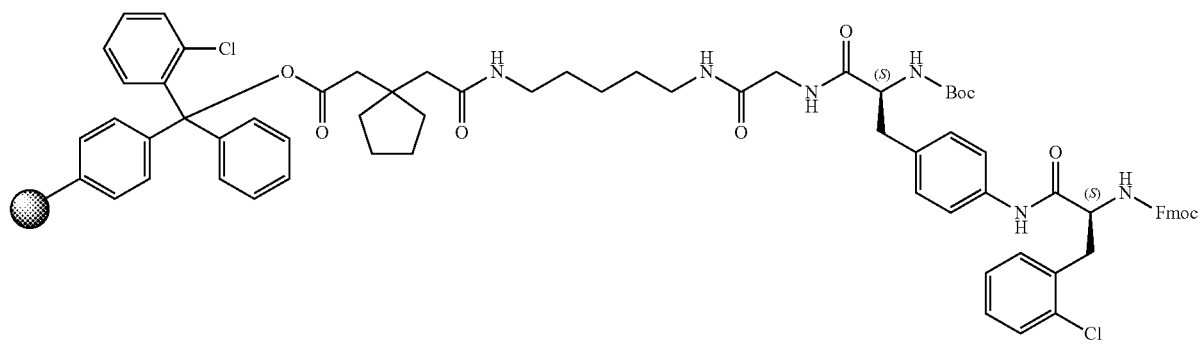

32

Resin 30 (0.075 mmol, 125 mg) was suspended in DMF (2 mL×5 min) and mixed with a stream of N₂ every 30 seconds. The Fmoc group was removed from the resin-supported building block by mixing the resin twice with a solution of 2% DBU, 2% piperidine in DMF (2 mL×5 min) while agitating with a stream of N₂ every 30 seconds. The resin was washed six times with DMF (2 mL×30 sec). Fmoc-2-chlorophenyla-lanine (31; 0.1 M solution in DMF, 2.5 mL, 3.3 equiv, 0.25 mmol), followed by HATU (0.2M solution in DMF, 1.15 mL, 3.1 equiv, 0.23 mmol) and N-methyl morpholine (1.0 M in DMF, 0.5 mL, 6.7 equiv, 0.5 mmol) were added to the resin. The reaction mixture was agitated by a stream of nitrogen for 5 hr. The reagents were drained from the reaction vessel, and the resin 32 was washed six times with DMF (2 mL×30 sec).

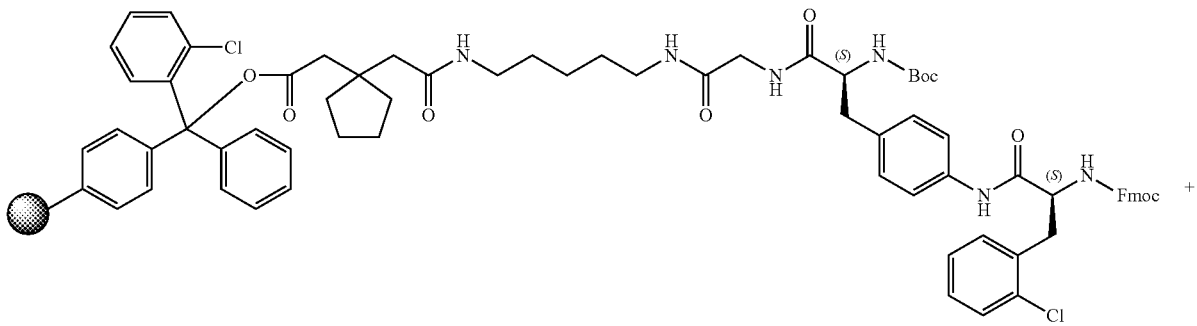

32

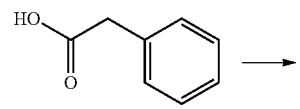

33

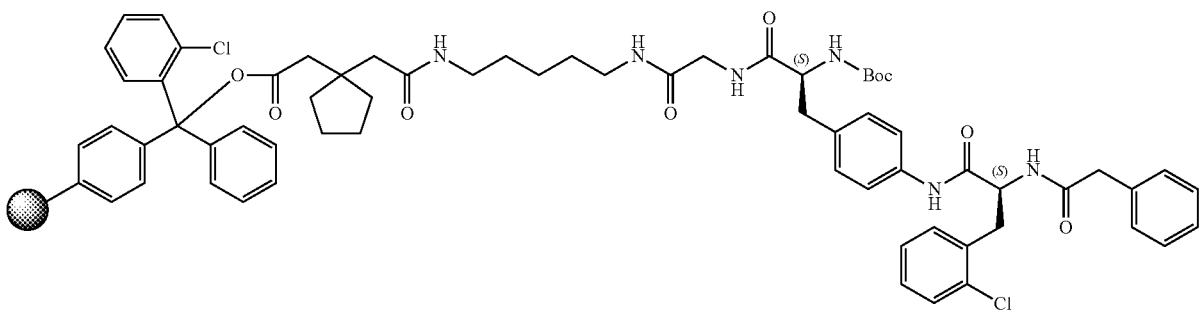

34

Resin 32 (0.075 mmol, 125 mg) was suspended in DMF (2 mL×5 min) and mixed with a stream of N₂ every 30 seconds. The Fmoc group was removed from the resin-supported building block by mixing the resin twice with a solution of 2% DBU, 2% piperidine in DMF (2 mL×5 min) while agitating with a stream of N₂ every 30 seconds. The resin was washed six times with DMF (2 mL×30 sec). Phenylacetic acid (33; 0.1M solution in DMF, 2.5 mL, 3.3 equiv, 0.25 mmol), followed by HATU (0.2M solution in DMF, 1.15 mL, 3.1 equiv, 0.23 mmol) and N-methyl morpholine (1.0 M in DMF, 0.5 mL, 6.7 equiv, 0.5 mmol) were added to the resin. The reaction mixture was agitated by a stream of nitrogen for 30 min. The reagents were drained from the reaction vessel, and the resin 34 was washed six times with DMF (2 mL×30 sec), and six times with DCM (2 mL×30 sec).

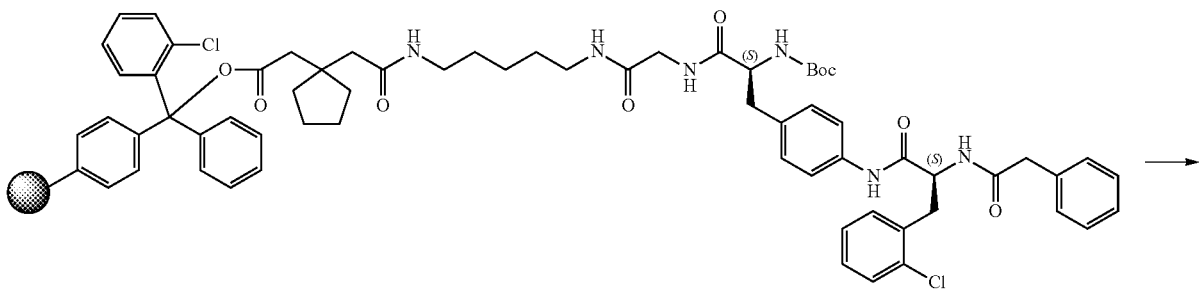

34

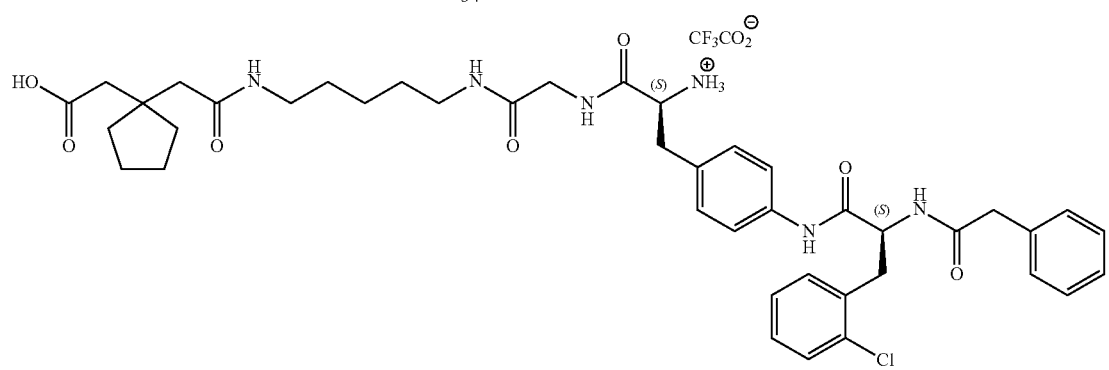

35

Resin 34 (0.075 mmol, 125 mg) was treated with 5% TFA in CH₂Cl₂ (4 mL×5 min) then washed with DCM (4 mL). Treatment with TFA was repeated two more times and the fractions combined. TFA (1 mL) was added and solvent was removed by evaporation using a Genevac EZ2.2 evaporator. The crude reaction mixture 35 was carried on to the next reaction.

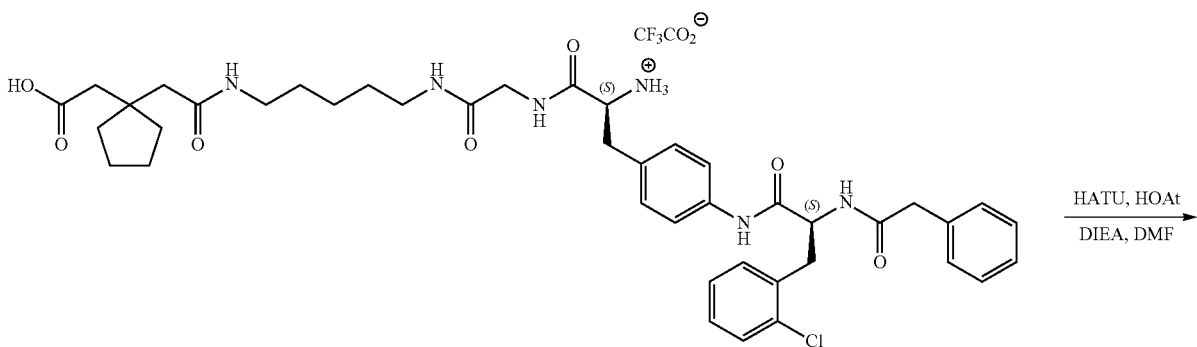

35

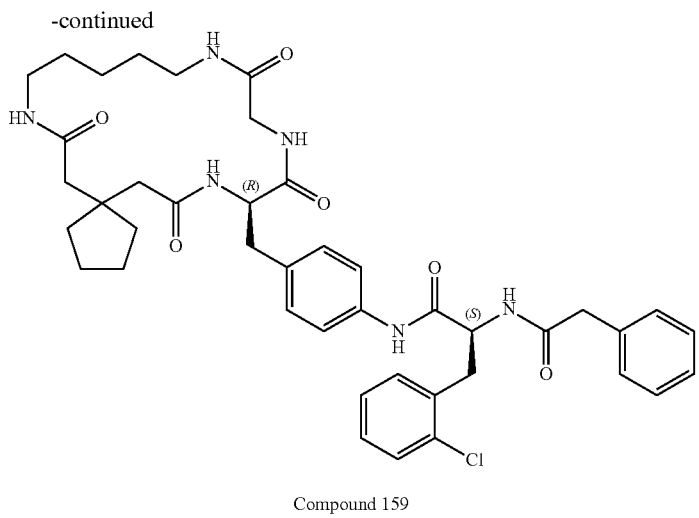

Compound 159

Crude reaction product 35 (0.075 mmol) and DIEA (0.13 mL, 10 equiv) were dissolved in DMF (5 mL). This solution was added to a solution containing HATU (34 mg, 0.090 mmol, 1.2 equiv) and HOAt (12 mg, 0.090 mmol, 1.2 equiv) dissolved in DMF (30 mL). After 30 minutes, the volatiles were evaporated on a Genevac EZ2.2 evaporator at 50° C. The resultant crude mixture was dissolved in DMSO and purified on a Waters HPLC. Evaporation of volatiles followed by lyophilization resulted in Compound 159 (32 mg, 0.042 mmol, 56% yield) as a white powder.

Example 3

Synthesis of 2-(1-(2-((5-((((9H-fluoren-9-yl)methoxy)carbonyl)(methyl)amino)pentyl)(methyl)amino)-2-oxoethyl)cyclopentyl)acetic Acid (Intermediate 39)

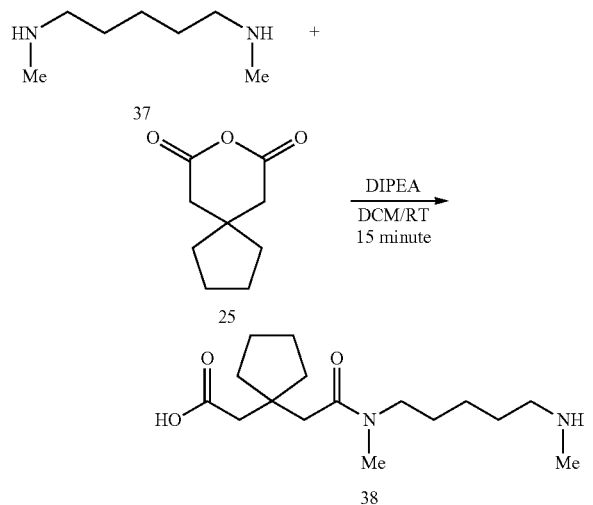

A 250 mL flask with magnetic stirring bar is charged with 1,5-di(methylamino)pentane (37; 1.0 g, 7.7 mmol), followed by 120 mL of dichloromethane. The mixture is stirred at room temperature for 5 minutes followed by addition of 8-oxazpiro [4.5]decane-7,9-dione (25; 1.29 g, 7.7 mmol) and diisopropylethylamine (1.34 mL, 30.8 mmol). The solution is allowed to stir for 15 minutes and the resulting 2-(1-(2-(methyl(5-(methylamino)pentyl)amino)-2-oxoethyl)cyclopentyl)acetic acid 38 is used directly for the next reaction without any purification.

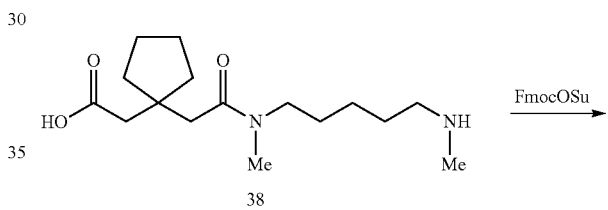

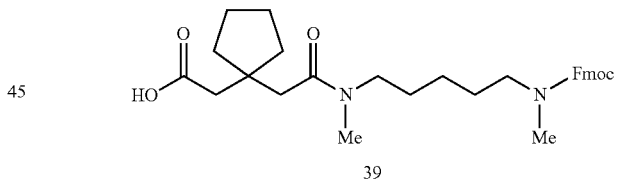

To the above solution is introduced (9H-fluoren-9-yl)methyl (2,5-dioxopyrrolidin-1-yl) carbonate (3.1 g, 9.2 mmol). The solution is stirred for 15 minutes. The resulting mixture is treated with 1.2N HCl solution and the pH adjusted to 3.0. The organic layer is separated and dried with $Na_2SO_4$. The crude product is purified by silica gel chromatography (acetonitrile/methylene chloride: 0-30%) providing a white powder (1.8 g, 3.4 mmol, 45% from diamine) consistent with desired product 39. The desired product 39 can be utilized in general Scheme 1 as a version of intermediate 11, or in general Scheme 2, as a version of intermediate 15.

Other compounds of Formula I were made by a similar process as described above with the appropriate substitution for one or more of reagents 20, 24, 25, 27, 29, 31, 33 and/or 37. Those of ordinary skill in the art should make reference to Schemes 1-4 herein, commercially available reagents/compounds and standard organic chemistry protocols to obtain appropriate substitutions for any of these reagents.

Example 4

Synthesis of 7-oxaspir[3.5]nonane-6,8-dione

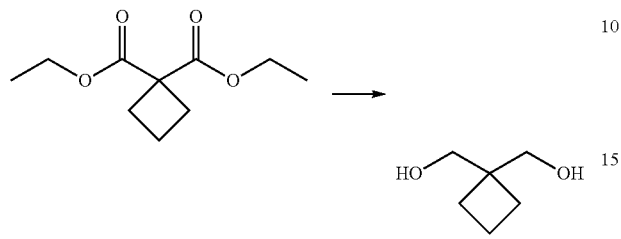

A solution of diethyl cyclobutane-1,1-dicarboxylate (4.76 ml, 24.97 mmol) in diethyl ether was cooled to 0° C. Aluminum(III) lithium hydride (49.9 ml, 100 mmol) in THF was added over 15 min. The reaction was warmed to room temperature and left to stir for 3 hours. A 20% solution of sodium hydroxide was added followed by diethyl ether. The organic layer was isolated, dried with magnesium sulfate, and concentrated under vacuum. Recovered cyclobutane-1,1-diyldimethanol (23.86 mmol, 96% yield) as pure material.

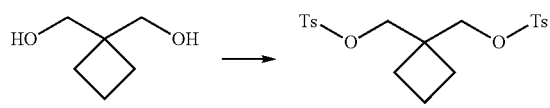 [SMILES: OCC1(CO)CCC1 ; Cc1ccc(S(=O)(=O)OCC2(COS(=O)(=O)c3ccc(C)cc3)CCC2)cc1]

4-methylbenzene-1-sulfonyl chloride (13.79 g, 72.3 mmol) was dissolved in pyridine and cooled to 0° C. Cyclobutane-1,1-diyldimethanol (2.8 g, 24.11 mmol) in pyridine was added over 10 min. The mixture was stirred for 2 hours at 0° C. and then for 48 h at room temperature. The material was partitioned between 50 ml DCM and 50 ml water. The aqueous layer was washed with 1× with 50 ml DCM. The organic layers were combined and washed with 50 ml 1.2 M HCl and brine and then dried over MgSO$_4$, filtered, and concentrated under reduced pressure. The material was then purified on Companion Combiflash using a gradient of 0-10% ethyl acetate in hexanes. The desired fractions were combined and dried down to give a white solid. Solvents were removed under reduced pressure to give cyclobutane-1,1-diylbis(methylene)bis(4-methylbenzenesulfonate) (8.72 mmol, 36.2% yield).

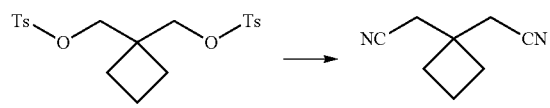 [SMILES: Cc1ccc(S(=O)(=O)OCC2(COS(=O)(=O)c3ccc(C)cc3)CCC2)cc1 ; N#CCC1(CC#N)CCC1]

Cyclobutane-1,1-diylbis(methylene)bis(4-methylbenzenesulfonate) (3.7 g, 8.72 mmol) was dissolved in 5 ml DMSO. KCN (1.703 g) was added and the mixture stirred overnight at 90° C. The reaction mixture was diluted with water (100 mL) and extracted with dichloromethane (50 ml×3). The organic extracts were combined, washed with brine (50 ml), dried over MgSO$_4$, and concentrated under vacuum to give 2,2'-(cyclobutane-1,1-diyl)diacetonitrile (8.71 mmol, 100% yield).

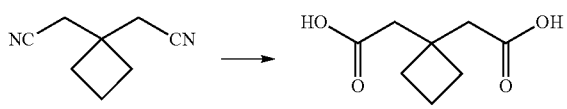 [SMILES: N#CCC1(CC#N)CCC1 ; O=C(O)CC1(CC(=O)O)CCC1]

2,2'-(cyclobutane-1,1-diyl)diacetonitrile (1.169 g, 8.71 mmol) was dissolved in 20% KOH, heated to reflux and refluxed for 48 h. Concentrated HCl was added dropwise until solution reached a pH of 1 and the solution was extracted with DCM (3×10 ml). Organic layers were combined and dried over MgSO$_4$, filtered, and concentrated to give 2,2'-(cyclobutane-1,1-diyl)diacetic acid (4.07 mmol, 46.7% yield).

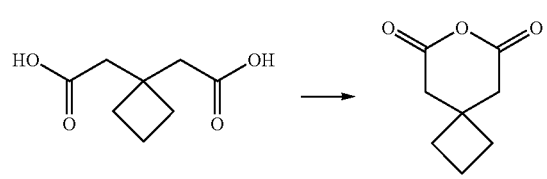 [SMILES: O=C(O)CC1(CC(=O)O)CCC1 ; O=C1CC2(CCC2)CC(=O)O1]

2,2'-(cyclobutane-1,1-diyl)diacetic acid (0.7 g, 4.07 mmol) was dissolved in acetic anhydride (5.75 mL, 61.0 mmol) and refluxed overnight. The solution was cooled to r.t. Acetic anhydride was removed under reduced pressure to give a brown oil, which was then recrystallized by dissolving in ether/hexanes, cooling to 0° C. and collecting crystals by vacuum filtration. The crystals were dried under vacuum overnight producing 7-oxaspiro[3.5]nonane-6,8-dione (2.147 mmol, 52.8% yield) as a light brown solid.

The resulting 7-oxaspiro[3.5]nonane-6,8-dione was used as intermediate 9 in Schemes 4A and 4B set forth previously to produce compounds of the invention having a cyclobutyl glutarate moiety (e.g, Compound Nos. 535 and 536).

Example 5

Synthesis of cyclopropane-1,1-diylbis(methylene) dimethanesulfonate

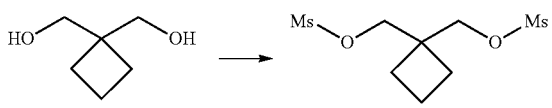 [SMILES: OCC1(CO)CCC1 ; CS(=O)(=O)OCC1(COS(C)(=O)=O)CCC1]

Cyclopropane-1,1-diyldimethanol (0.5 g, 4.90 mmol) was dissolved in DCM (6 ml). Triethylamine (2.73 mL, 19.58 mmol) was added, as was a solution of methanesulfonyl chloride (1.141 mL, 14.69 mmol) in DCM (4 ml) at 0° C. The mixture was stirred for 2 h at room temperature. After 2 h, 1.2N HCl was added, and the aqueous layer removed and washed 3× with DCM. The resulting organic layers were combined with the original layer, dried over MgSO$_4$, filtered, and concentrated to give 1.31 g crude material. The crude material was washed with hexanes to produce cyclopropane-1,1-diylbis(methylene)dimethanesulfonate (2.323 mmol, 47.4% yield).

The resulting cyclopropane-1,1-diylbis(methylene)dimethanesulfonate was used in place of cyclobutane-1,1-diylbis(methylene)bis(4-methylbenzenesulfonate) in Example 4 and, following the procedures set forth in Example 4, ultimately produced 6-oxaspiro[2.5]octane-5,7-dione.

6-oxaspiro[2.5]octane-5,7-dione was used as intermediate 9 in Schemes 4A and 4B set forth previously to produce compounds of the invention having a cyclopropyl glutarate moiety (e.g., Compound No. 554).

Example 6

Synthesis of 3-(1-(5-(((9H-fluoren-9-yl)methoxy)carbonylamino)pentylcarbamoyl)cyclopentyl)propanoic Acid

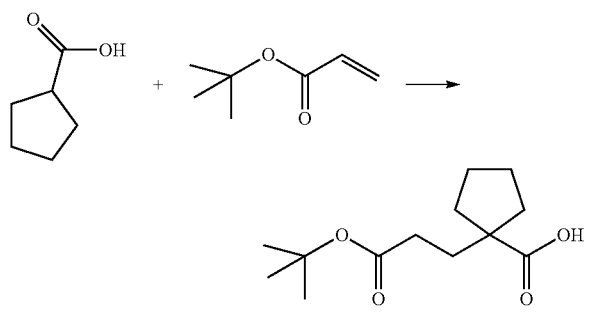

To a 50 ml round-bottomed flask under nitrogen was added lithium diisopropylamide (10.95 mL, 21.90 mmol). The solution was cooled to −20° using a controlled dry ice/acetonitrile bath. Cyclopentanecarboxylic acid (1.187 mL, 10.95 mmol) in dry THF (10 mL) was added over 5 minutes, keeping the temperature at −20° C. The mixture was warmed to room temperature, stirred for one hour, then cooled to −78° C. Tert-butyl acrylate (1.685 mL, 10.95 mmol) in dry THF (10 mL) was added dropwise over 5 min, keeping the temperature at −70° C. After 2 hours at −70° C., the mixture was quickly warmed to 0° C., acidified with 5N HCl, and extracted with hexane. The hexane extract was washed with water and saturated sodium bicarbonate, water, and dried over $MgSO_4$, and then recrystallized from hexanes. Recovered 1-(3-tert-butoxy-3-oxopropyl)cyclopentanecarboxylic acid (1.8 g, 7.43 mmol, 67.8% yield).

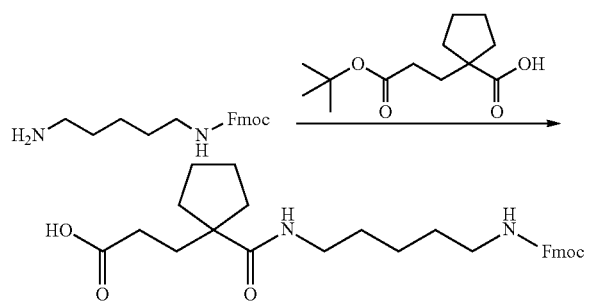

To a solution of (9H-fluoren-9-yl)methyl 5-aminopentylcarbamate (0.683 g, 2.105 mmol) in 15 ml DMF was added HATU (0.800 g, 2.105 mmol), 1-(3-tert-butoxy-3-oxopropyl)cyclopentanecarboxylic acid (0.425 g, 1.754 mmol) in 5 ml DMF, and DIEA (1.532 mL, 8.77 mmol). The solution was stirred for 10 minutes and material purified by HPLC using a gradient of 0-50% acetonitrile in DCM. Solvents were removed under reduced pressure to give 1.2 g crude tert-butyl 3-(1-(5-(((9H-fluoren-9-yl)methoxy)carbonylamino)-pentylcarbamoyl)cyclopentyl)propanoate. The crude material was dissolved in 20 ml DCM and 10 ml TFA was added to remove t-Bu group. Solvent was removed under reduced pressure and material purified by reverse phase chromatography to give 3-(1-(5-(((9H-fluoren-9-yl)methoxy)carbonylamino)pentylcarbamoyl)cyclopentyl)propanoic acid (16 mg, 0.032 mmol, 1.852% yield).

The resulting 3-(1-(5-(((9H-fluoren-9-yl)methoxy)carbonylamino)pentylcarbamoyl)cyclopentyl)propanoic acid was employed as intermediate 15 in Scheme 2 to produce compounds of the invention where $R^3$ is

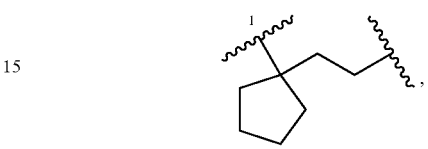

e.g. (Compound 543).

Example 7

Synthesis of 1-(3-(5-(((9H-fluoren-9-yl)methoxy)carbonylamino)pentylamino)-3-oxopropyl)cyclopentane Carboxylic Acid

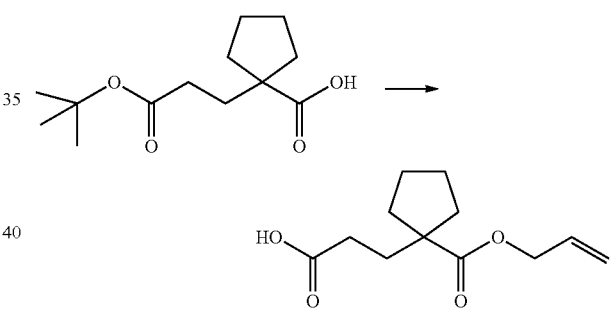

1-(3-tert-butoxy-3-oxopropyl)cyclopentanecarboxylic acid (1.275 g, 5.26 mmol) and 3-bromoprop-1-ene (0.911 mL, 10.52 mmol) were dissolved in 25 mL of acetone. Potassium carbonate (2.55 g, 18.42 mmol) was then added in one portion. The resulting suspension was stirred at reflux for 3 hours. The insoluble inorganic salts were removed by filtration and the reaction mixture was concentrated under reduced pressure to yield crude product. The crude product was dissolved in dichloromethane (10 mL) to which was added TFA (2.5 ml) to remove Boc group. The reaction was stirred for 15 min then the solvent removed under reduced pressure to give crude material (1.04 g, quantitative yield), which was used without further purification.

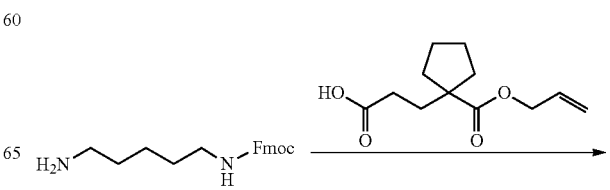

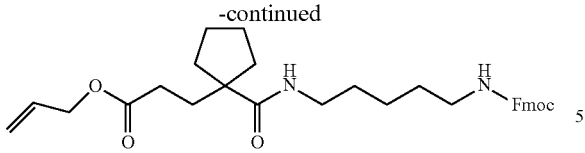

To a solution of 3-(1-(allyloxycarbonyl)cyclopentyl)propanoic acid (1.191 g, 5.26 mmol) in 40 ml DMF was added (9H-fluoren-9-yl)methyl 5-aminopentylcarbamate (2.049 g, 6.32 mmol), DIEA (4.60 mL, 26.3 mmol) and HATU (2.402 g, 6.32 mmol). After stirring for 10 minutes, DMF was removed under reduced pressure. The material was subjected to normal-phase purification using a gradient of 0-100% acetonitrile in DCM. Fractions containing the desired material were combined and solvent removed under reduced pressure to give crude allyl 1-(3-(5-(((9H-fluoren-9-yl)methoxy)carbonylamino)pentylamino)-3-oxopropyl)cyclopentanecarboxylate (360 mg, 0.676 mmol, 12.84% yield) that was used in the next step without further purification.

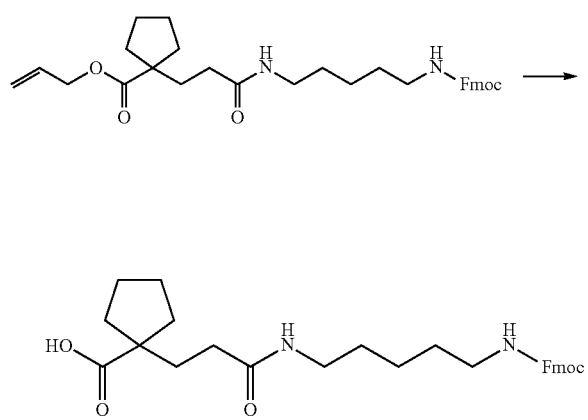

Allyl 1-(3-(5-(((9H-fluoren-9-yl)methoxy)carbonylamino)pentylamino)-3-oxopropyl)cyclopentanecarboxylate (360 mg, 0.676 mmol) was dissolved in DMF (15 mL) and cooled to 0° C. under nitrogen. Tetratritylpalladium (122 mg, 0.113 mmol) and morpholine (941 mg, 10.8 mmol) were added and the mixture stirred for 2 h. Solvent was removed under reduced pressure and material was purified by reverse-phase chromatography. Recovered 1-(3-(5-(((9H-fluoren-9-yl)methoxy)carbonylamino)pentylamino)-3-oxopropyl)cyclopentanecarboxylic acid (54.4 mg, 0.110 mmol, 16.34% yield).

The resulting 1-(3-(5-(((9H-fluoren-9-yl)methoxy)carbonylamino)pentylamino)-3-oxopropyl)cyclopentanecarboxylic acid was employed as intermediate 15 in Scheme 2 to produce compounds of the invention where $R^3$ is

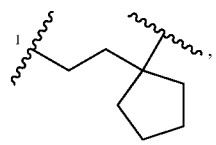 [SMILES: *CCC1(*)CCCC1]

e.g., Compound 561.

Example 8

Synthesis of 2-(1-(2-((5-(((9H-fluoren-9-yl)methoxy)carbonyl)pentyl)(methyl)amino)-2-oxoethyl)cyclopentyl)acetic Acid (47)

To a solution of 41 (20 g, 194 mmol) in DCM (0.2 L) was added (Boc)₂O dropwise (42.3 g, 194 mmol) under an ice bath. The reaction was stirred at RT over night. Then the mixture solution was extracted with DCM and washed with water. The combined organic layers were washed with saturated NaCl, dried over Na₂SO₄, and filtered. The solvent was removed in vacuum to give 42 as an oil (37 g, yield 93.1%). ¹H NMR (300 MHz, CDCl₃) δ: 3.5 (m, 2H), 3.2 (m, 2H), 1.6-1.5 (m, 4H), 1.4-1.3 (m, 11H).

To a solution of 42 (10 g, 49.2 mmol) in DCM (100 mL) and Et₃N (9.9 g, 98.5 mmol) was added methanesulfonyl chloride (6.7 g, 59.1 mmol) in portions over 20 minutes under an ice bath. The reaction was stirred for 1 hour. The mixture was extracted with DCM. The combined organic layers were washed with saturated NaCl, dried over Na₂SO₄, and filtered. The filtrate was concentrated to give 43 (12 g, yield: 86.9%). ¹H NMR (300 MHz, CDCl₃) δ: 4.0 (m, 2H), 3.1-3.0 (m, 3H), 3.2-3.1 (m, 2H), 1.6-1.5 (m, 4H), 1.4-1.3 (m, 11H).

To a solution of 43 (12 g, 42 mmol) in 1,4-dioxane (100 mL) was added CH$_3$NH$_2$ aqueous slowly (30%, 100 ml) at 60° C. The mixture was stirred at 60° C. for 1 h. The reaction was concentrated and purified by a silica gel column (eluting with 3% Et$_3$N/THF) to give 44 (5.2 g, yield 56.5%). $^1$H NMR (300 MHz, CDCl$_3$) δ: 3.2-3.1 (s, 2H) 2.9-2.9 (m, 3H), 2.6-2.5 (m, 2H), 1.6-1.5 (s, 2H), 1.4-1.3 (s, 11H).

To a solution of 44 (3.2 g, 14.8 mmol) was added 8-oxas-piro[4.5]decane-7,9-dione (2.9 g, 17.7 mmol) in DCM (30 mL). The resulting mixture was stirred at RT for 1 h. Then, the mixture was extracted with DCM. The combined organic layers were washed with saturated NaCl, dried over Na$_2$SO$_4$, and filtered. The filtrate was concentrated and purified by a silica gel column (eluting with 20-30% EA/PE, 2% AcOH) to give 45 (3.5 g, yield 62.5%). $^1$H NMR (300 MHz, CDCl$_3$) δ: 3.5-3.4 (m, 2H), 3.3 (m, 2H), 3.1 (m, 2H), 3.0 (m, 1H), 2.5 (m, 4H), 1.8-1.4 (s, 25H).

To a solution of 45 (3.5 g, 9.1 mmol) in 40 mL DCM was added Et$_2$O/HCl slowly (4 mol/L, 40 ml) under ice bath. Then, the mixture was stirred at room temperature overnight. The mixture was concentrated and washed with Et$_2$O to give 46 (2.2 g, yield 75.8%). $^1$H NMR (300 MHz, DMSO) δ: 3.5-3.4 (m, 2H), 3.3 (m, 2H), 3.1 (m, 2H), 3.0 (m, 1H), 2.5 (m, 4H), 1.8-1.4 (s, 16H).

To a solution of 46 (2.2 g, 6.8 mmol) and potassium carbonate (1.9 g, 13.7 mmol) in acetonitrile (20 mL) and water (40 mL) was added Fmoc-osu (2.5 g, 7.5 mmol) in acetonitrile (20 mL) over 10 minutes under an ice bath. The mixture was stirred under ice bath for about 1 h. Then, the mixture was extracted with EA. The combined organic layers were washed with saturated NaCl, dried over Na$_2$SO$_4$, and filtered. The filtrate was concentrated and purified by a silica gel column (eluting with 20-30% EA/PE, 2% AcOH) to give 47 (2 g, yield 58.8%). $^1$H NMR (300 MHz, CDCl$_3$) δ: 7.9-7.8 (d, 2H), 7.7-7.6 (d, 2H), 7.6-7.5 (d, 2H), 7.4-7.3 (m, 2H), 7.3-7.2 (d, 2H), 4.5-4.4 (m, 2H), 4.2 (m, 1H), 3.5-3.4 (m, 2H), 3.2 (m, 2H), 3.1 (m, 2H), 3.0 (m, 1H), 2.6-2.5 (m, 4H), 1.8-1.4 (s, 12H), 1.4-1.2 (s, 2H). LC-MS: m/z=529.2 (M+23)$^+$.

The resulting product 47 was employed as intermediate 15 in Scheme 2 to produce compounds of the invention, such as Compound 421. Alternatively, the resulting product was employed as intermediate 11 in Scheme 1 to produce compounds wherein R$^1$ is —N(CH$_3$)— and R$^2$ is —(CH$_2$)$_5$—N(H)—C(O)—C(H)(R$^{11}$)—(CH$_2$)$_{0-2}$—. For other compounds of the invention, the resulting product was used as set forth in Example 9, below.

Example 9

Synthesis of Resin-Linked Intermediate 51

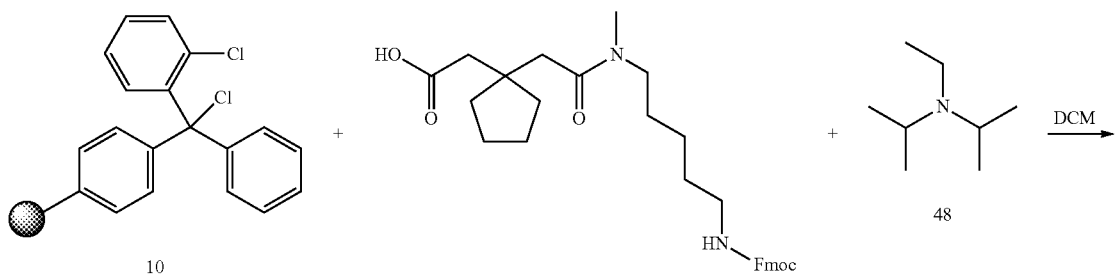

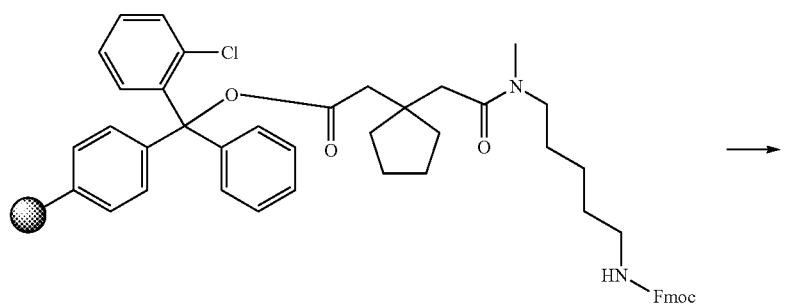

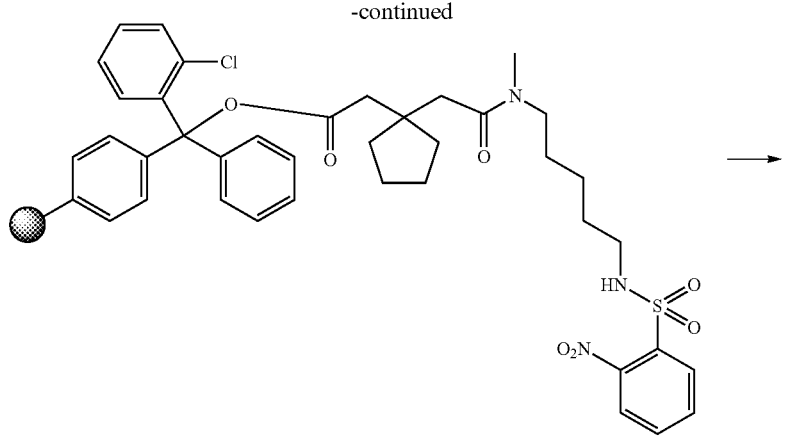

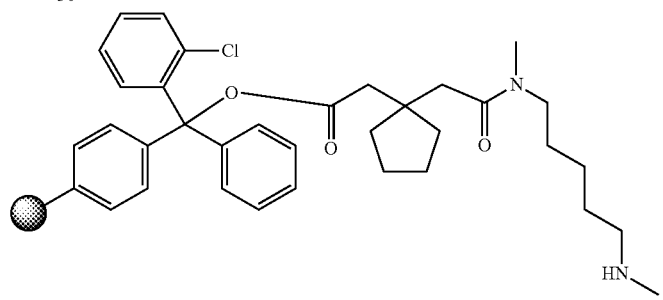

50

51

2-Chlorotrityl chloride resin (10; 0.658 g, 0.790 mmol) was added to a 20 mL plastic column. The resin was swelled with 10 mL anhydrous DCM and let sit for 20 minutes. The DCM was drained and the resin washed with 10 mL of DCM. 2-(1-(2-((5-(((9H-Fluoren-9-yl)methoxy)carbonylamino) pentyl)(methyl)amino)-2-oxoethyl)cyclopentyl)acetic acid (47; 0.400 g, 0.790 mmol) and N-ethyl-N-isopropylpropan-2-amine (48; 0.688 mL, 3.95 mmol) were dissolved in DCM (30 mL) in a 10 mL vial. The solution was loaded onto column containing the resin and rocked overnight. The solution was drained from the column, which was then washed with 85:10:5 DCM:MeOH:DIPEA (10 mL×2) and DCM (10 mL×3), and dried under light vacuum to produce resin 49. Resin loading was measured to be 0.3 mmol/g.

850 mg of resin 49 from the previous step was swelled in DMF (8 ml) for 15 min. The DMF was drained and 8 ml of 2% piperidine/2% DBU in DMF was added. After rotation for 5 min, the solution was drained and the resin washed 1× with DMF. 8 ml of 2% piperidine/2% DMF in DMF was added to the resin and rotated for 15 min. The solution was drained and the resin washed 5× with DMF. In a separate vial, 2-nitrobenzenesulfonyl chloride (0.222 g, 1.000 mmol) was dissolved in DMF (8 mL). To that was added 2,4,6-Collidine (0.330 mL, 2.500 mmol) and the mixture was vortexed. The NBS/collidine solution was added to the resin and rotated for 15 min.

After draining the resin was washed 1× with DMF, and the treatment with NBS/collidine was repeated. The resulting resin 50 was washed 5× with DMF.

The resin 50 from the previous step was rinsed 2× with THF. In a vial, triphenylphosphine (0.328 g, 1.250 mmol) was dissolved in DMF (5 mL), MeOH (0.101 mL, 2.500 mmol) added, and the solution mixed well. The solution was added to the resin and rotated vigorously for 2 min. Diisopropyl azodicarboxylate (0.246 mL, 1.250 mmol) dissolved in THF (1 mL) was added to the resin in 200 µL portions and rocked for 10 min between each addition. The resin was then rocked overnight. The solution was drained from resin and resin was washed with THF (5×5 mL) followed by DCM (3×5 mL). The additions of triphenylphosphine and diisopropyl azodicarboxylate were repeated and the resin rocked for an additional 8 hours. In a separate vial, 2-mercaptoethanol (0.176 mL, 2.500 mmol) was dissolved in DMF (5 mL) and then DBU (0.188 mL, 1.250 mmol) was added. This solution was added to the resin and rotated for 5 min. The reaction solution was drained from the resin and the resin washed with DMF (2×5 ml). The resulting resin 51 was then washed thoroughly with DMF, followed by DCM.

For certain compounds of the invention, the resulting resin 51 was used as resin 12 in general Scheme 1. For other compounds of the invention, the resulting resin 51 was used as resin 16 in general Scheme 2, e.g., Compounds 387, 488, 489, 524, 525, 566, 570, 600, 601, 602, 623, 625, 626, 627, 628, 629, 630, 631, 644, 645, 646, 653, 665, 669, and 670.

Example 10

Synthesis of 2-(1-(1-(9H-fluoren-9-yl)-13-methyl-3,14-dioxo-2,7,10-trioxa-4,13-diazapentadecan-15-yl)cyclopentyl)acetic Acid (63)

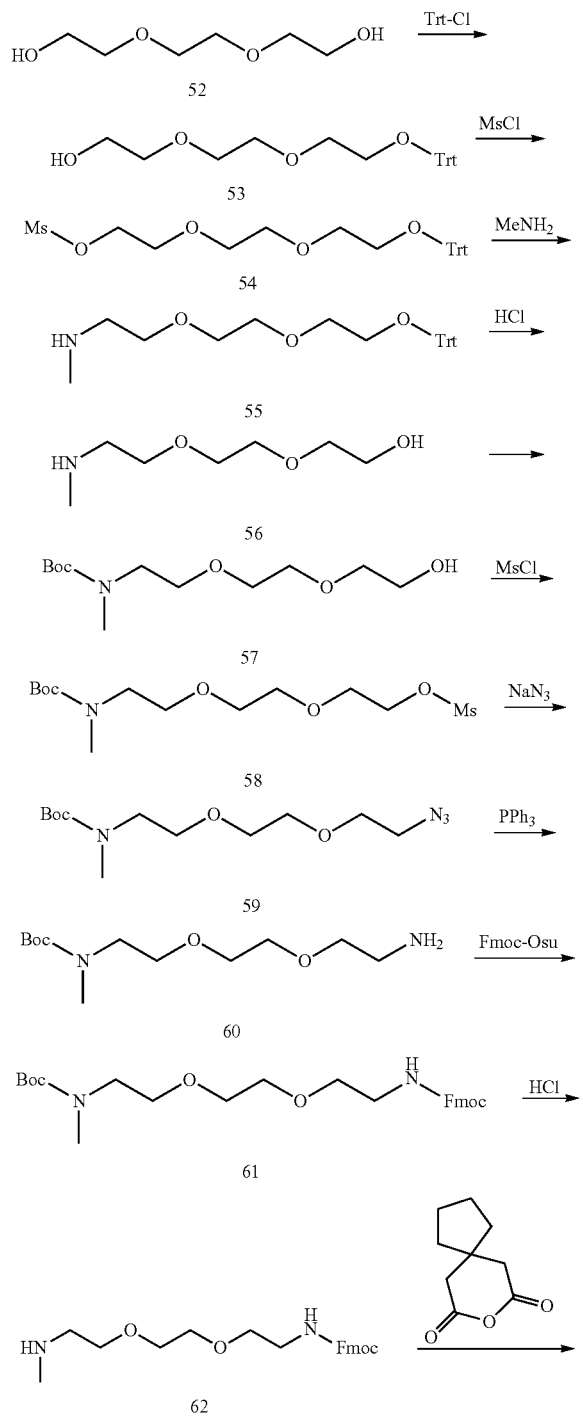

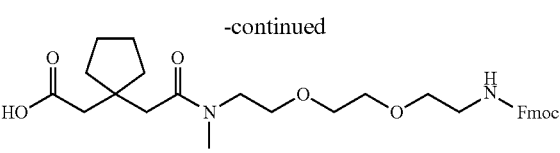

To a solution of 2,2'-(ethane-1,2-diylbis(oxy))diethanol (52; 100 g, 667 mmol) and $Et_3N$ (18.5 mL, 133 mmol) in DCM (500 mL) was added triphenylmethyl chloride (abbreviated as (Trt-Cl) (18.6 g, 66.7 mmol) in DCM (10 mL) over 20 minutes under an ice bath. The progress of the reaction was checked by TLC. The solution was extracted with DCM. The combined organic layers were washed with saturated NaCl, dried over $Na_2SO_4$, and filtered. The filtrate was concentrated and purified by a silica gel column (eluting with 5-15% EA/PE, 1% $Et_3N$) to provide 53 (15 g, yield: 57.3%). $^1$H NMR (300 MHz, $CDCl_3$) δ: 7.6-7.4 (m, 5H), 7.4-7.2 (m, 10H), 3.8-3.6 (m, 6H), 3.6-3.5 (m, 2H), 3.3-3.1 (m, 2H), 2.5-2.3 (s, 1H).

To a solution of 53 (15 g, 38.2 mmol) in DCM (100 mL) and $Et_3N$ (8 mL, 45.9 mmol) was added methanesulfonyl chloride (5.2 g, 45.9 mmol) in portions over 10 minutes under an ice bath. The reaction was stirred for 1 hour. The mixture was extracted with DCM. The combined organic layers were washed with saturated NaCl, dried over $Na_2SO_4$, and filtered. The filtrate was concentrated to give 54 (17 g, yield: 94.7%). $^1$H NMR (300 MHz, $CDCl_3$) δ: 7.6-7.4 (m, 5H), 7.4-7.2 (m, 10H), 4.5-4.3 (m, 2H), 3.9-3.8 (m, 2H), 3.8-3.6 (m, 6H), 3.0 (s, 3H).

To a solution of 54 (17 g, 36 mmol) in THF (20 mL) was added $CH_3NH_2$ aqueous solution slowly (30%, 80 ml) at 60° C. The mixture was stirred at 60° C. for 4 h. The mixture was concentrated to provide 55 (14.5 g, yield: 99.8%). $^1$H NMR (300 MHz, $CDCl_3$) δ: 7.7-7.4 (m, 7H), 7.4-7.2 (m, 8H), 3.9-3.7 (m, 8H), 3.3-3.2 (m, 2H), 2.8-2.8 (m, 2H), 2.5-2.4 (s, 3H).

To a solution of 55 (4.5 g, 36.1 mmol) in 30 mL DCM was added $Et_2O$/HCl (5.2 mol/L, 50 mL) at room temperature. Then, the mixture was stirred at room temperature over night. The mixture was filtered and the residue was washed with $Et_2O$ to give 56 (7.2 g, yield: 99.6%).

To a solution of 56 (7.2 g, 36.1 mmol) in DCM (0.2 L) was added $(Boc)_2O$ dropwise (42.3 g, 194 mmol) under ice bath. The reaction was stirred at RT overnight. Then the mixture solution was extracted with DCM and washed with water. The combined organic layers were washed with saturated NaCl, dried over $Na_2SO_4$, and filtered. The solvent was removed in vacuum and purified by a silica gel column (eluting with 20-50% EA/PE) to provide 57 (7 g, yield: 73.7%). $^1$H NMR (300 MHz, $CDCl_3$) δ: 3.8-3.6 (m, 11H), 3.5-3.3 (m, 2H), 3-2.8 (s, 3H), 1.6-1.5 (s, 9H).

To a solution of 57 (7 g, 26.6 mmol) in DCM (100 mL) and $Et_3N$ (5.5 mL, 40 mmol) was added methanesulfonyl chloride (3.6 g, 32 mmol) in portions over 10 minutes under ice bath. The reaction was stirred for 1 hour. The mixture was extracted with DCM. The combined organic layers were washed with saturated NaCl, dried over $Na_2SO_4$, and filtered. The filtrate was concentrated to give 58 (8 g, yield: 89.4%). $^1$H NMR (300 MHz, $CDCl_3$) δ: 4.5-4.3 (m, 2H), 3.9-3.7 (m, 2H), 3.7-3.5 (m, 6H), 3.5-3.3 (s, 2H), 3.1 (s, 3H), 3-2.8 (s, 3H), 1.6-1.5 (s, 9H).

To a solution of 58 (8 g, 30.4 mmol) in DMF (0.1 L) was added sodium azide (3.2 g, 49.7 mmol) under an ice bath. The reaction was stirred ice bath for 4 h, $H_2O$ (5 mL) was added and the mixture was stirred at room temperature for overnight. Then, the mixture was extracted with EA. The combined organic layers were washed with saturated NaCl, dried over Na$_2$SO$_4$, and filtered. The solvent was removed in vacuum to provide 59 (7 g, yield: 79.9%). $^1$H NMR (300 MHz, CDCl$_3$) δ: 3.8-3.5 (m, 6H), 3.5-3.4 (m, 2H), 3.1-2.8 (m, 5H), 1.6-1.5 (s, 9H).

To a solution of 59 (7.0 g, 24.3 mmol) in THF (50 mL) was added PPh$_3$ (7.6 g, 29.1 mmol) under an ice bath. The reaction was stirred ice bath for 4 h, H$_2$O (5 mL) was added and the mixture was stirred at room temperature for overnight. Then, the mixture was extracted with EA. The combined organic layers were washed with saturated NaCl, dried over Na$_2$SO$_4$, and filtered. The solvent was removed in vacuum to provide 60 (5.6 g, yield: 62.3%).

To a solution of 60 (5.6 g, 21.4 mmol) and potassium carbonate (4.4 g, 32 mmol) in acetonitrile (25 mL) and water (25 mL) was added Fmoc-Osu (7.9 g, 23.5 mmol) in acetonitrile (25 mL) over 10 minutes under ice bath. The mixture was stirred for 30 minutes. After TLC, the mixture was extracted with EA. The combined organic layers were washed with saturated NaCl, dried over Na$_2$SO$_4$, and filtered. The filtrate was concentrated and purified by a silica gel column (eluting with 50/90% EA, 10% MeOH) to provide 61 (9.5 g, yield: 91.7%). $^1$H NMR (300 MHz, CDCl$_3$) δ: 7.8-7.7 (d, 2H), 7.7-7.6 (d, 2H), 7.5-7.3 (m, 4H), 4.6-4.4 (m, 2H), 4.4-4.3 (m, 1H), 3.8-3.5 (m, 7H), 3.5-3.2 (m, 4H), 3.0-2.8 (s, 3H), 1.6-1.5 (s, 9H).

To a solution of 61 (9.5 g, 19.6 mmol) in 30 mL DCM was added Et$_2$O/HCl (5.2 mol/L, 40 mL) at room temperature. Then, the mixture was stirred at room temperature overnight. The mixture was filtered and the residue was washed with Et$_2$O to give of 62 (8.6 g, yield: 99.6%).

To a solution of 62 (8.6 g, 19.5 mmol) and DIEA (3.3 g, 25.2 mmol) in DCM (50 mL) was added 8-oxaspiro[4.5]decane-7,9-dione (4.2 g, 25.2 mmol) in DCM (10 mL) over 5 minutes under an ice bath. The progress of the reaction was checked by TLC. The solution was extracted with DCM. The combined organic layers were washed with saturated NaCl, dried over Na$_2$SO$_4$, and filtered. The filtrate was concentrated and purified by a silica gel column (eluting with 20-50% EA/PE, 2% AcOH) to provide 63 (10 g, yield: 92.9%). $^1$H NMR (300 MHz, CDCl$_3$) δ: 7.9-7.7 (d, 2H), 7.7-7.5 (m, 2H), 7.5-7.2 (m, 4H), 4.6-4.4 (m, 2H), 4.3-4.1 (m, 1H), 3.7-3.5 (m, 9H), 3.5-3.3 (m, 2H), 3.2-3.1 (m, 2H), 3.0-2.9 (m, 1H), 2.7-2.4 (m, 4H), 1.8-1.6 (m, 6H) 1.6-1.4 (m, 2H). LC-MS: m/z=575 (M+23)$^+$.

The resulting product 63 is used as intermediate 15 in Scheme 2 to produce compounds of the invention, such as Compounds 565, 568, 581, 582, and 585.

Example 11

Alternate Synthesis of 2-(1-(2-((5-((((9H-fluoren-9-yl)methoxy)carbonyl)(methyl)amino)pentyl)(methyl)amino)-2-oxoethyl)cyclopentyl)acetic Acid (70)

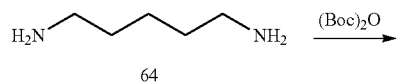

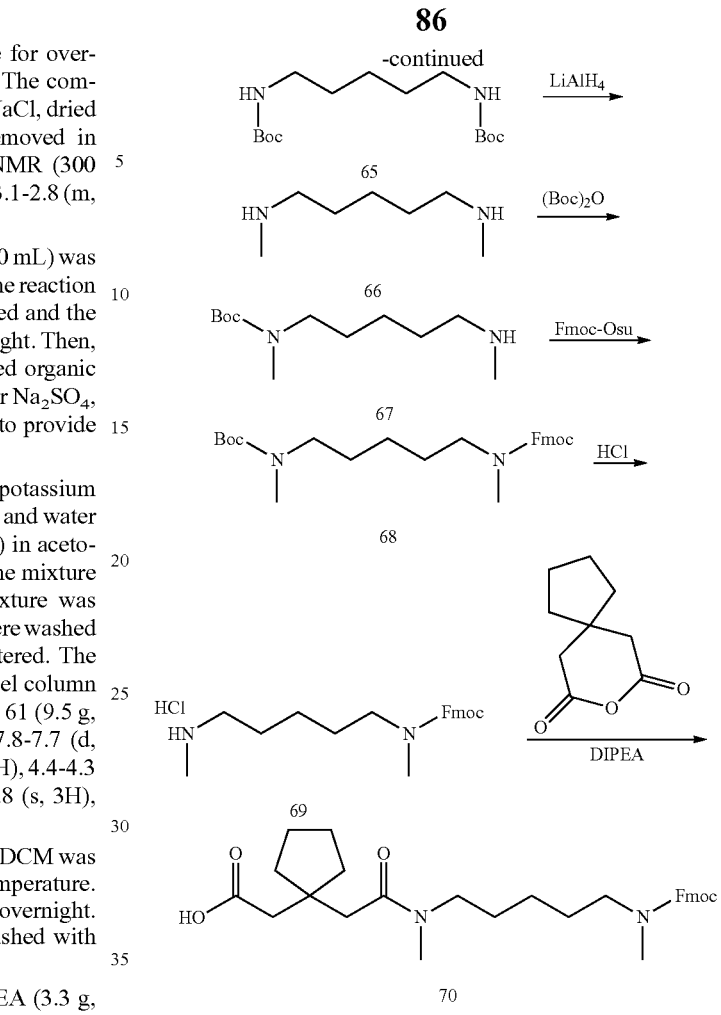

To a solution of pentane-1,5-diamine (64; 10 g, 98 mmol) and potassium carbonate (27 g, 196 mmol) in 1,4-dioxane (50 mL) and H$_2$O (50 mL) was added (Boc)$_2$O (42.8 g, 196 mmol) in 1,4-dioxane (50 mL) over 10 minutes under an ice bath. The reaction was stirred at room temperature for overnight. Then, the mixture solution was extracted with EA. The combined organic layers were washed with saturated NaCl, dried over Na$_2$SO$_4$, and filtered. The solvent was removed in vacuum to give 65 (26.1 g, yield 88.2%). $^1$H NMR (300 MHz, CDCl$_3$) δ: 4.7-4.5 (m, 2H), 3.2-3.0 (m, 6H), 1.8-1.7 (m, 2H), 1.6-1.4 (s, 18H), 1.4-1.3 (m, 2H).

To a solution of 65 (26.1 g, 86 mmol) in THF (200 mL) was added LiAlH$_4$ (13 g, 344 mmol) over 20 minutes under an ice bath. The reaction was refluxed for 16 h. After the reaction mixture was cooled, saturated NaOH (10 mL) was added. The mixture was filtered and the residue was washed with THF. Then, the filtrate was concentrated under vacuum to give 66 without purification (7 g, yield: 61.9%). $^1$H NMR (300 MHz, CDCl$_3$) δ: 4.7-4.5 (m, 2H), 3.2-3.0 (m, 6H), 2.9-2.8 (m, 6H), 1.7-1.6 (m, 2H), 1.3-1.2 (m, 2H).

To a solution of 66 (7 g, 53.4 mmol) and potassium carbonate (14.7 g, 106.8 mmol) in 1,4-dioxane (30 mL) and H$_2$O (30 mL) was added (Boc)$_2$O (11.6 g, 53.4 mmol) in 1,4-dioxane (30 mL) over 20 minutes under ice bath. The mixture was stirred at room temperature overnight. The reaction was extracted with EA. The combined organic layers were washed with saturated NaCl, dried over Na$_2$SO$_4$, and filtered. The filtrate was concentrated and purified by a silica gel column (eluting with 50% EA/PE, 5% MeOH) to give 67 (6.2 g, yield: 50%).

To a solution of 67 (6.2 g, 26.9 mmol) and potassium carbonate (3.7 g, 26.9 mmol) in acetonitrile (25 mL) and water (25 mL) was added Fmoc-Osu (8.1 g, 24.3 mmol) in acetonitrile (25 mL) over 10 minutes under ice bath. The mixture was stirred for 30 minutes. After TLC, the mixture was extracted with EA. The combined organic layers were washed with saturated NaCl, dried over $Na_2SO_4$, and filtered. The filtrate was concentrated and purified by a silica gel column (eluting with 20-50% EA/PE) to provide 68 (9.8 g, yield: 89.3%). $^1$H NMR (300 MHz, $CDCl_3$) δ: 7.8-7.7 (d, 2H), 7.7-7.6 (m, 2H), 7.5-7.2 (m, 4H), 4.6-4.2 (m, 3H), 3.4-3.0 (m, 4H), 2.9-2.8 (m, 6H), 1.6-1.5 (s, 9H), 1.4-1.0 (m, 6H), 1-0.8 (m, 4H).

To a solution of 68 (9.8 g, 21.7 mmol) in 20 mL DCM was added $Et_2O$/HCl (5.2 mol/L, 20 mL) at room temperature. Then, the mixture was stirred at room temperature overnight. The mixture was filtered and the residue was washed with $Et_2O$ to give 69 as a white solid (8.2 g, yield 97.6%). $^1$H NMR (300 MHz, $D_2O$) δ: 7.9-7.7 (d, 2H), 7.7-7.5 (m, 2H), 7.5-7.3 (m, 4H), 4.6-4.4 (m, 2H), 4.3-4.2 (m, 1H), 3.4-3.2 (m, 1H), 3.2-3.0 (m, 1H), 2.9-2.8 (m, 3H), 1.7-1.6 (m, 2H), 1.6-1.2 (m, 3H), 1.0-0.8 (m, 3H).

To a solution of 69 (8.6 g, 22.1 mmol) and DIEA (8.5 g, 66.3 mmol) in DCM (50 mL) was added 8-oxaspiro[4.5]decane-7,9-dione (3.7 g, 22.1 mmol) in DCM (10 mL) over 5 minutes under an ice bath. The progress of the reaction was checked by TLC. Next, the solution was extracted with DCM. The combined organic layers were washed with saturated NaCl, dried over $Na_2SO_4$, and filtered. The filtrate was concentrated and purified by a silica gel column (eluting with 20-50% EA/PE, 2% AcOH) to provide 70 (10 g, yield: 86.9%). $^1$H NMR (300 MHz, $CDCl_3$) δ: 7.9-7.7 (d, 2H), 7.7-7.5 (m, 2H), 7.5-7.2 (m, 4H), 4.6-4.4 (m, 2H), 4.4-4.1 (m, 1H), 3.5-3.2 (m, 2H), 3.1-2.8 (m, 6H), 2.6-2.5 (m, 4H), 1.8-1.5 (m, 6H), 1.5-1.4 (m, 2H), 1.4-1.2 (m, 2H). LC-MS: m/z=520.4 $(M+23)^+$.

The resulting product 70 is used as intermediate 15 in Scheme 2 to produce compounds of the invention such as Compounds 600, 601, 623, 625, 626, 627, 628, 629, 630, 631, 644, 645, 646, 653, 665, 669, and 670.

Example 12

Synthesis of 2-(1-(2-(5-(((9H-fluoren-9-yl)methoxy)carbonyl)pentylamino)-2-oxoethyl)cyclopentyl)acetic Acid (73)

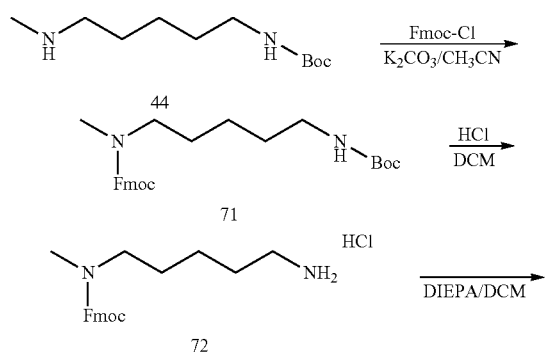

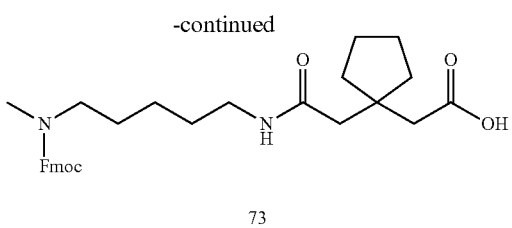

73

To a solution of 44 (from Example 8; 3.2 g, 14.8 mmol) and potassium carbonate (4.1 g, 29.6 mmol) in acetonitrile (20 mL) and water (40 mL) was added Fmoc-Cl (4.2 g, 16.3 mmol) in acetonitrile (20 mL) over 10 minutes under an ice bath. The mixture was stirred under an ice bath for about 2 h. The mixture was extracted with EA. The combined organic layers were washed with saturated NaCl, dried over $Na_2SO_4$, and filtered. The filtrate was concentrated and purified by a silica gel column (eluting with 20-30% EA/PE) to give 71 (4.3 g, yield: 66.2%). $^1$H NMR (300 MHz, $CDCl_3$) δ: 7.9-7.8 (d, 2H), 7.7-7.6 (d, 2H), 7.5-7.4 (d, 2H), 7.4-7.3 (m, 2H), 4.5-4.4 (m, 1H), 4.4 (m, 1H), 4.3 (m, 1H), 3.3-3.2 (m, 3H), 2.9-2.8 (m, 3H), 2.4 (m, 2H), 2.2 (m, 1H), 1.8-1.4 (s, 11H).

To a solution of 71 (4.3 g, 9.8 mmol) in 40 mL DCM was added $Et_2O$/HCl slowly (4 mol/L, 40 ml) under ice bath. Then, the mixture was stirred at RT overnight. The mixture was concentrated and washed with $Et_2O$ to give 72 (3 g, yield 83.4%). $^1$H NMR (300 MHz, $CDCl_3$) δ: 7.9-7.8 (d, 2H), 7.7-7.6 (d, 2H), 7.5-7.4 (d, 2H), 7.4-7.3 (m, 2H), 4.5 (m, 1H), 4.4 (m, 1H), 4.3 (m, 1H), 3.3-3.2 (m, 3H), 2.9-2.8 (m, 3H), 2.4 (m, 2H), 2.2 (m, 1H), 1.8-1.4 (s, 2H).

To a solution of 72 (3 g, 8.0 mmol) and DIEA (2 g, 16.0 mmol) in DCM (20 mL) was added 8-oxaspiro[4.5]decane-7,9-dione (1.5 g, 8.8 mmol). The mixture was stirred at RT for 1 h. The mixture was extracted with DCM. The combined organic layers were washed with saturated NaCl, dried over $Na_2SO_4$, and filtered. The filtrate was concentrated and purified by a silica gel column (eluting with 20-30% EA/PE, 2% AcOH) to give 73 (3.1 g, yield 77.5%). $^1$H NMR (300 MHz, $CDCl_3$) δ: 7.9-7.8 (d, 2H), 7.7-7.6 (d, 2H), 7.6-7.5 (d, 2H), 7.4-7.3 (m, 2H), 7.3-7.2 (d, 2H), 4.5 (m, 1H), 4.4 (m, 1H), 4.3 (m, 1H), 3.3-3.2 (m, 3H), 2.9-2.8 (m, 3H), 2.4 (m, 2H), 2.2 (m, 1H), 1.8-1.5 (s, 9H), 1.5-1.3 (s, 5H). LC-MS: m/z=529.2 $(M+23)^+$.

The resulting product 73 is used as intermediate 15 in Scheme 2 to produce compounds of the invention such as Compound 422. Alternatively, 73 was used as intermediate 11 in general Scheme 11 to produce compounds of the invention, such as Compounds 281, 307, 308, 335, 351, 363, 470 and 518.

Example 13

Synthesis of 2-(1-(2-(8-(((9H-fluoren-9-yl)methoxy)carbonylamino)octylamino)-2-oxoethyl)cyclopentyl)acetic Acid (78)

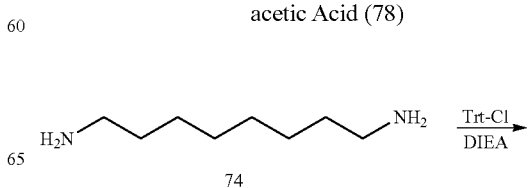

74

89

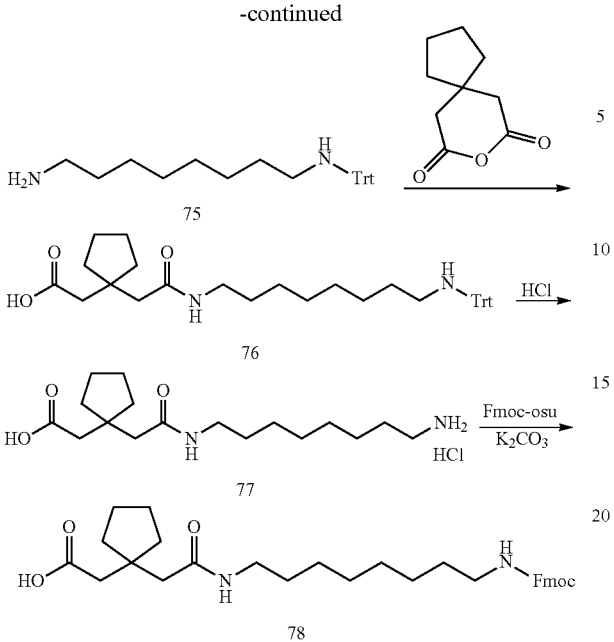

To a solution of 74 (10 g, 69.5 mmol) and DIEA (8.9 g, 69.5 mmol) in DCM (100 mL) was added triphenylmethyl chloride (abbreviated as Trt-Cl) (9.66 g, 34.75 mmol) in DCM (20 mL) over 10 minutes under an ice bath. The mixture was stirred overnight at room temperature. After TLC, the mixture was extracted with DCM. The combined organic layers were washed with saturated NaCl, dried over $Na_2SO_4$, and filtered. The filtrate was concentrated and purified by a silica gel column (eluting with 50% EA/PE-10% MeOH) to give 75 (8.8 g, yield 65.7%).

To a solution of 75 (8.8 g, 22.7 mmol) and DIEA (2.94 g, 22.7 mmol) in DCM (50 mL) was added 8-oxaspiro[4.5]decane-7,9-dione (3.82 g, 22.7 mmol) in DCM (10 mL) over 5 minutes under an ice bath. The progress of the reaction was checked by TLC. Next, the solution was extracted with DCM. The combined organic layers were washed with saturated NaCl, dried over $Na_2SO_4$, and filtered. The filtrate was concentrated and purified by a silica gel column (eluting with 20-50% EA/PE, 2% AcOH) to give 76 (8.6 g, yield 68.3%).

To a solution of 76 (8.6 g, 15.5 mmol) in 20 mL DCM was added $Et_2O$/HCl (5.2 mol/L, 10 mL) at room temperature. Then, the mixture was stirred at room temperature overnight. Next, the mixture was filtered and the residue was washed with $Et_2O$ to give 77 as a white solid (4.6 g, yield 85%).

To a solution of 77 (4.6 g, 13.2 mmol) and potassium carbonate (3.6 g, 26.3 mmol) in acetonitrile (30 mL) and water (30 mL) was added Fmoc-Osu (4.44 g, 13.2 mmol) in acetonitrile (20 mL) over 10 minutes under ice bath. The mixture was stirred for 30 minutes. After TLC, the mixture was extracted with EA. The combined organic layers were washed with saturated NaCl, dried over $Na_2SO_4$, and filtered. The filtrate was concentrated and purified by a silica gel column (eluting with 20-50% EA/PE) to give 78 (5.8 g, yield 82.3%). $^1$H NMR (300 MHz, $CDCl_3$) δ: 7.8-7.7 (d, 2H), 7.7-7.6 (d, 2H), 7.5-7.3 (m, 4H), 4.5-4.4 (m, 2H), 4.4-4.3 (m, 2H), 3.3-3.1 (m, 4H), 2.5-2.4 (s, 2H), 2.4-2.3 (s, 2H), 1.8-1.7 (m, 4H), 1.7-1.6 (m, 2H), 1.6-1.4 (m, 6H), 1.4-1.3 (m, 9H). LC-MS: m/z=557.4 (M+23)$^+$.

90

The resulting product 78 is used as intermediate 15 in Scheme 2 to produce compounds of the invention, such as Compounds 337, 366, 441, 442, 505, 597, 598, and 599.

Example 14

Synthesis of 2-(1-(2-((5-((((9H-fluoren-9-yl)methoxy)carbonyl)amino)pentyl)oxy)-2-oxoethyl)cyclopentyl)acetic Acid

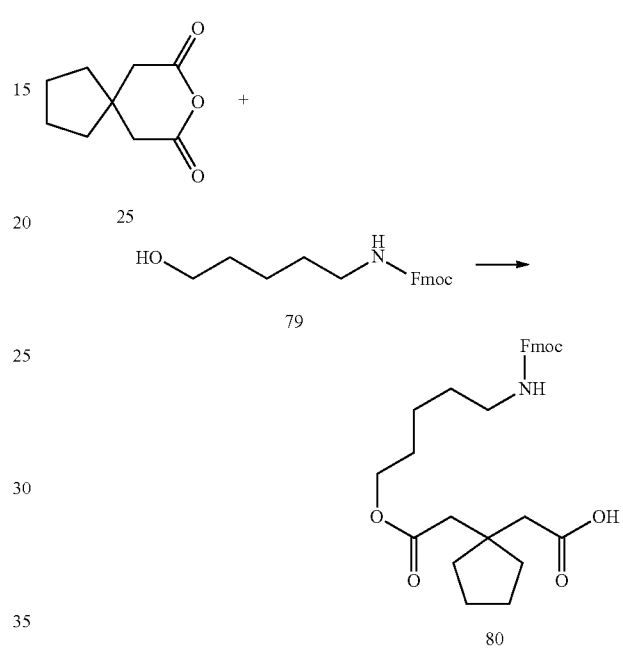

A 250-mL round bottom flask, equipped with magnetic stirring bar, is charged with 8-oxaspiro[4.5]decane-7,9-dione (25; 1.2 g, 7.1 mmoles), (9H-fluoren-9-yl)methyl(5-hydroxypentylcarbamate (79; 2.3 g, 7.1 mmoles), N,N-dimethylpyridin-4-amine (0.9 g, 7.4 mmoles), and dichloromethane (125 mL). The resulting mixture is stirred at room temperature for overnight. Next, the solvent was removed by rotary evaporation. The crude product is purified by silica gel chromatography (40 g, dichloromethane/acetonitrile: 100:0 to 50:50 ratio.) to obtain desired product 80 (1.67 g, 47.7%).

The resulting product 80 was then used as intermediate 11 in general Scheme 1 to produce compounds of the invention wherein —$R^1$-$R^2$— is —O—$(CH_2)_5$—NH—C(O)—C(H)($R^{11}$)—$(CH_2)_{0-2}$—, such as Compounds 671, 672, 673, 674, 675, 676, 677, 678, 679, 680 and 681.

Mass Spectrometry values for exemplary compounds of the invention are set forth in Table 2. NMR data for select compounds are set forth after Table 2.

TABLE 2

Physical data for Exemplary Compounds of the Invention.

| Cmpd No. | Exact Mass (M + H) | Observed Mass (M + H) |
|---|---|---|
| 100 | 756.38 | 756.33 |
| 101 | 841.43 | 841.34 |
| 102 | 742.36 | 742.21 |
| 103 | 827.42 | 827.3 |

TABLE 2-continued

Physical data for Exemplary Compounds of the Invention.

| Cmpd No. | Exact Mass (M + H) | Observed Mass (M + H) |
|---|---|---|
| 104 | 823.44 | 823.38 |
| 105 | 841.42 | 841.34 |
| 106 | 841.42 | 841.34 |
| 107 | 841.42 | 841.34 |
| 108 | 813.39 | 813.32 |
| 109 | 827.41 | 827.37 |
| 110 | 855.44 | 855.39 |
| 111 | 869.46 | 869.36 |
| 112 | 857.39 | 857.31 |
| 113 | 843.37 | 843.26 |
| 114 | 823.44 | 823.3 |
| 115 | 809.43 | 809.33 |
| 116 | 841.43 | 841.34 |
| 117 | 827.42 | 827.3 |
| 118 | 841.25 | 841.34 |
| 119 | 827.42 | 827.3 |
| 120 | 901.35 | 901.29 |
| 121 | 887.34 | 887.25 |
| 122 | 789.46 | 789.37 |
| 123 | 775.44 | 775.33 |
| 124 | 899.47 | 899.44 |
| 125 | 885.46 | 885.4 |
| 126 | 837.46 | 837.35 |
| 127 | 823.44 | 823.38 |
| 128 | 827.42 | 827.37 |
| 129 | 756.38 | 756.33 |
| 130 | 742.36 | 742.28 |
| 131 | 742.36 | 742.28 |
| 132 | 875.42 | 875.34 |
| 133 | 861.40 | 861.37 |
| 134 | 861.40 | 861.37 |
| 135 | 875.42 | 875.34 |
| 136 | 827.42 | 827.3 |
| 137 | 827.42 | 827.37 |
| 138 | 823.44 | 823.38 |
| 139 | 809.43 | 809.33 |
| 140 | 891.43 | 891.31 |
| 141 | 829.37 | 829.22 |
| 142 | 815.36 | 815.25 |
| 143 | 829.37 | 829.22 |
| 144 | 815.36 | 815.25 |
| 145 | 857.40 | 857.31 |
| 146 | 843.39 | 843.26 |
| 147 | 859.38 | 859.23 |
| 148 | 845.37 | 845.26 |
| 149 | 813.40 | 813.25 |
| 150 | 799.39 | 799.28 |
| 151 | 799.39 | 799.28 |
| 152 | 667.30 | 667.18 |
| 153 | 695.33 | 695.20 |
| 154 | 709.35 | 709.17 |
| 155 | 723.37 | 723.21 |
| 156 | 743.33 | 743.17 |
| 157 | 757.35 | 757.22 |
| 158 | 771.37 | 771.19 |
| 159 | 771.37 | 771.34 |
| 160 | 785.38 | 785.23 |
| 161 | 799.40 | 799.20 |
| 162 | 757.35 | 757.14 |
| 163 | 681.32 | 681.15 |
| 164 | 771.37 | 771.19 |
| 165 | 695.33 | 695.2 |
| 166 | 785.38 | 785.23 |
| 167 | 709.35 | 709.17 |
| 168 | 815.39 | 815.25 |
| 169 | 739.36 | 739.18 |
| 170 | 829.41 | 829.22 |
| 171 | 753.38 | 753.22 |
| 172 | 843.42 | 843.26 |
| 173 | 767.39 | 767.27 |
| 174 | 827.42 | 827.22 |
| 175 | 827.42 | 827.22 |
| 176 | 827.42 | 827.22 |
| 177 | 799.39 | 799.20 |
| 178 | 871.44 | 871.28 |
| 179 | 742.36 | 742.21 |
| 180 | 815.36 | 815.17 |
| 181 | 815.36 | 815.25 |
| 182 | 843.39 | 843.26 |
| 183 | 753.40 | 753.22 |
| 184 | 773.39 | 773.18 |
| 185 | 805.33 | 805.35 |
| 186 | 729.44 | 729.97 |
| 187 | 815.32 | 815.71 |
| 188 | 785.38 | 785.75 |
| 189 | 769.39 | 769.77 |
| 190 | 789.38 | 789.96 |
| 191 | 821.32 | 821.92 |
| 192 | 745.43 | 745.95 |
| 193 | 801.38 | 801.95 |
| 194 | 758.34 | 758.83 |
| 195 | 758.34 | 758.83 |
| 196 | 748.31 | 748.84 |
| 197 | 771.34 | 771.84 |
| 198 | 775.33 | 775.91 |
| 199 | 772.35 | 772.95 |
| 200 | 759.33 | 759.86 |
| 201 | 759.33 | 759.86 |
| 202 | 772.35 | 772.95 |
| 203 | 775.33 | 775.91 |
| 204 | 791.30 | 791.89 |
| 205 | 791.30 | 791.89 |
| 206 | 737.37 | 737.35 |
| 207 | 763.39 | 763.37 |
| 208 | 758.34 | 758.9 |
| 209 | 773.35 | 773.92 |
| 210 | 807.31 | 807.72 |
| 211 | 831.31 | 831.91 |
| 212 | 772.35 | 772.95 |
| 213 | 772.35 | 772.95 |
| 214 | 773.34 | 773.84 |
| 215 | 773.34 | 773.84 |
| 216 | 787.35 | 787.89 |
| 217 | 787.35 | 787.89 |
| 218 | 801.37 | 801.95 |
| 219 | 787.35 | 787.31 |
| 220 | 765.37 | 765.92 |
| 221 | 717.32 | 717.38 |
| 222 | 745.35 | 745.4 |
| 223 | 785.38 | 785.39 |
| 224 | 806.31 | 806.31 |
| 225 | 822.26 | 822.27 |
| 226 | 772.35 | 772.3 |
| 227 | 775.33 | 775.4 |
| 228 | 743.36 | 743.40 |
| 229 | 743.36 | 743.40 |
| 230 | 727.38 | 727.43 |
| 231 | 703.42 | 703.48 |
| 232 | 744.36 | 744.36 |
| 233 | 793.38 | 793.37 |
| 234 | 725.34 | 725.36 |
| 235 | 748.31 | 748.35 |
| 236 | 777.40 | 777.33 |
| 237 | 737.40 | 737.34 |
| 238 | 751.42 | 751.38 |
| 239 | 771.37 | 771.34 |
| 240 | 771.37 | 771.34 |
| 241 | 805.33 | 805.27 |
| 242 | 772.35 | 772.30 |
| 243 | 711.37 | 711.32 |
| 244 | 701.40 | 701.19 |
| 245 | 675.39 | 675.39 |
| 246 | 715.42 | 715.38 |
| 247 | 689.40 | 689.36 |
| 248 | 753.34 | 753.16 |
| 249 | 845.37 | 845.34 |
| 250 | 816.35 | 816.29 |
| 251 | 703.42 | 703.41 |

TABLE 2-continued

Physical data for Exemplary Compounds of the Invention.

| Cmpd No. | Exact Mass (M + H) | Observed Mass (M + H) |
|---|---|---|
| 252 | 627.39 | 627.42 |
| 253 | 719.42 | 719.45 |
| 254 | 690.40 | 690.4 |
| 255 | 717.35 | 717.38 |
| 256 | 641.31 | 641.39 |
| 257 | 733.34 | 733.35 |
| 258 | 704.33 | 704.37 |
| 259 | 756.39 | 756.34 |
| 260 | 802.37 | 802.32 |
| 261 | 861.41 | 861.38 |
| 262 | 877.41 | 877.34 |
| 263 | 772.39 | 772.38 |
| 264 | 739.32 | 739.26 |
| 265 | 831.35 | 831.29 |
| 266 | 802.34 | 802.24 |
| 267 | 834.47 | 834.39 |
| 268 | 825.47 | 825.37 |
| 269 | 901.46 | 901.29 |
| 270 | 731.30 | 731.28 |
| 271 | 793.32 | 793.30 |
| 272 | 807.33 | 807.30 |
| 273 | 710.34 | 710.28 |
| 274 | 724.36 | 724.26 |
| 275 | 779.39 | 779.33 |
| 276 | 793.42 | 793.30 |
| 277 | 791.33 | 791.22 |
| 278 | 791.33 | 791.29 |
| 279 | 787.36 | 787.16 |
| 280 | 785.38 | 785.31 |
| 281 | 785.38 | 785.31 |
| 282 | 787.44 | 787.38 |
| 283 | 754.37 | 754.38 |
| 284 | 856.38 | 856.28 |
| 285 | 829.37 | 829.30 |
| 286 | 785.38 | 785.31 |
| 288 | 785.38 | 785.31 |
| 289 | 799.40 | 799.29 |
| 290 | 785.38 | 785.31 |
| 291 | 799.40 | 799.36 |
| 292 | 760.35 | 760.30 |
| 293 | 743.45 | 743.40 |
| 294 | 759.45 | 759.22 |
| 295 | 747.43 | 747.24 |
| 296 | 807.34 | 807.27 |
| 297 | 793.33 | 793.30 |
| 298 | 807.34 | 807.27 |
| 299 | 801.34 | 801.28 |
| 300 | 778.41 | 778.29 |
| 301 | 764.39 | 764.32 |
| 302 | 786.37 | 786.48 |
| 303 | 738.37 | 738.30 |
| 304 | 780.39 | 780.29 |
| 305 | 789.36 | 789.23 |
| 306 | 789.36 | 789.23 |
| 307 | 801.38 | 801.28 |
| 308 | 789.36 | 789.31 |
| 309 | 865.39 | 865.30 |
| 310 | 703.42 | 703.33 |
| 311 | 703.42 | 703.33 |
| 312 | 703.42 | 703.33 |
| 313 | 689.40 | 689.36 |
| 314 | 689.40 | 689.36 |
| 315 | 729.44 | 729.36 |
| 316 | 773.42 | 773.34 |
| 317 | 861.41 | 861.50 |
| 318 | 772.35 | 772.40 |
| 319 | 801.38 | 801.40 |
| 320 | 857.44 | 857.60 |
| 321 | 815.39 | 815.40 |
| 322 | 829.37 | 829.50 |
| 323 | 786.37 | 786.40 |
| 324 | 795.31 | 795.30 |
| 325 | 825.34 | 825.23 |
| 326 | 811.32 | 811.26 |
| 327 | 759.34 | 759.29 |
| 328 | 811.32 | 811.26 |
| 329 | 811.32 | 811.26 |
| 330 | 773.34 | 773.27 |
| 331 | 819.48 | 819.53 |
| 332 | 743.45 | 743.44 |
| 333 | 718.42 | 718.45 |
| 334 | 714.46 | 714.45 |
| 335 | 743.45 | 743.40 |
| 336 | 849.49 | 849.60 |
| 337 | 744.47 | 744.40 |
| 338 | 772.36 | 772.43 |
| 339 | 815.35 | 815.39 |
| 340 | 801.37 | 801.38 |
| 341 | 842.40 | 842.45 |
| 342 | 743.45 | 743.59 |
| 343 | 773.46 | 773.61 |
| 344 | 748.43 | 748.54 |
| 345 | 728.36 | 728.28 |
| 346 | 686.43 | 686.50 |
| 347 | 742.37 | 742.41 |
| 348 | 700.44 | 700.55 |
| 349 | 770.37 | 770.50 |
| 350 | 728.48 | 728.58 |
| 351 | 773.46 | 773.54 |
| 352 | 774.42 | 774.50 |
| 353 | 772.36 | 772.43 |
| 354 | 758.37 | 758.45 |
| 355 | 716.44 | 716.51 |
| 356 | 772.38 | 772.50 |
| 357 | 730.46 | 730.57 |
| 358 | 800.42 | 800.53 |
| 359 | 758.49 | 758.60 |
| 360 | 773.46 | 773.54 |
| 361 | 730.43 | 730.47 |
| 362 | 716.42 | 716.45 |
| 363 | 841.44 | 841.55 |
| 364 | 770.37 | 770.43 |
| 365 | 784.38 | 784.48 |
| 366 | 742.37 | 742.48 |
| 367 | 829.37 | 829.42 |
| 368 | 816.35 | 816.41 |
| 369 | 787.44 | 787.47 |
| 370 | 774.42 | 774.43 |
| 371 | 806.46 | 806.51 |
| 372 | 812.45 | 812.50 |
| 373 | 765.42 | 765.55 |
| 374 | 765.42 | 765.55 |
| 375 | 759.44 | 759.56 |
| 376 | 731.41 | 731.39 |
| 377 | 653.40 | 653.38 |
| 378 | 745.43 | 745.36 |
| 379 | 715.42 | 715.37 |
| 380 | 747.62 | 747.41 |
| 381 | 730.43 | 730.43 |
| 382 | 733.41 | 733.38 |
| 383 | 805.47 | 805.48 |
| 384 | 760.41 | 760.45 |
| 385 | 865.34 | 865.45 |
| 386 | 789.36 | 789.44 |
| 387 | 799.40 | 799.49 |
| 388 | 807.35 | 807.47 |
| 390 | 785.38 | 785.51 |
| 391 | 700.33 | 700.48 |
| 392 | 714.34 | 714.53 |
| 393 | 730.34 | 730.50 |
| 394 | 744.35 | 744.48 |
| 395 | 735.45 | 735.48 |
| 396 | 749.38 | 749.51 |
| 397 | 716.32 | 716.38 |
| 398 | 686.31 | 686.36 |
| 399 | 729.35 | 729.42 |
| 400 | 746.33 | 746.40 |
| 401 | 716.32 | 716.53 |

TABLE 2-continued

Physical data for Exemplary Compounds of the Invention.

| Cmpd No. | Exact Mass (M + H) | Observed Mass (M + H) |
|---|---|---|
| 402 | 759.36 | 759.49 |
| 403 | 733.41 | 733.53 |
| 404 | 783.41 | 783.52 |
| 405 | 933.44 | 933.62 |
| 406 | 747.33 | 747.30 |
| 407 | 715.46 | 715.50 |
| 408 | 819.37 | 819.38 |
| 409 | 645.38 | 645.39 |
| 410 | 676.39 | 676.58 |
| 411 | 715.34 | 715.27 |
| 412 | 745.35 | 745.29 |
| 413 | 785.38 | 785.44 |
| 414 | 815.39 | 815.46 |
| 415 | 723.39 | 723.55 |
| 416 | 890.44 | 890.59 |
| 417 | 705.40 | 705.40 |
| 418 | 740.36 | 740.39 |
| 420 | 687.31 | 687.28 |
| 421 | 673.41 | 673.41 |
| 422 | 673.41 | 673.41 |
| 423 | 660.34 | 660.40 |
| 424 | 736.41 | 736.40 |
| 425 | 871.43 | 871.50 |
| 425 | 871.43 | 871.83 |
| 426 | 891.42 | 891.47 |
| 427 | 829.39 | 829.51 |
| 428 | 822.37 | 822.49 |
| 429 | 822.37 | 822.49 |
| 430 | 982.58 | 982.71 |
| 431 | 948.48 | 948.62 |
| 432 | 842.44 | 842.52 |
| 433 | 876.42 | 876.54 |
| 434 | 821.36 | 821.52 |
| 435 | 880.40 | 880.42 |
| 436 | 807.46 | 807.44 |
| 437 | 906.55 | 906.63 |
| 438 | 1024.51 | 1024.56 |
| 439 | 990.49 | 990.55 |
| 440 | 827.28 | 827.37 |
| 441 | 772.39 | 772.43 |
| 442 | 743.37 | 743.39 |
| 443 | 786.37 | 786.48 |
| 444 | 863.39 | 863.52 |
| 445 | 877.41 | 877.50 |
| 446 | 770.35 | 770.43 |
| 447 | 772.36 | 772.44 |
| 448 | 699.42 | 699.46 |
| 449 | 766.43 | 766.51 |
| 450 | 766.43 | 766.51 |
| 451 | 832.35 | 832.39 |
| 452 | 771.37 | 771.39 |
| 453 | 776.34 | 776.40 |
| 454 | 815.36 | 815.46 |
| 455 | 875.38 | 875.49 |
| 456 | 682.30 | 682.29 |
| 457 | 801.38 | 801.41 |
| 458 | 697.41 | 697.52 |
| 459 | 844.38 | 844.52 |
| 460 | 776.32 | 776.60 |
| 461 | 774.33 | 774.60 |
| 462 | 857.44 | 857.92 |
| 463 | 775.36 | 775.66 |
| 464 | 699.33 | 699.59 |
| 465 | 700.31 | 700.40 |
| 466 | 731.33 | 731.62 |
| 467 | 745.35 | 745.61 |
| 468 | 709.35 | 709.73 |
| 469 | 817.39 | 817.80 |
| 470 | 817.39 | 817.80 |
| 471 | 871.43 | 871.98 |
| 472 | 887.39 | 887.96 |
| 473 | 873.40 | 873.90 |
| 474 | 803.37 | 803.84 |
| 475 | 796.33 | 796.81 |
| 476 | 783.43 | 783.86 |
| 477 | 792.36 | 792.82 |
| 478 | 758.40 | 758.86 |
| 479 | 860.39 | 860.90 |
| 480 | 831.40 | 831.90 |
| 481 | 728.37 | 728.70 |
| 482 | 845.38 | 845.44 |
| 483 | 801.38 | 801.44 |
| 484 | 776.34 | 776.41 |
| 485 | 744.37 | 744.44 |
| 486 | 817.39 | 817.48 |
| 487 | 815.39 | 815.50 |
| 488 | 831.40 | 831.47 |
| 489 | 845.42 | 845.42 |
| 490 | 778.34 | 778.45 |
| 491 | 810.38 | 810.47 |
| 492 | 803.37 | 803.45 |
| 493 | 851.37 | 851.43 |
| 494 | 774.37 | 774.46 |
| 495 | 774.37 | 774.46 |
| 496 | 774.37 | 774.46 |
| 497 | 756.33 | 756.40 |
| 498 | 796.37 | 796.50 |
| 499 | 885.45 | 885.50 |
| 500 | 759.33 | 759.40 |
| 501 | 799.37 | 799.50 |
| 502 | 796.33 | 796.40 |
| 503 | 743.37 | 743.50 |
| 504 | 818.37 | 818.53 |
| 505 | 814.41 | 814.54 |
| 506 | 899.46 | 899.64 |
| 507 | 877.43 | 877.54 |
| 508 | 838.38 | 838.57 |
| 509 | 837.47 | 837.61 |
| 510 | 798.42 | 798.57 |
| 511 | 823.46 | 823.63 |
| 512 | 815.43 | 815.57 |
| 513 | 873.38 | 873.47 |
| 514 | 929.44 | 929.51 |
| 515 | 840.45 | 840.56 |
| 516 | 731.38 | 731.60 |
| 518 | 831.40 | 831.54 |
| 519 | 771.36 | 771.58 |
| 520 | 849.37 | 849.59 |
| 521 | 764.32 | 764.46 |
| 522 | 746.33 | 746.44 |
| 523 | 769.39 | 769.54 |
| 523 | 769.39 | 769.58 |
| 523 | 769.39 | 769.51 |
| 524 | 908.43 | 908.70 |
| 525 | 817.39 | 817.60 |
| 526 | 771.36 | 771.60 |
| 527 | 930.40 | 930.55 |
| 528 | 904.38 | 904.54 |
| 529 | 847.36 | 847.51 |
| 530 | 814.32 | 814.46 |
| 531 | 820.38 | 820.51 |
| 532 | 802.39 | 802.51 |
| 533 | 848.37 | 848.54 |
| 534 | 830.38 | 830.43 |
| 535 | 789.35 | 789.47 |
| 536 | 807.34 | 807.45 |
| 537 | 762.33 | 762.41 |
| 538 | 780.32 | 780.45 |
| 539 | 846.41 | 846.63 |
| 540 | 864.40 | 864.67 |
| 541 | 830.38 | 830.45 |
| 542 | 848.37 | 848.51 |
| 543 | 803.37 | 803.60 |
| 544 | 776.34 | 776.53 |
| 545 | 776.34 | 776.53 |
| 546 | 730.34 | 730.54 |
| 547 | 730.34 | 730.54 |
| 548 | 774.33 | 774.53 |

TABLE 2-continued

Physical data for Exemplary Compounds of the Invention.

| Cmpd No. | Exact Mass (M + H) | Observed Mass (M + H) |
|---|---|---|
| 549 | 799.36 | 799.60 |
| 550 | 801.37 | 801.60 |
| 551 | 801.37 | 801.60 |
| 552 | 828.42 | 828.66 |
| 553 | 803.39 | 803.60 |
| 554 | 775.34 | 775.50 |
| 555 | 784.36 | 784.56 |
| 556 | 916.40 | 916.67 |
| 557 | 840.37 | 840.64 |
| 558 | 764.33 | 764.55 |
| 559 | 814.32 | 814.46 |
| 560 | 839.35 | 839.53 |
| 561 | 803.37 | 803.60 |
| 562 | 871.46 | 871.63 |
| 563 | 872.43 | 872.58 |
| 564 | 775.34 | 775.57 |
| 565 | 810.34 | 810.54 |
| 566 | 849.39 | 849.66 |
| 567 | 851.37 | 851.60 |
| 568 | 714.33 | 714.53 |
| 569 | 755.35 | 755.54 |
| 570 | 753.37 | 753.59 |
| 571 | 762.33 | 762.43 |
| 572 | 780.32 | 780.45 |
| 573 | 842.40 | 842.56 |
| 574 | 830.40 | 830.58 |
| 575 | 805.35 | 805.59 |
| 576 | 801.37 | 801.60 |
| 577 | 739.36 | 739.56 |
| 578 | 753.37 | 753.53 |
| 579 | 714.33 | 714.49 |
| 580 | 728.34 | 728.54 |
| 581 | 790.36 | 790.43 |
| 582 | 817.41 | 817.49 |
| 583 | 831.38 | 831.47 |
| 584 | 858.43 | 858.53 |
| 585 | 788.34 | 788.43 |
| 586 | 787.36 | 787.40 |
| 587 | 844.42 | 844.54 |
| 588 | 768.39 | 768.47 |
| 589 | 788.38 | 788.44 |
| 590 | 806.37 | 806.47 |
| 591 | 824.36 | 824.45 |
| 592 | 789.35 | 789.47 |
| 593 | 818.34 | 818.38 |
| 594 | 829.37 | 829.62 |
| 595 | 754.40 | 754.49 |
| 596 | 761.46 | 761.52 |
| 597 | 792.37 | 792.50 |
| 598 | 750.44 | 750.50 |
| 599 | 757.50 | 757.60 |
| 600 | 807.46 | 807.59 |
| 601 | 814.52 | 814.68 |
| 602 | 809.44 | 809.58 |
| 603 | 816.50 | 816.61 |
| 604 | 822.47 | 822.60 |
| 605 | 829.53 | 829.68 |
| 606 | 787.38 | 787.50 |
| 607 | 755.37 | 755.47 |
| 608 | 773.36 | 773.50 |
| 609 | 741.35 | 741.48 |
| 610 | 759.34 | 759.45 |
| 611 | 768.41 | 768.47 |
| 612 | 636.38 | 636.41 |
| 613 | 782.43 | 782.45 |
| 614 | 789.49 | 789.54 |
| 615 | 754.40 | 754.42 |
| 616 | 761.46 | 761.52 |
| 617 | 789.35 | 789.47 |
| 618 | 803.37 | 803.45 |
| 619 | 817.39 | 817.49 |
| 620 | 777.35 | 777.42 |
| 621 | 817.39 | 817.49 |
| 622 | 819.36 | 819.42 |
| 623 | 789.47 | 789.54 |
| 624 | 672.40 | 672.49 |
| 625 | 711.44 | 711.38 |
| 626 | 871.54 | 871.48 |
| 627 | 926.45 | 926.42 |
| 628 | 814.41 | 814.36 |
| 629 | 891.43 | 891.38 |
| 630 | 821.39 | 821.39 |
| 631 | 841.45 | 841.45 |
| 632 | 658.38 | 658.33 |
| 633 | 872.34 | 872.36 |
| 634 | 872.34 | 872.36 |
| 635 | 836.34 | 836.33 |
| 636 | 850.35 | 850.32 |
| 637 | 928.40 | 928.37 |
| 638 | 928.40 | 928.37 |
| 639 | 881.38 | 881.39 |
| 640 | 775.48 | 775.45 |
| 641 | 936.46 | 936.51 |
| 642 | 908.43 | 908.47 |
| 643 | 790.40 | 790.41 |
| 644 | 848.51 | 848.47 |
| 645 | 906.41 | 906.54 |
| 646 | 844.50 | 844.55 |
| 647 | 734.41 | 734.39 |
| 649 | 943.36 | 943.39 |
| 650 | 886.47 | 886.42 |
| 651 | 904.38 | 904.33 |
| 652 | 722.29 | 722.20 |
| 653 | 858.51 | 858.46 |
| 654 | 814.37 | 814.36 |
| 655 | 839.45 | 839.44 |
| 656 | 902.39 | 902.40 |
| 657 | 936.41 | 936.51 |
| 658 | 942.36 | 942.43 |
| 659 | 978.42 | 978.45 |
| 660 | 901.43 | 901.44 |
| 661 | 974.42 | 974.38 |
| 662 | 925.40 | 925.41 |
| 663 | 772.44 | 772.40 |
| 664 | 742.43 | 742.38 |
| 665 | 770.46 | 770.42 |
| 666 | 822.36 | 822.29 |
| 667 | 950.40 | 950.34 |
| 668 | 908.47 | 908.41 |
| 669 | 892.40 | 892.34 |
| 670 | 850.47 | 850.42 |
| 671 | 766.39 | 766.42 |
| 672 | 690.36 | 690.37 |
| 673 | 654.38 | 654.41 |
| 674 | 808.32 | 808.30 |
| 675 | 732.29 | 732.31 |
| 676 | 696.31 | 696.14 |
| 677 | 718.39 | 718.27 |
| 678 | 822.34 | 822.20 |
| 679 | 780.41 | 780.33 |
| 680 | 732.41 | 732.24 |
| 681 | 668.39 | 688.39 |

NMR Data.

Compound 159:

$^1$H NMR (300 MHz, DMSO-d6) δ 9.96 (1H, s), 8.51 (3H, m), 8.01 (1H, t), 7.44 (2H, d), 7.37 (1H, dd), 7.27 (1H, dd), 7.24-7.12 (8H, m), 6.95 (1H, t), 4.76 (1H, q), 4.20 (1H, m), 3.76 (1H, dd), 3.50 (1H, dd), 3.44 (2H, d), 3.17-2.87 (7H, m), 2.76 (1H, m), 2.21 (2H, q), 2.12 (1H, d), 1.76 (1H, d), 1.65 (1H, m), 1.60-1.47 (3H, m), 1.45-1.29 (7H, m), 1.19 (3H, m), 0.86 (1H, m).

Compound 181:

$^1$H NMR (300 MHz, DMSO-d6) δ 12.46 (1H, br), 9.98 (1H, s), 8.51 (3H, m), 8.23 (1H, d), 7.46 (2H, d), 7.37 (1H, dd), 7.28 (1H, dd), 7.26-7.12 (9H), 7.06 (1H, t), 4.76 (1H, q), 4.19 (2H, m), 3.75 (1H, dd), 3.49 (1H, dd), 3.44 (2H, d), 3.18-2.93 (5H), 2.76 (1H, m), 2.21 (2H, d), 2.14 (1H, d), 1.85 (1H, d), 1.70-1.58 (3H), 1.58-1.47 (3H), 1.47-1.16 (7H), 0.91 (1H, m).

Compound 239:
$^1$H NMR (300 MHz, DMSO-d6) δ 10.07 (1H, s), 8.54 (3H, m), 8.01 (1H, t), 7.45 (2H, d), 7.36 (1H, s), 7.26-7.15 (8H, m), 7.09 (2H, d), 6.95 (1H, t), 4.65 (1H, m), 4.20 (1H, m), 3.76 (1H, dd), 3.52-3.35 (4H, m), 3.30-2.70 (8H, m), 2.21 (2H, dd), 2.12 (1H, d), 1.77 (1H, d), 1.65 (1H, m), 1.60-1.30 (11H, m), 1.18 (2H, m), 0.86 (1H, m).

Compound 242:
$^1$H NMR (300 MHz, DMSO-d6) δ 9.96 (1H, s), 8.48 (2H, m), 8.29 (1H, d), 7.43 (2H, d), 7.37 (1H, dd), 7.27 (1H, dd), 7.24-7.10 (9H, m), 4.75 (1H, m), 4.27 (1H, m), 4.11 (1H, m), 3.79 (2H, m), 3.43 (2H, q), 3.35 (1H, d), 3.20-2.60 (8H, m), 2.28 (1H, d), 2.16 (1H, d), 2.12 (1H, s), 1.65-1.36 (12H, m), 1.25 (1H, m), 1.06 (1H, m).

Compound 244:
$^1$H NMR (300 MHz, DMSO-d6) δ 9.97 (1H, s), 8.53 (2H, m), 8.34 (1H, d), 8.01 (1H, t), 7.87 (2H, d), 7.27 (3H, m), 7.20 (2H, d), 6.95 (1H, t), 4.46 (1H, q), 4.20 (1H, m), 3.76 (1H, dd), 3.49 (3H, m), 3.09 (2H, m), 2.95 (1H, dd), 2.88 (1H, m), 2.76 (1H, m), 2.21 (2H, q), 2.12 (1H, d), 1.76 (1H, d), 1.63 (2H, m), 1.57-1.30 (11H, m), 1.18 (2H, m), 0.86 (1H, m), 0.70 (1H, m), 0.32 (2H, m), 0.06 (2H, m).

Compound 256:
$^1$H NMR (300 MHz, DMSO-d6) δ 12.50 (1H, br), 9.97 (1H, s), 9.23 (1H, br), 8.54 (2H, m), 8.37 (1H, d), 8.10 (1H, m), 7.44 (2H, d), 7.37 (1H, dd), 7.27 (1H, dd), 7.24-7.14 (4H, m), 7.06 (1H, t), 6.92 (2H, d), 6.60 (2H, d), 4.73 (1H, q), 4.22 (1H, m), 4.13 (1H, q), 3.75 (1H, dd), 3.48 (1H, dd), 3.17-2.93 (6H, m), 2.77 (1H, dd), 2.24 (2H, d), 2.12 (1H, d), 1.87 (1H, d), 1.69-1.16 (15H, m), 0.93 (1H, m).

Compound 181:
$^1$H NMR (300 MHz, DMSO-d6) δ 12.46 (1H, br), 9.98 (1H, s), 8.51 (3H, m), 8.23 (1H, d), 7.44 (2H, d), 7.37 (1H, dd), 7.27 (1H, dd), 7.25-7.11 (8H, m), 7.06 (1H, t), 4.76 (1H, q), 4.19 (2H, m), 3.75 (1H, dd), 3.49 (1H, dd), 3.44 (1H, d), 3.18-2.93 (5H, m), 2.76 (1H, m), 2.24 (1H, d), 2.14 (1H, d), 1.85 (1H, d), 1.70-1.6 (3H, m), 1.58-1.47 (3H, m), 1.46-1.16 (7H, m), 0.91 (1H, m).

Compound 453:
$^1$H NMR (300 MHz, DMSO-d6) δ 9.93 (1H, s), 9.24 (1H, s), 8.41 (2H, q), 8.23 (1H, q), 7.59 (1H, t), 7.41 (2H, d), 7.36 (1H, dd), 7.26 (1H, dd), 7.20 (1H, td), 7.15 (2H, m), 7.00 (1H, t), 6.61 (1H, m), 6.56 (2H, m), 4.74 (1H, q), 4.37 (1H, m), 3.53-3.33 (12H, m), 3.16-2.94 (5H, m), 2.71 (1H, q), 2.37 (1H, d), 2.23 (1H, d), 2.01 (1H, d), 1.69 (1H, d), 1.64-1.36 (5H, m), 1.09 (1H, m), 1.00 (1H, m), 0.77 (1H, m).

Compound 474:
$^1$H NMR (300 MHz, DMSO-d6) δ 9.98 (1H, s), 8.49 (1H, d), 8.20 (1H, d), 7.99 (2H, m), 7.44 (2H, d), 7.37 (1H, d), 7.25 (2H, td), 7.18 (5H, m), 7.05 (2H, t), 7.56 (1H, m), 4.76 (1H, m), 4.21 (2H, m), 3.42 (4H, m), 3.27-2.83 (8H, m), 2.27 (1H, t), 2.05 (1H, d), 1.75 (2H, m), 1.52 (3H, m), 1.44-1.28 (6H, m), 1.22 (2H, d), 1.16 (2H, m), 0.83 (1H, m).

Compound 566:
$^1$H NMR (300 MHz, DMSO-d6) δ 9.97 (1H, s), 8.54 (2H, m), 8.37 (1H, d), 8.10 (1H, br), 7.44 (2H, d), 7.37 (1H, dd), 7.27 (1H, dd), 7.22 (1H, dd), 7.18 (3H, m), 7.06 (1H, t), 6.92 (2H, d), 6.61 (2H, d), 4.74 (1H, q), 4.22 (1H, m), 4.13 (1H, q), 3.76 (1H, dd), 3.48 (1H, dd), 3.29 (5H, m), 3.18-2.94 (6H, m), 2.77 (1H, q), 2.24 (2H, d), 2.13 (1H, d), 1.87 (1H, d), 1.68-1.19 (15H, m), 0.93 (1H, m).

Compound 406:
$^1$H NMR (300 MHz, DMSO-d6) δ 10.01 (1H, s), 9.05 (1H, d), 8.99 (1H, dd), 8.72 (1H, dd), 8.43 (1H, d), 8.22 (2H, m), 7.59 (1H, t), 7.55 (1H, q), 7.46 (2H, d), 7.40 (2H, m), 7.22 (2H, m), 7.17 (2H, d), 4.97 (1H, m), 4.37 (1H, m), 3.51-3.28 (11H, m), 3.19 (1H, q), 3.09 (1H, m), 2.97 (2H, m), 2.71 (1H, q), 2.36 (1H, d), 2.23 (1H, d), 2.00 (1H, d), 1.68 (1H, d), 1.61 (1H, m), 1.55-1.33 (4H, m), 1.08 (1H, m), 1.00 (1H, m), 0.77 (1H, m).

Compound 528:
$^1$H NMR (300 MHz, DMSO-d6) δ 12.41 (1H, br), 9.99 (1H, s), 8.50 (1H, d), 8.38 (1H, d), 8.25 (1H, d), 8.00 (1H, d), 7.46 (1H, d), 7.41-7.11 (9H), 7.06 (2H, t), 6.77 (1H, s), 4.78 (1H, m), 4.17 (3H, m), 3.24-3.08 (3H), 3.08-2.90 (3H), 2.72 (1H, m), 2.29 (2H, dd), 2.10 (3H, m), 1.95 (1H, m), 1.88-1.22 (15H), 1.79 (1H, m), 1.05 (1H, m), 0.74 (1H, m).

Compound 556:
$^1$H NMR (300 MHz, DMSO-d6) δ 10.28 (1H, s), 8.56 (1H), 8.43 (1H), 8.01 (1H), 7.82 (1H), 7.47 (2H, d), 7.38 (1H, d), 7.30 (2H), 7.26-7.14 (4H), 7.10 (2H), 6.88-6.7 (2H), 5.12 (1H), 4.77 (1H), 4.44 (2H), 4.30-4.10 (2H), 4.00 (1H), 3.43 (2H), 3.24-3.00 (4H), 2.90 (1H), 2.71 (1H), 2.43 (2H), 2.27 (2H), 2.07 (2H), 1.95 (2H), 1.86-1.00 (15H), 0.76 (1H).

Example 15

Evaluation of Biological Activity

Exemplary compounds were tested for the ability to bind to and modulate IL-17 activity in one or more of the below-described assays. Experimental procedures and results are provided below.

Experimental Procedures:

A. IL-17 ELISA Assay.

ELISA I: The ability of the compounds to block binding of IL17a to its receptor, IL17R, was analyzed in a competition ELISA format. High binding 96-well plates (Costar #9018) were coated with 20 nM of recombinant human IL17a (R&D Systems #317-ILB) in PBS (0.64 µg/mL), 100 µL/well, for 30 min at 37'C followed by 5 min at 4'C. Plates were then washed in PBST (PBS/0.05% Tween-20) on a plate washer, (Biotech EL-450) blocked with protein-free blocking buffer (Thermo Scientific #37573) in 250 µL/well for 30 min on shaker at room temperature, and then washed again. Compound dilutions prepared in PBST were added into the wells in duplicates followed by the addition of IL17R/Fc (R&D Systems #177-IR) at a final concentration of 12 nM. Plates were then incubated for 30 min at room temperature on the shaker. Wells with no compound served as a positive "no competitor" control, while wells with no IL17R/Fc and no compound served as a blank negative control. After an additional PBST wash, 50 ng/mL HRP-conjugated goat anti-human Fc IgG (KPL #04-10-20) was added to the plate for 30 min at room temperature, followed by PBST wash and addition of SureBlue™ TMB (KPL #52-00-03). After the sufficient color development, the reaction was fixed by the addition of 100 µL/well 0.5 N HCl and absorbance was measured at 450 nm on Biotek plate reader. The absorbances of 'no competitor' control and blank control did not exceed 1.0 A.U. and 0.05 A.U. respectively.

Data were processed using BioAssay Enterprise v10.1.4 (CambridgeSoft) software. Linear OD λ450 were plotted against log concentration (x) and fitted to a 4-parameter logistic equation. $IC_{50}$ was calculated using positive 'no competitor' control data as an upper limit and blank control as a lower limit in each assay.

ELISA II:

In this version, a high binding 96-well plate (Costar #9018) was coated with 20 nM of goat anti-human IgG (KPL 01-10-02) in PBS, 100 µL/well, for 30 min at 37° C. followed by 5 min at 4° C. The plate was then washed in PBST (PBS/0.05% Tween-20) on a plate washer, (BioTek ELx450) then blocked with protein-free blocking buffer (Thermo Scientific #37573) in 250 µL/well for 30 min on a shaker at room temperature, and then washed again. IL17R/Fc (R&D Systems #177-IR; 10 nM in PBST, 100 µL/well) was then added to all wells. The plate was then incubated for 30 minutes at room temperature on the shaker.

While the receptor capture step was underway, compound dilutions were prepared in PBST to a concentration of 1 µM in 1.5 mL tubes. After the receptor capture step, the plate was washed and 50 µL PBST was added to the wells in row B down to row H. Then, 62.5 µL of the 1 µM compound dilutions were added to the wells of row A. From row A, 12.5 µL of the compound solution was removed and added to row B with mixing and this process of 5-fold dilutions was continued, by row, to row G. One of the wells in row A received only PBST (62.5 µL) and this dilution series served as the no competitor control. Then, going up from row G to row A, 50 µL of b-IL-17 (biotinylated human IL-17, R&D Systems #317-ILB; 20 nM) was added to all wells. Row H received 50 µL of PBST and served as the blank row, i.e., no compound and no b-IL-17. The plate was then incubated for 30 minutes at room temperature on the shaker.

After the wash, 100 µL Streptavidin-Horseradish Peroxidase (SA-HRP) (KPL #14-30-00) at 25 ng/mL in PBST was added to each well in the plate and the plate incubated for 30 minutes at room temperature followed by wash and 100 µL SureBlue™ TMB (KPL #52-00-03). After sufficient color development (approx 3-6 minutes), the reaction was fixed by the addition of 100 µL/well 0.5 N HCl and absorbance was measured at 450 nm on a BioTek Synergy 2 plate reader. The absorbances of 'no competitor' control and blank control should not exceed 1.5 A.U. and 0.06 A.U., respectively.

Data was processed using BioAssay Enterprise v10.1.4 (CambridgeSoft) software. Linear OD λ450 were plotted against log concentration (x) and fitted to a 4-parameter logistic equation. IC50 was calculated using positive 'no competitor' control data as an upper limit and blank control as a lower limit in each assay.

B. Surface Plasmon Resonance (SPR) Analysis of Compound Interactions with IL17A

SPR analysis was carried out with a GE Healthcare (Piscataway, N.J.) Biacore X100 system. Typically, the chip (NTA Biacore Biosensor chip; GE Healthcare BR-1000-34) was first conditioned by injection of 0.35 M EDTA, which also served to remove any immobilized proteins from previous runs. Before immobilization of the recombinant 6-His-tagged IL17, the chip was washed with 0.5 mM nickel chloride in NTA buffer (10 mM HEPES buffer, 0.15 M sodium chloride, 10 µM ethylene diamine tetraacetic acid, 0.005% v/v surfactant P20 (GE Healthcare BR-1000-54)) to form a nickel chelate on the chip. IL17 protein was immobilized onto a NTA chip through its 6-His tag. IL17A was typically injected at 0.25 µM for 60-120 seconds, followed by a stabilization step washing with NTA+0.5% DMSO for 120 seconds or longer.

Five 2-fold or 3-fold serial dilutions of test compound were injected serially onto the chip. All steps were conducted using NTA buffer containing 0.5% v/v dimethylsulfoxide (DMSO). Compounds were diluted from stock solutions of 10 mM concentration in 100% DMSO with NTA buffer to obtain 50 µM solutions in NTA+0.5% DMSO. Subsequent 2× or 3× dilutions were made in NTA+0.5% DMSO. Compound was generally injected for 180 seconds followed by washing the chip in buffer alone for 120 seconds. The rate of refractive index change (RU units/time) and the maximum extend of RU change was measured during the "on" phase of analyte injection, followed by measuring the rate during the "off" phase.

Kinetic parameter fits were conducted using the Biacore SPR Evaluation Program (GE Healthcare) for 1:1 molecular binding fits, after subtracting the baseline average of 2 or more runs in which no analyte was injected. This program then reports the best fit average for the "on" rate (Ka), the "off" rate (Kd) and the dissociation constant (KD) (Chaiken, I et al., Anal Biochem 201, 197-210 (1992)). A separate program in the Biacore SPR Evaluation Program then calculates the best fit for Kd based upon the extent of binding alone (RU units bound) at each concentration of analyte and reports the best fit Kd by best fit to a Lineweaver-Burke plot. Typically, the Kd value calculated through both means agreed within a factor of three.

The presence and activity of IL17 on the NTA chip was routinely confirmed three ways:

1) An increase in response units (RU) upon immobilization confirms that the IL17 was immobilized on the chip;

2) Anti-IL17 was also injected on the chip to confirm the presence of IL17; and

3) IL17R was injected onto the chip to confirm that the immobilized IL17 retained its binding activity for its receptor.

Negative controls to access specificity for compound binding were conducted by immobilizing unrelated, but his-tagged, proteins (such as cyclophilin D) and conducting the same analysis as done with IL17A.

C. Inhibition of IL17A Induced Secretion of IL6 in Human Rheumatoid Arthritis Synovial Fibroblast Cells This assay was used to determine the extent of inhibition of IL-17A induced secretion of IL-6 in primary human rheumatoid synovial fibroblast (RASF) cells by compounds of the invention. IL-17A is known to stimulate IL-6 production in RASF cells.

Low passage (passage 2-8) Primary human RASF cells (Asterand) were maintained in maintenance medium. Cells were detached from flasks by tryptic digestion and the cell density of the suspension determined. To each well of a 96 well culture plate was added 100 µL of seeding medium containing 50,000 cells/mL and the plate incubated overnight in a humidified 37° C., 5% $CO_2$ incubator. The medium was replaced with fresh assay medium and cells were incubated for additional 5 hours in a humidified 37° C., 5% $CO_2$ incubator prior to stimulation with recombinant human IL-17A ("rhIL-17A"). Prior to addition to cells, rhIL-17A (30 ng/mL) in assay medium was incubated with either DMSO alone, compounds, or anti-IL17 receptor antibody (3 µg/mL) for 1 hour at 37° C. The final concentration of DMSO in all samples was 0.25%. The final concentration of compounds varied from 0.03 µM to 25 µM.

Immediately before stimulation, cells were washed once with fresh assay medium. Then, 100 µL of the test samples was added in triplicate wells and the plates incubated for 20 hours in a humidified 37° C., 5% $CO_2$ incubator. The assay medium from each well was collected and the IL-6 concentration in cell culture supernatants was determined by ELISA either immediately or after storage at −20° C.

A water-soluble tetrazolium salt (WST1) viability assay was immediately performed on the cells after the conditioned medium was collected using a WST1 reagent purchased from Roche. The concentration of IL-6 obtained from ELISA was normalized by the WST1 data.

D. HT-29 Cellular Assay

To test the ability of a compound of the invention to neutralize or antagonize IL-17 bioactivity, the following cell-based assay was used. IL-17 can stimulate epithelial cells and other cells to secrete GROα. The ability of a compound of the invention to neutralize IL-17-induced GROα secretion from the human colorectal adenocarcinoma epithelial cell line HT-29 is tested in this assay.

HT-29 cells (human colorectal adenocarcinoma epithelial cells, ATCC #HTB-38), were maintained in culture/assay medium in tissue culture-treated flasks using standard techniques. HT-29 cells were grown in tissue culture flasks until they were 50-80% confluent on the day before the assay. The day before the assay, the cells were detached from the culture flasks with trypsin+EDTA. The trypsin was inactivated with complete assay medium. HT-29 cells were then centrifuged at 500×g for 5 minutes at room temperature. The cell pellet was then re-suspended in Defined Keratinocyte SFM (Invitrogen #10766019)+10% FCS and 50,000 HT-29 cells (in 100 μl) were added to each treatment well of the 96-well plates. The 96-well plates were placed in a tissue culture incubator (37° C., 5% $CO_2$) overnight. The next day, the media was removed from the cells and the cells were washed twice with Defined Keratinocyte SFM. In a separate 96-well plate, compounds to be tested were serially diluted in Defined Keratinocyte SFM and run in triplicate in 100 μL total volume. To these compound samples were then added 100 μL of human IL-17 at a concentration of 20 ng/mL in Defined Keratinocyte SFM for serum-free assays. 150 μL of the compound/IL-17 mixture was then added to the cells from which the media has previously been removed. The cells were grown for 48 hours in Defined Keratinocyte SFM in a tissue culture incubator (37° C., 5% $CO_2$).

At the end of the incubation, the plates are centrifuged (500×g for 5 minutes at room temperature), and the cell culture media is transferred to polypropylene 96-well plates. The supernatant was used neat in the ELISA. GROα levels are measured with a GROα sandwich ELISA (R+D Systems DuoSet #DY275E), as per the manufacturer's instructions. The ELISA plates were previously coated with mAb 275 (R+D Systems) at 4 μg/mL. GROα is detected using biotinylated goat anti-human GROα (R+D Systems BAF275) at 200 ng/mL using TMB as a substrate. At the end of the ELISA reactions, plates are read at 450 nm on a microplate reader and compared to a standard calibration curve.

The results of the biochemical and cellular assays are set forth in Table 3 below. For each of the ELISA, SPR and RASF assays, "A" indicates a value of less than 100 nM; "B" a value of between 100 nM and 1 μM; "C" a value between greater than 1 μM and 10 μM; and "D" a value of greater than 10 μM. For the HT-29 assay, "A" indicates a value of less than 1 μM; "B" a value of between 1 μM and 10 μM; "C" a value greater than 10 μM. For every assay, a "*" indicates that some binding or activity was observed, but compound concentration was not taken high enough to calculate an IC50 value. Blank cells indicate that the compound was not tested in that particular assay. Some compounds appear more than once in the Table below because they were tested in more than one run in one or more assays.

TABLE 3

Assay Results for Select Compounds of Formula I

| Cmpd No. | ELISA I | ELISA II | SPR | RASF | HT-29 |
|---|---|---|---|---|---|
| 100 | | | * | | |
| 101 | | | C | | * |
| 101 | | | C | | |
| 102 | | | D | | |
| 103 | | | D | | |
| 104 | | | C | | |
| 105 | | | C | | * |
| 105 | | | B | | |
| 106 | B | | B | D | C |
| 106 | | | B | | |
| 107 | | | B | | C |
| 107 | | | B | | |
| 108 | | | A | | B |
| 108 | | | A | | B |
| 109 | | | B | | B |
| 110 | | | B | | C |
| 111 | | | B | | |
| 112 | | | A | | B |
| 113 | | | B | | C |
| 114 | | | B | | |
| 115 | | | B | | |
| 116 | | | B | | |
| 117 | | | B | | |
| 118 | | | B | | |
| 119 | | | B | | |
| 120 | | | * | | B |
| 121 | | | B | | |
| 122 | C | | C | C | |
| 123 | * | | C | * | |
| 124 | | | B | | |
| 125 | | | B | | |
| 126 | | | B | | |
| 127 | | | B | | |
| 128 | | | B | | |
| 129 | | | * | | |
| 130 | | | * | | |
| 131 | | | * | | |
| 132 | | | * | | |
| 133 | | | * | | |
| 134 | | | B | | |
| 135 | | | B | | |
| 136 | | | A | | |
| 137 | | | B | | |
| 138 | | | B | | |
| 139 | | | B | | |
| 140 | | | B | | |
| 141 | | | A | | B |
| 142 | | | A | | B |
| 143 | A | | A | C | A |
| 144 | A | | A | C | B |
| 145 | | | A | | |
| 146 | | | A | | |
| 147 | | | B | | |
| 148 | | | B | | |
| 149 | | | A | | |
| 150 | | | A | | |
| 151 | | | A | | |
| 152 | | | B | | |
| 153 | A | | A | C | |
| 154 | | | A | | |
| 155 | | | A | | |
| 156 | | | A | | |
| 157 | | | A | | |
| 158 | A | | A | | |
| 159 | A | | A | C | A |
| 159 | A | | A | C | |
| 159 | A | | | | |
| 160 | | | A | | |
| 161 | | | A | | |
| 162 | | | A | | |
| 163 | | | A | | |
| 164 | A | | A | | |
| 165 | | | A | | |
| 166 | | | A | | |
| 167 | | | A | | |

TABLE 3-continued

Assay Results for Select Compounds of Formula I

| Cmpd No. | ELISA I | ELISA II | SPR | RASF | HT-29 |
|---|---|---|---|---|---|
| 168 | | | A | C | |
| 169 | B | | A | D | |
| 170 | | | A | | |
| 171 | | | A | | |
| 172 | | | A | | |
| 173 | | | A | | |
| 174 | | | B | | |
| 175 | | | B | | |
| 176 | | | B | | |
| 177 | | | A | | B |
| 178 | | | B | | |
| 179 | | A | B | | |
| 180 | A | | A | | A |
| 181 | A | A | A | C | A |
| 182 | | | B | | |
| 183 | C | | B | | |
| 184 | | | A | | B |
| 185 | A | | A | C | B |
| 185 | A | | A | C | |
| 186 | A | A | A | C | |
| 187 | A | | A | | B |
| 188 | C | | B | | |
| 189 | | | A | | |
| 190 | | | B | | |
| 191 | A | | A | C | A |
| 192 | A | | A | C | |
| 193 | B | | A | * | |
| 194 | A | A | A | B | |
| 195 | B | A | B | | |
| 196 | A | | A | | |
| 197 | | | B | | |
| 198 | A | | A | C | |
| 199 | A | | A | | |
| 200 | B | | B | | |
| 201 | B | | A | D | |
| 202 | A | | A | | |
| 203 | A | | A | | |
| 204 | B | | A | | |
| 205 | A | | A | | |
| 206 | A | | A | C | |
| 207 | B | | A | | |
| 208 | | | A | | |
| 209 | A | | A | C | |
| 210 | | | A | | |
| 211 | A | | A | C | |
| 212 | B | | B | | |
| 213 | D | | B | | |
| 214 | A | | A | * | |
| 215 | | | A | | |
| 216 | A | | A | C | |
| 217 | A | | * | | |
| 218 | A | A | * | A | |
| 219 | B | | * | | |
| 220 | B | | * | | |
| 221 | C | | B | | |
| 222 | A | | A | * | |
| 223 | A | | A | | |
| 224 | C | | B | | |
| 225 | C | | B | | |
| 226 | A | A | A | C | |
| 227 | B | | A | C | |
| 228 | A | | A | * | |
| 229 | A | | * | | |
| 230 | A | | A | | |
| 231 | * | B | B | | |
| 232 | C | | B | | |
| 233 | B | | A | | |
| 234 | B | | | | |
| 235 | B | | | | |
| 236 | A | | | C | |
| 237 | A | | | | |
| 238 | C | | | | |
| 239 | A | | | | |
| 240 | A | | | | |
| 241 | B | | | | |
| 242 | A | | | D | |
| 243 | * | | | | |
| 244 | B | A | | | |
| 245 | C | | | | |
| 246 | A | A | | D | |
| 247 | B | | | | |
| 248 | A | | | | |
| 249 | A | | | | |
| 250 | A | | | | |
| 251 | B | | | C | |
| 252 | C | | | | |
| 253 | B | | | C | |
| 254 | C | | | D | |
| 255 | C | | | | |
| 256 | D | | | | |
| 257 | B | | | | |
| 258 | C | | | | |
| 259 | B | A | | | |
| 260 | A | | | C | |
| 261 | A | | | C | |
| 262 | A | | | | |
| 263 | A | | | C | |
| 264 | A | A | | B | |
| 265 | A | | | | |
| 266 | A | A | | B | |
| 267 | | | B | | |
| 268 | | | A | | |
| 269 | | | A | | |
| 270 | C | | | | |
| 271 | C | | | | |
| 272 | B | | | | |
| 273 | B | A | | C | |
| 274 | A | A | | B | |
| 275 | B | | | | |
| 276 | C | | | | |
| 277 | B | | | | |
| 278 | C | | | | |
| 279 | A | | | | |
| 280 | A | | | | |
| 280 | A | A | | | |
| 281 | A | | | | |
| 282 | A | | | | |
| 283 | | B | | | |
| 284 | B | | | | |
| 285 | A | | | | |
| 286 | B | | | | |
| 288 | A | A | | A | |
| 289 | C | | | | |
| 290 | B | | | | |
| 291 | C | | | | |
| 292 | B | A | | B | |
| 292 | | A | | C | |
| 293 | B | A | | C | |
| 294 | A | | | | |
| 295 | | | | | |
| 296 | A | | | | |
| 297 | A | | | | |
| 298 | A | | | | |
| 299 | C | | | | |
| 300 | B | | | | |
| 301 | C | | | | |
| 302 | A | A | | B | |
| 303 | B | | | | |
| 304 | B | | | | |
| 305 | A | A | | B | |
| 306 | B | | | | |
| 307 | A | | | | |
| 308 | B | | | | |
| 309 | B | | | | |
| 310 | B | A | | | |
| 311 | B | A | | | |
| 312 | B | A | | | |
| 313 | B | A | | * | |
| 314 | B | A | | | |
| 315 | C | * | | | |

TABLE 3-continued

Assay Results for Select Compounds of Formula I

| Cmpd No. | ELISA I | ELISA II | SPR | RASF | HT-29 |
|---|---|---|---|---|---|
| 316 | A | A | | B | |
| 317 | A | | | | |
| 318 | B | | | | |
| 319 | B | | | | |
| 320 | B | | | | |
| 321 | B | | | | |
| 322 | B | | | | |
| 323 | B | | | | |
| 324 | B | | | | |
| 325 | A | A | | | |
| 326 | B | | | | |
| 327 | A | | | | |
| 328 | B | | | | |
| 329 | B | | | | |
| 330 | B | | | | |
| 331 | B | | | | |
| 332 | B | A | | C | |
| 333 | B | A | | | |
| 334 | C | * | | | |
| 335 | B | A | | | |
| 336 | B | A | | B | |
| 337 | B | | | | |
| 338 | B | A | | D | |
| 339 | A | A | | B | |
| 340 | A | A | | B | |
| 341 | A | A | | A | |
| 342 | B | A | | B | |
| 343 | B | | | | |
| 344 | C | B | | | |
| 345 | B | A | | | |
| 346 | C | A | | | |
| 347 | B | A | | | |
| 348 | C | B | | | |
| 349 | C | A | | | |
| 350 | * | B | | | |
| 351 | B | | | | |
| 352 | C | | | D | |
| 353 | B | A | | C | |
| 354 | B | A | | | |
| 355 | C | A | | | |
| 356 | B | A | | | |
| 357 | B | A | | | |
| 358 | B | A | | | |
| 359 | C | A | | | |
| 360 | B | A | | | |
| 361 | B | A | | C | |
| 362 | C | B | | | |
| 363 | * | B | | | |
| 364 | B | A | | | |
| 365 | * | A | | | |
| 366 | * | B | | | |
| 367 | A | A | | A | |
| 368 | B | A | | B | |
| 369 | A | A | | A | |
| 370 | B | A | | | |
| 371 | * | C | | | |
| 372 | C | B | | | |
| 373 | A | A | | | |
| 374 | A | A | | | |
| 375 | B | A | | | |
| 376 | B | A | | | |
| 377 | A | B | | | |
| 378 | B | A | | B | |
| 379 | C | A | | | |
| 380 | A | A | | B | |
| 381 | B | A | | | |
| 382 | B | A | | | |
| 383 | * | C | | | |
| 384 | B | A | | | |
| 385 | | | | | |
| 386 | | A | | C | |
| 387 | | A | | * | |
| 388 | | A | | A | |
| 390 | | * | | | |
| 391 | | A | | | |
| 392 | | A | | | |
| 393 | | A | | | |
| 394 | | A | | | |
| 395 | | A | | | |
| 396 | | A | | | |
| 397 | | A | | | |
| 398 | | A | | | * |
| 399 | | A | | | C |
| 400 | | A | | | |
| 401 | | A | | | |
| 402 | | A | | | |
| 403 | | A | | | |
| 404 | | A | | | |
| 405 | | A | | | B |
| 406 | | A | | | C |
| 407 | | B | | | |
| 408 | | A | | | B |
| 409 | | B | | | |
| 410 | | B | | | |
| 411 | | A | | | |
| 412 | | B | | | |
| 413 | | A | | | D |
| 414 | | | | | |
| 415 | | B | | | |
| 416 | | A | | | |
| 417 | | B | | | * |
| 418 | | A | | | |
| 420 | | B | | | * |
| 421 | | C | | | |
| 422 | | C | | | |
| 423 | | C | | | |
| 424 | | A | | | D |
| 425 | | A | | | B |
| 425 | | * | | | |
| 426 | | B | | | |
| 427 | | A | | | C |
| 428 | | A | | | |
| 429 | | A | | | |
| 430 | | A | | | |
| 431 | | A | | | |
| 432 | | A | | | |
| 433 | | A | | | |
| 434 | | A | | | B |
| 435 | | A | | | |
| 436 | | B | | | |
| 437 | | B | | | C |
| 438 | | A | | | B |
| 439 | | A | | | B |
| 440 | | B | | | |
| 441 | | A | | | B |
| 442 | | A | | | C |
| 443 | | A | | | B |
| 444 | | A | | | |
| 445 | | A | | | |
| 446 | | A | | | B |
| 447 | | A | | | |
| 448 | | B | | | |
| 449 | | B | | | |
| 450 | | A | | | |
| 451 | | A | | | |
| 452 | | C | | | |
| 453 | | A | | | B |
| 454 | | C | | | |
| 455 | | A | | | A |
| 456 | | B | | | |
| 457 | | A | | | C |
| 458 | | C | | | |
| 459 | | A | | | |
| 460 | | A | | | |
| 461 | | A | | | |
| 462 | | A | | | |
| 463 | | A | | | |
| 464 | | A | | | |
| 465 | | A | | | * |
| 466 | | A | | | |

TABLE 3-continued

Assay Results for Select Compounds of Formula I

| Cmpd No. | ELISA I | ELISA II | SPR | RASF | HT-29 |
|---|---|---|---|---|---|
| 467 | | A | | | |
| 468 | | A | | | |
| 469 | | A | | C | |
| 470 | | A | | B | |
| 471 | | B | | | |
| 472 | | A | | | |
| 473 | | A | | B | |
| 474 | | A | | B | |
| 475 | | A | | B | |
| 476 | | A | | B | |
| 477 | | A | | | |
| 478 | | A | | C | |
| 479 | | A | | A | |
| 480 | | A | | C | |
| 481 | | B | | | |
| 482 | | A | | | |
| 483 | | A | | | |
| 484 | | A | | B | |
| 485 | | A | | | |
| 486 | | A | | | |
| 487 | | A | | A | |
| 488 | | A | | C | |
| 489 | | A | | | |
| 490 | | A | | C | |
| 491 | | C | | | |
| 492 | | B | | | |
| 493 | | | | | |
| 494 | | A | | B | |
| 495 | | A | | C | |
| 496 | | A | | | |
| 497 | | A | | C | |
| 498 | | C | | | |
| 499 | | A | | B | |
| 500 | | A | | | |
| 501 | | | | | |
| 502 | | A | | C | |
| 503 | | C | | | |
| 504 | | B | | | |
| 505 | | C | | | |
| 506 | | * | | | |
| 507 | | A | | C | |
| 508 | | B | | | |
| 509 | | B | | | |
| 510 | | B | | | |
| 511 | | A | | | |
| 512 | | A | | B | |
| 513 | | A | | B | |
| 514 | | B | | | |
| 515 | | A | | A | |
| 516 | | D | | | |
| 518 | | A | | | |
| 519 | | A | | | |
| 520 | | A | | | |
| 521 | | A | | | |
| 522 | | A | | C | |
| 523 | | * | | * | |
| 523 | | * | | | |
| 524 | | A | | | |
| 525 | | A | | | |
| 526 | | B | | | |
| 527 | | A | | | |
| 528 | | A | | A | |
| 529 | | A | | A | |
| 530 | | A | | | |
| 531 | | B | | | |
| 532 | | B | | | |
| 533 | | B | | | |
| 534 | | A | | | |
| 535 | | A | | C | |
| 536 | | A | | B | |
| 537 | | A | | | |
| 538 | | B | | | |
| 539 | | A | | C | |
| 540 | | A | | C | |
| 541 | | A | | | |
| 542 | | A | | | |
| 543 | | A | | | |
| 544 | | A | | | |
| 545 | | A | | | |
| 546 | | B | | | |
| 547 | | B | | | |
| 548 | | A | | | |
| 549 | | A | | A | |
| 550 | | A | | C | |
| 551 | | A | | C | |
| 552 | | A | | A | |
| 553 | | A | | B | |
| 554 | | A | | * | |
| 555 | | A | | A | |
| 556 | | A | | A | |
| 557 | | B | | | |
| 558 | | A | | * | |
| 559 | | A | | | |
| 560 | | A | | A | |
| 561 | | A | | C | |
| 562 | | A | | C | |
| 563 | | B | | | |
| 564 | | B | | | |
| 565 | | A | | | |
| 566 | | A | | B | |
| 567 | | A | | B | |
| 568 | | A | | | |
| 569 | | A | | | |
| 570 | | A | | | |
| 571 | | A | | C | |
| 572 | | A | | | |
| 573 | | A | | | |
| 574 | | A | | | |
| 575 | | A | | | |
| 576 | | A | | | |
| 577 | | A | | | |
| 578 | | A | | | |
| 579 | | A | | | |
| 580 | | A | | | |
| 581 | | A | | | |
| 582 | | A | | C | |
| 583 | | A | | | |
| 584 | | A | | C | |
| 585 | | A | | | |
| 586 | | A | | | |
| 587 | | A | | | |
| 588 | | A | | | |
| 589 | | A | | | |
| 590 | | A | | | |
| 591 | | A | | | |
| 592 | | B | | | |
| 593 | | A | | B | |
| 594 | | A | | | |
| 595 | | A | | | |
| 596 | | A | | | |
| 597 | | A | | | |
| 598 | | * | | | |
| 599 | | A | | | |
| 600 | | A | | C | |
| 601 | | A | | C | |
| 602 | | A | | | |
| 603 | | A | | | |
| 604 | | A | | | |
| 605 | | A | | | |
| 606 | | D | | | |
| 607 | | D | | | |
| 608 | | D | | | |
| 609 | | D | | | |
| 610 | | D | | | |
| 611 | | A | | | |
| 612 | | A | | | |
| 613 | | A | | | |
| 614 | | A | | | |
| 615 | | A | | | |
| 616 | | A | | | |

TABLE 3-continued

Assay Results for Select Compounds of Formula I

| Cmpd No. | ELISA I | ELISA II | SPR | RASF | HT-29 |
|---|---|---|---|---|---|
| 617 |  | A |  |  |  |
| 618 |  | A |  |  |  |
| 619 |  | A |  |  |  |
| 620 |  | A |  |  |  |
| 621 |  | A |  |  |  |
| 622 |  | B |  |  |  |
| 623 |  | A |  |  |  |
| 624 |  | D |  |  |  |
| 625 |  | B |  |  |  |
| 626 |  | A |  | B |  |
| 627 |  | A |  | B |  |
| 628 |  | A |  |  |  |
| 629 |  | A |  |  |  |
| 630 |  | A |  |  |  |
| 631 |  | A |  |  |  |
| 632 |  | B |  |  |  |
| 633 |  | A |  |  |  |
| 634 |  | A |  |  |  |
| 635 |  | A |  |  |  |
| 636 |  | A |  |  |  |
| 637 |  | A |  |  |  |
| 638 |  | A |  |  |  |
| 639 |  | A |  | C |  |
| 640 |  | A |  |  |  |
| 641 |  | A |  |  |  |
| 642 |  | A |  |  |  |
| 643 |  | A |  |  |  |
| 644 |  | A |  |  |  |
| 645 |  | A |  | B |  |
| 646 |  | A |  | C |  |
| 647 |  | A |  |  |  |
| 649 |  | A |  |  |  |
| 650 |  | A |  |  |  |
| 651 |  | A |  |  |  |
| 652 |  | B |  |  |  |
| 653 |  | A |  | C |  |
| 654 |  | A |  |  |  |
| 655 |  | A |  |  |  |
| 656 |  | A |  | A |  |
| 657 |  | A |  | A |  |
| 658 |  | A |  | A |  |
| 659 |  | A |  |  |  |
| 660 |  | A |  | A |  |
| 661 |  | A |  | A |  |
| 662 |  | A |  | A |  |
| 663 |  | A |  |  |  |
| 664 |  | A |  |  |  |
| 665 |  | A |  |  |  |
| 666 |  | A |  |  |  |
| 667 |  | A |  |  |  |
| 668 |  | A |  |  |  |
| 669 |  | A |  |  |  |
| 670 |  | A |  |  |  |
| 671 |  | A |  |  |  |
| 672 |  | A |  |  |  |
| 673 |  | A |  |  |  |
| 674 |  | A |  |  |  |
| 675 |  | A |  |  |  |
| 676 |  | A |  |  |  |
| 677 |  | B |  |  |  |
| 678 |  | A |  |  |  |
| 679 |  | A |  |  |  |
| 680 |  | B |  |  |  |
| 681 |  | A |  |  |  |

E. Murine Model of Delayed Hypersensitivity

We used a murine model of fluorodinitrobenzene (DNFB)-induced ear edema to test the anti-inflammatory activity of both orally dosed and intraperitoneally dosed exemplary compounds of the invention. BALB/c mice (Harlan Sprague-Dawley, Inc., male, 6-8 weeks old) were topically treated on their shaved abdomen with 30 μL of 0.5% 1-fluoro-2,4-dinitrobenzene (DNFB) (4:1 acetone:olive oil) once on Day 0 and once on Day 1.

For oral dosing ("PO"), exemplary compounds of the invention were either suspended at 3 mg/mL in 20% Cremophor EL (Sigma) (20:80; Cremophor:water) or dissolved at 1 mg/mL or 3 mg/mL in D-α-tocopherol polyethylene glycol 1000 succinate (TPGS; Sigma)/PEG-400/water (20:60:20). For intraperitoneal dosing ("IP"), exemplary compounds of the invention were dissolved in DMSO at a concentration of 5 mg/mL. On day 7, the test compound was administered (PO at either 10 mg/kg or 30 mg/kg; IP at 1, 3, or 10 mg/kg) to DNFB-treated mice. Commercially available anti-mouse IL-17A (BioLegend) administered intraperitoneally at 5 mg/kg in PBS was used as a positive control. Thirty minutes later, 20 μL of 0.2% DNFB was applied to the right ear of animals and vehicle (DNFB:olive oil) was applied to the left ear. One and four hours after DNFB challenge, a subset of mice was exsanguinated and plasma prepared from the blood. Twenty-four hours after challenge, the remaining mice were euthanized, and their ears were removed and weighed to determine the amount of edema. Plasma was assayed for interleukin-6, TNF-α, CXCL1, and interferon-γ concentrations using commercially-available assays. The results are shown in FIGS. 1-5 and summarized in Table 4, below.

TABLE 4

Delayed Hypersensitivity Assay Results for Select Compounds of Formula I

| Cmpd No. | Route | Dose (mg/kg) | IL6 Reduction (%) | IFNγ Reduction (%) | CXCL1 Reduction (%) | TNFα Reduction (%) | Reduction in edema (%) |
|---|---|---|---|---|---|---|---|
| 159 | po | 10 | 29.8 | 24.2 |  |  | 19.0 |
|  | po | 30 | 58.3 | 64.5 |  |  | 53.7 |
| 465 | po | 30 | 42.5 | 47.4 |  |  | 23.5 |
| 453 | po | 3 | 9.3 | 29.2 | −17.0 |  | 7.7 |
|  | po | 10 | 35.9 | 35.6 | 31.0 |  | 36.7 |
|  | po | 30 | 66.5 | 67.7 | 64.3 |  | 66.7 |
| 474 | po | 3 | 6.5 | 9.3 | 25.9 |  | 9.7 |
|  | po | 10 | 22.5 | 29.5 | 44.6 |  | 23.1 |
|  | po | 30 | 70.8 | 82.9 | 87.0 |  | 67.3 |
| 475 | po | 10 | 29.7 | 11.3 | 61.4 |  | 19.2 |
|  | po | 30 | 51.9 | 45.0 | 63.0 |  | 49.5 |
| 159* | ip | 10 |  | 28.5 |  | 21.7 | 54.1 |
|  | ip | 10 | 78.6 | 82.2 |  |  | 54 |

TABLE 4-continued

Delayed Hypersensitivity Assay Results for Select Compounds of Formula I

| Cmpd No. | Route | Dose (mg/kg) | IL6 Reduction (%) | IFNγ Reduction (%) | CXCL1 Reduction (%) | TNFα Reduction (%) | Reduction in edema (%) |
|---|---|---|---|---|---|---|---|
| | ip | 3 | 72.2 | 85.5 | | | 44 |
| | ip | 1 | 62.6 | 54.2 | | | 17 |
| 181 | ip | 10 | | 38.9 | | 25.5 | 50.1 |

*Compound 159 was tested in this assay on two separate occasions.

Figure 2:
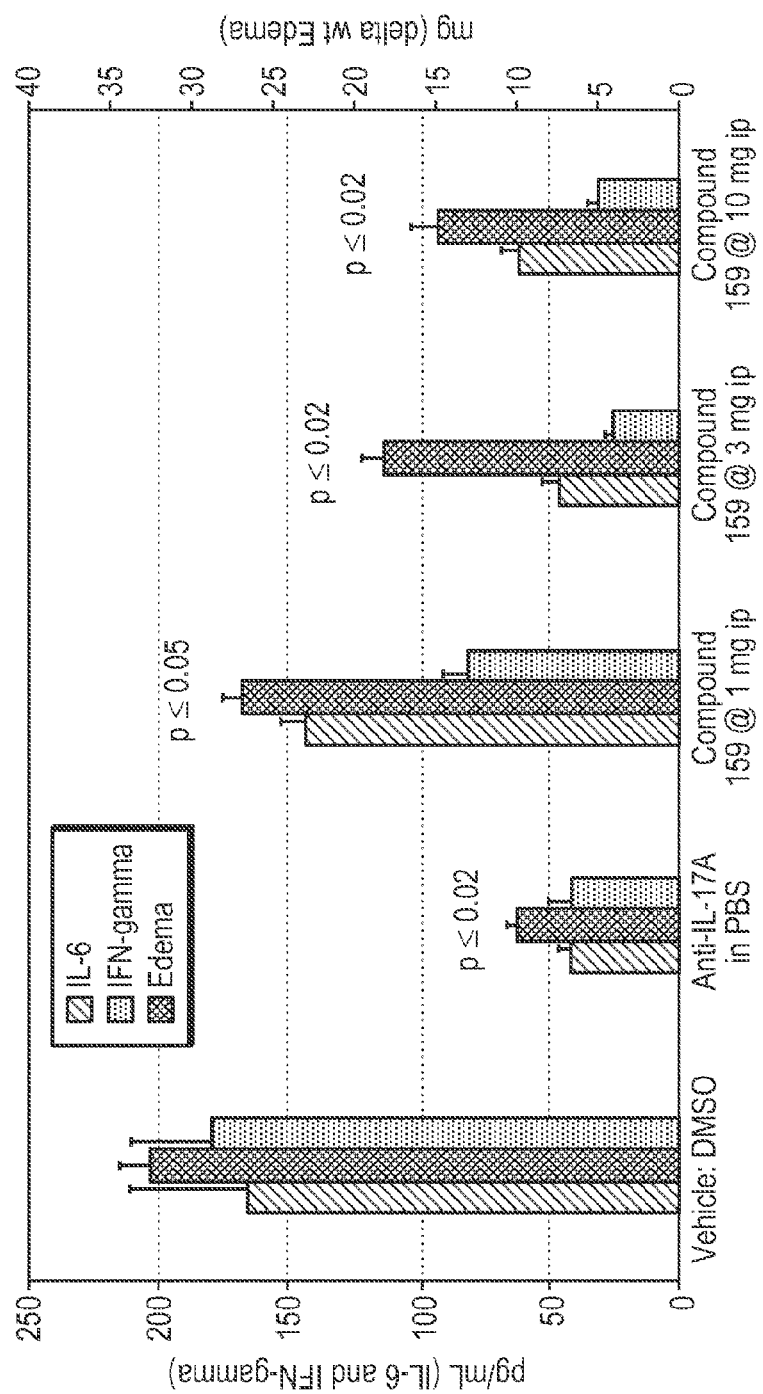
FIG. 2 depicts the dose-dependent effect of an intraperitoneally dosed exemplary compound of the invention (i.e., compound 159) on edema, IL-6, and IFN-γ in a murine delayed hypersensitivity assay, as compared to an IL-17 antibody and a vehicle control.
Figure 3:
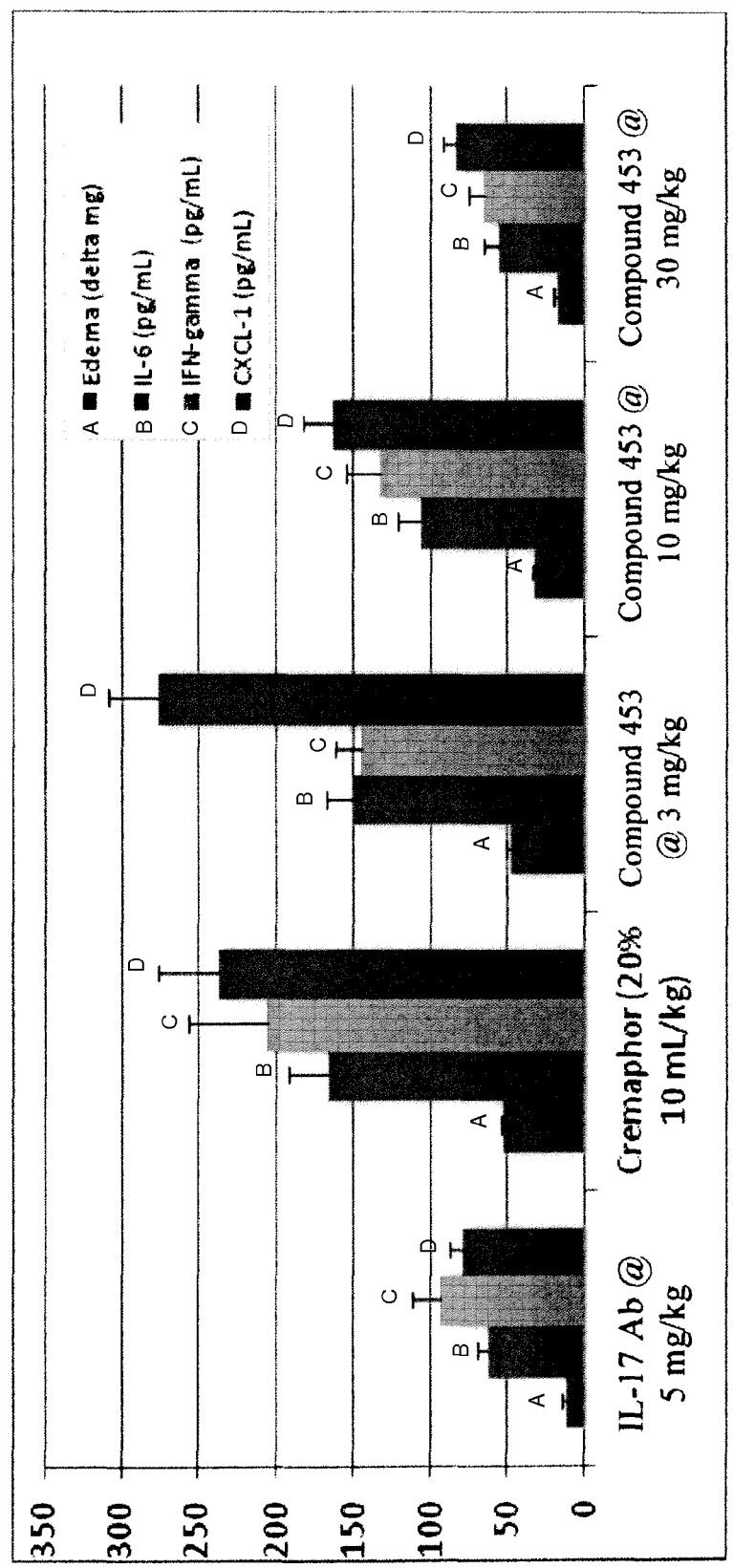
FIG. 3 depicts the dose-dependent effect of an orally dosed exemplary compound of the invention on edema, IL-6, and IFN-γ in a murine delayed hypersensitivity assay, as compared to an IL-17 antibody and a vehicle control.
Figure 4:
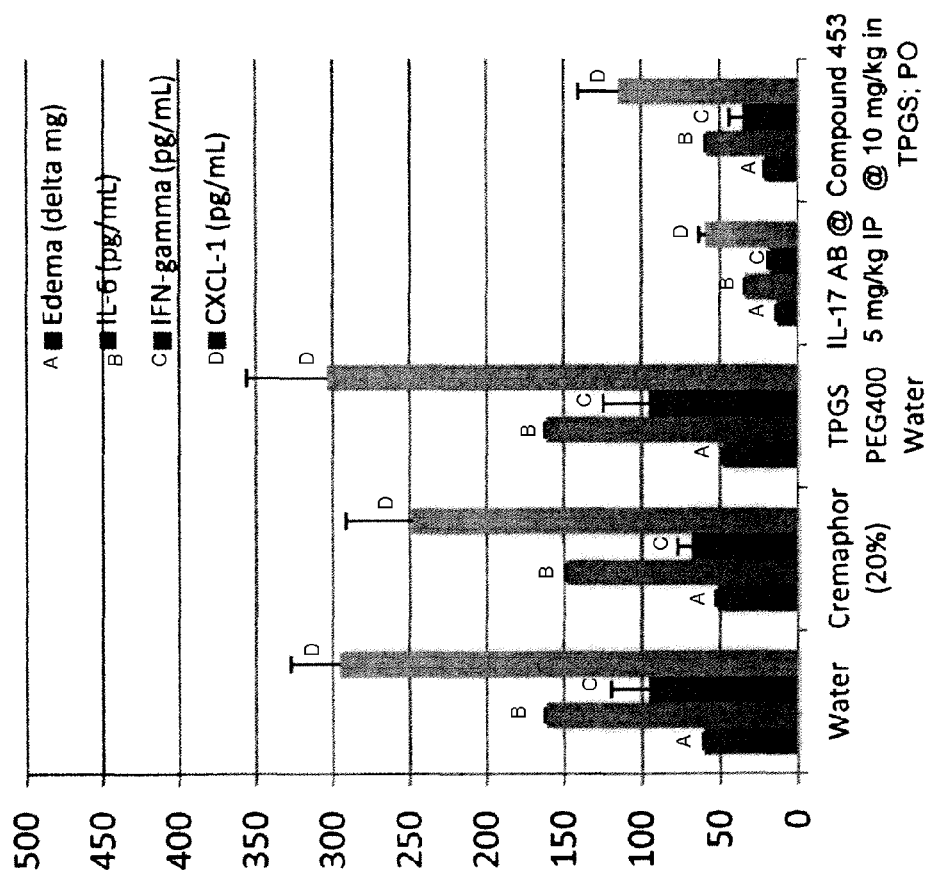
FIG. 4 depicts the effect of an orally dosed exemplary compound of the invention on edema, IL-6, IFN-γ and CXCL-1 in a murine delayed hypersensitivity assay, as compared to an IL-17 antibody and various vehicle controls.
Figure 5:
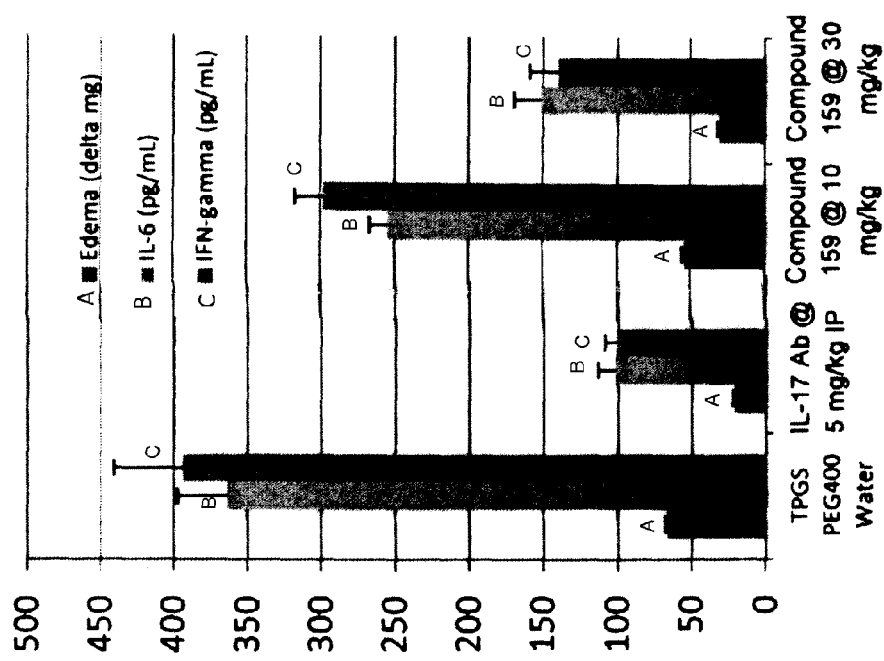
FIG. 5 depicts the dose-dependent effect of an orally dosed exemplary compound of the invention on edema, IL-6, and IFN-γ in a murine delayed hypersensitivity assay, as compared to an IL-17 antibody and various vehicle controls.

FIG. 1 demonstrates that Compounds 159 and 181 administered i.p. at 10 mg/kg both produced a statistically significant reduction in TNF-α, IFN-γ and edema as compared to a PBS control or DMSO control. FIG. 2 demonstrates that Compound 159 administered i.p. at 1 mg/kg, 3 mg/kg, or 10 mg/kg, produced a statistically significant reduction in IL-6, IFN-γ and edema compared to a DMSO control. FIG. 3 demonstrates that Compound 453 in a 20% Cremophor Cremophor vehicle demonstrated an effective, dose-dependent decrease in IL-6, IFN-γ, CXCL-1, and edema when administered orally. At oral doses of 30 mg/kg, Compound 453 exhibited edema and biomarker suppression equivalent to anti-IL-17A antibody (anti-mouse IL-17 monoclonal antibody, BioLegend, Inc.) administered at 5 mg/kg (i.p.). FIG. 4 demonstrates that switching to the TPGS-PEG400 oral formulation improved the oral activity of Compound 453 relative to the Cremophor results in FIG. 3. Compound 453 administered orally at 10 mg/kg in a TPGS/PEG400/Water vehicle decreased IL-6, IFN-γ, CXCL-1, and edema as compared to any of water, 20% Cremophor vehicle alone, or TPGS/PEG400/Water vehicle alone. FIG. 5 shows that orally dosed Compound 159 in TPGS/PEG400/Water vehicle effectively reduced IL-6, IFN-γ, and edema in a dose-dependent manner.

F. Mouse Collagen-Induced Arthritis Model

Exemplary compounds of the invention were evaluated in a murine CIA model. DAB-1 mice (10/group) were anaesthetized with Isoflurane, shaved at the base of the tail, and injected intradermally with 150 μL of Freund's Complete Adjuvant (Sigma) containing bovine type II collagen (Elastin Products, Owensville, Mo.) (2 mg/mL) at the base of the tail on day 0 and again on day 21. On study days 24-25, onset of arthritis occurred and mice were randomized into treatment groups. Randomization into each group was done after swelling was obviously established in at least one paw (score of 1), and attempts were made to ensure approximately equal mean scores of 0.25 across the groups at the time of enrollment. Once a day oral treatment with 10 or 30 mg/kg of test compound in 20% Cremophor EL was initiated after enrollment and continued once a day as indicated through arthritis day 10. Mice were terminated on day 11. Clinical scores were calculated for each of the paws (right front, left front, right rear, and left rear) on arthritis days 1-11 and the results were summarized as a reduction in clinical arthritis score for all paws over the time period of dosing.

Figure 6:
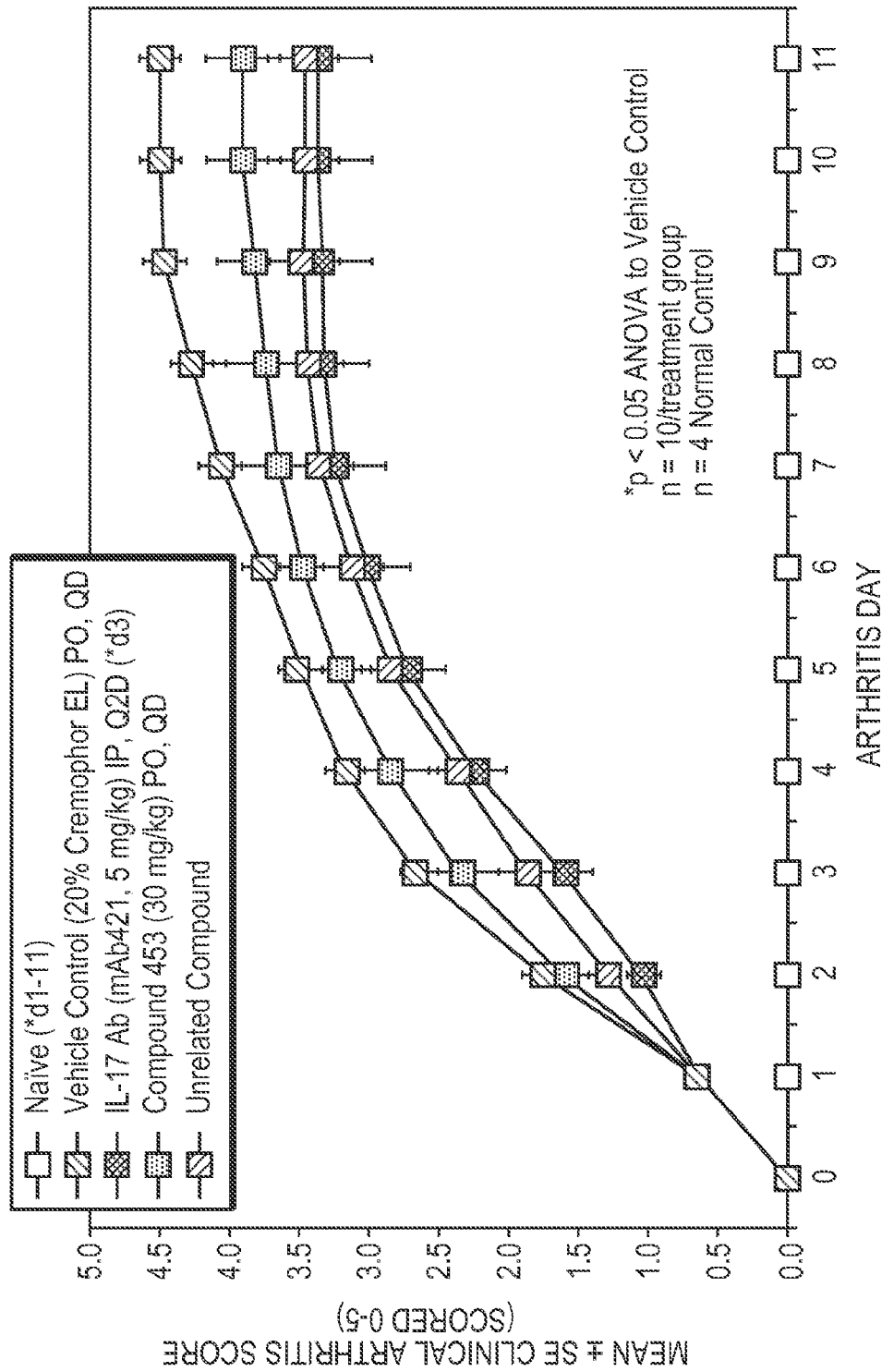
FIG. 6 depicts the effect over time on all paws of an orally dosed exemplary compound of the invention on Mean Clinical Arthritis Score in a murine collagen-induced arthritis ("CIA") assay, as compared to an IL-17 antibody and various vehicle controls.
Figure 7:
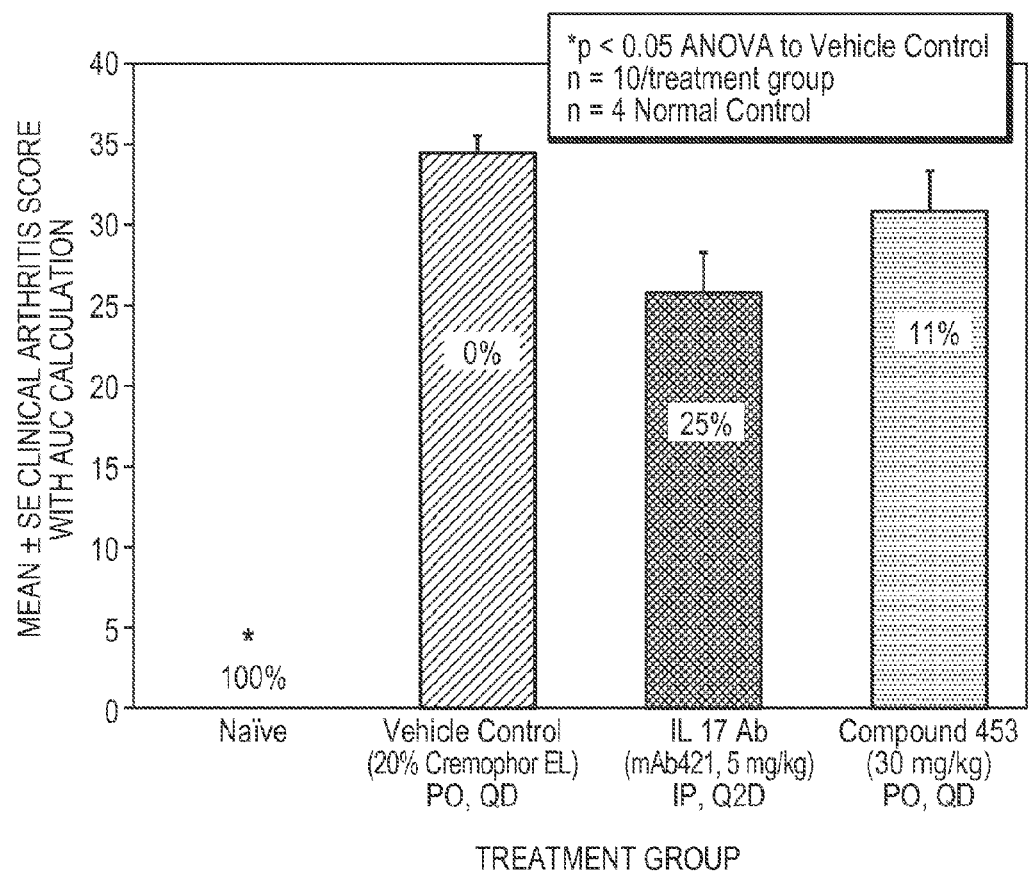
FIG. 7 depicts the effect on all paws of an orally dosed exemplary compound of the invention on Clinical Arthritis Score in a murine collagen-induced arthritis ("CIA") assay, as compared to an IL-17 antibody and a vehicle control.
Figure 8:
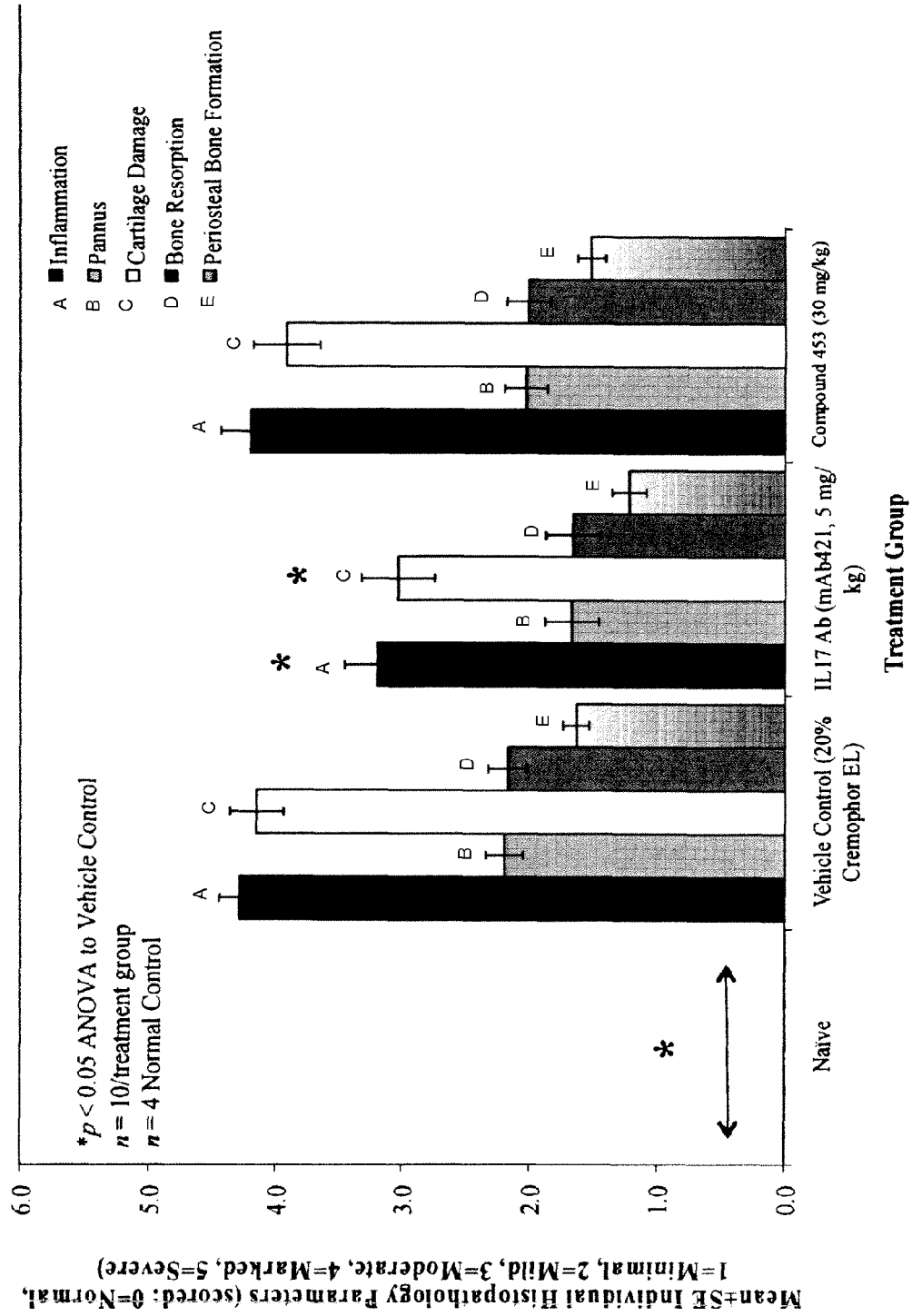
FIG. 8 depicts the effect on all joints of an orally dosed exemplary compound of the invention on various pathological parameters in a murine collagen-induced arthritis ("CIA") assay, as compared to an IL-17 antibody and a vehicle control.
Figure 9:
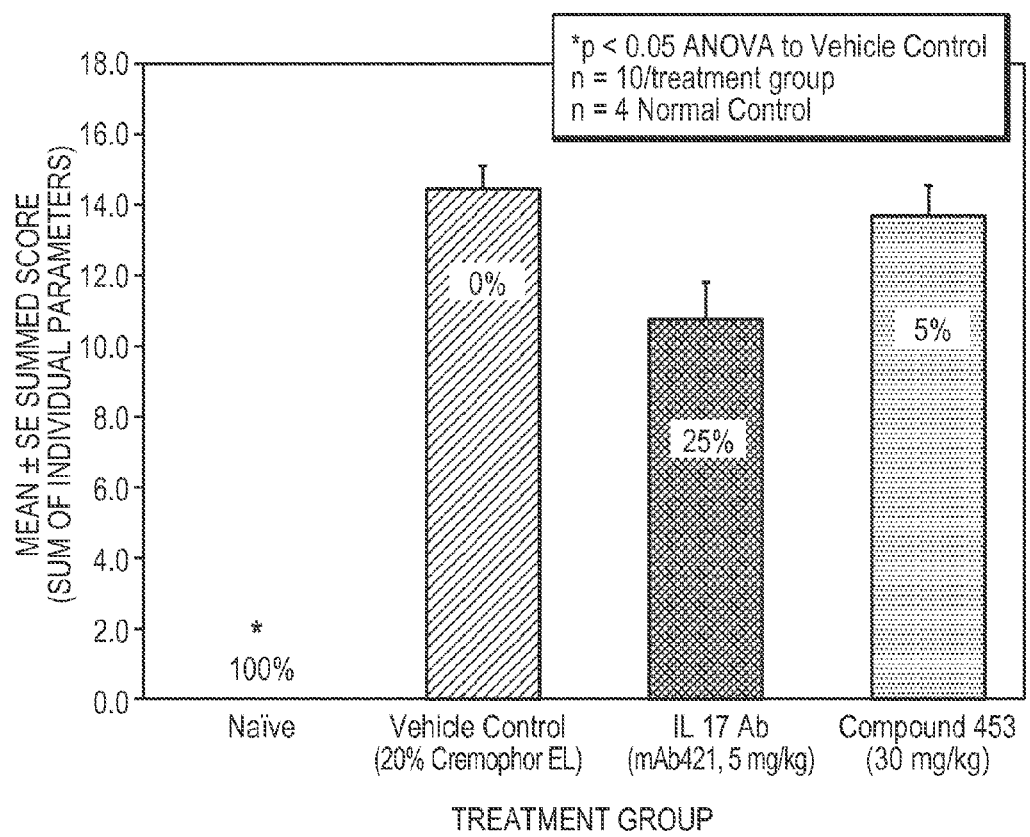
FIG. 9 depicts the sum effect of an orally dosed exemplary compound of the invention on measured pathological parameters in a murine collagen-induced arthritis ("CIA") assay, as compared to an IL-17 antibody and a vehicle control.
Figure 10:
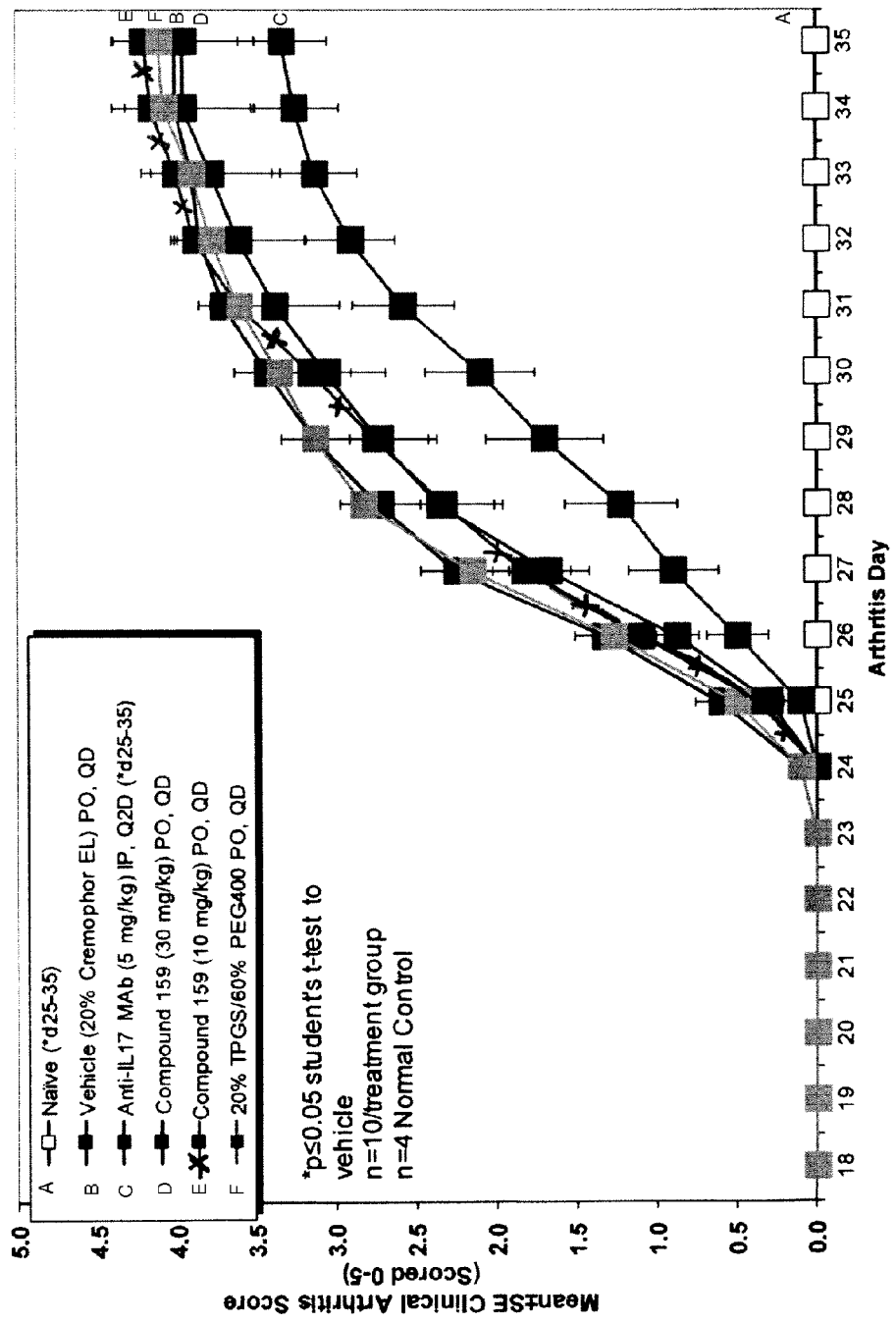
FIG. 10 depicts the effect over time on all paws of two different dosages of an orally dosed exemplary compound of the invention on Mean Clinical Arthritis Score in a murine collagen-induced arthritis ("CIA") assay, as compared to an IL-17 antibody and vehicle controls.
Figure 11:
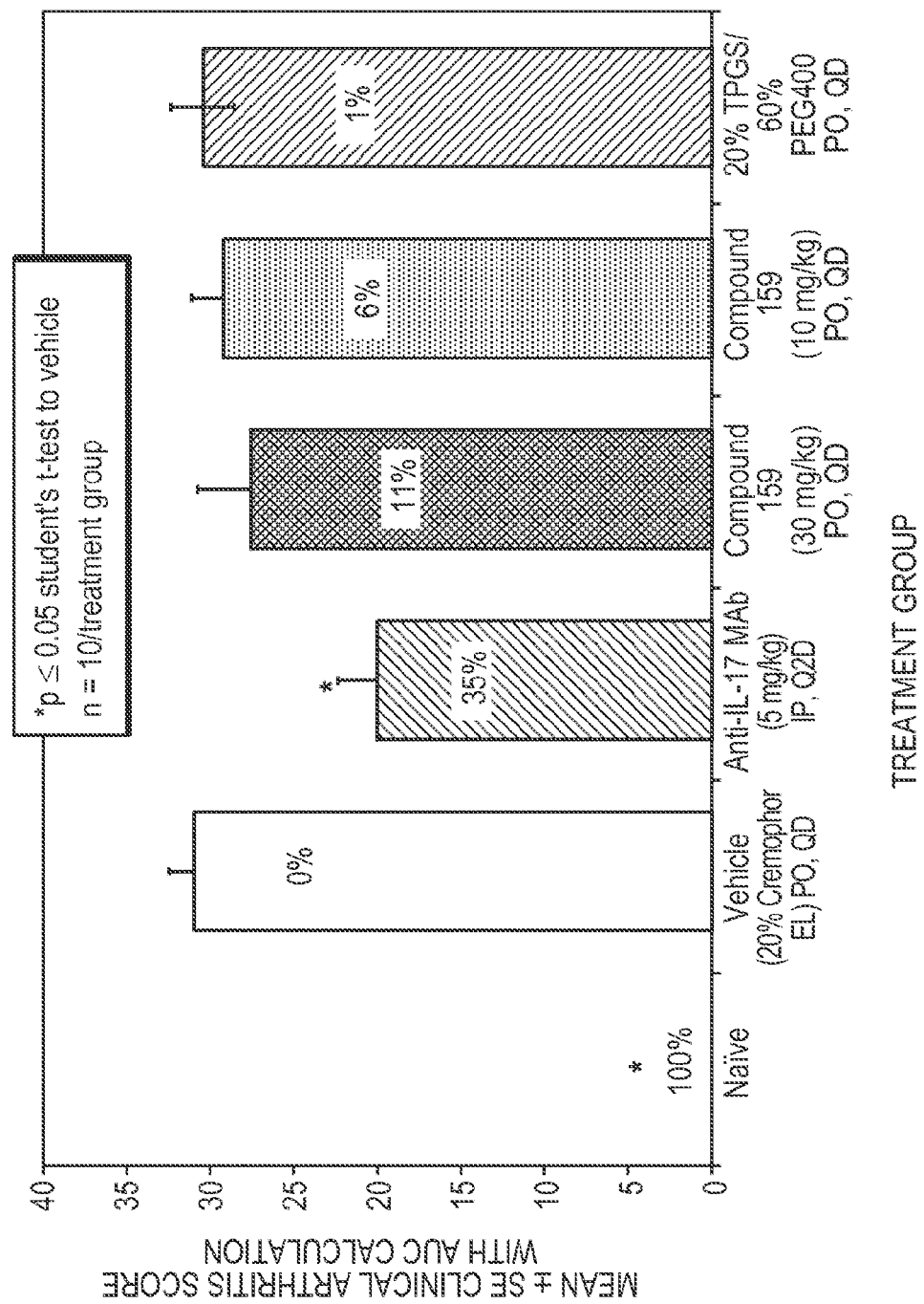
FIG. 11 depicts the overall effect on all paws of two different dosages of an orally dosed exemplary compound of the invention on Mean Clinical Arthritis Score in a murine collagen-induced arthritis ("CIA") assay, as compared to an IL-17 antibody and vehicle controls.

As shown in FIG. 6, Compound 453 administered orally at 30 mg/kg in 20% Cremophor EL reduced mean Clinical Arthritis Score over time as compared to the vehicle control. FIG. 7 shows that this reduction was 11%. FIG. 8, however, suggests that Compound 453 administered orally at 30 mg/kg in 20% Cremophor EL had little effect on histological parameters. The overall effect on histological parameters was 5% as shown in FIG. 9. FIG. 10 demonstrates that Compound 159 administered orally at 10 and 30 mg/kg in 20% Cremophor EL demonstrated superior reduction in mean Clinical Arthritis Score on days 27-30 as compared to either TPGS/PEG400 vehicle control or 20% Cremophor EL vehicle control. FIG. 11 shows that Compound 159 reduced the overall mean Clinical Arthritis Score by 6% at 10 mg/kg and 11% at 30 mg/kg.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound represented by Formula I:

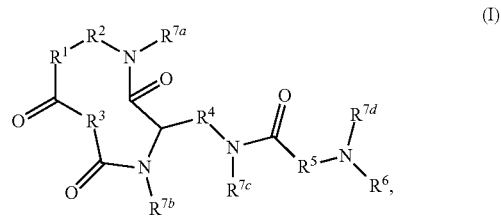

or a pharmaceutically acceptable salt thereof, wherein:
$R^1$ is selected from —O— and —N(($C_0$-$C_3$ alkylene)-Q)-, wherein
Q is selected from hydrogen, —N($R^{7e}$), —OH, —O—$C_1$-$C_4$ alkyl, aryl, heteroaryl, carbocyclyl, and heterocyclyl;
the alkylene portion of $R^1$, if present, is optionally substituted; and
when the —C(O)— group adjacent to $R^1$ is bound directly to an —N($R^{7b}$)— in $R^3$, $R^1$ is additionally selected from —$CH_2$—;
$R^2$ is an optionally substituted $C_3$-$C_{12}$ alkylene, optionally substituted $C_3$-$C_{12}$ alkenylene, or optionally substituted $C_3$-$C_{12}$ alkynylene, wherein:
up to three methylene units of $R^2$ are optionally and independently replaced with —O—, —N($R^c$)—, —S—, —S(O)—, or —S(O)$_2$—, wherein
$R^c$ is selected from hydrogen, $C_1$-$C_4$ alkyl, —C(O)—$C_1$-$C_3$ alkyl, —C(O)—($C_1$-$C_3$ alkylene)-aryl, —C(O)—

($C_1$-$C_3$ alkylene)-heteroaryl, —C(O)—O—$C_1$-$C_3$ alkyl, —C(O)—O—$C_1$-$C_3$ alkenyl, —S(O)$_2$—$C_1$-$C_3$ alkyl, —S(O)$_2$—($C_1$-$C_3$ alkylene)-aryl, and —S(O)$_2$—($C_1$-$C_3$ alkylene)-heteroaryl; or when $R^1$ is —N(($C_0$-$C_3$ alkylene)-Q)-, $R^c$ is optionally taken together with $R^1$ and any intervening atoms to form a heterocyclyl;

any two substituents bound to a common carbon atom in $R^2$ are optionally taken together to form =O, carbocyclyl, or heterocyclyl;

any two substituents bound to different carbon atoms in $R^2$ are optionally taken together with any intervening atoms to form an aryl, heteroaryl, carbocyclyl, or heterocyclyl;

any two $R^c$ are optionally taken together with the nitrogen atoms to which they are bound and any intervening atoms to form a heterocyclyl; and any substituent bound to a carbon atom in $R^2$ is optionally taken together with any one $R^c$ or with $R^{7a}$ and any intervening atoms to form heteroaryl or heterocyclyl;

$R^3$ is —[C($R^d$)($R^d$)]$_p$—[N($R^{7h}$)]$_{0-1}$—[C($R^d$)($R^d$)]$_q$—, wherein:

each $R^d$ is independently selected from hydrogen and a suitable alkylene substituent; and any two $R^d$ are optionally taken together with any intervening atoms to form aryl, heteroaryl, carbocyclyl, or heterocyclyl;

p is 0, 1 or 2;

q is 0, 1 or 2; and p+q is 2 or more;

$R^4$ is —[C($R^e$)($R^e$)]$_n$—Y—[C($R^e$)($R^e$)]$_m$—, wherein:

each $R^e$ is independently selected from hydrogen and a suitable alkylene substituent;

Y is selected from aryl, heteroaryl, carbocyclyl, heterocyclyl, and optionally substituted $C_1$-$C_3$ alkylene;

each of n and m are independently selected from 0, 1, 2, 3, 4, 5, and 6; and n+m is 6 or less;

$R^5$ is $C_1$-$C_2$ alkylene substituted with one or more —($C_0$-$C_5$ alkylene)-$R^f$, wherein each $R^f$ is independently selected from —CH$_3$, —O—$C_1$-$C_3$ alkyl, aryl, heteroaryl, carbocyclyl, and heterocyclyl;

$R^6$ is selected from heteroaryl, —CH$_2$-aryl, —C(O)—$R^8$, —C(O)—O—$R^8$, —C(O)—C(O)—$R^8$, —S(O)—$R^8$, —S(O)$_2$—$R^8$, C(O)—N($R^{7f}$)—$R^8$, and —S(O)$_2$—N($R^{7f}$)—$R^8$;

each $R^{7a}$, $R^{7b}$, $R^{7c}$, $R^{7d}$, $R^{7e}$, $R^{7f}$, and $R^{7g}$ is independently selected from hydrogen and $C_1$-$C_4$ alkyl;

$R^{7h}$ is independently selected from hydrogen, $C_1$-$C_4$ alkyl, phenyl, and benzyl;

$R^8$ is selected from —($C_0$-$C_6$ alkylene)-aryl, —($C_0$-$C_6$ alkylene)-heteroaryl, —($C_0$-$C_6$ alkylene)-carbocyclyl, —($C_0$-$C_6$ alkylene)-heterocyclyl, and $C_1$-$C_6$ alkyl, wherein when $R^8$ is $C_1$-$C_6$ alkyl, up to two methylene units in the alkyl are optionally and independently replaced with —O—, —N($R^{7g}$)—, —S—, —S(O)—, or —S(O)$_2$—; and any alkyl or alkylene portion of $R^8$ is optionally substituted with an appropriate alkyl or alkylene substituent other than =O; or $R^{7d}$ and $R^6$ are optionally taken together to form a heterocyclyl; and any aryl, heteroaryl, carbocyclyl, or heterocyclyl portion of the compound is optionally substituted.

2. The compound of claim 1, wherein $R^1$ is selected from —O—, —N(H)— and —N(CH$_3$)—.

3. The compound of claim 1, wherein $R^2$ is selected from *—CH($R^{10}$)—Z— and *—C(H)($R^{10}$)—X—C(H)($R^{10}$)—N($R^{12}$)—C(O)—C(H)($R^{11}$)—(CH$_2$)$_{0-2}$—, wherein:

X is selected from —CH$_2$—O—CH$_2$—, —CH$_2$—N(H)—CH$_2$—, —CH$_2$—N(CH$_3$)—CH$_2$—, —CH$_2$—, —(CH$_2$)$_2$—, and —(CH$_2$)$_3$—;

Z is selected from $C_2$-$C_8$ alkylene, $C_2$-$C_8$ alkenylene, or $C_2$-$C_8$ alkynylene, wherein up to 2 methylene units in Z are optionally and independently replaced with —O—, —N(H)— or —N(CH$_3$)—;

each $R^{10}$ is independently selected from hydrogen and —(R)—COOH, wherein at least one $R^{10}$ is hydrogen;

$R^{11}$ is selected from hydrogen, (S)—CH$_2$OH, (S)—CH$_3$, (S)—C(CH$_3$)$_3$, (S)-benzyl, (R)-benzyl, (S)—CH$_2$-pyridinyl, (S)-cyclohexyl, (S)—CH$_2$-cyclohexyl, (S)—(CH$_2$)$_2$—COOH, (S)—(CH$_2$)$_2$—C(O)NH$_2$, and (S)—(CH$_2$)$_4$—NH$_2$;

$R^{12}$ is selected from hydrogen and —CH$_3$; and

"*" represents a terminus of $R^2$ bound to $R^1$.

4. The compound of claim 1, wherein $R^2$ is selected from *—(CH$_2$)$_{3-9}$—, *—CH(COOH)—(CH$_2$)$_{2-8}$—, *—(CH$_2$)$_2$—O—(CH$_2$)$_2$—, *—(CH$_2$)$_2$—O—(CH$_2$)$_2$—O—(CH$_2$)$_2$—, *—(CH$_2$)$_2$—NH—(CH$_2$)$_2$—, *—(CH$_2$)$_2$—N(CH$_3$)—(CH$_2$)$_2$—, *—CH$_2$—C≡C—(CH$_2$)$_{4-5}$, and *—CH$_2$—CH=CH—(CH$_2$)$_{4-5}$.

5. The compound of claim 1, wherein the portion of the compound represented by —$R^1$-$R^2$ is selected from:

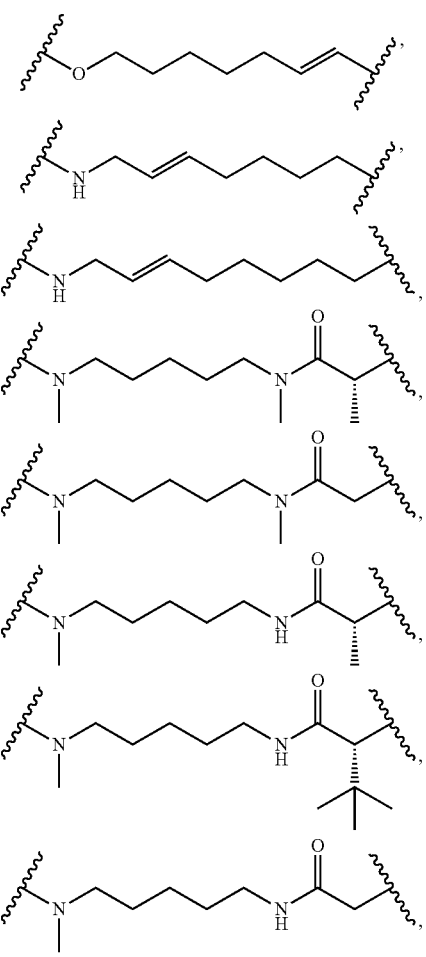

117
-continued
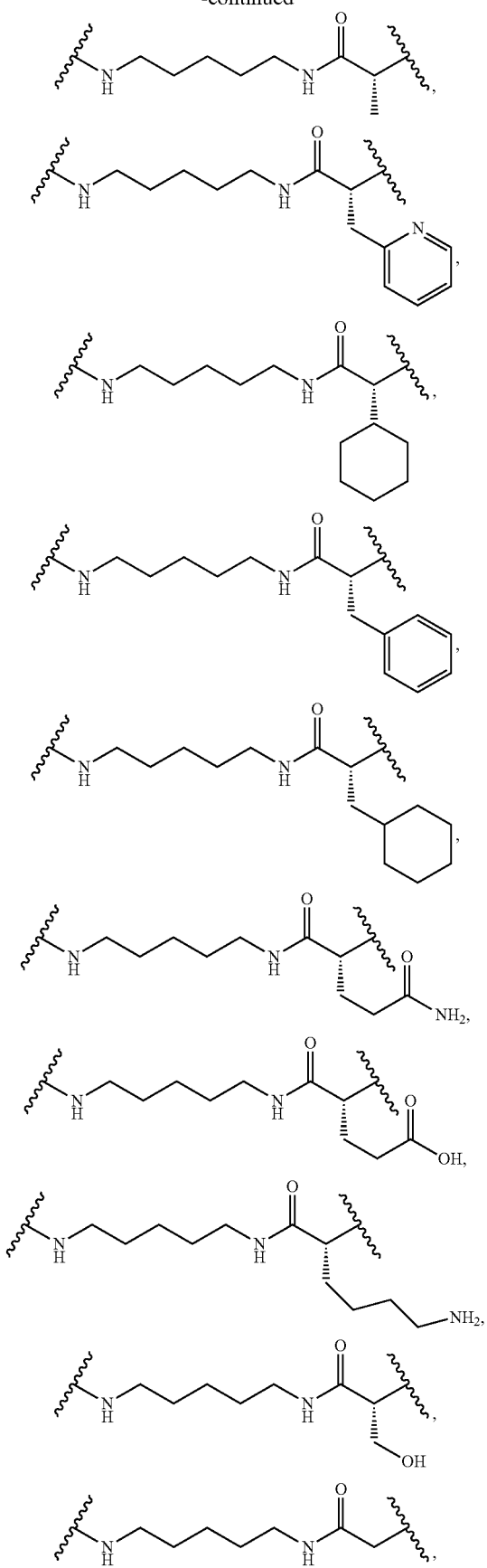
118
-continued
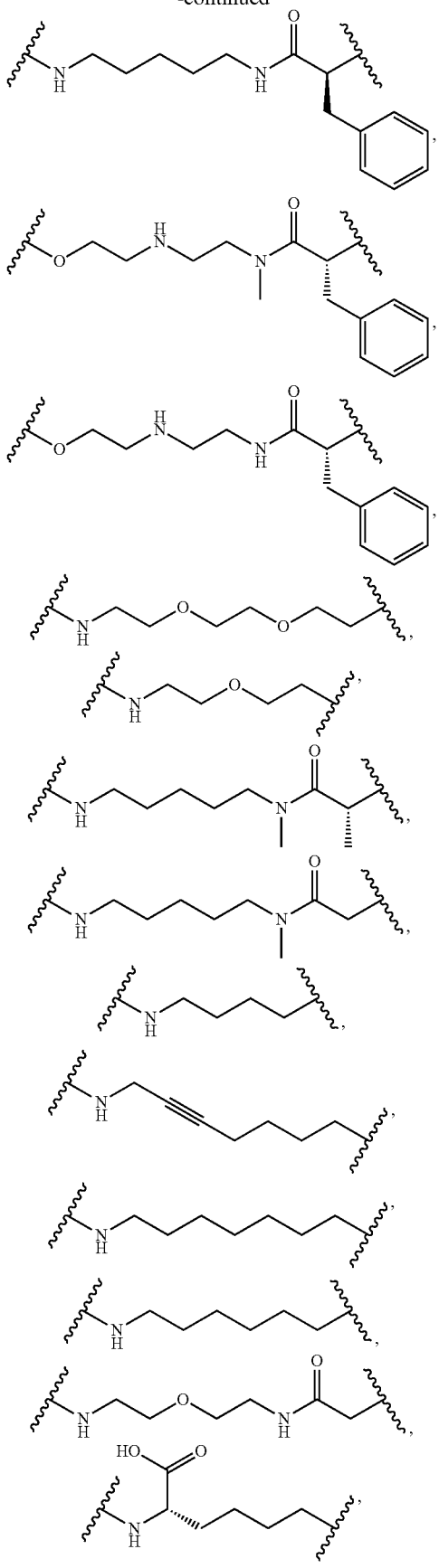

119
-continued
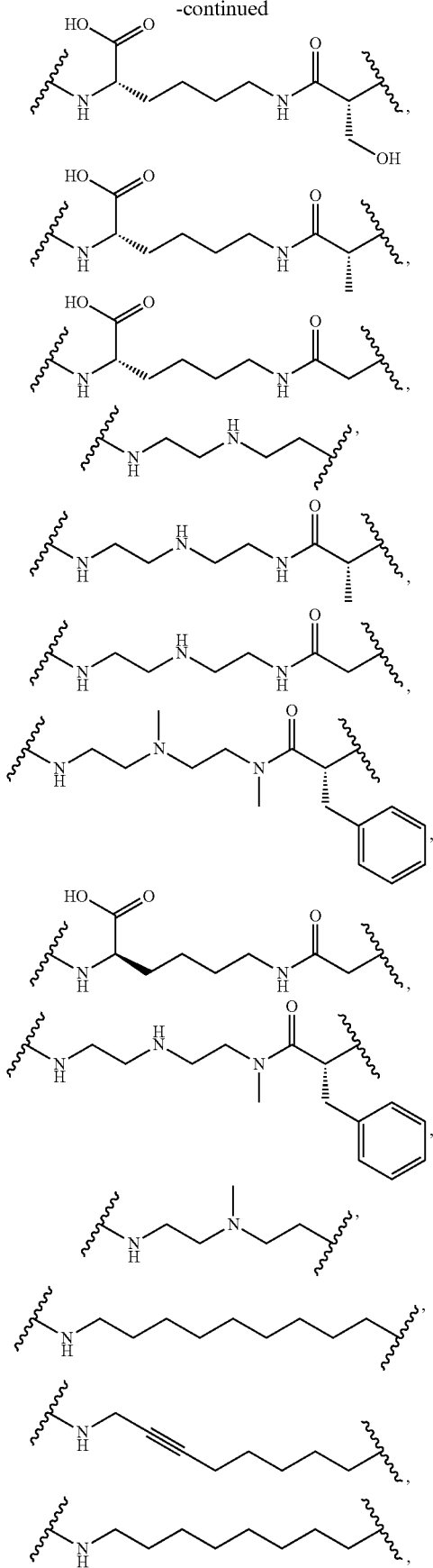
120
-continued
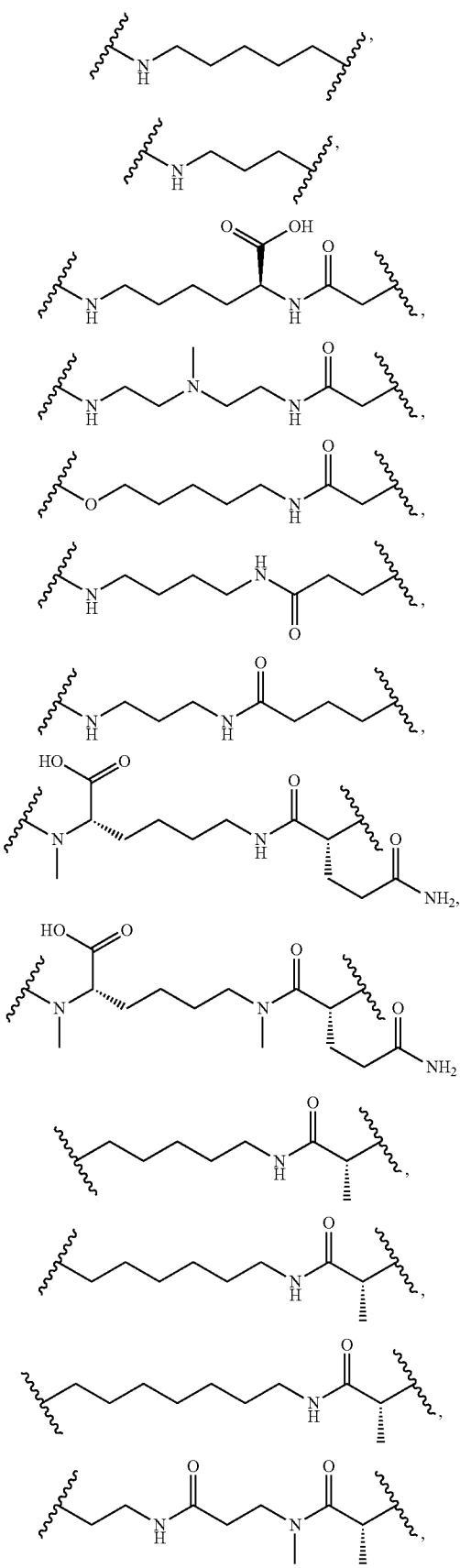

121
-continued
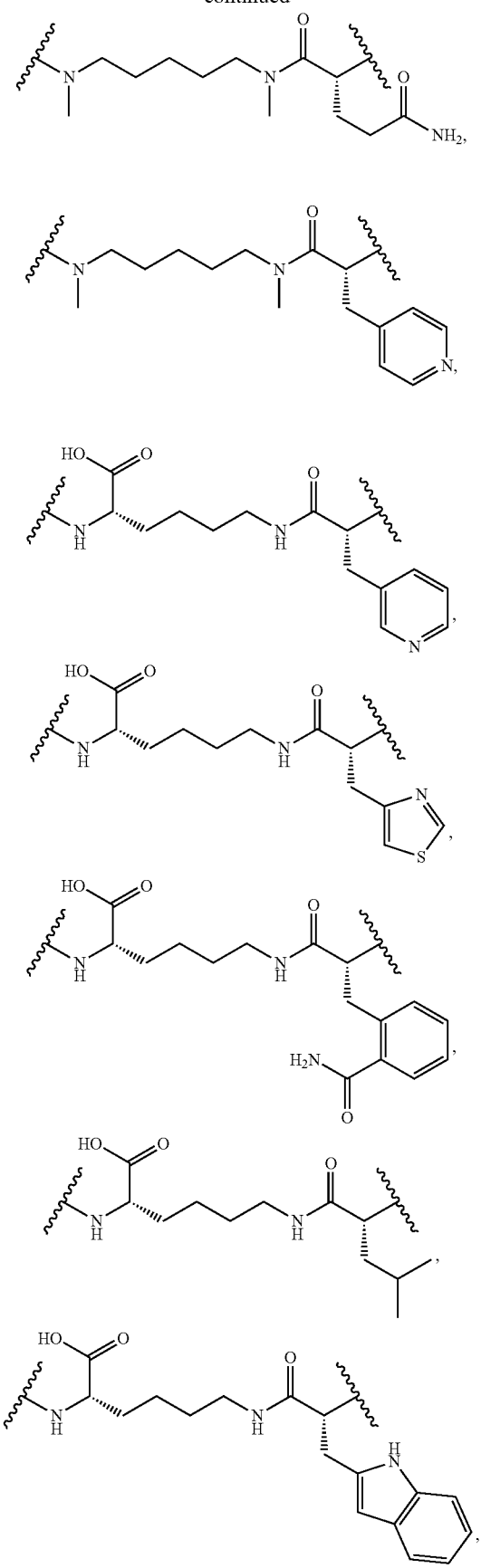
122
-continued
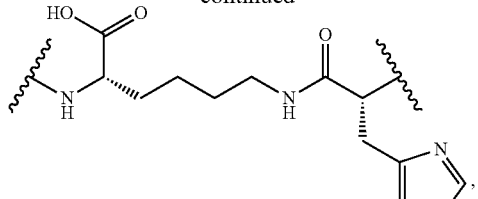
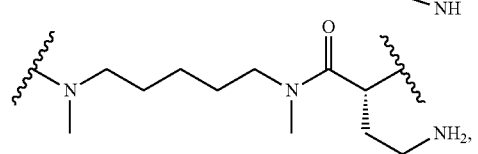
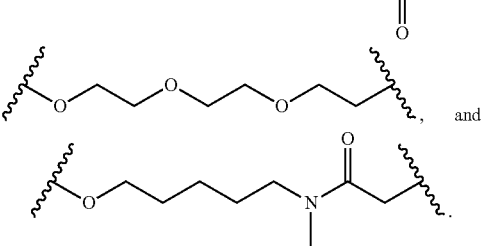
6. The compound of claim 1, wherein $R^3$ is selected from —CH$_2$—C(CH$_3$)$_2$—CH$_2$—, —CH$_2$—N(CH$_3$)—CH$_2$—,
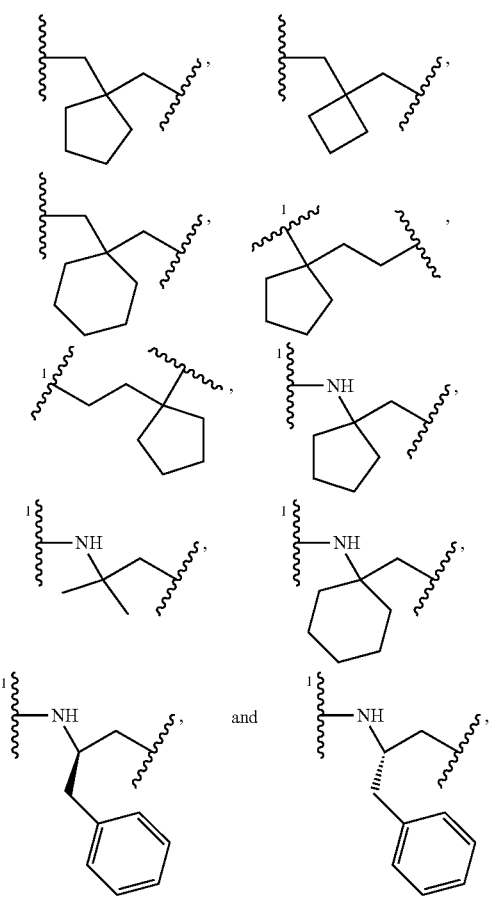
wherein "1" represents a portion of $R^3$ bound to the carbonyl moiety that is bound to $R^1$.

7. The compound of claim 1, wherein $R^4$ is selected from —$(CH_2)_4$— and —$CH_2$-(1,4-phenylene)-†, wherein "†" represents a portion of $R^4$ bound to $N(R^{7c})$.

8. The compound of claim 1, wherein $R^4$ is —$CH_2$-(1,4-phenylene)-†; and the stereochemistry of the carbon adjacent to $R^4$ is (S).

9. The compound of claim 1, wherein $R^5$ is —C(H)((R)-benzyl)- wherein a phenyl portion of the benzyl is optionally substituted with up to two substituents independently selected from bromo, chloro, fluoro, methyl, and —$CF_3$; or $R^5$ is selected from —C(H)($CH_2$—($C_4$-$C_6$ cycloalkyl))-, —C(H)($C_4$-$C_6$ cycloalkyl)-, —C(H)($CH_2$-thienyl)-, —C(H)($CH_2$-furanyl)-, —C(H)(heterocyclyl)-, —C(H)(CH($CH_3$)-(aryl))-, —C(H)(CH($CH_3$)-(heteroaryl))-, —C(H)(CH($CH_3$)-(heterocyclyl))-, —C(H)(CH($CH_3$)-(carbocyclyl))-, and —C(H)($C_3$-$C_4$ alkyl)-.

10. The compound of claim 1, wherein $R^5$ is selected from:

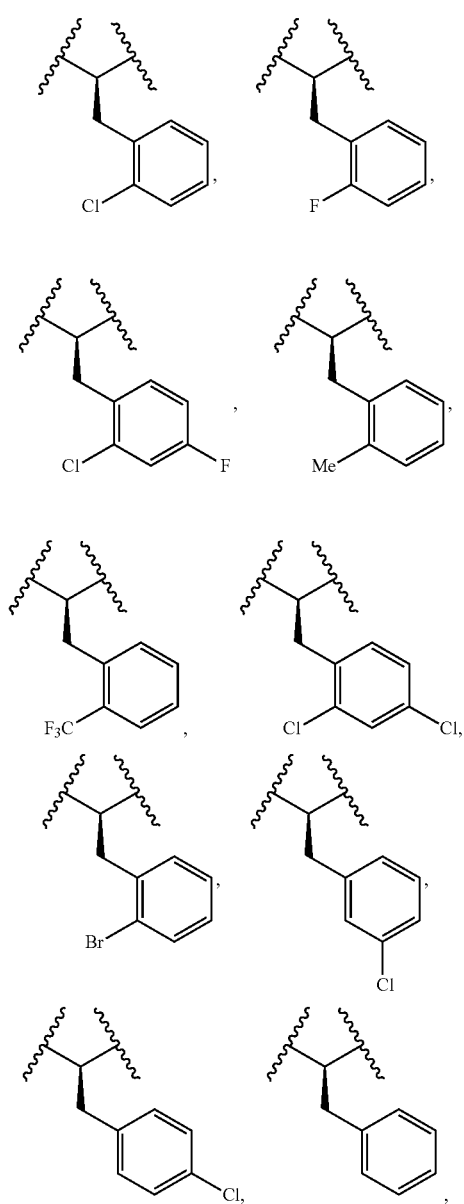

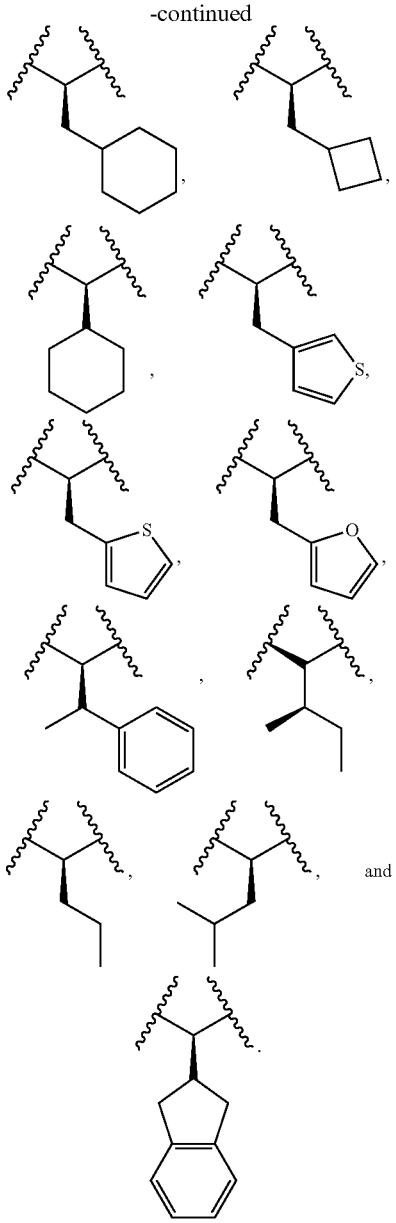

11. The compound of claim 1, wherein $R^6$ is —C(O)—[C($R^{13}$)$_2$]$_{0-1}$—$R^{9a}$; wherein $R^{9a}$ is selected from aryl, heteroaryl, cycloalkyl, saturated heterocyclyl, $C_1$-$C_4$ alkyl, —O—$C_1$-$C_4$ alkyl, —N(H)—$CH_3$, —N($CH_3$)$_2$, and —N(H)—$CH_2$-aryl, wherein $R^{9a}$ is optionally substituted with up to 2 substituents independently selected from halogen, $C_1$-$C_4$ alkyl, $C_1$-$C_4$ haloalkyl, hydroxy, $C_1$-$C_4$ alkoxy, —O—$(CH_2)_2$-morpholin-4-yl, —O—$(CH_2)_2$—N($R^{14}$)—$CH_2$-phenyl, —N(H)—C(O)—$CH_2$—N(H)—$CH_2$-phenyl, and —O—$(CH_2)_2$—N($R^{14}$)$_2$; each $R^{13}$ is independently hydrogen or fluoro, or two $R^{13}$ are taken together to form a $C_3$-$C_6$ cycloalkyl or =O; and each $R^{14}$ is independently hydrogen or —$CH_3$.

12. The compound of claim 11, wherein $R^{9a}$ is selected from phenyl, pyridyl, quinolinyl, isoquinolinyl, cyclohexyl, 3,3-difluorocyclopropyl, —$CH_3$, —C($CH_3$)$_3$, —$OCH_3$, —N($CH_3$)$_2$, —N(H)($CH_3$), and —N(H)-benzyl, wherein $R^{9a}$ is optionally substituted with up to 2 substituents independently selected from fluoro, chloro, methyl, methoxy, hydroxy, —O—(CH$_2$)$_2$-morpholin-4-yl, —O—(CH$_2$)$_2$—N(CH$_3$)—CH$_2$-phenyl, and —O—(CH$_2$)$_2$—N(CH$_3$)$_2$.

13. The compound of claim 1, wherein R$^6$ is —C(O)-benzyl or —C(O)— phenyl, wherein said benzyl and phenyl in R$^6$ are each optionally substituted with one or more substituents independently selected from the group consisting of halogen, hydroxyl, C$_1$-C$_4$ alkoxyl, and C$_1$-C$_4$ alkyl.

14. The compound of claim 1, wherein R$^6$ is selected from:

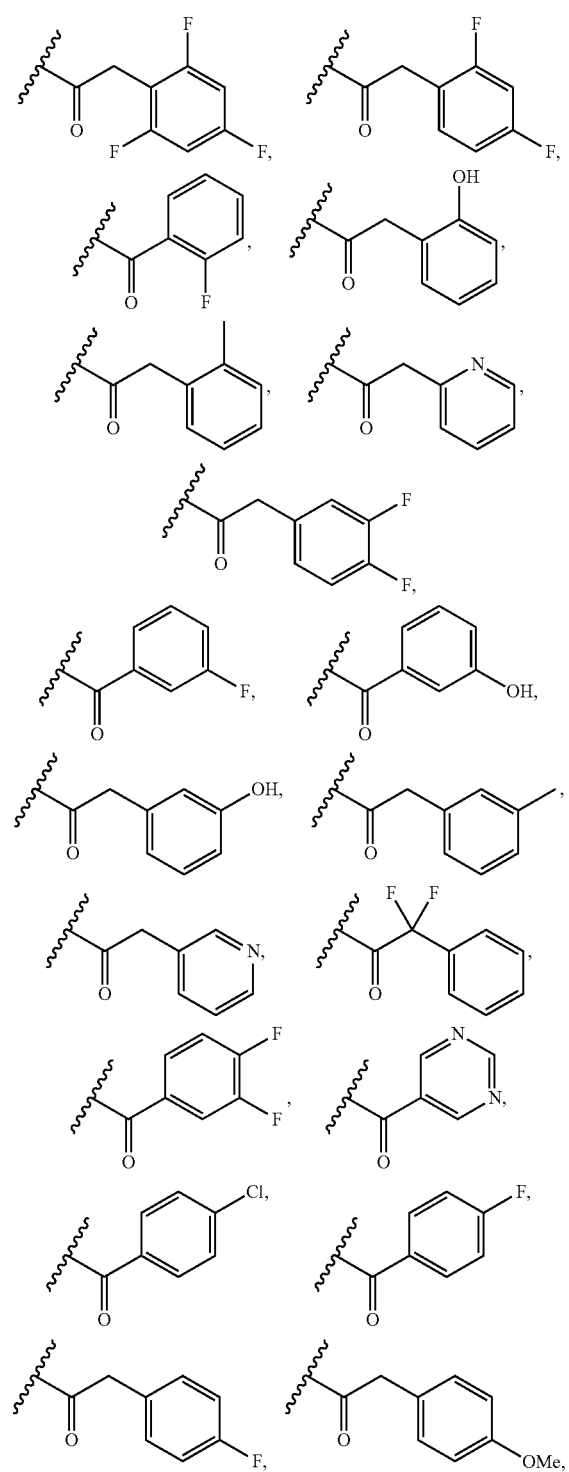

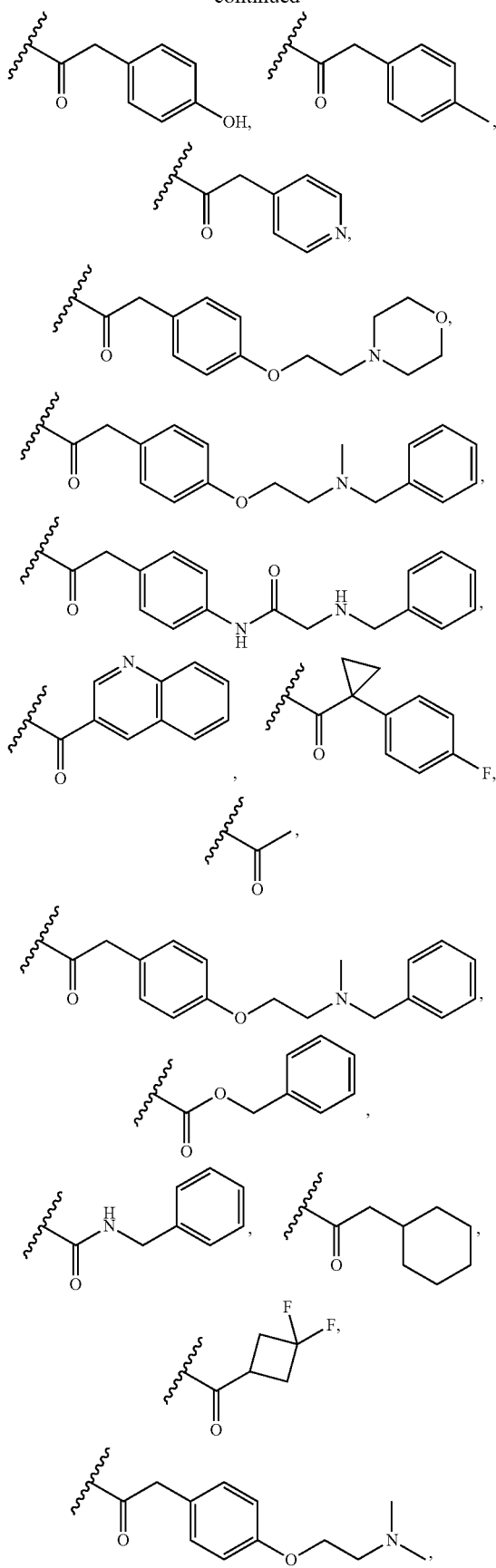

-continued
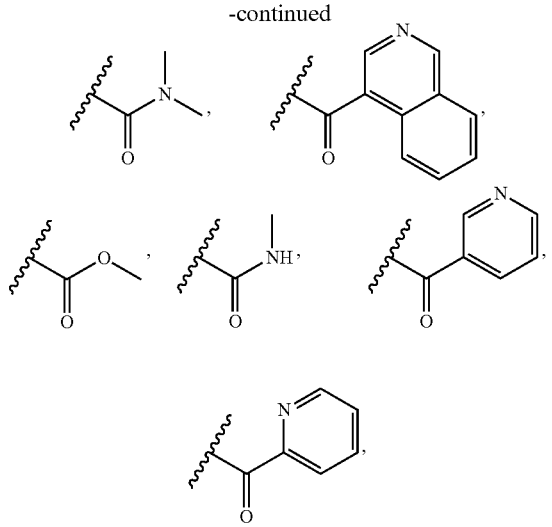
-continued
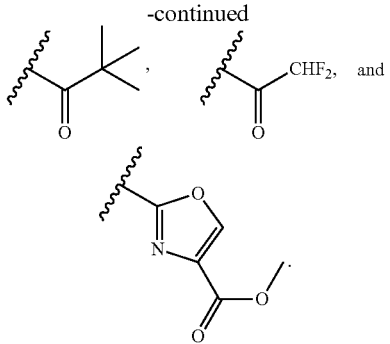
15. The compound of claim 1, wherein $R^{7a}$, $R^{7b}$, $R^{7c}$, $R^{7d}$, $R^{7e}$, $R^{7f}$, and $R^{7g}$ are independently selected from methyl and hydrogen.
16. A pharmaceutical composition comprising a compound of claim 1, and a pharmaceutically acceptable carrier.
* * * * *